US008846656B2

(12) United States Patent
Adams et al.

(10) Patent No.: US 8,846,656 B2
(45) Date of Patent: Sep. 30, 2014

(54) TETRAHYDROPYRIDO-PYRIDINE AND TETRAHYDROPYRIDO-PYRIMIDINE COMPOUNDS AND USE THEREOF AS C5A RECEPTOR MODULATORS

(75) Inventors: Christopher Michael Adams, Somerville, MA (US); Veronique Darsigny, Somerville, MA (US); Alec Nathanson Flyer, Cambridge, MA (US); Christine Fang Gelin, San Diego, CA (US); Timothy Brian Hurley, Boston, MA (US); Nan Ji, Arlington, MA (US); Rajeshri Ganesh Karki, Somerville, MA (US); Toshio Kawanami, Boston, MA (US); Erik Meredith, Hudson, MA (US); Chang Rao, Waltham, MA (US); Michael H. Serrano-Wu, Belmont, MA (US); Catherine Fooks Solovay, Arlington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/553,120

(22) Filed: Jul. 19, 2012

(65) Prior Publication Data
US 2013/0184253 A1   Jul. 18, 2013

Related U.S. Application Data

(60) Provisional application No. 61/539,732, filed on Sep. 27, 2011, provisional application No. 61/510,643, filed on Jul. 22, 2011.

(51) Int. Cl.
*C07D 471/04* (2006.01)
*C07D 491/107* (2006.01)
*C07D 491/044* (2006.01)
*C07D 471/10* (2006.01)
*C07D 471/08* (2006.01)

(52) U.S. Cl.
CPC ............ *C07D 471/04* (2013.01); *C07D 471/08* (2013.01); *C07D 491/044* (2013.01); *C07D 471/10* (2013.01); *C07D 491/107* (2013.01)
USPC .............. 514/210.21; 514/234.2; 514/252.16; 514/264.11; 514/300; 544/117; 544/230; 544/279; 546/122

(58) Field of Classification Search
USPC ............... 514/210.21, 234.2, 252.16, 264.11, 514/300; 300/117, 230, 279; 546/122
See application file for complete search history.

(56) References Cited

U.S. PATENT DOCUMENTS

| 4,727,149 A | 2/1988 | Shepherd |
| 2005/0277644 A1 | 12/2005 | Leblanc |

FOREIGN PATENT DOCUMENTS

| WO | 9805300 A2 | 2/1998 |
| WO | 0222608 A1 | 3/2002 |
| WO | 2004016596 A1 | 2/2004 |
| WO | 2004087056 A2 | 10/2004 |
| WO | 2005/014558 A1 | 2/2005 |
| WO | 2005/110416 A2 | 11/2005 |
| WO | 2006035061 A1 | 4/2006 |
| WO | 2007125320 A1 | 11/2007 |
| WO | 2009018466 A1 | 2/2009 |
| WO | 2009023669 A1 | 2/2009 |
| WO | 2010/014939 A1 | 2/2010 |
| WO | 2010014939 A1 | 2/2010 |
| WO | 2010028174 A1 | 3/2010 |
| WO | 2010120994 A2 | 10/2010 |
| WO | 2010126833 A1 | 11/2010 |
| WO | 2010138430 A1 | 12/2010 |
| WO | 2011022213 A1 | 2/2011 |
| WO | 2011062253 A1 | 5/2011 |
| WO | 2013016197 A1 | 1/2013 |
| WO | 2013049352 A2 | 4/2013 |
| WO | 2013082535 A2 | 6/2013 |

OTHER PUBLICATIONS

Gong et al., Bioorganic Medicinal Chemistry Letters, 18(14):3852-3855 (2008).
Barbay et al., Bioorganic Medicinal Chemistry Letters, 18(8):2544-2548 (2008).

*Primary Examiner* — San-Ming Hui
*Assistant Examiner* — Kathrien Cruz
(74) *Attorney, Agent, or Firm* — Joshua Roth

(57) ABSTRACT

The present invention provides a compound of formula I:

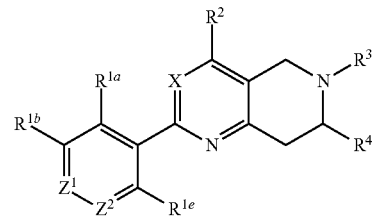

(I)
a method for manufacturing the compounds of the invention, and its therapeutic uses. The present invention further provides a combination of pharmacologically active agents and a pharmaceutical composition.

3 Claims, 39 Drawing Sheets

XRPD of Example 19-F of the initial precipitate (upper pattern) and dried material (lower pattern) from Me-THF

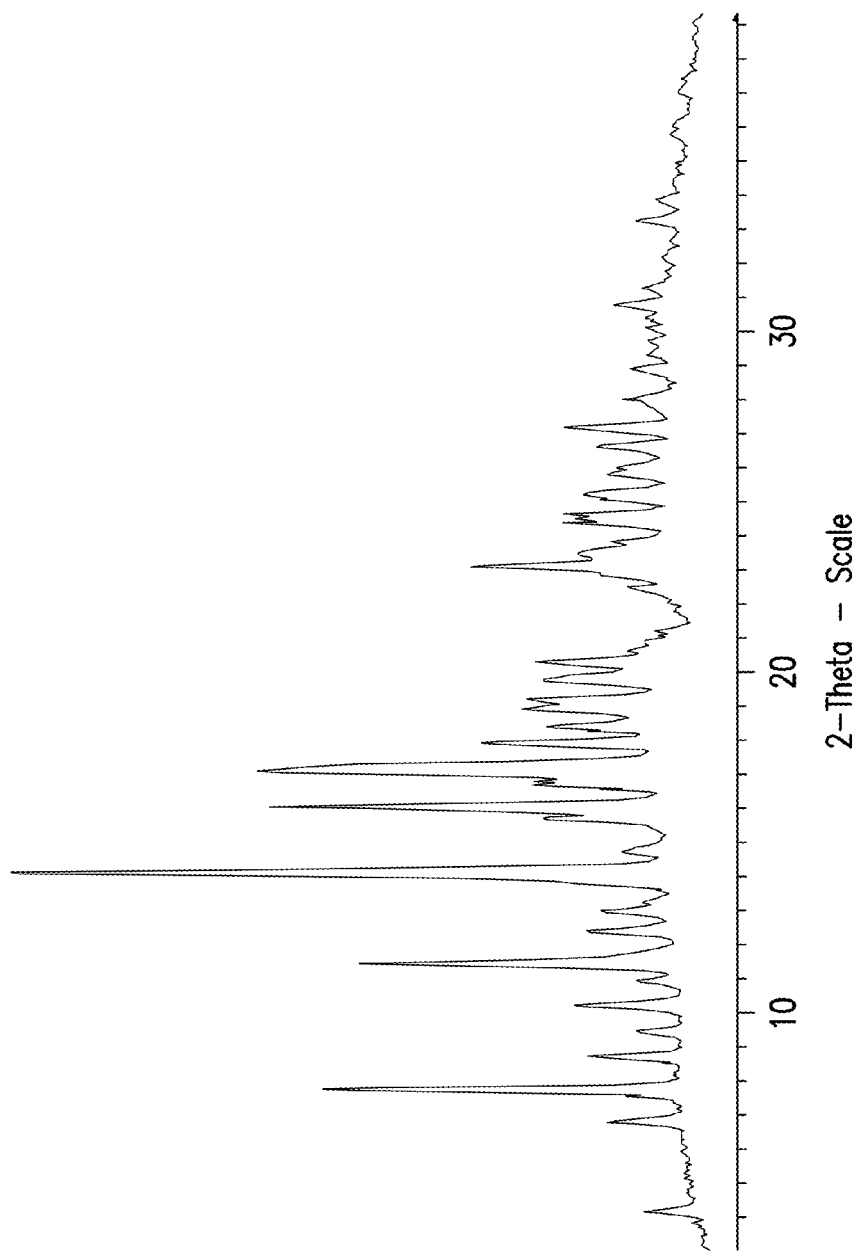

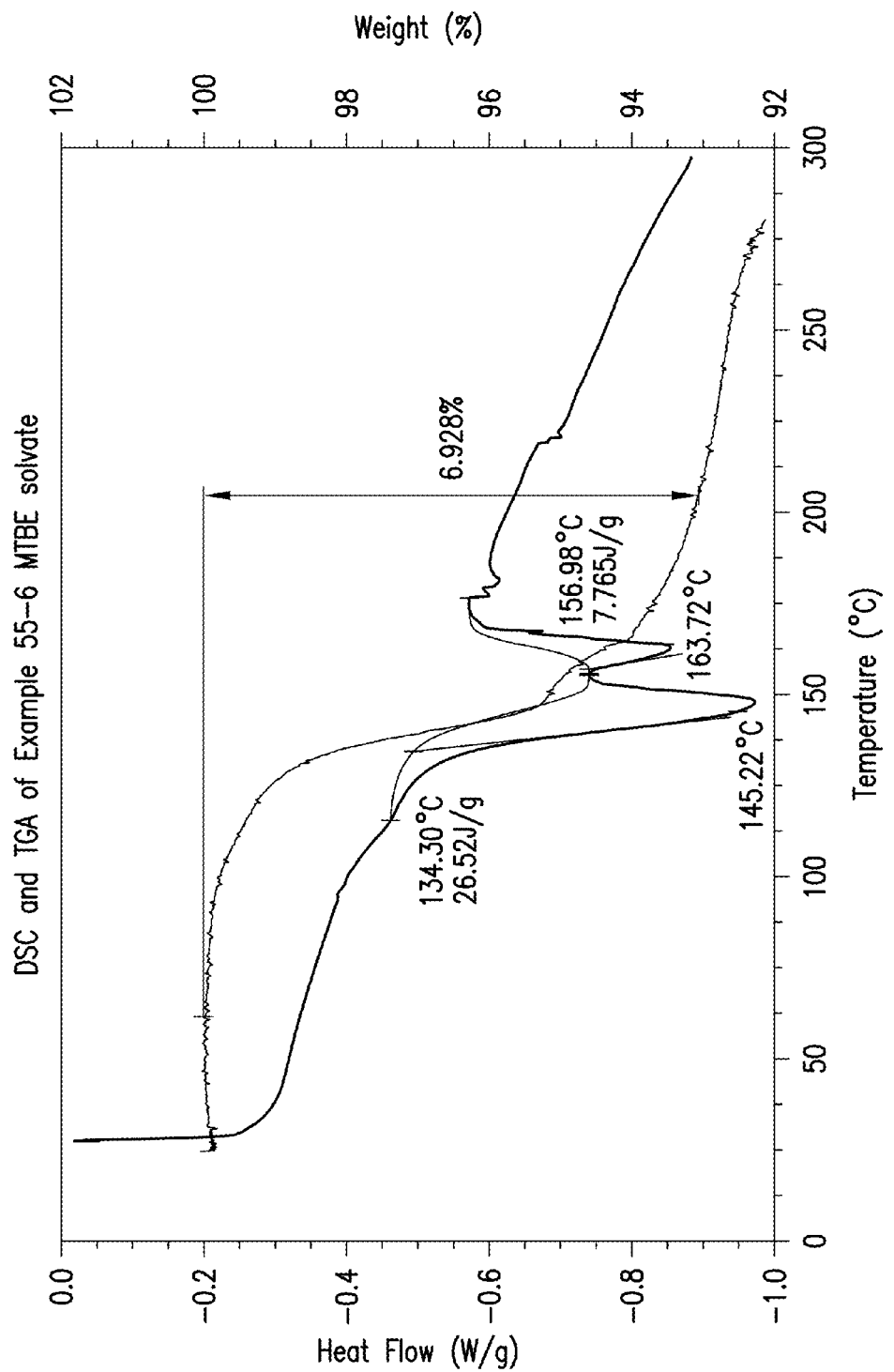

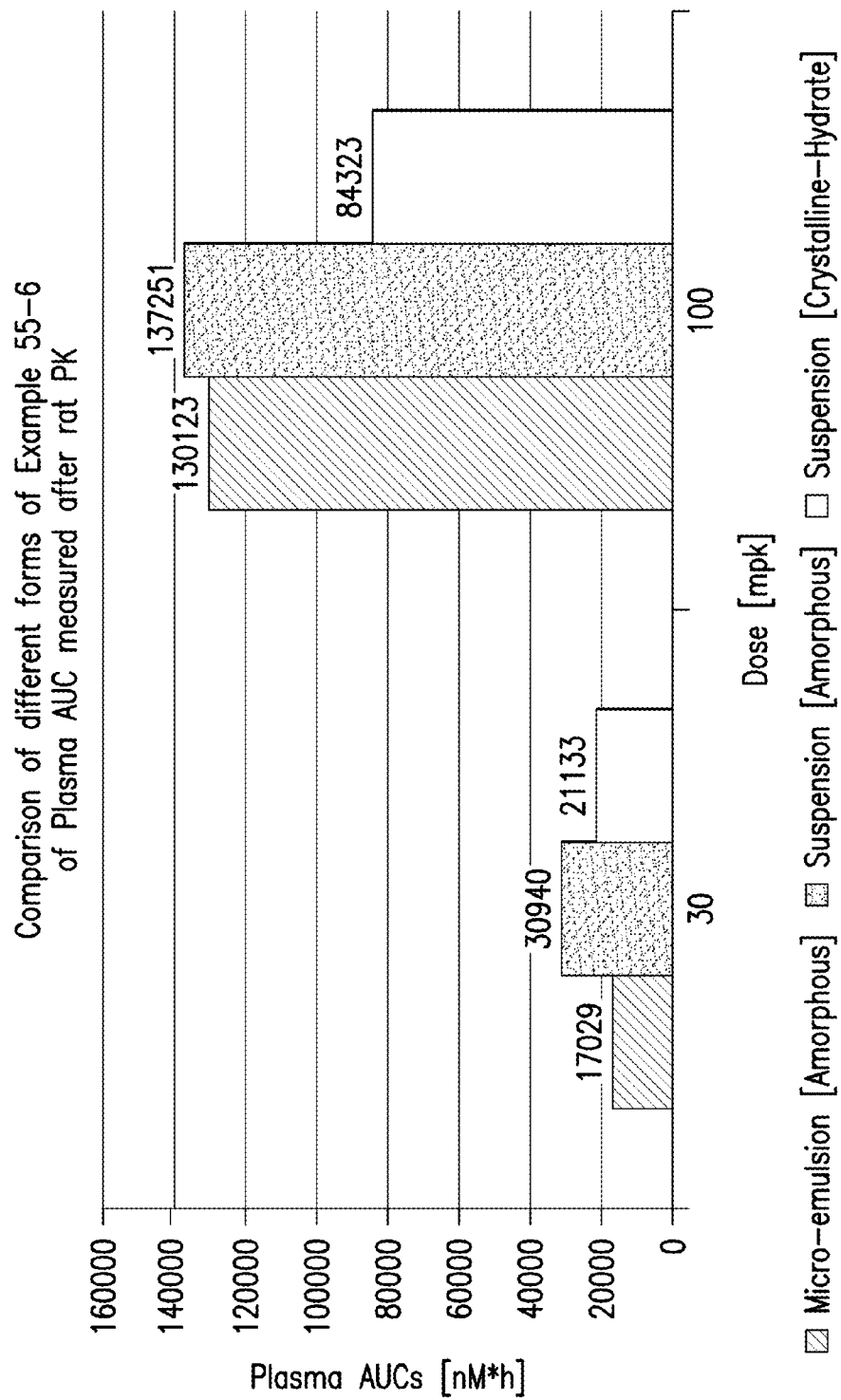

TETRAHYDROPYRIDO-PYRIDINE AND TETRAHYDROPYRIDO-PYRIMIDINE COMPOUNDS AND USE THEREOF AS C5A RECEPTOR MODULATORS

FIELD OF THE INVENTION

This invention relates generally to tetrahydropyrido-pyridine, tetrahydropyrido-pyrimidine and related heterocyclic compounds that act as modulators of mammalian complement C5a receptors, and to pharmaceutical compositions comprising such modulators. The present invention further relates to the use of such modulators in treating a variety of inflammatory and immune system disorders and as probes for the localization of C5a receptors.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H(CFH) (Edwards A O, et al. Complement factor H polymorphism and age-related macular degeneration. Science. 2005 Apr. 15; 308(5720):421-4; Hageman G S, et al A common haplotype in the complement regulatory gene factor H(HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol V is Sci. 2006 August; 47(8): 3242-6; Simonelli F, et al. Polymorphism p. 402Y>H in the complement factor H protein is a risk factor for age related macular degeneration in an Italian population. Br J. Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53), complement factor B (CFB) and complement C2 (Gold B, et al. Variation in factor B (BF) and complement component 2 (C2) genes is associated with age-related macular degeneration. Nat. Genet. 2006 April; 38(4):458-62 and Jakobsdottir J, et al. C2 and CFB genes inage-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Maller J B, et al Variation in complement factor 3 is associated with risk of age-related macular degeneration. Nat. Genet. 2007 October; 39(10): 1200-1 and Park K H, et al Complement component 3 (C3) haplotypes and risk of advanced age-related macular degeneration. Invest Ophthalmol Vis Sci. 2009 July; 50(7):3386-93. Epub 2009 Feb. 21). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, C5a receptor activation and/or C5a receptor-mediated signal transduction. Such C5a receptor modulators are preferably high affinity C5a receptor ligands and act as antagonists (e.g., inverse agonists) of complement C5a receptors, such as human C5a receptors. Within certain aspects, C5a receptor modulators provided herein are tetrahydropyrido-pyridines and tetrahydropyrido-pyrimidines.

Various embodiments of the invention are described herein. It will be recognized that features specified in each embodiment may be combined with other specified features to provide further embodiments.

Within certain aspects, C5a receptor modulators provided herein are compounds of Formula I and salts thereof:

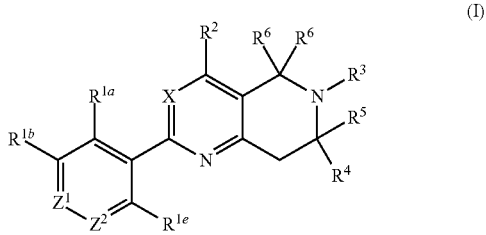

(I)

wherein
X is N or CH;
$Z^1$ is N or $CR^{1c}$;
$Z^2$ is N or $CR^{1d}$, wherein at least one of $Z^1$ and $Z^2$ is not N;
$R^{1a}$ is selected from the group consisting of hydrogen, $C_1$-$C_6$alkyl, $C_1$-$C_6$alkoxy, halo$C_1$-$C_6$alkyl, halo$C_1$-$C_6$alkoxy, cyano or halogen;
$R^{1b}$ is selected from the group consisting of hydrogen, amino, hydroxy, $C_1$-$C_6$alkyl, $C_1$-$C_6$alkoxy, and mono- and di-$C_1$-$C_4$alkylamino;
$R^{1c}$ is hydrogen, halogen or $C_1$-$C_6$alkyl;

$R^{1d}$ is selected from the group consisting of hydrogen, halogen, $C_1$-$C_6$alkyl, and $C_1$-$C_6$alkoxy;
$R^{1e}$ is selected from hydrogen, halogen, cyano, $C_1$-$C_6$alkyl, halo$C_1$-$C_6$alkyl, $C_1$-$C_6$alkoxy and halo$C_1$-$C_6$alkoxy; or
$R^{1a}$ and $R^{1b}$ taken in combination form a 5 member saturated or unsaturated heterocyclic ring having one or two ring heteroatoms selected from N, O or S, which heterocyclic ring is substituted with 0, 1, or 2 independently selected $C_1$-$C_6$alkyl or halogen substituents;
wherein at least one of $R^{1a}$ and $R^{1e}$ is not hydrogen;
$R^2$ is selected from the group consisting of hydrogen, $C_1$-$C_6$alkyl, $C_1$-$C_6$alkoxy, $C_1$-$C_6$alkylthio, $C_3$-$C_7$cycloalkyl, $C_3$-$C_7$cycloalkyl$C_1$-$C_4$alkyl and $(CH_2)_pNR^{2a}R^{2b}$, wherein each alkyl and alkoxy group is substituted with 0 or 1 substituents selected from the group consisting of hydroxy, halogen, and $C_1$-$C_4$alkoxy;
p is 0 or 1;
$R^{2a}$ is hydrogen, $C_1$-$C_6$alkyl or hydroxy$C_1$-$C_6$alkyl;
$R^{2b}$ is hydrogen, $C_1$-$C_6$alkyl, $C_3$-$C_7$cycloalkyl or $C_3$-$C_7$cycloalkyl$C_1$-$C_4$alkyl, wherein each alkyl is unsubstituted or substituted with hydroxy, $C_1$-$C_4$alkoxy, $C_1$-$C_4$alkoxycarbonyl, or heterocycle wherein the heterocycle is a saturated, unsaturated or aromatic five or six member ring having 1 or 2 ring heteroatoms selected from N, O or S and is unsubstituted or substituted with 1 or 2 independently selected $C_1$-$C_4$alkyl substituents; or
$NR^{2a}R^{2b}$ taken in combination form a 4 to 8 member saturated heterocyclic ring system having 1 or 2 rings and 0 or 1 additional ring heteroatoms selected from N, O or S, the saturated heterocyclic ring system is unsubstituted or substituted with 1-4 substituents independently selected from the group consisting of $C_1$-$C_4$alkyl, hydroxy, $C_1$-$C_4$alkoxy, $C_1$-$C_4$alkoxy$C_1$-$C_4$alkyl, hydroxy$C_1$-$C_4$alkyl, halogen, amino, mono- and di-$C_1$-$C_4$alkylamino, $C_1$-$C_4$alkoxycarbonyl, $C_1$-$C_4$alkanoyl, $S(O)_2C_1$-$C_4$alkyl, and $CH_2C(O)NH_2$;
$R_3$ is selected from the group consisting of substituted phenyl, substituted heteroaryl, and phenyl$C_1$-$C_3$alkyl, wherein the heteroaryl is selected from pyridyl, pyrazolyl, imidazolyl, tetrazolyl, oxazolyl, and isoxazolyl, and wherein each phenyl or heteroaryl group is substituted with 1, 2 or 3 substituents which are independently selected from the group consisting of $C_1$-$C_4$alkyl, $C_1$-$C_4$alkoxy, halogen, cyano, halo$C_1$-$C_4$alkyl, halo$C_1$-$C_4$alkoxy, hydroxy$C_1$-$C_4$alkyl, $C_1$-$C_4$alkoxy$C_1$-$C_4$alkyl, $C_3$-$C_6$cycloalkyl, and saturated oxacycle having 4, 5, or 6 ring atoms and one ring oxygen, which oxacycle is unsubstituted or substituted with 1 or 2 independently selected $C_1$-$C_4$alkyl substituents, and wherein each phenyl or heteroaryl comprises at least one non-hydrogen substituent ortho to the point of attachment to the remainder of the compound of formula (I);
$R_4$ is hydrogen or $C_1$-$C_4$alkyl;
$R^5$ is hydrogen; or
$R^4$ and $R^5$ taken in combination are oxo; and
$R^6$ is hydrogen at each occurrence or $CR^6_2$, taken in combination, form a divalent carbonyl.

In another embodiment, the invention provides a pharmaceutical composition comprising a therapeutically effective amount of a compound according to the definition of formula (I) or sub formulae thereof and one or more pharmaceutically acceptable carriers.

In another embodiment, the invention provides a combination, in particular a pharmaceutical combination, comprising a therapeutically effective amount of the compound according to the definition of formula (I) or sub formulae thereof and one or more therapeutically active agents.

The invention further provides methods of treating or preventing complement mediated diseases, the method comprising the steps of identifying a patient in need of complement modulation therapy and administering a compound of Formula (I) or a sub formulae thereof. Complement mediated diseases include ophthalmic diseases (including early or neovascular age-related macular degeneration and geographic atrophy), autoimmune diseases (including arthritis, rheumatoid arthritis), Respiratory diseases, cardiovascular diseases.

Other aspects of the invention are discussed infra.

BRIEF DESCRIPTION OF THE DRAWINGS

FIG. 37. illustrates the x-ray powder diffraction patterns of Example 55-G MTBE solvate.
FIG. 38. illustrates the differential scanning calorimetry (DSC) and thermogravimetric analysis (TGA) of Example 55-G MTBE solvate.
FIG. 39. illustrates a comparison of different forms of Example 55-G of Plasma AUC measured after rat PK.

DETAILED DESCRIPTION OF THE INVENTION

Figure 1:
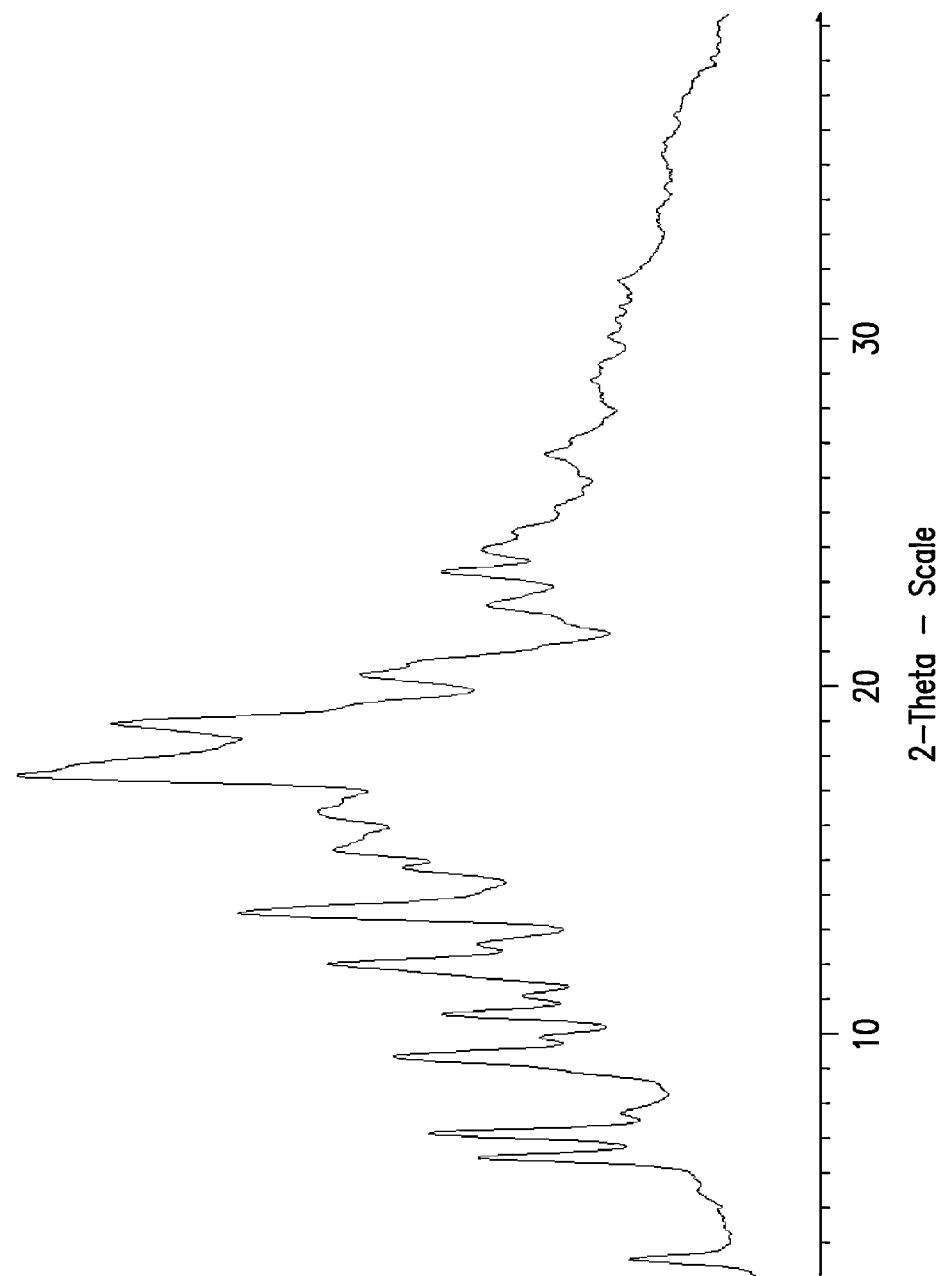
FIG. 1. illustrates the x-ray powder diffraction patterns of Example 19-F from MTBE.

As noted above, the present invention provides tetrahydropyrido-pyrimidines, tetrahydropyridopyridines and related heterocyclic compounds that modulate C5a receptor activation and/or C5a receptor-mediated signal transduction. Such compounds may be used in vitro or in vivo to modulate (preferably inhibit) C5a receptor activity (sometimes referred to hereinafter as C5aR) in a variety of contexts.

In a first embodiment, the invention provides compounds of Formula I and pharmaceutically acceptable salts thereof, which modulate the complement system. More particularly, the compounds of the invention modulate the C5a mediated response induced by activation of any one of the classical, alternative or lectin pathways of the complement system.

In a first embodiment, compounds of Formula I and salts thereof are provided which are represented by the structure:

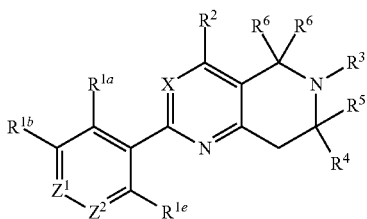

(I)

wherein
X is N or CH;
$Z^1$ is N or $CR^{1c}$;
$Z^2$ is N or $CR^{1d}$, wherein at least one of $Z^1$ and $Z^2$ is not N;
$R^{1a}$ is selected from the group consisting of hydrogen, $C_1$-$C_6$alkyl, $C_1$-$C_6$alkoxy, halo$C_1$-$C_6$alkyl, halo$C_1$-$C_6$alkoxy, cyano or halogen;
$R^{1b}$ is selected from the group consisting of hydrogen, amino, hydroxy, $C_1$-$C_6$alkyl, $C_1$-$C_6$alkoxy, and mono- and di-$C_1$-$C_4$alkylamino;
$R^{1c}$ is hydrogen, halogen or $C_1$-$C_6$alkyl;
$R^{1d}$ is selected from the group consisting of hydrogen, halogen, $C_1$-$C_6$alkyl, and $C_1$-$C_6$alkoxy;
$R^{1e}$ is selected from hydrogen, halogen, cyano, $C_1$-$C_6$alkyl, halo$C_1$-$C_6$alkyl, $C_1$-$C_6$alkoxy and halo$C_1$-$C_6$alkoxy; or
$R^{1a}$ and $R^{1b}$ taken in combination form a 5 member saturated or unsaturated heterocyclic ring having one or two ring heteroatoms selected from N, O or S, which heterocyclic ring is substituted with 0, 1, or 2 independently selected $C_1$-$C_6$alkyl or halogen substituents;
wherein at least one of $R^{1a}$ and $R^{1e}$ is not hydrogen;
$R^2$ is selected from the group consisting of hydrogen, $C_1$-$C_6$alkyl, $C_1$-$C_6$alkoxy, $C_1$-$C_6$alkylthio, $C_3$-$C_7$cycloalkyl, $C_3$-$C_7$cycloalkyl$C_1$-$C_4$alkyl and $(CH_2)_p NR^{2a}R^{2b}$, wherein each alkyl and alkoxy group is substituted with 0 or 1 substituents selected from the group consisting of hydroxy, halogen, and $C_1$-$C_4$alkoxy;
p is 0 or 1;
$R^{2a}$ is hydrogen, $C_1$-$C_6$alkyl or hydroxy$C_1$-$C_6$alkyl;
$R^{2b}$ is hydrogen, $C_1$-$C_6$alkyl, $C_3$-$C_7$cycloalkyl or $C_3$-$C_7$cycloalkyl$C_1$-$C_4$alkyl, wherein each alkyl is unsubstituted or substituted with hydroxy, $C_1$-$C_4$alkoxy, $C_1$-$C_4$alkoxycarbonyl, or heterocycle wherein the heterocycle is a saturated, unsaturated or aromatic five or six member ring having 1 or 2 ring heteroatoms selected from N, O or S and is unsubstituted or substituted with 1 or 2 independently selected $C_1$-$C_4$alkyl substituents; or
$NR^{2a}R^{2b}$ taken in combination form a 4 to 8 member saturated heterocyclic ring system having 1 or 2 rings and 0 or 1 additional ring heteroatoms selected from N, O or S, the saturated heterocyclic ring system is unsubstituted or substituted with 1-4 substituents independently selected from the group consisting of $C_1$-$C_4$alkyl, hydroxy, $C_1$-$C_4$alkoxy, $C_1$-$C_4$alkoxy$C_1$-$C_4$alkyl, hydroxy$C_1$-$C_4$alkyl, halogen, amino, mono- and di-$C_1$-$C_4$alkylamino, $C_1$-$C_4$alkoxycarbonyl, $C_1$-$C_4$alkanoyl, $S(O)_2 C_1$-$C_4$alkyl, $CH_2C(O)(C_1$-$C_4$alkoxy) and $CH_2C(O)NH_2$;
$R_3$ is selected from the group consisting of substituted phenyl, substituted heteroaryl, and phenyl$C_1$-$C_3$alkyl, wherein the heteroaryl is selected from pyridyl, pyrazolyl, imidazolyl, tetrazolyl, oxazolyl, and isoxazolyl, and wherein each phenyl or heteroaryl group is substituted with 1, 2 or 3 substituents which are independently selected from the group consisting of $C_1$-$C_4$alkyl, $C_1$-$C_4$alkoxy, halogen, cyano, halo$C_1$-$C_4$alkyl, halo$C_1$-$C_4$alkoxy, hydroxy$C_1$-$C_4$alkyl, $C_1$-$C_4$alkoxy$C_1$-$C_4$alkyl, $C_3$-$C_6$cycloalkyl, and saturated oxacycle having 4, 5, or 6 ring atoms and one ring oxygen, which oxacycle is unsubstituted or substituted with 1 or 2 independently selected $C_1$-$C_4$alkyl substituents, and wherein each phenyl or heteroaryl comprises at least one non-hydrogen substituent ortho to the point of attachment to the remainder of the compound of formula (I);
$R_4$ is hydrogen or $C_1$-$C_4$alkyl;
$R^5$ is hydrogen; or
$R^4$ and $R^5$ taken in combination are oxo; and
$R^6$ is hydrogen at each occurrence or $CR^6_2$, taken in combination, form a divalent carbonyl.

In another embodiment, compounds of Formula I and salts thereof are provided which are represented by the structure:

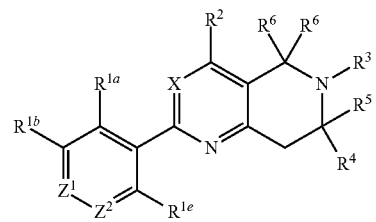

(I)

wherein
X is N or CH;
$Z^1$ is N or $CR^{1c}$;
$Z^2$ is N or $CR^{1d}$, wherein at least one of $Z^1$ and $Z^2$ is not N;
$R^{1a}$ is selected from the group consisting of hydrogen, $C_1$-$C_6$alkyl, $C_1$-$C_6$alkoxy, halo$C_1$-$C_6$alkyl, halo$C_1$-$C_6$alkoxy, cyano or halogen;
$R^{1b}$ is selected from the group consisting of hydrogen, amino, hydroxy, $C_1$-$C_6$alkyl, $C_1$-$C_6$alkoxy, and mono- and di-$C_1$-$C_4$alkylamino;
$R^{1c}$ is hydrogen, halogen or $C_1$-$C_6$alkyl;
$R^{1d}$ is selected from the group consisting of hydrogen, halogen, $C_1$-$C_6$alkyl, and $C_1$-$C_6$alkoxy;
$R^{1e}$ is selected from hydrogen, halogen, cyano, $C_1$-$C_6$alkyl, halo$C_1$-$C_6$alkyl, $C_1$-$C_6$alkoxy and halo$C_1$-$C_6$alkoxy, sulfone, $C_3$-$C_7$cycloalkyl; or
$R^{1a}$ and $R^{1b}$ taken in combination form a 5 member saturated or unsaturated heterocyclic ring having one or two ring heteroatoms selected from N, O or S, which heterocyclic ring is substituted with 0, 1, or 2 independently selected $C_1$-$C_6$alkyl or halogen substituents;
wherein at least one of $R^{1a}$ and $R^{1e}$ is not hydrogen;
$R^2$ is selected from the group consisting of hydrogen, $C_1$-$C_6$alkyl, $C_1$-$C_6$alkoxy, $C_1$-$C_6$alkylthio, $C_3$-$C_7$cycloalkyl, $C_3$-$C_7$cycloalkyl$C_1$-$C_4$alkyl and $(CH_2)_p NR^{2a}R^{2b}$, wherein each alkyl and alkoxy group is substituted with 0 or 2 substituents selected from the group consisting of hydroxy, halogen, and $C_1$-$C_4$alkoxy, amino, mono- and di-$C_1$-$C_4$ alkylamino;
p is 0 or 1;
$R^{2a}$ is hydrogen, $C_1$-$C_6$alkyl or hydroxy$C_1$-$C_6$alkyl;
$R^{2b}$ is hydrogen, $C_1$-$C_6$alkyl, $C_3$-$C_7$cycloalkyl or $C_3$-$C_7$cycloalkyl$C_1$-$C_4$alkyl, wherein each alkyl is unsubstituted or substituted with hydroxy, $C_1$-$C_4$alkoxy, $C_1$-$C_4$alkoxycarbonyl, or heterocycle wherein the heterocycle is a saturated, unsaturated or aromatic five or six member ring having 1 or 2 ring heteroatoms selected from N, O or S and is unsubstituted or substituted with 1 or 2 independently selected $C_1$-$C_4$alkyl substituents; or $NR^{2a}R^{2b}$ taken in combination form a 4 to 8 member saturated heterocyclic ring system having 1 or 2 rings and 0 or 1 additional ring heteroatoms selected from N, O or S, the saturated heterocyclic ring system is unsubstituted or substituted with 1-4 substituents independently selected from the group consisting of $C_1$-$C_4$alkyl, hydroxy, $C_1$-$C_4$alkoxy, $C_1$-$C_4$alkoxy$C_1$-$C_4$alkyl, hydroxy$C_1$-$C_4$alkyl, halogen, amino, mono- and di-$C_1$-$C_4$alkylamino, $C_1$-$C_4$alkoxycarbonyl, $C_1$-$C_4$alkanoyl, $S(O)_2C_1$-$C_4$alkyl, $CH_2C(O)(C_1$-$C_4$alkoxy) and $CH_2C(O)NH_2$;

$R_3$ is selected from the group consisting of substituted phenyl, substituted heteroaryl, and phenyl$C_1$-$C_3$alkyl, wherein the heteroaryl is selected from pyridyl, pyrazolyl, imidazolyl, tetrazolyl, oxazolyl, and isoxazolyl, and wherein each phenyl or heteroaryl group is substituted with 1, 2 or 3 substituents which are independently selected from the group consisting of $C_1$-$C_4$alkyl, $C_1$-$C_4$alkoxy, halogen, halo$C_1$-$C_4$alkyl, halo$C_1$-$C_4$alkoxy, hydroxy$C_1$-$C_4$alkyl, $C_1$-$C_4$alkoxy$C_1$-$C_4$alkyl, $C_3$-$C_6$cycloalkyl, and saturated oxacycle having 4, 5, or 6 ring atoms and one ring oxygen, which oxacycle is unsubstituted or substituted with 1 or 2 independently selected $C_1$-$C_4$alkyl substituents, and wherein each phenyl or heteroaryl comprises at least one non-hydrogen substituent ortho to the point of attachment to the remainder of the compound of formula (I);

$R_4$ is hydrogen or $C_1$-$C_4$alkyl;
$R^5$ is hydrogen; or
$R^4$ and $R^5$ taken in combination are oxo; and
$R^6$ is hydrogen at each occurrence or $CR^6{}_2$, taken in combination, form a divalent carbonyl.

The language "wherein each phenyl or heteroaryl comprises at least one non-hydrogen substituent ortho to the point of attachment to the remainder of the compound of formula (I)" shall mean that the phenyl or heteroaryl ring bears at least one substituent ortho to the tetrahydropyrido-pyridine or tetrahydropyrido-pyrimidine ring of Formula (I).

In a second embodiment, a compound of Formula (I) of embodiment one is provided, which compound is a compound of formula (II) or formula (III), or a salt thereof:

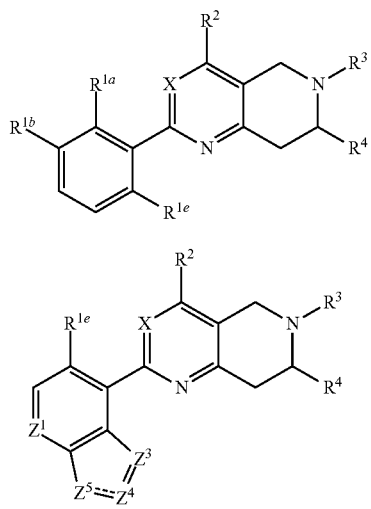

wherein
$Z^1$ is N or CH;
$Z^3$ is N(H), N($C_1$-$C_4$alkyl), or $C(R^{1f})$;
$Z^4$ is N or CH;
$Z^5$ is N(H), N($C_1$-$C_4$alkyl) or $C(R^{1g})$, wherein one or two of $Z^3$, $Z^4$ and $Z^5$ is nitrogen;

$R^{1f}$ is hydrogen, $C_1$-$C_4$alkyl or halogen; and
$R^{1g}$ is hydrogen or $C_1$-$C_4$alkyl.

In a third embodiment, a compound of embodiment one or two is provided in which $R^3$ is phenyl or 1H-pyrazolyl, each of which is substituted with 1 or 2 independently selected $C_1$-$C_4$alkyl groups and 0, 1 or 2 additional substituents selected from the group consisting of halogen, cyano, $C_1$-$C_4$alkyl, halo$C_1$-$C_4$alkyl, $C_1$-$C_4$alkoxy, cyclopropyl, oxetanyl or 1-methyl-oxetanyl. In certain compounds of the third embodiment, $R^3$ is phenyl or 1H-pyrazolyl, each of which is substituted with 1 or 2 independently selected $C_1$-$C_4$alkyl groups and 0 or 1 additional substituents selected from the group consisting of halogen, $C_1$-$C_4$alkyl, halo$C_1$-$C_4$alkyl, $C_1$-$C_4$alkoxy, cyclopropyl, oxetanyl or 1-methyl-oxetanyl.

In a fourth embodiment, a compound of embodiment two or three is provided in which $R^{1a}$ is hydrogen or methyl;
$R^{1e}$ is hydrogen, methyl or trifluoromethyl, wherein at least one of $R^{1a}$ and $R^{1e}$ is not hydrogen;
$Z^3$ is $C(R^{1f})$;
$Z^4$ is N or CH;
$Z^5$ is N(H); and
$R^{1f}$ is hydrogen or methyl.

In a fifth embodiment, a compound of any one of embodiments one to three is provided in which the

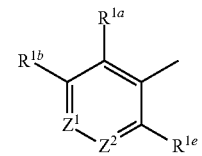

fragment of Formula (I) or the

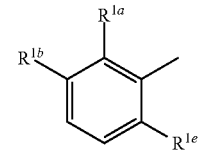

fragment of Formula (II) is 2,6-dimethylphenyl or 2,6-diethylphenyl;
Or the

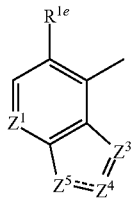

fragment of Formula (I) or the

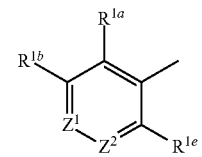

fragment of Formula (III) is 5-methyl-1H-indazol-4-yl, 3-methyl-1H-indol-4-yl, 3,5-dimethyl-1H-indazol-4-yl, 3,5-dimethyl-1H-indol-4-yl, 3,5-dimethyl-1H-indol-4-yl, or 3,5- dimethyl-1H-pyrazolo[3,4-b]pyridin-4-yl, 5-trifluoromethyl-3H-pyrrolo[2,3-b]pyridin-4-yl.

In certain aspects of the fifth embodiment, the

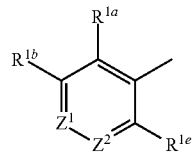

fragment of Formula (I) is 2,6-dimethylphenyl, 2,6-diethylphenyl 5-methyl-1H-indazol-4-yl, 3-methyl-1H-indol-4-yl, 3,5-dimethyl-1H-pyrazolo[3,4-b]pyridin-4-yl or 5-methyl-1H-indazol-4-yl.

In a sixth embodiment, a compound of any one of embodiments one to five is provided in which $R^4$ is hydrogen.

In a seventh embodiment, a compound of any one of embodiments one to five is provided in which X is N.

In certain aspects, compounds of any one of embodiments one to seven include those compounds in which $R^2$ is methyl, methoxy, or methoxy-piperidin-1-yl which are further substituted with one or two methyl groups. In certain compounds, $R^2$ is selected from methyl, methoxy, 2-methyl-4-methoxy-piperidin-1-yl, 3,3-dimethyl-4-methoxy-piperidin-1-yl, 2,5-dimethyl-4-methoxy-piperidin-1-yl and 2,5,5-trimethyl-4-methoxy-piperidin-1-yl.

In an eighth embodiment, a compound of any one of embodiments one to seven is provided which compound is a compound of Formula (IV) or (V), or a salt thereof:

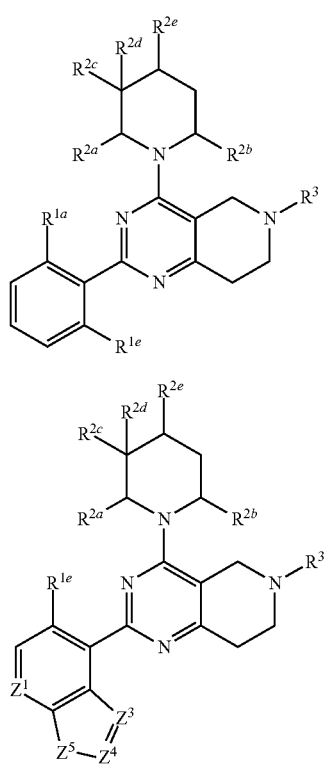

wherein
$R^{2a}$, $R^{2b}$, $R^{2c}$, and $R^{2d}$ are independently selected from hydrogen and $C_1$-$C_4$alkyl; or $R^{2a}$ and $R^{2b}$, taken in combination, form a divalent $C_1$-$C_3$alkylene group; and
$R^{2e}$ is hydroxy or $C_1$-$C_4$alkoxy.

In a ninth embodiment, a compound of any one of embodiments one to five is provided in which X is CH.

In a tenth embodiment, a compound of any one of embodiments one to five or nine is provided in which $R^2$ is hydrogen or methyl.

In an eleventh embodiment, a compound of any one of embodiments one to five, nine or ten is provided which compound is a compound of Formula (VI) or (VII), or a salt thereof:

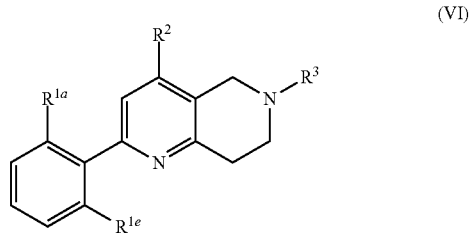

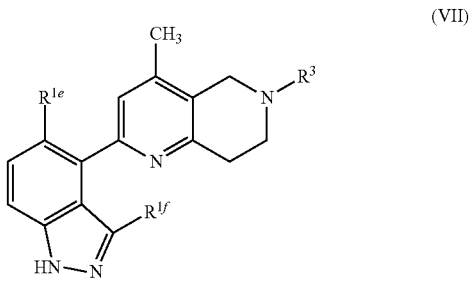

wherein
in Formula (VI), $R^{1a}$ and $R^{1e}$ are methyl or ethyl; or
in Formula (VII), $R^{1e}$ and $R^{1f}$ are hydrogen or methyl, wherein at least one $R^{1e}$ or $R^{1f}$ is methyl.

In a twelfth embodiment, a compound or a salt thereof according to Formula (I), in which $R^6$ is deuterium.

In yet another embodiment, compounds of any one of embodiments 9 to 11 are provided in which $R^3$ is phenyl or 1H-pyrazolyl, each of which is substituted with 1 or 2 independently selected $C_1$-$C_4$alkyl groups and 0 or 1 additional substituents selected from the group consisting of halogen, $C_1$-$C_4$alkyl, halo$C_1$-$C_4$alkyl, $C_1$-$C_4$alkoxy, cyclopropyl, oxetanyl or 1-methyl-oxetanyl.

In certain other embodiments according to any one of embodiments one to twelve $R^3$ is 2-methyl-5-trifluorophenyl, 2-methyl-5-chlorophenyl, 2-methyl-5-isopropyl-phenyl, 3-cyclopropyl-1H-pyrazol-5-yl, 3-propyl-1H-pyrazol-5-yl, 4-chloro-3-cyclopropyl-1H-pyrazol-5-yl, or 4-chloro-3-propyl-1H-pyrazol-5-yl.

In a thirteenth embodiment, individual compounds according to the invention are those listed in the Examples section below. In certain aspects the compound is selected from the group consisting of:
racemic 1-(2-(2,6-dimethylphenyl)-6-(3-isopropyl-1-methyl-1H-pyrazol-5-yl)-5,6,7,8-tetrahydropyrido[4,3-d]pyrimidin-4-yl)-2-methylpiperidin-4-ol;
2-(2,6-dimethylphenyl)-4-(3,3-dimethylpiperidin-1-yl)-6-(3-isopropyl-1-methyl-1H-pyrazol-5-yl)-5,6,7,8-tetrahydropyrido[4,3-d]pyrimidine;
(S)-2-(2,6-dimethylphenyl)-6-(3-isopropyl-1-methyl-1H-pyrazol-5-yl)-4-(2-methylpiperidin-1-yl)-5,6,7,8-tetrahydropyrido[4,3-d]pyrimidine;

2-(2,6-dimethylphenyl)-6-(3-isopropyl-1-methyl-1H-pyrazol-5-yl)-4-(4-methylpiperidin-1-yl)-5,6,7,8-tetrahydropyrido[4,3-d]pyrimidine;

racemic 2-(2,6-dimethylphenyl)-6-(3-isopropyl-1-methyl-1H-pyrazol-5-yl)-4-(4-methoxy-3-methylpiperidin-1-yl)-5,6,7,8-tetrahydropyrido[4,3-d]pyrimidine;

racemic 1-(2-(2,6-dimethylphenyl)-6-(3-isopropyl-1-methyl-1H-pyrazol-5-yl)-5,6,7,8-tetrahydropyrido[4,3-d]pyrimidin-4-yl)-3-methylpiperidin-4-ol;

2-(2,6-dimethylphenyl)-6-(3-isopropyl-1-methyl-1H-pyrazol-5-yl)-4-(3-methoxyazetidin-1-yl)-5,6,7,8-tetrahydropyrido[4,3-d]pyrimidine;

6-(1,3-dimethyl-1H-pyrazol-5-yl)-2-(2,6-dimethylphenyl)-4-(3,3-dimethylpiperidin-1-yl)-5,6,7,8-tetrahydropyrido[4,3-d]pyrimidine;

2-(2,6-dimethylphenyl)-6-(3-isopropyl-1-methyl-1H-pyrazol-5-yl)-N-(2-methoxyethyl)-N-methyl-5,6,7,8-tetrahydropyrido[4,3-d]pyrimidin-4-amine;

1-((2-(2,6-dimethylphenyl)-6-(3-isopropyl-1-methyl-1H-pyrazol-5-yl)-5,6,7,8-tetrahydropyrido[4,3-d]pyrimidin-4-yl)(methyl)amino)-2-methylpropan-2-ol;

2-(2,6-dimethylphenyl)-4-(3,3-dimethylpiperidin-1-yl)-6-(3-(2-methoxyethyl)-1-methyl-1H-pyrazol-5-yl)-5,6,7,8-tetrahydropyrido[4,3-d]pyrimidine;

2-(2,6-dimethylphenyl)-4-(3,3-dimethylpiperidin-1-yl)-6-(1-methyl-3-(tetrahydrofuran-2-yl)-1H-pyrazol-5-yl)-5,6,7,8-tetrahydropyrido[4,3-d]pyrimidine;

N-cyclopentyl-2-(2,6-dimethylphenyl)-6-(3-isopropyl-1-methyl-1H-pyrazol-5-yl)-N-methyl-5,6,7,8-tetrahydropyrido[4,3-d]pyrimidin-4-amine;

2-(2,6-dimethylphenyl)-6-(3-isopropyl-1-methyl-1H-pyrazol-5-yl)-4-(2-methylpiperidin-1-yl)-5,6,7,8-tetrahydropyrido[4,3-d]pyrimidine;

racemic 1-(2-(2,6-dimethylphenyl)-6-(3-isopropyl-1-methyl-1H-pyrazol-5-yl)-5,6,7,8-tetrahydropyrido[4,3-d]pyrimidin-4-yl)piperidin-3-ol;

(R)-2-(2,6-dimethylphenyl)-6-(3-isopropyl-1-methyl-1H-pyrazol-5-yl)-4-(2-methylpyrrolidin-1-yl)-5,6,7,8-tetrahydropyrido[4,3-d]pyrimidine;

2-(2,6-dimethylphenyl)-6-(3-isopropyl-1-methyl-1H-pyrazol-5-yl)-N-methyl-N-((tetrahydrofuran-2-yl)methyl)-5,6,7,8-tetrahydropyrido[4,3-d]pyrimidin-4-amine;

racemic 2-(2,6-dimethylphenyl)-6-(3-isopropyl-1-methyl-1H-pyrazol-5-yl)-4-(3-(methoxymethyl)piperidin-1-yl)-5,6,7,8-tetrahydropyrido[4,3-d]pyrimidine;

2-(2,6-dimethylphenyl)-6-(3-isopropyl-1-methyl-1H-pyrazol-5-yl)-4-(4-(methoxymethyl)piperidin-1-yl)-5,6,7,8-tetrahydropyrido[4,3-d]pyrimidine;

(S)-1-(2-(2,6-dimethylphenyl)-6-(3-isopropyl-1-methyl-1H-pyrazol-5-yl)-5,6,7,8-tetrahydropyrido[4,3-d]pyrimidin-4-yl)piperidin-3-ol;

(S)-6-(5-isopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

1-((2-(2,6-dimethylphenyl)-6-(o-tolyl)-5,6,7,8-tetrahydropyrido[4,3-d]pyrimidin-4-yl)(methyl)amino)-2-methylpropan-2-ol;

ethyl 1-(2-(2,6-dimethylphenyl)-6-(o-tolyl)-5,6,7,8-tetrahydropyrido[4,3-d]pyrimidin-4-yl)-3-methylpiperidine-3-carboxylate;

2,2'-((2-(2,6-dimethylphenyl)-6-(o-tolyl)-5,6,7,8-tetrahydropyrido[4,3-d]pyrimidin-4-yl)azanediyl)diethanol;

2-(2,6-dimethylphenyl)-N-propyl-6-(o-tolyl)-5,6,7,8-tetrahydropyrido[4,3-d]pyrimidin-4-amine;

methyl 2-((2-(2,6-dimethylphenyl)-6-(o-tolyl)-5,6,7,8-tetrahydropyrido[4,3-d]pyrimidin-4-yl)(methyl)amino)acetate;

(R)-2-((6-(5-isopropyl-2-methylphenyl)-2-(3-methyl-1H-indol-4-yl)-5,6,7,8-tetrahydropyrido[4,3-d]pyrimidin-4-yl)amino)-3-methylbutan-1-ol;

4-(3,3-dimethylpiperidin-1-yl)-2-(3-methyl-1H-indol-4-yl)-6-(o-tolyl)-5,6,7,8-tetrahydropyrido[4,3-d]pyrimidine;

6-(5-isopropyl-2-methylphenyl)-4-((2R,4S)-4-methoxy-2-methylpiperidin-1-yl)-2-(3-methyl-1H-indol-4-yl)-5,6,7,8-tetrahydropyrido[4,3-d]pyrimidine;

6-(5-isopropyl-2-methylphenyl)-4-((2R,4S)-4-methoxy-2-methylpiperidin-1-yl)-2-(3-methyl-1H-indol-4-yl)-5,6,7,8-tetrahydropyrido[4,3-d]pyrimidine;

1-(6-(5-isopropyl-2-methylphenyl)-2-(3-methyl-1H-indol-4-yl)-5,6,7,8-tetrahydropyrido[4,3-d]pyrimidin-4-yl)-3-methylpiperidin-3-ol;

6-(5-isopropyl-2-methylphenyl)-4-((2R,4R)-4-methoxy-2-methylpiperidin-1-yl)-2-(3-methyl-1H-indol-4-yl)-5,6,7,8-tetrahydropyrido[4,3-d]pyrimidine;

6-(5-isopropyl-2-methylphenyl)-4-((2S,4S)-4-methoxy-2-methylpiperidin-1-yl)-2-(3-methyl-1H-indol-4-yl)-5,6,7,8-tetrahydropyrido[4,3-d]pyrimidine;

2-(2,6-dimethylphenyl)-N,N-dimethyl-6-(o-tolyl)-5,6,7,8-tetrahydropyrido[4,3-d]pyrimidin-4-amine;

2-(2,6-dimethylphenyl)-N-(2-methoxyethyl)-N-methyl-6-(o-tolyl)-5,6,7,8-tetrahydropyrido[4,3-d]pyrimidin-4-amine;

2-(2,6-dimethylphenyl)-4-(3,3-dimethylpiperidin-1-yl)-6-(o-tolyl)-5,6,7,8-tetrahydropyrido[4,3-d]pyrimidine;

2-(2,6-dimethylphenyl)-4-(4-methoxypiperidin-1-yl)-6-(o-tolyl)-5,6,7,8-tetrahydropyrido[4,3-d]pyrimidine;

2-(2,6-dimethylphenyl)-4-(3,3-dimethylpyrrolidin-1-yl)-6-(o-tolyl)-5,6,7,8-tetrahydropyrido[4,3-d]pyrimidine;

4-(2-(2,6-dimethylphenyl)-6-(o-tolyl)-5,6,7,8-tetrahydropyrido[4,3-d]pyrimidin-4-yl)-2,2-dimethylmorpholine;

4-(azetidin-1-yl)-2-(2,6-dimethylphenyl)-6-(o-tolyl)-5,6,7,8-tetrahydropyrido[4,3-d]pyrimidine;

6-(5-chloro-2-methylphenyl)-4-(3,3-dimethylpiperidin-1-yl)-2-(3-methyl-1H-indol-4-yl)-5,6,7,8-tetrahydropyrido[4,3-d]pyrimidine;

4-(4-methoxypiperidin-1-yl)-2-(3-methyl-1H-indol-4-yl)-6-(o-tolyl)-5,6,7,8-tetrahydropyrido[4,3-d]pyrimidine;

6-(5-chloro-2-methylphenyl)-4-(4-methoxypiperidin-1-yl)-2-(3-methyl-1H-indol-4-yl)-5,6,7,8-tetrahydropyrido[4,3-d]pyrimidine;

2-methyl-1-(methyl(2-(3-methyl-1H-indol-4-yl)-6-(o-tolyl)-5,6,7,8-tetrahydropyrido[4,3-d]pyrimidin-4-yl)amino)propan-2-ol;

1-((6-(5-chloro-2-methylphenyl)-2-(3-methyl-1H-indol-4-yl)-5,6,7,8-tetrahydropyrido[4,3-d]pyrimidin-4-yl)(methyl)amino)-2-methylpropan-2-ol;

6-(5-chloro-2-methylphenyl)-4-(3,3-dimethylpiperidin-1-yl)-2-(5-methyl-1H-indazol-4-yl)-5,6,7,8-tetrahydropyrido[4,3-d]pyrimidine;

4-(6-(5-isopropyl-2-methylphenyl)-2-(3-methyl-1H-indol-4-yl)-5,6,7,8-tetrahydropyrido[4,3-d]pyrimidin-4-yl)-2,2-dimethylmorpholine;

6-(5-isopropyl-2-methylphenyl)-N,N-dimethyl-2-(3-methyl-1H-indol-4-yl)-5,6,7,8-tetrahydropyrido[4,3-d]pyrimidin-4-amine;

1-(6-(5-isopropyl-2-methylphenyl)-2-(3-methyl-1H-indol-4-yl)-5,6,7,8-tetrahydropyrido[4,3-d]pyrimidin-4-yl)-3,3-dimethylpiperidin-4-ol;

6-(5-isopropyl-2-methylphenyl)-N-methyl-2-(3-methyl-1H-indol-4-yl)-5,6,7,8-tetrahydropyrido[4,3-d]pyrimidin-4-amine;

N-isopropyl-6-(5-isopropyl-2-methylphenyl)-2-(3-methyl-1H-indol-4-yl)-5,6,7,8-tetrahydropyrido[4,3-d]pyrimidin-4-amine;

4-(azetidin-1-yl)-6-(5-isopropyl-2-methylphenyl)-2-(3-methyl-1H-indol-4-yl)-5,6,7,8-tetrahydropyrido[4,3-d]pyrimidine;

(R)-6-(5-isopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

racemic-1-(6-(5-isopropyl-2-methylphenyl)-2-(3-methyl-1H-indol-4-yl)-5,6,7,8-tetrahydropyrido[4,3-d]pyrimidin-4-yl)-3-methylpiperidin-4-ol;

6-(5-isopropyl-2-methylphenyl)-N-(2-methoxyethyl)-N-methyl-2-(3-methyl-1H-indol-4-yl)-5,6,7,8-tetrahydropyrido[4,3-d]pyrimidin-4-amine;

1-(6-(5-isopropyl-2-methylphenyl)-2-(3-methyl-1H-indol-4-yl)-5,6,7,8-tetrahydropyrido[4,3-d]pyrimidin-4-yl)azetidin-3-ol;

racemic 6-(5-isopropyl-2-methylphenyl)-4-(4-methoxy-3-methylpiperidin-1-yl)-2-(3-methyl-1H-indol-4-yl)-5,6,7,8-tetrahydropyrido[4,3-d]pyrimidine;

4-(3-fluoroazetidin-1-yl)-6-(5-isopropyl-2-methylphenyl)-2-(3-methyl-1H-indol-4-yl)-5,6,7,8-tetrahydropyrido[4,3-d]pyrimidine;

6-(5-isopropyl-2-methylphenyl)-4-((3-endo)-3-methoxy-8-azabicyclo[3.2.1]octan-8-yl)-2-(3-methyl-1H-indol-4-yl)-5,6,7,8-tetrahydropyrido[4,3-d]pyrimidine;

(S)-1-(6-(5-isopropyl-2-methylphenyl)-2-(3-methyl-1H-indol-4-yl)-5,6,7,8-tetrahydropyrido[4,3-d]pyrimidin-4-yl)-3,3-dimethylpiperidin-4-ol;

(S)-4-(6-(5-isopropyl-2-methylphenyl)-2-(3-methyl-1H-indol-4-yl)-5,6,7,8-tetrahydropyrido[4,3-d]pyrimidin-4-yl)-3-methylmorpholine;

(S)-1-(6-(5-isopropyl-2-methylphenyl)-2-(3-methyl-1H-indol-4-yl)-5,6,7,8-tetrahydropyrido[4,3-d]pyrimidin-4-yl)piperidin-3-ol;

(R)-1-(6-(5-isopropyl-2-methylphenyl)-2-(3-methyl-1H-indol-4-yl)-5,6,7,8-tetrahydropyrido[4,3-d]pyrimidin-4-yl)piperidin-3-ol;

6-(5-isopropyl-2-methylphenyl)-4-((3R,4R)-4-methoxy-3-methylpiperidin-1-yl)-2-(3-methyl-1H-indol-4-yl)-5,6,7,8-tetrahydropyrido[4,3-d]pyrimidine;

6-(5-isopropyl-2-methylphenyl)-4-((3S,4S)-4-methoxy-3-methylpiperidin-1-yl)-2-(3-methyl-1H-indol-4-yl)-5,6,7,8-tetrahydropyrido[4,3-d]pyrimidine;

(R)-(1-(6-(5-isopropyl-2-methylphenyl)-2-(3-methyl-1H-indol-4-yl)-5,6,7,8-tetrahydropyrido[4,3-d]pyrimidin-4-yl)pyrrolidin-2-yl)methanol;

(R)-6-(5-isopropyl-2-methylphenyl)-2-(3-methyl-1H-indol-4-yl)-4-(2-methylpiperidin-1-yl)-5,6,7,8-tetrahydropyrido[4,3-d]pyrimidine;

(S)-6-(5-isopropyl-2-methylphenyl)-2-(3-methyl-1H-indol-4-yl)-4-(2-methylpiperidin-1-yl)-5,6,7,8-tetrahydropyrido[4,3-d]pyrimidine;

6-(5-isopropyl-2-methylphenyl)-4-(3-methoxy-3-methylazetidin-1-yl)-2-(3-methyl-1H-indol-4-yl)-5,6,7,8-tetrahydropyrido[4,3-d]pyrimidine;

1-(6-(5-isopropyl-2-methylphenyl)-2-(3-methyl-1H-indol-4-yl)-5,6,7,8-tetrahydropyrido[4,3-d]pyrimidin-4-yl)-3-methylazetidin-3-ol;

6-(6-(5-isopropyl-2-methylphenyl)-2-(3-methyl-1H-indol-4-yl)-5,6,7,8-tetrahydropyrido[4,3-d]pyrimidin-4-yl)-2-oxa-6-azaspiro[3.3]heptane;

6-(5-isopropyl-2-methylphenyl)-4-(3-methoxyazetidin-1-yl)-2-(3-methyl-1H-indol-4-yl)-5,6,7,8-tetrahydropyrido[4,3-d]pyrimidine;

1-(6-(5-isopropyl-2-methylphenyl)-2-(3-methyl-1H-indol-4-yl)-5,6,7,8-tetrahydropyrido[4,3-d]pyrimidin-4-yl)-N,N-dimethylazetidin-3-amine;

(3-endo)-8-(6-(5-isopropyl-2-methylphenyl)-2-(3-methyl-1H-indol-4-yl)-5,6,7,8-tetrahydropyrido[4,3-d]pyrimidin-4-yl)-8-azabicyclo[3.2.1]octan-3-ol;

(S)-2-(2,5-dimethylphenyl)-6-(5-isopropyl-2-methylphenyl)-4-(4-methoxy-3,3-dimethylpiperidin-1-yl)-5,6,7,8-tetrahydropyrido[4,3-d]pyrimidine;

(S)-6-(5-chloro-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

(R)-6-(5-chloro-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

6-(5-isopropyl-2-methylphenyl)-4-methoxy-2-(3-methyl-1-tosyl-1H-indol-4-yl)-5,6,7,8-tetrahydropyrido[4,3-d]pyrimidine;

2-(3,5-dimethyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine;

4-(3,3-dimethylpiperidin-1-yl)-6-(5-isopropyl-2-methylphenyl)-2-(5-(trifluoromethyl)-1H-pyrrolo[2,3-b]pyridin-4-yl)-5,6,7,8-tetrahydropyrido[4,3-d]pyrimidine;

2-(5-chloro-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine;

(S)-6-(5-isopropyl-2-methylphenyl)-4-(4-methoxy-3,3-dimethylpiperidin-1-yl)-2-(5-methyl-1H-indazol-4-yl)-5,6,7,8-tetrahydropyrido[4,3-d]pyrimidine;

(S)-6-(5-isopropyl-2-methylphenyl)-4-(4-methoxy-3,3-dimethylpiperidin-1-yl)-2-(1-methyl-1H-indazol-7-yl)-5,6,7,8-tetrahydropyrido[4,3-d]pyrimidine;

(S)-6-(5-cyclopropyl-2-methylphenyl)-4-(4-methoxy-3,3-dimethylpiperidin-1-yl)-2-(2-(trifluoromethyl)phenyl)-5,6,7,8-tetrahydropyrido[4,3-d]pyrimidine'

(S)-4-(4-methoxy-3,3-dimethylpiperidin-1-yl)-2-(1-methyl-1H-indazol-7-yl)-6-(2-methyl-5-(3-methyloxetan-3-yl)phenyl)-5,6,7,8-tetrahydropyrido[4,3-d]pyrimidine;

(S)-6-(5-isopropyl-2-methylphenyl)-4-(4-methoxy-3,3-dimethylpiperidin-1-yl)-2-(2-(trifluoromethyl)phenyl)-5,6,7,8-tetrahydropyrido[4,3-d]pyrimidine;

(S)-6-(5-cyclopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

4-(3,3-dimethylpiperidin-1-yl)-6-(5-isopropyl-2-methylphenyl)-2-(3-methyl-1H-indol-4-yl)-5,6,7,8-tetrahydropyrido[4,3-d]pyrimidine;

4-(3,3-dimethylpiperidin-1-yl)-6-(5-isopropyl-2-methylphenyl)-2-(2-methoxyphenyl)-5,6,7,8-tetrahydropyrido[4,3-d]pyrimidine;

2-(5-chloro-2-methoxyphenyl)-4-(3,3-dimethylpiperidin-1-yl)-6-(5-isopropyl-2-methylphenyl)-5,6,7,8-tetrahydropyrido[4,3-d]pyrimidine;

2-(5-chloro-2-methylphenyl)-4-(3,3-dimethylpiperidin-1-yl)-6-(5-isopropyl-2-methylphenyl)-5,6,7,8-tetrahydropyrido[4,3-d]pyrimidine;

4-(3,3-dimethylpiperidin-1-yl)-2-(5-fluoro-2-methylphenyl)-6-(5-isopropyl-2-methylphenyl)-5,6,7,8-tetrahydropyrido[4,3-d]pyrimidine;

6-(5-isopropyl-2-methylphenyl)-4-((3-endo)-3-methoxy-8-azabicyclo[3.2.1]octan-8-yl)-2-(5-methyl-1H-indazol-4-yl)-5,6,7,8-tetrahydropyrido[4,3-d]pyrimidine;

2-(5-isopropyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine;

4-(3,3-dimethylpiperidin-1-yl)-6-(5-isopropyl-2-methylphenyl)-2-(3-methyl-1H-pyrrolo[2,3-b]pyridin-4-yl)-5,6,7,8-tetrahydropyrido[4,3-d]pyrimidine;

(S)-6-(5-cyclopropyl-2-methylphenyl)-4-(4-methoxy-3,3-dimethylpiperidin-1-yl)-2-(5-(trifluoromethyl)-1H-pyrrolo[2,3-b]pyridin-4-yl)-5,6,7,8-tetrahydropyrido[4,3-d]pyrimidine;

(S)-2-(5-chloro-1H-pyrrolo[2,3-b]pyridin-4-yl)-6-(5-cyclopropyl-2-methylphenyl)-4-(4-methoxy-3,3-dimethylpiperidin-1-yl)-5,6,7,8-tetrahydropyrido[4,3-d]pyrimidine;

2-(5-Cyclopropyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine;

2-(2,6-Dimethylphenyl)-6-(5-isopropyl-2-methylphenyl)-4-((2R,4R)-4-methoxy-2-methylpiperidin-1-yl)-5,6,7,8-tetrahydropyrido[4,3-d]pyrimidine;

2-(2,5-dimethylphenyl)-6-(5-isopropyl-2-methylphenyl)-4-((2R,4R)-4-methoxy-2-methylpiperidin-1-yl)-5,6,7,8-tetrahydropyrido[4,3-d]pyrimidine;

2-(2,5-dimethylphenyl)-6-(5-isopropyl-2-methylphenyl)-4-((3S,4S)-4-methoxy-3-methylpiperidin-1-yl)-5,6,7,8-tetrahydropyrido[4,3-d]pyrimidine;

2-(2,5-dimethylphenyl)-4-((3S,4S)-4-methoxy-3-methylpiperidin-1-yl)-6-(2-methyl-5-(3-methyloxetan-3-yl)phenyl)-5,6,7,8-tetrahydropyrido[4,3-d]pyrimidine;

2-(2,6-dimethylphenyl)-4-((3S,4S)-4-methoxy-3-methylpiperidin-1-yl)-6-(2-methyl-5-(3-methyloxetan-3-yl)phenyl)-5,6,7,8-tetrahydropyrido[4,3-d]pyrimidine;

2-(2,6-dimethylphenyl)-6-(5-isopropyl-2-methylphenyl)-4-((3S,4S)-4-methoxy-3-methylpiperidin-1-yl)-5,6,7,8-tetrahydropyrido[4,3-d]pyrimidine;

(R)-2-(2,4-dimethylpyridin-3-yl)-6-(5-isopropyl-2-methylphenyl)-4-(4-methoxy-3,3-dimethylpiperidin-1-yl)-5,6,7,8-tetrahydropyrido[4,3-d]pyrimidine;

2-(2,6-dimethylphenyl)-4-((2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine;

2-(2,5-dimethylphenyl)-4-((2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine;

(R)-2-(3,5-dimethylpyridin-4-yl)-6-(5-isopropyl-2-methylphenyl)-4-(4-methoxy-3,3-dimethylpiperidin-1-yl)-5,6,7,8-tetrahydropyrido[4,3-d]pyrimidine;

2-(2,6-dimethylphenyl)-6-(5-methoxy-2-methylphenyl)-4-((2R,4R)-4-methoxy-2-methylpiperidin-1-yl)-5,6,7,8-tetrahydropyrido[4,3-d]pyrimidine;

2-(2,6-dimethylphenyl)-4-((2R,4R)-4-methoxy-2-methylpiperidin-1-yl)-6-(2-methyl-5-(trifluoromethyl)phenyl)-5,6,7,8-tetrahydropyrido[4,3-d]pyrimidine;

6-(5-isopropyl-2-methylphenyl)-4-((2R,4R)-4-methoxy-2-methylpiperidin-1-yl)-2-(5-methyl-1H-indazol-4-yl)-5,6,7,8-tetrahydropyrido[4,3-d]pyrimidine;

6-(5-chloro-2-methylphenyl)-2-(2,6-dimethylphenyl)-4-((2R,4R)-4-methoxy-2-methylpiperidin-1-yl)-5,6,7,8-tetrahydropyrido[4,3-d]pyrimidine;

2-(3,5-dimethyl-1H-indazol-4-yl)-6-(5-isopropyl-2-methylphenyl)-4-((2R,4R)-4-methoxy-2-methylpiperidin-1-yl)-5,6,7,8-tetrahydropyrido[4,3-d]pyrimidine;

2-(3,5-dimethyl-1H-indazol-4-yl)-4-(2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine;

2-(2,4-dimethylpyridin-3-yl)-6-(5-isopropyl-2-methylphenyl)-4-((2R,4R)-4-methoxy-2-methylpiperidin-1-yl)-5,6,7,8-tetrahydropyrido[4,3-d]pyrimidine;

2-(2,6-dimethylphenyl)-6-(5-fluoro-2-methylphenyl)-4-((2R,4R)-4-methoxy-2-methylpiperidin-1-yl)-5,6,7,8-tetrahydropyrido[4,3-d]pyrimidine;

2-(2,6-dimethylphenyl)-6-(4-fluoro-2-methylphenyl)-4-((2R,4R)-4-methoxy-2-methylpiperidin-1-yl)-5,6,7,8-tetrahydropyrido[4,3-d]pyrimidine;

2-(2,6-dimethylphenyl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine;

6-(5-cyclopropyl-2-methylphenyl)-2-(2,6-dimethylphenyl)-4-((3-endo)-3-methoxy-8-azabicyclo[3.2.1]octan-8-yl)-5,6,7,8-tetrahydropyrido[4,3-d]pyrimidine;

2-(2,6-dimethylphenyl)-4-((3-endo)-3-methoxy-8-azabicyclo[3.2.1]octan-8-yl)-6-(2-methyl-5-(3-methyloxetan-3-yl)phenyl)-5,6,7,8-tetrahydropyrido[4,3-d]pyrimidine;

6-(5-isopropyl-2-methylphenyl)-4-((3-endo)-3-methoxy-8-azabicyclo[3.2.1]octan-8-yl)-2-(5-(trifluoromethyl)-1H-pyrrolo[2,3-b]pyridin-4-yl)-5,6,7,8-tetrahydropyrido[4,3-d]pyrimidine;

(S)-6-(5-cyclopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine;

(R)-2-(2,6-dimethylphenyl)-6-(5-isopropyl-2-methylphenyl)-4-(4-methoxy-3,3-dimethylpiperidin-1-yl)-5,6,7,8-tetrahydropyrido[4,3-d]pyrimidine;

(R)-2-(2,6-dimethylphenyl)-4-(4-methoxy-3,3-dimethylpiperidin-1-yl)-6-(2-methyl-5-(trifluoromethyl)phenyl)-5,6,7,8-tetrahydropyrido[4,3-d]pyrimidine;

(R)-6-(5-chloro-2-methylphenyl)-2-(2,6-dimethylphenyl)-4-(4-methoxy-3,3-dimethylpiperidin-1-yl)-5,6,7,8-tetrahydropyrido[4,3-d]pyrimidine;

(R)-2-(2,6-dimethylphenyl)-4-(4-methoxy-3,3-dimethylpiperidin-1-yl)-6-(2-methyl-5-(3-methyloxetan-3-yl)phenyl)-5,6,7,8-tetrahydropyrido[4,3-d]pyrimidine;

6-(5-isopropyl-2-methylphenyl)-4-((2R,4R)-4-methoxy-2-methylpiperidin-1-yl)-2-(5-(trifluoromethyl)-1H-pyrrolo[2,3-b]pyridin-4-yl)-5,6,7,8-tetrahydropyrido[4,3-d]pyrimidine;

(S)-2-(2,6-dimethylphenyl)-6-(3-isopropyl-1-methyl-1H-pyrazol-5-yl)-4-(4-methoxy-3,3-dimethylpiperidin-1-yl)-5,6,7,8-tetrahydropyrido[4,3-d]pyrimidine;

6-(3-cyclopropyl-1-methyl-1H-pyrazol-5-yl)-2-(2,6-dimethylphenyl)-4-((3S,4S)-4-methoxy-3-methylpiperidin-1-yl)-5,6,7,8-tetrahydropyrido[4,3-d]pyrimidine;

2-(2,6-dimethylphenyl)-6-(3-isopropyl-1-methyl-1H-pyrazol-5-yl)-4-((2R,4R)-4-methoxy-2-methylpiperidin-1-yl)-5,6,7,8-tetrahydropyrido[4,3-d]pyrimidine;

6-(3-cyclopropyl-1-methyl-1H-pyrazol-5-yl)-2-(2,6-dimethylphenyl)-4-((2R,4R)-4-methoxy-2-methylpiperidin-1-yl)-5,6,7,8-tetrahydropyrido[4,3-d]pyrimidine;

(R)-2-(2,6-dimethylphenyl)-6-(3-isopropyl-1-methyl-1H-pyrazol-5-yl)-4-(4-methoxy-3,3-dimethylpiperidin-1-yl)-5,6,7,8-tetrahydropyrido[4,3-d]pyrimidine;

(R)-2-(4-(2-(2,5-Dimethylphenyl)-6-(5-isopropyl-2-methylphenyl)-5,6,7,8-tetrahydropyrido[4,3-d]pyrimidin-4-yl)-3-methylpiperazin-1-yl)acetamide;

(R)-2-(4-(2-(2,6-dimethylphenyl)-6-(2-methyl-5-(3-methyloxetan-3-yl)phenyl)-5,6,7,8-tetrahydropyrido[4,3-d]pyrimidin-4-yl)-2-methylpiperazin-1-yl)acetamide;

(R)-2-(2-methyl-4-(2-(3-methyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)acetamide;

(R)-2-(4-(2-(2,6-dimethylphenyl)-6-(o-tolyl)-5,6,7,8-tetrahydropyrido[4,3-d]pyrimidin-4-yl)-2-methylpiperazin-1-yl)acetamide;

(R)-2-(2-methyl-4-(2-(3-methyl-1H-indol-4-yl)-6-(o-tolyl)-5,6,7,8-tetrahydropyrido[4,3-d]pyrimidin-4-yl)piperazin-1-yl)acetamide;

(R)-2-(4-(6-(5-chloro-2-methylphenyl)-2-(3-methyl-1H-indol-4-yl)-5,6,7,8-tetrahydropyrido[4,3-d]pyrimidin-4-yl)-2-methylpiperazin-1-yl)acetamide;

(R)-2-(4-(6-(5-chloro-2-methylphenyl)-2-(2,6-dimethylphenyl)-5,6,7,8-tetrahydropyrido[4,3-d]pyrimidin-4-yl)-2-methylpiperazin-1-yl)acetamide;
(R)-2-(4-(6-(5-chloro-2-methylphenyl)-2-(5-methyl-1H-indazol-4-yl)-5,6,7,8-tetrahydropyrido[4,3-d]pyrimidin-4-yl)-2-methylpiperazin-1-yl)acetamide;
(R)-2-(2-methyl-4-(2-(3-methyl-1H-indol-4-yl)-6-(2-(trifluoromethyl)phenyl)-5,6,7,8 tetrahydropyrido[4,3-d]pyrimidin-4-yl)piperazin-1-yl)acetamide;
(R)-2-(4-(6-(5-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide;
(R)-2-(4-(6-(4-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide;
(R)-2-(2-methyl-4-(2-(3-methyl-1H-indol-4-yl)-6-(2-methyl-5-(trifluoromethyl)phenyl)-5,6,7,8-tetrahydropyrido[4,3-d]pyrimidin-4-yl)piperazin-1-yl)acetamide;
(R)-2-(4-(6-(3-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide;
(R)-2-(4-(6-(2,4-difluorophenyl)-2-(3-methyl-1H-indol-4-yl)-5,6,7,8-tetrahydropyrido[4,3-d]pyrimidin-4-yl)-2-methylpiperazin-1-yl)acetamide;
(R)-2-(4-(6-(5-isopropyl-2-methylphenyl)-2-(2-(trifluoromethyl)phenyl)-5,6,7,8-tetrahydropyrido[4,3-d]pyrimidin-4-yl)-2-methylpiperazin-1-yl)acetamide;
(R)-2-(4-(6-(5-isopropyl-2-methylphenyl)-2-(3-methyl-1H-indol-4-yl)-5,6,7,8-tetrahydropyrido[4,3-d]pyrimidin-4-yl)-2-methylpiperazin-1-yl)acetamide;
(R)-2-(4-(2-(2,5-dimethylphenyl)-6-(5-isopropyl-2-methylphenyl)-5,6,7,8-tetrahydropyrido[4,3-d]pyrimidin-4-yl)-2-methylpiperazin-1-yl)acetamide;
(R)-2-(4-(6-(5-isopropyl-2-methylphenyl)-2-(3-methyl-1H-indol-4-yl)-5,6,7,8-tetrahydropyrido[4,3-d]pyrimidin-4-yl)-3-methylpiperazin-1-yl)acetamide;
(R)-2-(4-(6-(5-isopropyl-2-methylphenyl)-2-(5-methyl-1H-indazol-4-yl)-5,6,7,8-tetrahydropyrido[4,3-d]pyrimidin-4-yl)-3-methylpiperazin-1-yl)acetamide;
(R)-1-(4-(6-(5-isopropyl-2-methylphenyl)-2-(3-methyl-1H-indol-4-yl)-5,6,7,8-tetrahydropyrido[4,3-d]pyrimidin-4-yl)-3-methylpiperazin-1-yl)ethanone;
(R)-1-(4-(6-(5-isopropyl-2-methylphenyl)-2-(3-methyl-1H-indol-4-yl)-5,6,7,8-tetrahydropyrido[4,3-d]pyrimidin-4-yl)-2-methylpiperazin-1-yl)ethanone;
(R)-1-(4-(6-(5-cyclopropyl-2-methylphenyl)-2-(3-methyl-1H-indol-4-yl)-5,6,7,8-tetrahydropyrido[4,3-d]pyrimidin-4-yl)-3-methylpiperazin-1-yl)ethanone;
1-(4-(6-(5-isopropyl-2-methylphenyl)-2-(2-(trifluoromethyl)phenyl)-5,6,7,8-tetrahydropyrido[4,3-d]pyrimidin-4-yl)piperazin-1-yl)ethanone;
(R)-1-(4-(6-(5-isopropyl-2-methylphenyl)-2-(2-(trifluoromethyl)phenyl)-5,6,7,8-tetrahydropyrido[4,3-d]pyrimidin-4-yl)-2-methylpiperazin-1-yl)ethanone;
(R)-1-(4-(6-(5-isopropyl-2-methylphenyl)-2-(2-(trifluoromethyl)phenyl)-5,6,7,8-tetrahydropyrido[4,3-d]pyrimidin-4-yl)-3-methylpiperazin-1-yl)ethanone;
(R)-1-(4-(2-(2,5-dimethylphenyl)-6-(5-isopropyl-2-methylphenyl)-5,6,7,8-tetrahydropyrido[4,3-d]pyrimidin-4-yl)-2-methylpiperazin-1-yl)ethanone;
(R)-1-(4-(6-(5-isopropyl-2-methylphenyl)-2-(5-methyl-1H-indazol-4-yl)-5,6,7,8-tetrahydropyrido[4,3-d]pyrimidin-4-yl)-2-methylpiperazin-1-yl)ethanone;
(R)-1-(4-(2-(2,5-dimethylphenyl)-6-(5-isopropyl-2-methylphenyl)-5,6,7,8-tetrahydropyrido[4,3-d]pyrimidin-4-yl)-3-methylpiperazin-1-yl)ethanone;
(R)-1-(3-methyl-4-(2-(3-methyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)ethanone;
racemic 1-(4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)ethanone;
racemic 1-((trans)-4-(6-(5-isopropyl-2-methylphenyl)-2-(3-methyl-1H-indol-4-yl)-5,6,7,8-tetrahydropyrido[4,3-d]pyrimidin-4-yl)-2,5-dimethylpiperazin-1-yl)ethanone;
racemic 2-(4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)acetamide;
racemic 2-(4-(6-(5-isopropyl-2-methylphenyl)-2-(3-methyl-1H-indol-4-yl)-5,6,7,8-tetrahydropyrido[4,3-d]pyrimidin-4-yl)-(trans)-2,5-dimethylpiperazin-1-yl)acetamide;
(R)-6-(5-isopropyl-2-methylphenyl)-2-(3-methyl-1H-indol-4-yl)-4-(3-methyl-4-(methylsulfonyl)piperazin-1-yl)-5,6,7,8-tetrahydropyrido[4,3-d]pyrimidine;
(R)-6-(5-isopropyl-2-methylphenyl)-2-(3-methyl-1H-indol-4-yl)-4-(3-;
methyl-4-(oxetan-3-yl)piperazin-1-yl)-5,6,7,8-tetrahydropyrido[4,3-d]pyrimidine;
(R)-6-(5-chloro-2-methylphenyl)-4-(4-ethyl-3-methylpiperazin-1-yl)-2-(3-methyl-1H-indol-4-yl)-5,6,7,8-tetrahydropyrido[4,3-d]pyrimidine;
(R)-6-(5-chloro-2-methylphenyl)-2-(3-methyl-1H-indol-4-yl)-4-(3-methyl-4-(oxetan-3-yl)piperazin-1-yl)-5,6,7,8-tetrahydropyrido[4,3-d]pyrimidine;
(R)-6-(5-chloro-2-methylphenyl)-2-(3-methyl-1H-indol-4-yl)-4-(3-methyl-4-(oxetan-3-yl)piperazin-1-yl)-5,6,7,8-tetrahydropyrido[4,3-d]pyrimidine;
6-(5-isopropyl-2-methylphenyl)-4-methoxy-2-(5-methyl-1H-indazol-4-yl)-5,6,7,8-; tetrahydropyrido[4,3-d]pyrimidine;
2-(5-isopropyl-1H-indazol-4-yl)-6-(5-isopropyl-2-methylphenyl)-4-methoxy-5,6,7,8-tetrahydropyrido[4,3-d]pyrimidine;
2-(5-isopropyl-1H-indazol-4-yl)-4-methoxy-6-(2-methyl-5-(3-methyloxetan-3-yl)phenyl)-5,6,7,8-tetrahydropyrido[4,3-d]pyrimidine;
2-(3-chloro-5-methyl-1H-indazol-4-yl)-6-(5-isopropyl-2-methylphenyl)-4-methoxy-5,6,7,8 tetrahydropyrido[4,3-d]pyrimidine;
(S)-2-(3-chloro-5-methyl-1H-indazol-4-yl)-6-(5-isopropyl-2-methylphenyl)-4-(4-methoxy-3,3-dimethylpiperidin-1-yl)-5,6,7,8-tetrahydropyrido[4,3-d]pyrimidine;
racemic 2-(2,6-dimethylphenyl)-4-(4-methoxy-3,3-dimethylpiperidin-1-yl)-6-((S)-1-phenylethyl)-5,6,7,8-tetrahydropyrido[4,3-d]pyrimidine;
racemic 2-(2,6-dimethylphenyl)-4-(4-methoxy-3,3-dimethylpiperidin-1-yl)-6-((R) 1-phenylethyl)-5,6,7,8-tetrahydropyrido[4,3-d]pyrimidine;
6-(4-chloro-3-isopropyl-1-methyl-1H-pyrazol-5-yl)-4-(3,3-dimethylpiperidin-1-yl)-2-(3-methyl-1H-indol-4-yl)-5,6,7,8-tetrahydropyrido[4,3-d]pyrimidine;
(R)-4-methyl-1-(2-(3-methyl-1-tosyl-1H-indol-4-yl)-4-(3-methyl-4-((2-nitrophenyl)sulfonyl)piperazin-1-yl)-7,8-dihydropyrido[4,3-d]pyrimidin-6(5H)-yl)pentane-1,3-dione;
(R)-6-(3-isopropyl-1-methyl-1H-pyrazol-5-yl)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine;
(R)-6-(3-isopropyl-1-methyl-1H-pyrazol-5-yl)-2-(3-methyl-1-tosyl-1H-indol-4-yl)-4-(3-methylpiperazin-1-yl)-5,6,7,8-tetrahydropyrido[4,3-d]pyrimidine;

(R)-2-(4-(6-(3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperazin-1-yl)acetamide;

(R)-2-(4-(2-(2,6-dimethylphenyl)-6-(3-isopropyl-1-methyl-1H-pyrazol-5-yl)-5,6,7,8-tetrahydropyrido[4,3-d]pyrimidin-4-yl)-2-methylpiperazin-1-yl)acetamide;

(R)-2-(4-(6-(4-chloro-3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperazin-1-yl)acetamide;

(S)-6-(3-isopropyl-1-methyl-1H-pyrazol-5-yl)-2-(3-methyl-1H-indol-4-yl)-4-(2-methylpiperidin-1-yl)-5,6,7,8-tetrahydropyrido[4,3-d]pyrimidine;

(6-(3-isopropyl-1-methyl-1H-pyrazol-5-yl)-4-((3R,4R)-4-methoxy-3-methylpiperidin-1-yl)-2-(3-methyl-1H-indol-4-yl)-5,6,7,8-tetrahydropyrido[4,3-d]pyrimidine;

(S)-6-(3-isopropyl-1-methyl-1H-pyrazol-5-yl)-4-(4-methoxy-3,3-dimethylpiperidin-1-yl)-2-(3-methyl-1H-indol-4-yl)-5,6,7,8-tetrahydropyrido[4,3-d]pyrimidine;

racemic 1-(6-(3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperidin-4-ol;

2-(2,6-dimethylphenyl)-6-(5-isopropyl-2-methylphenyl)-4-(3-methoxypropoxy)-5,6,7,8-tetrahydropyrido[4,3-d]pyrimidine;

6-(5-isopropyl-2-methylphenyl)-4-methyl-2-(3-methyl-1H-indol-4-yl)-5,6,7,8-tetrahydro-1,6-naphthyridine;

2-(2,6-diethylphenyl)-4-methyl-6-(o-tolyl)-5,6,7,8-tetrahydro-1,6-naphthyridine;

2-(2,6-diethylphenyl)-6-(1-ethyl-3,5-dimethyl-1H-pyrazol-4-yl)-4-methyl-5,6,7,8-tetrahydro-1,6-naphthyridine-2-(2,6-diethylphenyl)-6-(1-ethyl-3,5-dimethyl-1H-pyrazol-4-yl)-4-methyl-5,6,7,8-tetrahydro-1,6-naphthyridine;

2-(2,6-diethylphenyl)-6-(1,3-dimethyl-1H-pyrazol-5-yl)-4-methyl-5,6,7,8-tetrahydro-1,6-naphthyridine;

2-(2,6-diethylphenyl)-6-(5-methoxy-2-methylphenyl)-4-methyl-5,6,7,8-tetrahydro-1,6-naphthyridine;

2-(2,6-diethylphenyl)-6-(2,5-dimethylphenyl)-4-methyl-5,6,7,8-tetrahydro-1,6-naphthyridine;

2-(2,6-diethylphenyl)-6-(1-ethyl-3-methyl-1H-pyrazol-5-yl)-4-methyl-5,6,7,8-tetrahydro-1,6-naphthyridine;

2-(2,6-diethylphenyl)-6-(2,4-dimethylphenyl)-4-methyl-5,6,7,8-tetrahydro-1,6-naphthyridine;

6-(5-cyclopropyl-2-methylphenyl)-2-(2,6-diethylphenyl)-4-methyl-5,6,7,8-tetrahydro-1,6-naphthyridine;

6-(5-chloro-2-methylphenyl)-2-(2,6-diethylphenyl)-4-methyl-5,6,7,8-tetrahydro-1,6-naphthyridine;

2-(2,6-diethylphenyl)-4-methyl-6-(1,3,5-trimethyl-1H-pyrazol-4-yl)-5,6,7,8-tetrahydro-1,6-naphthyridine;

6-(1-ethyl-3,5-dimethyl-1H-pyrazol-4-yl)-4-methyl-2-(5-methyl-1H-indazol-4-yl)-5,6,7,8-tetrahydro-1,6-naphthyridine;

6-(3-cyclopropyl-1-methyl-1H-pyrazol-5-yl)-4-methyl-2-(5-methyl-1H-indazol-4-yl)-5,6,7,8-tetrahydro-1,6-naphthyridine;

6-(1-ethyl-3,5-dimethyl-1H-pyrazol-4-yl)-4-methyl-2-(3-methyl-1H-indol-4-yl)-5,6,7,8-tetrahydro-1,6-naphthyridine;

2-(2,6-diethylphenyl)-6-(5-fluoro-2-methylphenyl)-4-methyl-5,6,7,8-tetrahydro-1,6-naphthyridine;

2-(3-methyl-1H-indol-4-yl)-6-(5-isopropyl-2-methylphenyl)-4-methyl-5,6,7,8-tetrahydro($^2$H$_2$)-1,6-naphthyridine;

6-(5-isopropyl-2-methylphenyl)-4-methyl-2-(5-methyl-1H-indazol-4-yl)-5,6,7,8-tetrahydro-1,6-naphthyridine;

6-(5-isopropyl-2-methylphenyl)-4-methyl-2-(3-methyl-1H-indazol-4-yl)-5,6,7,8-tetrahydro-1,6-naphthyridine;

2-(2-chloro-5-methoxyphenyl)-6-(5-isopropyl-2-methylphenyl)-4-methyl-5,6,7,8-tetrahydro-1,6-naphthyridine;

2-(5-isopropyl-1H-indazol-4-yl)-6-(5-isopropyl-2-methylphenyl)-4-methyl-5,6,7,8-tetrahydro-1,6-naphthyridine;

4-methyl-2-(5-methyl-1H-indazol-4-yl)-6-(2-methyl-5-(3-methyloxetan-3-yl)phenyl)-5,6,7,8-tetrahydro-1,6-naphthyridine;

6-(5-isopropyl-2-methylphenyl)-2-(5-methyl-1H-indazol-4-yl)-5,6,7,8-tetrahydro-1,6-naphthyridine;

2-(2,6-diethylphenyl)-6-(5-isopropyl-2-methylphenyl)-4-methyl-5,6,7,8-tetrahydro-1,6-naphthyridine;

6-(3-cyclopropyl-1-methyl-1H-pyrazol-5-yl)-2-(2,6-diethylphenyl)-4,7-dimethyl-5,6,7,8-tetrahydro(5,5-$^2$H$_2$)-1,6-naphthyridine;

6-(4-chloro-3-cyclopropyl-1-methyl-1H-pyrazol-5-yl)-2-(2,6-diethylphenyl)-4-methyl-5,6,7,8-tetrahydro(5,5-$^2$H$_2$)-1,6-naphthyridine;

2-(2,6-diethylphenyl)-6-(5-isopropyl-2-methylphenyl)-4,7-dimethyl-5,6,7,8-tetrahydro(5,5-$^2$H$_2$)-1,6-naphthyridine;

6-(5-isopropyl-2-methylphenyl)-4-methyl-2-(5-methyl-1H-indazol-4-yl)-5,6,7,8-tetrahydro(5,5-$^2$H$_2$)-1,6-naphthyridine;

6-(5-isopropyl-2-methylphenyl)-4-methyl-2-(3-methyl-1H-indazol-4-yl)-5,6,7,8-tetrahydro(5,5-$^2$H$_2$)-1,6-naphthyridine;

2-(5-chloro-1H-pyrrolo[2,3-b]pyridin-4-yl)-6-(5-isopropyl-2-methylphenyl)-4-methyl-5,6,7,8-tetrahydro(5,5-$^2$H$_2$)-1,6-naphthyridine;

6-(5-isopropyl-2-methylphenyl)-4-methyl-2-(5-methyl-1H-pyrrolo[2,3-b]pyridin-4-yl)-5,6,7,8-tetrahydro(5,5-$^2$H$_2$)-1,6-naphthyridine;

2-(2,6-diethylphenyl)-6-(2,4-dimethylpyridin-3-yl)-4-methyl-5,6,7,8-tetrahydro(5,5-$^2$H$_2$)-1,6-naphthyridine;

2-(3-methyl-1H-indol-4-yl)-6-(2,6-dimethylphenyl)-4-methyl-5,6,7,8-tetrahydro(5,5-$^2$H$_2$)-1,6-naphthyridine;

6-(5-methoxy-2-methylphenyl)-4-methyl-2-(5-methyl-1H-indazol-4-yl)-5,6,7,8-tetrahydro(5,5-$^2$H$_2$)-1,6-naphthyridine;

6-(3-cyclopropyl-1-methyl-1H-pyrazol-5-yl)-2-(5-isopropyl-1H-indazol-4-yl)-4-methyl-5,6,7,8-tetrahydro-1,6-naphthyridine;

6-(4-chloro-3-cyclopropyl-1-methyl-1H-pyrazol-5-yl)-2-(5-isopropyl-1H-indazol-4-yl)-4-methyl-5,6,7,8-tetrahydro-1,6-naphthyridine;

2-(2,6-diethylphenyl)-6-(1-ethyl-3,5-dimethyl-1H-pyrazol-4-yl)-4-methyl-5,6,7,8-tetrahydro(5,5-$^2$H$_2$)-1,6-naphthyridine;

2-(3-methyl-1H-indol-4-yl)-6-(1-ethyl-3,5-dimethyl-1H-pyrazol-4-yl)-4-methyl-5,6,7,8-tetrahydro(5,5-$^2$H$_2$)-1,6-naphthyridine;

2-(2,6-diethylphenyl)-4-methyl-6-(1-methyl-1H-tetrazol-5-yl)-5,6,7,8-tetrahydro-1,6-naphthyridine;

2-(2,6-dimethylphenyl)-6-(5-isopropyl-2-methylphenyl)-4-methoxy 5,6,7,8-tetrahydro-1,6-naphthyridine;

2-(2,6-dimethylphenyl)-6-(5-isopropyl-2-methylphenyl)-4-methoxy 5,6,7,8-tetrahydro(5,5-$^2$-1,6-naphthyridine;

(S)-2-(2,6-dimethylphenyl)-6-(5-isopropyl-2-methylphenyl)-4-(4-methoxy-3,3-dimethylpiperidin-1-yl)-7,8-dihydro-1,6-naphthyridin-5(6H)-one;

2-(2,6-dimethylphenyl)-4-((2-hydroxy-2-methylpropyl)(methyl)amino)-6-(5-isopropyl-2-methylphenyl)-7,8-dihydro-1,6-naphthyridin-5(6H)-one;

4-((cyclopropylmethyl)(propyl)amino)-2-(2,6-dimethylphenyl)-6-(5-isopropyl-2-methylphenyl)-7,8-dihydro-1,6-naphthyridin-5(6H)-one;

2-(2,6-dimethylphenyl)-6-(5-isopropyl-2-methylphenyl)-4-((2-methoxyethyl)(methyl)amino)-7,8-dihydro-1,6-naphthyridin-5(6H)-one;

2-(2,6-dimethylphenyl)-6-(5-isopropyl-2-methylphenyl)-4-((2R,4R)-4-methoxy-2-methylpiperidin-1-yl)-7,8-dihydro-1,6-naphthyridin-5(6H)-one;

(S)-2-(2,6-dimethylphenyl)-6-(5-isopropyl-2-methylphenyl)-4-(4-methoxy-3,3-dimethylpiperidin-1-yl)-5,6,7,8-tetrahydro-1,6-naphthyridine;

1-((2-(2,6-dimethylphenyl)-6-(5-isopropyl-2-methylphenyl)-5,6,7,8-tetrahydro-1,6-naphthyridin-4-yl)(methyl)amino)-2-methylpropan-2-ol;

N-(cyclopropylmethyl)-2-(2,6-dimethylphenyl)-6-(5-isopropyl-2-methylphenyl)-N-propyl-5,6,7,8-tetrahydro-1,6-naphthyridin-4-amine;

2-(2,6-dimethylphenyl)-6-(5-isopropyl-2-methylphenyl)-N-(2-methoxyethyl)-N-methyl-5,6,7,8-tetrahydro-1,6-naphthyridin-4-amine;

2-(2,6-dimethylphenyl)-6-(5-isopropyl-2-methylphenyl)-4-((2R,4R)-4-methoxy-2-methylpiperidin-1-yl)-5,6,7,8-tetrahydro-1,6-naphthyridine;

2-(3,5-dimethyl-1H-indazol-4-yl)-4-(2R,4R)-4-ethoxy-2-methylpiperidin-1-yl)-6-(5-isopropyl-2-methylphenyl)-5,6,7,8-tetrahydropyrido[4,3-d]pyrimidine;

(R)-6-(3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

2-(3,5-dimethyl-1H-indazol-4-yl)-4-(2R,4R)-4-methoxy-2-methylpiperidin-1-yl)-6-(1-methyl-3-(trifluoromethyl)-1H-pyrazol-5-yl)-5,6,7,8-tetrahydropyrido[4,3-d]pyrimidine;

(S)-2-(3,5-dimethyl-1H-indazol-4-yl)-4-(4-methoxy-3,3-dimethylpiperidin-1-yl)-6-(1-methyl-3-(trifluoromethyl)-1H-pyrazol-5-yl)-5,6,7,8-tetrahydropyrido[4,3-d]pyrimidine;

(R)-6-(3-(difluoromethyl)-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(3-cyclopropyl-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine;

(R)-6-(4-chloro-3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(4-chloro-3-cyclopropyl-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine;

(R)-6-(4-chloro-3-(difluoromethyl)-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

6-(4-chloro-3-cyclopropyl-1-methyl-1H-pyrazol-5-yl)-2-(3,5-dimethyl-1H-indazol-4-yl)-4-((2R,4R)-4-ethoxy-2-methylpiperidin-1-yl)-5,6,7,8-tetrahydropyrido[4,3-d]pyrimidine;

6-(4-chloro-3-cyclopropyl-1-methyl-1H-pyrazol-5-yl)-4-((2R,4R)-4-methoxy-2-methylpiperidin-1-yl)-2-(5-methyl-1H-indazol-4-yl)-5,6,7,8-tetrahydropyrido[4,3-d]pyrimidine;

(S)-6-(4-chloro-3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

6-(4-chloro-3-cyclopropyl-1-methyl-1H-pyrazol-5-yl)-2-(3,5-dimethyl-1H-indazol-4-yl)-4-((2R,4R)-4-methoxy-2-methylpiperidin-1-yl)-5,6,7,8-tetrahydropyrido[4,3-d]pyrimidine;

(R)-2-(3,5-dimethyl-1H-indazol-4-yl)-4-(4-ethoxy-3,3-dimethylpiperidin-1-yl)-6-(1-methyl-3-(trifluoromethyl)-1H-pyrazol-5-yl)-5,6,7,8-tetrahydropyrido[4,3-d]pyrimidine;

6-(3-cyclopropyl-4-fluoro-1-methyl-1H-pyrazol-5-yl)-2-(3,5-dimethyl-1H-indazol-4-yl)-4-(3-endo)-3-methoxy-8-azabicyclo[3.2.1]octan-8-yl)-5,6,7,8-tetrahydropyrido[4,3-d]pyrimidine;

(S)-6-(3-cyclopropyl-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(3-cyclopropyl-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine; and (R)-6-(3-cyclopropyl-4-fluoro-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine;

(S)-6-(3-cyclopropyl-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

racemic (cis)-3-(2-(3,5-dimethyl-1H-indazol-4-yl)-6-(1-methyl-3-(trifluoromethyl)-1H-pyrazol-5-yl)-5,6,7,8-tetrahydropyrido[4,3-d]pyrimidin-4-yl)-1-methyl-7-oxa-3-azabicyclo[4.2.0]octane;

(R)-2-(3,5-dimethyl-1H-indazol-4-yl)-6-(5-isopropyl-2-methylphenyl)-4-(2-methylpiperidin-1-yl)-5,6,7,8-tetrahydropyrido[4,3-d]pyrimidine;

4-cyclopropyl-2-(2-(3,5-dimethyl-1H-indazol-4-yl)-4-((4S,6R)-6-methyl-1-oxa-7-azaspiro[3.5]nonan-7-yl)-7,8-dihydropyrido[4,3-d]pyrimidin-6(5H)-yl)benzonitrile;

(R)-1-(2-(3,5-dimethyl-1H-indazol-4-yl)-6-(5-methoxy-2-methylphenyl)-5,6,7,8-tetrahydropyrido[4,3-d]pyrimidin-4-yl)-N,N-dimethylpyrrolidin-3-amine;

(R)-6-(4-chloro-1-methyl-3-(trifluoromethyl)-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(3-(difluoromethyl)-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-2-(3,5-dimethyl-1H-indazol-4-yl)-6-(4-fluoro-1-methyl-3-(trifluoromethyl)-1H-pyrazol-5-yl)-4-(4-methoxy-3,3-dimethylpiperidin-1-yl)-5,6,7,8-tetrahydropyrido[4,3-d]pyrimidine;

2-(3,5-dimethyl-1H-indazol-4-yl)-4-(2-fluoroethoxy)-6-(5-isopropyl-2-methylphenyl)-5,6,7,8-tetrahydropyrido[4,3-d]pyrimidine;

4-(2,2-difluoroethoxy)-2-(3,5-dimethyl-1H-indazol-4-yl)-6-(5-isopropyl-2-methylphenyl)-5,6,7,8-tetrahydropyrido[4,3-d]pyrimidine;

2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)ethanamine;

2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)-N-methylethanamine;

(S)-2-(3,5-dimethyl-1H-indazol-4-yl)-6-(5-isopropyl-2-methylphenyl)-4-((1-methylpyrrolidin-2-yl)methoxy)-5,6,7,8-tetrahydropyrido[4,3-d]pyrimidine;

4-(2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)ethyl)morpholine;

(R)-3-((2-(3,5-dimethyl-1H-indazol-4-yl)-6-(5-isopropyl-2-methylphenyl)-5,6,7,8-tetrahydropyrido[4,3-d]pyrimidin-4-yl)oxy)propane-1,2-diol;

1-(2-(3,5-dimethyl-1H-indazol-4-yl)-6-(5-isopropyl-2-methylphenyl)-5,6,7,8-tetrahydropyrido[4,3-d]pyrimidin-4-yl)-N,N-dimethylazetidin-3-amine;

(R)-1-(2-(3,5-dimethyl-1H-indazol-4-yl)-6-(5-isopropyl-2-methylphenyl)-5,6,7,8-tetrahydropyrido[4,3-d]pyrimidin-4-yl)-N,N-dimethylpyrrolidin-3-amine;

1-(2-(3,5-dimethyl-1H-indazol-4-yl)-6-(5-isopropyl-2-methylphenyl)-5,6,7,8-tetrahydropyrido[4,3-d]pyrimidin-4-yl)-3,3-difluoropiperidin-4-ol;

(R)-1-(2-(3,5-dimethyl-1H-pyrazolo[3,4-b]pyridin-4-yl)-6-(5-isopropyl-2-methylphenyl)-5,6,7,8-tetrahydropyrido[4,3-d]pyrimidin-4-yl)-N,N-dimethylpyrrolidin-3-amine;

(3S,4S)-1-(2-(3,5-dimethyl-1H-indazol-4-yl)-6-(5-methoxy-2-methylphenyl)-5,6,7,8-tetrahydropyrido[4,3-d]pyrimidin-4-yl)-4-methoxy-N,N-dimethylpyrrolidin-3-amine;

(3R,4R)-1-(2-(3,5-dimethyl-1H-indazol-4-yl)-6-(5-methoxy-2-methylphenyl)-5,6,7,8-tetrahydropyrido[4,3-d]pyrimidin-4-yl)-4-methoxy-N,N-dimethylpyrrolidin-3-amine;

(3R,4R)-1-(2-(3,5-dimethyl-1H-indazol-4-yl)-6-(5-isopropyl-2-methylphenyl)-5,6,7,8-tetrahydropyrido[4,3-d]pyrimidin-4-yl)-4-methoxy-N,N-dimethylpyrrolidin-3-amine;

(3S,4S)-1-(2-(3,5-dimethyl-1H-indazol-4-yl)-6-(5-isopropyl-2-methylphenyl)-5,6,7,8-tetrahydropyrido[4,3-d]pyrimidin-4-yl)-4-methoxy-N,N-dimethylpyrrolidin-3-amine;

(R)-2-(3,5-dimethyl-1H-indazol-4-yl)-6-(5-isopropyl-2-methylphenyl)-4-(2-methylazetidin-1-yl)-5,6,7,8-tetrahydropyrido[4,3-d]pyrimidine;

(S)-2-(3,5-dimethyl-1H-indazol-4-yl)-6-(5-isopropyl-2-methylphenyl)-4-(2-methylazetidin-1-yl)-5,6,7,8-tetrahydropyrido[4,3-d]pyrimidine;

(R)-4-(2-(3,5-dimethyl-1H-indazol-4-yl)-6-(5-isopropyl-2-methylphenyl)-5,6,7,8-tetrahydropyrido[4,3-d]pyrimidin-4-yl)-3-methylmorpholine;

2-(3,5-dimethyl-1H-indazol-4-yl)-6-(5-isopropyl-2-methylphenyl)-4-(4-(methylsulfonyl)piperidin-1-yl)-5,6,7,8-tetrahydropyrido[4,3-d]pyrimidine;

6-(4-chloro-3-cyclopropyl-1-methyl-1H-pyrazol-5-yl)-4-(2,2-difluoroethoxy)-2-(3,5-dimethyl-1H-indazol-4-yl)-5,6,7,8-tetrahydropyrido[4,3-d]pyrimidine;

6-(4-chloro-3-cyclopropyl-1-methyl-1H-pyrazol-5-yl)-2-(3,5-dimethyl-1H-indazol-4-yl)-4-(3-ethoxyazetidin-1-yl)-5,6,7,8-tetrahydropyrido[4,3-d]pyrimidine;

(R)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-N,N-dimethylpyrrolidin-3-amine;

(R)-6-(4-chloro-3-cyclopropyl-1-methyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine;

(S)-6-(4-chloro-3-cyclopropyl-1-methyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine;

(3R,4R)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-4-methoxy-N,N-dimethylpyrrolidin-3-amine;

(3S,4S)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-4-methoxy-N,N-dimethylpyrrolidin-3-amine;

racemic (trans)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-2-methylazetidin-3-ol;

racemic 6-(4-chloro-3-cyclopropyl-1-methyl-1H-pyrazol-5-yl)-2-(3,5-dimethyl-1H-indazol-4-yl)-4-((trans)-3-methoxy-2-methylazetidin-1-yl)-5,6,7,8-tetrahydropyrido[4,3-d]pyrimidine;

1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-N,N-dimethylazetidin-3-amine;

(R)-6-(4-chloro-3-cyclopropyl-1-methyl-1H-pyrazol-5-yl)-2-(3,5-dimethyl-1H-indazol-4-yl)-4-(2,4-dimethylpiperazin-1-yl)-5,6,7,8-tetrahydropyrido[4,3-d]pyrimidine;

racemic (1S*,6S*)-3-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-1-methyl-7-oxa-3-azabicyclo[4.2.0]octane;

racemic (cis)-3-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-7-oxa-3-azabicyclo[4.2.0]octane;

(R)-4-(6-(4-Chloro-3-cyclopropyl-1-ethyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine;

(R)-6-(4-chloro-3-cyclopropyl-1-ethyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine;

(S)-6-(4-chloro-3-cyclopropyl-1-ethyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine;

(R)-4-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine;

1-(6-(4-chloro-3-cyclopropyl-1-ethyl-1H-pyrazol-5-yl)-2-(3,5-dimethyl-1H-indazol-4-yl)-5,6,7,8-tetrahydropyrido[4,3-d]pyrimidin-4-yl)-N,N-dimethylazetidin-3-amine;

(R)-6-(3-cyclopropyl-1-ethyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(3-cyclopropyl-1-ethyl-4-fluoro-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-6-(4-chloro-3-cyclopropyl-1-ethyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine;

(R)-3-(difluoromethyl)-5-(2-(3,5-dimethyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbonitrile Racemic (1S*,6S*)-3-(6-(3-(difluoromethyl)-1-methyl-1H-pyrazol-5-yl)-2-(3,5-dimethyl-1H-indazol-4-yl)-5,6,7,8-tetrahydropyrido[4,3-d]pyrimidin-4-yl)-1-methyl-7-oxa-3-azabicyclo[4.2.0]octane;

(R)-4-(6-(3-cyclopropyl-4-fluoro-1-methyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine;

(R)-6-(3-cyclopropyl-1-methyl-1H-pyrazol-5-yl)-2-(3,5-dimethyl-1H-indazol-4-yl)-4-(2-methylpiperidin-1-yl)-5,6,7,8-tetrahydropyrido[4,3-d]pyrimidine; and (R)-6-(4-chloro-3-cyclopropyl-1-methyl-1H-pyrazol-5-yl)-2-(3,5-dimethyl-1H-indazol-4-yl)-4-(2-methylpiperidin-1-yl)-5,6,7,8-tetrahydropyrido[4,3-d]pyrimidine.

In a fourteenth embodiment, a pharmaceutical composition is provided which comprises one or more pharmaceutically acceptable carriers and a therapeutically effective amount of a compound of any one of embodiments 1 to 13.

In a fifteenth embodiment, a combination, in particular a pharmaceutical combination, is provided which comprises a therapeutically effective amount of the compound according to any one of embodiments 1 to 13 and a second therapeutically active agent.

In a sixteenth embodiment, a method of inhibiting C5a induced anaphalaxis in a subject is provided, the method comprises administering to the subject a therapeutically effective amount of the compound according to any one of embodiments 1 to 13.

In a seventeenth embodiment, a method of treating a disorder or a disease in a subject mediated by complement activation, in particular mediated by C5a activation is provided, the method comprises administering to the subject a therapeutically effective amount of the compound according to any one of embodiments 1 to 13.

In an eighteenth embodiment, the method of embodiment seventeen is provided in which the disease or disorder is selected from the group consisting of age-related macular degeneration, geographic atrophy, diabetic retinopathy, uveitis, retinitis pigmentosa, macular edema, Behcet's uveitis, multifocal choroiditis, Vogt-Koyanagi-Harada syndrome, intermediate uveitis, birdshot retino-choroiditis, sympathetic ophthalmia, ocular cicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome (ARDS), myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity.

In a nineteenth embodiment, a method of treating age related macular degeneration is provided, the method comprising administering to a subject in need thereof an effective amount of a composition comprising a compound of the $1^{st}$ through $14^{th}$ embodiments.

In a twentieth embodiment, a compound according to any one of embodiment 1 to 13 is provided for use as a medicament.

In a twenty first embodiment the use of a compound according to any one of embodiments 1 to 13 is provided in the manufacture of a medicament for the treatment of a disorder or disease in a subject mediated by complement activation or activation of the complement alternative pathway.

In a twenty second embodiment, the use of a compound according to any one of embodiments 1 to 13 is provided for the treatment of age-related macular degeneration In another embodiment, pharmaceutical compositions are provided which comprise one or more pharmaceutically acceptable carriers and a therapeutically effective amount of a compound of any one of formulae (I), (Ia), (II), (III), (IV), (V), (VI), (VII), or a sub formulae thereof, e.g., a compound of any one of embodiments one to eleven listed supra.

In another embodiment, combinations, in particular pharmaceutical combinations, are provided which comprise a therapeutically effective amount of the compound of any one of formulae (I), (Ia), (II), (III), (IV), (V), (VI), (VII), or a sub formulae thereof, e.g., a compound of any one of embodiments one to eleven listed supra.

In another embodiment, methods of modulating complement activity in a subject are provided which methods comprise administering to the subject a therapeutically effective amount of the compound of any one of formulae (I), (Ia), (II), (III), (IV), (V), (VI), (VII), or a sub formulae thereof, e.g., a compound of any one of embodiments one to eleven listed supra.

In yet other embodiments, methods of treating a disorder or a disease in a subject mediated by complement activation, in particular mediated by activation of the complement system, are provided, which methods comprise administering to the subject a therapeutically effective amount of the compound of any one of formulae (I), (Ia), (II), (III), (IV), (V), (VI), (VII), or a sub formulae thereof, e.g., a compound of any one of embodiments one to eleven listed supra.

In another embodiment, methods of treating age related macular degeneration in a subject are provided which methods comprise administering to the subject a therapeutically effective amount of the compound of any one of formulae (I), (Ia), (II), (III), (IV), (V), (VI), (VII), or a sub formulae thereof, e.g., a compound of any one of embodiments one to eleven listed supra.

In another aspect, the invention provides for the use of compounds of any one of formulae (I), (Ia), (II), (III), (IV), (V), (VI), (VII), or a sub formulae thereof, e.g., a compound of any one of embodiments one to eleven listed supra, for use in the preparation of a medicament and more particularly for use in the manufacture of a medicament for the treatment of a disorder or disease in a subject mediated by complement activation or activation of the complement system. In certain other aspects, the invention provides for the use of a compound according to any one of formulae (I), (Ia), (II), (III), (IV), (V), (VI), (VII), or a sub formulae thereof, e.g., a compound of any one of embodiments one to eleven listed supra, in the treatment of age-related macular degeneration.

In one embodiment, the invention provides a combination, in particular a pharmaceutical combination, comprising a therapeutically effective amount of the compound according to the definition of formula (I), (Ia), (II), (III), (IV), (V), (VI), (VII), or a sub formulae thereof, e.g., a compound of any one of embodiments one to eleven listed supra, or any one of the specifically disclosed compounds of the invention and one or more therapeutically active agents (preferably selected from those listed infra).

In twenty third embodiment, the invention is a solvate form of Example 19-F isolated from MTBE.

In a twenty fourth embodiment, the invention is a solvate form of Example 19-F isolated from MTBE characterized by a x-ray powder diffraction pattern comprising four or more 2θ values selected from the group consisting of 6.369±0.2°, 7.058±0.2°, 9.306±0.2°, 10.522±0.2°, 11.908±0.2°, 12.511±0.2°, 13.434±0.2°, 15.527±0.2°, 16.385±0.2°, 17.390±0.2°, 18.883±0.2°, 20.285±0.2°, 22.351±0.2° and 23.297±0.2°, at a temperature of about 22° C.

In a twenty fifth embodiment, the invention is a solvate form of Example 19-F isolated from MTBE characterized by a x-ray powder diffraction pattern comprising five or more 2θ values selected from the group consisting of 6.369±0.2°, 7.058±0.2°, 9.306±0.2°, 10.522±0.2°, 11.908±0.2°, 12.511±0.2°, 13.434±0.2°, 15.527±0.2°, 16.385±0.2°, 17.390±0.2°, 18.883±0.2°, 20.285±0.2°, 22.351±0.2° and 23.297±0.2°, at a temperature of about 22° C.

In a twenty sixth embodiment, the invention is a solvate form of Example 19-F isolated from MTBE having a X-ray diffraction spectrum substantially the same as the X-ray powder diffraction spectrum shown in FIG. 1.

Figure 2:
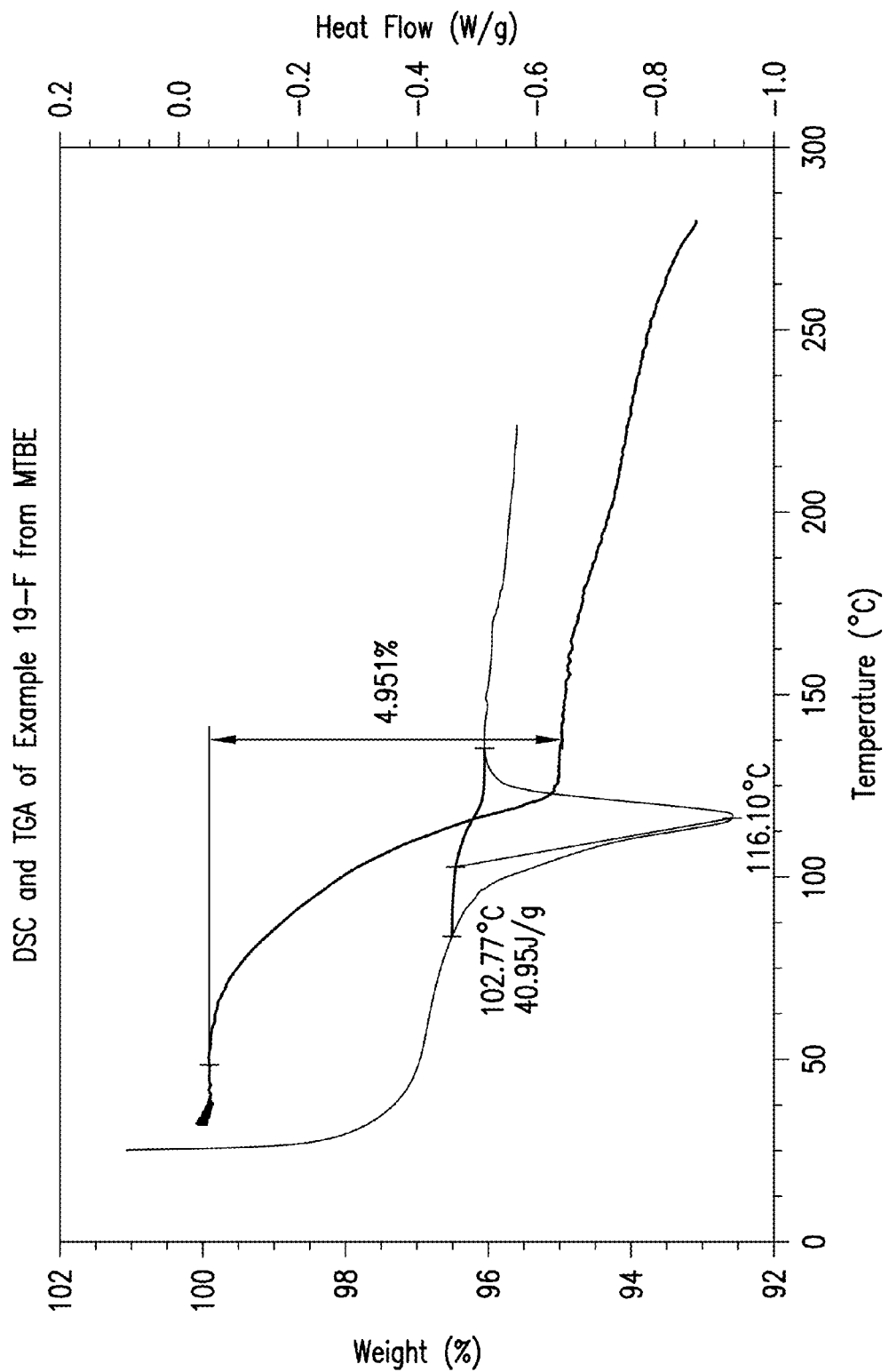
FIG. 2. illustrates the differential scanning calorimetry (DSC) and thermogravimetric analysis (TGA) of Example 19-F from MTBE.

In a twenty seventh embodiment, the invention is a solvate form of Example 19-F isolated from MTBE having a differential scanning calorimetry (DSC) thermogram substantially the same as that shown in shown in FIG. 2.

In a twenty eighth embodiment, the invention is a solvate form of Example 19-F isolated from MTBE having a thermo gravimetric analysis (TGA) diagram substantially the same as that shown in shown in FIG. 2.

In a thirtieth embodiment, the invention is a solvate form of Example 19-F isolated from Me-THF.

In a thirty first embodiment, the invention is a solvate form of Example 19-F isolated from Me-THF characterized by a x-ray powder diffraction pattern comprising four or more 2θ values selected from the group consisting of 6.959±0.2°, 8.629±0.2° 11.310±0.2°, 13.387±0.2°, 16.778±0.2°, 17.287±0.2°, 17.865±0.2°, 18.849±0.2°, 19.452±0.2°, 22.353±0.2°, 22.830±0.2° and 26.312±0.2° at a temperature of about 22° C.

In a thirty second embodiment, the invention is a solvate form of Example 19-F isolated from Me-THF characterized by a x-ray powder diffraction pattern comprising five or more 2θ values selected from the group consisting of 6.959±0.2°, 8.629±0.2° 11.310±0.2°, 13.387±0.2°, 16.778±0.2°, 17.287±0.2°, 17.865±0.2°, 18.849±0.2°, 19.452±0.2°, 22.353±0.2°, 22.830±0.2° and 26.312±0.2° at a temperature of about 22° C.

Figure 3:
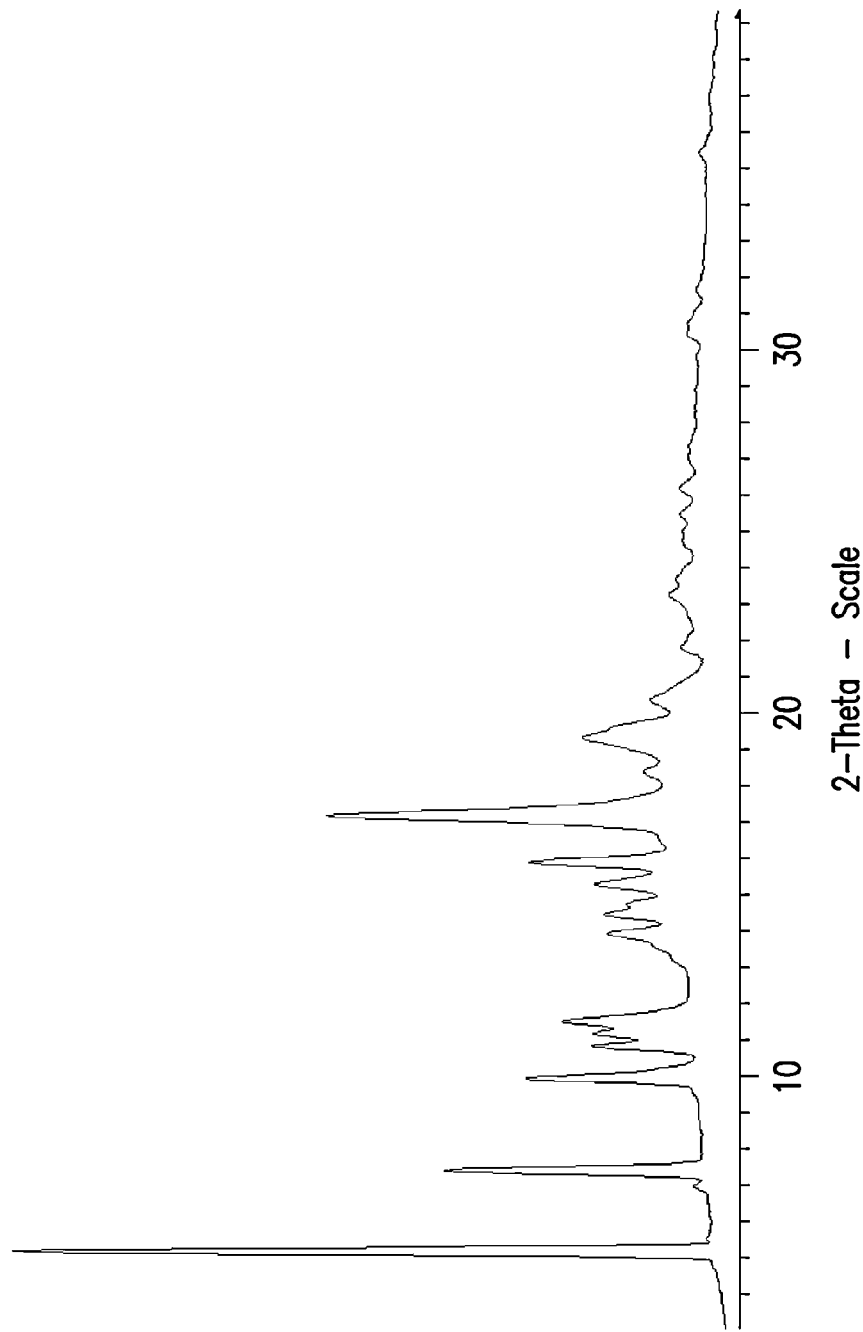
FIG. 3. illustrates the x-ray powder diffraction patterns of Example 19-F from Me-THF.

In a thirty third embodiment, the invention is a solvate form of Example 19-F isolated from Me-THF having a X-ray diffraction spectrum substantially the same as the X-ray powder diffraction spectrum shown in FIG. 3.

Figure 4:
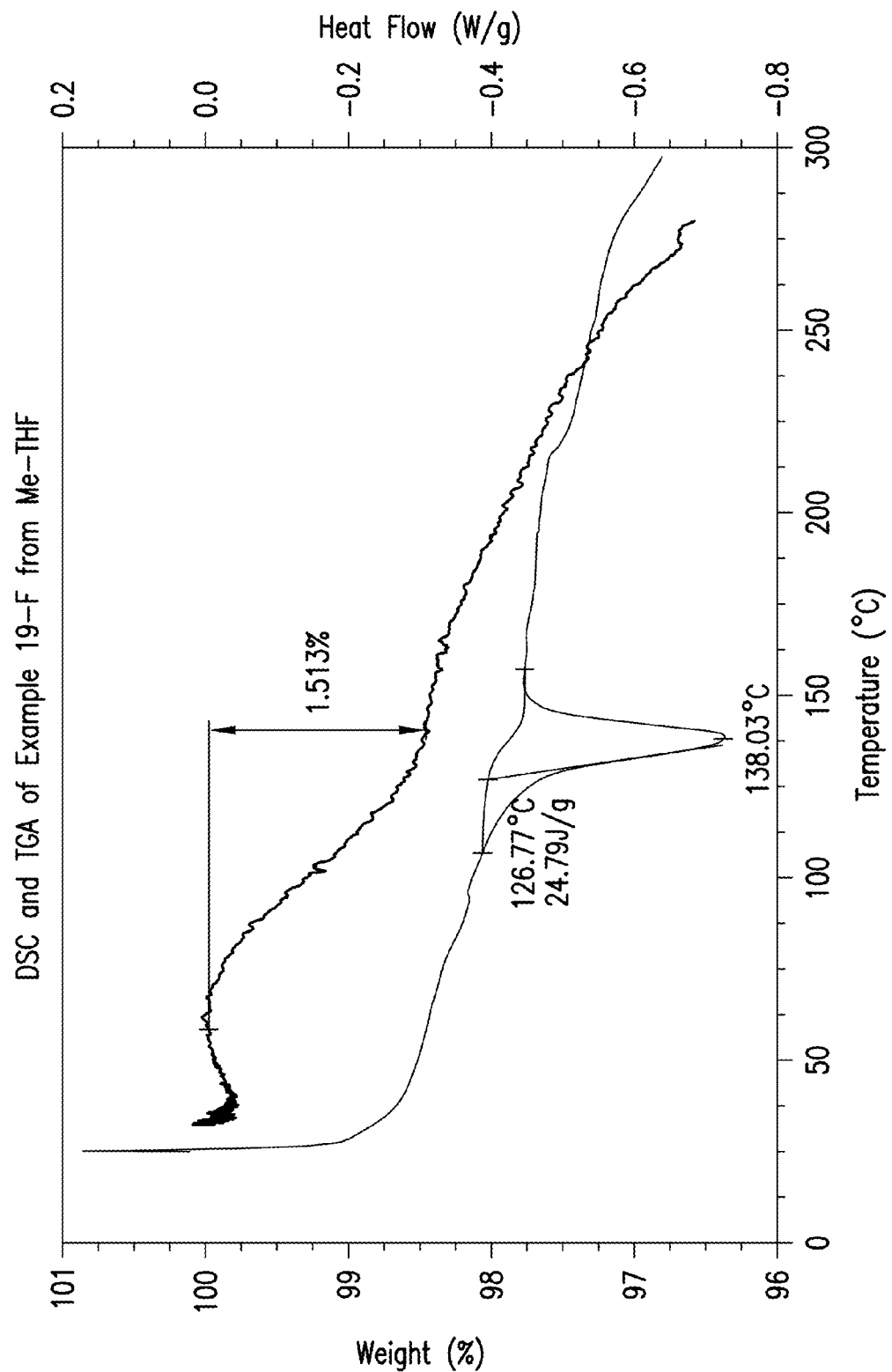
FIG. 4. illustrates the differential scanning calorimetry (DSC) and thermogravimetric analysis (TGA) of Example 19-F from Me-THF.

In a thirty fourth embodiment, the invention is a solvate form of Example 19-F isolated from Me-THF having a differential scanning calorimetry (DSC) thermogram substantially the same as that shown in shown in FIG. 4.

In a thirty fifth embodiment, the invention is a solvate form of Example 19-F isolated from Me-THF having a thermo gravimetric analysis (TGA) diagram substantially the same as that shown in shown in FIG. 4.

In a thirty sixth embodiment, the invention is a solvate form of Example 19-F isolated from Toluene.

In thirty seventh embodiment, the invention is a solvate form of Example 19-F isolated from Toluene characterized by a x-ray powder diffraction pattern comprising four or more 2θ values selected from the group consisting of 7.431±0.2°, 9.970±0.2°, 10.975±0.2°, 11.562±0.2°, 12.209±0.2°, 13.632±0.2° 14.448±0.2°, 15.032±0.2°, 15.865±0.2°, 16.974±0.2°, 17.280±0.2°, 18.829±0.2°, 22.402±0.2° and 23.165±0.2°, at a temperature of about 22° C.

In a thirty eighth embodiment, the invention is a solvate form of Example 19-F isolated from Toluene characterized by a x-ray powder diffraction pattern comprising five or more 2θ values selected from the group consisting of 7.431±0.2°, 9.970±0.2°, 10.975±0.2°, 11.562±0.2°, 12.209±0.2°, 13.632±0.2° 14.448±0.2°, 15.032±0.2°, 15.865±0.2°, 16.974±0.2°, 17.280±0.2°, 18.829±0.2°, 22.402±0.2° and 23.165±0.2°, at a temperature of about 22° C.

Figure 6:
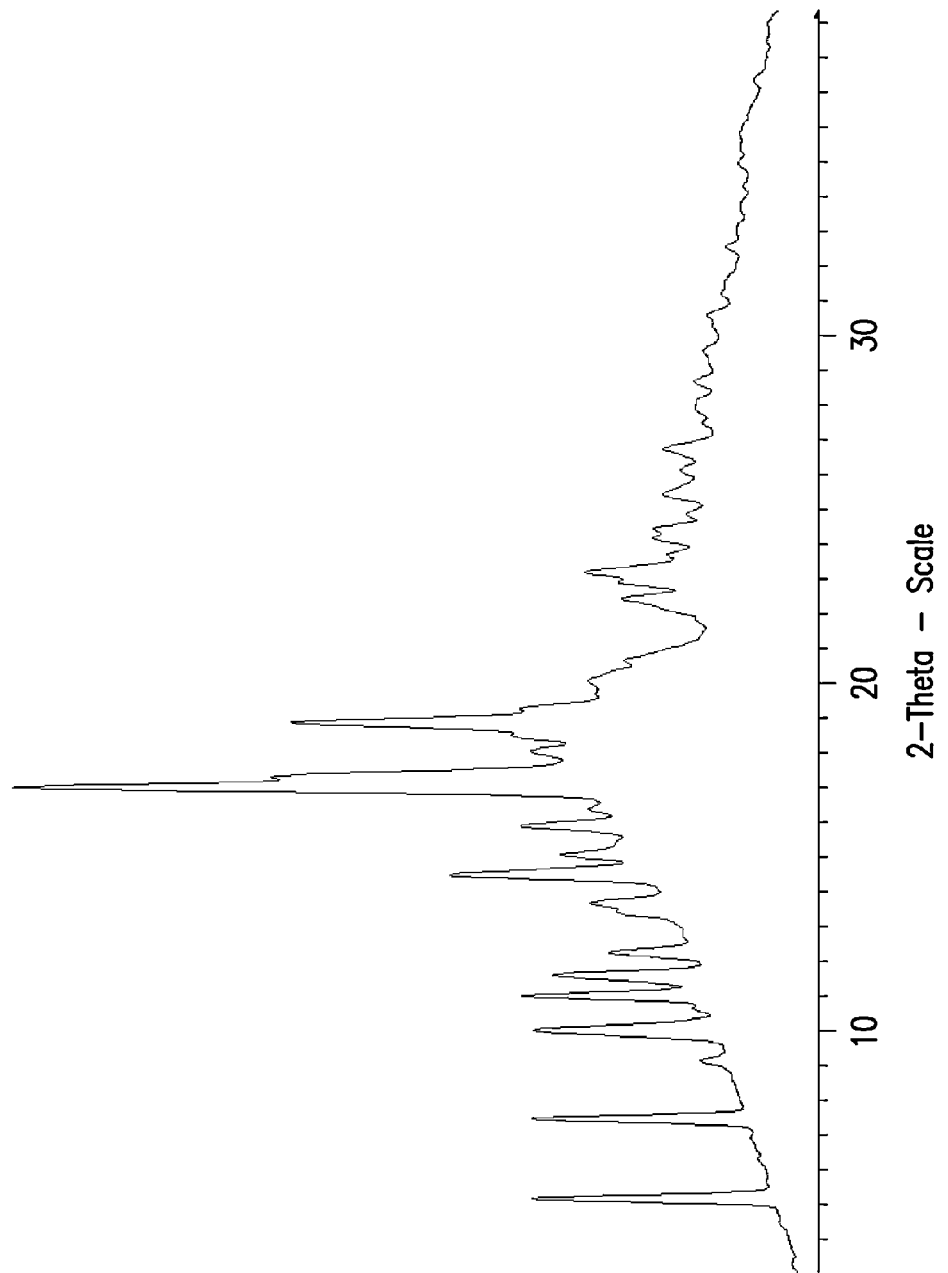
FIG. 6. illustrates the x-ray powder diffraction patterns of Example 19-F from toluene.

In a thirty ninth embodiment, the invention is a solvate form of Example 19-F isolated from Toluene having a X-ray diffraction spectrum substantially the same as the X-ray powder diffraction spectrum shown in FIG. 6.

Figure 7:
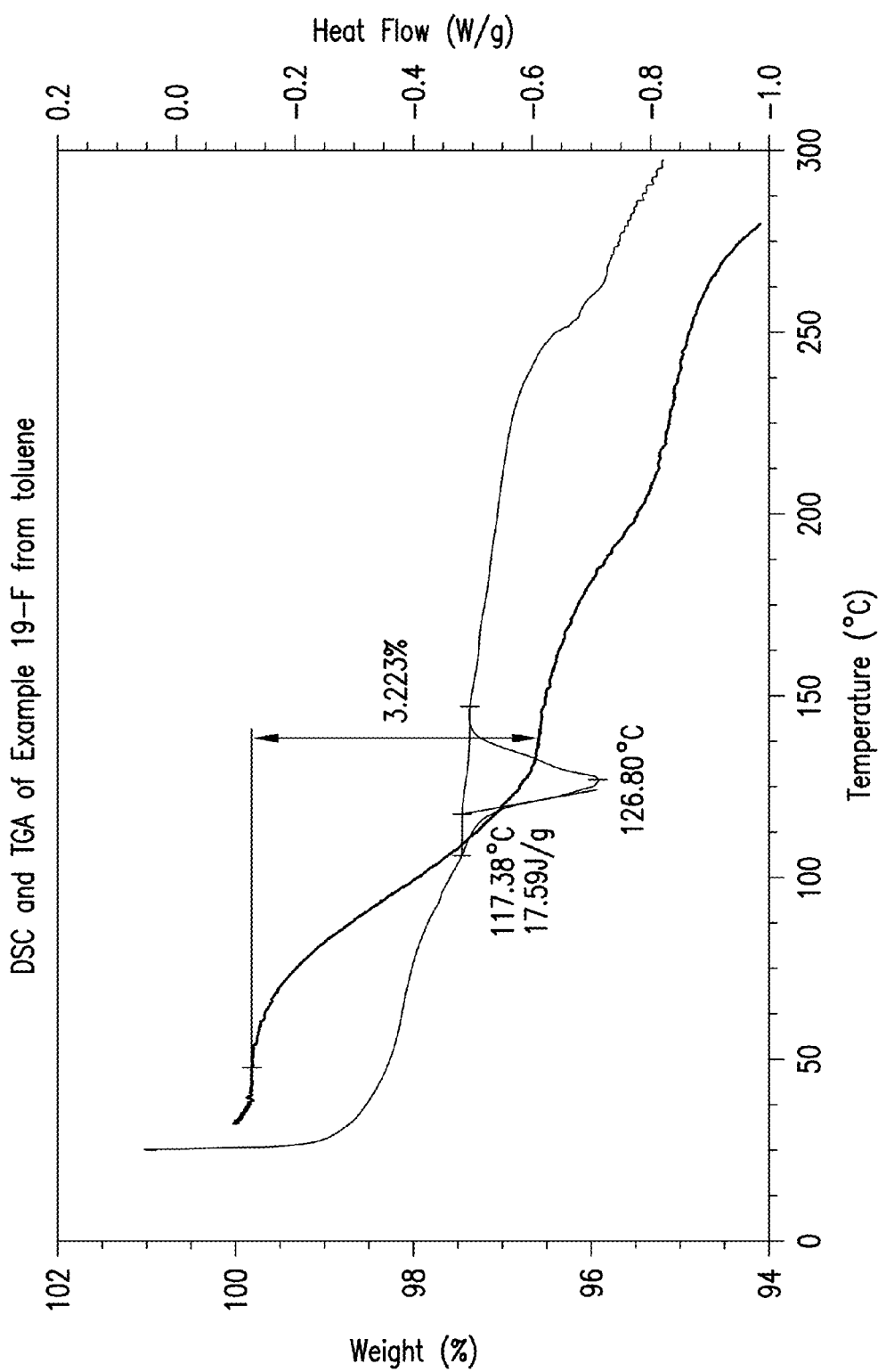
FIG. 7. illustrates the differential scanning calorimetry (DSC) and thermogravimetric analysis (TGA) of Example 19-F from toluene.

In a fortieth embodiment, the invention is a solvate form of Example 19-F isolated from Toluene having a differential scanning calorimetry (DSC) thermogram substantially the same as that shown in shown in FIG. 7.

In a forty first embodiment, the invention is a solvate form of Example 19-F isolated from Toluene having a thermo gravimetric analysis (TGA) diagram substantially the same as that shown in shown in FIG. 7.

Ina forty second embodiment, the invention is a solvate form of Example 19-F isolated from EtOAc.

In a forty third embodiment, the invention is a solvate form of Example 19-F isolated from EtOAc characterized by a x-ray powder diffraction pattern comprising four or more 2θ values selected from the group consisting of 7.430±0.2°, 9.171±0.2°, 10.048±0.2°, 11.070±0.2°, 11.555±0.2°, 12.318±0.2°, 13.778±0.2°, 14.490±0.2°, 15.972±0.2°, 17.394±0.2°, 19.025±0.2° and 23.283±0.2°, at a temperature of about 22° C.

In a forty fourth embodiment, the invention is a solvate form of Example 19-F isolated from EtOAc characterized by a x-ray powder diffraction pattern comprising five or more 2θ values selected from the group consisting of 7.430±0.2°, 9.171±0.2°, 10.048±0.2°, 11.070±0.2°, 11.555±0.2°, 12.318±0.2°, 13.778±0.2°, 14.490±0.2°, 15.972±0.2°, 17.394±0.2°, 19.025±0.2° and 23.283±0.2°, at a temperature of about 22° C.

Figure 8:
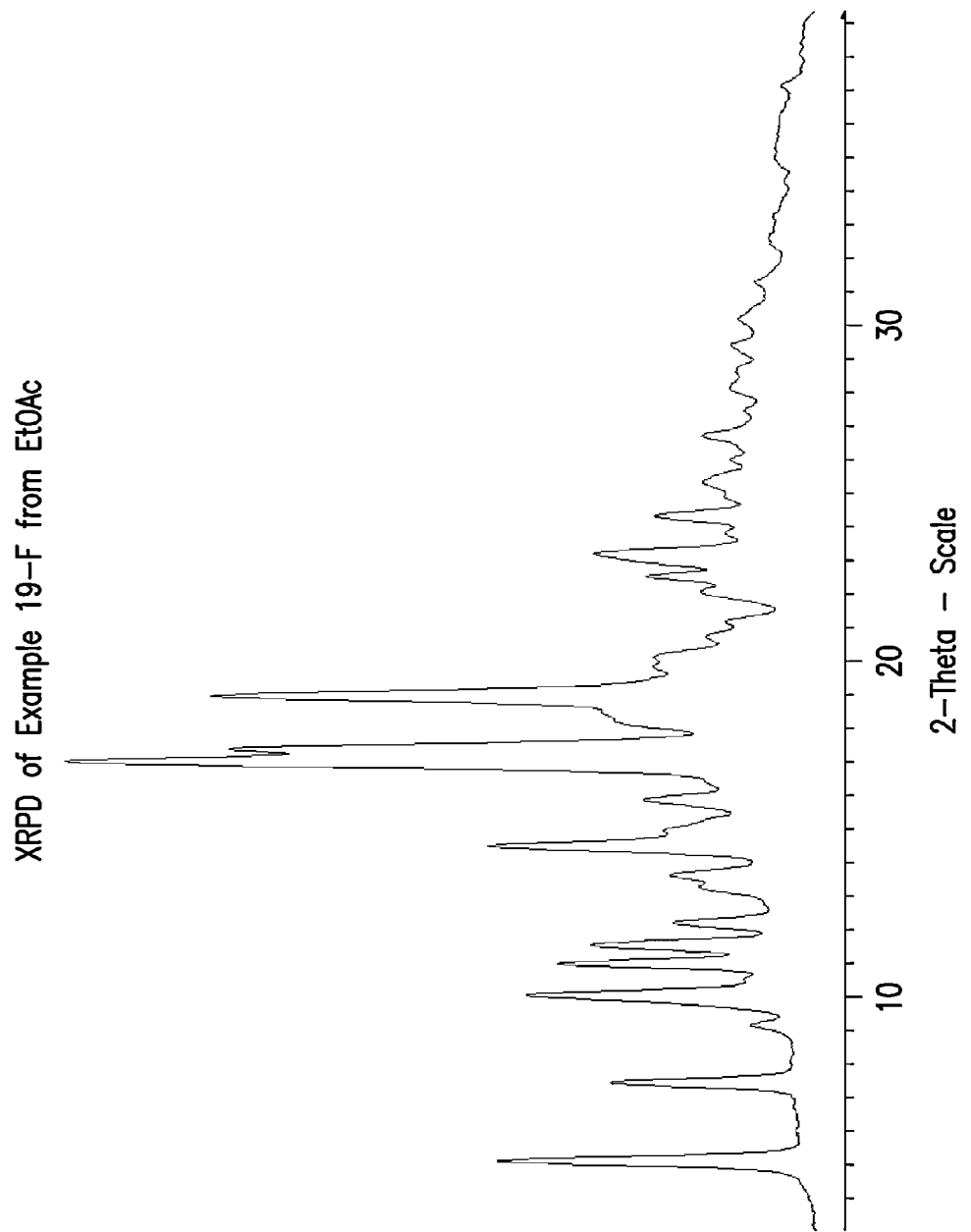
FIG. 8. illustrates the x-ray powder diffraction patterns of Example 19-F from EtOAc.

In a forty fifth embodiment, the invention is a solvate form of Example 19-F isolated from EtOAc having a X-ray diffraction spectrum substantially the same as the X-ray powder diffraction spectrum shown in FIG. 8.

Figure 9:
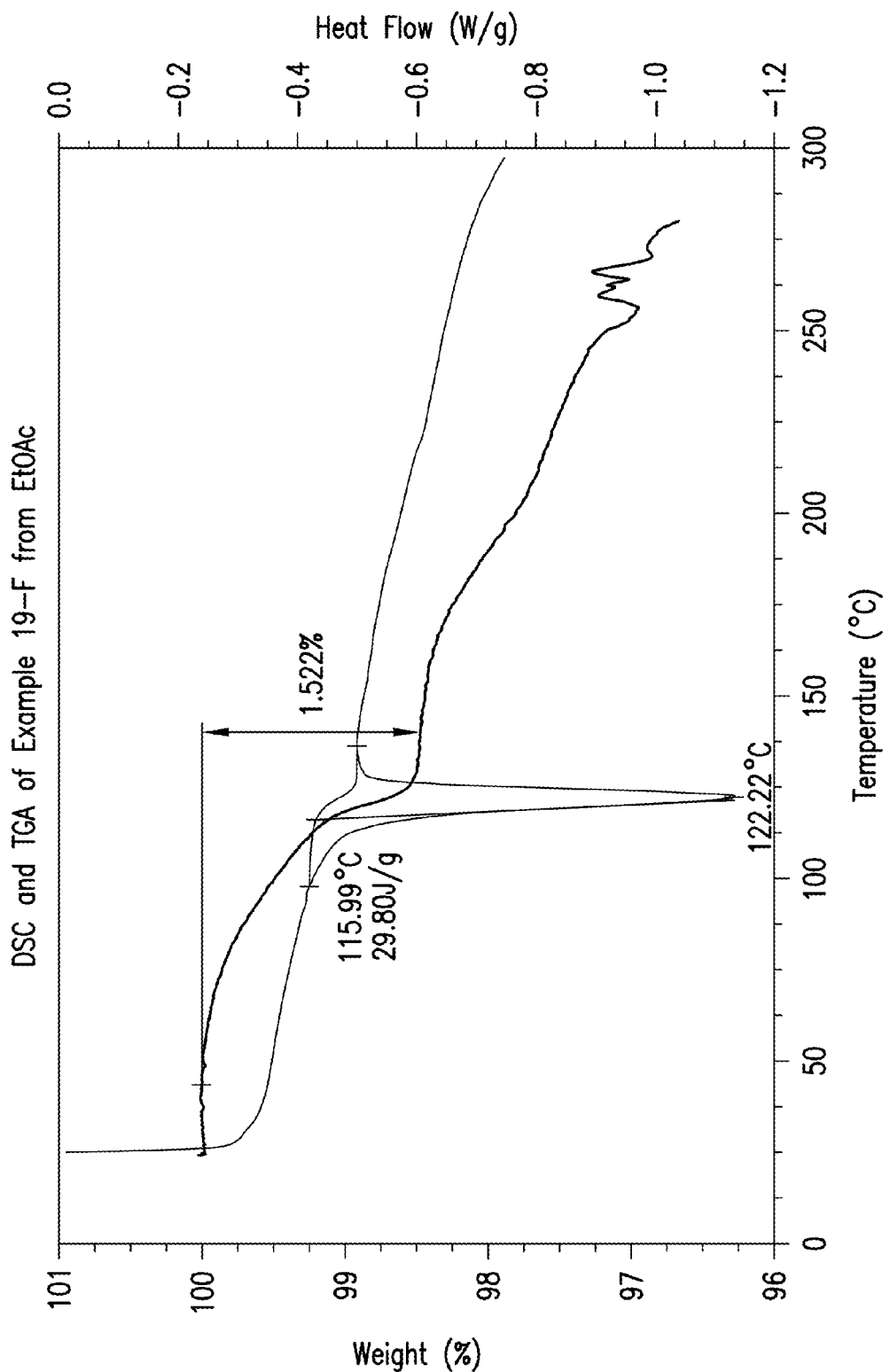
FIG. 9. illustrates the differential scanning calorimetry (DSC) and thermogravimetric analysis (TGA) of Example 19-F from EtOAc.
Figure 10:
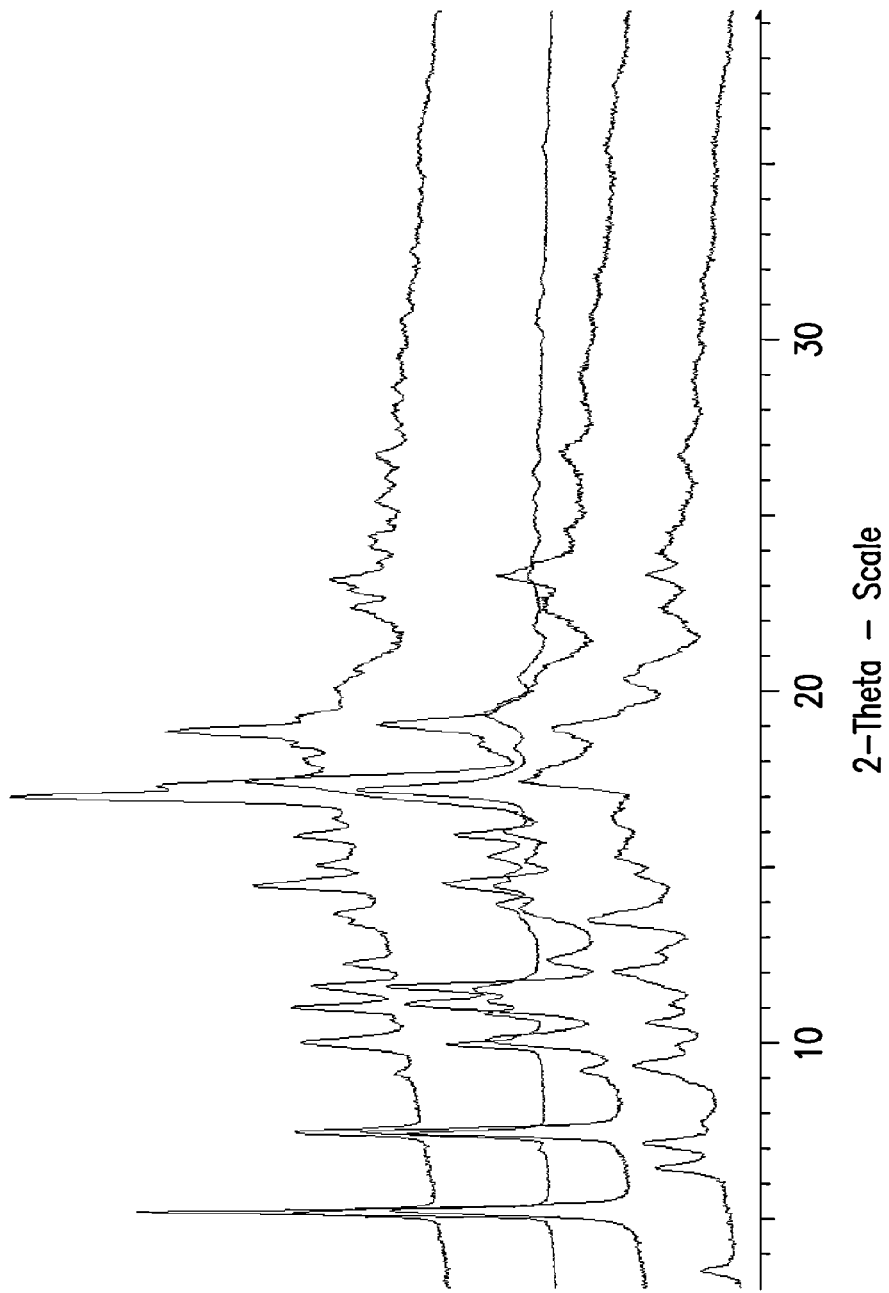
FIG. 10. overlays the x-ray powder diffraction patterns of Example 19-F solid forms.

In a forty sixth embodiment, the invention is a solvate form of Example 19-F isolated from EtOAc having a differential scanning calorimetry (DSC) thermogram substantially the same as that shown in FIG. 9.

In a forty seventh embodiment, the invention is a solvate form of Example 19-F isolated from EtOAc having a thermo gravimetric analysis (TGA) diagram substantially the same as that shown in shown in FIG. 9.

In a forty eighth embodiment, the invention is a crystalline Hydrochloride Form A of Example 19-F.

In a forty ninth embodiment, the invention is a crystalline Hydrochloride Form A of Example 19-F characterized by a x-ray powder diffraction pattern comprising four or more 2θ values selected from the group consisting of 6.928±0.2°, 7.630±0.2°, 9.394±0.2°, 10.875±0.2°, 12.252±0.2°, 14.236±0.2°, 15.378±0.2°, 17.227±0.2°, 18.146±0.2°, 19.187±0.2° and 26.521±0.2°, at a temperature of about 22° C.

In a fiftieth embodiment, the invention is a crystalline Hydrochloride Form A of Example 19-F characterized by a x-ray powder diffraction pattern comprising five or more 2θ values selected from the group consisting of 6.928±0.2°, 7.630±0.2°, 9.394±0.2°, 10.875±0.2°, 12.252±0.2°, 14.236±0.2°, 15.378±0.2°, 17.227±0.2°, 18.146±0.2°, 19.187±0.2° and 26.521±0.2°, at a temperature of about 22° C.

Figure 11:
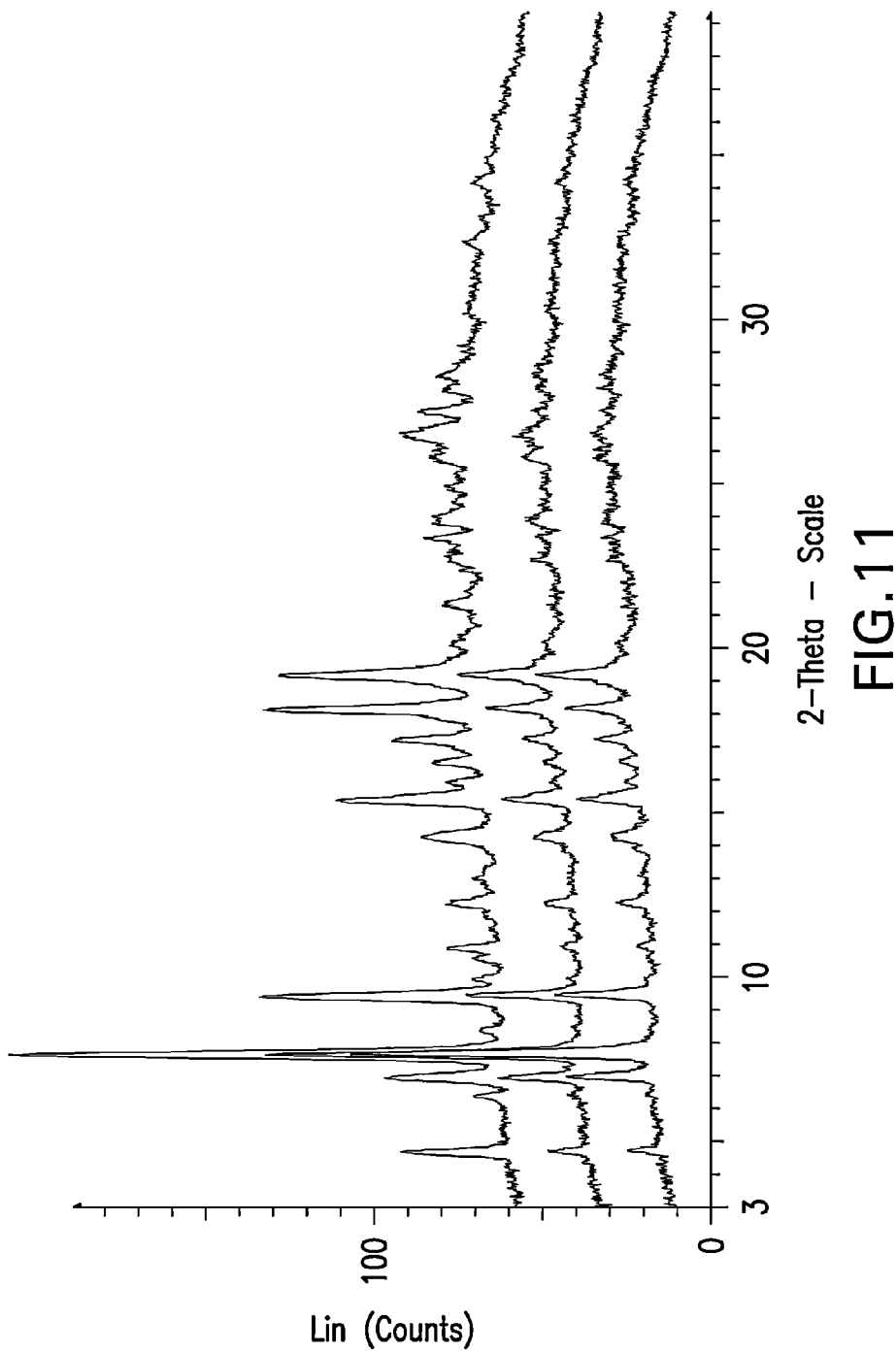
FIG. 11. illustrates the x-ray powder diffraction patterns of Example 19-F Hydrochloride Form A.

In a fifty first embodiment, the invention is a crystalline Hydrochloride Form A of Example 19-F having a X-ray diffraction spectrum substantially the same as the X-ray powder diffraction spectrum shown in FIG. 11.

Figure 13:
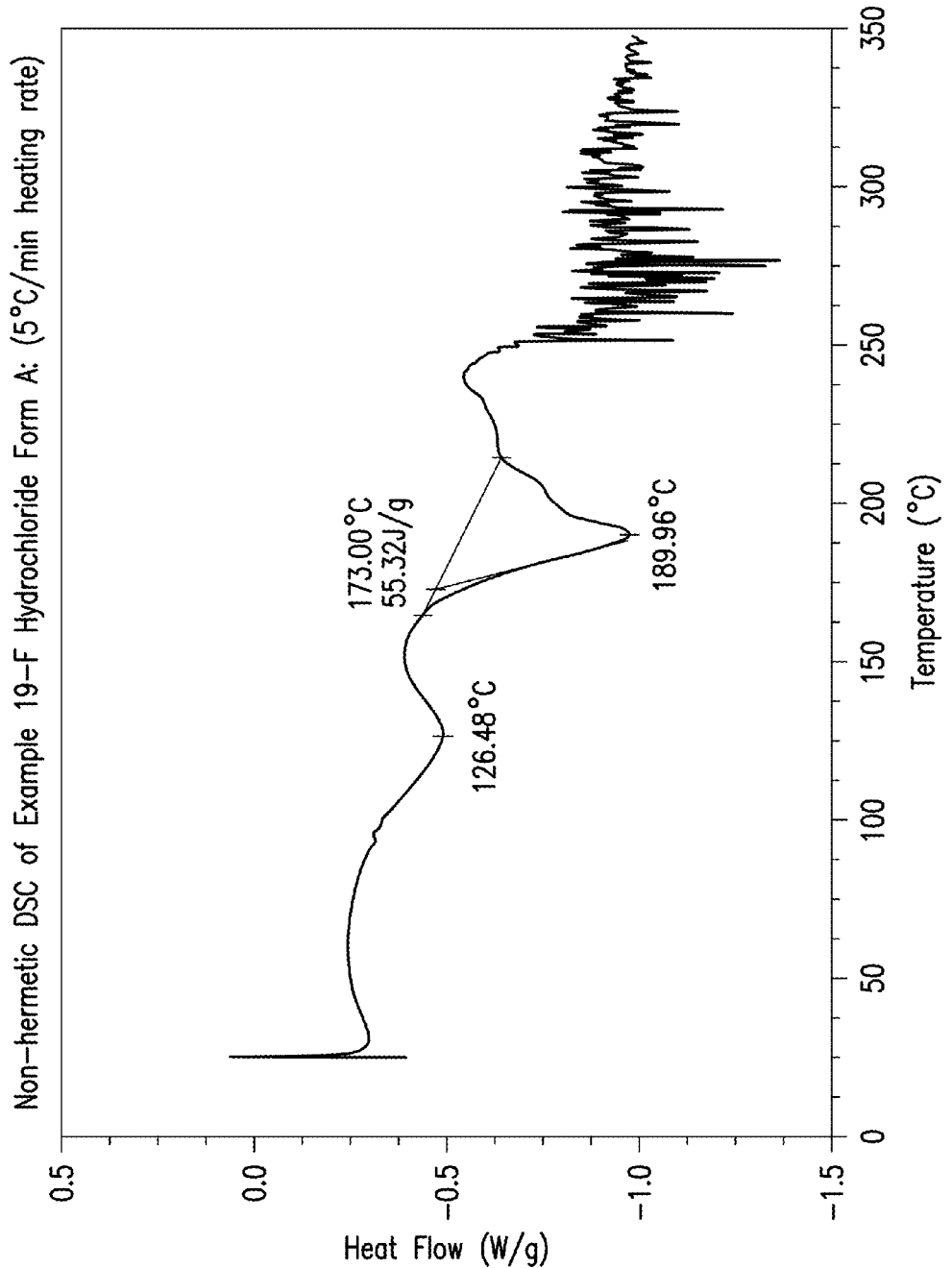
FIG. 13. illustrates the non-hermetic differential scanning calorimetry (DSC) of Example 19-F Hydrochloride Form A: (5° C./min heating rate).
Figure 14:
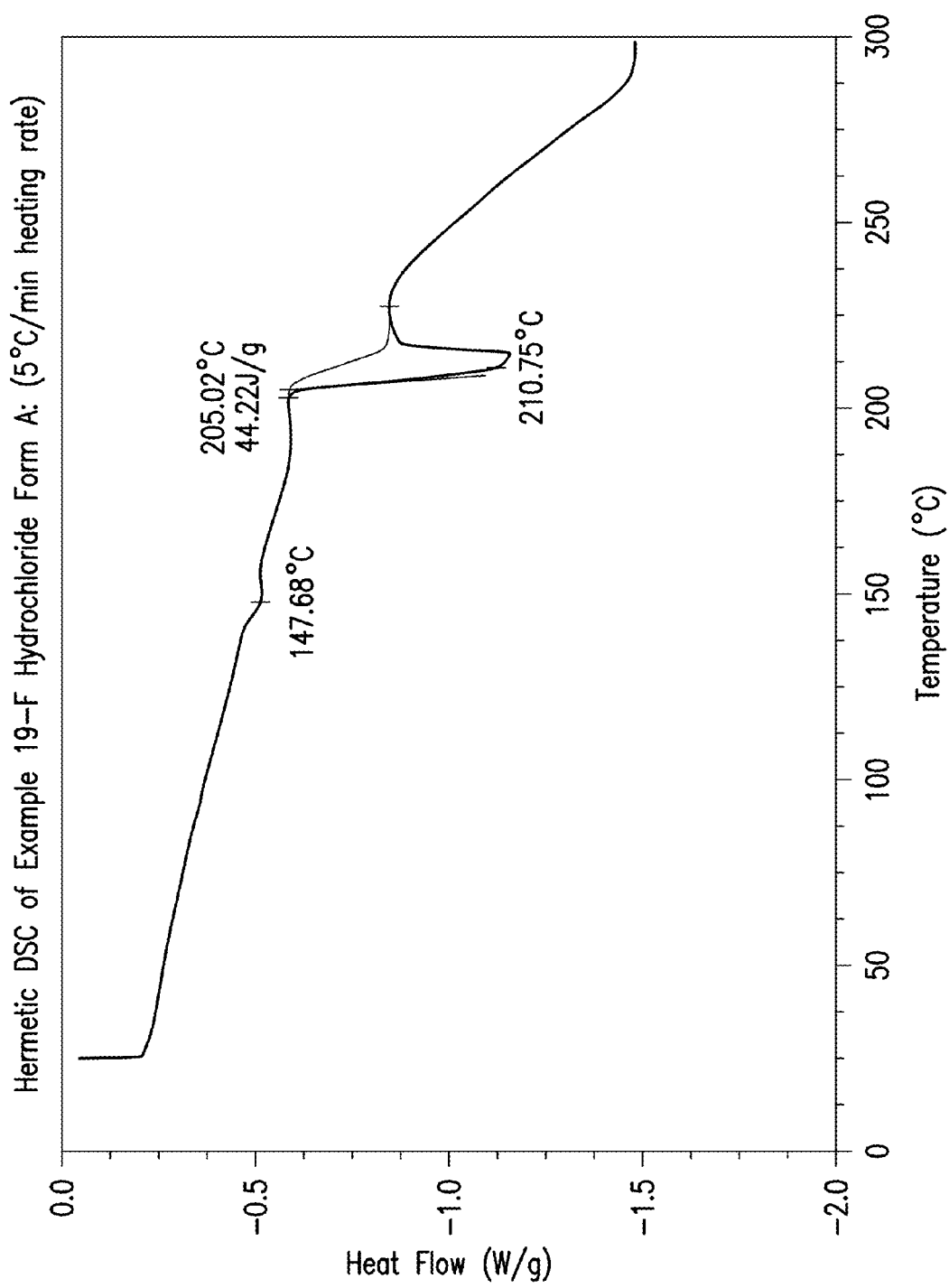
FIG. 14. illustrates the hermetic differential scanning calorimetry (DSC) of Example 19-F Hydrochloride Form A (5° C./min heating rate).

In a fifty second embodiment, the invention is a crystalline Hydrochloride Form A of Example 19-F having a differential scanning calorimetry (DSC) thermogram substantially the same as that shown in shown in FIGS. 13 and 14.

Figure 12:
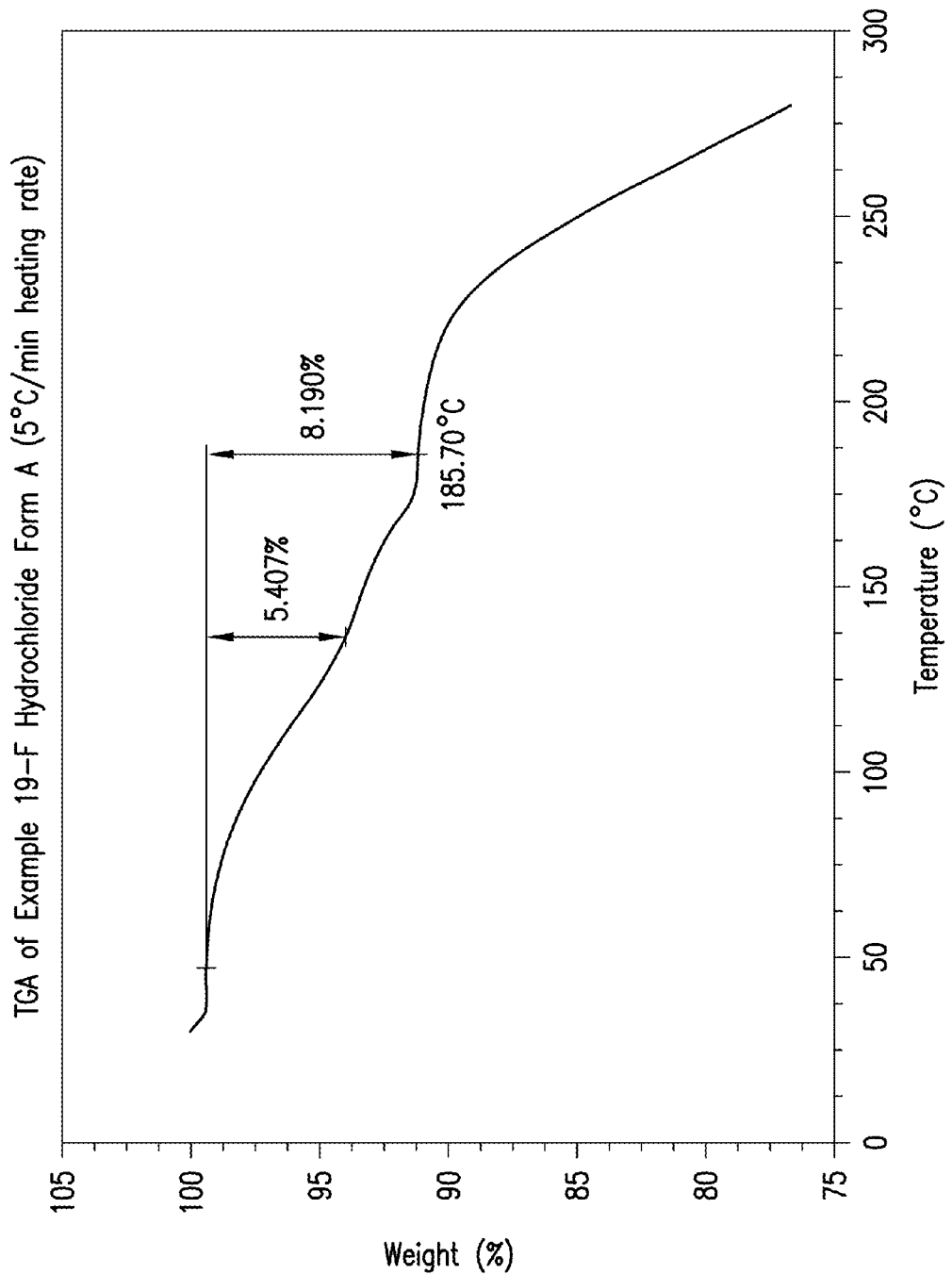
FIG. 12. illustrates the thermogravimetric analysis (TGA) of Example 19-F Hydrochloride Form A (5° C./min heating rate).

In a fifty third embodiment, the invention is a crystalline Hydrochloride Form A of Example 19-F having a thermo gravimetric analysis (TGA) diagram substantially the same as that shown in shown in FIG. 12.

In a fifty fourth embodiment, the invention is a crystalline Hydrochloride Form B of Example 19-F.

In a fifty fifth embodiment, the invention is a crystalline Hydrochloride Form B of Example 19-F characterized by a x-ray powder diffraction pattern comprising four or more 2θ values selected from the group consisting of 7.407±0.2°, 8.041±0.2°, 8.368±0.2°, 9.681±0.2°, 9.983±0.2°, 13.252±0.2°, 15.006±0.2°, 15.554±0.2°, 19.271±0.2° and 20.137±0.2°, at a temperature of about 22° C.

In a fifty sixth embodiment, the invention is a crystalline Hydrochloride Form B of Example 19-F characterized by a x-ray powder diffraction pattern comprising five or more 2θ values selected from the group consisting of 7.407±0.2°, 8.041±0.2°, 8.368±0.2°, 9.681±0.2°, 9.983±0.2°, 13.252±0.2°, 15.006±0.2°, 15.554±0.2°, 19.271±0.2° and 20.137±0.2°, at a temperature of about 22° C.

Figure 15:
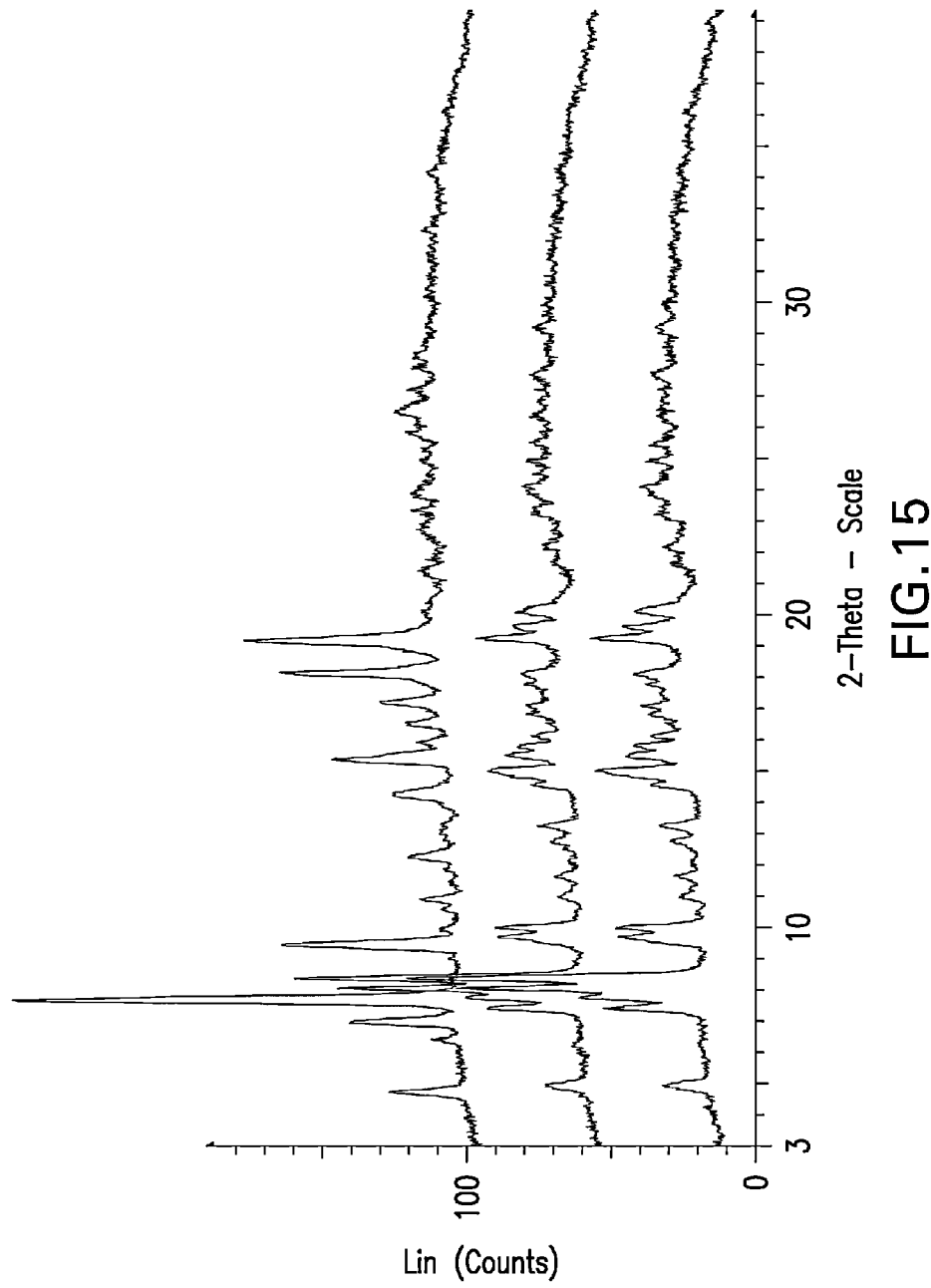
FIG. 15. illustrates the x-ray powder diffraction patterns of two scans of Example 19-F Hydrochloride Form B compared to one scan of Form A.

In fifty seventh embodiment, the invention is a crystalline Hydrochloride Form B of Example 19-F having a X-ray diffraction spectrum substantially the same as the X-ray powder diffraction spectrum shown in FIG. 15.

Figure 17:
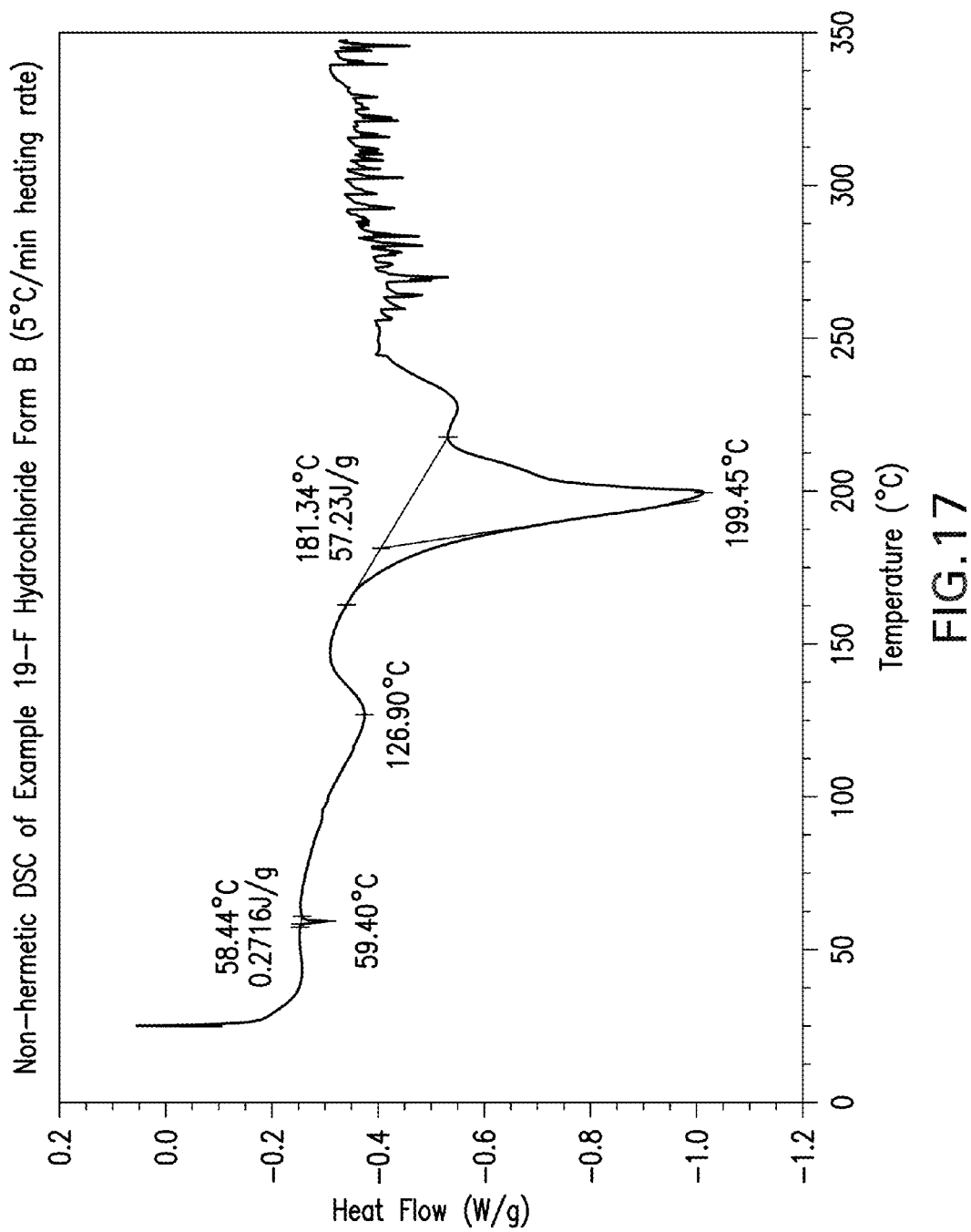
FIG. 17. illustrates the non-hermetic differential scanning calorimetry (DSC) of Example 19-F Hydrochloride Form B (5° C./min heating rate).

In a fifty eighth embodiment, the invention is a crystalline Hydrochloride Form B of Example 19-F having a differential scanning calorimetry (DSC) thermogram substantially the same as that shown in shown in FIG. 17.

Figure 16:
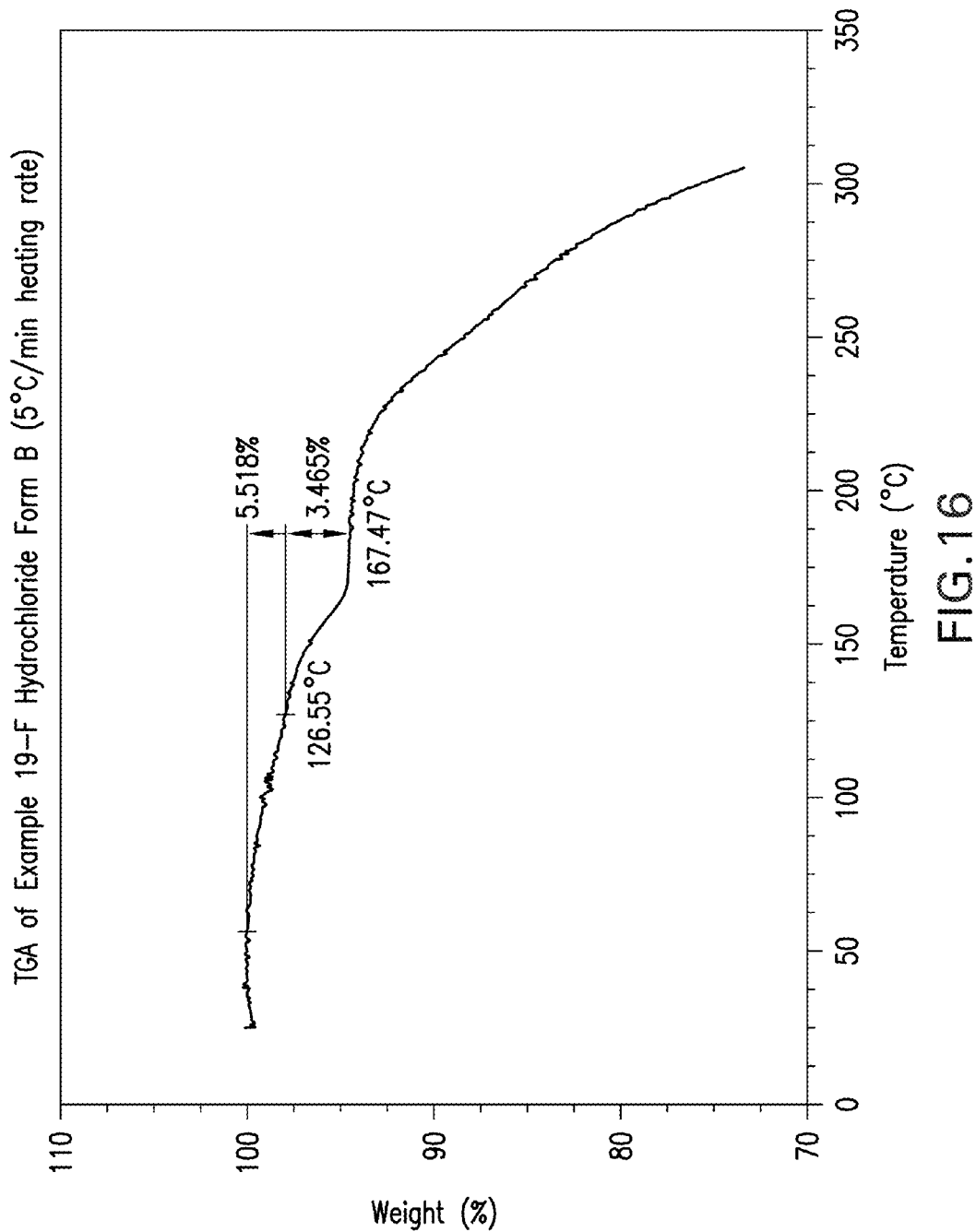
FIG. 16. illustrates the thermogravimetric analysis (TGA) of Example 19-F Hydrochloride Form B (5° C./min heating rate).

In a fifty ninth embodiment, the invention is a crystalline Hydrochloride Form B of Example 19-F having a thermo gravimetric analysis (TGA) diagram substantially the same as that shown in shown in FIG. 16.

In a sixtieth embodiment, the invention is a crystalline Phosphate Form A of Example 19-F.

In a sixty first embodiment, the invention is a crystalline Phosphate Form A of Example 19-F characterized by a x-ray powder diffraction pattern comprising four or more 2θ values selected from the group consisting of 4.730±0.2°, 7.956±0.2°, 9.584±0.2°, 10.644±0.2°, 13.588±0.2°, 14.548±0.2°, 16.287±0.2°, 17.266±0.2°, 11.835±0.2° and 18.948±0.2°, at a temperature of about 22° C.

In a sixty second embodiment, the invention is a crystalline Phosphate Form A of Example 19-F characterized by a x-ray powder diffraction pattern comprising five or more 2θ values selected from the group consisting of 7.956±0.2°, 9.584±0.2°, 10.644±0.2°, 13.588±0.2°, 14.548±0.2°, 16.287±0.2°, 17.266±0.2°, 11.835±0.2° and 18.948±0.2°, at a temperature of about 22° C.

Figure 18:
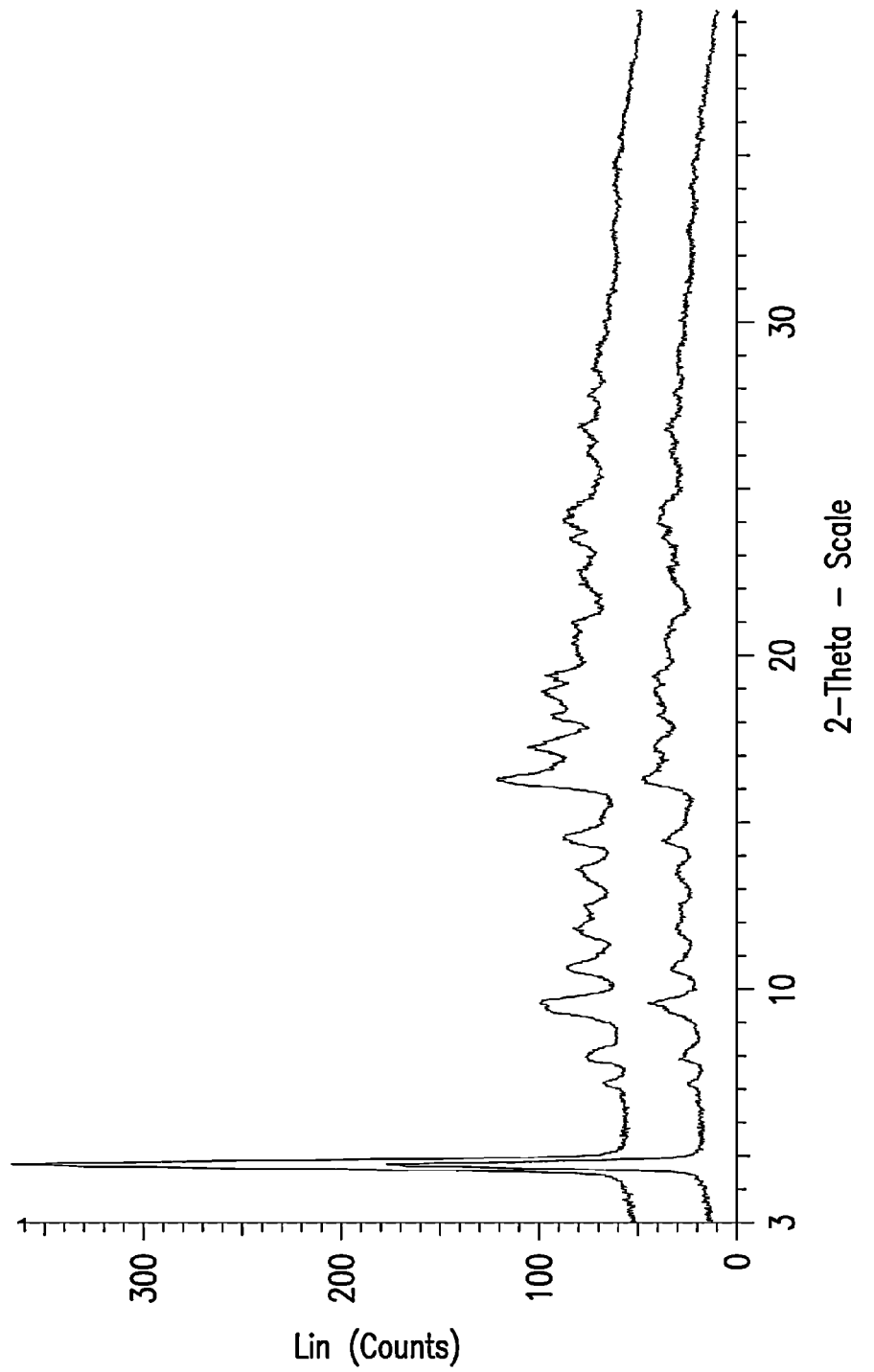
FIG. 18. illustrates the x-ray powder diffraction patterns of Example 19-F Phosphate Form A.

In a sixty third embodiment, the invention is a crystalline Phosphate Form A of Example 19-F having a X-ray diffraction spectrum substantially the same as the X-ray powder diffraction spectrum shown in FIG. 18.

Figure 19:
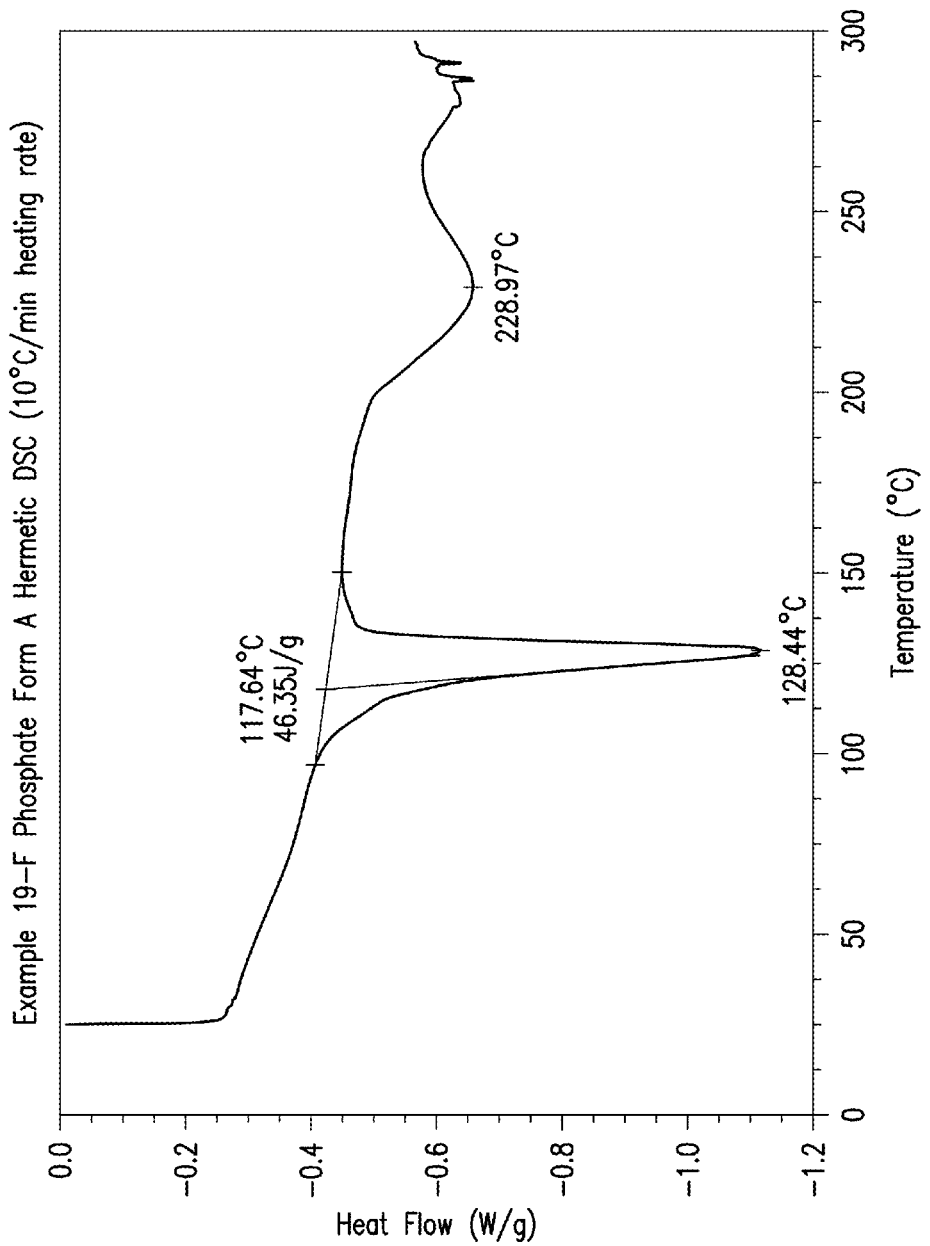
FIG. 19. illustrates the hermetic differential scanning calorimetry (DSC) of Example 19-F Phosphate Form A (10° C./min heating rate).

In a sixty fourth embodiment, the invention is a crystalline Phosphate Form A of Example 19-F having a differential scanning calorimetry (DSC) thermogram substantially the same as that shown in shown in FIG. 19.

In a sixty fifth embodiment, the invention is a crystalline Phosphate Form B of Example 19-F.

In a sixty sixth embodiment, the invention is a crystalline Phosphate Form B of Example 19-F characterized by a x-ray powder diffraction pattern comprising four or more 2θ values selected from the group consisting of 5.873±0.2°, 7.086±0.2°, 7.993±0.2°, 10.188±0.2°, 11.865±0.2°, 13.382±0.2°, 14.434±0.2°, 16.946±0.2°, 18.742±0.2°, 20.709±0.2°, 21.718±0.2° and 22.728±0.2°, at a temperature of about 22° C.

In a sixty seventh embodiment, the invention is a crystalline Phosphate Form B of Example 19-F characterized by a x-ray powder diffraction pattern comprising five or more 2θ values selected from the group consisting of 5.873±0.2°, 7.086±0.2°, 7.993±0.2°, 10.188±0.2°, 11.865±0.2°, 13.382±0.2°, 14.434±0.2°, 16.946±0.2°, 18.742±0.2°, 20.709±0.2°, 21.718±0.2° and 22.728±0.2°, at a temperature of about 22° C.

Figure 20:
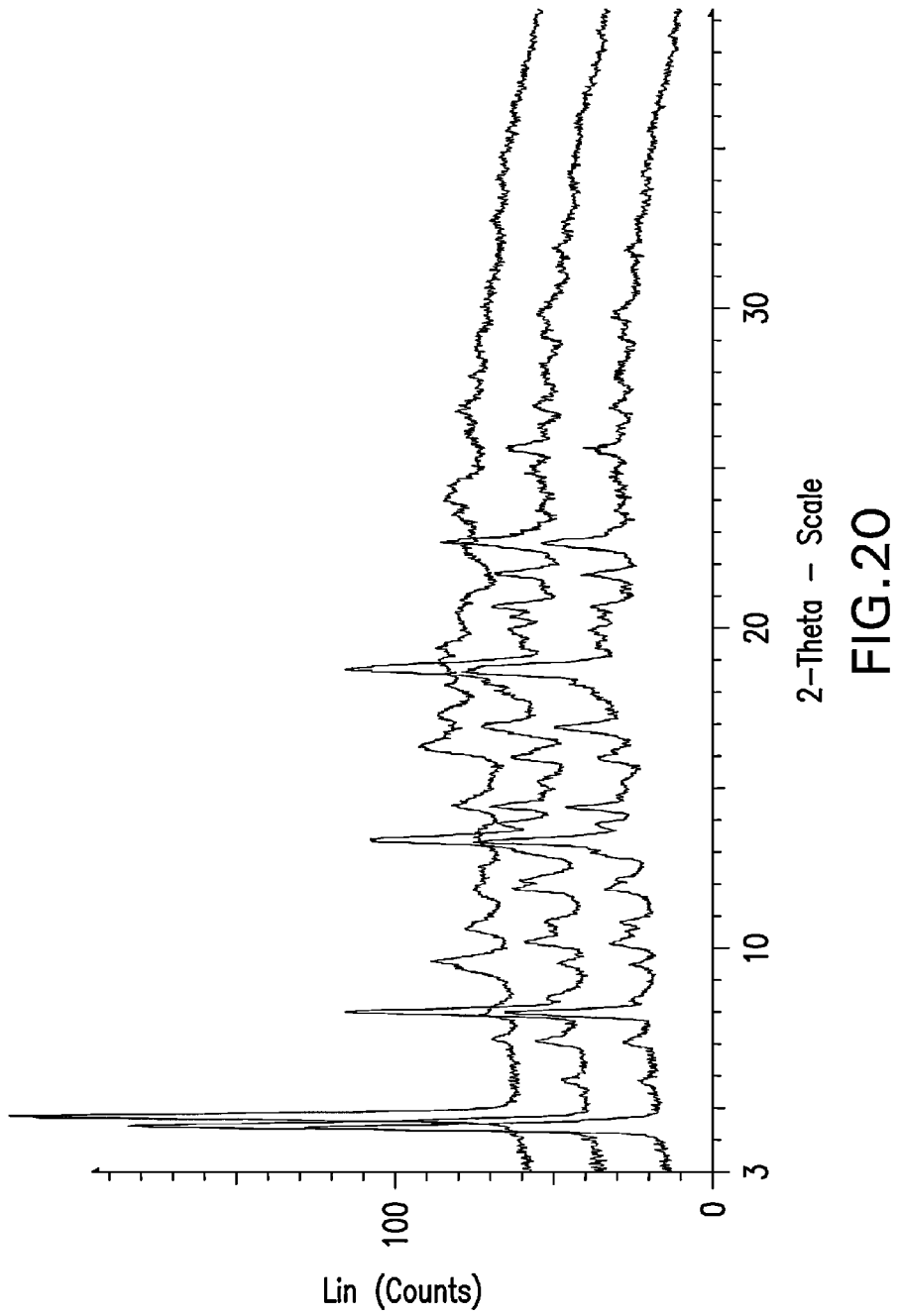
FIG. 20. illustrates the x-ray powder diffraction patterns of Example 19-F Phosphate Form B with Example 19-F Phosphate Form A for comparison.

In a sixty eighth embodiment, the invention is a crystalline Phosphate Form B of Example 19-F having a X-ray diffraction spectrum substantially the same as the X-ray powder diffraction spectrum shown in FIG. 20.

Figure 21:
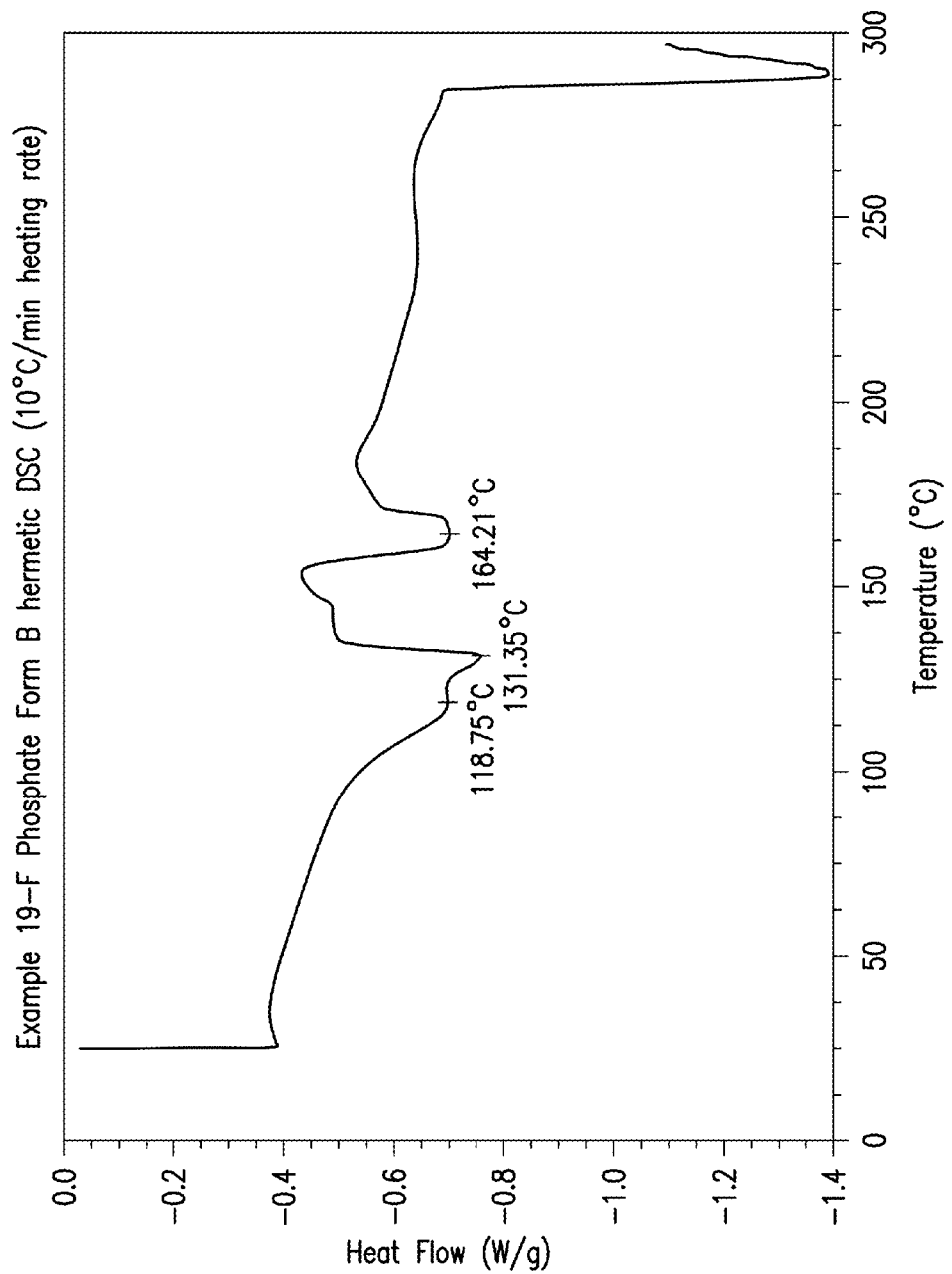
FIG. 21. illustrates the hermetic differential scanning calorimetry (DSC) of Example 19-F Phosphate Form B (10° C./min heating rate).

In a sixty ninth embodiment, the invention is a crystalline Phosphate Form B of Example 19-F having a differential scanning calorimetry (DSC) thermogram substantially the same as that shown in shown in FIG. 21.

In a seventieth embodiment, the invention is a crystalline Phosphate Form C of Example 19-F.

In a seventy first embodiment, the invention is a crystalline Phosphate Form C of Example 19-F characterized by a x-ray powder diffraction pattern comprising four or more 2θ values selected from the group consisting of 7.93±0.2°, 8.65±0.2°, 10.63±0.2°, 12.00±0.2°, 13.85±0.2°, 15.35±0.2°, 16.06±0.2°, 17.65±0.2° and 18.82±0.2°, at a temperature of about 22° C.

In a seventy second embodiment, the invention is a crystalline Phosphate Form C of Example 19-F characterized by a x-ray powder diffraction pattern comprising five or more 2θ values selected from the group consisting of 4.50±0.2°, 7.93±0.2°, 8.65±0.2°, 10.63±0.2°, 12.00±0.2°, 13.85±0.2°, 15.35±0.2°, 16.06±0.2°, 17.65±0.2° and 18.82±0.2°, at a temperature of about 22° C.

Figure 22:
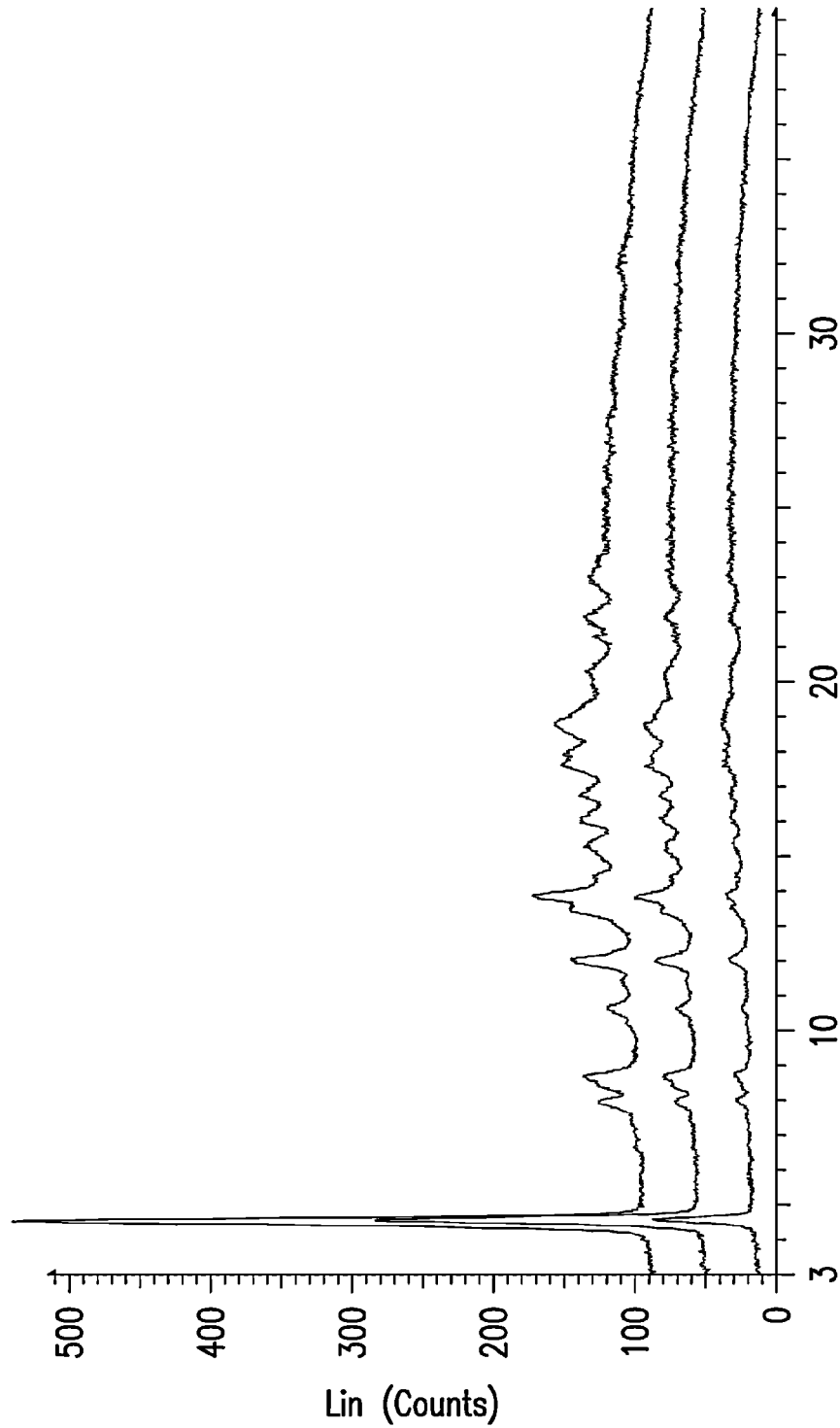
FIG. 22. illustrates the x-ray powder diffraction patterns of Example 19-F Phosphate Form C.

In a seventy third embodiment, the invention is a crystalline Phosphate Form C of Example 19-F having a X-ray diffraction spectrum substantially the same as the X-ray powder diffraction spectrum shown in FIG. 22.

Figure 23:
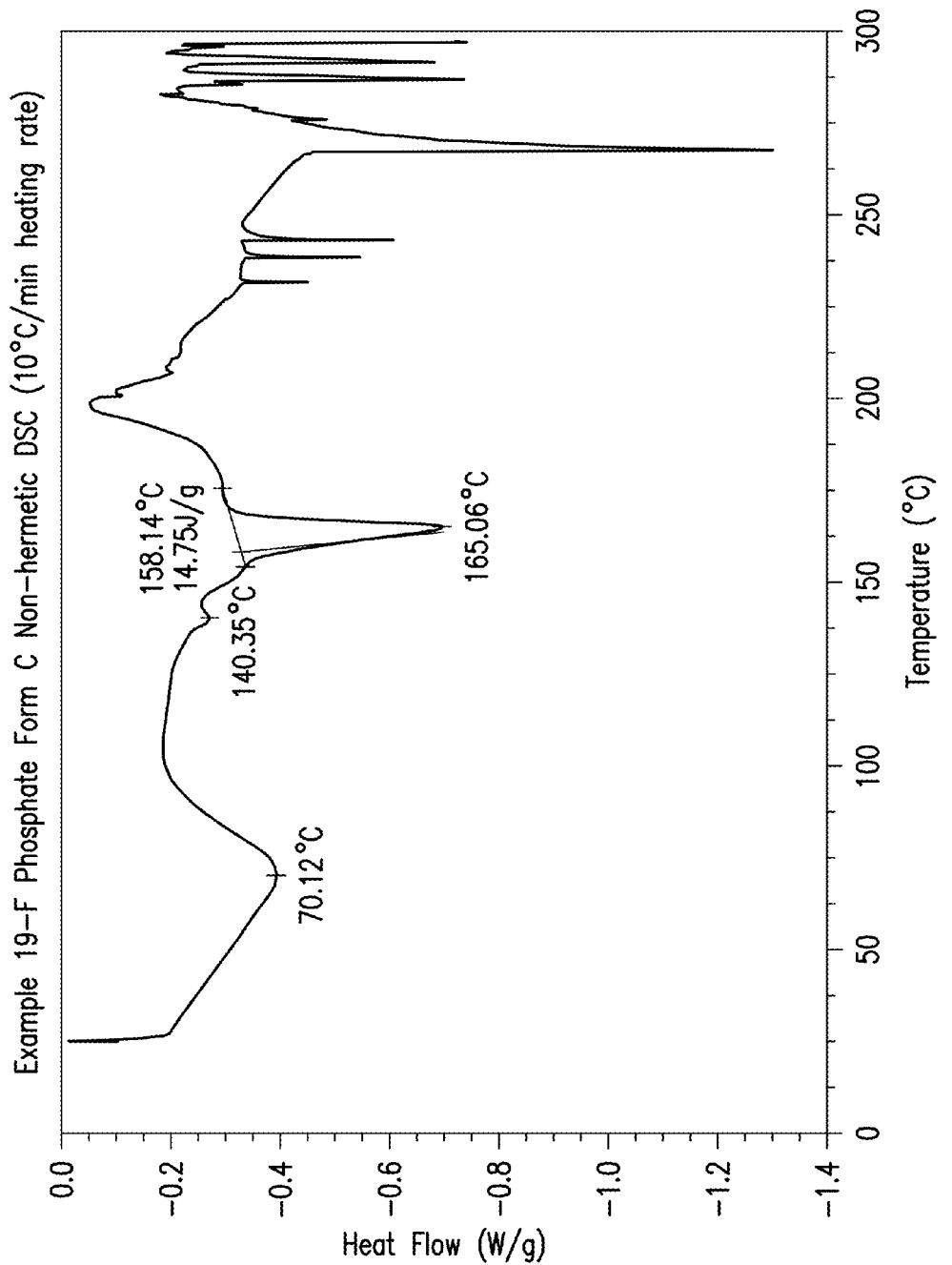
FIG. 23. illustrates the non-hermetic differential scanning calorimetry (DSC) of Example 19-F Phosphate Form C (10° C./min heating rate).

In a seventy fourth embodiment, the invention is a crystalline Phosphate Form C of Example 19-F having a differential scanning calorimetry (DSC) thermogram substantially the same as that shown in shown in FIG. 23.

Figure 24:
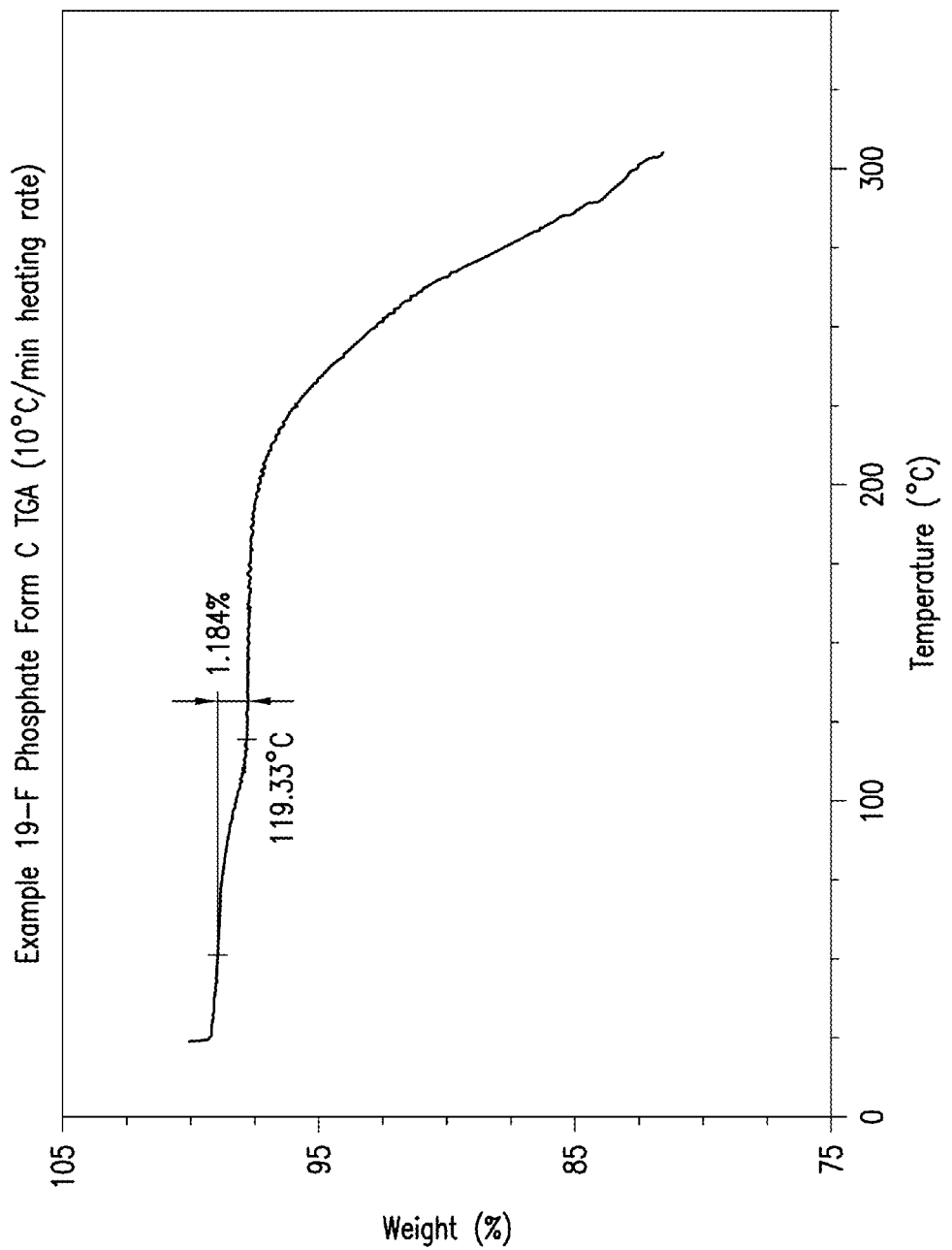
FIG. 24. illustrates the thermogravimetric analysis (TGA) of Example 19-F Phosphate Form C (10° C./min heating rate).

In a seventy fifth embodiment, the invention is a crystalline Hydrochloride Form C of Example 19-F having a thermo gravimetric analysis (TGA) diagram substantially the same as that shown in shown in FIG. 24.

In a seventy sixth embodiment, the invention is a solvate form of Example 55-G isolated from EtOAc in Heptane.

In a seventy seventh embodiment, the invention is a solvate form of Example 55-G isolated from EtOAc in Heptane characterized by a x-ray powder diffraction pattern comprising four or more 2θ values selected from the group consisting of 7.752±0.2°, 8.750±0.2°, 10.211±0.2°, 10.909±0.2°, 11.635±0.2°, 12.485±0.2°, 12.972±0.2°, 14.159±0.2°, 14.831±0.2°, 15.714±0.2°, 16.227±0.2°, 17.249±0.2°, 17.899±0.2°, 18.411±0.2°, 19.351±0.2°, 20.094±0.2°, 22.443±0.2°, 23.089±0.2°, 23.813±0.2°, 24.303±0.2°, 25.326±0.2°, 25.809±0.2°, 27.193±0.2°, 27.973 and 28.863±0.2°, at a temperature of about 22° C.

In a seventy eighth embodiment, the invention is a solvate form of Example 55-G isolated from EtOAc in Heptane characterized by a x-ray powder diffraction pattern comprising five or more 2θ values selected from the group consisting of 7.752±0.2°, 8.750±0.2°, 10.211±0.2°, 10.909±0.2°, 11.635±0.2°, 12.485±0.2°, 12.972±0.2°, 14.159±0.2°, 14.831±0.2°, 15.714±0.2°, 16.227±0.2°, 17.249±0.2°, 17.899±0.2°, 18.411±0.2°, 19.351±0.2°, 20.094±0.2°, 22.443±0.2°, 23.089±0.2°, 23.813±0.2°, 24.303±0.2°, 25.326±0.2°, 25.809±0.2°, 27.193±0.2°, 27.973 and 28.863±0.2°, at a temperature of about 22° C.

Figure 26:
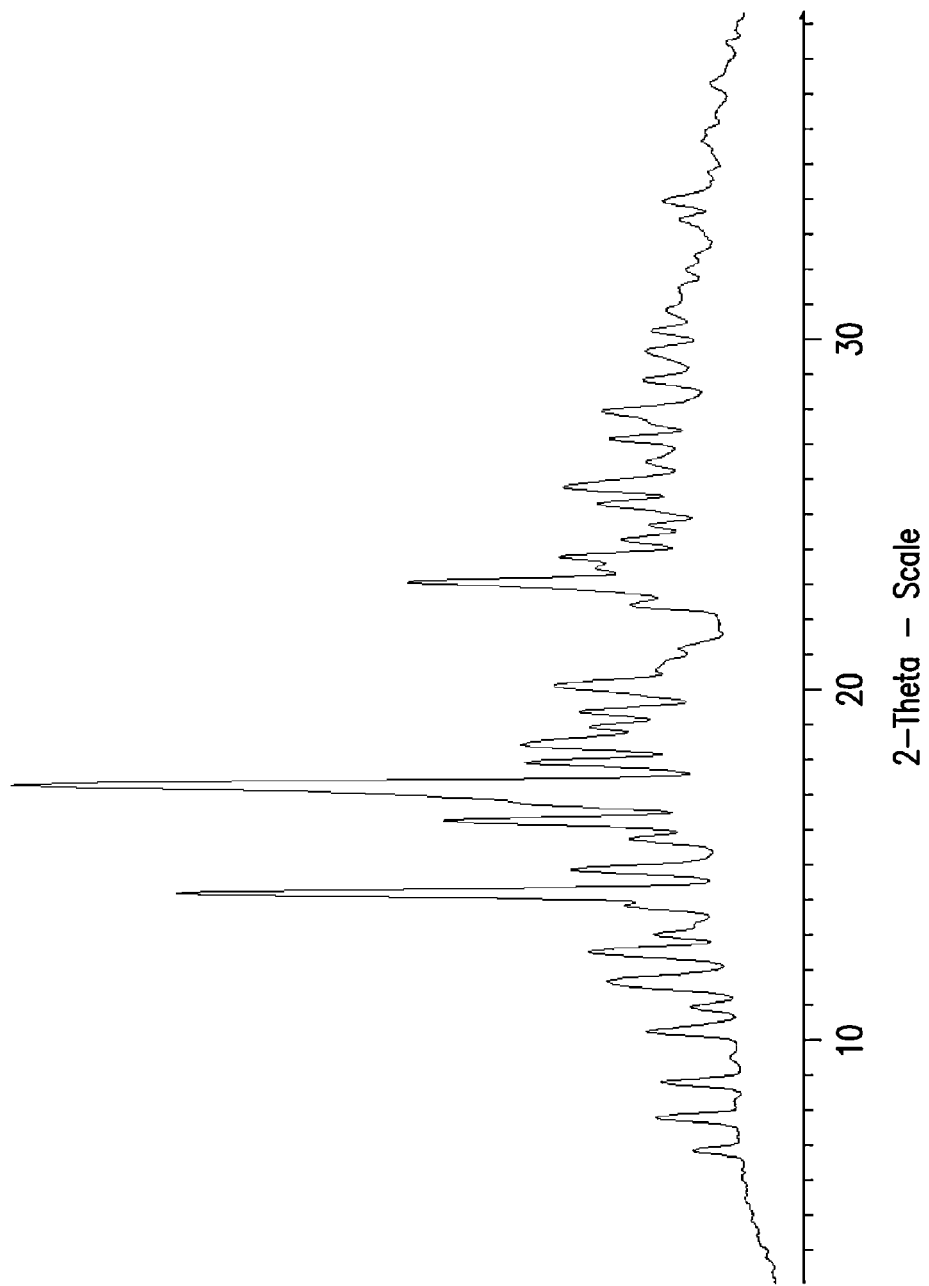
FIG. 26. illustrates the x-ray powder diffraction patterns of Example 55-G from 10% EtOAc in heptane.

In a seventy ninth embodiment, the invention is a solvate form of Example 55-G isolated from EtOAc in Heptane having a X-ray diffraction spectrum substantially the same as the X-ray powder diffraction spectrum shown in FIG. 26.

Figure 27:
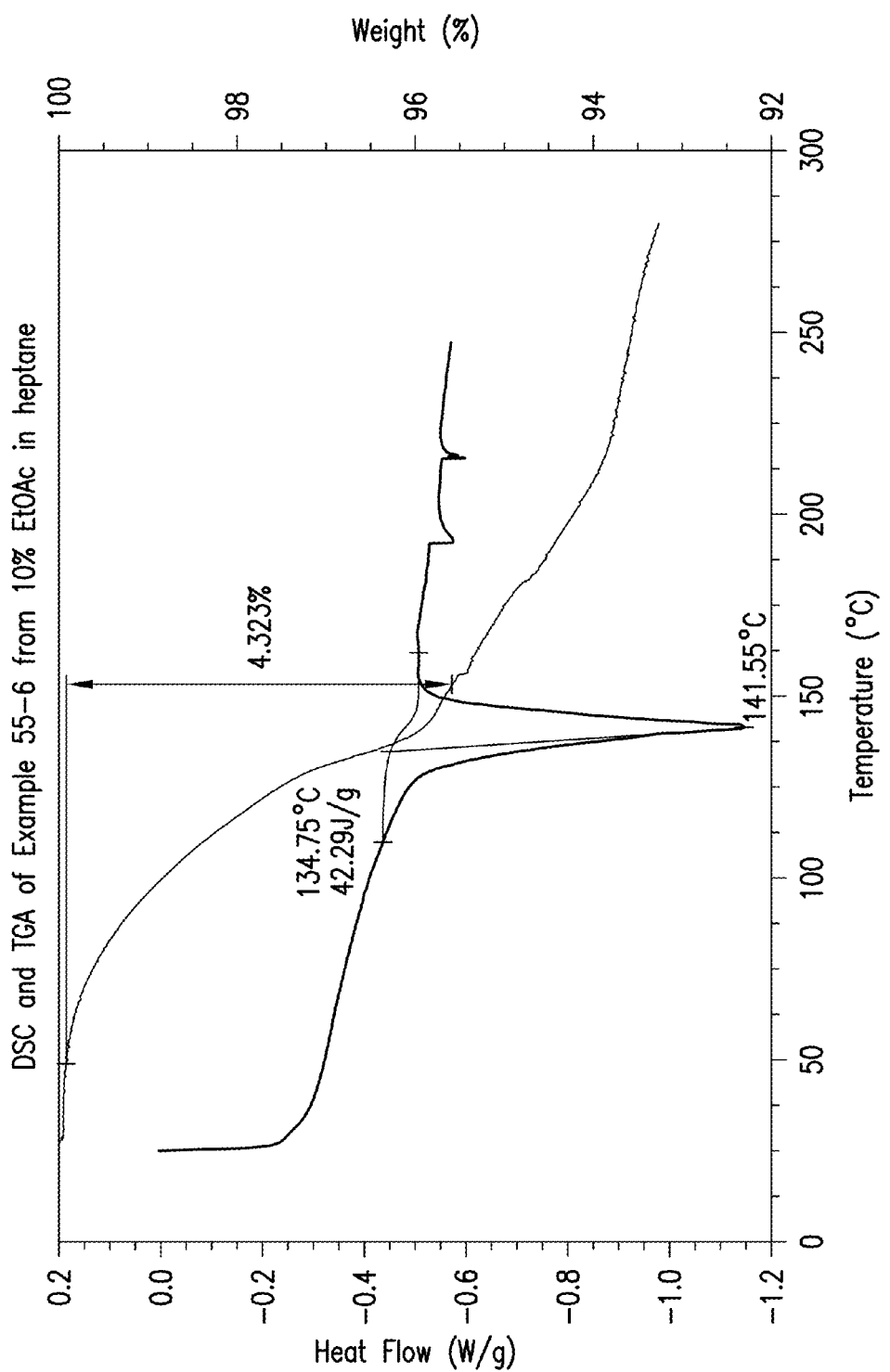
FIG. 27. illustrates the differential scanning calorimetry (DSC) and thermogravimetric analysis (TGA) of Example 55-G from 10% EtOAc in heptane.

In an eightieth embodiment, the invention is a solvate form of Example 55-G isolated from EtOAc in Heptane having a differential scanning calorimetry (DSC) thermogram substantially the same as that shown in shown in FIG. 27.

In an eighty first embodiment, the invention is a solvate form of Example 55-G isolated from EtOAc in Heptane having a thermo gravimetric analysis (TGA) diagram substantially the same as that shown in shown in FIG. 27.

In an eighty second embodiment, the invention is a tri-hydrate form of Example 55-G isolated from 50% MeOH in Water.

In an eighty third embodiment, the invention is a tri-hydrate form of Example 55-G isolated from 50% MeOH in Water characterized by a x-ray powder diffraction pattern comprising four or more 2θ values selected from the group consisting of 8.161±0.2°, 9.746±0.2°, 12.689±0.2°, 13.109±0.2°, 13.910±0.2°, 14.544±0.2°, 16.441±0.2°, 16.999±0.2°, 17.517±0.2°, 19.318±0.2°, 21.222±0.2°, 22.710±0.2°, 23.065±0.2°, 24.253±0.2°, 25.351±0.2° and 27.787±0.2°, at a temperature of about 22° C.

In an eighty fourth embodiment, the invention is a tri-hydrate form of Example 55-G isolated from 50% MeOH in Water characterized by a x-ray powder diffraction pattern comprising five or more 2θ values selected from the group consisting of 6.602±0.2°, 8.161±0.2°, 9.746±0.2°, 12.689±0.2°, 13.109±0.2°, 13.910±0.2°, 14.544±0.2°, 16.441±0.2°, 16.999±0.2°, 17.517±0.2°, 19.318±0.2°, 21.222±0.2°, 22.710±0.2°, 23.065±0.2°, 24.253±0.2°, 25.351±0.2° and 27.787±0.2°, at a temperature of about 22° C.

Figure 28:
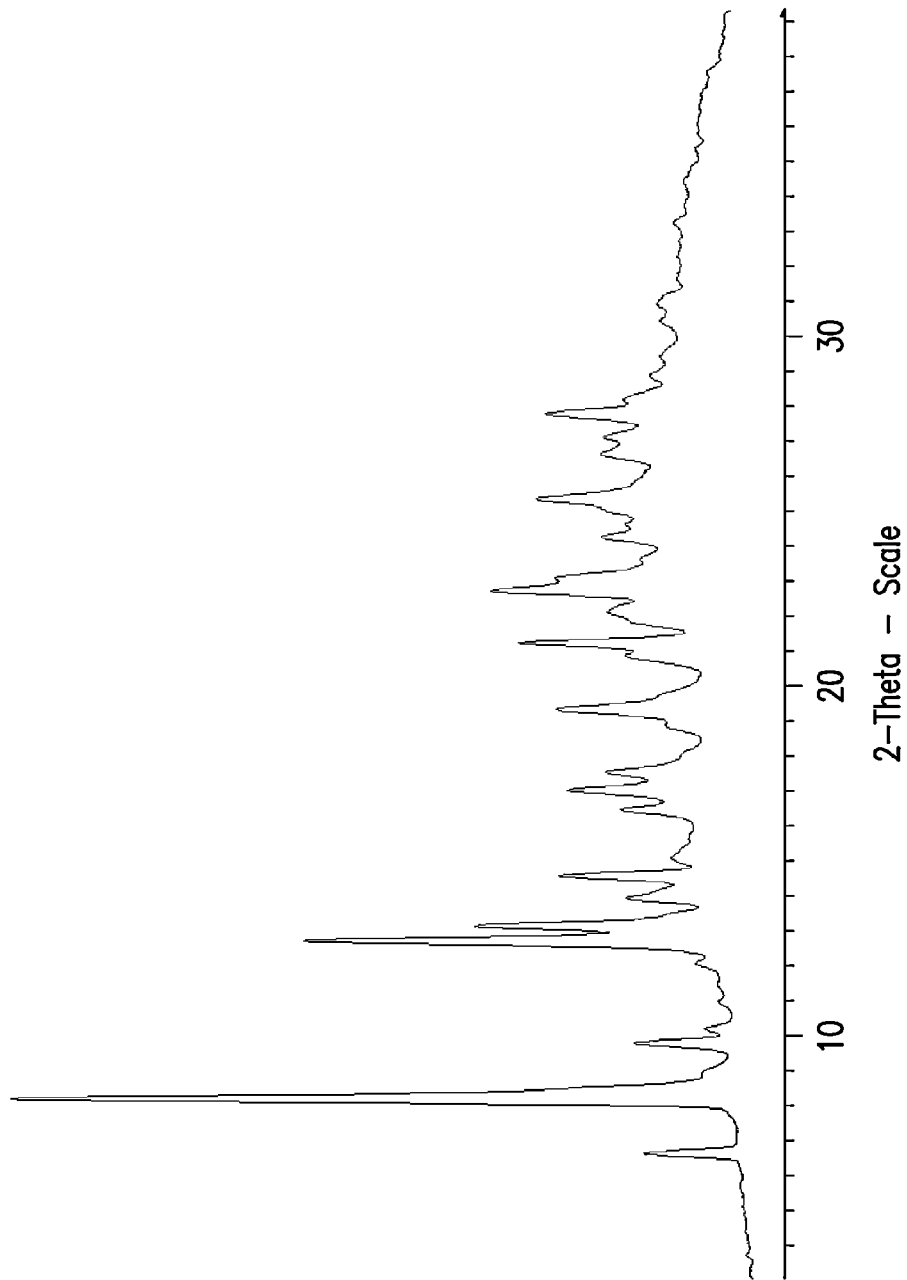
FIG. 28. illustrates the x-ray powder diffraction patterns of Example 55-G from 50% MeOH in water.

In an eighty fifth embodiment, the invention is a tri-hydrate form of Example 55-G isolated from 50% MeOH in Water having a X-ray diffraction spectrum substantially the same as the X-ray powder diffraction spectrum shown in FIG. 28.

Figure 29:
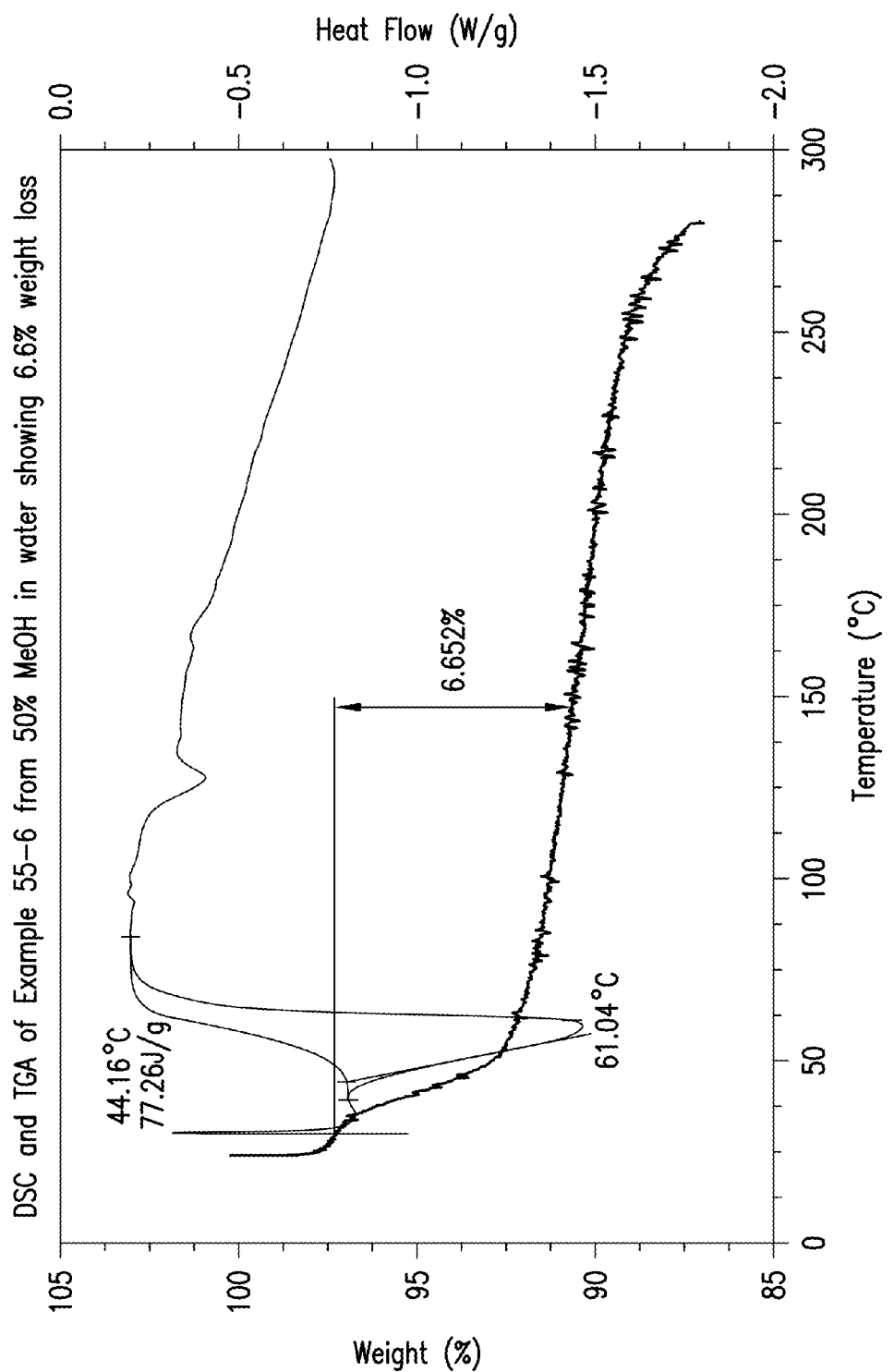
FIG. 29. illustrates the differential scanning calorimetry (DSC) and thermogravimetric analysis (TGA) of Example 55-G from 50% MeOH in water showing 6.6% weight loss.
Figure 30:
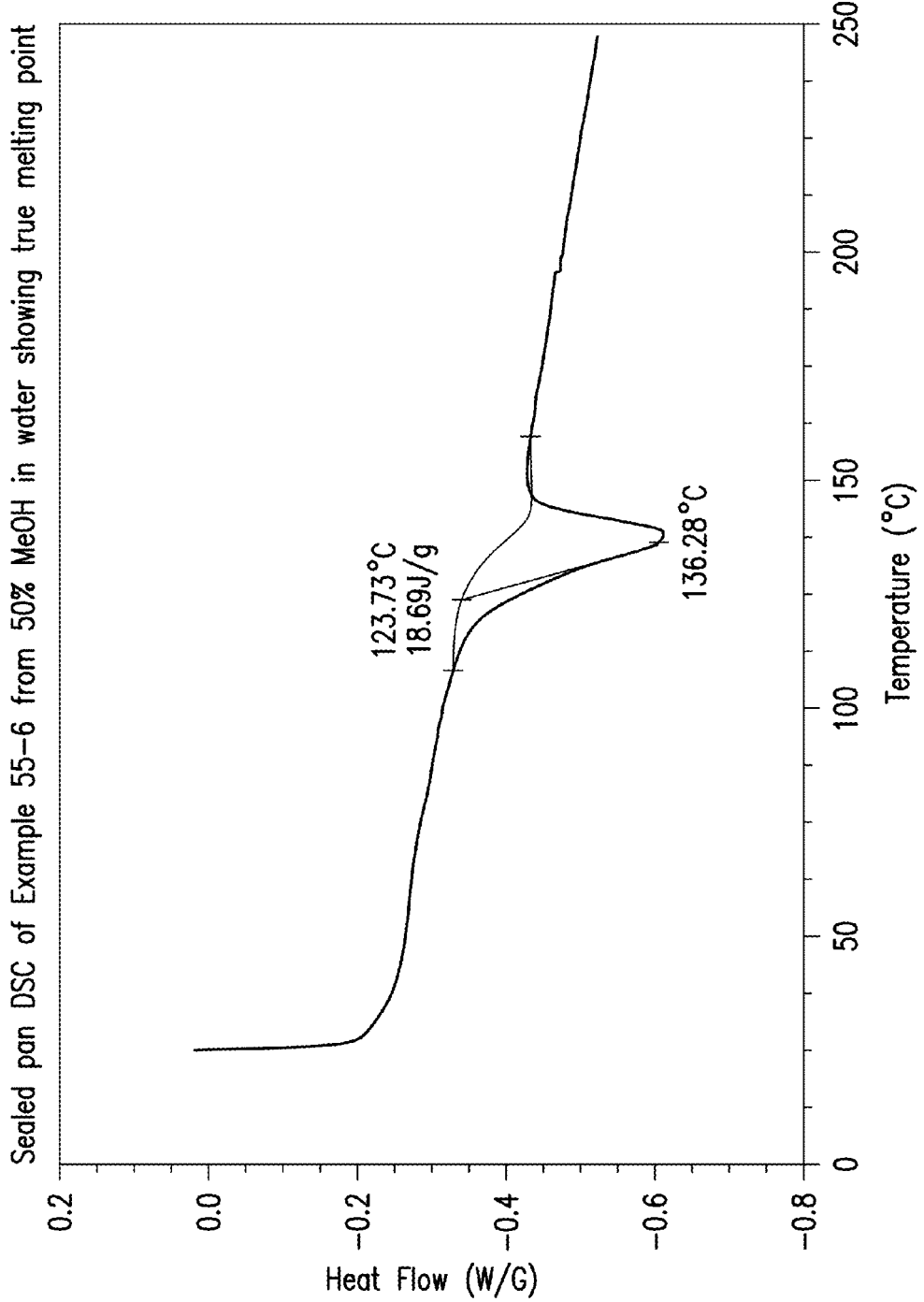
FIG. 30. illustrates sealed pan differential scanning calorimetry (DSC) of Example 55-G from 50% MeOH in water showing true melting point.

In an eighty sixth embodiment, the invention is a tri-hydrate form of Example 55-G isolated from 50% MeOH in Water having a differential scanning calorimetry (DSC) thermogram substantially the same as that shown in shown in FIGS. 29 and 30.

In an eighty seventh embodiment, the invention is a tri-hydrate form of Example 55-G isolated from 50% MeOH in Water having a thermo gravimetric analysis (TGA) diagram substantially the same as that shown in shown in FIG. 30.

In an eighty eighth embodiment, the invention is a crystalline Sulfate Form of Example 55-G.

In an eighty ninth embodiment, the invention is a crystalline Sulfate Form of Example 55-G characterized by a x-ray powder diffraction pattern comprising four or more 2θ values selected from the group consisting of 6.198±0.2°, 8.648±0.2°, 10.047±0.2°, 11.452±0.2°, 12.769±0.2°, 14.551±0.2°, 16.203±0.2°, 17.059±0.2°, 17.827±0.2° 19.214±0.2° and 19.952±0.2°, at a temperature of about 22° C.

In a ninetieth embodiment, the invention is a crystalline Sulfate Form of Example 55-G characterized by a x-ray powder diffraction pattern comprising five or more 2θ values selected from the group consisting of 6.198±0.2°, 8.648±0.2°, 10.047±0.2°, 11.452±0.2°, 12.769±0.2°, 14.551±0.2°, 16.203±0.2°, 17.059±0.2°, 17.827±0.2° 19.214±0.2° and 19.952±0.2°, at a temperature of about 22° C.

Figure 31:
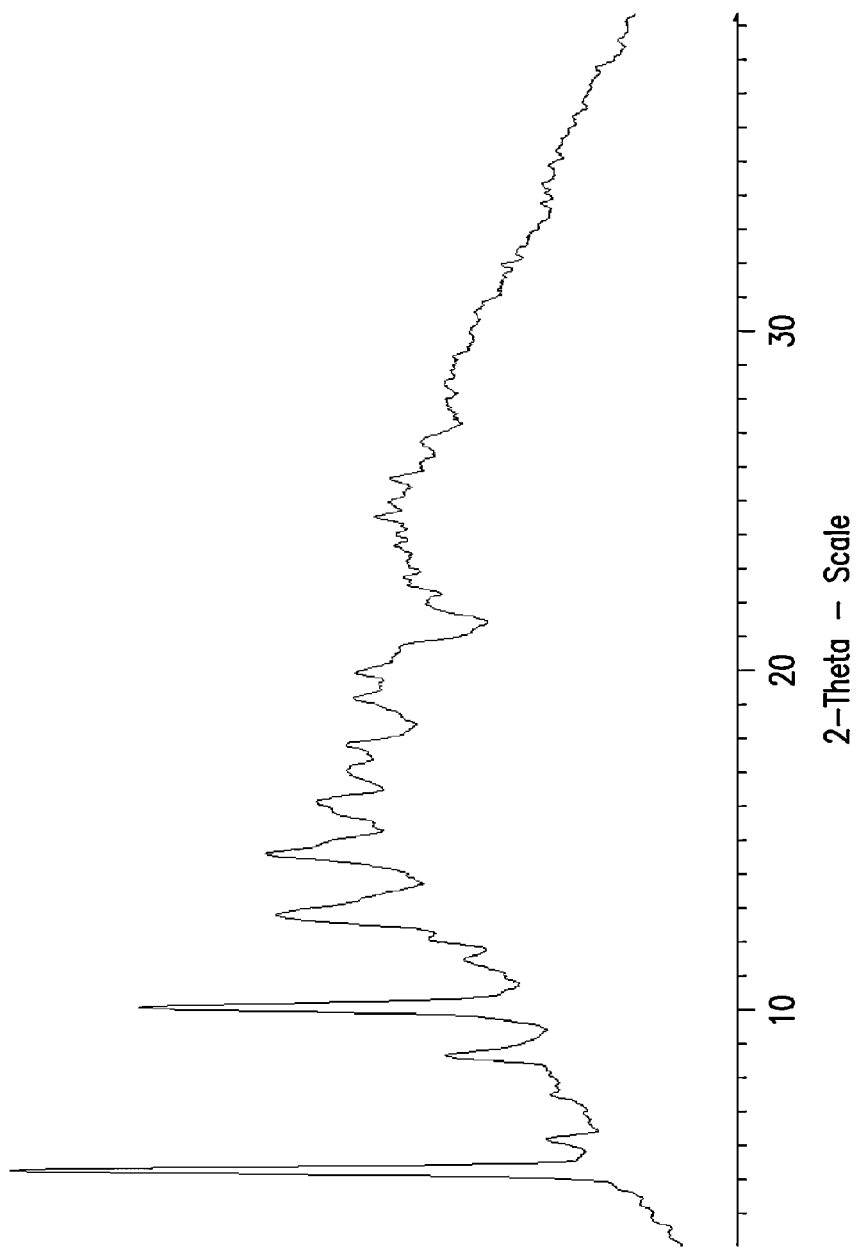
FIG. 31. illustrates the x-ray powder diffraction patterns of Example 55-G sulfate.

In a ninety first embodiment, the invention is a crystalline Sulfate Form of Example 55-G having a X-ray diffraction spectrum substantially the same as the X-ray powder diffraction spectrum shown in FIG. 31.

Figure 32:
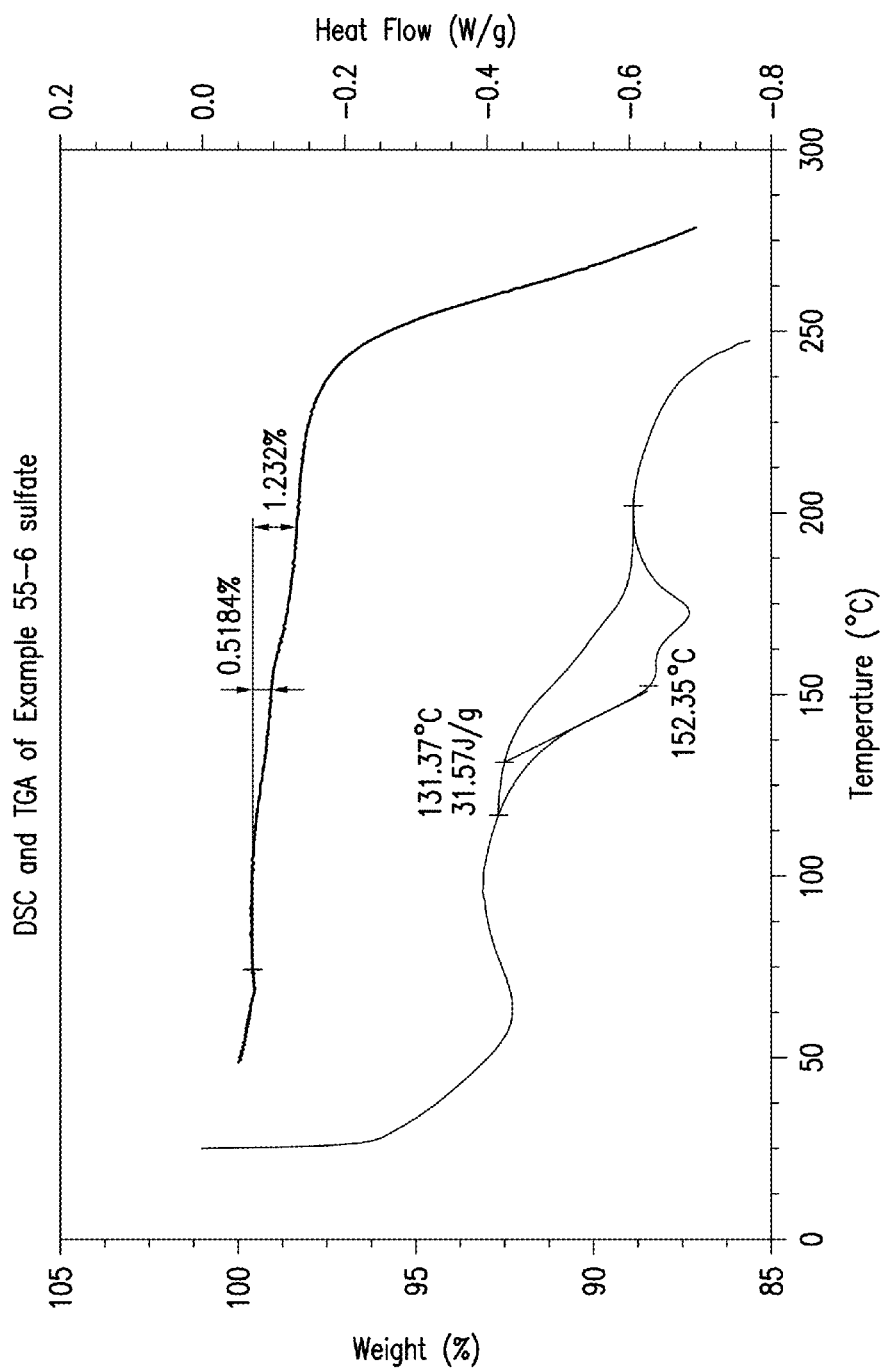
FIG. 32. illustrates the differential scanning calorimetry (DSC) and thermogravimetric analysis (TGA) of Example 55-G sulfate.

In a ninety second embodiment, the invention is a crystalline Sulfate Form of Example 55-G having a differential scanning calorimetry (DSC) thermogram substantially the same as that shown in shown in FIG. 32.

In a ninety third embodiment, the invention is a crystalline Sulfate Form of Example 55-G having a thermo gravimetric analysis (TGA) diagram substantially the same as that shown in shown in FIG. 32.

In a ninety fourth embodiment, the invention is a crystalline Tosylate Form of Example 55-G.

In a ninety fifth embodiment, the invention is a crystalline Tosylate Form of Example 55-G characterized by a x-ray powder diffraction pattern comprising four or more 2θ values selected from the group consisting of 6.405±0.2°, 8.264±0.2°, 9.769±0.2°, 12.366±0.2°, 13.724±0.2°, 14.639±0.2°, 16.026±0.2°, 18.069 and 18.889±0.2°, at a temperature of about 22° C.

In a ninety sixth embodiment, the invention is a crystalline Tosylate Form of Example 55-G characterized by a x-ray powder diffraction pattern comprising five or more 2θ values selected from the group consisting of 6.405±0.2°, 8.264±0.2°, 9.769±0.2°, 12.366±0.2°, 13.724±0.2°, 14.639±0.2°, 16.026±0.2°, 18.069 and 18.889±0.2°, at a temperature of about 22° C.

Figure 33:
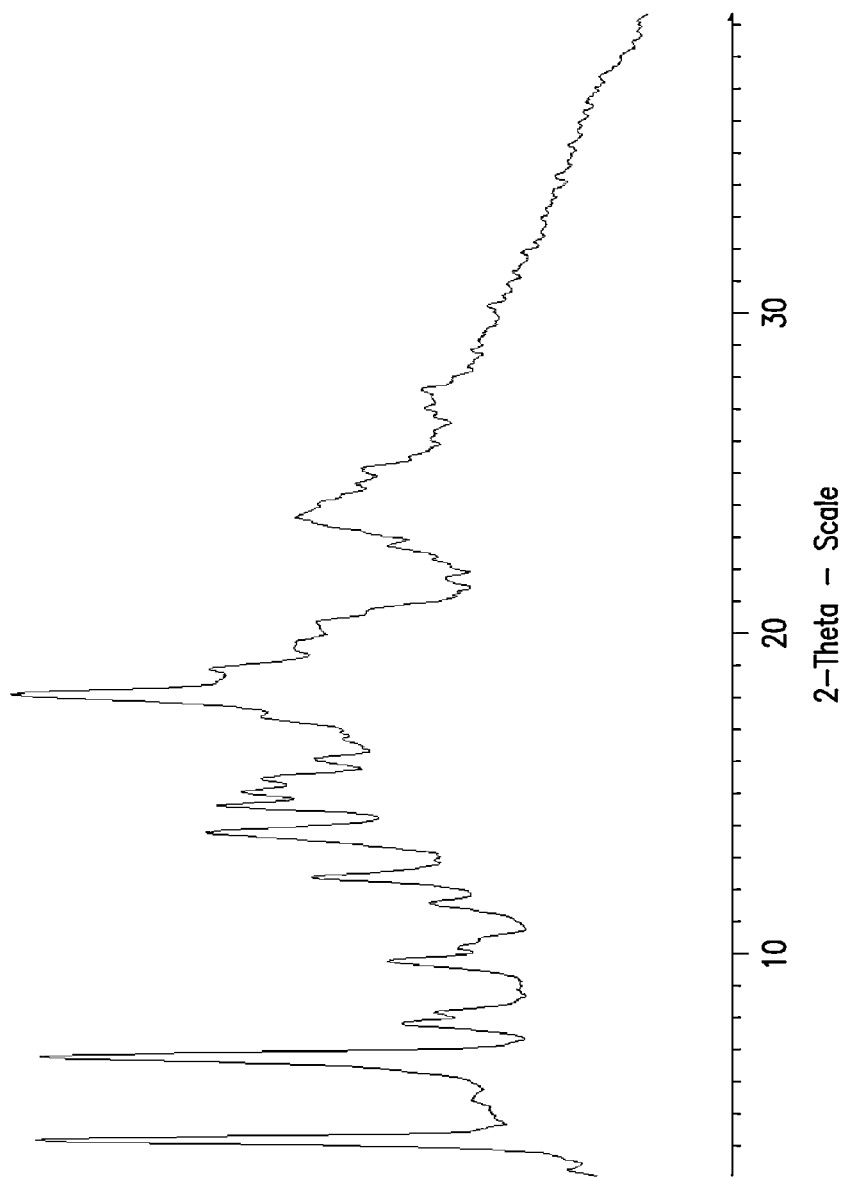
FIG. 33. illustrates the x-ray powder diffraction patterns of Example 55-G tosylate.

In a ninety seventh embodiment, the invention is a crystalline Tosylate Form of Example 55-G having a X-ray diffraction spectrum substantially the same as the X-ray powder diffraction spectrum shown in FIG. 33.

Figure 34:
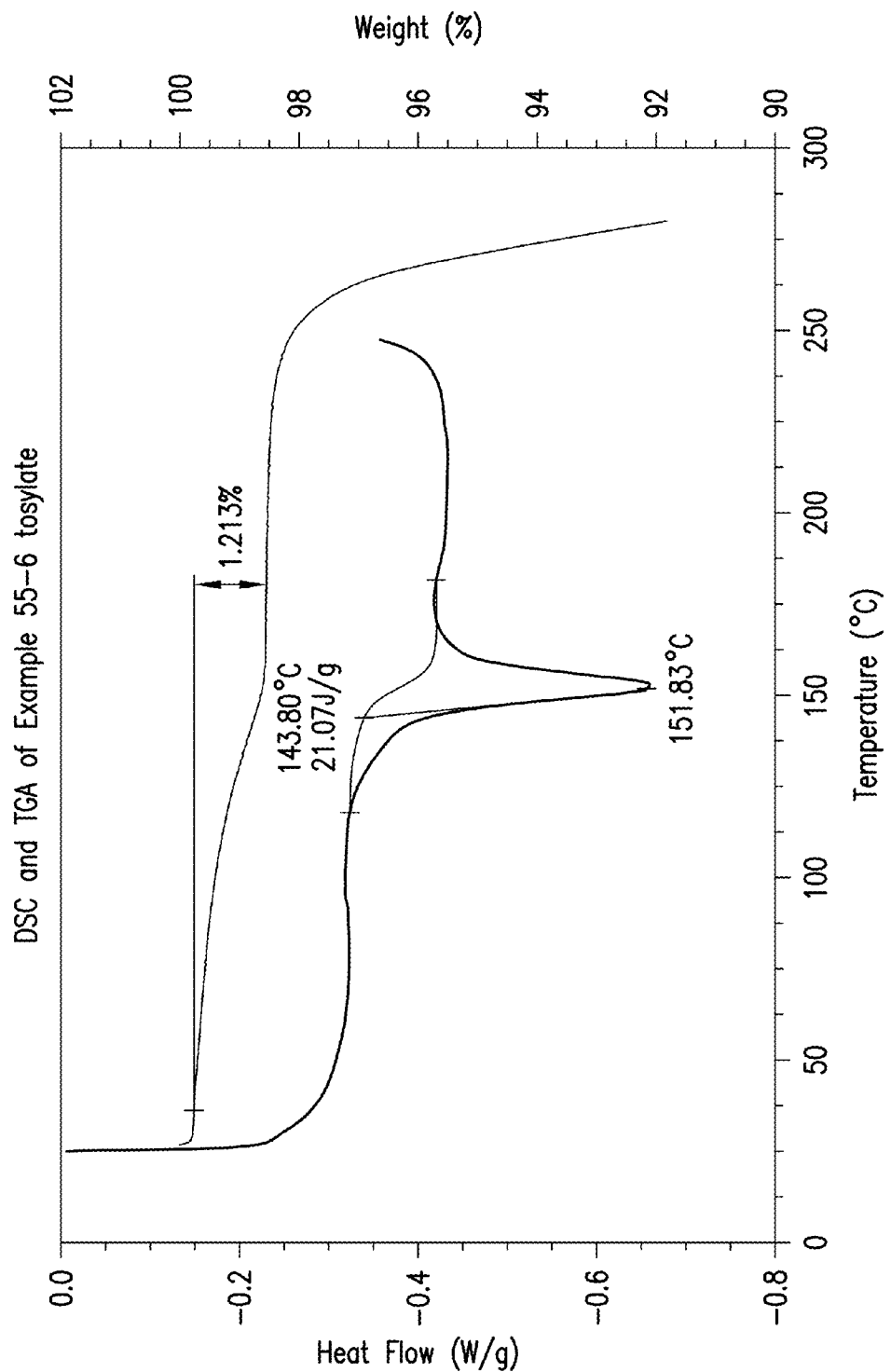
FIG. 34. illustrates the differential scanning calorimetry (DSC) and thermogravimetric analysis (TGA) of Example 55-G tosylate.

In a ninety eighth embodiment, the invention is a crystalline Tosylate Form of Example 55-G having a differential scanning calorimetry (DSC) thermogram substantially the same as that shown in shown in FIG. 34.

In a ninety ninth embodiment, the invention is a crystalline Tosylate Form of Example 55-G having a thermo gravimetric analysis (TGA) diagram substantially the same as that shown in shown in FIG. 34.

In a one hundredth embodiment, the invention is a crystalline Besylate Form of Example 55-G.

In a one hundred first embodiment, the invention is a crystalline Besylate Form of Example 55-G characterized by a x-ray powder diffraction pattern comprising four or more 2θ values selected from the group consisting of 7.624±0.2°, 8.215±0.2°, 9.196±0.2°, 10.674±0.2°, 11.177±0.2°, 11.715±0.2°, 13.324±0.2°, 13.710±0.2°, 14.352±0.2°, 14.912±0.2°, 15.358±0.2°, 16.169±0.2°, 16.706±0.2°, 17.160±0.2°, 17.465±0.2°, 17.737±0.2°, 18.952±0.2°, 19.915±0.2°, 21.568±0.2°, 22.119±0.2°, 22.422±0.2°, 23.656±0.2°, 24.450±0.2°, 25.535±0.2°, 27.668±0.2°, 28.393±0.2°, 29.209±0.2°, 29.832, 30.595 and 33.143±0.2°, at a temperature of about 22° C.

In a one hundred second embodiment, the invention is a crystalline Besylate Form of Example 55-G characterized by a x-ray powder diffraction pattern comprising five or more 2θ values selected from the group consisting of 7.624±0.2°, 8.215±0.2°, 9.196±0.2°, 10.674±0.2°, 11.177±0.2°, 11.715±0.2°, 13.324±0.2°, 13.710±0.2°, 14.352±0.2°, 14.912±0.2°, 15.358±0.2°, 16.169±0.2°, 16.706±0.2°, 17.160±0.2°, 17.465±0.2°, 17.737±0.2°, 18.952±0.2°, 19.915±0.2°, 21.568±0.2°, 22.119±0.2°, 22.422±0.2°, 23.656±0.2°, 24.450±0.2°, 25.535±0.2°, 27.668±0.2°, 28.393±0.2°, 29.209±0.2°, 29.832, 30.595 and 33.143±0.2°, at a temperature of about 22° C.

Figure 35:
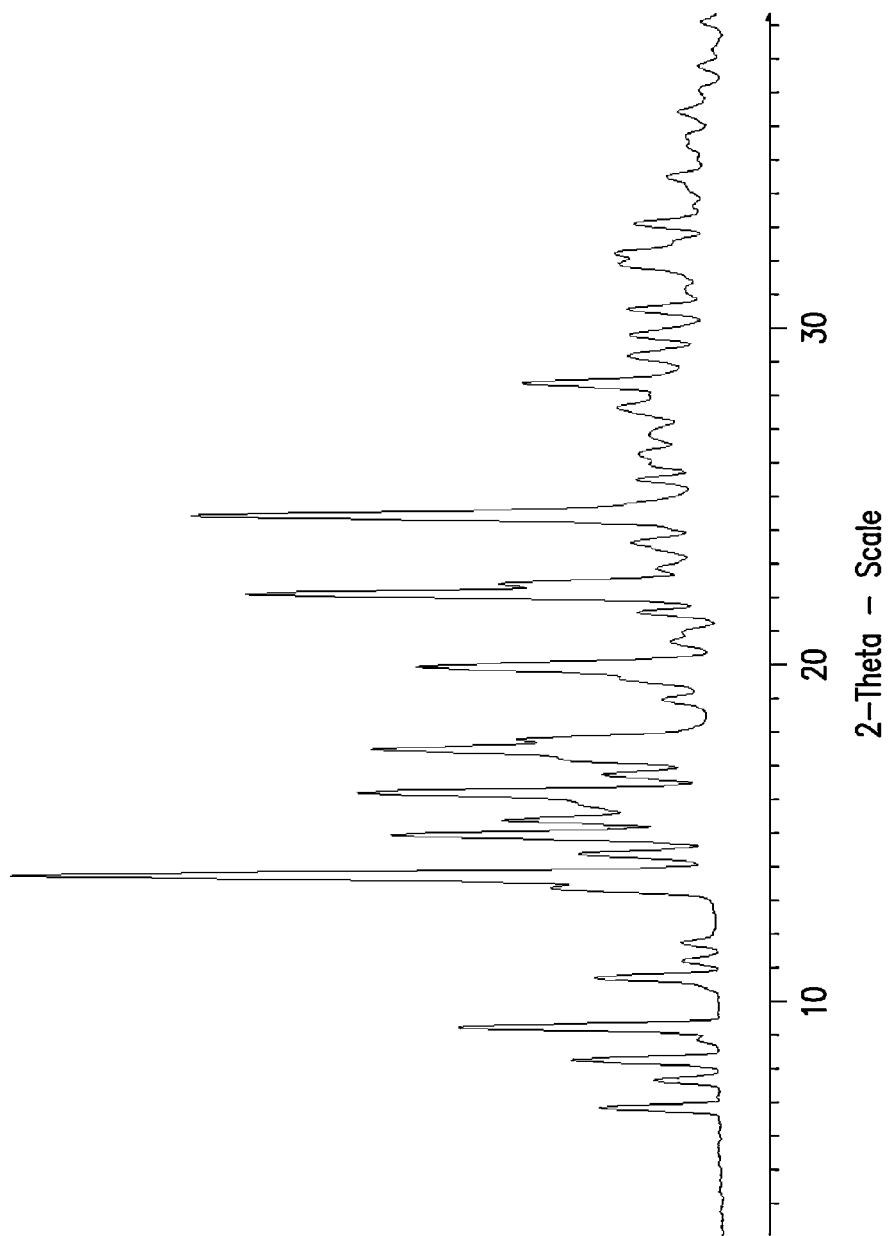
FIG. 35. illustrates the x-ray powder diffraction patterns of Example 55-G besylate.

In a one hundred third embodiment, the invention is a crystalline Besylate Form of Example 55-G having a X-ray diffraction spectrum substantially the same as the X-ray powder diffraction spectrum shown in FIG. 35.

Figure 36:
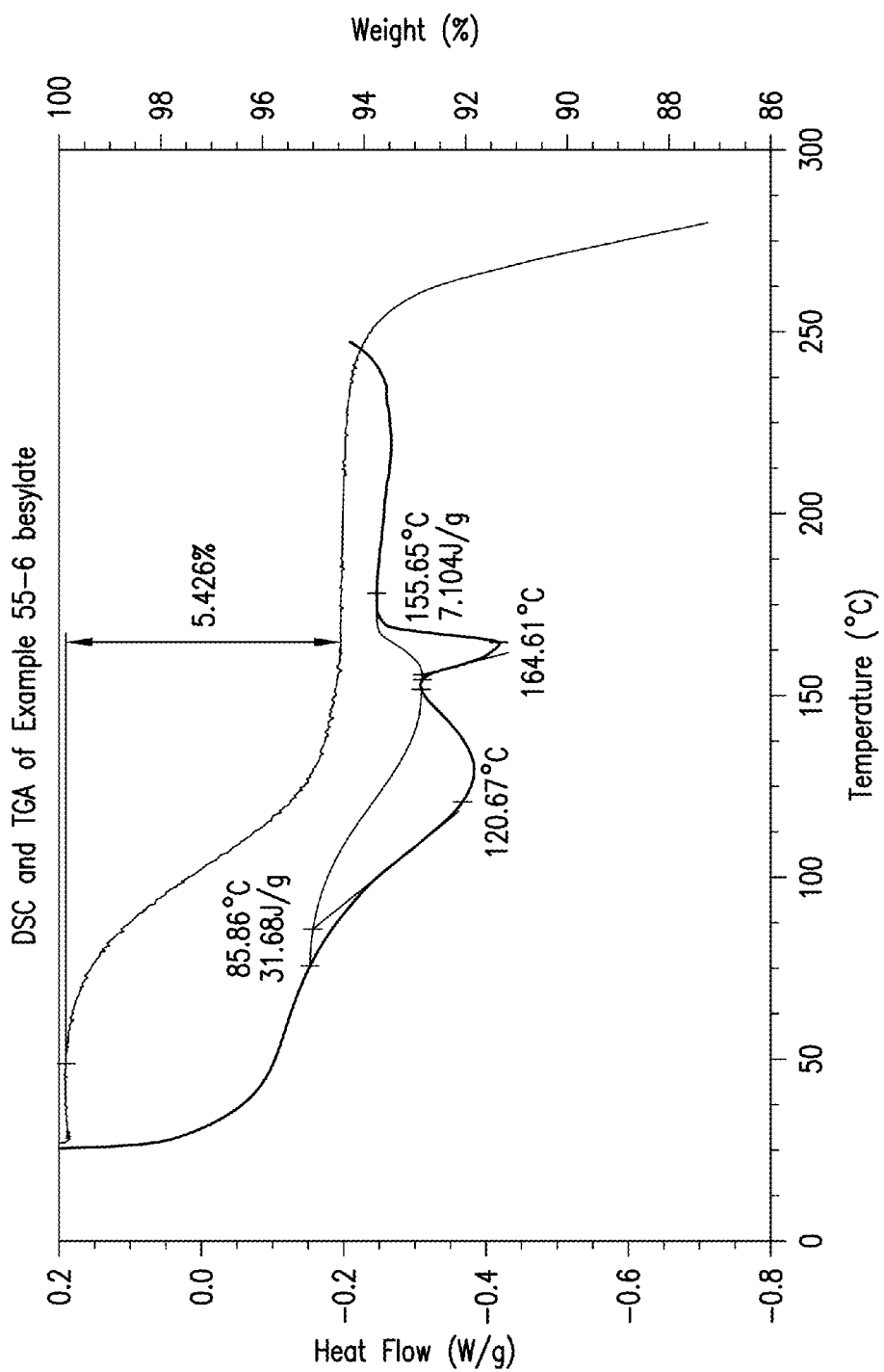
FIG. 36. illustrates the differential scanning calorimetry (DSC) and thermogravimetric analysis (TGA) of Example 55-G besylate.

In a one hundred fourth embodiment, the invention is a crystalline Besylate Form of Example 55-G having a differential scanning calorimetry (DSC) thermogram substantially the same as that shown in shown in FIG. 36.

In a one hundred fifth embodiment, the invention is a crystalline Besylate Form of Example 55-G having a thermo gravimetric analysis (TGA) diagram substantially the same as that shown in shown in FIG. 36.

In a one hundred sixth embodiment, the invention is a solvate form of Example 55-G isolated from MTBE.

In a one hundred seventh embodiment, the invention is a solvate form of Example 55-G isolated from MTBE characterized by a x-ray powder diffraction pattern comprising four or more 2θ values selected from the group consisting of 6.728±0.2°, 7.659±0.2°, 8.627±0.2°, 10.148±0.2°, 10.853±0.2°, 11.418±0.2°, 12.313±0.2°, 12.889±0.2°, 14.043±0.2°, 14.684±0.2°, 15.969±0.2°, 16.689±0.2°, 17.149±0.2°, 17.842±0.2°, 18.338±0.2°, 19.119±0.2°, 19.752±0.2°, 23.113±0.2°, 24.397±0.2°, 25.187±0.2°, 25.794±0.2° and 27.159±0.2°, at a temperature of about 22° C.

In a one hundred eighth embodiment, the invention is a solvate form of Example 55-G isolated from MTBE characterized by a x-ray powder diffraction pattern comprising five or more 2θ values selected from the group consisting of 6.728±0.2°, 7.659±0.2°, 8.627±0.2°, 10.148±0.2°, 10.853±0.2°, 11.418±0.2°, 12.313±0.2°, 12.889±0.2°, 14.043±0.2°, 14.684±0.2°, 15.969±0.2°, 16.689±0.2°, 17.149±0.2°, 17.842±0.2°, 18.338±0.2°, 19.119±0.2°, 19.752±0.2°, 23.113±0.2°, 24.397±0.2°, 25.187±0.2°, 25.794±0.2° and 27.159±0.2°, at a temperature of about 22° C.

In a one hundred ninth embodiment, the invention is a solvate form of Example 55-G isolated from MTBE having a X-ray diffraction spectrum substantially the same as the X-ray powder diffraction spectrum shown in FIG. 37.

In a one hundred tenth embodiment, the invention is a solvate form of Example 55-G isolated from MTBE having a differential scanning calorimetry (DSC) thermogram substantially the same as that shown in shown in FIG. 38.

In a one hundred eleventh embodiment, the invention is a solvate form of Example 55-G isolated from MTBE having a thermo gravimetric analysis (TGA) diagram substantially the same as that shown in shown in FIG. 38.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 12 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 12 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-pyrimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and (x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture. "Diastereoisomers" are stereoisomers that have at least two asymmetric atoms, but which are not mirror-images of each other. The absolute stereochemistry is specified according to the Cahn-lngold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isothionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}F$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include those compounds in which $R^{6}$ is deuterium. In certain additional embodiments, compounds of any one of formulae (I), (Ia), (II), (III), (IV), (V), (VI), (VII), or a sub formulae thereof, e.g., a compound of any one of embodiments one to eleven listed supra may be bis-deuterated at the 5 position of either the tetrahydropyrido-pyridine or tetrahydropyrido-pyrimidine ring system.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by C5a receptor activity, or (ii) associated C5a receptor activity, or (iii) characterized by activity (normal or abnormal) of the complement system; or (2) reducing or inhibiting the activity of C5a receptor activity; or (3) reducing or inhibiting activation of the complement system and particularly reducing or inhibiting the interaction of C5a and it's receptor.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity C5a receptor and/or the complement system.

As used herein, the term "subject" refers to an animal. Typically the animal is a mammal A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Protein" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and ophthalmic administration, etc. In addition, the pharmaceutical compositions of the present invention can be made up in a solid form (including without limitation capsules, tablets, pills, granules, powders or suppositories), or in a liquid form (including without limitation solutions, suspensions, emulsions, each of which may be suitable for ophthalmic administration). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ophthalmic application, e.g., for the treatment of eye diseases e.g., for therapeutic or prophylactic use in treating age related macular degeneration and other complement mediated ophthalmic disorders. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of Formula I in free form or in pharmaceutically acceptable salt form, exhibit valuable pharmacological properties, e.g. C5a receptor modulating properties, complement pathway modulating properties and modulation of the complement system, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing complement mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyanagi-Harada syndrome, intermediate uveitis, birdshot retino-chorioditis, sympathetic ophthalmia, ocular cicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by complement activation. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement system, wherein the medicament is prepared for administration with another therapeutic agent. The invention also provides the use of another therapeutic agent for treating a disease or condition mediated by the complement system, wherein the medicament is administered with a compound of formula (I).

The invention also provides a compound of formula (I) for use in a method of treating a disease or condition mediated by the complement system, wherein the compound of formula (I) is prepared for administration with another therapeutic agent. The invention also provides another therapeutic agent for use in a method of treating a disease or condition mediated by the complement system and/or, wherein the other therapeutic agent is prepared for administration with a compound of formula (I). The invention also provides a compound of formula (I) for use in a method of treating a disease or condition mediated by the complement system and/or C5a mediated inflammation, wherein the compound of formula (I) is administered with another therapeutic agent. The invention also provides another therapeutic agent for use in a method of treating a disease or condition mediated by the complement system and/or C5a mediated inflammation, wherein the other therapeutic agent is administered with a compound of formula (I).

The invention also provides the use of a compound of formula (I) for treating a disease or condition mediated by the complement system and/or C5a mediated inflammation, wherein the patient has previously (e.g. within 24 hours) been treated with another therapeutic agent. The invention also provides the use of another therapeutic agent for treating a disease or condition mediated by the complement system and/or C5a mediated inflammation wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neurotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysabri, laquinimod, rebif, avonex and the like.

In one embodiment, the invention provides a method of modulating activity of the complement system in a subject, wherein the method comprises administering to the subject a therapeutically effective amount of the compound according to the definition of formula (I). The invention further provides methods of modulating the activity of the complement system in a subject by modulating the activity of C5a receptor, wherein the method comprises administering to the subject a therapeutically effective amount of the compound according to the definition of Formula (I).

In one embodiment, the invention provides a compound according to the definition of formula (I), (Ia), (VII) or any sub formulae thereof, for use as a medicament.

In one embodiment, the invention provides the use of a compound according to the definition of formula (I), (Ia), (VII) or any sub formulae thereof, for the treatment of a disorder or disease in a subject mediated by complement activation. In particular, the invention provides the use of a compound according to the definition of formula (I), (Ia), (VII) or any sub formulae thereof, for the treatment of a disorder or disease mediated by activation of the complement system.

In one embodiment, the invention provides the use of a compound according to the definition of formula (I), (Ia), in the manufacture of a medicament for the treatment of a disorder or disease in a subject characterized by activation of the complement system. More particularly in the manufacture of a medicament for the treatment of a disease or disorder in a subject characterized by over activation of the complement system.

In one embodiment, the invention provides the use of a compound according to the definition of formula (I), (Ia), or sub formulae thereof for the treatment of a disorder or disease in a subject characterized by activation of the complement system. More particularly, the invention provides uses of the compounds provided herein in the treatment of a disease or disorder characterized by over activation of the complement system or the C3 amplification loop of the system. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing complement mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyanagi-Harada syndrome, intermediate uveitis, birdshot retino-chorioditis, sympathetic ophthalmia, ocular cicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The following Examples serve to illustrate the invention without limiting the scope thereof.

General Synthetic Aspects

Typically, the compounds of formula (I) can be prepared according to the Schemes provided infra

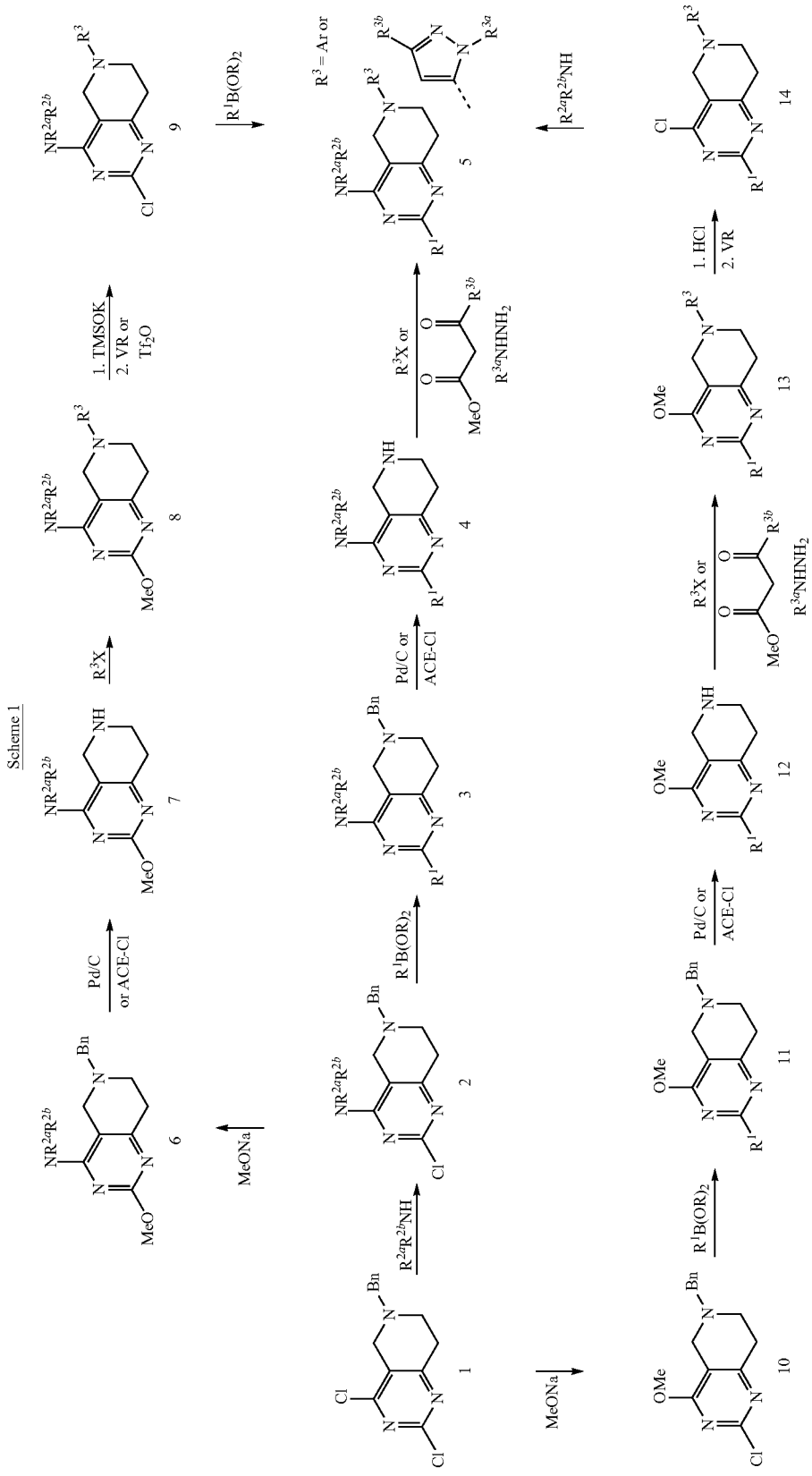

Amination of the pyrimidine core, to provide intermediates such as 2, can be accomplished by treatment of dichloropyrimidine 1 with either primary or secondary amines ($R^{2a}R^{2b}NH$), and DIEA or TEA in solvents such as DMA or IPA at elevated temperature. In a similar manner treatment of dichloropyrimidine 1 with MeONa in MeOH provides methoxy derivative 10. Installation of $R^1$ into either intermediate 2 or 10 can be accomplished with palladium catalyzed cross-coupling of boronic acids or the corresponding borate esters to give 3 and 12 respectively. Alternatively, 2 can be reacted with MeONa at elevated temperature to give methoxy intermediate 6. Removal of the benzyl protecting group from 3, 11, or 6 can be accomplished upon treatment with ACE-Cl or palladium catalyzed hydrogenolysis to give the corresponding secondary amines 4, 7, or 12. The $R^3$ group can then be installed by a palladium catalyzed amination with the appropriate aryl triflate or aryl halide and one of 4, 7, or 12 to give 5, 8 or 13. Alternatively, an $R^3$ pyrazole can be constructed by the reaction of amines 4, 7, or 12 with the appropriate β-ketoester and then subsequent condensation the β-ketoamide intermediate with alkylhydrazine facilitated by Lawesson's reagent. The methoxy group of 8 can be removed upon treatment with TMSOK at elevated temperature and the hydroxyl pyrimidine is then converted to the chloride upon reaction with Vilsmeier Reagent, $POCl_3$, $PPh_3/CCl_4$ or the like. An analogous sequence is employed with methoxy intermediate 13 to provide the 4-chloropyrimidine 14. The 2-chloropyrimidine 9 can then undergo installation of the $R^1$ group as described above to provide 5. The 4-chloropyrimidine 14 can undergo nucleophilic displacement either primary or secondary amines ($R^{2a}R^{2b}NH$) and DIEA or TEA in solvents such as DMA or IPA at elevated temperature to provide 5

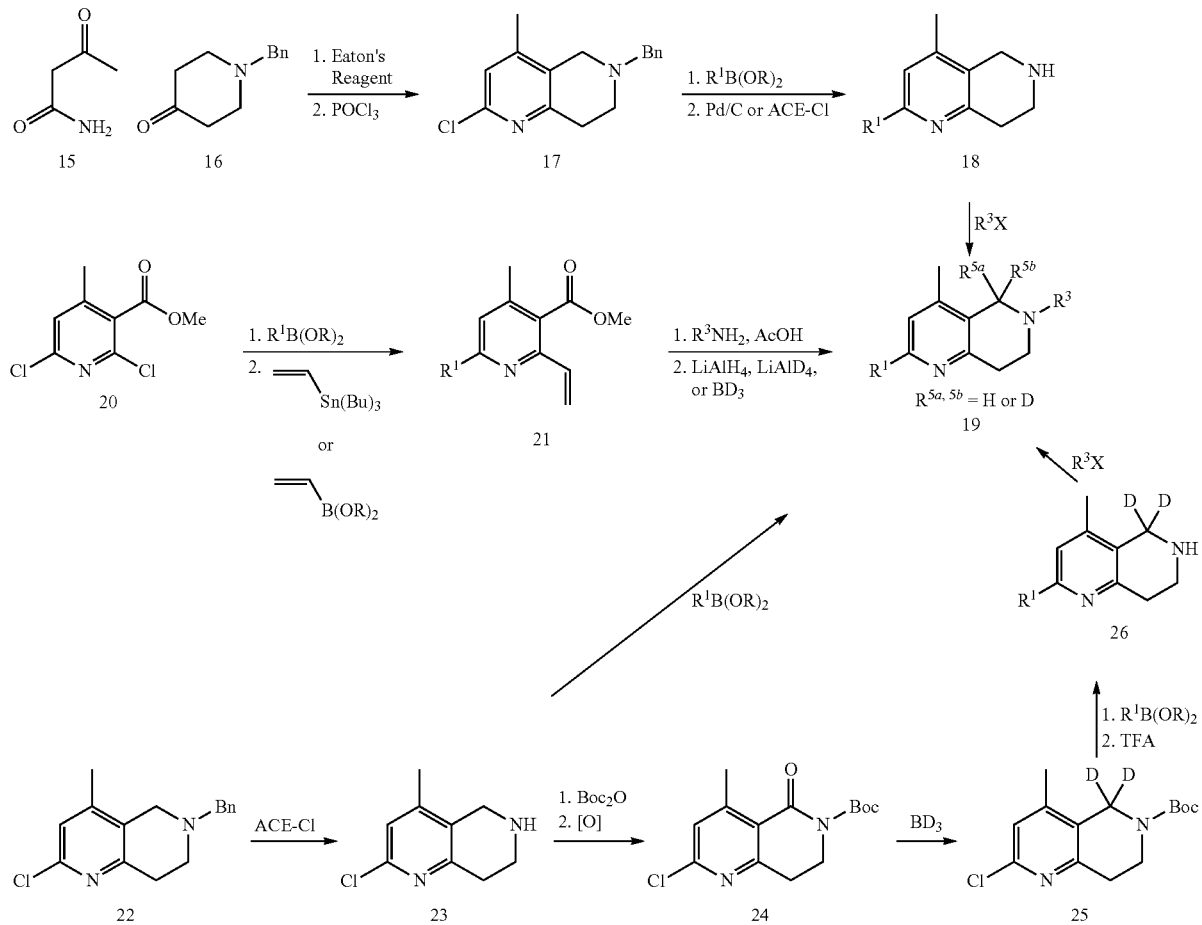

Scheme 2

The pyridine core 17 can be prepared by the condensation of 15 and 16 in Eaton's Reagent at elevated temperature followed by chlorination of the resulting hydroxypyridine with $POCl_3$. Palladium catalyzed cross-coupling reaction of chloropyridine 17 with the appropriate $R^1$ boronic acid or ester enables installation of $R^1$. Removal of the benzyl protecting group from 17 can be accomplished upon treatment with ACE-Cl or palladium catalyzed hydrogenolysis to give the corresponding secondary amines 18. The $R^3$ group can then be installed by a palladium catalyzed amination with the appropriate aryl triflate or aryl halide and 18 to provide 19. Alternatively, an $R^3$ pyrazole can be constructed by the reaction of amines 18 with the appropriate β-ketoester and then subsequent condensation the 13-ketoamide intermediate with alkylhydrazine facilitated by Lawesson's reagent to provide 19.

Intermediate 19 can also be prepared from 20 palladium catalyzed cross-coupling reaction with the appropriate $R^1$ boronic acid or ester to install $R^1$, a second palladium catalyzed cross-coupling reaction with either a vinyl borate ester or vinyl stannane reagent to give 21. Heating of the appropriate R³ amine with 21 in AcOH facilitates ring formation to give the intermediate lactam corresponding to 19. The lactam can then be reduced with LiAlH₄, LiAlD₄, or BD₃ to give the desired compounds 19. An alternative approach to 19 utilizes a selective palladium catalyzed amination of 23 with an appropriate aryl triflate or aryl bromide followed by palladium catalyzed cross-coupling to install R¹.

Deuterated intermediate can be accessed by the protection, oxidation, and reduction sequence from 23-25. The R¹ group is installed as above on intermediate 25 and then deprotection provides 26. Palladium catalyzed amination as described above provides 19 definitions mentioned hereinbefore may reasonably be used, for example, to replace one or more up to all more general definitions with more specific definitions or especially with definitions characterized as being preferred.

Compounds of formula I are prepared analogously to methods that, for other compounds, are in principle known in the art, but are novel when applied in the manufacture of the compounds of the present invention, and are especially prepared according to the methods described hereinbelow under 'Examples' or by analogous methods.

Prodrug derivatives of the compounds of the invention can be prepared by methods known to those of ordinary skill in the art (e.g., for further details see Saulnier et al., (1994),

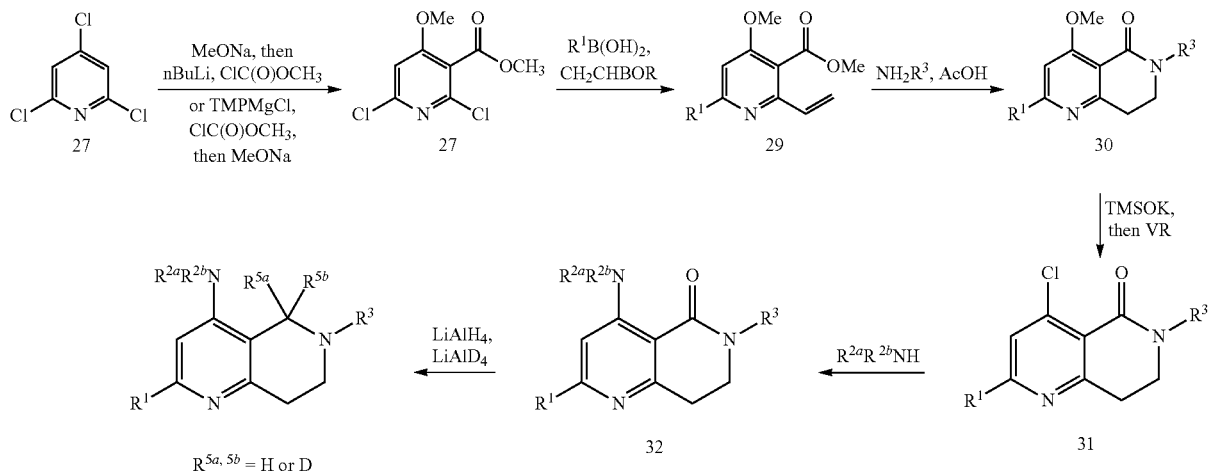

Scheme 3

Treatment of 27 with MeONa and then nbutyllithim and methyl chloroformate provides dichloropyridine 28. Alternatively, 28 can be prepared from 27 by metallation with TMP-MgCl, esterification, and then methanolysis with MeONa. The R¹ group can be installed with palladium catalyzed cross-coupling with the corresponding boronic acid or ester. In a second cross-coupling step the vinyl group can be installed to give 29. As described above, 29 undergoes cyclization upon reaction with the corresponding amine in acetic acid at elevated temperature to provide lactam 30. The 4-methoxypyridine is then converted to a 4-chloropyridine 31 by treatment with TMSOK and then Vilsmeier Reagent. Displacement of the chloro group is facilitated by heating 31 with the appropriate primary or secondary amine to give the intermediate lactam, which then undergoes reduction as described above to provide 33.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

With the groups of preferred compounds of formula I mentioned hereinafter, definitions of substituents from the general Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999. Corresponding protecting groups can be introduced, used and removed at appropriate stages at any stage in the manufacture of a compound of the formula I. Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as acetonitrile, methanol, ethanol, ethyl acetate, heptane, or tetrahydrofuran. Intermediates and final products can be worked up and/or purified according to standard methods, e.g. using chromatographic methods, distribution methods, (re-) crystallization, and the like.

Abbreviations
ACECl 2-chloroethyl chlroformate
app apparent
aq aqueous
atm atmosphere BHT 2,6-di-tert-butyl-4-methylphenol
BINAP 2,2'-bis(diphenylphosphino)-1,1'-binaphthalene
Bn benzyl
BOC tertiary butyl carboxy
br broad
BSA bovine serum albumin
Cbz carbobenzyloxy
C5aR C5a receptor
d doublet
D deuterium
DCE 1,2-dichloroethane
dd doublet of doublets
DCM dichloromethane
DEA diethylamine
DIEA, DIPEA diisopropylethylamine
DMA N,N-dimethylacetamide
DMAP 4,4-dimethylaminopyridine
DME 1,2-dimethoxyethane
DMEM Dulbecco's Modified Eagle Medium
DMF N,N-dimethylformamide
DMSO dimethylsulfoxide
ee enantiomeric excess
ESI electrospray ionization
EtOAc ethyl acetate
FACS fluorescence-activated cell sorting
FCC flash column chromatography
FITC fluorescein isothiocyanate
FLIPR Fluorescent Imaging Plate Reader
g grams
h hour(s)
HBSS Hanks' Balanced Salt Solution
HEPES 4-(2-hydroxyethyl)-1-piperazineethanesulfonic acid
HPLC high pressure liquid chromatography
IR infrared spectroscopy
LAD lithium aluminum deuteride
LAH lithium aluminum hydride
Lawesson's reagent 2,4-bis-(4-methoxyophenyl)-1,3-dithia-2,4-diphosphetane 2,4-disulfide
LCMS liquid chromatography and mass spectrometry
LTMP lithium 2,2',6,6'-tetramethylpiperidine
M molar
m multiplet
MeCN, CH$_3$CN acetonitrile
MeOH methanol
Me-THF 2-Methyl Tetra Hydro Furan
MTBE Methyl tert-butyl ether
min minutes
mL milliliter(s)
mmol millimoles
MS mass spectrometry
MsOH methanesulfonic acid
MW microwave
m/z mass to charge ratio
N normal
NCS N-chlorosuccinimide
NMR nuclear magnetic resonance
obs obscured; partially obscured
PBS phosphate buffer solution
Pd/C palladium on carbon
ppm parts per million
rac racemic
rt room temperature
R$_t$ retention time
s singlet
sat saturated
SFC Supercritical Fluid Chromatography
S-Phos 2-Dicyclohexylphosphino-2',6'-dimethoxybiphenyl
t triplet
TBSCl tert-butyldimethylsilyl chloride
Tf trifluoromethanesulfonate
TFA trifluoroacetic acid
THF tetrahydrofuran
TMP 2,2,6,6-tetramethylpiperidine
TMS trimethylsilyl
Ts, Tos tosyl
VR Vilsmeier Reagent; (Chlormethylene)dimethylammonium chloride
X-Phos 2-Dicyclohexylphosphino-2',4',6'-triisopropylbiphenyl Example 1

3,5-Dimethyl-4-(4,4,5,5-tetramethyl-1,3,2-dioxaborolan-2-yl)pyridine

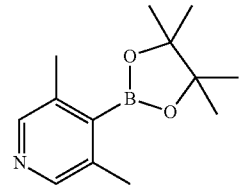 [SMILES: Cc1cncc(C)c1B1OC(C)(C)C(C)(C)O1]

To a solution of 4-bromo-3,5-dimethylpyridine (600 mg, 2.70 mmol) in dioxane (9 mL) was added bis(pinocolato)diboron (1.37 g, 5.39 mmol), potassium acetate (1.06 g, 10.8 mmol), S-phos (221 mg, 0.539 mmol) and PdCl$_2$(MeCN)$_2$ (35 mg, 0.14 mmol). Reaction was heated at 95° C. for 16 h. Water was added and the aqueous phase was extracted with EtOAc (3×). The combined organic layers were washed with brine, dried over anhydrous sodium sulfate, filtered, and concentrated under reduced pressure. The residue was purified via FCC (40-60% EtOAc/heptane) to give the title compound. MS (ESI+) m/z 234.1 (M+H)$^+$.

Example 2

2,4-Dimethyl-3-(4,4,5,5-tetramethyl-1,3,2-dioxaborolan-2-yl)pyridine

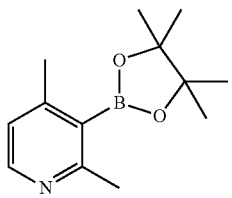 [SMILES: Cc1ccnc(C)c1B1OC(C)(C)C(C)(C)O1]

To a solution of 3-bromo-2,4-dimethylpyridine (476 mg, 2.56 mmol) in DMSO (14 mL) was added bis(pinocolato)diboron (3.25 g, 12.8 mmol), potassium acetate (1.26 g, 12.8 mmol) and PdCl$_2$(dppf).CH$_2$Cl$_2$ adduct (209 mg, 0.256 mmol). Reaction was heated at 95° C. for 16 h. Water was added and the aqueous phase was extracted with EtOAc (3×). The combined organic layers were washed with brine, dried over anhydrous sodium sulfate, filtered, and concentrated under reduce pressure. The residue was purified via FCC (40-70% EtOAc/heptane) to give the title compound. $^1$H NMR (400 MHz, CDCl$_3$) δ ppm 8.35 (d, J=5.1 Hz, 1 H), 6.91

(d, J=5.1 Hz, 1 H), 2.64 (s, 3 H), 2.42 (s, 3 H); 1.43 (s, 12 H); MS (ESI+) m/z 234.1 (M+H)⁺.

Example 3

3,5-Dimethyl-4-(4,4,5,5-tetramethyl-1,3,2-dioxaborolan-2-yl)-1-tosyl-1H-indazole

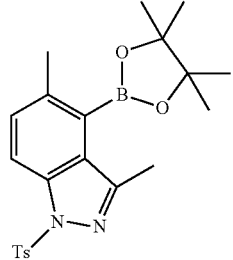 [SMILES: Cc1ccc(S(=O)(=O)n2nc(C)c3c(B4OC(C)(C)C(C)(C)O4)c(C)ccc32)cc1]

A solution of 1-(2-chloro-6-fluoro-3-methylphenyl)ethanone (10 g, 53.6 mmol) and hydrazine (5.05 mL, 161 mmol) in DMSO (50 mL) was heated at 80° C. overnight. The reaction mixture was then partitioned between EtOAc and water. The aqueous layer was extracted with EtOAc. The combined organic layers were washed with brine, dried (Na₂SO₄) and concentrated to provide crude 4-chloro-3,5-dimethyl-1H-indazole as a white solid, which was used in the next step directly. MS (ESI+) m/z 180.9 (M+H)⁺. NaH (60% dispersion in mineral oil, 3.87 g, 97 mmol) was added portion wise to a solution of crude 4-chloro-3,5-dimethyl-1H-indazole (9.7 g, 53.7 mmol) in THF (200 mL) at −20° C. The mixture was allowed to warm to 0° C. and stir for 20 min, then TsCl (14.33 g, 75 mmol) was added. The reaction mixture was allowed to warm to rt and stir overnight. The reaction mixture was cooled to −20° C. and sat. NH₄Cl aqueous solution was added to quench excess base. The resulting mixture was extracted with CH₂Cl₂ (2×). The combined organics were washed with brine, dried (Na₂SO₄) and concentrated. The residue was triturated with EtOAc and filtered to provide 4-chloro-3,5-dimethyl-1-tosyl-1H-indazole. ¹H NMR (400 MHz, CDCl₃) δ ppm 7.98 (d, J=8.34 Hz, 1 H) 7.84 (m, J=8.34 Hz, 2 H) 7.39 (d, J=8.59 Hz, 1 H) 7.25 (m, J=7.83 Hz, 2 H) 2.73 (s, 3 H) 2.46 (s, 3 H) 2.38 (s, 3 H); MS (ESI+) m/z 334.7 (M+H)⁺.

A mixture of 4-chloro-3,5-dimethyl-1-tosyl-1H-indazole (1.5 g, 4.48 mmol), dioxaborolane (3.41 g, 13.44 mmol), S-Phos palladacycle (CAS: 1028206-58-7, 0.151 g, 0.224 mmol), and K₃PO₄ (2.85 g, 13.44 mmol) in DMSO (20 mL) was heated at 110° C. for 70 min. The reaction mixture was then partitioned between DCM and water. The aqueous layer was extracted with DCM (2×). The combined organics were washed with brine, dried (Na₂SO₄) and concentrated. The residue was purified by FCC (0-30% EtOAc/heptanes) to provide 3,5-dimethyl-4-(4,4,5,5-tetramethyl-1,3,2-dioxaborolan-2-yl)-1-tosyl-1H-indazole. ¹H NMR (400 MHz, CDCl₃) δ ppm 8.09 (d, J=8.59 Hz, 1 H) 7.78 (m, J=8.34 Hz, 2 H) 7.35 (d, J=8.84 Hz, 1 H) 7.19 (m, J=8.08 Hz, 2 H) 2.59 (s, 3 H) 2.54 (s, 3 H) 2.35 (s, 3 H) 1.44 (s, 12 H); (ESI+) m/z 426.9 (M+H)⁺.

Example 4

4-A. 4-Bromo-5-isopropyl-1-tosyl-1H-indazole

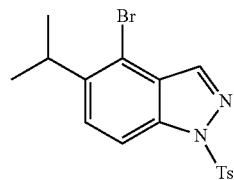 [SMILES: Cc1ccc(S(=O)(=O)n2ncc3c(Br)c(C(C)C)ccc32)cc1]

NaH (60% dispersion in mineral oil, 241 mg, 6.02 mmol) was added to a solution of 4-bromo-5-isopropyl-1H-indazole (720 mg, 3.01 mmol) in THF (15 mL) at 0° C. After 10 min, TsCl (861 mg, 4.52 mmol) was added and the resulting mixture was stirred at 0° C. for 1 h, then at room temperature overnight. Saturated aqueous NH₄Cl was added and the mixture was extracted with EtOAc (2×). The combined organics were washed with brine, dried (Na₂SO₄) and concentrated. Ther residue was purified by silica gel chromatography (0-30% EtOAc/heptanes) to provide 4-bromo-5-isopropyl-1-tosyl-1H-indazole. MS (ESI+) m/z 394.8 (M+H)⁺.

4-B. 5-Isopropyl-4-(4,4,5,5-tetramethyl-1,3,2-dioxaborolan-2-yl)-1-tosyl-1H-indazole

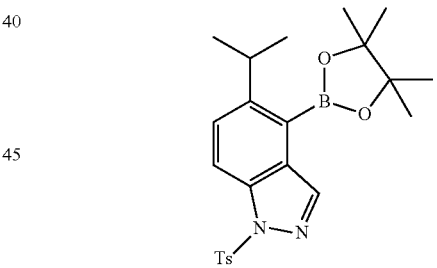

A mixture of 4-bromo-5-isopropyl-1-tosyl-1H-indazole (550 mg, 1.398 mmol), bis(pinacolato)diboron (710 mg, 2.80 mmol), PdCl₂(dppf).CH₂Cl₂ adduct (91 mg, 0.112 mmol) and potassium acetate (412 mg, 4.20 mmol) in DMSO (8 mL) was heated at 110° C. for 24 h. The reaction mixture was partitioned between EtOAc and water. The aqueous layer was extracted with EtOAc. The combined organics were washed with brine, dried (Na₂SO₄) and concentrated. The residue was purified by silica gel chromatography (0-30% EtOAc/heptane) to provide 5-isopropyl-4-(4,4,5,5-tetramethyl-1,3,2-dioxaborolan-2-yl)-1-tosyl-1H-indazole. ¹H NMR (400 MHz, CDCl₃) δ ppm 8.57 (s, 1 H) 8.24 (d, J=8.84 Hz, 1 H) 7.87 (d, J=8.59 Hz, 2 H) 7.57 (d, J=8.84 Hz, 1 H) 7.24 (d, J=8.59 Hz, 2 H) 3.71-3.88 (m, 1 H) 2.38 (s, 3 H) 1.41 (s, 12 H) 1.29-1.32 (m, 6 H); MS (ESI+) m/z 440.9 (M+H)⁺.

Example 5

5-Isopropyl-4-(4,4,5,5-tetramethyl-1,3,2-dioxaborolan-2-yl)-1H-indazole

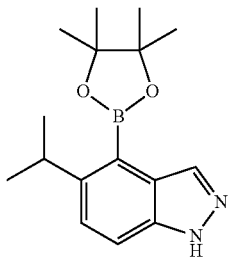 [SMILES: CC(C)c1ccc2[nH]ncc2c1B1OC(C)(C)C(C)(C)O1]

A suspension of 4-bromo-5-isopropyl-1H-indazole (396 mg, 1.656 mmol), bis(pinacolato)diboron (841 mg, 3.31 mmol), KOAc (488 mg, 4.97 mmol), PdCl$_2$(CH$_3$CN)$_2$ (21.48 mg, 0.083 mmol) and S-Phos (136 mg, 0.331 mmol) in DMSO (6 mL) was allowed to stir at 110° C. for 23 h under nitrogen. The reaction mixture was cooled to rt, and diluted with EtOAc and half-saturated brine. The products were extracted three times with EtOAc. The combined organic layer was washed with brine, and concentrated. After the residue was diluted with THF (10 mL) and MeOH (1.5 mL), 1 M aq LiOH (4.5 mL) was added. After stirring for 0.5 h, the reaction was quenched with sat aq NH$_4$Cl, and diluted with EtOAc and brine. The mixture was extracted twice with EtOAc. The combined organic layer were washed with a 1:1 solution of sat aq NH$_4$Cl and saturated brine, dried over Na$_2$SO$_4$, filtered, and concentrated. The residue was purified by flash column chromatography on 40 g of silica gel (0-20% EtOAc/heptane) to give 5-isopropyl-4-(4,4,5,5-tetramethyl-1,3,2-dioxaborolan-2-yl)-1H-indazole along with 20 mol % of debromonated product (345 mg) as a yellow solid. $^1$H NMR (400 MHz, CDCl$_3$, the desired boronic ester) δ ppm 9.93 (br s, 1 H), 8.39 (d, J=1.01 Hz, 1 H), 7.50-7.52 (m, 1 H), 7.41 (d, J=8.84 Hz, 1 H), 3.75-3.85 (m, 1 H), 1.42 (s, 12 H), 1.28 (d, J=6.82 Hz, 6 H); MS (ESI+) m/z 287.30 (M+H)$^+$. The obtained material was used without further purification.

Example 6

6-A. 3-Methyl-4-(4,4,5,5-tetramethyl-1,3,2-dioxaborolan-2-yl)-1-tosyl-1H-indole

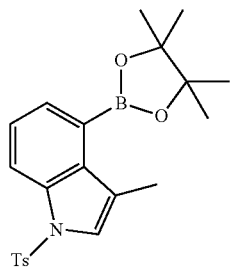 [SMILES: Cc1ccc(S(=O)(=O)n2cc(C)c3c(B4OC(C)(C)C(C)(C)O4)cccc32)cc1]

To a solution of 4-bromo-1H-indole-3-carbaldehyde (7.5 g, 66.9 mmol) in THF (125 mL) was added LiAlH$_4$ (40 mL, 1.0 M THF) dropwise at rt. The mixture was then heated at reflux for 2 h and was then cooled to 0° C. At that point 15% NaOH (2 mL) and water (7 mL) were added in sequence and the mixture was stirred vigorously for 1 h. At that point the suspension was filtered over Celite® and the filtrate was concentrated to provide crude 4-bromo-3-methyl-1H-indole, which was taken to the next step. A solution of crude 4-bromo-3-methyl-1H-indole (14.0 g, 66.9 mmol) in THF (50 mL) was added to a suspension of NaH (2.94 g, 73.6 mmol, 60% in mineral oil) in THF (200 mL) at 0° C. The mixture was stirred for 0.5 h at that temperature before a solution of p-toluene sulfonylcholoride (13.4 g, 70.2 mmol) in THF (50 mL) was added. After stirring for an additional 1 h sat aq NH$_4$Cl was added slowly. The reaction mixture was then diluted with EtOAc and sat aq NH$_4$Cl and the layers were separated. The organic layer was dried (Na$_2$SO$_4$), filtered and concentrated. The residue was then purified by FCC (0-50% EtOAc/heptane) to give 4-bromo-3-methyl-1-tosyl-1H-indole.

To a solution of 4-bromo-3-methyl-1-tosyl-1H-indole (8.66 g, 23.8 mmol) in DMSO (100 mL), 4,4,4',4',5,5,5',5'-octamethyl-2,2'-bi(1,3,2-dioxaborolane) (7.85 g, 30.9 mmol), potassium acetate (3.50 g, 35.7 mmol) and PdCl$_2$(dppf).CH$_2$Cl$_2$ (0.97 g, 1.19 mmol) were added. The reaction mixture was placed under a nitrogen atmosphere and then heated at 100° C. for 4 h. The mixture was then allowed to cool to rt and then poured into ice water (600 mL). The precipitate was filtered and the solid was then purified by FCC (0-25% EtOAc/heptanes) to give 3-methyl-4-(4,4,5,5-tetramethyl-1,3,2-dioxaborolan-2-yl)-1-tosyl-1H-indole. MS (ESI+) m/z 412.2 (M+H)$^+$.

The following compounds were prepared in a similar manner.

6-B. 7-Fluoro-3-methyl-4-(4,4,5,5-tetramethyl-1,3,2-dioxaborolan-2-yl)-1-tosyl-1H-indole

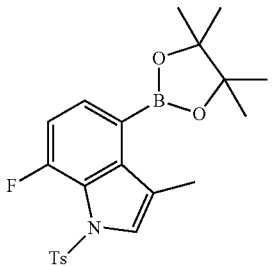 [SMILES: Cc1ccc(S(=O)(=O)n2cc(C)c3c(B4OC(C)(C)C(C)(C)O4)ccc(F)c32)cc1]

MS (ESI+) m/z 429.8 (M+H)$^+$. Prepared as described for Example 6-A from 4-bromo-7-fluoro-1H-indole-3-carbaldehyde which was prepared by the following method. POCl$_3$ (0.85 mL, 9.11 mmol) was added to DMF (4.4 ml, 56.1 mmol) which had been cooled in an ice bath. After stirring for 15 min a solution of 4-bromo-7-fluoro-1H-indole (1.50 g, 7.01 mmol) in DMF (1.5 mL) was added and the mixture was then heated at 35° C. for 1.25 h. The reaction mixture was then cooled in an ice bath and treated with ice and 20% w/w aq NaOH to pH 14 and heated at reflux for 8 h. After allowing the reaction to cool to rt the mixture was neutralized with HCl to pH 7 and extracted with EtOAc (2×). The combined organic layers were then concentrated under reduced pressure and the residue was purified with FCC to give 4-bromo-7-fluoro-1H-indole-3-carbaldehyde.

Example 7

7-A. (S)-Tert-butyl 4-hydroxy-3,3-dimethylpiperidine-1-carboxylate

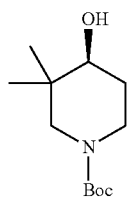 [SMILES: CC(C)(C)OC(=O)N1CC[C@H](O)C(C)(C)C1]

To a solution of tert-butyl 3,3-dimethyl-4-oxopiperidine-1-carboxylate (10.0 g, 44.0 mmol) in THF (45 mL) at 0° C. was added dropwise (–)-DIP-Chloride (50-65 wt. % in heptane, 48.9 mL, 79.0 mmol), and the reaction mixture was stirred at 5° C. for 4 days. The reaction mixture was then diluted with Et$_2$O (250 mL) and diethanol amine (8.0 g) was added to give a massive amount of white precipitate. The resulting mixture was vigorously stirred at room temperature for 3 h. The heterogeneous mixture was then filtered through a Buchner funnel packed with Celite®, and the resulting filtrate was concentrated to give a yellow residue. The residue was purified by silica gel chromatography (25-70% EtOAc/heptane) to provide (S)-tert-butyl 4-hydroxy-3,3-dimethylpiperidine-1-carboxylate. (90% ee). Enantiomeric excess determined by Mosher ester analysis. $^1$H NMR (400 MHz, CDCl$_3$) δ ppm 3.79-3.94 (m, 1 H), 3.53 (d, J=13.4 Hz, 1 H), 3.42 (dd, J=9.2, 4.2 Hz, 1 H), 3.05 (ddd, J=13.2, 9.8, 3.5 Hz, 1 H), 2.74 (d, J=13.1 Hz, 1 H), 1.69-1.80 (m, 2 H), 1.58 (m, 1 H), 1.46 (s, 9 H), 0.97 (s, 3 H), 0.90 (s, 3 H).

7-B. (S)-Tert-butyl 4-hydroxy-3,3-dimethylpiperidine-1-carboxylate

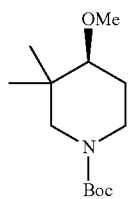 [SMILES: CO[C@H]1CCN(C(=O)OC(C)(C)C)CC1(C)C]

To a solution of (S)-tert-butyl 4-hydroxy-3,3-dimethylpiperidine-1-carboxylate (6.43 g, 28.0 mmol) in DMF (100 mL) at 0° C. was added NaH (60% dispersion in mineral oil, 2.24 g, 56.1 mmol), and the reaction mixture was stirred at room temperature for 15 min. Then, MeI (3.16 mL, 50.5 mmol) was added dropwise and the resulting mixture was stirred at room temperature for 1.5 h. The reaction mixture was then cooled to 0° C. and sat. aq. NH$_4$Cl was added slowly and stirred for 5 min. The solution was warmed to room temperature and diluted with water (250 mL) and extracted with Et$_2$O (3×200 mL). The combined organic extracts were washed with brine (100 mL), dried (Na$_2$SO$_4$), filtered, and concentrated. The residue was purified by silica gel chromatography (5-30% EtOAc/heptane) to provide (S)-tert-butyl 4-methoxy-3,3-dimethylpiperidine-1-carboxylate. $^1$H NMR (400 MHz, CDCl$_3$) δ ppm 3.75 (br. s., 1 H), 3.41 (d, J=13.1 Hz, 1 H), 3.35 (s, 3 H), 3.09 (ddd, J=13.3, 9.3, 3.7 Hz, 1 H), 2.86 (dd, J=8.5, 3.7 Hz, 1 H), 2.80 (d, J=13.1 Hz, 1 H), 1.74-1.85 (m, 1 H), 1.48-1.59 (m, 1 H), 1.46 (s, 9 H), 0.94 (s, 3 H), 0.88 (s, 3 H).

7-C. (S)-4-Methoxy-3,3-dimethylpiperidin-1-ium chloride

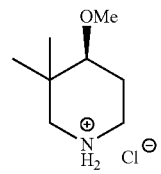

To neat (S)-tert-butyl 4-methoxy-3,3-dimethylpiperidine-1-carboxylate (5.87 g, 24.1 mmol) was added 4.0 M HCl in dioxane (24.1 mL, 96.0 mmol), and the reaction mixture was stirred at room temperature for 16 h. Then, the reaction mixture was diluted with heptanes (60 mL) and Et$_2$O (10 mL) and stirred at room temperature until a white solid crashed out. The heterogeneous mixture was then filtered and the white solid was collected to afford (S)-4-methoxy-3,3-dimethylpiperidin-1-ium chloride. $^1$H NMR (400 MHz, CDCl$_3$) δ ppm 9.58 (br. s., 1 H), 9.23 (br. s., 1 H), 3.34 (s, 3 H), 3.09-3.24 (m, 2 H), 3.05 (t, J=10.0 Hz, 1 H), 2.97 (dd, J=5.4, 2.4 Hz, 1 H), 2.76 (d, J=13.1 Hz, 1 H), 2.04-2.17 (m, 1 H), 1.84-1.96 (m, 1 H), 1.19 (s, 3 H), 1.05 (s, 3 H).

The corresponding TFA salt was also prepared with a similar method using TFA in DCM.

The following compounds were prepared in a similar manner.

7-D. (R)-4-Methoxy-3,3-dimethylpiperidin-1-ium chloride

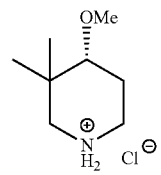

$^1$H NMR (400 MHz, CD$_2$Cl$_2$) δ ppm 9.62 (br. s., 1 H) 9.36 (br. s., 1 H) 3.33 (s, 3 H) 3.15 (d, J=8.84 Hz, 1 H) 2.90-3.08 (m, 3 H) 2.65-2.77 (m, 1 H) 1.98-2.11 (m, 1 H) 1.81-1.93 (m, 1 H) 1.15 (s, 3 H) 1.04 (s, 3 H).

7-E. (R)-4-Ethoxy-3,3-dimethylpiperidin-1-ium chloride

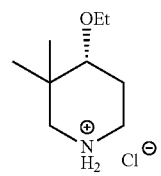

$^1$H NMR (400 MHz, CDCl$_3$) δ ppm 9.56 (br. s., 1 H) 9.14 (br. s., 1 H) 3.53-3.65 (m, 1 H) 3.30-3.40 (m, 1 H) 3.10-3.27

(m, 2 H) 3.06 (d, J=4.93 Hz, 2 H) 2.75 (d, J=12.25 Hz, 1 H) 2.01-2.16 (m, 1 H) 1.79-1.92 (m, 1 H) 1.20 (s, 3 H) 1.18 (t, J=5.40 Hz, 3 H) 1.04 (s, 3 H).

Example 8

8-A. (2R,4R)-2-Methyl-1-((R)-1-phenylethyl)piperidin-4-ol and 8-B. (2R,4S)-2-Methyl-1-((R)-1-phenylethyl)piperidin-4-ol

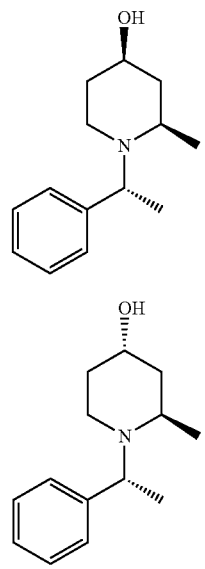

Preparation of (R)-2-methyl-1-((R)-1-phenylethyl)piperidin-4-one and (S)-2-methyl-1-((R)-1-phenylethyl)piperidin-4-one done done as described in WO2004/94380. The mixture of diastereomers was separated by FCC (0-15% EtOAc/heptane) to provide (R)-2-methyl-1-((R)-1-phenylethyl)piperidin-4-one as the first eluting diastereomer. Analytical data for (R)-2-methyl-1-((R)-1-phenylethyl)piperidin-4-one: $^1$H NMR (400 MHz, CDCl$_3$) δ ppm 7.46 (d, J=7.07 Hz, 2 H) 7.35 (t, J=7.45 Hz, 2 H) 7.23-7.28 (m, 1 H) 4.02 (q, J=6.57 Hz, 1 H) 3.39 (m, 1 H) 2.73-2.83 (m, 1 H) 2.61-2.72 (m, 2 H) 2.30-2.40 (m, 1 H) 2.16-2.30 (m, 2 H) 1.35 (d, J=6.82 Hz, 3 H) 1.15 (d, J=6.57 Hz, 3 H); $[α]^{25}_D$+46.28 (c 1.0, MeOH).

To a precooled (0° C.) solution of (R)-2-methyl-1-((R)-1-phenylethyl)piperidin-4-one, prepared as above, (2.64 g, 12.1 mmol) in EtOH (50 mL) was added sodium borohydride (551 mg, 14.6 mmol). After 2 h, reaction was quenched with a saturated solution of ammonium chloride and allowed to warm to room temperature. The pH was then adjusted to 9 by the addition of 4 N NaOH and then extracted with EtOAc (3×). The combined organic layers were washed with brine, dried over anhydrous sodium sulfate, filtered, and concentrated under reduced pressure. The diasteromers 8-A and 8-B were then purified by FCC (0-50% EtOAc/heptane) with 8-A being the major product and the first eluting diastereomer followed by 8-B as the minor diastereomer product.

8-A: $^1$H NMR (400 MHz, CDCl$_3$) δ ppm 7.49 (d, J=8.1 Hz, 2 H), 7.31-7.40 (m, 2 H), 7.21-7.28 (m, 1 H), 4.34 (q, J=6.8 Hz, 1 H), 3.62 (tq, J=10.5, 5.1 Hz, 1 H), 2.60-2.72 (m, 1 H), 2.47 (dt, J=11.8, 3.7 Hz, 1 H), 2.13 (td, J=11.9, 2.3 Hz, 1 H), 2.00 (ddt, J=11.9, 4.7, 2.5 Hz, 1 H), 1.74-1.85 (m, 1 H), 1.36-1.45 (m, 1 H), 1.30-1.36 (m, 2 H), 1.23-1.30 (m, 6 H); MS (ESI+) m/z 220.2 (M+H)$^+$; $[α]^{25}_D$-51.66 (c 1.0, MeOH).

8-B: $^1$H NMR (400 MHz, CDCl$_3$) δ ppm 7.40-7.46 (m, 2 H), 7.33 (t, J=7.6 Hz, 2 H), 7.21-7.27 (m, 1 H), 3.99 (br. s., 1 H), 3.89 (q, J=6.7 Hz, 1 H), 3.32 (sxt, J=6.0 Hz, 1 H), 2.48-2.58 (m, 1 H), 2.32 (ddd, J=12.1, 8.5, 3.4 Hz, 1 H), 1.77 (t, J=5.6 Hz, 2 H), 1.66-1.74 (m, J=12.6, 3.4, 3.4 Hz, 1 H), 1.47 (dtd, J=12.3, 8.1, 3.8 Hz, 1 H), 1.29-1.35 (m, 4 H), 1.13 (d, J=6.6 Hz, 3 H); MS (ESI+) m/z 220.2 (M+H)$^+$.

8-C. (2R,4R)-4-Methoxy-2-methyl-1-((R)-1-phenylethyl)piperidine

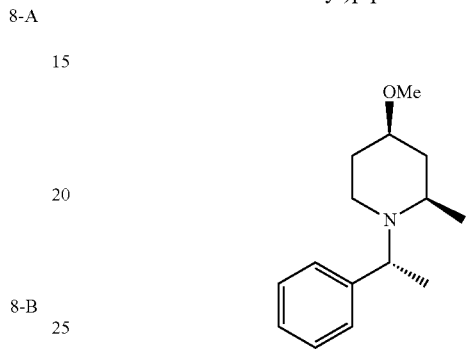

Sodium hydride (710 mg, 17.7 mmol; 60% dispersion in mineral oil) was added to a solution of (2R,4R)-2-methyl-1-((R)-1-phenylethyl)piperidin-4-ol (1.95 g, 8.87 mmol) in DMF (47 mL) at 0° C. After 15 min, iodomethane (666 μL, 10.7 mmol) was added and the solution was allowed to warm to room temperature. After 1 h, water was slowly added at 0° C. The aqueous phase was extracted with a 4:1 mixture of EtOAc/n-heptane (3×). The combined organic layers were washed with brine (3×), dried over anhydrous sodium sulfate, filtered, and concentrated under reduce pressure. The residue was purified via FCC (0-30% EtOAc/heptane) to give the title compound. $^1$H NMR (400 MHz, CDCl$_3$) δ ppm 7.49 (d, J=7.8 Hz, 2H), 7.35 (t, J=7.6 Hz, 2 H), 7.21-7.28 (m, 1 H), 4.33 (q, J=6.8 Hz, 1 H), 3.36 (s, 3 H), 3.11-3.22 (m, 1 H), 2.59-2.71 (m, 1 H), 2.49 (dt, J=11.9, 3.8 Hz, 1 H), 1.99-2.16 (m, 2 H), 1.85 (d, J=12.1 Hz, 1 H), 1.33-1.42 (m, 1 H), 1.28 (d, J=7.1 Hz, 4 H), 1.25 (d, J=6.3 Hz, 3 H); MS (ESI+) m/z 234.2 (M+H)$^+$; $[α]^{25}_D$-49.17 (c 1.0, MeOH).

8-D. (+)-(2R,4R)-4-Methoxy-2-methylpiperidine hydrochloride

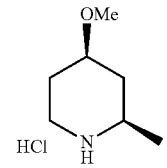

Palladium on carbon (5%) (857 mg, 0.403 mmol) and HCl (concentrated) (734 μL, 24.3 mmol) were added to (2R,4R)-4-methoxy-2-methyl-1-((R)-1-phenylethyl)piperidine (1.88 g, 8.05 mmol) in MeOH (80 mL). Hydrogen was bubbled through the reaciton mixture for 15 min. After 1 h, the reaction mixture was filtered through Celite®. The filtrate was washed with a solution of DCM/MeOH (4:1) and concentrated in vacuo to give the title compound. $^1$H NMR (400

MHz, MeOD) δ ppm 3.40-3.51 (m, 2 H), 3.38 (s, 3 H), 3.19-3.28 (m, 1 H), 3.01 (td, J=13.5, 2.7 Hz, 1 H), 2.19-2.36 (m, 2 H), 1.48 (tdd, J=13.7, 10.7, 4.5 Hz, 1 H), 1.35 (d, J=6.6 Hz, 3 H), 1.25-1.33 (m, 1 H); [α]$^{25}_D$+15.03 (c 1.0, MeOH).

The following compounds were prepared in a similar manner.

8-E. (2R,4S)-4-Methoxy-2-methylpiperidine hydrochloride

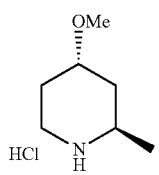

$^1$H NMR (400 MHz, MeOD) δ ppm 3.66 (quin, J=2.9 Hz, 1 H), 3.39-3.47 (m, 1 H), 3.35 (s, 3 H), 3.16-3.23 (m, 2 H), 2.03-2.18 (m, 2 H), 1.69-1.82 (m, 1 H), 1.53-1.63 (m, 1 H), 1.29 (d, J=6.6 Hz, 3 H).

8-F. (2S,4S)-4-Methoxy-2-methylpiperidine hydrochloride

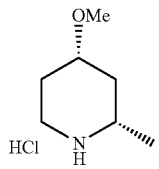

$^1$H NMR (400 MHz, CDCl$_3$) δ ppm 9.88 (br. s., 1 H), 9.41 (br. s., 1 H), 3.54 (br. s., 1 H), 3.38 (s, 3 H), 3.38 (obs m, 1 H) 3.21 (br. s., 1 H), 2.88 (br. s., 1 H), 2.21 (d, J=11.9 Hz, 2 H), 1.91 (br. s., 1 H), 1.71 (br. s., 1 H), 1.61 (br. s., 3 H).

8-G. (2S,4R)-4-Methoxy-2-methylpiperidine hydrochloride

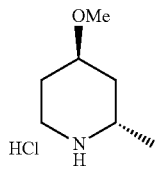

$^1$H NMR (400 MHz, CDCl$_3$) δ ppm 9.50 (br. s., 1 H), 9.17 (br. s., 1 H), 3.77 (q, J=7.0 Hz, 1 H), 3.66 (br. s., 1 H), 3.48-3.61 (m, 1 H), 3.35 (s, 3 H), 3.26 (br. s., 1 H), 2.06 (d, J=8.8 Hz, 2 H), 1.17-1.34 (m, 3 H).

8-H. (2R,4R)-4-Ethoxy-2-methylpiperidine hydrochloride

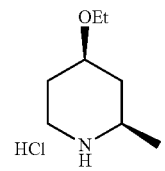

$^1$H NMR (400 MHz, MeOD) δ ppm $^1$H NMR (400 MHz, DMSO-d$_6$) δ ppm 9.18 (br. s., 1 H) 8.80 (br. s., 1 H) 3.46 (q, J=6.99 Hz, 3 H) 3.19-3.30 (m, 1 H) 3.03-3.16 (m, 1 H) 2.75-2.90 (m, 1 H) 1.98-2.14 (m, 2 H) 1.40-1.55 (m, 1 H) 1.28-1.37 (m, 1 H) 1.25 (d, J=6.57 Hz, 3 H) 1.09 (t, J=6.95 Hz, 3 H).

Example 9

9-A. (3S,4S)-Benzyl 4-hydroxy-3-methylpiperidine-1-carboxylate

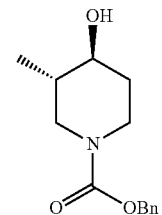 [SMILES: C[C@H]1CN(C(=O)OCc2ccccc2)CC[C@@H]1O]

To a solution of (3S,4S)-3-methylpiperidin-4-yl pivalate [6.6 g, 33.1 mmol (CAS#863249-31-4; prepared as described in WO 2005077932)] in THF (200 mL) at 0° C. under an atmosphere of argon was added LiAlH$_4$ (2.51 g, 66.2 mmol) in 3 portions. The reaction mixture was then allowed to warm to room temperature and then heated at 55° C. for ca. 14 hours. The reaction mixture was then cooled to 0° C. and quenched via slow drop-wise addition of a 9:1 mixture of THF/H$_2$O (20 mL). Then 2 N aq. NaOH (7 mL) was added and the reaction was put at room temperature. Next, water (13.2 mL) and THF (60 mL) were added and the mixture was stirred for 10 minutes. Celite® (30 grams) was added and the heterogeneous mixture was stirred for 2 minutes and then filtered through a pad of Celite®, washing the pad with 10% MeOH/THF (200 mL). The eluent was then concentrated to give a semi-solid which was dissolved in water (165 mL). To the resulting solution was added 2N aq. Na$_2$CO$_3$ (99 mL, 198 mmol), then CbzCl (9.42 mL, 66.0 mmol). The mixture was stirred at room temperature for 3.5 h. The mixture was then poured into dichloromethane and the resulting layers were separated. The aqueous layer was re-extracted with dichloromethane and the organic layers were combined, dried over Na$_2$SO$_4$, filtered and concentrated. The resulting residue was purified by silica gel flash chromatography (35-80% {Et$_2$O (2% EtOH)}/DCM) to provide: (3S,4S)-benzyl 4-hydroxy-3-methylpiperidine-1-carboxylate. $^1$H NMR (400 MHz, CD$_2$Cl$_2$) δ ppm 0.98 (d, J=6.6 Hz, 3 H) 1.31-1.53 (m, 2 H) 1.89 (dq, J=12.8, 3.6 Hz, 1 H) 2.54 (br. s., 1 H) 2.73-3.02 (m, 1 H) 3.28 (td, J=9.7, 4.3 Hz, 1 H) 3.89-4.20 (m, 2 H) 4.93-5.23 (m, 2 H) 7.19-7.47 (m, 5 H); MS (ESI+) m/z 250.1 (M+H)$^+$.

9-B. (3S,4S)-Benzyl 4-methoxy-3-methylpiperidine-1-carboxylate

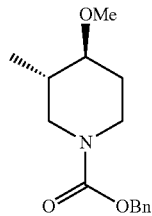 [SMILES: CO[C@H]1CCN(C(=O)OCc2ccccc2)C[C@@H]1C]

To a solution of (3S,4S)-benzyl 4-methoxy-3-methylpiperidine-1-carboxylate (4.45 g, 17.85 mmol) in DMF (100 mL) at 0° C. was added NaH (60% dispersion in oil, 1.285 g, 32.1 mmol). The reaction mixture was then put at room temperature for 10 min and then re-cooled to 0° C. MeI (1.674 mL, 26.8 mmol) was then added and the reaction was allowed to warm to room temperature. After stirring for ca. 40 minutes the reaction mixture was cooled to 0° C. and quenched with saturated aq NH$_4$Cl and diluted with Et$_2$O. The mixture was further diluted with water and the resulting layers were separated. The aqueous layer was re-extracted with Et$_2$O and the organic layers were combined, washed with brine, then dried over MgSO$_4$, filtered and concentrated. The resulting residue was purified by silica gel flash chromatography (50% Et$_2$O/Heptane) to provide: (3S,4S)-benzyl 4-methoxy-3-methylpiperidine-1-carboxylate. $^1$H NMR (400 MHz, CD$_2$Cl$_2$) δ ppm 0.95 (d, J=6.6 Hz, 3 H) 1.25-1.40 (m, 1 H) 1.56-1.68 (m, 1 H) 1.94-2.05 (m, 1 H) 2.67 (br. s., 1 H) 2.87 (td, J=8.8, 4.0 Hz, 1 H) 2.97 (ddd, J=13.6, 10.8, 3.2 Hz, 1 H) 3.33 (s, 3 H) 3.79-4.10 (m, 2 H) 4.96-5.18 (m, 2 H) 7.20-7.46 (m, 5 H); MS (ESI+) m/z 264.0 (M+H)$^+$.

9-C. (3S,4S)-4-Methoxy-3-methylpiperidine

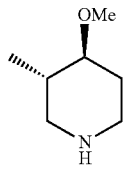

To a solution of (3S,4S)-benzyl 4-methoxy-3-methylpiperidine-1-carboxylate (4.0 g, 15.19 mmol) in MeOH (150 mL) under an argon atmosphere was added wet Pd/C [(5% dry basis) (1.617 g, 0.759 mmol)] The atmosphere was replaced with hydrogen gas via a balloon. The heterogeneous mixture was stirred for 1 hour at room temperature, and then filtered through Celite®. The filter cake was washed with dichloromethane (150 mL) followed by 20% MeOH/DCM (150 mL). The eluent was concentrated to afford (3S,4S)-4-methoxy-3-methylpiperidine which was used without the need for further purification. $^1$H NMR (400 MHz, CD$_2$Cl$_2$) δ ppm 0.91 (d, J=6.6 Hz, 3 H) 1.20 (tdd, J=12.2, 12.2, 10.5, 4.3 Hz, 1 H) 1.37-1.55 (m, 1 H) 2.03 (ddt, J=12.6, 4.2, 3.0, 3.0 Hz, 1 H) 2.21 (dd, J=12.6, 10.6 Hz, 1 H) 2.53 (td, J=12.4, 2.8 Hz, 1 H) 2.70-2.81 (m, 1 H) 2.95 (ddd, J=12.5, 4.3, 1.6 Hz, 1 H) 3.01-3.11 (m, 1 H) 3.31 (s, 3 H).

The following compounds were prepared by similar method.

9-D. (3R,4R)-4-Methoxy-3-methylpiperidine

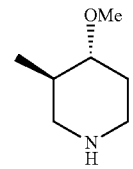

The same procedures employed to synthesize (3S,4S)-4-methoxy-3-methylpiperidine Examples 9-C were utilized, however the starting material used was (3R,4R)-3-methylpiperidin-4-yl pivalate (CAS#863249-35-8, prepared as described in WO 2005077932). $^1$H NMR (400 MHz, CD$_2$Cl$_2$) δ ppm 0.92 (d, J=6.6 Hz, 3 H) 1.22 (tdd, J=12.3, 12.3, 10.4, 4.3 Hz, 1 H) 1.39-1.55 (m, 1 H) 2.04 (dq, J=12.4, 3.5 Hz, 1 H) 2.23 (dd, J=12.6, 10.6 Hz, 1 H) 2.55 (td, J=12.4, 2.8 Hz, 1 H) 2.75 (td, J=9.7, 4.2 Hz, 1 H) 2.96 (ddd, J=12.6, 4.2, 1.4 Hz, 1 H) 3.02-3.11 (m, 1 H) 3.31 (s, 3 H).

Example 10

(3-endo)-3-Methoxy-8-azabicyclo[3.2.1]octane

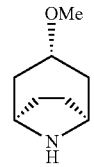

A solution of nortropine (5 g, 39.3 mmol) and Boc$_2$O (9.44 g, 43.2 mmol) in THF (100 mL) was stirred at room temperature overnight. The mixture was concentrated under reduced pressure and the residue was triturated with heptanes to provide crude (3-endo)-tert-butyl 3-hydroxy-8-azabicyclo[3.2.1]octane-8-carboxylate as a off white solid. MS (ESI+) m/z 228.0 (M+H)$^+$.

NaH (60% dispersion in mineral oil, 1.5 g, 38 mmol) was added portion wise to a solution of crude (3-endo)-tert-butyl 3-hydroxy-8-azabicyclo[3.2.1]octane-8-carboxylate (4.3 g, 19 mmol) in DMF (43 mL) at 0° C. After 30 min methyl iodide (4.8 g, 34.1 mmol) was added and the mixture was allowed to warm to room temperature. After 1.5 hours the reaction mixture was cooled to 0° C. and sat. NH$_4$Cl aqueous solution was added slowly to quench excess base. The resulting mixture was diluted with H$_2$O (100 mL) and Et$_2$O (100 mL). The layers were mixed and then separated. The aqueous layer was further extracted with Et$_2$O (2×). The combined organics were washed with brine, dried (Na$_2$SO$_4$) and concentrated to provide crude (3-endo)-tert-butyl 3-methoxy-8-azabicyclo[3.2.1]octane-8-carboxylate. MS (ESI+) m/z 242.0 (M+H)$^+$.

A solution of (3-endo)-tert-butyl 3-methoxy-8-azabicyclo[3.2.1]octane-8-carboxylate (1.9 g, 8.0 mmol in DCM (20 mL) and TFA (10 mL) was stirred at room temperature for 3 h. The reaction mixture was then concentrated in vacuo to provide (3-endo)-3-methoxy-8-abicyclo[3.2.1]octane TFA salt. $^1$H NMR (400 MHz, DMSO) δ ppm 3.91 (s, 2 H) 3.46 (t, J=2.78 Hz, 1 H) 3.22 (s, 3 H) 2.10 (d, J=7.33 Hz, 2 H) 2.00 (t, J=3.03 Hz, 4 H) 1.84-1.92 (m, 2 H).

Example 11

11-A. Racemic (cis)-tert-butyl 4-methoxy-3-methylpiperidine-1-carboxylate

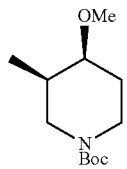

To a solution of racemic (cis)-tert-butyl 4-hydroxy-3-methylpiperidine-1-carboxylate (310 mg, 1.44 mmol) (CAS#955028-93-0; prepared as described in US 20070249589)] in DMF (5 mL) at 0° C. was added NaH (60% dispersion in mineral oil, 75 mg, 1.87 mmol). The reaction mixture was stirred at 0° C. for 10 minutes and MeI (0.13 mL, 2.02 mmol) was added. After 2 h the reaction was quenched with saturated aqueous NH$_4$Cl. The aqueous phase was washed three times with EtOAc. The combined organic extracts were washed with brine, dried over Na$_2$SO$_4$, filtered, and concentrated. The resulting residue was purified by silica gel flash chromatography (0-100% EtOAc/heptanes) to provide racemic (cis)-tert-butyl 4-methoxy-3-methylpiperidine-1-carboxylate. $^1$H NMR (400 MHz, CDCl$_3$) δ ppm 3.36-3.50 (m, 6 H), 3.34 (dt, J=6.6, 3.3 Hz, 1 H), 3.22-3.29 (m, 1 H), 1.78-1.96 (m, 2 H), 1.49 (s, 9 H), 0.95 (d, J=6.8 Hz, 3 H).

11-B. Racemic (cis)-4-methoxy-3-methylpiperidine 2,2,2-trifluoroacetate

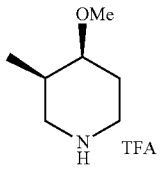

A solution of racemic (cis)-tert-butyl 4-methoxy-3-methylpiperidine-1-carboxylate (230 mg, 1.0 mmol) in DCM (2 mL) with TFA (0.23 mL, 3.01 mmol) was stirred at room temperature overnight. The reaction mixture was then concentrated to give racemic (cis)-4-methoxy-3-methylpiperidine 2,2,2-trifluoroacetate. $^1$H NMR (400 MHz, DMSO-d$_6$) δ ppm 3.27 (s, 3 H), 3.01-3.09 (m, 1 H), 2.93-3.00 (m, 1 H), 2.81-2.93 (m, 1 H), 2.69-2.77 (m, 1 H), 1.90-2.08 (m, 2 H), 1.57-1.67 (m, 1 H), 0.90 (d, J=7.1 Hz, 3 H).

Example 12

(R)-1-(3-Methylpiperazin-1-yl)ethanone 2,2,2-trifluoroacetate

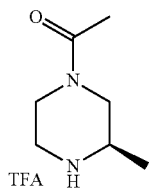

A mixture of (R)-tert-butyl 2-methylpiperazine-1-carboxylate (4.8 g, 23.97 mmol), Ac$_2$O (3.39 mL, 36.0 mmol) and pyridine (3.88 mL, 47.9 mmol) in DCM (30 mL) was stirred at rt for 30 min. Reaction was diluted with EtOAc, washed with diluted HCl, brine and sat NaHCO$_3$, brine, and dried over Na$_2$SO$_4$, concentrated. Resulting residue was treated with 1N NaOH in ether, extracted with ether, washed with brine, dried over Na$_2$SO$_4$, concentrated and purified by FCC (0-10% MeOH in DCM) to give (R)-tert-butyl 4-acetyl-2-methylpiperazine-1-carboxylate. $^1$H NMR (400 MHz, CD$_2$Cl$_2$) δ ppm 4.14-4.46 (m, 2 H) 3.74-3.91 (m, 1 H) 3.46-3.72 (m, 1 H) 2.92-3.35 (m, 2 H) 2.56-2.91 (m, 1 H) 2.05 (d, J=16.67 Hz, 3 H) 1.44 (s, 9 H) 1.03-1.18 (m, 3 H). MS (ESI+) m/z 243.2 (M+H)$^+$.

A mixture of (R)-tert-butyl 4-acetyl-2-methylpiperazine-1-carboxylate (1.34 g, 5.53 mmol) and TFA (10 mL, 130 mmol) in DCM (30 mL) was stirred at rt for 45 min, then concentrated, diluted with DCM, and then concentrated again which was repeated 3 times. Dried under high vacuum at 80° C. to give (R)-1-(3-methylpiperazin-1-yl)ethanone 2,2,2-trifluoroacetate (1.95 g). MS (ESI+) m/z 143.0 (M+H)$^+$.

Example 13

13-A. 3-((Phenylsulfonyl)methylene)oxetane

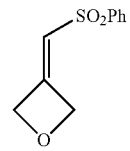

A solution of BuLi (2.5 M in hexanes, 22.5 mL, 56.3 mmol) was added over 10 min to a solution of methylphenylsulfone (4.00 g, 25.6 mmol) in THF (70 mL) at 0° C. The solution went from clear to light green to a heterogeneous yellow suspension. The mixture was stirred for 30 min at 0° C. and then chlorodiethylphosphonate (4.46 mL, 30.7 mmol) was added dropwise and the stirring was continued for 30 min, at which point the solution turned clear orange. The reaction mixture was then cooled to −78° C. and oxetan-3-one (1.85 g, 25.6 mmol) was added in THF (3 mL). The reaction mixture turned pale brown/yellow in color. After stirring for another 1.5 h, the reaction mixture was filtered through a plug of silica gel. The filtrate was triturated with solid NH$_4$Cl until pH reached 7. The mixture was then filtered and the filtrate was concentrated. The residue was purified by silica gel chromatography (0-60% EtOAc/heptane) to provide 3-((phenylsulfonyl)methylene)oxetane. $^1$H NMR (400 MHz, CD$_2$Cl$_2$) δ ppm 7.86-7.99 (m, 2 H) 7.68-7.77 (m, 1 H) 7.57-7.68 (m, 2 H) 6.18 (t, J=2.40 Hz, 1 H) 5.59-5.70 (m, 2 H) 5.30 (td, J=3.41, 2.27 Hz, 2 H)

13-B. 2-Methyl-5-(3-((phenylsulfonyl)methyl)oxetan-3-yl)phenol

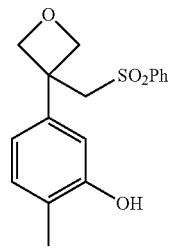

A solution of KOH (1.5 M in water, 14.2 mL, 21.3 mmol) was added to a solution of [Rh(cod)Cl]$_2$ (0.525 g, 1.07 mmol) in dioxane (60 mL). The resulting yellow solution was stirred for 1 min. Then, 3-hydroxy-4-methylphenyl boronic acid (6.48 g, 42.6 mmol) and a solution of 3-((phenylsulfonyl)methylene)oxetane (4.48 g, 21.3 mmol) in dioxane (40 mL) were added in that order. After 1 h, a solution of KOH (1.5 M in water, 14.2 mL, 21.3 mmol) was added. After another 10 min, [Rh(cod)Cl]$_2$ (0.525 g, 1.07 mmol) was added. The resulting mixture was stirred at room temperature overnight, and then partitioned between Et$_2$O and aqueous NH$_4$Cl. The aqueous layer was extracted with Et$_2$O (3×). (During extractions, some solids crashed out in the organic layer, but went back into solution over time). The combined organic layers were dried (Na$_2$SO$_4$), filtered, and concentrated. The dark orange residue was purified by silica gel chromatography (30-100% EtOAc/heptane) to provide 2-methyl-5-(3-((phenylsulfonyl)methyl)oxetan-3-yl)phenol. $^1$H NMR (400 MHz, CD$_2$Cl$_2$) δ ppm 7.52-7.63 (m, 3 H) 7.41 (t, J=7.71 Hz, 2 H) 6.99 (d, J=7.83 Hz, 1 H) 6.57 (dd, J=7.83, 1.77 Hz, 1 H) 6.50 (d, J=2.02 Hz, 1 H) 4.99 (d, J=6.57 Hz, 2 H) 4.91 (d, J=6.57 Hz, 2 H) 4.03 (s, 2 H) 2.20 (s, 3 H)

13-C. 2-Methyl-5-(3-methyloxetan-3-yl)phenol

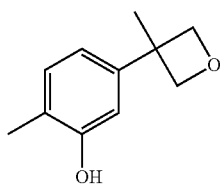

Magnesium (granulate) (8.70 g, 358 mmol) was added to a solution of crude 2-methyl-5-(3-((phenylsulfonyl)methyl)oxetan-3-yl)phenol (7.6 g, 23.9 mmol) in MeOH (100 mL). The resulting mixture was stirred for 2 min in an ultrasound bath. The flask was then fitted with a condenser. Stirring was continued for 3 h, at which point the reaction mixture turned cloudy and off white in color. The reaction was exothermic, which caused the solvent to reflux. Water bath was added to lower the reaction mixture temperature to room temperature. The reaction mixture was then stirred overnight and became heterogeneous and pale orange in color. Et$_2$O (525 mL) was added, followed by Na$_2$SO$_4$.10H$_2$O (85 g). The resulting mixture was stirred for 2 h at room temperature and Celite® was then added. The resulting mixture was stirred for another 1 h and filtered through a Buchner funnel packed with Celite®. The cake was washed with EtOAc (2×) and MeOH (1×). The light yellow filtrate was concentrated and the residue was triturated with CHCl$_3$ (220 mL) and filtered. The filtrate was concentrated to provide 2-methyl-5-(3-methyloxetan-3-yl)phenol. $^1$H NMR (400 MHz, CD$_2$Cl$_2$) δ ppm 7.14 (d, J=7.83 Hz, 1 H) 6.73 (d, J=7.58 Hz, 1 H) 6.69 (d, J=1.77 Hz, 1 H) 4.92 (d, J=5.31 Hz, 2 H) 4.61 (d, J=5.56 Hz, 2 H) 2.26 (s, 3 H) 1.72 (s, 3 H)

13-D. 2-Methyl-5-(3-methyloxetan-3-yl)phenyl trifluoromethanesulfonate

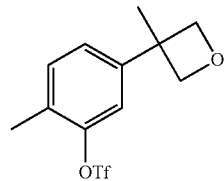

Tf$_2$O (3.07 mL, 18.2 mmol) was added dropwise to a solution of 2-methyl-5-(3-methyloxetan-3-yl)phenol (2.70 g, 15.2 mmol) and pyridine (1.71 mL, 21.2 mmol) in DCM (25 mL) at 0° C. The red/orange mixture was stirred at 0° C. for 1.5 h, then partitioned between DCM and water. The aqueous layer was extracted with DCM (2×). The combined organic layers were dried (Na$_2$SO$_4$), filtered, and concentrated. The residue was purified by silica gel chromatography (0-40% EtOAc/heptane) to provide 2-methyl-5-(3-methyloxetan-3-yl)phenyl trifluoromethanesulfonate. $^1$H NMR (400 MHz, CD$_2$Cl$_2$) δ ppm 7.38 (d, J=8.08 Hz, 1 H) 7.26 (dd, J=7.96, 1.89 Hz, 1 H) 7.14 (d, J=1.77 Hz, 1 H) 4.89 (d, J=5.56 Hz, 2 H) 4.66 (d, J=5.81 Hz, 2 H) 2.41 (s, 3 H) 1.75 (s, 3 H).

Example 14

5-Cyclopropyl-2-methylphenyl trifluoromethanesulfonate

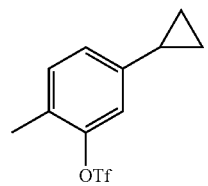 [SMILES: Cc1ccc(C2CC2)cc1OS(=O)(=O)C(F)(F)F]

A solution of 5-bromo-2-methylphenol (2.00 g, 10.7 mmol), potassium cyclopropyltrifluoroborate (2.85 g, 19.2 mmol), bis(di-tert-butyl(4-dimethylaminophenyl)phosphine)dichloropalladium(II) (0.379 g, 0.535 mmol) and K$_3$PO$_4$ (5.67 g, 26.7 mmol) in toluene (40 mL) and water (10 mL) was allowed to stir at 100° C. for 17 h under nitrogen. The reaction was monitored by $^1$H NMR. The mixture was cooled to rt, and diluted with 1 M HCl aq (100 mL), brine and EtOAc. The products were extracted twice with EtOAc. The combined organic layers were washed with brine, dried over MgSO$_4$, filtered, and concentrated to give crude as red oil (1.73 g). The crude was used without further purification.

To a solution of the crude product (1.73 g) and pyridine (1.21 mL, 15.0 mmol) in DCM (15 mL), Tf$_2$O (2.17 mL, 12.8 mmol) was added at 0° C. under nitrogen. The mixture was allowed to stir for 1 h. The reaction was monitored by TLC (25% EtOAc/heptane). The mixture was diluted with brine and DCM. The organic layer was separated and concentrated. The residue was purified by flash column chromatography on 40 g silica gel (with 15 g pre-column of silica gel; eluent:

heptane/EtOAc=100:0 to 85:15) to give 5-cyclopropyl-2-methylphenyl trifluoromethanesulfonate. ¹H NMR (400 MHz, CDCl₃) δ ppm 7.16 (d, J=7.87 Hz, 1 H), 6.96 (dd, J=1.64, 7.87 Hz, 1 H), 6.92 (d, J=1.64 Hz, 1 H), 2.32 (s, 3 H), 1.85-1.92 (m, 1 H), 0.97-1.01 (m, 2 H), 0.65-0.69 (m, 2 H).

Example 15

15-A. 5-Isopropyl-2-methylphenyl trifluoromethanesulfonate

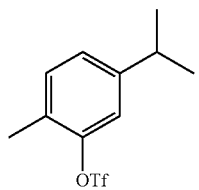 [SMILES: Cc1ccc(C(C)C)cc1OS(=O)(=O)C(F)(F)F]

To a solution of the carvacrol (5.0 g, 33.3 mmol) and pyridine (20 mL) in DCM (40 mL) was added Tf₂O (8.44 mL, 33.3 mmol) at 0° C. under nitrogen. The solution was stirred for 0.5 h at that temperature and then 0.5 h at room temperature. At that point the reaction was diluted with DCM (250 mL) and 1 M HCl (250 mL). The layers were mixed and then separated. The aqueous layer was further extracted with DCM (250 mL) and the combined organic layers were then dried (Na₂SO₄), filtered, and concentrated. The residue was then purified by FCC (10-30% EtOAc/heptane) to give the title compound. ¹H NMR (400 MHz, CDCl₃) δ ppm 7.19-7.24 (m, 1 H) 7.12-7.17 (m, 1 H) 7.08 (d, J=1.52 Hz, 1 H) 2.92 (spt, J=6.91 Hz, 1 H) 2.35 (s, 3 H) 1.25 (d, J=6.82 Hz, 6 H).

15-B. 2-cyano-5-cyclopropylphenyl trifluoromethanesulfonate

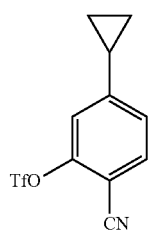 [SMILES: N#Cc1ccc(C2CC2)cc1OS(=O)(=O)C(F)(F)F]

Step 1: A solution of 4-bromo-2-hydroxybenzonitrile (1 g, 5.05 mmol), potassium cyclopropyltrifluoroborate (1.495 g, 10.10 mmol), K₃PO₄ (5.05 ml, 15.15 mmol) and PdCl₂(Amphos)₂ (0.358 g, 0.505 mmol) in toluene (25 mL) was allowed to stir at 100° C. under nitrogen overnight. The mixture was then cooled to room temperature, diluted with EtOAc/NH₄Cl (aq), and filtered through a pad of Celite. The organic layer was seperated, dried over Na₂SO₄, filtered and concentrated. The residue was purified by FCC (0-50% EtOAc/heptane) to provide 4-cyclopropyl-2-hydroxybenzonitrile, ¹H NMR (400 MHz, CH₂Cl₂) δ 12.17 (br. s., 1H), 7.23 (d, J=8.34 Hz, 1H), 6.51-6.58 (m, 2H), 1.82 (tt, J=5.02, 8.37 Hz, 1H), 0.94-1.00 (m, 2H), 0.68-0.73 (m, 2H).

Step 2: The title compound was prepared from 4-cyclopropyl-2-hydroxybenzonitrile in a similar manner as example 15-A. ¹H NMR (400 MHz, CD₃Cl) δ ppm 7.63 (d, J=8.08 Hz, 1H), 7.16 (dd, J=1.52, 8.08 Hz, 1H), 7.13 (d, J=1.77 Hz, 1H), 2.01 (tt, J=4.93, 8.34 Hz, 1H), 1.19-1.26 (m, 2H), 0.82-0.88 (m, 2H).

Example 16

16-A. 6-Benzyl-2-chloro-4-methoxy-5,6,7,8-tetrahydropyrido[4,3-d]pyrimidine

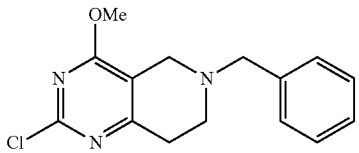 [SMILES: COc1nc(Cl)nc2c1CN(Cc1ccccc1)CC2]

To a solution of 6-benzyl-2,4-dichloro-5,6,7,8-tetrahydropyrido[4,3-d]pyrimidine (6.38 g, 21.69 mmol) in anhydrous methanol (100 mL), was added 4.67 N sodium methoxide (5.57 mL, 26 mmol) slowly at 0° C. The reaction mixture was stirred at 0° C. for 15 min, then at rt for 30 min. The reaction mixture was concentrated under reduced pressure. The residue was dissolved in DCM and washed with brine, dried over Na₂SO₄, filtered, and concentrated to give 6-benzyl-2-chloro-4-methoxy-5,6,7,8-tetrahydropyrido[4,3-d]pyrimidine which was used without the need for purification. ¹H NMR (400 MHz, CD₂Cl₂) δ ppm 7.31-7.40 (m, 4 H), 7.23-7.31 (m, 1 H), 3.95 (s, 3 H), 3.72 (br. s., 2 H), 3.43 (br. s., 2 H), 2.84 (d, J=4.5 Hz, 2 H), 2.78 (d, J=4.0 Hz, 2 H). MS (ESI+) m/z 290.4 (M+H)⁺.

16-B. 6-Benzyl-2-(2,6-dimethylphenyl)-4-methoxy-5,6,7,8-tetrahydropyrido[4,3-d]pyrimidine

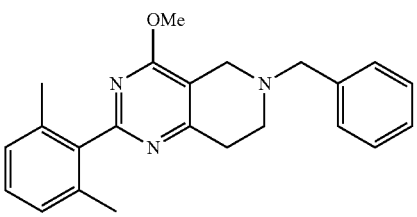 [SMILES: COc1nc(-c2c(C)cccc2C)nc2c1CN(Cc1ccccc1)CC2]

To a suspension of 6-benzyl-2-chloro-4-methoxy-5,6,7,8-tetrahydropyrido[4,3-d]pyrimidine (6.52 g, 22.5 mmol) and 2,6-dimethylphenylboronic acid (3.90 g, 26.0 mmol) in 1,2-dimethoxyethane (175 mL), was added 2 M aqueous Na₂CO₃ (35.2 mL, 70.5 mmol) and tetrakis(triphenylphosphine)palladium(0) (0.751 g, 0.651 mmol). The reaction was flushed with nitrogen, then heated to 100° C. for 48 h. The reaction mixture was cooled to r.t., then ethyl acetate and brine were added. The aqueous layer was extracted by ethyl acetate twice. The combined ethyl acetate layers were dried over Na₂SO₄, filtered, and concentrated. The resulting residue was purified via silica gel FCC (0-40% EtOAc/heptane) to give 6-benzyl-2-(2,6-dimethylphenyl)-4-methoxy-5,6,7,8-tetrahydropyrido[4,3-d]pyrimidine. ¹H NMR (400 MHz, CD₂Cl₂) δ ppm 7.23-7.46 (m, 5 H), 7.12-7.21 (m, 1 H), 7.04-7.10 (m, 1 H), 6.97 (d, J=7.6 Hz, 1 H), 3.94 (d, J=10.1 Hz, 3 H), 3.73 (d, J=16.4 Hz, 2 H), 3.36-3.56 (m, 2 H), 2.91 (d, J=4.8 Hz, 1 H), 2.84 (br. s., 2 H), 2.77 (t, J=5.4 Hz, 1 H), 2.35 (s, 3 H), 2.08 (s, 3 H). MS (ESI+) m/z 360.3 (M+H)+.

16-C. 2-(2,6-Dimethylphenyl)-4-methoxy-5,6,7,8-tetrahydropyrido[4,3-d]pyrimidine

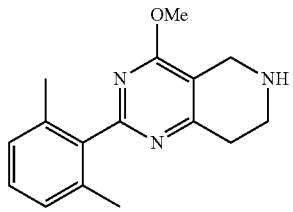 [SMILES: COc1nc(-c2c(C)cccc2C)nc2c1CNCC2]

To a solution of 6-benzyl-2-(2,6-dimethylphenyl)-4-methoxy-5,6,7,8-tetrahydropyrido[4,3-d]pyrimidine (7.08 g, 19.70 mmol) in THF (100 mL) and H₂O (12.50 mL), was added 20% Pd(OH)₂ wet (50% dry basis, 2.77 g, 1.970 mmol), followed by acetic acid (2.26 mL, 39.4 mmol). The reaction was stirred at r.t. under hydrogen atmosphere for 30 min, then heated to 40° C. for 16 h. The reaction mixture was cooled to r.t. and filtered through a Celite® pad which was washed with methanol. The organic solvent in the filtrate was removed under reduced pressure. The reaction mixture was diluted by 200 mL DCM and neutralized by saturated aqueous NaHCO₃. The mixture was extracted twice by DCM. The combined organic layers were dried over Na₂SO₄. After filtration and concentration, the resulting residue was purified via silica gel FCC (Methanol/DCM=0 to 10%) to provide 2-(2,6-dimethylphenyl)-4-methoxy-5,6,7,8-tetrahydropyrido[4,3-d]pyrimidine. ¹H NMR (400 MHz, DMSO-d₆) δ ppm 7.14-7.22 (m, 1 H), 7.05-7.11 (m, 2 H), 5.75 (s, 1 H), 3.88 (s, 3 H), 3.72 (s, 2 H), 3.01 (t, J=5.8 Hz, 2 H), 2.68 (t, J=5.7 Hz, 2 H), 2.03 (s, 6 H). MS (ESI+) m/z 270.5 (M+H)+.

16-D. 1-(2-(2,6-Dimethylphenyl)-4-methoxy-7,8-dihydropyrido[4,3-d]pyrimidin-6(5H)-yl)-4-methylpentane-1,3-dione

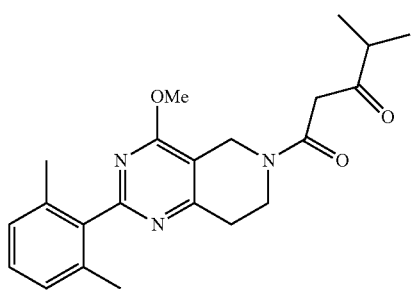 [SMILES: COc1nc(-c2c(C)cccc2C)nc2c1CN(C(=O)CC(=O)C(C)C)CC2]

A mixture of 2-(2,6-dimethylphenyl)-4-methoxy-5,6,7,8-tetrahydropyrido[4,3-d]pyrimidine (4.8 g, 17.82 mmol), methyl 4-methyl-3-oxopentanoate (5.14 g, 35.6 mmol), and DMAP (0.327 g, 2.67 mmol) was dissolved in toluene (70 mL). The mixture was evenly divided into four 20 mL microwave vials. Each vial was heated to 150° C. for 30 min via microwave irradiation. The reaction mixtures were combined and directly concentrated. The resulting residue was purified via silica gel FCC (0-80% EtOAc/heptane) to give 1-(2-(2,6-dimethylphenyl)-4-methoxy-7,8-dihydropyrido[4,3-d]pyrimidin-6(5H)-yl)-4-methylpentane-1,3-dione. MS (ESI+) m/z 382.3 (M+H)+.

16-E. 2-(2,6-Dimethylphenyl)-6-(3-isopropyl-1-methyl-1H-pyrazol-5-yl)-4-methoxy-5,6,7,8-tetrahydropyrido[4,3-d]pyrimidine

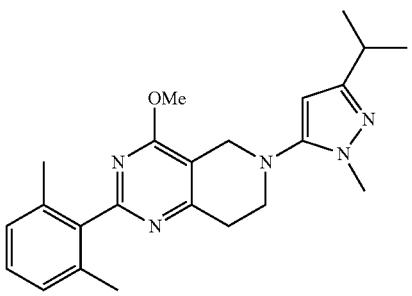 [SMILES: COc1nc(-c2c(C)cccc2C)nc2c1CN(c1cc(C(C)C)nn1C)CC2]

To a solution of 1-(2-(2,6-dimethylphenyl)-4-methoxy-7,8-dihydropyrido[4,3-d]pyrimidin-6(5H)-yl)-4-methylpentane-1,3-dione (5.92 g, 15.52 mmol) in THF (80 mL) was added pyridine (5 mL). the resulting solution was evenly divided into four microwave 20 mL vials. To each microwave via was added, methyl hydrazine (0.312 mL, 5.81 mmol) and 2,4-bis(4-methoxyphenyl)-1,3,2,4-dithiadiphosphetane 2,4-disulfide (Lawesson's reagent) (1.88 g, 4.66 mmol). The vials were immediately capped and heated to 125° C. for 10 min via microwave irradiation. The reaction vials were cooled to r.t. and the reaction mixtures were combined and diluted with brine. The mixture was extracted with DCM three times. The combined organic layers were dried over Na₂SO₄. After filtration and concentration, the resulting residue was purified via silica gel FCC ((1% MeOH in EtOAc):n-heptane=0 to 100%) to provide 2-(2,6-dimethylphenyl)-6-(3-isopropyl-1-methyl-1H-pyrazol-5-yl)-4-methoxy-5,6,7,8-tetrahydropyrido[4,3-d]pyrimidine. ¹H NMR (400 MHz, CD₂Cl₂) δ ppm 7.15-7.24 (m, 1 H), 7.05-7.12 (m, 2 H), 5.77 (s, 1 H), 4.00-4.04 (m, 2 H), 3.98 (s, 3 H), 3.70 (s, 3 H), 3.28 (t, J=5.8 Hz, 2 H), 3.05 (t, J=5.8 Hz, 2 H), 2.87 (dt, J=13.9, 6.9 Hz, 1 H), 2.12 (s, 6 H), 1.23 (d, J=7.1 Hz, 6 H). MS (ESI+) m/z 392.4 (M+H)+.

16-F. 2-(2,6-Dimethylphenyl)-6-(3-isopropyl-1-methyl-1H-pyrazol-5-yl)-5,6,7,8-tetrahydropyrido[4,3-d]pyrimidin-4-ol

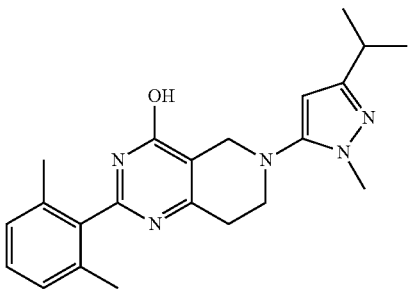 [SMILES: Cc1cccc(C)c1-c1nc(O)c2c(n1)CCN(c1cc(C(C)C)nn1C)C2]

To a solution of 2-(2,6-dimethylphenyl)-6-(3-isopropyl-1-methyl-1H-pyrazol-5-yl)-4-methoxy-5,6,7,8-tetrahydropyrido[4,3-d]pyrimidine (3.3 g, 8.51 mmol) in EtOH (30 mL) in a 150 mL sealed tube was added concentrated hydrochloride (21 mL). The tube was sealed, stirred, and heated at 90° C. for 16 h. The reaction mixture was cooled to r.t. and poured onto iced-water. Solid NaHCO$_3$ was added to neutralize the mixture. The mixture was extracted by DCM three times. The combined organic layers were dried over Na$_2$SO$_4$. After filtration and concentration, the resulting residue was purified via silica gel FCC (0-100% EtOAc/heptane) to give 2-(2,6-dimethylphenyl)-6-(3-isopropyl-1-methyl-1H-pyrazol-5-yl)-5,6,7,8-tetrahydropyrido[4,3-d]pyrimidin-4-ol. $^1$H NMR (400 MHz, CD$_2$Cl$_2$) δ ppm 9.95 (br. s., 1 H), 7.21-7.36 (m, 1 H), 7.13 (d, J=7.3 Hz, 2 H), 5.76 (s, 1 H), 3.87 (s, 2 H), 3.68 (s, 3 H), 3.22 (t, J=5.7 Hz, 2 H), 2.77-2.97 (m, 3 H), 2.22 (s, 6 H), 1.22 (d, J=7.1 Hz, 6 H). MS (ESI+) m/z 378.3 (M+H)$^+$.

16-G. 4-Chloro-2-(2,6-dimethylphenyl)-6-(3-isopropyl-1-methyl-1H-pyrazol-5-yl)-5,6,7,8-tetrahydropyrido[4,3-d]pyrimidine

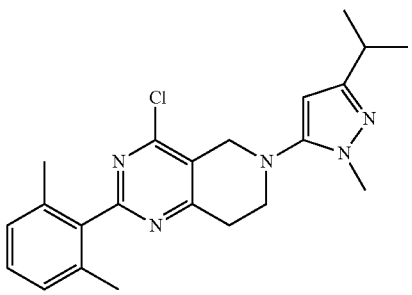 [SMILES: Cc1cccc(C)c1-c1nc(Cl)c2c(n1)CCN(c1cc(C(C)C)nn1C)C2]

To a solution of 2-(2,6-dimethylphenyl)-6-(3-isopropyl-1-methyl-1H-pyrazol-5-yl)-5,6,7,8-tetrahydropyrido[4,3-d]pyrimidin-4-ol (2.38 g, 6.3 mmol) in DCM (50 mL) at 0° C., was added (1-chloro-ethylidene)-dimethylammonium chloride (Vilsmeier reagent) (2.421 g, 18.91 mmol). The reaction was stirred at 0° C. for 5 min, then at r.t. for 30 min. Saturated aqueous NaHCO$_3$ was added to quench the reaction. The mixture was extracted with DCM three times. The combined organic layers was dried over Na$_2$SO$_4$. After filtration and concentration, the resulting residue was purified via silica gel FCC (0-100% EtOAc/heptane) to give 4-chloro-2-(2,6-dimethylphenyl)-6-(3-isopropyl-1-methyl-1H-pyrazol-5-yl)-5, 6,7,8-tetrahydropyrido[4,3-d]pyrimidine. $^1$H NMR (400 MHz, CD$_2$Cl$_2$) δ ppm 7.19-7.27 (m, 1 H), 7.11 (d, J=7.6 Hz, 2 H), 5.80 (s, 1 H), 4.16 (s, 2 H), 3.72 (s, 3 H), 3.32 (t, J=5.9 Hz, 2 H), 3.16 (t, J=5.8 Hz, 2 H), 2.88 (dt, J=13.9, 6.9 Hz, 1 H), 2.11 (s, 6 H), 1.23 (d, J=6.8 Hz, 6 H). MS (ESI+) m/z 396.3 (M+H)$^+$.

16-H. (±)-1-(2-(2,6-Dimethylphenyl)-6-(3-isopropyl-1-methyl-1H-pyrazol-5-yl)-5,6,7,8-tetrahydropyrido [4,3-d]pyrimidin-4-yl)-2-methylpiperidin-4-ol

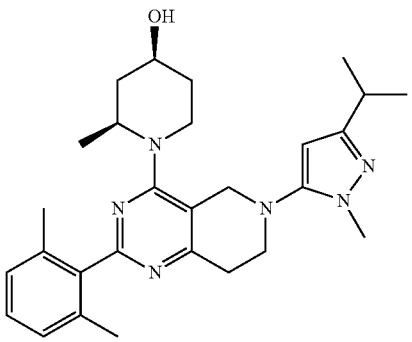 [SMILES: Cc1cccc(C)c1-c1nc2c(c(N3CC[C@H](O)C[C@@H]3C)n1)CN(c1cc(C(C)C)nn1C)CC2]

To a solution of 4-chloro-2-(2,6-dimethylphenyl)-6-(3-isopropyl-1-methyl-1H-pyrazol-5-yl)-5,6,7,8-tetrahydropyrido[4,3-d]pyrimidine (40 mg, 0.101 mmol) in N,N-dimethylacetamide (1.5 mL), was added diisopropylethylamine (0.141 mL, 0.808 mmol) and cis racemic-2-methylpiperidin-4-ol hydrochloride, (CAS#344329-35-7, 30.6 mg, 0.202 mmol). The reaction was heated to 125° C. for 42 h. After cooling, the mixture was directly purified via HPLC ((0.1% ammonium hydroxide in acetonitrile/water 35%-100%) to give 26 mg of product. $^1$H NMR (400 MHz, CD$_2$Cl$_2$) δ ppm 7.14-7.24 (m, 1 H), 7.04-7.12 (m, 2 H), 5.70 (s, 1 H), 4.15 (d, J=15.2 Hz, 1 H), 3.94 (d, J=15.4 Hz, 1 H), 3.78-3.91 (m, 1 H), 3.69 (s, 3H), 3.57-3.67 (m, 1 H), 3.27-3.39 (m, 2 H), 3.19-3.27 (m, 1 H), 3.02-3.12 (m, 2 H), 2.96 (ddd, J=12.8, 9.3, 3.2 Hz, 1 H), 2.86 (ddd, J=13.8, 7.1, 6.9 Hz, 1 H), 2.09 (s, 6 H), 1.87-2.02 (m, 2 H), 1.82 (d, J=3.0 Hz, 1 H), 1.56-1.71 (m, 1 H), 1.49 (dt, J=12.9, 8.3 Hz, 1 H), 1.22 (d, J=7.1 Hz, 6 H), 1.14 (d, J=6.3 Hz, 3 H); MS (ESI+) m/z 475.4 (M+H)$^+$.

The following compounds were prepared in a similar manner

| | Structure | Chemical Name & Analytical Data |
|---|---|---|
| 16-I | 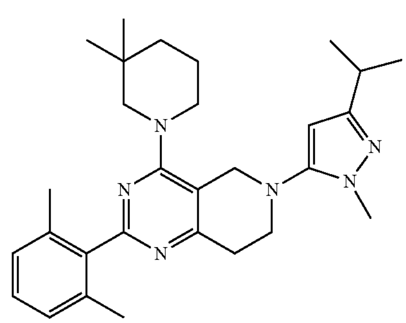 [SMILES: Cc1cccc(C)c1-c1nc2c(c(N3CCCC(C)(C)C3)n1)CN(c1cc(C(C)C)nn1C)CC2] | 2-(2,6-Dimethylphenyl)-4-(3,3-dimethylpiperidin-1-yl)-6-(3-isopropyl-1-methyl-1H-pyrazol-5-yl)-5,6,7,8-tetrdhydropyrido[4,3-d]pyrimidine. HCl salt $^1$H NMR (400 MHz, DMSO-d$_6$) δ ppm 7.39-7.43 (m, 1 H), 7.25 (d, J = 7.8 Hz, 2 H), 5.76 (s, 1 H), 4.15 (s, 2 H), 3.73 (br. s., 2 H), 3.61 (s, 3 H), 3.31 (t, J = 5.8 Hz, 2 H), 3.01 (br. s., 2 H), 2.77 (spt, J = 6.9 Hz, 1 H), 2.17 (s, 6 H), 1.68 (br. s., 2 H), 1.48 (br. s., 2 H), 1.15 (d, J = 7.1 Hz, 6 H), 0.89 (s, 6 H); MS (ESI+) m/z 473.2 (M + H)$^+$. |

| | Structure | Chemical Name & Analytical Data |
|---|---|---|
| 16-J | 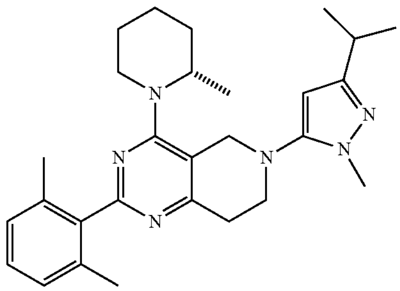 [SMILES: Cc1cccc(C)c1-c1nc2c(c(N3CCCC[C@@H]3C)n1)CN(c1cc(C(C)C)nn1C)CC2] | (S)-2-(2,6-dimethylphenyl)-6-(3-isopropyl-1-methyl-1H-pyrazol-5-yl)-4-(2-methylpiperidin-1-yl)-5,6,7,8-tetrahydropyrido[4,3-d]pyrimidine. TFA salt $^1$H NMR (400 MHz, DMSO-d$_6$) δ ppm 7.39 (t, J = 7.6 Hz, 1 H), 7.24 (d, J = 7.8 Hz, 2 H), 5.78 (s, 1 H), 4.26 (d, J = 14.1 Hz, 2 H), 3.96 (d, J = 14.9 Hz, 2 H), 3.62 (s, 3 H), 3.29-3.43 (m, 3 H), 3.18-3.29 (m, 1 H), 2.91-3.13 (m, 3 H), 2.72-2.82 (m, 1 H), 2.18 (s, 6 H), 1.67-1.82 (m, 3 H), 1.55-1.67 (m, 2 H), 1.50 (dd, J = 14.9, 5.3 Hz, 1 H), 1.32 (d, J = 6.6 Hz, 3 H), 1.16 (d, J = 6.8 Hz, 6 H); MS (ESI+) m/z 459.5 (M + H)$^+$. |
| 16-K | 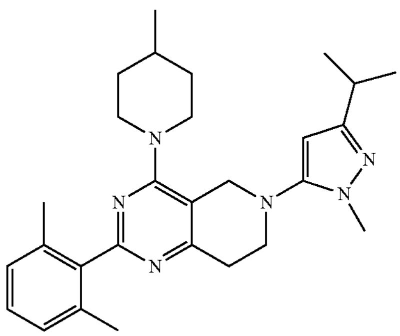 [SMILES: Cc1cccc(C)c1-c1nc2c(c(N3CCC(C)CC3)n1)CN(c1cc(C(C)C)nn1C)CC2] | 2-(2,6-dimethylphenyl)-6-(3-isopropyl-1-methyl-1H-pyrazol-5-yl)-4-(4-methylpiperidin-1-yl)-5,6,7,8-tetrahydropyrido[4,3-d]pyrimidine. TFA salt $^1$H NMR (400 MHz, DMSO-d$_6$) δ ppm 7.40 (t, J = 7.6 Hz, 1 H), 7.24 (d, J = 7.8 Hz, 2 H), 5.83 (s, 1 H), 4.19-4.43 (m, 2 H), 4.11 (s, 2 H), 3.61 (s, 3 H), 3.14-3.33 (m, 4 H), 3.02 (t, J = 5.7 Hz, 2 H), 2.73-2.83 (m, 1 H), 2.18 (s, 6 H), 1.70-1.83 (m, 4 H), 1.18-1.24 (m, 1 H), 1.16 (d, J = 7.1 Hz, 6 H), 0.92 (d, J = 6.1 Hz, 3 H); MS (ESI+) m/z 459.5 (M + H)$^+$. |
| 16-L | 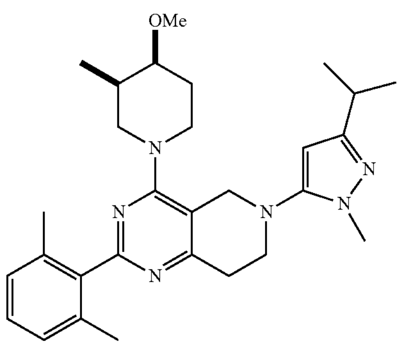 [SMILES: CO[C@H]1CCN(c2nc(-c3c(C)cccc3C)nc3c2CN(c2cc(C(C)C)nn2C)CC3)C[C@H]1C] | (±)-2-(2,6-dimethylphenyl)-6-(3-isopropyl-1-methyl-1H-pyrazol-5-yl)-4-(4-methoxy-3-methylpiperidin-1-yl)-5,6,7,8-tetrahydropyrido[4,3-d]pyrimidine. TFA salt $^1$H NMR (400 MHz, DMSO-d$_6$) δ ppm 7.40 (t, J = 7.6 Hz, 1 H), 7.25 (d, J = 7.8 Hz, 2 H), 5.80 (s, 1 H), 4.05-4.25 (m, 2 H), 3.64-3.84 (m, 3 H), 3.62 (s, 3 H), 3.53-3.61 (m, 1 H), 3.40-3.49 (m, 1 H), 3.22-3.37 (m, 5 H), 3.03 (t, J = 5.9 Hz, 2 H), 2.72-2.84 (m, 1 H), 2.18 (s, 6 H), 1.99-2.11 (m, 1 H), 1.81-1.94 (m, 1 H), 1.63-1.77 (m, 1 H), 1.17 (d, J = 7.1 Hz, 6 H), 0.86 (d, J = 6.8 Hz, 3 H); MS (ESI+) m/z 489.5 (M + H)$^+$. |
| 16-M | 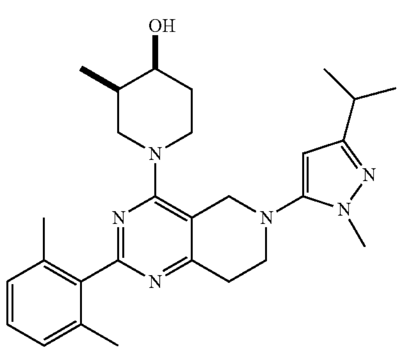 [SMILES: Cc1cccc(C)c1-c1nc2c(c(N3CC[C@H](O)[C@H](C)C3)n1)CN(c1cc(C(C)C)nn1C)CC2] | racemic 1-(2-(2,6-dimethylphenyl)-6-(3-isopropyl-1-methyl-1H-pyrazol-5-yl)-5,6,7,8-tetrahydropyrido[4,3-d]pyrimidin-4-yl)-3-methylpiperidin-4-ol. TFA salt $^1$H NMR (400 MHz, DMSO-d$_6$) δ ppm 7.40 (t, J = 7.6 Hz, 1 H), 7.24 (d, J = 7.6 Hz, 2 H), 5.79 (s, 1 H), 4.05-4.22 (m, 2 H), 3.75-3.98 (m, 3 H), 3.63-3.75 (m, 1 H), 3.61 (s, 3 H), 3.48 (dd, J = 12.6, 9.9 Hz, 1 H), 3.21-3.38 (m, 2 H), 3.01 (t, J = 5.9 Hz, 2 H), 2.77 (quin, J = 6.9 Hz, 1 H), 2.18 (s, 6 H), 1.79-1.92 (m, 1 H), 1.67-1.78 (m, 2 H), 1.16 (d, J = 6.8 Hz, 6 H), 0.86 (d, J = 6.8 Hz, 3 H); MS (ESI+) m/z 475.5 (M + H)$^+$. |

| | Structure | Chemical Name & Analytical Data |
|---|---|---|
| 16-N | 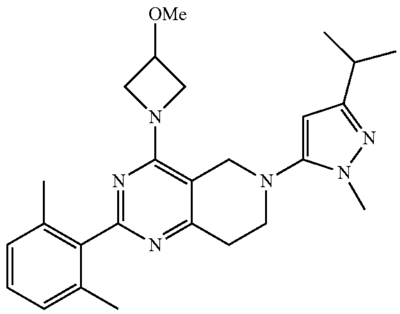 [SMILES: COC1CN(c2nc(-c3c(C)cccc3C)nc3c2CN(c2cc(C(C)C)nn2C)CC3)C1] | 2-(2,6-dimethylphenyl)-6-(3-isopropyl-1-methyl-1H-pyrazol-5-yl)-4-(3-methoxyazetidin-1-yl)-5,6,7,8-tetrdhydropyrido[4,3-d]pyrimidine. TFA salt $^1$H NMR (400 MHz, DMSO-d$_6$) δ ppm 7.39 (t, J = 7.6 Hz, 1 H), 7.23 (d, J = 7.6 Hz, 2 H), 5.92 (s, 1 H), 4.59-5.13 (m, 2 H), 4.36-4.59 (m, 1 H), 4.26-4.36 (m, 1 H), 4.18 (br. s., 2 H), 3.88-4.13 (m, 1 H), 3.62 (s, 3 H), 3.25 (s, 3 H), 3.18 (t, J = 5.7 Hz, 2 H), 2.95 (t, J = 4.3 Hz, 2 H), 2.78 (quin, J = 6.9 Hz, 1 H), 2.17 (s, 6 H), 1.17 (d, J = 6.9 Hz, 6 H); MS (ESI+) m/z 447.5 (M + H)$^+$. |
| 16-O | 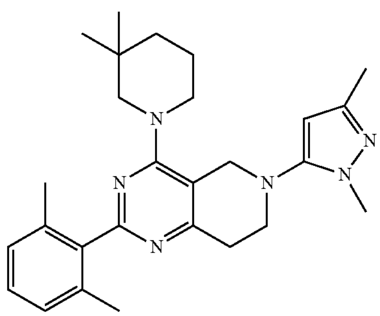 [SMILES: Cc1cc(N2CCc3nc(-c4c(C)cccc4C)nc(N4CCCC(C)(C)C4)c3C2)n(C)n1] | 6-(1,3-dimethyl-1H-pyrazol-5-yl)-2-(2,6-dimethylphenyl)-4-(3,3-dimethylpiperidin-1-yl)-5,6,7,8-tetrahydropyrido[4,3-d]pyrimidine. TFA salt $^1$H NMR (400 MHz, CD$_2$Cl$_2$) δ ppm 7.34 (t, J = 7.6 Hz, 1 H), 7.16 (d, J = 7.6 Hz, 2 H), 5.86 (s, 1 H), 4.05 (s, 2 H), 3.82 (s, 3 H), 3.73 (app. t, J = 5.1 Hz, 2 H), 3.53 (s, 2 H), 3.40 (br. s., 4 H), 2.33 (s, 3 H), 2.22 (s, 6 H), 1.73-1.81 (m, 2 H), 1.52-1.58 (m, 2 H), 0.94 (s, 6 H); MS (ESI+) m/z 445.3 (M + H)$^+$. |
| 16-P | 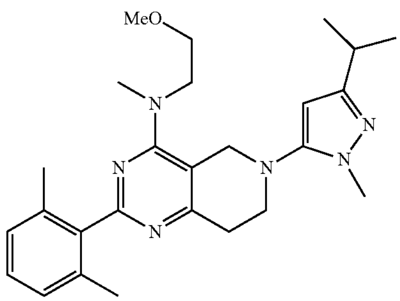 [SMILES: COCCN(C)c1nc(-c2c(C)cccc2C)nc2c1CN(c1cc(C(C)C)nn1C)CC2] | 2-(2,6-dimethylphenyl)-6-(3-isopropyl-1-methyl-1H-pyrazol-5-yl)-N-(2-methoxyethyl)-N-methyl-5,6,7,8-tetrahydropyrido[4,3-d]pyrimidin-4-amine. $^1$H NMR HCl salt (400 MHz, DMSO-d$_6$) δ ppm 7.40 (t, J = 8.6 Hz, 1 H), 7.24 (d, J = 7.6 Hz, 2 H), 5.88 (br. s., 1 H), 4.35 (br. s., 2 H), 3.66 (s, 3 H), 3.56-3.63 (m, 2 H), 3.38-3.45 (m, 3 H), 3.31 (br. s., 2 H), 3.23 (s, 3 H), 3.04 (br. s., 2 H), 2.81 (spt, J = 6.6 Hz, 1 H), 2.18 (s, 6 H), 1.18 (d, J = 7.1 Hz, 6 H); MS (ESI+) m/z 449.2 (M + H)$^+$. |
| 16-Q | 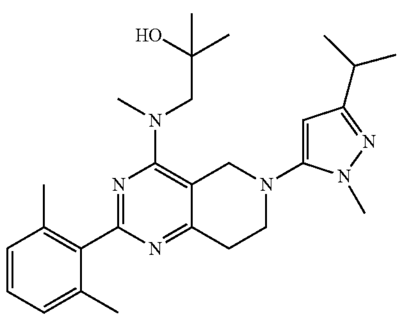 [SMILES: Cc1cccc(C)c1-c1nc2c(c(N(C)CC(C)(C)O)n1)CN(c1cc(C(C)C)nn1C)CC2] | 1-((2-(2,6-dimethylphenyl)-6-(3-isopropyl-1-methyl-1H-pyrazol-5-yl)-5,6,7,8-tetrahydropyrido[4,3-d]pyrimidin-4-yl)(methyl)amino)-2-methylpropan-2-ol. $^1$H NMR (400 MHz, DMSO-d$_6$) δ ppm 7.12-7.19 (m, 1 H), 7.06 (d, J = 7.6 Hz, 2 H), 5.55 (s, 1 H), 4.64 (s, 1 H), 4.15 (br. s, 2 H), 3.63 (s, 2 H), 3.60 (s, 3 H), 3.28-3.33 (m, 2 H), 2.84 (t, J = 5.7 Hz, 2 H), 2.74 (spt, J = 7.1 Hz, 1 H), 2.02 (s, 6 H), 1.11 (d, J = 6.8 Hz, 6 H), 1.02 (s, 6 H); MS (ESI+) m/z 463.2 (M + H)$^+$. |
| 16-R | 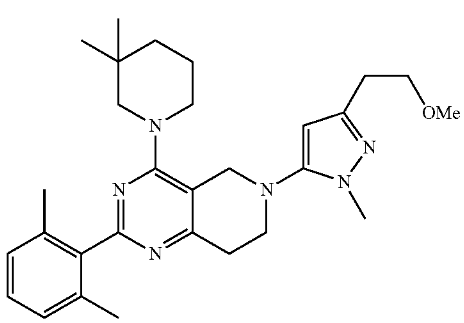 [SMILES: COCCc1cc(N2CCc3nc(-c4c(C)cccc4C)nc(N4CCCC(C)(C)C4)c3C2)n(C)n1] | 2-(2,6-dimethylphenyl)-4-(3,3-dimethylpiperidin-1-yl)-6-(3-(2-methoxyethyl)-1-methyl-1H-pyrazol-5-yl)-5,6,7,8-tetrahydiopyrido[4,3-d]pyrimidine. $^1$H NMR (400 MHz, DMSO-d$_6$) δ ppm 7.17 (m, J = 7.1 Hz, 1 H), 7.08 (d, J = 7.6 Hz, 2 H), 5.73 (s, 1 H), 4.00 (s, 2 H), 3.59 (s, 3 H), 3.51 (t, J = 7.1 Hz, 2 H), 3.22-3.32 (m, 7 H), 3.04 (s, 2 H), 2.93 (t, J = 5.9 Hz, 2 H), 2.66 (t, J = 7.1 Hz, 2 H), 2.04 (s, 6 H), 1.58-1.68 (m, 2 H), 1.39 (t, J = 5.8 Hz, 2 H), 0.91 (s, 6 H); MS (ESI+) m/z 489.3 (M + H)$^+$. |

| | Structure | Chemical Name & Analytical Data |
|---|---|---|
| 16-S | 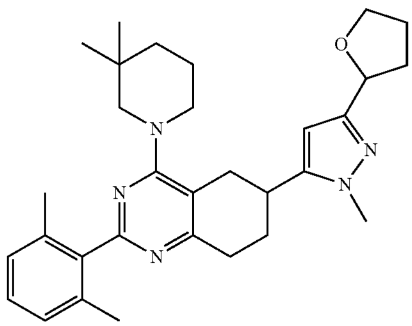 [SMILES: Cc1cccc(C)c1-c1nc2c(c(N3CCCC(C)(C)C3)n1)CC(c1cc(C3CCCO3)nn1C)CC2] | 2-(2,6-dimethylphenyl)-4-(3,3-dimethylpiperidin-1-yl)-6-(1-methyl-3-(tetrahydrofuran-2-yl)-1H-pyrazol-5-yl)-5,6,7,8-tetrahydropyrido[4,3-d]pyrimidine. $^1$H NMR (400 MHz, DMSO-$d_6$) δ ppm 7.17 (dd, J = 8.6, 7.1 Hz, 1 H), 7.07 (d, J = 7.6 Hz, 2 H), 5.80 (s, 1 H), 4.63-4.68 (m, 1 H), 4.02 (br. s, 2 H), 3.76-3.84 (m, 1 H), 3.66-3.74 (m, 1 H), 3.62 (s, 3 H), 3.24-3.32 (m, 4 H), 3.05 (d, J = 2.8 Hz, 2 H), 2.92 (t, J = 6.1 Hz, 2 H), 2.06-2.15 (m, 1 H), 2.04 (s, 6 H), 1.84-1.96 (m, 3 H), 1.58-1.67 (m, 2 H), 1.37-1.41 (m, 2 H), 0.90 (s, 6 H); MS (ESI+) m/z 501.3 (M + H)$^+$. |
| 16-T | 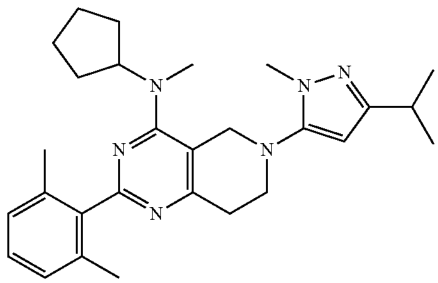 [SMILES: Cc1cccc(C)c1-c1nc2c(c(N(C)C3CCCC3)n1)CN(c1cc(C(C)C)nn1C)CC2] | N-cyclopentyl-2-(2,6-dimethylphenyl)-6-(3-isopropyl-1-methyl-1H-pyrazol-5-yl)-N-methyl-5,6,7,8-tetrahydropyrido[4,3-d]pyrimidin-4-amine. TFA salt $^1$H NMR (400 MHz, DMSO-$d_6$) δ ppm 7.41 (t, J = 7.8 Hz, 1 H), 7.25 (d, J = 7.6 Hz, 2 H), 5.79 (s, 1 H), 4.88 (br. s., 1 H), 4.25 (s, 3 H), 3.62 (s, 3 H), 3.29 (t, J = 5.9 Hz, 2 H), 3.18 (s, 2 H), 2.94-3.08 (m, 2 H), 2.72-2.84 (m, 1 H), 2.18 (s, 6 H), 1.79-1.93 (m, 1 H), 1.79-1.94 (m, 2 H), 1.62-1.79 (m, 4 H), 1.46-1.62 (m, 2 H), 1.17 (d, J = 6.8 Hz, 6 H); MS (ESI+) m/z 459.5 (M + H)$^+$. |
| 16-U | 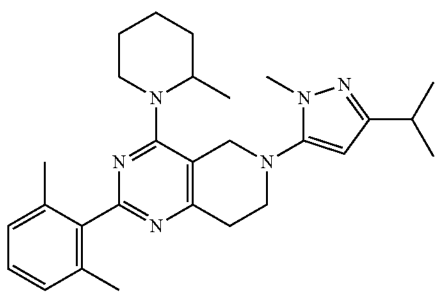 [SMILES: Cc1cccc(C)c1-c1nc2c(c(N3CCCCC3C)n1)CN(c1cc(C(C)C)nn1C)CC2] | 2-(2,6-dimethylphenyl)-6-(3-isopropyl-1-methyl-1H-pyrazol-5-yl)-4-(2-methylpiperidin-1-yl)-5,6,7,8-tetrahydropyrido[4,3-d]pyrimidine. TFA salt $^1$H NMR (400 MHz, DMSO-$d_6$) δ ppm 7.40 (t, J = 7.6 Hz, 1 H), 7.25 (d, J = 7.6 Hz, 2 H), 5.78 (s, 1 H), 4.70 (br. s., 1 H), 3.87-4.37 (m, 2 H), 3.62 (s, 3 H), 3.36 (ddd, J = 12.3, 6.1, 5.9 Hz, 2 H), 3.15-3.29 (m, 1 H), 2.91-3.15 (m, 3 H), 2.72-2.85 (m, 1 H), 2.18 (s, 6 H), 1.65-1.84 (m, 3 H), 1.54-1.65 (m, 2 H), 1.42-1.54 (m, 1 H), 1.33 (d, J = 6.6 Hz, 3 H), 1.16 (d, J = 6.8 Hz, 6 H); MS (ESI+) m/z 459.4 (M + H)$^+$. |
| 16-V | 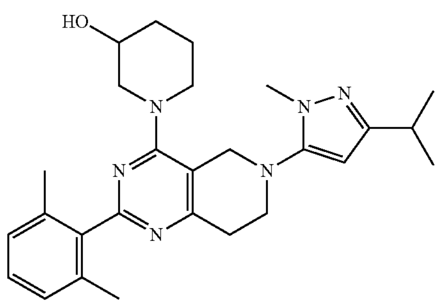 [SMILES: Cc1cccc(C)c1-c1nc2c(c(N3CCCC(O)C3)n1)CN(c1cc(C(C)C)nn1C)CC2] | racemic 1-(2-(2,6-dimethylphenyl)-6-(3-isopropyl-1-methyl-1H-pyrazol-5-yl)-5,6,7,8-tetrahydropyrido[4,3-d]pyrimidin-4-yl)piperidin-3-ol. TFA salt $^1$H NMR (400 MHz, DMSO-$d_6$) δ ppm 7.40 (t, J = 7.6 Hz, 1 H), 7.25 (d, J = 7.6 Hz, 2 H), 5.81 (s, 1 H), 4.27 (d, J = 14.7 Hz, 1 H), 4.01 (d, J = 14.9 Hz, 1 H), 3.79-3.98 (m, 2 H), 3.73 (br. s., 1 H), 3.66 (br. s., 1 H), 3.61 (s, 3 H), 3.49 (br. s., 1 H), 3.18-3.39 (m, 2 H), 3.03 (t, J = 5.3 Hz, 2 H), 2.71-2.84 (m, 1 H), 2.18 (s, 6 H), 1.85 (d, J = 8.6 Hz, 2 H), 1.41-1.65 (m, 2 H), 1.16 (d, J = 6.8 Hz, 6 H); MS (ESI+) m/z 461.4 (M + H)$^+$. |
| 16-W | 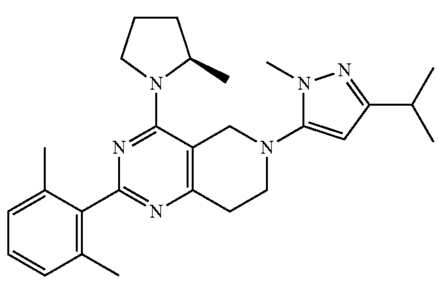 [SMILES: Cc1cccc(C)c1-c1nc2c(c(N3CCC[C@H]3C)n1)CN(c1cc(C(C)C)nn1C)CC2] | (R)-2-(2,6-dimethylphenyl)-6-(3-isopropyl-1-methyl-1H-pyrazol-5-yl)-4-(2-methylpyrrolidin-1-yl)-5,6,7,8-tetrahydropyrido[4,3-d]pyrimidine. TFA salt $^1$H NMR (400 MHz, DMSO-$d_6$) δ ppm 7.41 (t, J = 7.6 Hz, 1 H), 7.26 (d, J = 7.8 Hz, 2 H), 5.88 (s, 1 H), 4.52 (br. s., 1 H), 4.20-4.44 (m, 2 H), 3.89-4.18 (m, 2 H), 3.63 (s, 3 H), 3.22-3.36 (m, 1 H), 2.87-3.21 (m, 2 H), 2.73-2.87 (m, 1 H), 2.19 (s, 6 H), 1.78-2.13 (m, 4 H), 1.62 (br. s., 1 H), 1.22 (d, J = 6.1 Hz, 3 H), 1.18 (d, J = 6.8 Hz, 6 H); MS (ESI+) m/z 445.4 (M + H)$^+$. |

| | Structure | Chemical Name & Analytical Data |
|---|---|---|
| 16-X | 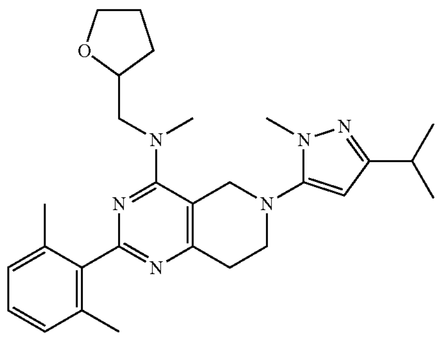 [SMILES: Cc1cccc(C)c1-c1nc2c(c(N(C)CC3CCCO3)n1)CN(c1cc(C(C)C)nn1C)CC2] | 2-(2,6-dimethylphenyl)-6-(3-isopropyl-1-methyl-1H-pyrazol-5-yl)-N-methyl-N-((tetrahydrofuran-2-yl)methyl)-5,6,7,8-tetrahydropyrido[4,3-d]pyrimidin-4-amine. TFA salt $^1$H NMR (400 MHz, DMSO-d$_6$) δ ppm 7.39 (t, J = 7.6 Hz, 1 H), 7.23 (d, J = 7.6 Hz, 2 H), 5.76 (s, 1 H), 4.32-4.45 (m, 1 H), 4.23 (d, J = 14.9 Hz, 1 H), 4.10-4.20 (m, 1 H), 3.73-3.86 (m, 2 H), 3.63-3.73 (m, 1 H), 3.55-3.63 (m, 4 H), 3.41 (s, 3 H), 3.26 (t, J = 5.9 Hz, 2 H), 2.99 (t, J = 4.9 Hz, 2 H), 2.69-2.83 (m, 1 H), 2.16 (s, 6 H), 1.87-2.01 (m, 1 H), 1.68-1.87 (m, 2 H), 1.43-1.60 (m, 1 H), 1.14 (d, J = 7.1 Hz, 6 H); MS (ESI+) m/z 475.5 (M + H)$^+$. |
| 16-Y | 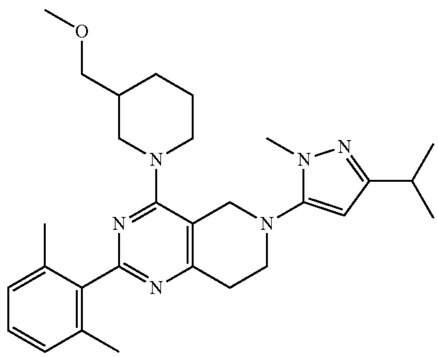 [SMILES: COCC1CCCN(c2nc(-c3c(C)cccc3C)nc3c2CN(c2cc(C(C)C)nn2C)CC3)C1] | racemic 2-(2,6-dimethylphenyl)-6-(3-isopropyl-1-methyl-1H-pyrazol-5-yl)-4-(3-(methoxymethyl)piperidin-1-yl)-5,6,7,8-tetrahydropyrido[4,3-d]pyrimidine. TFA salt $^1$H NMR (400 MHz, DMSO-d$_6$) δ ppm 7.40 (t, J = 7.6 Hz, 1 H), 7.25 (d, J = 7.6 Hz, 2 H), 5.80 (s, 1 H), 4.25 (br. s., 2 H), 4.19 (d, J = 15.2 Hz, 1 H), 4.02-4.10 (m, 1 H), 3.62 (s, 3 H), 3.22-3.39 (m, 4 H), 3.16-3.22 (m, 4 H), 3.09-3.16 (m, 2 H), 2.93-3.08 (m, 2 H), 2.72-2.85 (m, 1 H), 2.19 (s, 6 H), 1.89-2.06 (m, 1 H), 1.71-1.86 (m, 2 H), 1.47-1.65 (m, 1 H), 1.28-1.44 (m, 1 H), 1.17 (d, J = 6.8 Hz, 6 H); MS (ESI+) m/z 489.4 (M + H)$^+$. |
| 16-Z | 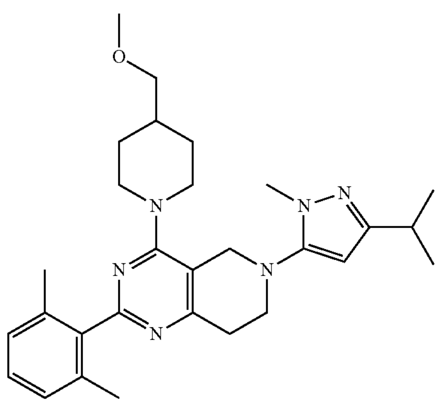 [SMILES: COCC1CCN(c2nc(-c3c(C)cccc3C)nc3c2CN(c2cc(C(C)C)nn2C)CC3)CC1] | 2-(2,6-dimethylphenyl)-6-(3-isopropyl-1-methyl-1H-pyrazol-5-yl)-4-(4-(methoxymethyl)piperidin-1-yl)-5,6,7,8-tetrahydropyrido[4,3-d]pyrimidine. TFA salt $^1$H NMR (400 MHz, DMSO-d$_6$) δ ppm 7.39 (t, J = 7.6 Hz, 1 H), 7.24 (d, J = 7.8 Hz, 2 H), 5.82 (s, 1 H), 4.33 (d, J = 13.6 Hz, 2 H), 4.12 (s, 2 H), 3.61 (s, 3 H), 3.24-3.34 (m, 4 H), 3.23 (s, 3 H), 3.20 (d, J = 6.3 Hz, 2 H), 3.02 (t, J = 5.7 Hz, 2 H), 2.77 (quin, J = 6.9 Hz, 1 H), 2.17 (s, 6 H), 1.86-2.02 (m, 1 H), 1.81 (d, J = 14.1 Hz, 2 H), 1.19-1.34 (m, 2 H), 1.16 (d, J = 6.8 Hz, 6 H); MS (ESI+) m/z 489.5 (M + H)$^+$. |
| 16-AA | 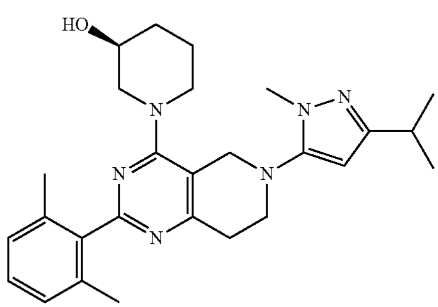 [SMILES: Cc1cccc(C)c1-c1nc2c(c(N3CCC[C@H](O)C3)n1)CN(c1cc(C(C)C)nn1C)CC2] | (S)-1-(2-(2,6-dimethylphenyl)-6-(3-isopropyl-1-methyl-1H-pyrazol-5-yl)-5,6,7,8-tetrahydropyrido[4,3-d]pyrimidin-4-yl)piperidin-3-ol. TFA salt $^1$H NMR (400 MHz, DMSO-d$_6$) δ ppm 7.39 (t, J = 7.6 Hz, 1 H), 7.24 (d, J = 7.6 Hz, 2 H), 5.80 (s, 1 H), 4.27 (d, J = 15.2 Hz, 1 H), 4.01 (d, J = 14.7 Hz, 1 H), 3.93 (d, J = 14.9 Hz, 1 H), 3.78-3.90 (m, 1 H), 3.70-3.78 (m, 1 H), 3.62-3.70 (m, 1 H), 3.61 (s, 3 H), 3.42-3.55 (m, 1 H), 3.18-3.38 (m, 2 H), 2.97-3.08 (m, 2 H), 2.73-2.81 (m, 1 H), 2.18 (s, 6 H), 1.85 (d, J = 11.4 Hz, 2 H), 1.42-1.63 (m, 2 H), 1.16 (d, 6 H); MS (ESI+) m/z 461.5 (M + H)$^+$. |

| Structure | Chemical Name & Analytical Data |
|---|---|
| 16-AB LLN0 36 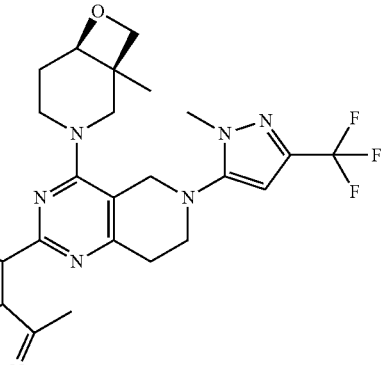 | racemic (cis)-3-(2-(3,5-dimethyl-1H-indazol-4-yl)-6-(1-methyl-3-(trifluoromethyl)-1H-pyrazol-5-yl)-5,6,7,8-tetrahydropyrido[4,3-d]pyrimidin-4-yl)-1-methyl-7-oxa-3-azabicyclo[4.2.0]octane. ¹H NMR (400 MHz,CD₂Cl₂) δ ppm 9.78 (br. s, 1H), 7.27 (d, J = 8.59 Hz, 1H), 7.16 (d, J = 8.59 Hz, 1H), 6.08 (s, 1H), 4.57 (t, J = 3.03 Hz, 1H), 4.44 (d, J = 5.81 Hz, 1H), 4.23 (d, J = 6.06 Hz, 1H), 4.12 (q, J = 14.70 Hz, 2H), 3.89-4.00 (m, 1H), 3.73 (s, 3H), 3.65 (d, J = 13.64 Hz, 1H), 3.43 (td, J = 4.36, 11.24 Hz, 1H), 3.24-3.37 (m, 2H), 3.20 (d, J = 13.64 Hz, 1H), 2.92-3.09 (m, 2H), 2.19 (s, 3H), 1.88-1.97 (m, 2H), 1.92 (s, 3H), 1.18 (s, 3H); MS (ESI+) m/z 553.3 (M + H)⁺. |

Example 17

17-A. 6-Benzyl-2-chloro-4-methoxy-5,6,7,8-tetrahydropyrido[4,3-d]pyrimidine

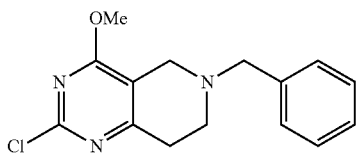 [SMILES: COc1nc(Cl)nc2c1CN(Cc1ccccc1)CC2]

To a solution of 6-benzyl-2,4-dichloro-5,6,7,8-tetrahydropyrido[4,3-d]pyrimidine (CAS#778574-06-4 2.0 g, 6.80 mmol) in MeOH (70 mL) at 0° C. was added 25% sodium methoxide in methanol (1.9 mL, 8.2 mmol) to give a suspension. After 15 minutes the reaction became a homogeneous solution, at which time an additional aliquot of 25% sodium methoxide in methanol (0.25 mL, 1.1 mmol) was added and the reaction was stirred for 15 minutes. The reaction was then diluted with water and diethyl ether and the resulting layers were separated. The organic layer was washed with brine, dried over MgSO₄, filtered, and concentrated. The resulting yellow oil was used without further purification. ¹H NMR (400 MHz, CD₂Cl₂) δ ppm 2.71-2.91 (m, 4 H) 3.43 (m, 2 H) 3.72 (m, 2 H) 3.95 (s, 3 H) 7.24-7.42 (m, 5 H). MS (ESI+) m/z 290.2 (M+H)⁺.

17-B. 6-Benzyl-4-methoxy-2-(3-methyl-1-tosyl-1H-indol-4-yl)-5,6,7,8-tetrahydropyrido[4,3-d]pyrimidine

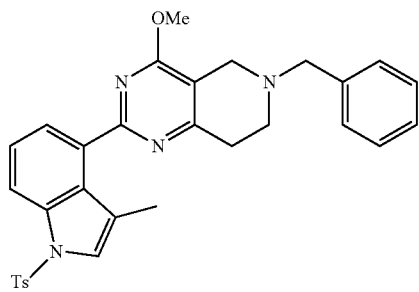 [SMILES: COc1nc(-c2cccc3c2c(C)cn3S(=O)(=O)c2ccc(C)cc2)nc2c1CN(Cc1ccccc1)CC2]

To a solution of 6-benzyl-2-chloro-4-methoxy-5,6,7,8-tetrahydropyrido[4,3-d]pyrimidine (1.0 g, 3.45 mmol) in DME (10.0 mL) in a 20 mL microwave reaction vial was added 3-methyl-4-(4,4,5,5-tetramethyl-1,3,2-dioxaborolan-2-yl)-1-tosyl-1H-indole (1.57 g, 3.80 mmol). Then 2 M aqueous Na₂CO₃ (5.6 mL, 11.22 mmol) was added. The reaction mixture was degassed via a series of 3 argon/vacuum cycles and then placed under an atmosphere of argon. Then Pd(Ph₃P)₄ (0.399 g, 0.345 mmol) was added and the vial was sealed and heated via microwave irradiation at 140° C. for 90 minutes. The reaction mixture was cooled to room temperature and diluted with Et₂O and water. The layers were separated and the organic layer was washed with brine, dried over MgSO₄, filtered, and concentrated. The resulting residue was purified by silica gel flash chromatography (27-48% ethyl acetate/heptanes) to provide 6-benzyl-4-methoxy-2-(3-methyl-1-tosyl-1H-indol-4-yl)-5,6,7,8-tetrahydropyrido[4,3-d]pyrimidine as a white solid. MS (ESI+) m/z 539.3 (M+H)⁺.

17-C. 4-Methoxy-2-(3-methyl-1-tosyl-1H-indol-4-yl)-5,6,7,8-tetrahydropyrido[4,3-d]pyrimidine

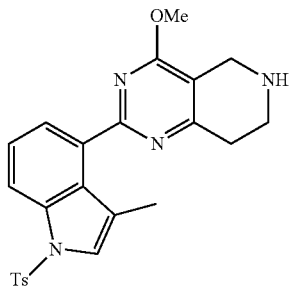 [SMILES: COc1nc(-c2cccc3c2c(C)cn3S(=O)(=O)c2ccc(C)cc2)nc2c1CNCC2]

To a solution of 6-benzyl-4-methoxy-2-(3-methyl-1-tosyl-1H-indol-4-yl)-5,6,7,8-tetrahydropyrido[4,3-d]pyrimidine (1.1 g, 2.0 mmol) in THF (15 mL) was added water (3.75 mL) and acetic acid (0.34 mL, 5.9 mmol), then 20 mol % Pd(OH)₂/carbon (50% wet) (0.86 g, 0.61 mmol) was added. The reaction mixture was placed under an atmosphere of hydrogen gas via balloon. After 1.5 hours the mixture was diluted with ethyl acetate and neutralized with saturated aqueous NaHCO₃. The mixture was then filtered through a pad of Celite®. The eluent was then further diluted with ethyl acetate and brine and the layers were separated. The organic layer was dried over Na₂SO₄, filtered, and concentrated. The resulting residue was purified by silica gel flash chromatography (0-20% MeOH/DCM) to provide 4-methoxy-2-(3-methyl-1-tosyl-1H-indol-4-yl)-5,6,7,8-tetrahydropyrido[4,3-d]pyrimidine. $^1$H NMR (400 MHz, DMSO-d$_6$) δ ppm 1.91 (d, J=1.0 Hz, 3 H) 2.32 (s, 3 H) 2.68 (t, J=5.6 Hz, 2 H) 3.00 (t, J=5.7 Hz, 2 H) 3.72 (s, 2H) 3.92 (s, 3 H) 7.30-7.48 (m, 4 H) 7.65 (d, J=1.0 Hz, 1 H) 7.85 (d, J=8.3 Hz, 2 H) 8.04 (dd, J=7.3, 2.0 Hz, 1 H). MS (ESI+) m/z 449.2 (M+H)$^+$.

17-D. 6-(5-Isopropyl-2-methylphenyl)-4-methoxy-2-(3-methyl-1-tosyl-1H-indol-4-yl)-5,6,7,8-tetrahydropyrido[4,3-d]pyrimidine

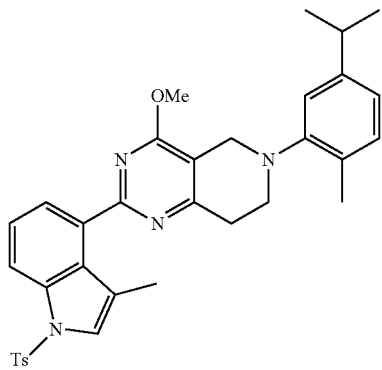 [SMILES: COc1nc(-c2cccc3c2c(C)cn3S(=O)(=O)c2ccc(C)cc2)nc2c1CN(c1cc(C(C)C)ccc1C)CC2]

To a solution of 4-methoxy-2-(3-methyl-1-tosyl-1H-indol-4-yl)-5,6,7,8-tetrahydropyrido[4,3-d]pyrimidine (1.32 g, 2.94 mmol) in THF (11 mL) in a 20 mL microwave vial was added 5-isopropyl-2-methylphenyl trifluoromethanesulfonate, prepared as described in Example 15 (1.25 g, 4.41 mmol). Then cesium carbonate (2.4 g, 7.36 mmol) was added followed by X-Phos (CAS#564483-18-7, 0.28 g, 0.59 mmol). The reaction mixture was degassed via several vacuum/nitrogen cycles and then Pd(OAc)$_2$ (53 mg, 0.235 mmol) was added. The vial was sealed and heated via microwave irradiation at 120° C. for 90 minutes. The reaction was then diluted with ethyl acetate and water. The layers were separated and the aqueous layer was extracted two additional times with ethyl acetate. The organic layers were combined, dried over Na$_2$SO$_4$, filtered, and concentrated. The resulting residue was purified by silica gel flash chromatography (0-50% ethyl acetate/heptanes) to provide: 6-(5-isopropyl-2-methylphenyl)-4-methoxy-2-(3-methyl-1-tosyl-1H-indol-4-yl)-5,6,7,8-tetrahydropyrido[4,3-d]pyrimidine. MS (ESI+) m/z 581.2 (M+H)$^+$.

17-E. 4-Chloro-6-(5-isopropyl-2-methylphenyl)-2-(3-methyl-1-tosyl-1H-indol-4-yl)-5,6,7,8-tetrahydropyrido[4,3-d]pyrimidine

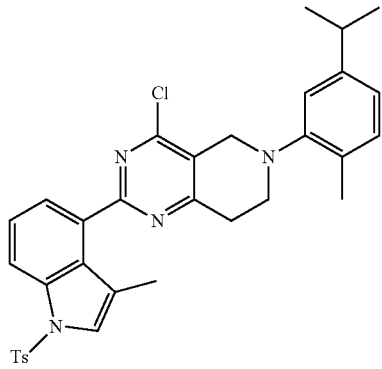 [SMILES: Cc1ccc(S(=O)(=O)n2cc(C)c3c(-c4nc(Cl)c5c(n4)CCN(c4cc(C(C)C)ccc4C)C5)cccc32)cc1]

Ethanol (4 mL) was added to 6-(5-isopropyl-2-methylphenyl)-4-methoxy-2-(3-methyl-1-tosyl-1H-indol-4-yl)-5,6,7,8-tetrahydropyrido[4,3-d]pyrimidine (0.92 g, 1.58 mmol) and then 12 N aqueous HCl (2 mL, 24 mmol) was added and the mixture was heated to 68° C. for ca. 15 hours. The reaction was then cooled to room temperature, diluted with dichloromethane, and neutralized via the slow addition of saturated aqueous sodium bicarbonate. The resulting layers were separated and the aqueous layer was extracted two additional times with dichloromethane. The organic layers were combined, dried over Na$_2$SO$_4$, filtered, and concentrated. The resulting residue was then dissolved in dichloromethane (20 mL) and cooled to 0° C. and N-chloromethylene-N,N-dimethyl ammonium chloride (Vilsmeier reagent) (0.41 g, 3.21 mmol) was added. The reaction was then placed at room temperature for 25 minutes. The reaction was then diluted with dichloromethane and saturated aqueous sodium bicarbonate. The resulting layers were separated and the aqueous layer was extracted one additional time with dichloromethane. The organic layers were combined, dried over Na$_2$SO$_4$ filtered and concentrated. The resulting residue was purified by silica gel flash chromatography (0-45% ethyl acetate/heptanes) to provide 4-chloro-6-(5-isopropyl-2-methylphenyl)-2-(3-methyl-1-tosyl-1H-indol-4-yl)-5,6,7,8-tetrahydropyrido[4,3-d]pyrimidine. MS (ESI+) m/z 585.2 (M+H)$^+$.

17-F. (S)-6-(5-Isopropyl-2-methylphenyl)-4-(4-methoxy-3,3-dimethylpiperidin-1-yl)-2-(3-methyl-1-tosyl-1H-indol-4-yl)-5,6,7,8-tetrahydropyrido[4,3-d]pyrimidine

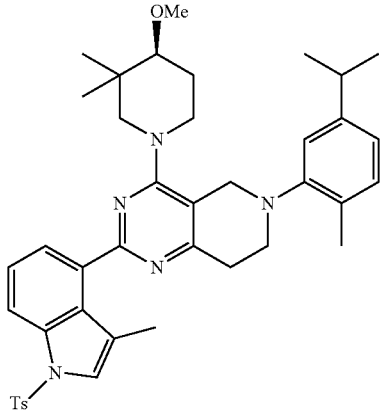 [SMILES: CO[C@H]1CCN(c2nc(-c3cccc4c3c(C)cn4S(=O)(=O)c3ccc(C)cc3)nc3c2CN(c2cc(C(C)C)ccc2C)CC3)CC1(C)C]

Isopropanol (2 mL) was added to a microwave vial containing a mixture of 4-chloro-6-(5-isopropyl-2-methylphenyl)-2-(3-methyl-1-tosyl-1H-indol-4-yl)-5,6,7,8-tetrahydropyrido[4,3-d]pyrimidine (150 mg, 0.256 mmol) and the trifluoroacetic acid salt of (S)-4-methoxy-3,3-dimethylpiperidine (120 mg, 0.461 mmol). Then diisopropylethylamine (0.32 mL, 1.8 mmol) was added and the vial was sealed and heated via microwave irradiation at 125° C. for 3.5 hours. The reaction was then cooled to room temperature and diluted with ethyl acetate and saturated aqueous NaHCO$_3$. The layers were separated and the organic layer was dried over Na$_2$SO$_4$, filtered and concentrated. The resulting residue was purified by silica gel chromatography (0-60% ethyl acetate/heptanes) to afford: (S)-6-(5-isopropyl-2-methylphenyl)-4-(4-methoxy-3,3-dimethylpiperidin-1-yl)-2-(3-methyl-1-tosyl-1H-indol-4-yl)-5,6,7,8-tetrahydropyrido[4,3-d]pyrimidine. MS (ESI+) m/z 692.5 (M+H)$^+$.

17-G. (S)-6-(5-Isopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine

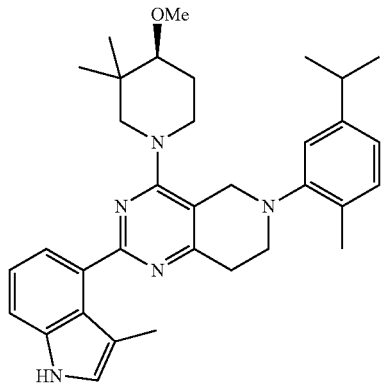 [SMILES: CO[C@H]1CCN(c2nc(-c3cccc4[nH]cc(C)c34)nc3c2CN(c2cc(C(C)C)ccc2C)CC3)CC1(C)C]

To a solution of (S)-6-(5-isopropyl-2-methylphenyl)-4-(4-methoxy-3,3-dimethylpiperidin-1-yl)-2-(3-methyl-1-tosyl-1H-indol-4-yl)-5,6,7,8-tetrahydropyrido[4,3-d]pyrimidine (135 mg, 0.195 mmol) in methanol (2 mL) in a microwave vial was added KOH (100 mg, 1.75 mmol) followed by 28% ammonium hydroxide in water (1 mL, 7.25 mmol). The vial was sealed and heated via microwave irradiation at 80° C. for 75 minutes. The reaction mixture was cooled to room temperature and diluted with dichloromethane and brine. The layers were separated and the aqueous layer was extracted two additional times with dichloromethane. The organic layers were combined, dried over $Na_2SO_4$, filtered, and concentrated. The resulting residue was purified by silica gel flash chromatography (0-70% ethyl acetate/heptanes) to furnish (S)-6-(5-isopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, DMSO-$d_6$) δ ppm 0.92 (s, 3 H) 0.98 (s, 3 H) 1.18 (d, J=6.8 Hz, 6 H) 1.51-1.62 (m, 1 H) 1.91-1.99 (m, 1 H) 2.01 (s, 3 H) 2.21 (s, 3 H) 2.78-2.88 (m, 2 H) 2.91-3.08 (m, 4 H) 3.29 (s, 3 H) 3.31-3.41 (m, 3 H) 3.60-3.71 (m, 1 H) 4.07 (s, 2 H) 6.86 (d, J=7.3 Hz, 1 H) 6.96 (s, 1 H) 7.07-7.15 (m, 3 H) 7.20 (d, J=7.1 Hz, 1H) 7.41 (d, J=7.8 Hz, 1 H) 10.89 (br. s., 1 H); MS (ESI+) m/z 538.4 (M+H)$^+$.

The following compounds were prepared in a similar manner

| | Structure | Chemical Name & Analytical Data |
|---|---|---|
| 17-H | 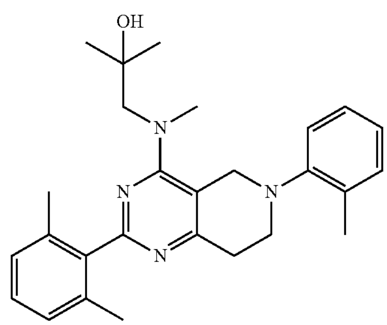 [SMILES: Cc1ccccc1N1CCc2nc(-c3c(C)cccc3C)nc(N(C)CC(C)(C)O)c2C1] | 1-((2-(2,6-Dimethylphenyl)-6-(o-tolyl)-5,6,7,8-tetrahydropyrido[4,3-d]pyrimidin-4-yl)(methyl)amino)-2-methylpropan-2-ol. $^1$H NMR (400 MHz, CD$_2$Cl$_2$) δ ppm 7.13-7.26 (m, 4 H), 7.00-7.11 (m, 3 H), 4.17 (s, 2 H), 3.54 (s, 2 H), 3.26-3.32 (m, 5 H), 3.05 (t, J = 5.8 Hz, 2 H), 2.34 (s, 3 H), 2.11 (s, 6 H), 1.14 (s, 6 H); MS (ESI+) m/z 431.2 (M + H)$^+$. |
| 17-I | 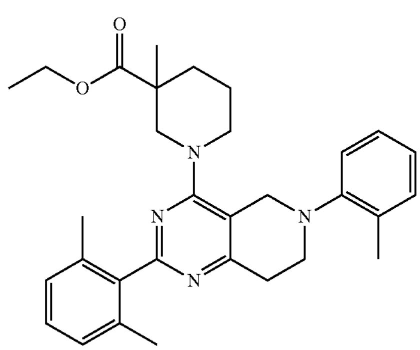 [SMILES: CCOC(=O)C1(C)CCCN(c2nc(-c3c(C)cccc3C)nc3c2CN(c2ccccc2C)CC3)C1] | Ethyl 1-(2-(2,6-dimethylphenyl)-6-(o-tolyl)-5,6,7,8-tetrahydropyrido[4,3-d]pyrimidin-4-yl)-3-methylpiperidine-3-carboxylate. $^1$H NMR (400 MHz, DMSO-$d_6$) δ ppm 7.14-7.25 (m, 4 H), 7.08 (d, J = 7.6 Hz, 2 H), 7.01 (t, J = 7.1 Hz, 1 H), 4.03-4.15 (m, 2 H), 3.81-3.96 (m, 2 H), 3.77 (d, J = 14.4 Hz, 1 H), 3.58-3.67 (m, 1 H), 3.19-3.28 (m, 1 H), 2.85-3.05 (m, 4 H), 2.24 (s, 3 H), 2.08-2.16 (m, 1 H), 2.05 (s, 6 H), 1.57-1.67 (m, 2 H), 1.35-1.44 (m, 1 H), 1.09 (s, 3 H), 0.97 (t, J = 7.1 Hz, 3 H); MS (ESI+) m/z 499.2 (M + H)$^+$. |
| 17-J | 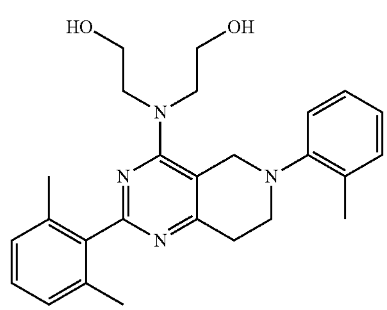 [SMILES: Cc1ccccc1N1CCc2nc(-c3c(C)cccc3C)nc(N(CCO)CCO)c2C1] | 2,2'-((2-(2,6-dimethylphenyl)-6-(o-tolyl)-5,6,7,8-tetrahydropyrido[4,3-d]pyrimidin-4-yl)azanediyl)diethanol. $^1$H NMR (400 MHz, DMSO-$d_6$) δ ppm 7.14-7.23 (m, 4 H), 7.07 (d, J = 7.6 Hz, 2 H), 6.97-7.02 (m, 1 H), 4.76 (t, J = 5.1 Hz, 2 H), 4.11 (s, 2 H), 3.49-3.60 (m, 8 H), 3.23 (t, J = 5.9 Hz, 2 H), 2.92 (t, J = 5.7 Hz, 2 H), 2.27 (s, 3 H), 2.04 (s, 6 H); MS (ESI+) m/z 433.1 (M + H)$^+$. |

| | Structure | Chemical Name & Analytical Data |
|---|---|---|
| 17-K | 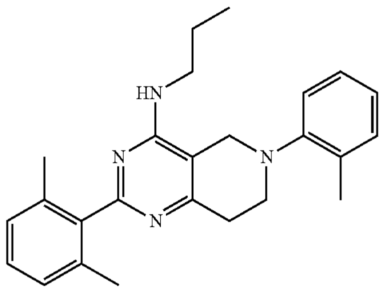 [SMILES: CCCNc1nc(-c2c(C)cccc2C)nc2c1CN(c1ccccc1C)CC2] | 2-(2,6-dimethylphenyl)-N-propyl-6-(o-tolyl)-5,6,7,8-tetrahydropyrido[4,3-d]pyrimidin-4-amine. $^1$H NMR (400 MHz, DMSO-$d_6$) δ ppm 7.12-7.29 (m, 4 H), 6.98-7.10 (m, 3 H), 3.80 (s, 2 H), 3.19 (t, J = 5.7 Hz, 2 H), 2.78-2.86 (m, 2 H), 2.31 (s, 3 H), 2.07 (br. s., 6 H), 1.53 (sxt, J = 7.1 Hz, 2 H), 0.85 (t, J = 7.3 Hz, 3 H); MS (ESI+) m/z 387.2 (M + H)$^+$. |
| 17-L | 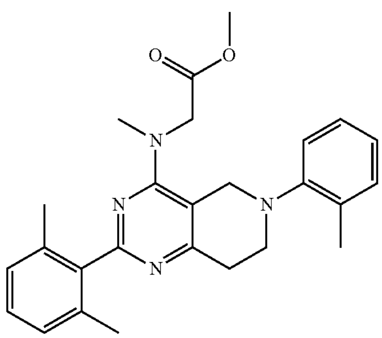 [SMILES: COC(=O)CN(C)c1nc(-c2c(C)cccc2C)nc2c1CN(c1ccccc1C)CC2] | methyl 2-((2-(2,6-dimethylphenyl)-6-(o-tolyl)-5,6,7,8-tetrahydropyrido[4,3-d]pyrimidin-4-yl)(methyl)amino)acetate. $^1$H NMR HCl salt (400 MHz, DMSO-$d_6$) ppm 7.39 (t, J = 7.7 Hz, 1 H), 7.19-7.27 (m, 5 H), 7.02-7.08 (m, 1 H), 4.47 (br. s., 2 H), 4.34 (br. s., 2 H), 3.61 (s, 3 H), 3.26 (t, J = 5.6 Hz, 2 H), 3.04 (br. s., 2 H), 2.28 (s, 3 H), 2.11 (s, 6 H); MS (ESI+) m/z 431.2 (M + H)$^+$. |
| 17-M | 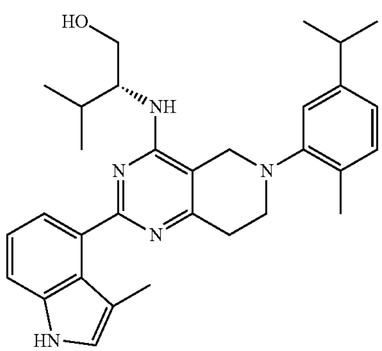 [SMILES: Cc1ccc(C(C)C)cc1N1CCc2nc(-c3cccc4[nH]cc(C)c34)nc(N[C@@H](CO)C(C)C)c2C1] | (R)-2-((6-(5-isopropyl-2-methylphenyl)-2-(3-methyl-1H-indol-4-yl)-5,6,7,8-tetrahydropyrido[4,3-d]pyrimidin-4-yl)amino)-3-methylbutan-1-ol. $^1$H NMR (400 MHz, CD$_2$Cl$_2$) δ ppm 7.52 (br. s., 1 H), 7.35 (d, J = 6.6 Hz, 1 H), 7.19-7.23 (m, 1 H), 7.16 (d, J = 7.8 Hz, 1 H), 7.08-7.14 (m, 2 H), 6.95 (dd, J = 7.8, 1.8 Hz, 1 H), 3.72-3.87 (m, 3 H), 3.26 (br. s., 1 H), 3.06 (br. s., 2 H), 2.90 (spt, J = 6.3 Hz, 1 H), 2.30 (s, 3 H), 2.13 (s, 3 H), 2.04 (spt, J = 6.6 Hz, 1 H), 1.26 (d, J = 7.1 Hz, 6 H), 0.99 (d, J = 6.8 Hz, 3 H), 0.96 (d, J = 6.8 Hz, 3 H); MS (ESI+) m/z 498.3 (M + H)$^+$. |
| 17-N | 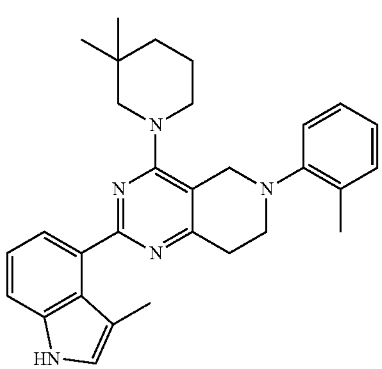 [SMILES: Cc1ccccc1N1CCc2nc(-c3cccc4[nH]cc(C)c34)nc(N3CCCC(C)(C)C3)c2C1] | 4-(3,3-dimethylpiperidin-1-yl)-2-(3-methyl-1H-indol-4-yl)-6-(o-tolyl)-5,6,7,8-tetrahydropyrido[4,3-d]pyrimidine. $^1$H NMR (400 MHz, CD$_2$Cl$_2$) δ ppm 7.46-7.54 (m, 1 H), 7.37-7.44 (m, 1 H), 7.22-7.30 (m, 3 H), 7.14-7.19 (m, 1 H), 7.09 (d, J = 12.9 Hz, 2 H), 4.03 (s, 2 H), 3.40 (br. s., 1 H), 3.35 (t, J = 5.9 Hz, 2 H), 3.20 (br. s., 4 H), 2.33 (s, 3 H), 2.10 (s, 3 H), 1.69-1.75 (m, 2 H), 1.45-1.51 (m, 2 H), 1.01 (s, 6 H); MS (ESI+) m/z 466.3 (M + H)$^+$. |

| | Structure | Chemical Name & Analytical Data |
|---|---|---|
| 17-O | | 6-(5-isopropyl-2-methylphenyl)-4-((2S,4R)-4-methoxy-2-methylpiperidin-1-yl)-2-(3-methyl-1H-indol-4-yl)-5,6,7,8-tetrahydropyrido[4,3-d]pyrimidine. $^1$H NMR (400 MHz, (CD$_3$)$_2$CO) δ ppm 9.96-10.13 (br. s., 1 H), 7.47 (dd, J = 8.1, 1.0 Hz, 1 H), 7.39 (dd, J = 7.3, 1.0 Hz, 1 H), 7.13-7.20 (m, 3 H), 7.11 (d, J = 1.8 Hz, 1 H), 6.92 (dd, J = 7.6, 1.8 Hz, 1 H), 4.34-4.42 (m, 1 H), 4.02-4.20 (m, 2 H), 3.82 (dt, J = 13.5, 4.2 Hz, 1 H), 3.62-3.72 (m, 1 H), 3.40-3.46 (m, 2 H), 3.33 (s, 3 H), 3.08 (t, J = 6.2 Hz, 2 H), 2.91 (dt, J = 13.9, 6.9 Hz, 1 H), 2.76 (m, 2 H), 2.30 (s, 3 H), 2.18 (s, 3 H), 1.94-2.01 (m, 1 H), 1.66 (ddd, J = 12.6, 10.4, 5.3 Hz, 1 H), 1.55 (m, 1 H), 1.32 (d, J = 6.8 Hz, 3 H), 1.26 (d, J = 6.8 Hz, 6 H); MS (ESI+) m/z 524.3 (M + H)$^+$. |
| 17-P | | 6-(5-isopropyl-2-methylphenyl)-4-((2R,4S)-4-methoxy-2-methylpiperidin-1-yl)-2-(3-methyl-1H-indol-4-yl)-5,6,7,8-tetrahydropyrido[4,3-d]pyrimidine. $^1$H NMR (400 MHz, (CD$_3$)$_2$CO) δ ppm 9.96-10.13 (br. s., 1 H), 7.47 (dd, J = 8.1, 1.0 Hz, 1 H), 7.39 (dd, J = 7.3, 1.0 Hz, 1 H), 7.13-7.20 (m, 3 H), 7.11 (d, J = 1.8 Hz, 1 H), 6.92 (dd, J = 7.6, 1.8 Hz, 1 H), 4.34-4.42 (m, 1 H), 4.02-4.20 (m, 2 H), 3.82 (dt, J = 13.5, 4.2 Hz, 1 H), 3.62-3.72 (m, 1 H), 3.40-3.46 (m, 2 H), 3.33 (s, 3 H), 3.08 (t, J = 6.2 Hz, 2 H), 2.91 (dt, J = 13.9, 6.9 Hz, 1 H), 2.76 (m, 2 H), 2.30 (s, 3 H), 2.18 (s, 3 H), 1.94-2.01 (m, 1 H), 1.66 (ddd, J = 12.6, 10.4, 5.3 Hz, 1 H), 1.55 (m, 1 H), 1.32 (d, J = 6.8 Hz, 3 H), 1.26 (d, J = 6.8 Hz, 6 H); MS (ESI+) m/z 524.3 (M + H)$^+$. |
| 17-Q | | 1-(6-(5-isopropyl-2-methylphenyl)-2-(3-methyl-1H-indol-4-yl)-5,6,7,8-tetrahydropyrido[4,3-d]pyrimidin-4-yl)-3-methylpiperidin-3-ol. $^1$H NMR (400 MHz, CD$_2$Cl$_2$) δ ppm 7.47 (d, J = 8.1 Hz, 1 H), 7.32 (d, J = 7.1 Hz, 1 H), 7.18-7.26 (m, 1 H), 7.14 (d, J = 7.8 Hz, 1 H), 7.07 (d, J = 1.3 Hz, 1 H), 7.00 (d, J = 1.8 Hz, 1 H), 6.92 (dd, J = 7.7, 1.6 Hz, 1 H), 3.98-4.13 (m, 2 H), 3.83-3.98 (m, 2 H), 3.35-3.46 (m, 1 H), 3.25-3.34 (m, 1 H), 3.12-3.25 (m, 2 H), 2.96-3.12 (m, 2 H), 2.89 (dt, J = 13.8, 6.9 Hz, 1 H), 2.27 (s, 3 H), 2.10 (s, 3 H), 1.81-1.96 (m, 1 H), 1.76 (d, J = 15.2 Hz, 1 H), 1.42-1.65 (m, 2 H), 1.25 (d, J = 7.1 Hz, 6 H), 1.20 (s, 3 H); MS (ESI+) m/z 510.2 (M + H)$^+$. |
| 17-R | | 6-(5-isopropyl-2-methylphenyl)-4-((2R,4S)-4-methoxy-2-methylpiperidin-1-yl)-2-(3-methyl-1H-indol-4-yl)-5,6,7,8-tetrahydropyrido[4,3-d]pyrimidine. $^1$H NMR (400 MHz, DMSO-d$_6$) δ ppm 10.81-11.02 (m, 1 H), 7.33-7.52 (m, 1 H), 7.22 (d, J = 1.0 Hz, 1 H), 7.07-7.16 (m, 3 H), 6.96 (d, J = 1.5 Hz, 1 H), 6.87 (dd, J = 7.6, 1.5 Hz, 1 H), 4.04-4.13 (m, 1 H), 3.93-4.02 (m, 1 H), 3.76-3.87 (m, 1 H), 3.41-3.50 (m, 1 H), 3.31-3.37 (m, 3 H), 3.26 (s, 3 H), 3.11-3.23 (m, 1 H), 2.96 (t, J = 5.7 Hz, 2 H), 2.84 (dt, J = 13.9, 6.9 Hz, 1 H), 2.22 (s, 3 H), 2.02 (s, 3 H), 1.84-1.95 (m, 2 H), 1.52-1.67 (m, 2 H), 1.15-1.23 (m, 9 H); MS (ESI+) m/z 524.2 (M + H)$^+$. |

-continued

| | Structure | Chemical Name & Analytical Data |
|---|---|---|
| 17-S | 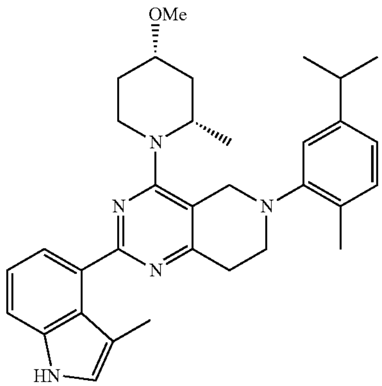 [SMILES: CO[C@H]1CCN(c2nc(-c3cccc4[nH]cc(C)c34)nc3c2CN(c2cc(C(C)C)ccc2C)CC3)[C@@H](C)C1] | 6-(5-isopropyl-2-methylphenyl)-4-((2S,4S)-4-methoxy-2-methylpiperidin-1-yl)-2-(3-methyl-1H-indol-4-yl)-5,6,7,8-tetrahydropyrido[4,3-d]pyrimidine. $^1$H NMR (400 MHz, (CD$_3$)$_2$CO) δ ppm 10.07 (br. s., 1 H), 7.48 (d, J = 9.1 Hz, 1 H), 7.41 (d, J = 7.3 Hz, 1 H), 7.13-7.22 (m, 3 H), 7.10 (d, J = 1.5 Hz, 1 H), 6.93 (dd, J = 1.6, 7.7 Hz, 1 H), 4.03-4.28 (m, 2 H), 3.90 (dd, J = 6.3, 10.9 Hz, 1 H), 3.49 (dt, J = 3.5, 7.2 Hz, 1 H), 3.39-3.46 (m, 2 H), 3.35 (s, 3 H), 3.18-3.26 (m, 1 H), 3.06-3.13 (m, 2 H), 2.91 (td, J = 6.9, 13.8 Hz, 1 H), 2.79 (d, J = 13.6 Hz, 2 H), 2.32 (s, 3 H), 2.18 (d, J = 0.8 Hz, 3 H), 1.98-2.04 (m, 1 H), 1.68-1.76 (m, 1 H), 1.59-1.68 (m, 1 H), 1.24-1.30 (m, 9 H); MS (ESI+) m/z 524.3 (M + H)$^+$. |
| 17-T | 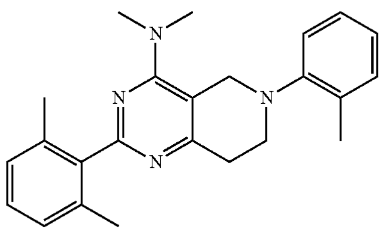 [SMILES: Cc1ccccc1N1CCc2nc(-c3c(C)cccc3C)nc(N(C)C)c2C1] | 2-(2,6-dimethylphenyl)-N,N-dimethyl-6-(o-tolyl)-5,6,7,8-tetrahydropyrido[4,3-d]pyrimidin-4-amine. $^1$H NMR (400 MHz, DMSO-d$_6$) δ ppm 7.14-7.23 (m, 4 H), 7.07 (d, J = 7.6 Hz, 2 H), 6.96-7.04 (m, 1 H), 4.08 (s, 2 H), 3.24 (t, J = 5.9 Hz, 2 H), 3.01 (s, 6 H), 2.91 (t, J = 5.8 Hz, 2 H), 2.26 (s, 3 H), 2.06 (s, 6 H); MS (ESI+) m/z 373.2 (M + H)$^+$. |
| 17-U | 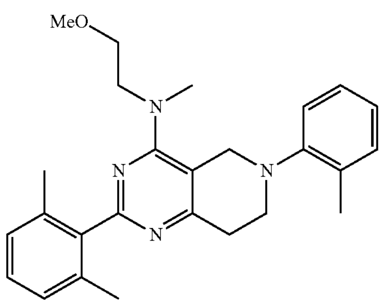 [SMILES: COCCN(C)c1nc(-c2c(C)cccc2C)nc2c1CN(c1ccccc1C)CC2] | 2-(2,6-dimethylphenyl)-N-(2-methoxyethyl)-N-methyl-6-(o-tolyl)-5,6,7,8-tetrahydropyrido[4,3-d]pyrimidin-4-amine. HCl salt $^1$H NMR (400 MHz, DMSO-d$_6$) δ ppm 7.39 (t, J = 7.1 Hz, 1 H), 7.17-7.28 (m, 5 H), 6.99-7.09 (m, 1 H), 4.31 (br. s., 2 H), 3.89 (t, J = 4.8 Hz, 2 H), 3.53-3.62 (m, 5 H), 3.19-3.29 (m, 5 H), 3.01-3.10 (m, 2 H), 2.28 (s, 3 H), 2.19 (s, 6 H); MS (ESI+) m/z 417.3 (M + H)$^+$. |
| 17-V | 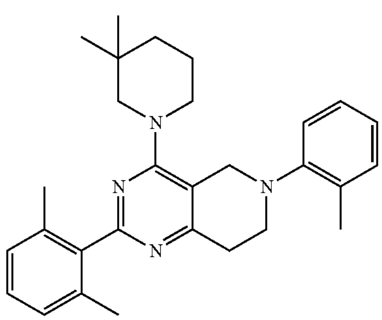 [SMILES: Cc1ccccc1N1CCc2nc(-c3c(C)cccc3C)nc(N3CCCC(C)(C)C3)c2C1] | 2-(2,6-dimethylphenyl)-4-(3,3-dimethylpiperidin-1-yl)-6-(o-tolyl)-5,6,7,8-tetrahydropyrido[4,3-d]pyrimidine. HCl salt $^1$H NMR (400 MHz, DMSO-d$_6$) δ ppm 7.40 (t, J = 6.8 Hz, 1 H), 7.19-7.28 (m, 5 H), 7.05 (td, J = 6.9, 2.0 Hz, 1 H), 4.16 (s, 2 H), 3.76 (br. s., 2 H), 3.59 (s, 2 H), 3.29 (t, J = 5.6 Hz, 2 H), 3.05-3.14 (m, 2 H), 2.28 (s, 3 H), 2.19 (s, 6 H), 1.62-1.73 (m, 2 H), 1.47 (t, J = 5.6 Hz, 2 H), 0.89 (s, 6 H); MS (ESI+) m/z 441.3 (M + H)$^+$. |
| 17-W | 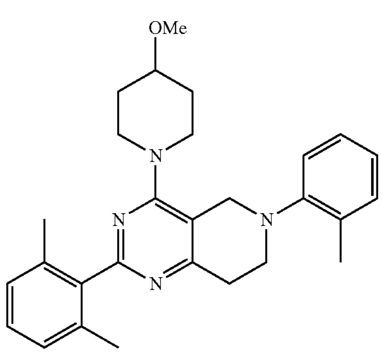 [SMILES: COC1CCN(c2nc(-c3c(C)cccc3C)nc3c2CN(c2ccccc2C)CC3)CC1] | 2-(2,6-dimethylphenyl)-4-(4-methoxypiperidin-1-yl)-6-(o-tolyl)-5,6,7,8-tetrahydropyrido[4,3-d]pyrimidine. $^1$H NMR (400 MHz, DMSO-d$_6$) δ ppm 7.39 (t, J = 7.6 Hz, 1 H), 7.17-7.30 (m, 5 H), 7.01-7.09 (m, 1 H), 4.14 (br. s., 2 H), 3.95-4.06 (m, 2 H), 3.64-3.73 (m, 2 H), 3.21-3.31 (m, 4 H), 3.10 (br. s., 2 H), 2.28 (s, 3 H), 2.20 (s, 6 H), 1.88-2.01 (m, 2 H), 1.59 (s, 3 H); MS (ESI+) m/z 443.3 (M + H)$^+$. |

| | Structure | Chemical Name & Analytical Data |
|---|---|---|
| 17-X | 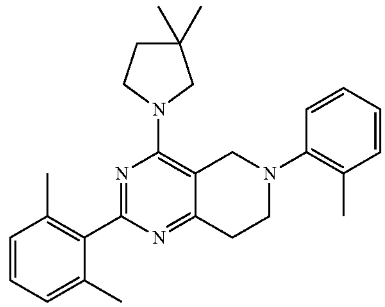 [SMILES: Cc1ccccc1N1CCc2nc(-c3c(C)cccc3C)nc(N3CCC(C)(C)C3)c2C1] | 2-(2,6-dimethylphenyl)-4-(3,3-dimethylpyrrolidin-1-yl)-6-(o-tolyl)-5,6,7,8-tetrahydropyrido[4,3-d]pyrimidine. $^1$H NMR (400 MHz, DMSO-d$_6$) δ ppm 7.18-7.27 (m, 3 H) 7.14 (d, J = 7.3 Hz, 1 H) 7.06 (d, J = 7.6 Hz, 2 H) 7.02 (br. s., 1 H) 4.23 (s, 2 H) 3.74 (t, J = 7.0 Hz, 2 H) 3.10-3.24 (m, 3 H) 2.87 (t, J = 5.3 Hz, 2 H) 2.28 (s, 3 H) 2.07 (s, 6 H) 1.65 (t, J = 7.0 Hz, 2 H) 1.05 (s, 6 H); MS (ESI+) m/z 427.29 (M + H)$^+$. |
| 17-Y | 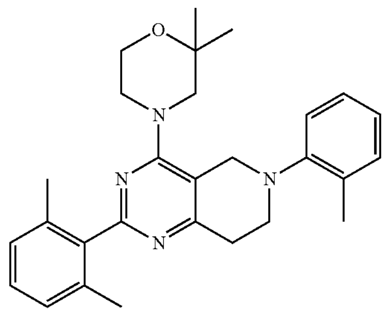 [SMILES: Cc1ccccc1N1CCc2nc(-c3c(C)cccc3C)nc(N3CCOC(C)(C)C3)c2C1] | 4-(2-(2,6-dimethylphenyl)-6-(o-tolyl)-5,6,7,8-tetrahydropyrido[4,3-d]pyrimidin-4-yl)-2,2-dimethylmorpholine. HCl salt $^1$H NMR (400 MHz, DMSO-d$_6$) δ ppm 7.40 (t, J = 7.8 Hz, 1 H), 7.19-7.29 (m, 5 H), 7.05 (dd, J = 7.6, 6.8 Hz, 1 H), 4.16 (s, 2 H), 3.84 (br. s., 2 H), 3.71 (br. s., 4 H), 3.21-3.29 (m, 2 H), 3.09 (br. s., 2 H), 2.28 (s, 3 H), 2.18 (s, 6 H), 1.16 (s, 6 H); MS (ESI+) m/z 443.3 (M + H)$^+$. |
| 17-Z | 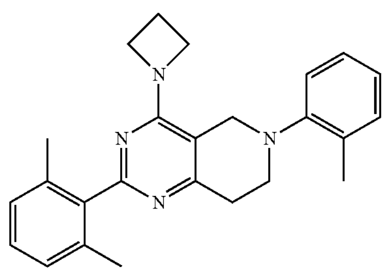 [SMILES: Cc1ccccc1N1CCc2nc(-c3c(C)cccc3C)nc(N3CCC3)c2C1] | 4-(azetidin-1-yl)-2-(2,6-dimethylphenyl)-6-(o-tolyl)-5,6,7,8-tetrahydropyrido[4,3-d]pyrimidine. HCl salt $^1$H NMR (400 MHz, DMSO-d$_6$) δ ppm 7.40 (t, J = 7.6 Hz, 1 H), 7.18-7.29 (m, 5 H), 7.01-7.09 (m, 1 H), 4.83-4.92 (m, 2 H), 4.22-4.31 (m, 2 H), 4.20 (s, 2 H), 3.15-3.21 (m, 2 H), 2.92-2.98 (m, 2 H), 2.32-2.41 (m, 2 H), 2.30 (s, 3 H), 2.19 (s, 6 H); MS (ESI+) m/z 385.3 (M + H)$^+$. |
| 17-AA | 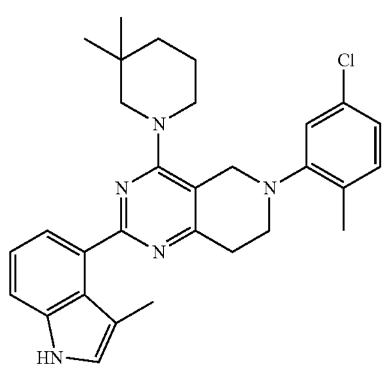 [SMILES: Cc1ccc(Cl)cc1N1CCc2nc(-c3cccc4[nH]cc(C)c34)nc(N3CCCC(C)(C)C3)c2C1] | 6-(5-chloro-2-methylphenyl)-4-(3,3-dimethylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 7.46 (d, J = 7.8 Hz, 1 H), 7.33-7.40 (m, 1 H), 7.19-7.25 (m, 1 H), 7.17 (d, J = 8.1 Hz, 1 H), 7.05-7.11 (m, 2 H), 7.02 (dd, J = 8.1, 2.0 Hz, 1 H), 4.00 (s, 2 H), 3.30-3.46 (m, 4 H), 3.09-3.28 (m, 4 H), 2.29 (s, 3 H), 2.10 (s, 3 H), 1.68-1.77 (m, 2 H), 1.42-1.48 (m, 2 H), 0.98 (s, 6 H); MS (ESI+) m/z 500.3 (M + H)$^+$. |

| Structure | Chemical Name & Analytical Data |
|---|---|
| 17-AB | 4-(4-methoxypiperidin-1-yl)-2-(3-methyl-1H-indol-4-yl)-6-(o-tolyl)-5,6,7,8-tetrahydropyrido[4,3-d]pyrimidine. $^1$H NMR (400 MHz, CD$_2$Cl$_2$) δ ppm 8.26 (br. s., 1 H), 7.46 (d, J = 9.3 Hz, 1 H), 7.38 (d, J = 6.3 Hz, 1 H), 7.19-7.24 (m, 3 H), 7.13 (d, J = 6.8 Hz, 1 H), 7.07 (s, 1 H), 7.02-7.05 (m, 1 H), 4.01 (s, 2 H), 3.76 (br. s., 2 H), 3.43 (br. s., 1 H), 3.30-3.37 (m, 6 H), 3.12-3.28 (br. s., 3 H), 2.32 (s, 3 H), 2.10 (s, 3 H), 1.93-2.01 (m, 2 H), 1.60-1.71 (m, 2 H); MS (ESI+) m/z 468.3 (M + H)$^+$. |
| 17-AC | 6-(5-chloro-2-methylphenyl)-4-(4-methoxypiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.20-8.29 (br. s., 1 H), 7.45 (d, J = 7.8 Hz, 1 H), 7.37 (d, J = 7.3 Hz, 1 H), 7.19-7.24 (m, 1 H), 7.16 (d, J = 0.5 Hz, 1 H), 7.11 (d, J = 2.3 Hz, 1 H), 7.07 (s, 1 H), 7.02 (dd, J = 7.8, 2.0 Hz, 1 H), 3.98 (s, 2 H), 3.69-3.79 (m, 2 H), 3.39-3.46 (m, 1 H), 3.31-3.37 (m, 5 H), 3.11-3.27 (m, 4 H), 2.28 (s, 3 H), 2.10 (d, J = 0.8 Hz, 3 H), 1.94-2.02 (m, 2 H), 1.60-1.70 (m, 2 H); MS (ESI+) m/z 502.3 (M + H)$^+$. |
| 17-AD | 2-methyl-1-(methyl(2-(3-methyl-1H-indol-4-yl)-6-(o-tolyl)-5,6,7,8-tetrahydropyrido[4,3-d]pyrimidin-4-yl)amino)propan-2-ol. $^1$H NMR (400 MHz, DMSO-d$_6$) δ ppm 10.89 (br. s., 1 H), 7.37 (d, J = 10.1 Hz, 1 H), 7.07-7.22 (m, 6 H), 7.00-7.03 (m, 1 H), 4.71 (s, 1 H), 4.09 (s, 2 H), 3.67 (s, 2 H), 3.19 (s, 3 H), 2.94 (s, 2 H), 2.26 (s, 3 H), 2.00 (s, 3 H), 1.05 (s, 6 H); MS (ESI+) m/z 456.2 (M + H)$^+$. |
| 17-AE | 1-((6-(5-chloro-2-methylphenyl)-2-(3-methyl-1H-indol-4-yl)-5,6,7,8-tetrahydropyrido[4,3-d]pyrimidin-4-yl)(methyl)amino)-2-methylpropan-2-ol. $^1$H NMR (400 MHz, DMSO-d$_6$) δ ppm 10.90 (br. s, 1 H), 7.39 (dd, J = 7.7, 1.4 Hz, 1 H), 7.23 (d, J = 8.1 Hz, 1 H), 7.03-7.16 (m, 5 H), 4.71 (s, 1 H), 4.15 (s, 2 H), 3.69 (s, 2 H), 3.19 (s, 3 H), 2.91 (t, J = 5.7 Hz, 2 H), 2.24 (s, 3 H), 1.99 (s, 3 H), 1.06 (s, 6 H); MS (ESI+) m/z 490.2 (M + H)$^+$. |

| | Structure | Chemical Name & Analytical Data |
|---|---|---|
| 17-AF | 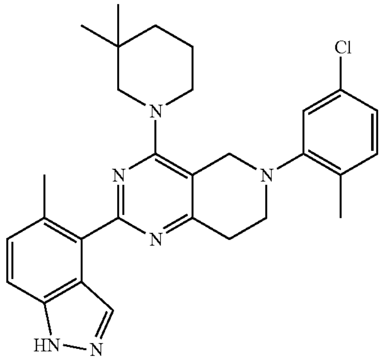 [SMILES: Cc1ccc(Cl)cc1N1CCc2nc(-c3c(C)ccc4[nH]ncc34)nc(N3CCCC(C)(C)C3)c2C1] | 6-(5-chloro-2-methylphenyl)-4-(3,3-dimethylpiperidin-1-yl)-2-(5-methyl-1H-indazol-4-yl)-5,6,7,8-tetrahydropyrido[4,3-d]pyrimidine. $^1$H NMR (400 MHz, CD$_2$Cl$_2$) δ ppm 7.83-7.87 (m, 1 H), 7.28 (d, J = 8.6 Hz, 1 H), 7.21 (d, J = 8.1 Hz, 1 H), 7.12-7.17 (m, 2 H), 7.09 (dd, J = 8.1, 2.0 Hz, 1 H), 4.02 (s, 2 H), 3.73-3.78 (m, 2 H), 3.58-3.64 (m, 2 H), 3.55 (s, 2 H), 3.37 (t, J = 5.8 Hz, 2 H), 2.67 (s, 3 H), 2.31 (s, 3 H), 1.75-1.81 (m, 2 H), 1.50-1.56 (m, 2 H), 0.95 (s, 6 H); MS (ESI+) m/z 501.2 (M + H)$^+$. |
| 17-AG | 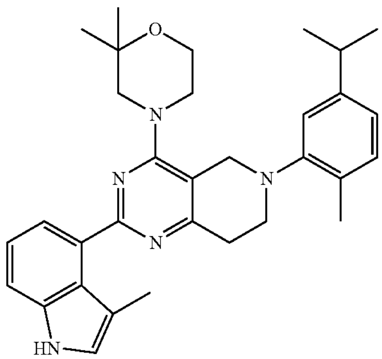 [SMILES: Cc1ccc(C(C)C)cc1N1CCc2nc(-c3cccc4[nH]cc(C)c34)nc(N3CCOC(C)(C)C3)c2C1] | 4-(6-(5-isopropyl-2-methylphenyl)-2-(3-methyl-1H-indol-4-yl)-5,6,7,8-tetrahydropyrido[4,3-d]pyrimidin-4-yl)-2,2-dimethylmorpholine. $^1$H NMR (400 MHz, CD$_2$Cl$_2$) δ ppm 1.24 (s, 3 H) 1.26 (s, 3 H) 1.28 (s, 6 H) 2.10 (s, 3 H) 2.29 (s, 3 H) 2.89 (dt, J = 13.9, 7.0 Hz, 1 H) 3.10-3.21 (m, 2 H) 3.22-3.31 (m, 2 H) 3.37 (t, J = 5.9 Hz, 2 H) 3.40-3.45 (m, 2 H) 3.78-3.87 (m, 2 H) 4.04 (s, 2 H) 6.91 (dd, J = 7.7, 1.6 Hz, 1 H) 6.97 (d, J = 1.5 Hz, 1 H) 7.07 (s, 1 H) 7.14 (d, J = 8.1 Hz, 1 H) 7.22 (t, J = 7.7 Hz, 1 H) 7.36 (d, J = 7.1 Hz, 1 H) 7.45 (d, J = 8.1 Hz, 1 H) 8.21 (br. s., 1 H); MS (ESI+) m/z 510.3 (M + H)$^+$. |
| 17-AH | 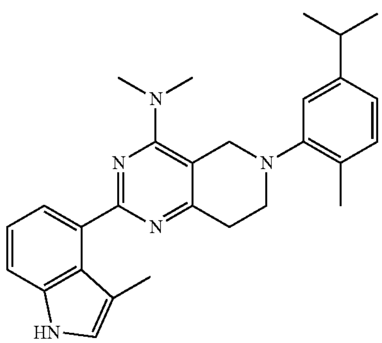 [SMILES: Cc1ccc(C(C)C)cc1N1CCc2nc(-c3cccc4[nH]cc(C)c34)nc(N(C)C)c2C1] | 6-(5-isopropyl-2-methylphenyl)-N,N-dimethyl-2-(3-methyl-1H-indol-4-yl)-5,6,7,8-tetrahydropyrido[4,3-d]pyrimidin-4-amine. $^1$H NMR (400 MHz, CD$_2$Cl$_2$) δ ppm 1.25 (d, J = 6.8 Hz, 6 H) 2.12 (s, 3 H) 2.28 (s, 3 H) 2.89 (spt, J = 6.9 Hz, 1 H) 3.06-3.24 (m, 8 H) 3.34 (t, J = 5.9 Hz, 2 H) 4.09 (s, 2 H) 6.92 (dd, J = 7.7, 1.6 Hz, 1 H) 7.01 (d, J = 1.8 Hz, 1 H) 7.06 (d, J = 1.0 Hz, 1 H) 7.14 (d, J = 7.6 Hz, 1 H) 7.21 (t, J = 7.7 Hz, 1 H) 7.38 (d, J = 7.1 Hz, 1 H) 7.45 (d, J = 8.1 Hz, 1 H) 8.27 (br. s., 1 H); MS (ESI+) m/z 440.2 (M + H)$^+$. |
| 17-AI | 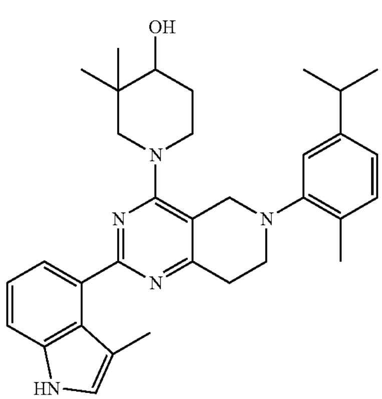 [SMILES: Cc1ccc(C(C)C)cc1N1CCc2nc(-c3cccc4[nH]cc(C)c34)nc(N3CCC(O)C(C)(C)C3)c2C1] | 1-(6-(5-isopropyl-2-methylphenyl)-2-(3-methyl-1H-indol-4-yl)-5,6,7,8-tetrahydropyrido[4,3-d]pyrimidin-4-yl)-3,3-dimethylpiperidin-4-ol. $^1$H NMR (400 MHz, DMSO-d$_6$) δ ppm 0.90 (s, 3 H) 0.93 (s, 3 H) 1.18 (d, J = 6.8 Hz, 6 H) 1.52-1.65 (m, 1 H) 1.70-1.78 (m, 1 H) 2.01 (s, 3 H) 2.21 (s, 3 H) 2.74 (d, J = 12.9 Hz, 1 H) 2.83 (dt, J = 13.6, 6.8 Hz, 1 H) 2.90-3.05 (m, 3 H) 3.26-3.36 (m, 3 H) 3.42 (d, J = 13.1 Hz, 1 H) 3.61-3.70 (m, 1 H) 4.06 (s, 2 H) 4.63 (d, J = 4.8 Hz, 1 H) 6.86 (dd, J = 7.6, 1.3 Hz, 1 H) 6.96 (s, 1 H) 7.07-7.15 (m, 3 H) 7.19 (dd, J = 7.1, 1.0 Hz, 1 H) 7.40 (dd, J = 8.0, 0.9 Hz, 1 H) 10.89 (br. s., 1 H); MS (ESI+) m/z 524.4 (M + H)$^+$. |

| Structure | Chemical Name & Analytical Data |
|---|---|
| 17-AJ | 6-(5-isopropyl-2-methylphenyl)-N-methyl-2-(3-methyl-1H-indol-4-yl)-5,6,7,8-tetrahydropyrido[4,3-d]pyrimidin-4-amine. $^1$H NMR (400 MHz, DMSO-$d_6$) δ ppm 8.23 (br. s., 1 H), 7.42 (dd, J = 8.1, 1.0 Hz, 1 H), 7.34 (dd, J = 7.3, 1.0 Hz, 1 H), 7.18-7.22 (m, 1 H), 7.16 (d, J = 7.8 Hz, 1 H), 7.03-7.07 (m, 2 H), 6.93 (dd, J = 7.7, 1.6 Hz, 1 H), 4.56 (br. s., 1 H), 3.85 (s, 2 H), 3.28 (t, J = 5.7 Hz, 2 H), 3.09 (d, J = 4.8 Hz, 3 H), 3.02 (t, J = 5.6 Hz, 2 H), 2.89 (spt, J = 6.9 Hz, 1 H), 2.32 (s, 3 H), 2.12 (d, J = 1.0 Hz, 3 H), 1.26 (d, J = 6.8 Hz, 6 H); MS (ESI+) m/z 426.2 (M + H)$^+$. |
| 17-AK | N-isopropyl-6-(5-isopropyl-2-methylphenyl)-2-(3-methyl-1H-indol-4-yl)-5,6,7,8-tetrahydropyrido[4,3-d]pyrimidin-4-amine. $^1$H NMR (400 MHz, DICHLOROMETHANE-$d_6$) δ ppm 8.23 (br. s., 1 H), 7.42 (dd, J = 8.1, 0.8 Hz, 1 H), 7.33 (d, J = 7.1 Hz, 1 H), 7.15-7.23 (m, 2 H), 7.08 (d, J = 1.8 Hz, 1 H), 7.05 (d, J = 1.0 Hz, 1 H), 6.94 (dd, J = 7.7, 1.6 Hz, 1 H), 4.48-4.57 (m, 1 H), 3.80 (s, 2 H), 3.28 (t, J = 5.7 Hz, 2 H), 2.99-3.07 (m, 2 H), 2.90 (spt, J = 6.9 Hz, 1 H), 2.33 (s, 3 H), 2.12 (d, J = 1.0 Hz, 3 H), 1.23-1.28 (m, 12 H); MS (ESI+) m/z 454.2 (M + H)$^+$. |
| 17-AL | 4-(azetidin-1-yl)-6-(5-isopropyl-2-methylphenyl)-2-(3-methyl-1H-indol-4-yl)-5,6,7,8-tetrahydropyrido[4,3-d]pyrimidine. $^1$H NMR (400 MHz, $CD_2Cl_2$) δ ppm 8.16-8.22 (m, 1 H), 7.41 (dd, J = 8.1, 1.0 Hz, 1 H), 7.29-7.32 (m, 1 H), 7.16-7.21 (m, 1 H), 7.14 (d, J = 7.6 Hz, 1 H), 7.02-7.05 (m, 1 H), 6.99 (d, J = 1.8 Hz, 1 H), 6.90 (dd, J = 7.7, 1.6 Hz, 1 H), 4.29 (t, J = 7.6 Hz, 4 H), 4.06 (s, 2 H), 3.28 (t, J = 5.7 Hz, 2 H), 2.99-3.05 (m, 2 H), 2.88 (spt, J = 6.9 Hz, 1 H), 2.29-2.40 (m, 5 H), 2.10 (d, J = 0.8 Hz, 3 H), 1.25 (d, J = 6.8 Hz, 6 H); MS (ESI+) m/z 452.1 (M + H)$^+$. |
| 17-AM | (R)-6-(5-Isopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, $CD_2Cl_2$) δ ppm 0.94-0.99 (m, 3 H) 1.01 (s, 3 H) 1.25 (d, J = 7.1 Hz, 6 H) 1.63-1.76 (m, 1 H) 1.91-2.03 (m, 1 H) 2.10 (s, 3 H) 2.28 (s, 3 H) 2.81-3.03 (m, 3 H) 3.11-3.25 (m, 3 H) 3.34 (s, 3 H) 3.35-3.39 (m, 2 H) 3.41-3.53 (m, 1 H) 3.74 (dd, J = 11.4, 6.3 Hz, 1 H) 4.05 (s, 2 H) 6.91 (dd, J = 7.6, 1.5 Hz, 1 H) 6.97 (d, J = 1.5 Hz, 1 H) 7.06 (d, J = 1.0 Hz, 1 H) 7.14 (d, J = 7.8 Hz, 1 H) 7.19-7.25 (m, 1 H) 7.36 (d, J = 7.1 Hz, 1 H) 7.45 (d, J = 8.1 Hz, 1 H) 8.27 (br. s., 1 H); MS (ESI+) m/z 538.4 (M + H)$^+$. |

| | Structure | Chemical Name & Analytical Data |
|---|---|---|
| 17-AN | 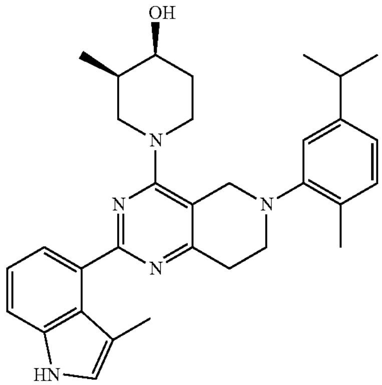 [SMILES: Cc1ccc(C(C)C)cc1N1CCc2nc(-c3cccc4[nH]cc(C)c34)nc(N3CC[C@H](O)[C@H](C)C3)c2C1] | racemic-1-(6-(5-isopropyl-2-methylphenyl)-2-(3-methyl-1H-indol-4-yl)-5,6,7,8-tetrahydropyrido[4,3-d]pyrimidin-4-yl)-3-methylpiperidin-4-ol. $^1$H NMR (400 MHz, CD$_2$Cl$_2$) δ ppm 8.24 (br. s., 1 H), 7.44 (d, J = 8.1 Hz, 1 H), 7.35 (d, J = 7.1 Hz, 1 H), 7.19-7.23 (m, J = 7.6 Hz, 1 H), 7.13 (d, J = 7.8 Hz, 1 H), 7.06 (d, J = 1.0 Hz, 1 H), 6.98 (d, J = 1.5 Hz, 1 H), 6.90 (dd, J = 8.1, 1.5 Hz, 1 H), 4.03 (d, J = 7.1 Hz, 2 H), 3.93 (br. s., 1 H), 3.39-3.61 (m, 1 H), 3.35 (t, J = 6.3 Hz, 2 H), 3.24 (app t, J = 11.9 Hz, 1 H), 3.15 (br. s., 1 H), 2.89 (spt, J = 7.1 Hz, 1 H), 2.27 (s, 3 H), 2.10 (s, 1 H), 1.92-2.00 (m, 1 H), 1.78-1.88 (m, 2 H), 1.25 (d, J = 7.1 Hz, 6 H), 0.99 (d, J = 7.1 Hz, 3 H); MS (ESI+) m/z 510.2 (M + H)$^+$. |
| 17-AO | 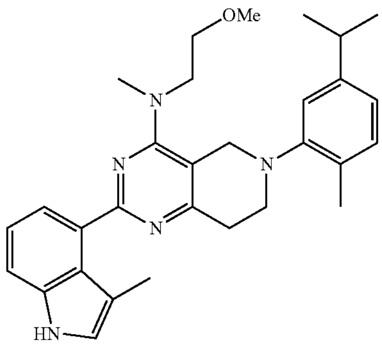 [SMILES: COCCN(C)c1nc(-c2cccc3[nH]cc(C)c23)nc2c1CN(c1cc(C(C)C)ccc1C)CC2] | 6-(5-isopropyl-2-methylphenyl)-N-(2-methoxyethyl)-N-methyl-2-(3-methyl-1H-indol-4-yl)-5,6,7,8-tetrahydropyrido[4,3-d]pyrimidin-4-amine. $^1$H NMR (400 MHz, CD$_2$Cl$_2$) δ ppm 8.37 (br. s., 1 H), 7.43 (dd, J = 8.1, 1.0 Hz, 1 H), 7.36 (dd, J = 7.1 Hz, 1 H), 7.17-7.23 (m, 1 H), 7.14 (d, J = 7.6 Hz, 1 H), 7.05 (d, J = 1.3 Hz, 1 H), 7.00 (d, J = 1.8 Hz, 1 H), 6.91 (dd, J = 7.7, 1.6 Hz, 1 H), 4.11 (s, 2 H), 3.72 (br. s., 2 H), 3.62 (app. t, J = 5.8 Hz, 2 H), 3.33 (app. t, J = 5.8 Hz, 2 H), 3.30 (s, 3 H), 3.20 (br. s., 4 H), 2.89 (spt, J = 7.1 Hz, 1 H), 2.27 (s, 3 H), 2.11 (d, J = 0.8, 3 H), 1.25 (d, J = 6.8 Hz, 6 H); MS (ESI+) m/z 484.22 (M + H)$^+$. |
| 17-AP | 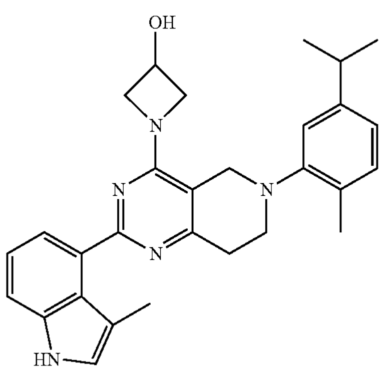 [SMILES: Cc1ccc(C(C)C)cc1N1CCc2nc(-c3cccc4[nH]cc(C)c34)nc(N3CC(O)C3)c2C1] | 1-(6-(5-isopropyl-2-methylphenyl)-2-(3-methyl-1H-indol-4-yl)-5,6,7,8-tetrahydropyrido[4,3-d]pyrimidin-4-yl)azetidin-3-ol. $^1$H NMR (400 MHz, CD$_2$Cl$_2$) δ ppm 7.43 (d, J = 7.3 Hz, 1 H), 7.31 (d, J = 7.3 Hz, 1 H), 7.15-7.19 (m, 2 H), 7.05 (s, 1 H), 6.99 (d, J = 1.8 Hz, 1 H), 6.93 (dd, J = 8.1, 1.5 Hz, 1 H), 4.65-4.74 (m, 1 H), 4.47 (dd, J = 8.6, 6.8 Hz, 2 H), 4.14 (br. s., 2 H), 4.01 (s, 2 H), 3.25 (t, J = 5.6 Hz, 2 H), 3.01-3.09 (m, 2 H), 2.89 (spt, J = 6.6 Hz, 1 H), 2.30 (s, 3 H), 2.09 (s, 3 H), 1.26 (d, J = 6.8 Hz, 6 H); MS (ESI+) m/z 468.3 (M + H)$^+$. |
| 17-AQ | 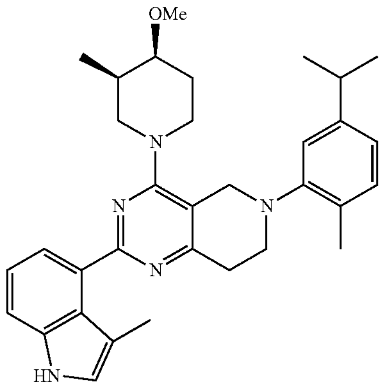 | racemic 6-(5-isopropyl-2-methylphenyl)-4-(4-methoxy-3-methylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.21 (br. s., 1 H), 7.43 (dd, J = 8.1, 1.0 Hz, 1 H), 7.34 (d, J = 6.6 Hz, 1 H), 7.18-7.22 (m, 1 H), 7.13 (d, J = 7.8 Hz, 1 H), 7.05 (dd, J = 2.0, 1.0 Hz, 1 H), 6.98 (d, J = 1.5 Hz, 1 H), 6.90 (dd, J = 7.6, 1.8 Hz, 1 H), 4.03 (AB q, J = 6.1 Hz, 2 H), 3.41-3.52 (m, 1 H), 3.29-3.40 (m, 9 H), 3.11 (br. s., 2 H), 2.89 (spt, J = 7.3 Hz, 1 H), 2.27 (s, 3 H), 2.09 (s, 3 H), 2.01-2.08 (m, 1 H), 1.89-1.99 (m, 1 H), 1.66-1.77 (m, 1 H), 1.25 (d, J = 6.8 Hz, 6 H), 0.98 (d, J = 6.8 Hz, 3 H); MS (ESI+) m/z 524.3 (M + H)$^+$. |

| | Structure | Chemical Name & Analytical Data |
|---|---|---|
| 17-AR | 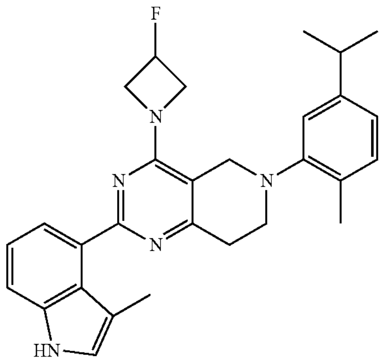 [SMILES: Cc1ccc(C(C)C)cc1N1CCc2nc(-c3cccc4[nH]cc(C)c34)nc(N3CC(F)C3)c2C1] | 4-(3-fluoroazetidin-1-yl)-6-(5-isopropyl-2-methylphenyl)-2-(3-methyl-1H-indol-4-yl)-5,6,7,8-tetrahydropyrido[4,3-d]pyrimidine. $^1$H NMR (400 MHz, DMSO-$d_6$) δ ppm 10.92 (br. s., 1 H), 7.41 (d, J = 8.1 Hz, 1 H), 7.21 (d, J = 8.1 Hz, 1 H), 7.06-7.16 (m, 3 H), 7.02 (d, J = 1.5 Hz, 1 H), 6.89 (dd, J = 7.8, 1.5 Hz, 1 H), 5.35-5.59 (m, 1 H), 4.49-4.66 (m, 2 H), 4.23-4.38 (m, 2 H), 4.05 (s, 2 H), 3.23 (t, J = 5.7 Hz, 2 H), 2.81-2.94 (m, 3 H), 2.24 (s, 3 H), 2.03 (d, J = 0.8 Hz, 3 H), 1.20 (d, J = 7.1 Hz, 6 H); MS (ESI+) m/z 470.1 (M + H)$^+$. |
| 17-AS | 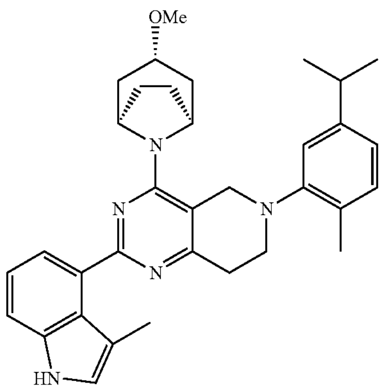 [SMILES: CO[C@H]1C[C@H]2CC[C@@H](C1)N2c1nc(-c2cccc3[nH]cc(C)c23)nc2c1CN(c1cc(C(C)C)ccc1C)CC2] | 6-(5-isopropyl-2-methylphenyl)-4-((3-endo)-3-methoxy-8-azabicyclo[3.2.1]octan-8-yl)-2-(3-methyl-1H-indol-4-yl)-5,6,7,8-tetrahydropyrido[4,3-d]pyrimidine. $^1$H NMR TFA salt (400 MHz, DMSO-$d_6$) δ ppm 10.88-10.92 (br. s., 1 H), 7.39 (dd, J = 8.0, 1.1 Hz, 1 H), 7.19 (dd, J = 7.2, 1.1 Hz, 1 H), 7.13 (s, 1 H), 7.07-7.13 (m, 2 H), 7.01 (d, J = 1.5 Hz, 1 H), 6.88 (dd, J = 7.6, 1.5 Hz, 1 H), 4.47 (br. s., 2 H), 4.02 (s, 2 H), 3.47 (br. s., 1 H), 3.21 (s, 3 H), 2.92 (t, J = 5.9 Hz, 2 H), 2.85 (quin, J = 6.9 Hz, 1 H), 2.22 (s, 3 H), 1.95-2.06 (m, 9 H), 1.79-1.95 (m, 4 H), 1.16-1.22 (m, 6 H); MS (ESI+) m/z 536.2 (M + H)$^+$. |
| 17-AT | 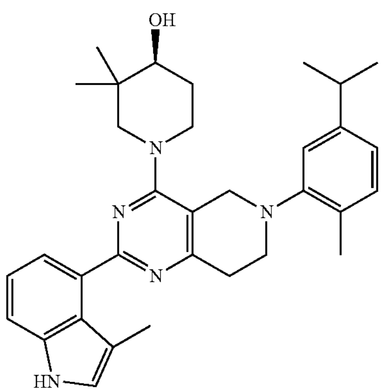 [SMILES: Cc1ccc(C(C)C)cc1N1CCc2nc(-c3cccc4[nH]cc(C)c34)nc(N3CC[C@H](O)C(C)(C)C3)c2C1] | (S)-1-(6-(5-isopropyl-2-methylphenyl)-2-(3-methyl-1H-indol-4-yl)-5,6,7,8-tetrahydropyrido[4,3-d]pyrimidin-4-yl)-3,3-dimethylpiperidin-4-ol. $^1$H NMR (400 MHz, DMSO-$d_6$) δ ppm 0.90 (s, 3 H) 0.93 (s, 3 H) 1.18 (d, J = 6.8 Hz, 6 H) 1.52-1.65 (m, 1 H) 1.70-1.78 (m, 1 H) 2.01 (s, 3 H) 2.21 (s, 3 H) 2.74 (d, J = 12.9 Hz, 1 H) 2.83 (dt, J = 13.6, 6.8 Hz, 1 H) 2.90-3.05 (m, 3 H) 3.26-3.36 (m, 3 H) 3.42 (d, J = 13.1 Hz, 1 H) 3.61-3.70 (m, 1 H) 4.06 (s, 2 H) 4.63 (d, J = 4.8 Hz, 1 H) 6.86 (dd, J = 7.6, 1.3 Hz, 1 H) 6.96 (s, 1 H) 7.07-7.15 (m, 3 H) 7.19 (dd, J = 7.1, 1.0 Hz, 1 H) 7.40 (dd, J = 8.0, 0.9 Hz, 1 H) 10.89 (br. s., 1 H); MS (ESI+) m/z 524.4 (M + H)$^+$. |
| 17-AU | 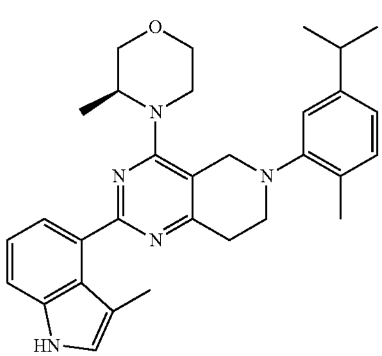 [SMILES: Cc1ccc(C(C)C)cc1N1CCc2nc(-c3cccc4[nH]cc(C)c34)nc(N3CCOC[C@@H]3C)c2C1] | (S)-4-(6-(5-isopropyl-2-methylphenyl)-2-(3-methyl-1H-indol-4-yl)-5,6,7,8-tetrahydropyrido[4,3-d]pyrimidin-4-yl)-3-methylmorpholine. $^1$H NMR (400 MHz, CD$_2$Cl$_2$) δ ppm 1.25 (d, J = 7.6 Hz, 6 H) 1.28 (d, J = 6.3 Hz, 3 H) 2.11 (s, 3 H) 2.28 (s, 3 H) 2.89 (dt, J = 13.8, 6.9 Hz, 1 H) 3.08-3.24 (m, 2 H) 3.29-3.43 (m, 3 H) 3.45-3.55 (m, 2 H) 3.57-3.71 (m, 2 H) 3.78 (dd, J = 11.2, 2.7 Hz, 1 H) 3.83-3.90 (m, 1 H) 3.92-4.10 (m, 2 H) 6.91 (dd, J = 7.7, 1.6 Hz, 1 H) 6.98 (d, J = 1.5 Hz, 1 H) 7.07 (s, 1 H) 7.14 (d, J = 7.8 Hz, 1 H) 7.22 (t, J = 7.8 Hz, 1 H) 7.36 (d, J = 7.3 Hz, 1 H) 7.45 (d, J = 7.8 Hz, 1 H) 8.21 (br. s., 1 H); MS (ESI+) m/z 496.3 (M + H)$^+$. |

| Structure | Chemical Name & Analytical Data |
|---|---|
| 17-AV | (S)-1-(6-(5-isopropyl-2-methylphenyl)-2-(3-methyl-1H-indol-4-yl)-5,6,7,8-tetrahydropyrido[4,3-d]pyrimidin-4-yl)piperidin-3-ol. $^1$H NMR (400 MHz, CD$_2$Cl$_2$) δ ppm 1.26 (d, J = 7.1 Hz, 6 H) 1.55-1.60 (m, 1 H) 1.67-1.94 (m, 3 H) 2.10 (s, 3 H) 2.26 (s, 3 H) 2.90 (spt, J = 7.0 Hz, 1 H) 3.08-3.16 (m, 2 H) 3.23-3.62 (m, 5 H) 3.76 (dd, J = 13.4, 4.3 Hz, 1 H) 3.86-3.94 (m, 1 H) 3.97-4.05 (m, 2 H) 6.92 (dd, J = 7.7, 1.6 Hz, 1 H) 7.01 (d, J = 1.5 Hz, 1 H) 7.08 (s, 1 H) 7.13 (d, J = 7.8 Hz, 1 H) 7.17-7.27 (m, 1 H) 7.34 (d, J = 7.3 Hz, 1 H) 7.48 (d, J = 8.3 Hz, 1 H) 8.43 (s, 1 H); MS (ESI+) m/z 496.5 (M + H)$^+$. |
| 17-AW | (R)-1-(6-(5-isopropyl-2-methylphenyl)-2-(3-methyl-1H-indol-4-yl)-5,6,7,8-tetrahydropyrido[4,3-d]pyrimidin-4-yl)piperidin-3-ol. $^1$H NMR (400 MHz, CD$_2$Cl$_2$) δ ppm 1.25 (d, J = 6.8 Hz, 6 H) 1.54-1.59 (m, 1 H) 1.66-1.93 (m, 3 H) 2.11 (s, 3 H) 2.27 (s, 3 H) 2.89 (dt, J = 13.7, 6.9 Hz, 1 H) 3.03-3.22 (m, 2 H) 3.24-3.57 (m, 5 H) 3.75 (dd, J = 13.5, 4.4 Hz, 1 H) 3.85-3.94 (m, 1 H) 4.01 (s, 2 H) 6.91 (dd, J = 7.7, 1.6 Hz, 1 H) 7.00 (d, J = 1.5 Hz, 1 H) 7.1 (s, 1 H) 7.14 (d, J = 7.8 Hz, 1 H) 7.18-7.26 (m, 1 H) 7.33 (d, J = 7.3 Hz, 1 H) 7.46 (d, J = 8.1 Hz, 1 H) 8.29 (br. s., 1 H); MS (ESI+) m/z 496.5 (M + H)$^+$. |
| 17-AX | 6-(5-isopropyl-2-methylphenyl)-4-((3R,4R)-4-methoxy-3-methylpiperidin-1-yl)-2-(3-methyl-1H-indol-4-yl)-5,6,7,8-tetrahydropyrido[4,3-d]pyrimidine. $^1$H (400 MHz, DMSO-d$_6$) δ ppm 0.97 (d, J = 6.6 Hz, 3 H) 1.19 (d, J = 6.8 Hz, 6 H) 1.33-1.44 (m, 1 H) 1.65-1.73 (m, 1 H) 2.02 (s, 3 H) 2.08-2.15 (m, 1 H) 2.21 (s, 3 H) 2.76 (dd, J = 13.1, 9.9 Hz, 1 H) 2.84 (dt, J = 13.8, 6.9 Hz, 1 H) 2.92-3.05 (m, 4 H) 3.28 (s, 3 H) 3.30-3.37 (m, 2 H) 3.70 (d, J = 12.6 Hz, 1 H) 3.80 (d, J = 13.4 Hz, 1 H) 3.94-4.11 (m, 2 H) 6.87 (dd, J = 7.6, 1.5 Hz, 1 H) 6.98 (s, 1 H) 7.07-7.16 (m, 3 H) 7.17-7.23 (m, 1 H) 7.41 (dd, J = 8.1, 1.0 Hz, 1 H) 10.88 (s, 1 H); MS (ESI+) m/z 524.3 (M + H)$^+$. |
| 17-AY | 6-(5-isopropyl-2-methylphenyl)-4-((3S,4S)-4-methoxy-3-methylpiperidin-1-yl)-2-(3-methyl-1H-indol-4-yl)-5,6,7,8-tetrahydropyrido[4,3-d]pyrimidine. $^1$H (400 MHz, DMSO-d$_6$) δ ppm 0.97 (d, J = 6.6 Hz, 3 H) 1.19 (d, J = 6.8 Hz, 6 H) 1.31-1.45 (m, 1 H) 1.63-1.74 (m, 1 H) 2.02 (s, 3 H) 2.07-2.15 (m, 1 H) 2.21 (s, 3 H) 2.76 (dd, J = 13.1, 9.9 Hz, 1 H) 2.84 (dt, J = 13.8, 6.9 Hz, 1 H) 2.91-3.06 (m, 4 H) 3.27 (s, 3 H) 3.30-3.39 (m, 2 H) 3.70 (d, J = 11.4 Hz, 1 H) 3.80 (d, J = 12.4 Hz, 1 H) 3.94-4.12 (m, 2 H) 6.87 (d, J = 7.8 Hz, 1 H) 6.98 (s, 1 H) 7.05-7.16 (m, 3 H) 7.20 (dd, J = 7.1, 0.8 Hz, 1 H) 7.41 (dd, J = 8.1, 0.8 Hz, 1 H) 10.89 (br. s., 1 H); MS (ESI+) m/z 524.4 (M + H)$^+$. |

-continued

| | Structure | Chemical Name & Analytical Data |
|---|---|---|
| 17-AZ | 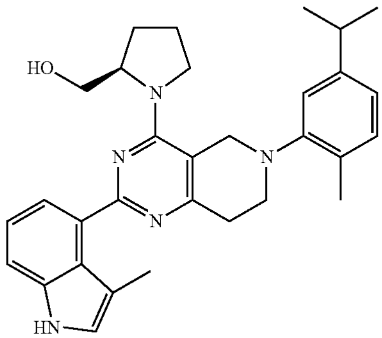 [SMILES: Cc1ccc(C(C)C)cc1N1CCc2nc(-c3cccc4[nH]cc(C)c34)nc(N3CCC[C@@H]3CO)c2C1] | (R)-(1-(6-(5-isopropyl-2-methylphenyl)-2-(3-methyl-1H-indol-4-yl)-5,6,7,8-tetrahydropyrido[4,3-d]pyrimidin-4-yl)pyrrolidin-2-yl)methanol. $^1$H (400 MHz, CD$_2$Cl$_2$) δ ppm 1.26 (d, J = 6.8 Hz, 6 H) 1.70-1.81 (m, 1 H) 1.84-1.94 (m, 1 H) 1.97-2.11 (m, 2 H) 2.12 (d, J = 1.0 Hz, 3 H) 2.29 (s, 3 H) 2.81-2.97 (m, 1 H) 3.05-3.17 (m, 1 H) 3.18-3.29 (m, 2 H) 3.33-3.44 (m, 1 H) 3.58-3.73 (m, 2 H) 3.76-3.87 (m, 2 H) 4.07-4.17 (m, 1 H) 4.23-4.33 (m, 1 H) 4.54-4.67 (m, 1 H) 6.93 (dd, J = 7.7, 1.64 Hz, 1 H) 7.01 (d, J = 1.8 Hz, 1 H) 7.07 (s, 1 H) 7.15 (d, J = 7.8 Hz, 1 H) 7.22 (t, J = 7.7 Hz, 1 H) 7.34 (d, J = 7.8 Hz, 1 H) 7.47 (d, J = 7.8 Hz, 1 H) 8.42 (br. s., 1 H); MS (ESI+) m/z 496.1 (M + H)$^+$. |
| 17-BA | 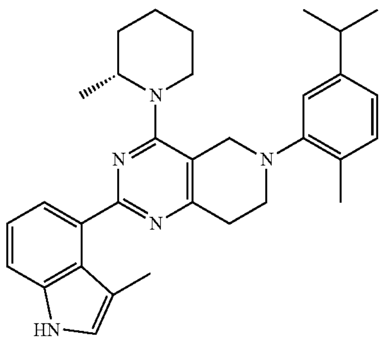 [SMILES: Cc1ccc(C(C)C)cc1N1CCc2nc(-c3cccc4[nH]cc(C)c34)nc(N3CCCC[C@H]3C)c2C1] | (R)-6-(5-isopropyl-2-methylphenyl)-2-(3-methyl-1H-indol-4-yl)-4-(2-methylpiperidin-1-yl)-5,6,7,8-tetrahydropyrido[4,3-d]pyrimidine. $^1$H (400 MHz, CD$_2$Cl$_2$) δ ppm 1.19-1.29 (m, 9 H) 1.50-1.89 (m, 6 H) 2.11 (s, 3 H) 2.28 (s, 3 H) 2.89 (spt, J = 6.9 Hz, 1 H) 3.07-3.17 (m, 2 H) 3.24 (ddd, J = 13.5, 10.7, 3.2 Hz, 1 H) 3.32-3.41 (m, 2 H) 3.53-3.63 (m, 1 H) 3.93-4.10 (m, 2 H) 4.11-4.21 (m, 1 H) 6.90 (dd, J = 7.71, 1.6 Hz, 1 H) 6.98 (d, J = 1.5 Hz, 1 H) 7.04 (d, J = 1.1 Hz, 1 H) 7.13 (d, J = 7.8 Hz, 1 H) 7.17-7.24 (m, 1 H) 7.34 (d, J = 6.6 Hz, 1 H) 7.42 (dd, J = 8.1, 1.0 Hz, 1 H) 8.22 (br. s., 1 H); MS (ESI+) m/z 494.4 (M + H)$^+$. |
| 17-BB | 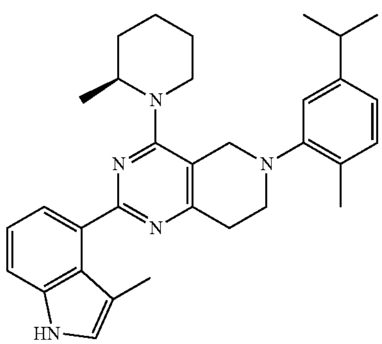 [SMILES: Cc1ccc(C(C)C)cc1N1CCc2nc(-c3cccc4[nH]cc(C)c34)nc(N3CCCC[C@@H]3C)c2C1] | (S)-6-(5-isopropyl-2-methylphenyl)-2-(3-methyl-1H-indol-4-yl)-4-(2-methylpiperidin-1-yl)-5,6,7,8-tetrahydropyrido[4,3-d]pyrimidine. $^1$H (400 MHz, CD$_2$Cl$_2$) δ ppm 1.19-1.31 (m, 9 H) 1.47-1.88 (m, 6 H) 2.11 (s, 3 H) 2.28 (s, 3 H) 2.83-2.96 (m, 1 H) 3.09-3.17 (m, 2 H) 3.24 (ddd, J = 13.5, 10.7, 3.2 Hz, 1 H) 3.32-3.41 (m, 2 H) 3.53-3.63 (m, 1 H) 3.93-4.10 (m, 2 H) 4.12-4.20 (m, 1 H) 6.90 (dd, J = 7.6, 1.8 Hz, 1 H) 6.98 (d, J = 1.5 Hz, 1 H) 7.03-7.07 (m, 1 H) 7.13 (d, J = 7.6 Hz, 1 H) 7.18-7.25 (m, 1 H) 7.34 (d, J = 7.3 Hz, 1 H) 7.43 (dd, J = 8.1, 0.8 Hz, 1 H) 8.20 (br. s., 1 H); MS (ESI+) m/z 494.1 (M + H)$^+$. |
| 17-BC | 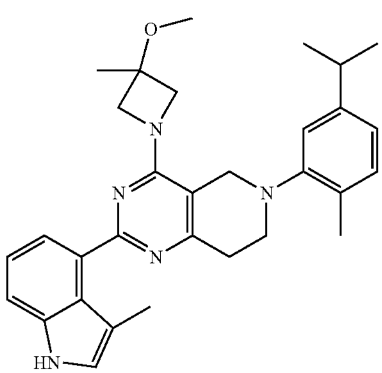 [SMILES: COC1(C)CN(c2nc(-c3cccc4[nH]cc(C)c34)nc3c2CN(c2cc(C(C)C)ccc2C)CC3)C1] | 6-(5-isopropyl-2-methylphenyl)-4-(3-methoxy-3-methylazetidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.27 (br. s., 1 H), 7.44 (d, J = 8.1 Hz, 1 H), 7.35 (d, J = 7.1 Hz, 1 H), 7.18-7.23 (m, 1 H), 7.15 (d, J = 7.8 Hz, 1 H), 7.05-7.07 (m, 1 H), 7.00 (d, J = 1.5 Hz, 1 H), 6.93 (dd, J = 7.8, 1.8 Hz, 1 H), 4.26 (d, J = 8.8 Hz, 2 H), 4.03-4.09 (m, 4 H), 3.29 (t, J = 5.6 Hz, 2 H), 3.24 (s, 3 H), 3.06-3.16 (m, 2 H), 2.89 (spt, J = 6.8 Hz, 1 H), 2.31 (s, 3 H), 2.11 (d, J = 0.8 Hz, 3 H), 1.51 (s, 3 H), 1.25 (d, J = 6.8 Hz, 6 H); MS (ESI+) m/z 496.1 (M + H)$^+$. |

| | Structure | Chemical Name & Analytical Data |
|---|---|---|
| 17-BD | 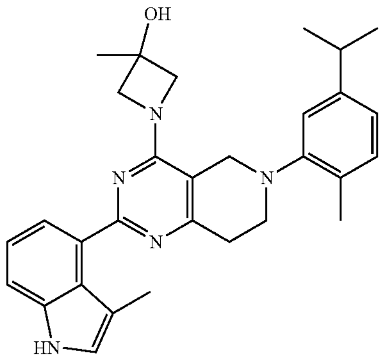 [SMILES: Cc1ccc(C(C)C)cc1N1CCc2nc(-c3cccc4[nH]cc(C)c34)nc(N3CC(C)(O)C3)c2C1] | 1-(6-(5-isopropyl-2-methylphenyl)-2-(3-methyl-1H-indol-4-yl)-5,6,7,8-tetrahydropyrido[4,3-d]pyrimidin-4-yl)-3-methylazetidin-3-ol. $^1$H NMR (400 MHz, DMSO-$d_6$) δ ppm 10.89 (br. s., 1 H), 7.40 (br. s., 1 H), 7.18 (d, J = 6.6 Hz, 1 H), 7.06-7.20 (m, 3 H), 7.02 (s, 1 H), 6.89 (d, J = 7.3 Hz, 1 H), 3.97-4.13 (m, 5 H), 3.18-3.25 (m, 2 H), 2.81-2.92 (m, 3 H), 2.24 (s, 3 H), 2.03 (s, 3 H), 1.42 (s, 3 H), 1.20 (d, J = 6.8 Hz, 6 H); MS (ESI+) m/z 482.1 (M + H)$^+$. |
| 17-BE | 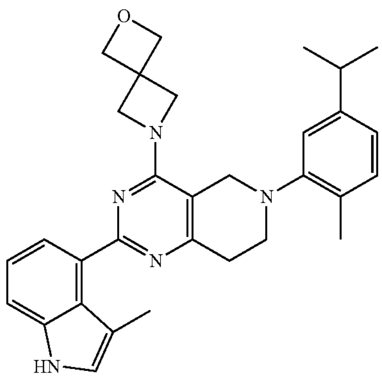 [SMILES: Cc1ccc(C(C)C)cc1N1CCc2nc(-c3cccc4[nH]cc(C)c34)nc(N3CC4(COC4)C3)c2C1] | 6-(6-(5-isopropyl-2-methylphenyl)-2-(3-methyl-1H-indol-4-yl)-5,6,7,8-tetrahydropyrido[4,3-d]pyrimidin-4-yl)-2-oxa-6-azaspiro[3.3]heptanes. $^1$H NMR (400 MHz, CD$_2$Cl$_2$) δ ppm 7.45-7.56 (m, 2 H), 7.21 (app. t, J = 7.8 Hz, 1 H), 7.17 (d, J = 7.6 Hz, 1 H), 7.11 (s, 1 H), 6.94-7.01 (m, 2 H), 4.79 (s, 4 H), 4.53 (br. s., 2 H), 4.09 (s, 2 H), 3.46 (br. s., 1 H), 3.28 (t, J = 8.8 Hz, 2 H), 2.86-2.96 (m, 1 H), 2.30 (s, 3 H), 2.14 (s, 3 H), 1.27 (d, J = 7.1 Hz, 6 H); MS (ESI+) m/z 494.1 (M + H)$^+$. |
| 17-BF | 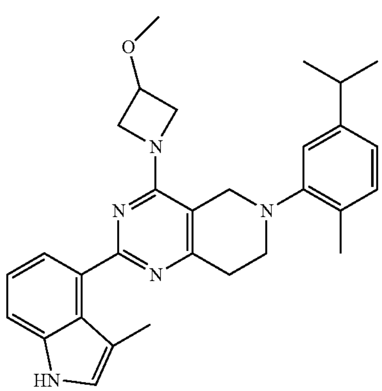 [SMILES: COC1CN(c2nc(-c3cccc4[nH]cc(C)c34)nc3c2CN(c2cc(C(C)C)ccc2C)CC3)C1] | 6-(5-isopropyl-2-methylphenyl)-4-(3-methoxyazetidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.32 (br. s., 1 H), 7.43 (d, J = 8.1 Hz, 1 H), 7.36 (d, J = 6.8 Hz, 1 H), 7.18-7.21 (m, 1 H), 7.05 (d, J = 0.5 Hz, 1 H), 6.99 (d, J = 1.5 Hz, 1 H), 6.93 (dd, J = 7.6, 1.5 Hz, 1 H), 4.46 (br. s., 2 H), 4.25-4.32 (m, 1 H), 4.18 (br. s., 2 H), 4.06 (s, 2 H), 3.26-3.32 (m, 5 H), 3.12 (br. s., 2 H), 2.88 (spt, J = 6.3 Hz, 1 H), 2.31 (s, 3 H), 2.11 (s, 3 H), 1.25 (d, J = 6.8 Hz, 6 H); MS (ESI+) m/z 482.1 (M + H)$^+$. |
| 17-BG | 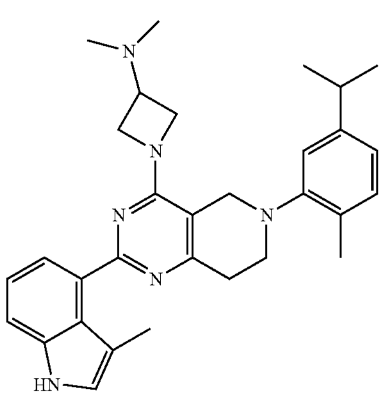 [SMILES: Cc1ccc(C(C)C)cc1N1CCc2nc(-c3cccc4[nH]cc(C)c34)nc(N3CC(N(C)C)C3)c2C1] | 1-(6-(5-isopropyl-2-methylphenyl)-2-(3-methyl-1H-indol-4-yl)-5,6,7,8-tetrahydropyrido[4,3-d]pyrimidin-4-yl)-N,N-dimethylazetidin-3-amine. $^1$H NMR (400 MHz, CD$_2$Cl$_2$) δ ppm 8.19 (br. s., 1 H), 7.41 (dd, J = 7.1, 1.0 Hz, 1 H), 7.31 (d, J = 6.8 Hz, 1 H), 7.17-7.21 (m, 1 H), 7.15 (d, J = 7.6 Hz, 1 H), 7.04 (d, J = 1.0 Hz, 1 H), 7.00 (d, J = 1.8 Hz, 1 H), 6.92 (dd, J = 7.6, 1.8 Hz, 1 H), 4.26 (app. t, J = 7.6 Hz, 2 H), 4.13 (br. s., 2 H), 4.05 (s, 2 H), 3.29 (t, J = 5.6 Hz, 2 H), 3.19 (br. s., 1 H), 3.03 (br. s., 2 H), 2.89 (spt, J = 7.1 Hz, 1 H), 2.31 (s, 3 H), 2.18 (br. s., 6 H), 2.10 (s, 3 H), 1.25 (d, J = 6.8 Hz, 6 H); MS (ESI+) m/z 495.2 (M + H)$^+$. |

| | Structure | Chemical Name & Analytical Data |
|---|---|---|
| 17-BH | 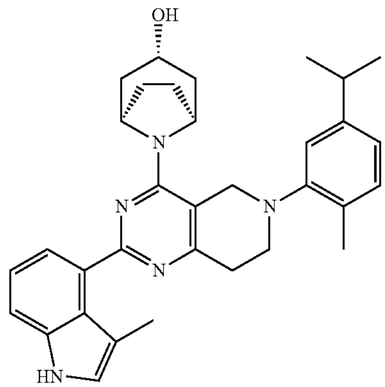 [SMILES: Cc1ccc(C(C)C)cc1N1CCc2nc(-c3cccc4[nH]cc(C)c34)nc(N3[C@@H]4CC[C@H]3C[C@@H](O)C4)c2C1] | (3-endo)-8-(6-(5-isopropyl-2-methylphenyl)-2-(3-methyl-1H-indol-4-yl)-5,6,7,8-tetrahydropyrido[4,3-d]pyrimidin-4-yl)-8-azabicyclo[3.2.1]octan-3-ol. $^1$H NMR (400 MHz, CD$_2$Cl$_2$) δ ppm 8.28 (br. s, 1 H), 7.43 (d, J = 8.1 Hz, 1 H), 7.34 (d, J = 7.6 Hz, 1 H), 7.22-7.18 (m, 1 H), 7.14 (d, J = 7.6 Hz, 1 H), 7.04 (d, J = 1.0 Hz, 1 H), 7.00 (d, J = 1.5 Hz, 1 H), 6.92 (dd, J = 7.6, 1.5 Hz, 1 H), 4.61 (br. s., 2 H), 4.11 (br. s., 1 H), 4.03 (s, 2 H), 3.34 (t, J = 5.8 Hz, 2 H), 3.15 (br. s., 2 H), 2.89 (spt, J = 7.1 Hz, 1 H), 2.29 (s, 3 H), 2.20-2.27 (m, 4 H), 2.10 (s, 3 H), 1.95-2.03 (m, 1 H), 1.79 (d, J = 14.4 Hz, 2 H), 1.25 (d, J = 7.1 Hz, 6 H); MS (ESI+) m/z 522.2 (M + H)$^+$. |
| 17-BI | 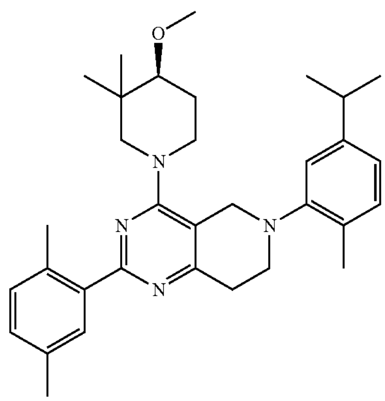 [SMILES: CO[C@H]1CCN(c2nc(-c3cc(C)ccc3C)nc3c2CN(c2cc(C(C)C)ccc2C)CC3)CC1(C)C] | (S)-2-(2,5-dimethylphenyl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 7.58 (s, 1 H), 7.05-7.18 (m, 3 H), 6.97 (d, J = 1.8 Hz, 1 H), 6.89 (dd, J = 7.7, 1.6 Hz, 1 H), 4.00 (s, 2 H), 3.69 (d, J = 10.6 Hz, 1 H), 3.27-3.42 (m, 6 H), 3.01-3.15 (m, 3 H), 2.91-2.99 (m, 1 H), 2.79-2.91 (m, 2 H), 2.49 (s, 3 H), 2.36 (s, 3 H), 2.27 (s, 4 H), 1.89-2.07 (m, 1 H), 1.60-1.78 (m, 1 H), 1.25 (d, J = 6.8 Hz, 7 H), 1.00 (s, 3 H), 0.96 (s, 3 H); MS (ESI+) m/z 513.3 (M + H)$^+$. |
| 17-BJ | 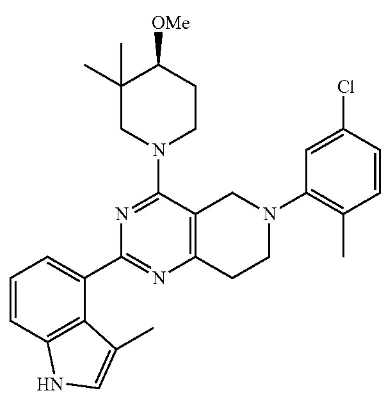 [SMILES: CO[C@H]1CCN(c2nc(-c3cccc4[nH]cc(C)c34)nc3c2CN(c2cc(Cl)ccc2C)CC3)CC1(C)C] | (S)-6-(5-chloro-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, CD$_3$CN) δ ppm 9.13 (br. s., 1 H) 7.45 (dd, J = 8.08, 1.01 Hz, 1 H) 7.22-7.26 (m, 1 H) 7.14-7.22 (m, 3 H) 7.01-7.09 (m, 2 H) 3.98-4.10 (m, 2 H) 3.64-3.75 (m, 1 H) 3.33-3.40 (m, 3 H) 3.32 (s, 3 H) 3.01-3.12 (m, 3 H) 2.98 (dd, J = 9.09, 4.04 Hz, 1 H) 2.86 (d, J = 12.88 Hz, 1 H) 2.27 (s, 3 H) 2.02 (d, J = 1.01 Hz, 3 H) 1.99 (dd, J = 5.43, 3.92 Hz, 1 H) 1.65 (dddd, J = 13.14, 9.60, 9.47, 3.92 Hz, 1 H) 0.98 (s, 3 H) 0.92 (s, 3 H); MS (ESI+) m/z 530.3 (M + H)$^+$. |
| 17-BK | 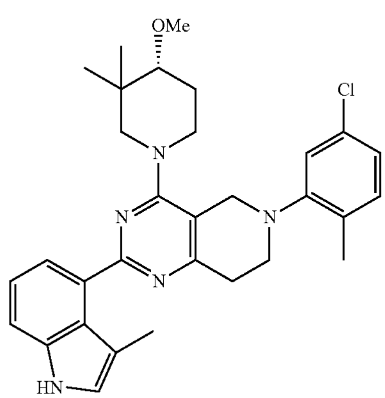 [SMILES: CO[C@@H]1CCN(c2nc(-c3cccc4[nH]cc(C)c34)nc3c2CN(c2cc(Cl)ccc2C)CC3)CC1(C)C] | (R)-6-(5-chloro-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, DMSO-d$_6$) δ ppm 10.89 (s, 1 H) 7.41 (dd, J = 8.1, 1.01 Hz, 1 H) 7.23 (d, J = 8.1 Hz, 1 H) 7.20 (dd, J = 7.3, 1.01 Hz, 1 H) 7.08-7.16 (m, 3 H) 7.06 (dd, J = 8.1, 2.0 Hz, 1 H) 3.96-4.14 (m, 2 H) 3.66 (d, J = 13.1 Hz, 1 H) 3.32-3.40 (m, 3 H) 3.28 (s, 3 H) 2.94-3.09 (m, 4 H) 2.83 (d, J = 12.9 Hz, 1 H) 2.23 (s, 3 H) 1.90-2.04 (m, 4 H) 1.50-1.64 (m, 1 H) 0.97 (s, 3 H) 0.89 (s, 3 H); MS (ESI+) m/z 530.3 (M + H)$^+$. |

Example 18

6-(5-Isopropyl-2-methylphenyl)-4-methoxy-2-(3-methyl-1-tosyl-1H-indol-4-yl)-5,6,7,8-tetrahydropyrido[4,3-d]pyrimidine

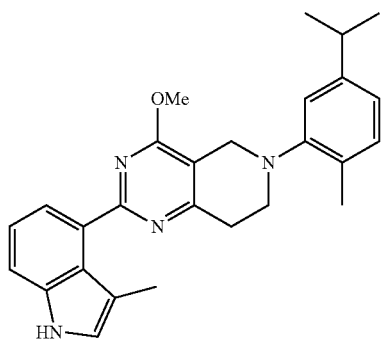 [SMILES: COc1nc(-c2cccc3[nH]cc(C)c23)nc2c1CN(c1cc(C(C)C)ccc1C)CC2]

To a solution of 4-chloro-6-(5-isopropyl-2-methylphenyl)-2-(3-methyl-1-tosyl-1H-indol-4-yl)-5,6,7,8-tetrahydropyrido[4,3-d]pyrimidine, prepared as described in Example 17 (110 mg, 0.188 mmol) in methanol (5 mL) was added 25% sodium methoxide in methanol (40.6 mg, 0.188 mmol). The reaction was stirred for ca. 40 minutes at room temperature at which time the mixture was diluted with EtOAc and water. The layers were separated, and the organic layer was washed with brine, dried over $Na_2SO_4$, filtered, and concentrated. The resulting residue was added to a microwave vial, and diluted with EtOH (2 mL) and charged with KOH (ca. 100 mg, 1.75 mmol) and 28% ammonium hydroxide in water (1 mL, 7.25 mmol). The vial was sealed and heated via microwave irradiation at 100° C. for 45 minutes. The reaction mixture was cooled to room temperature and diluted with dichloromethane and brine. The layers were separated and the aqueous layer was extracted two additional times with dichloromethane. The organic layers were combined, dried over $Na_2SO_4$, filtered, and concentrated. The resulting residue was purified by silica gel flash chromatography (0-100% ethyl acetate/heptanes) and then further purified by reverse phase HPLC (20-100% MeCN/0.1% $NH_4OH$ in water to afford 6-(5-isopropyl-2-methylphenyl)-4-methoxy-2-(3-methyl-1-tosyl-1H-indol-4-yl)-5,6,7,8-tetrahydropyrido[4,3-d]pyrimidine.

$^1$H NMR (400 MHz, $CD_2Cl_2$) δ ppm 8.16 (br. s., 1 H) 7.37-7.46 (m, 1 H) 7.27-7.38 (m, 1 H) 7.11-7.21 (m, 1 H) 7.07 (d, J=7.6 Hz, 1 H) 6.98-7.05 (m, 1 H) 6.96 (s, 1 H) 6.76-6.90 (m, 1 H) 4.00 (s, 3 H) 3.34 (s, 1 H) 3.17-3.28 (m, 1 H) 2.90-3.17 (m, 1 H) 2.76-2.90 (m, 1 H) 2.24 (s, 2 H) 2.05 (s, 2 H) 1.09-1.28 (m, 6 H); MS (ESI+) m/z 427.25 (M+H)$^+$.

Example 19

19-A. 6-Benzyl-2-methoxy-4-((3-endo)-3-methoxy-8-azabicyclo[3.2.1]octan-8-yl)-5,6,7,8-tetrahydropyrido[4,3-d]pyrimidine

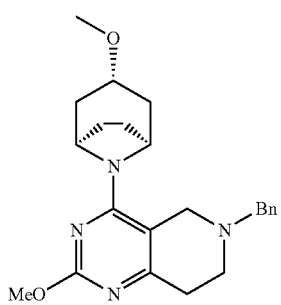 [SMILES: COc1nc2c(c(N3[C@@H]4CC[C@H]3C[C@@H](OC)C4)n1)CN(Cc1ccccc1)CC2]

To a microwave vial containing 6-benzyl-2-chloro-4-((3-endo)-3-methoxy-8-azabicyclo[3.2.1]octan-8-yl)-5,6,7,8-tetrahydropyrido[4,3-d]pyrimidine (1.6 g, 4.0 mmol), prepared in a similar manner to that described in Example 21 below, was added a 0.5 M solution of NaOMe in THF (40 mL, 20.0 mmol). The vial was sealed and heated in a microwave reactor at 130° C. for 30 min. The reaction mixture was cooled and concentrated. The residue was diluted with DCM and washed with sat aq $NH_4Cl$ solution. The aqueous layer was extracted with DCM (2×). The combined organics were dried ($Na_2SO_4$), filtered, and concentrated to provide 6-benzyl-2-methoxy-4-((3-endo)-3-methoxy-8-azabicyclo[3.2.1]octan-8-yl)-5,6,7,8-tetrahydropyrido[4,3-d]pyrimidine, which was used in the next step without further purification. MS (ESI+) m/z 395.3 (M+H)$^+$.

19-B. 2-Methoxy-4-((3-endo)-3-methoxy-8-azabicyclo[3.2.1]octan-8-yl)-5,6,7,8-tetrahydropyrido[4,3-d]pyrimidine

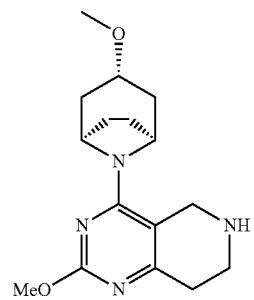 [SMILES: COc1nc2c(c(N3[C@@H]4CC[C@H]3C[C@@H](OC)C4)n1)CNCC2]

A mixture of 6-benzyl-2-methoxy-4-((3-endo)-3-methoxy-8-azabicyclo[3.2.1]octan-8-yl)-5,6,7,8-tetrahydropyrido[4,3-d]pyrimidine (crude, 4 mmol), 20% Pd(OH)$_2$ on carbon (wet) (2.25 g, 3.2 mmol) in THF (40 mL), water (10 mL) and acetic acid (0.69 mL) was stirred under a hydrogen atmosphere at room temperature for 2 h. The reaction mixture was filtered through Celite® and the solid were washed with DCM. The combined filtrate was washed with sat aq $NaHCO_3$ solution. Layers were separated and the aqueous layer was extracted with DCM. The combined organics were washed with brine, dried ($Na_2SO_4$), filtered, and concentrated. The residue was purified by silica gel chromatography (0-10% MeOH (10% $NH_4OH$)/DCM) to provide 2-methoxy-4-((3-endo)-3-methoxy-8-azabicyclo[3.2.1]octan-8-yl)-5,6,7,8-tetrahydropyrido[4,3-d]pyrimidine. MS (ESI+) m/z 305.0 (M+H)$^+$.

19-C. 6-(5-Isopropyl-2-methylphenyl)-2-methoxy-4-((3-endo)-3-methoxy-8-azabicyclo[3.2.1]octan-8-yl)-5,6,7,8-tetrahydropyrido[4,3-d]pyrimidine

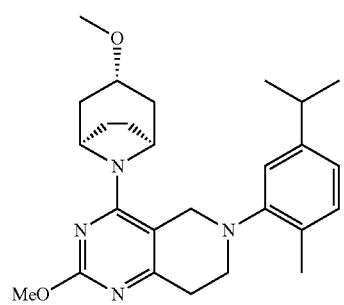 [SMILES: COc1nc2c(c(N3[C@@H]4CC[C@H]3C[C@@H](OC)C4)n1)CN(c1cc(C(C)C)ccc1C)CC2]

A mixture of 2-methoxy-4-((3-endo)-3-methoxy-8-azabicyclo[3.2.1]octan-8-yl)-5,6,7,8-tetrahydropyrido[4,3-d]pyrimidine (0.88 g, 2.89 mmol), 5-isopropyl-2-methylphenyl trifluoromethanesulfonate (1.22 g, 4.34 mmol), chloro(2-dicyclohexylphosphino-2'-4'-6'-triisopropyl-1,1'-biphenyl)[2-(2-aminoethyl)phenyl]palladium(II)-methyl-t-butylether adduct (CAS#1028206-56-5, 0.21 g, 0.30 mmol), and Cs$_2$CO$_3$ (1.88 g, 5.78 mmol) in THF (3 mL) was heated in a microwave reactor at 140° C. for 2 h. The reaction mixture was partitioned between EtOAc and water. The organic layer was washed with brine, dried (Na$_2$SO$_4$) and concentrated. The residue was purified by silica gel chromatography (0-50% EtOAc/heptane) to provide 6-(5-isopropyl-2-methylphenyl)-2-methoxy-4-((3-endo)-3-methoxy-8-azabicyclo[3.2.1]octan-8-yl)-5,6,7,8-tetrahydropyrido[4,3-d]pyrimidine. MS (ESI+) m/z 437.1 (M+H)$^+$.

19-D. 6-(5-Isopropyl-2-methylphenyl)-4-β3-endo)-3-methoxy-8-azabicyclo[3.2.1]octan-8-yl)-5,6,7,8-tetrahydropyrido[4,3-d]pyrimidin-2-ol

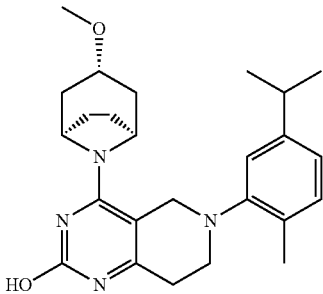 [SMILES: CO[C@H]1C[C@H]2CC[C@@H](C1)N2c1nc(O)nc2c1CN(c1cc(C(C)C)ccc1C)CC2]

A mixture of 6-(5-isopropyl-2-methylphenyl)-2-methoxy-4-((3-endo)-3-methoxy-8-azabicyclo[3.2.1]octan-8-yl)-5,6,7,8-tetrahydropyrido[4,3-d]pyrimidine (0.9 g, 2.06 mmol), and KOTMS (2.65 g, 20.6 mmol) in 1,4-dioxane (20 mL) was heated in a sealed tube at 140° C. for 24 h. The reaction mixture was diluted with DCM and quenched with sat aq NH$_4$Cl. The aqueous layer was extracted with DCM. The combined organics were washed with brine, dried (Na$_2$SO$_4$), filtered, and concentrated to provide 6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidin-2-ol, which was used in the next step without further purification. MS (ESI+) m/z 423.0 (M+H)$^+$.

19-E. 2-Chloro-6-(5-isopropyl-2-methylphenyl)-4-β3-endo)-3-methoxy-8-azabicyclo[3.2.1]octan-8-yl)-5,6,7,8-tetrahydropyrido[4,3-d]pyrimidine

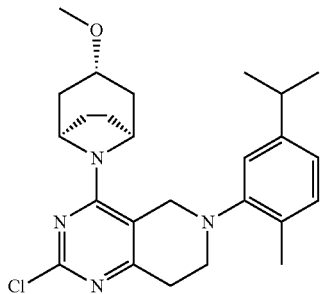 [SMILES: CO[C@H]1C[C@H]2CC[C@@H](C1)N2c1nc(Cl)nc2c1CN(c1cc(C(C)C)ccc1C)CC2]

To a solution of 6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidin-2-ol (crude, 2.06 mmol) in DCE was added Vilsmeier reagent (1.3 g, 10.3 mmol) and the reaction mixture was heated at 40° C. for 18 h. The reaction mixture was washed with water and the aqueous layer was extracted with DCM (2×). The combined organics were washed with brine, dried (Na$_2$SO$_4$), filtered, and concentrated. The residue was purified by silica gel chromatography (0-100% EtOAc/heptane) to provide 2-chloro-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. MS (ESI+) m/z 441.0 (M+H)$^+$.

19-F. 2-(3,5-Dimethyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine

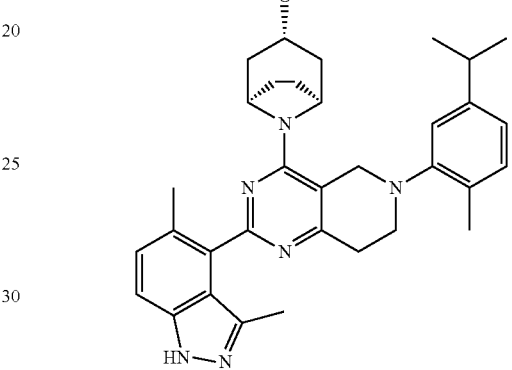

A mixture of 2-chloro-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine (26 mg, 0.06 mmol), 3,5-dimethyl-4-(4,4,5,5-tetramethyl-1,3,2-dioxaborolan-2-yl)-1-tosyl-1H-indazole (25 mg, 0.06 mmol), Pd(PPh$_3$)$_4$ (7.0 mg, 0.006 mmol), and Na$_2$CO$_3$ (2 M, 0.09 mL, 0.18 mmol) in DME (2 mL) was heated in a microwave reactor at 140° C. for 30 min. The reaction mixture was partitioned between EtOAc and water. The aqueous layer was extracted with EtOAc. The combined organic layers were washed with brine, dried (Na$_2$SO$_4$), filtered, and concentrated. The residue was purified by silica gel chromatography (20-100% EtOAc/heptane) to provide 2-(3,5-dimethyl-1-tosyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine, which was used in the next step without further purification. MS (ESI+) m/z 705.0 (M+H)$^+$.

A suspension of 2-(3,5-dimethyl-1-tosyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine (from previous step, theoretically 0.06 mmol) and K$_2$CO$_3$ (82 mg, 0.6 mmol) in MeOH (5 mL) was heated at 50° C. for 1 h. The reaction mixture was filtered and washed with MeOH. The filtrate was concentrated and the residue was purified by HPLC (CH$_3$CN-water with 0.1% NH$_4$OH 10-100%) to provide 2-(3,5-dimethyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, CD$_2$Cl$_2$) δ ppm 9.83 (br. s., 1 H) 7.35 (d, J=8.60 Hz, 1 H) 7.25 (d, J=8.60 Hz, 1 H) 7.15 (d, J=7.83 Hz, 1 H) 7.00 (d, J=1.77 Hz, 1 H) 6.92 (dd, J=7.71, 1.64 Hz, 1 H) 4.47 (br. s., 2 H) 4.05 (s, 2 H) 3.46 (t, J=4.80 Hz, 1 H) 3.36 (t, J=5.94 Hz, 2 H) 3.25 (s, 3 H) 3.01-3.10 (m, 2 H) 2.89 (spt, J=6.95 Hz, 1 H) 2.30 (s, 3 H)

2.29 (s, 3 H) 2.02-2.14 (m, 4 H) 2.00 (s, 3 H) 1.87-1.96 (m, 4 H) 1.26 (d, J=6.82 Hz, 6 H); MS (ESI+) m/z 551.1 (M+H)+.

The following compounds were prepared in a similar manner.

| | Structure | Chemical Name & Analytical Data |
|---|---|---|
| 19-G | 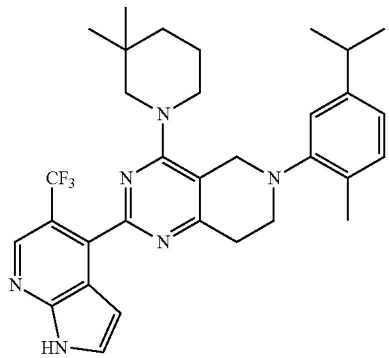 [SMILES: Cc1ccc(C(C)C)cc1N1CCc2nc(-c3c(C(F)(F)F)cnc4[nH]ccc34)nc(N3CCCC(C)(C)C3)c2C1] | 4-(3,3-dimethylpiperidin-1-yl)-6-(5-isopropyl-2-methylphenyl)-2-(5-(trifluoromethyl)-1H-pyrrolo[2,3-b]pyridin-4-yl)-5,6,7,8-tetrahydropyrido[4,3-d]pyrimidine. $^1$H NMR (400 MHz, DMSO-d$_6$) δ ppm 12.22 (br.s., 1 H), 8.63 (s, 1 H), 7.11 (d, J = 7.6 Hz, 1 H), 6.94 (s, 1 H), 6.87 (d, J = 7.6 Hz, 1 H), 6.44 (d, J = 3.3 Hz, 1 H), 4.09 (s, 2 H), 3.38-3.32 (m, 2 H), 3.10 (s, 2 H), 2.95 (t, J = 5.9 Hz, 2 H), 2.83 (td, J = 7.0, 14.0 Hz, 1 H), 2.23 (s, 3 H), 1.69-1.58 (m, 2 H), 1.44-1.34 (m, 2 H), 1.18 (d, J = 7.1 Hz, 6 H), 0.94 (s, 6 H); MS (ESI+) m/z 563.3 (M + H)+. |
| 19-H | 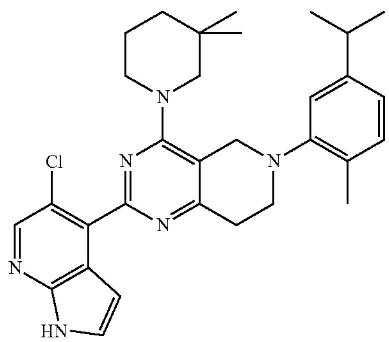 [SMILES: Cc1ccc(C(C)C)cc1N1CCc2nc(-c3c(Cl)cnc4[nH]ccc34)nc(N3CCCC(C)(C)C3)c2C1] | 2-(5-chloro-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 11.94 (br. s., 1 H), 8.30 (s, 1 H), 7.50-7.60 (m, 1 H), 7.11 (d, J = 7.8 Hz, 1 H), 6.98 (d, J = 1.5 Hz, 1 H), 6.87 (dd, J = 7.6, 1.5 Hz, 1 H), 6.41 (d, J = 5.3 Hz, 1 H), 4.08 (s, 2 H), 3.32-3.38 (m, 4 H), 3.11 (s, 2 H), 2.98 (t, J = 5.8 Hz, 2 H), 2.84 (dt, J = 13.7, 6.9 Hz, 1 H), 2.22 (s, 3 H), 1.65 (m, 2 H), 1.40 (t, J = 5.7 Hz, 2 H), 1.19 (d, J = 7.1 Hz, 6 H), 0.96 (s, 6 H); MS (ESI+) m/z 529.2 (M + H)+. |
| 19-I | 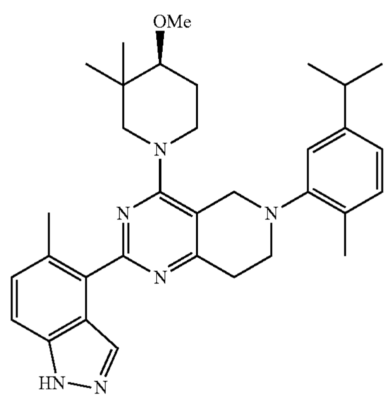 [SMILES: CO[C@H]1CCN(c2nc(-c3c(C)ccc4[nH]ncc34)nc3c2CN(c2cc(C(C)C)ccc2C)CC3)CC1(C)C] | (S)-6-(5-isopropyl-2-methylphenyl)-4-(4-methoxy-3,3-dimethylpiperidin-1-yl)-2-(5-methyl-1H-indazol-4-yl)-5,6,7,8-tetrahydropyrido[4,3-d]pyrimidine. $^1$H NMR (400 MHz, CD$_3$CN) δ ppm 8.00 (s, 1 H), 7.67 (d, J = 13.4 Hz, 1 H), 7.38 (d, J = 8.6 Hz, 1 H), 7.20-7.20 (m, 1 H), 7.15 (d, J = 7.8 Hz, 1 H), 7.07 (d, J = 1.8 Hz, 1 H), 6.95 (dd, J = 7.7, 1.6 Hz, 1 H), 4.09 (s, 2 H), 3.91-3.99 (m, 1 H), 3.70 (d, J = 12.6 Hz, 1 H), 3.48-3.57 (m, 1 H), 3.25-3.40 (m, 6 H), 3.14 (t, J = 5.8 Hz, 2 H), 3.07 (dd, J = 8.0, 3.7 Hz, 1 H), 2.91 (dt, J = 13.6, 6.8 Hz, 1 H), 2.53 (s, 3 H), 2.50 (s, 3 H), 1.64-1.75 (m, 1 H), 1.25 (d, J = 6.8 Hz, 6 H), 0.98 (s, 3 H), 0.91 (s, 3 H); MS (ESI+) m/z 539.2 (M + H)+. |
| 19-J | 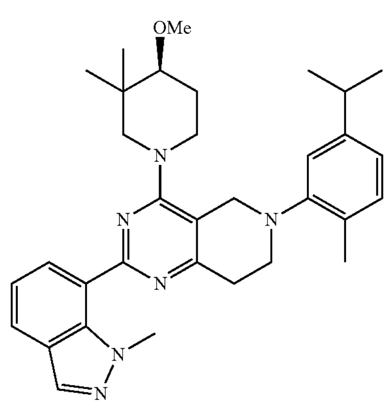 [SMILES: CO[C@H]1CCN(c2nc(-c3cccc4cnn(C)c34)nc3c2CN(c2cc(C(C)C)ccc2C)CC3)CC1(C)C] | (S)-6-(5-isopropyl-2-methylphenyl)-4-(4-methoxy-3,3-dimethylpiperidin-1-yl)-2-(1-methyl-1H-indazol-7-yl)-5,6,7,8-tetrahydropyrido[4,3-d]pyrimidine. $^1$H NMR (400 MHz, DMSO-d$_6$) δ ppm 8.17 (s, 1 H), 7.87 (dd, J = 8.1, 1.0 Hz, 1H), 7.69 (dd, J = 7.1, 1.01 Hz, 1 H), 7.23 (dd, J = 8.0, 7.2 Hz, 1 H), 7.11 (d, J = 8.1 Hz, 1 H), 7.00 (d, J = 1.3 Hz, 1 H), 6.87 (dd, J = 7.7, 1.4 Hz, 1 H), 4.07 (s, 2 H), 3.90 (s, 3 H), 3.71 (d, J = 13.4 Hz, 1 H), 3.42 (d, J = 12.9 Hz, 1 H), 3.29 (s, 3 H), 3.10 (t, J = 10.4 Hz, 1 H), 2.97-3.04 (m, 3 H), 2.80-2.92 (m, 2 H), 2.21 (s, 3 H), 1.93-2.02 (m, 1 H), 1.51-1.63 (m, 1 H), 1.19 (dd, J = 7.0, 0.6 Hz, 6 H), 0.99 (s, 3 H), 0.93 (s, 3 H); MS (ESI+) m/z 539.2 (M + H)+. |

| | Structure | Chemical Name & Analytical Data |
|---|---|---|
| 19-K | 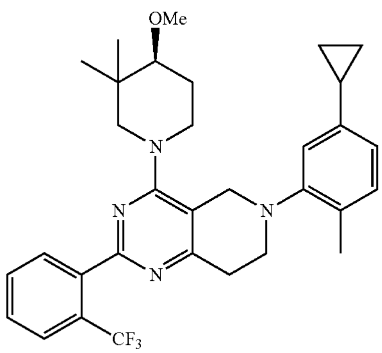 [SMILES: CO[C@H]1CCN(c2nc(-c3ccccc3C(F)(F)F)nc3c2CN(c2cc(C4CC4)ccc2C)CC3)CC1(C)C] | (S)-6-(5-cyclopropyl-2-methylphenyl)-4-(4-methoxy-3,3-dimethylpiperidin-1-yl)-2-(2-(trifluoromethyl)phenyl)-5,6,7,8-tetrahydropyrido[4,3-d]pyrimidine. $^1$H NMR (400 MHz, CD$_2$Cl$_2$) δ ppm 7.70-7.81 (m, 2 H), 7.64 (t, J = 7.3 Hz, 1 H), 7.50-7.59 (m, 1 H), 7.08 (d, J = 7.8 Hz, 1 H), 6.83 (d, J = 1.8 Hz, 1 H), 6.72 (dd, J = 7.6, 1.8 Hz, 1 H), 3.97 (s, 2 H), 3.71 (d, J = 12.9 Hz, 1 H), 3.29-3.41 (m, 6 H), 3.06 (br. s., 1 H), 2.94 (dd, J = 8.7, 3.9 Hz, 1 H), 2.85 (d, J = 11.9 Hz, 1 H), 2.25 (s, 3 H), 1.95 (ddt, J = 13.3, 6.1, 3.6 Hz, 1 H), 1.87 (tt, J = 8.5, 5.1 Hz, 1 H), 1.62-1.73 (m, 1 H), 0.97 (s, 3 H), 0.93-0.97 (m, 2 H), 0.93 (s, 3 H), 0.63-0.68 (m, 2 H); MS (ESI+) m/z 551.4 (M + H)$^+$. |
| 19-L | 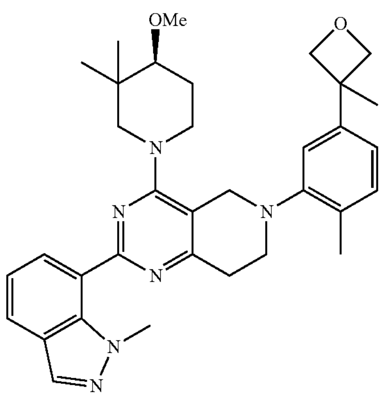 [SMILES: CO[C@H]1CCN(c2nc(-c3cccc4cnn(C)c34)nc3c2CN(c2cc(C4(C)COC4)ccc2C)CC3)CC1(C)C] | (S)-4-(4-methoxy-3,3-dimethylpiperidin-1-yl)-2-(1-methyl-1H-indazol-7-yl)-6-(2-methyl-5-(3-methyloxetan-3-yl)phenyl)-5,6,7,8-tetrahydropyrido[4,3-d]pyrimidine. $^1$HNMR (400 MHz, DMSO-d$_6$) δ ppm 8.17 (s, 1 H), 7.87 (dd, J = 8.0, 1.1 Hz, 1 H), 7.69 (dd, J = 7.1, 1.0 Hz, 1 H), 7.23 (dd, J = 8.0, 7.2 Hz, 1 H), 7.19 (d, J = 8.1 Hz, 1 H), 6.98 (d, J = 1.8 Hz, 1 H), 6.87 (dd, J = 7.8, 1.8 Hz, 1 H), 4.79 (dd, J = 5.6, 1.8 Hz, 2 H), 4.52 (dd, J = 5.6, 1.0 Hz, 2 H), 4.09 (s, 2 H), 3.91 (s, 3 H), 3.70 (d, J = 13.4 Hz, 1 H), 3.41 (d, J = 13.4 Hz, 1 H), 3.35-3.37 (m, 1 H), 3.29 (s, 3 H), 3.05-3.14 (m, 1 H), 2.97-3.04 (m, 3 H), 2.88 (d, J = 13.1 Hz, 1 H), 2.24 (s, 3 H), 1.93-2.03 (m, 1 H), 1.62 (s, 3 H), 1.50-1.60 (m, 1 H), 0.99 (s, 3 H), 0.92 (s, 3 H); MS (ESI+) m/z 567.0 (M + H)$^+$. |
| 19-M | 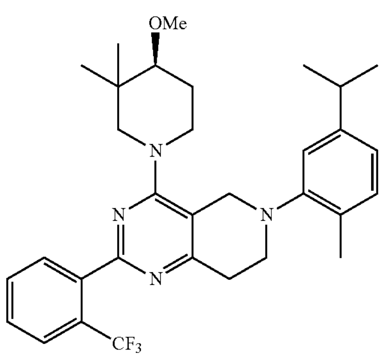 [SMILES: CO[C@H]1CCN(c2nc(-c3ccccc3C(F)(F)F)nc3c2CN(c2cc(C(C)C)ccc2C)CC3)CC1(C)C] | (S)-6-(5-isopropyl-2-methylphenyl)-4-(4-methoxy-3,3-dimethylpiperidin-1-yl)-2-(2-(trifluoromethyl)phenyl)-5,6,7,8-tetrahydropyrido[4,3-d]pyrimidine. $^1$H NMR (400 MHz, CD$_2$Cl$_2$) δ ppm 7.71-7.80 (m, 2 H), 7.64 (t, J = 7.5 Hz, 1 H), 7.55 (t, J = 1.0 Hz, 1 H), 7.13 (d, J = 7.8 Hz, 1 H), 6.96 (d, J = 1.5 Hz, 1 H), 6.90 (dd, J = 7.7, 1.6 Hz, 1 H), 4.01 (s, 2 H), 3.70 (d, J = 12.9 Hz, 1 H), 3.30-3.41 (m, 6 H), 3.06 (br. s., 2 H), 2.94 (dd, J = 8.8, 3.8 Hz, 1 H), 2.81-2.90 (m, 2 H), 2.26 (s, 3 H), 1.91-2.01 (m, 1 H), 1.61-1.73 (m, 1 H), 1.48-1.52 (m, 1 H), 1.24 (d, J = 7.1 Hz, 6 H), 0.98 (s, 3 H), 0.94 (s, 3 H); MS (ESI+) m/z 553.4 (M + H)$^+$. |
| 19-N | 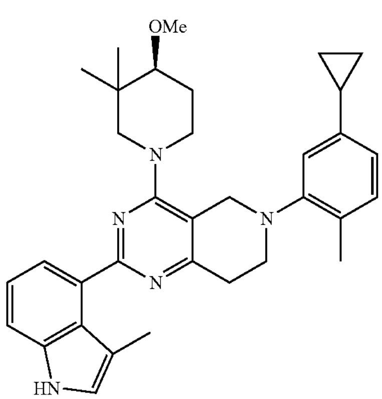 [SMILES: CO[C@H]1CCN(c2nc(-c3cccc4[nH]cc(C)c34)nc3c2CN(c2cc(C4CC4)ccc2C)CC3)CC1(C)C] | (S)-6-(5-cyclopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.22 (br. s., 1 H), 7.44 (d, J = 8.1 Hz, 1 H), 7.34 (d, J = 7.1 Hz, 1 H), 7.21 (t, J = 7.7 Hz, 1 H), 7.01-7.13 (m, 2 H), 6.84 (s, 1 H), 6.72 (d, J = 7.8 Hz, 1 H), 4.01 (s, 2 H), 3.71 (br. s., 1 H), 3.43 (d, J = 11.4 Hz, 1 H), 3.28-3.37 (m, 5 H), 3.13 (br. s., 3 H), 2.95 (dd, J = 8.7, 3.9 Hz, 2 H), 2.26 (s, 3 H), 209 (s, 3 H), 1.98 (dd, J = 12.8, 9.2 Hz, 1 H), 1.81-1.92 (m, 1 H), 1.63-1.74 (m, 1 H), 1.00 (s, 3 H), 0.96 (br. s., 3 H), 0.91-0.95 (m, 2 H), 0.62-0.69 (m, 2 H); MS (ESI+) m/z 536.0 (M + H)$^+$. |

-continued

| | Structure | Chemical Name & Analytical Data |
|---|---|---|
| 19-O | 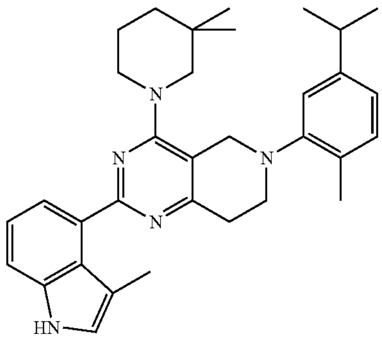 [SMILES: Cc1ccc(C(C)C)cc1N1CCc2nc(-c3cccc4[nH]cc(C)c34)nc(N3CCCC(C)(C)C3)c2C1] | 4-(3,3-dimethylpiperidin-1-yl)-6-(5-isopropyl-2-methylphenyl)-2-(3-methyl-1H-indol-4-yl)-5,6,7,8-tetrahydropyrido[4,3-d]pyrimidine. $^1$H NMR (400 MHz, CDCl$_3$) δ ppm 8.00 (br. s., 1 H), 7.44 (dd, J = 13.0, 7.7 Hz, 2 H), 7.22-7.27 (m, 1 H), 7.19 (d, J = 7.6 Hz, 1 H), 7.02 (d, J = 18.9 Hz, 2 H), 6.94 (d, J = 7.6 Hz, 1 H), 4.12 (s, 2 H), 3.42 (t, J = 6.1 Hz, 2 H), 3.31-3.38 (m, 2 H), 3.12-3.19 (m, 4 H), 2.92 (dt, J = 13.8, 6.8 Hz, 1 H), 2.34 (s, 3 H), 2.17 (s, 3 H), 1.70-1.79 (m, 2 H), 1.45 (t, J = 6.1 Hz, 2 H), 1.30 (d, J = 6.8 Hz, 6 H), 1.04 (s, 6 H); MS (ESI+) m/z 508.4 (M + H)$^+$. |
| 19-P | 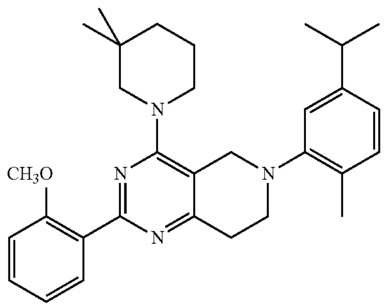 | 4-(3,3-dimethylpiperidin-1-yl)-6-(5-isopropyl-2-methylphenyl)-2-(3-methoxyphenyl)-5,6,7,8-tetrahydropyrido[4,3-d]pyrimidine. $^1$H NMR (400 MHz, DMSO-d$_6$) δ ppm 7.47 (dd, J = 7.6, 1.8 Hz, 1 H) 7.36-7.43 (m, 1 H) 7.11 (s, 1 H) 7.09 (s, 1 H) 6.98-7.04 (m, 2 H) 6.87 (dd, J = 7.6, 1.5 Hz, 1 H) 3.99 (s, 2 H) 3.76 (s, 3 H) 3.22-3.30 (m, 4 H) 3.04 (s, 2 H) 2.93 (t, 2 H) 2.85 (quin, J = 6.9 Hz, 1 H) 2.20 (s, 3 H) 1.60-1.68 (m, 2 H) 1.38 (t, J = 5.9 Hz, 2 H) 1.20 (d, J = 7.1 Hz, 6 H) 0.96 (s, 6 H); MS (ESI+) m/z 485.1 (M + H)$^+$. |
| 19-Q | 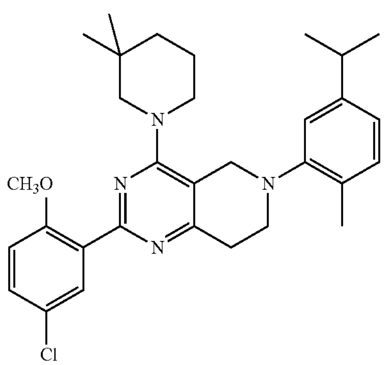 | 2-(5-chloro-2-methoxyphenyl)-4-(3,3-dimethylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 7.49 (d, J = 2.8 Hz, 1 H) 7.45 (dd, J = 9.2, 2.8 Hz, 1 H) 7.14 (d, J = 8.8 Hz, 1 H) 7.10 (d, J = 7.8 Hz, 1 H) 7.01 (d, J = 1.3 Hz, 1 H) 6.87 (dd, J = 7.7, 1.6 Hz, 1 H) 3.98-4.02 (m, 2 H) 3.77 (s, 3 H) 3.24-3.29 (m, 4 H) 3.04-3.08 (m, 2 H) 2.94 (t, J = 5.8 Hz, 2 H) 2.85 (dt, J = 13.7, 6.9 Hz, 1 H) 2.20 (s, 3 H) 1.59-1.68 (m, 2 H) 1.39 (t, J = 5.8 Hz, 2 H) 1.20 (d, 6 H) 0.95 (s, 6 H); MS (ESI+) m/z 519.1 (M + H)$^+$. |
| 19-R | 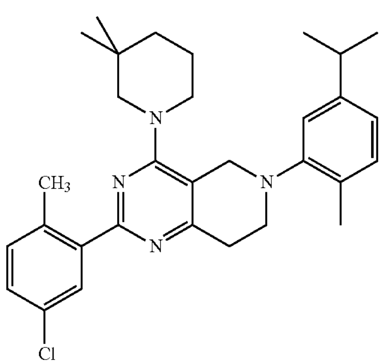 [SMILES: Cc1ccc(Cl)cc1-c1nc2c(c(N3CCCC(C)(C)C3)n1)CN(c1cc(C(C)C)ccc1C)CC2] | 2-(5-chloro-2-methylphenyl)-4-(3,3-dimethylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 7.80 (d, J = 2.3 Hz, 1 H) 7.39-7.42 (m, 1 H) 7.38 (d, J = 2.5 Hz, 1 H) 7.32 (d, J = 8.4 Hz, 1 H) 7.10 (d, J = 7.8 Hz, 1 H) 6.99 (d, J = 1.5 Hz, 1 H) 6.86 (dd, J = 7.8, 1.5 Hz, 1 H) 4.02 (s, 2 H) 3.26-3.31 (m, 4 H) 3.05-3.08 (m, 2 H) 2.98 (t, J = 5.8 Hz, 2 H) 2.84 (dq, J = 7.1, 6.9 Hz, 1 H) 2.51-2.53 (m, 2 H) 2.20 (s, 3 H) 1.62-1.70 (m, 2 H) 1.40 (t, J = 5.9 Hz, 2 H) 1.18 (d, J = 6.9 Hz, 6 H) 0.96 (s, 6 H); MS (ESI+) m/z 503.1 (M + H)$^+$. |

| | Structure | Chemical Name & Analytical Data |
|---|---|---|
| 19-S | 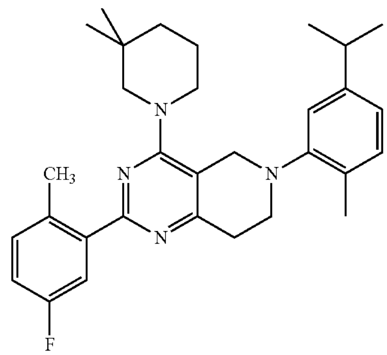 [SMILES: Cc1ccc(F)cc1-c1nc2c(c(N3CCCC(C)(C)C3)n1)CN(c1cc(C(C)C)ccc1C)CC2] | 4-(3,3-dimethylpiperidin-1-yl)-2-(5-fluoro-2-methylphenyl)-6-(5-isopropyl-2-methylphenyl)-5,6,7,8-tetrahydropyrido[4,3-d]pyrimidine. $^1$H NMR (400 MHz, DMSO-d$_6$) δ ppm 7.57 (dd, J = 10.2, 2.9 Hz, 1 H) 7.32 (dd, J = 8.5, 5.9 Hz, 1 H) 7.18 (td, J = 8.4, 2.9 Hz, 1 H) 7.10 (d, J = 7.8 Hz, 1 H) 7.00 (d, J = 1.3 Hz, 1 H) 6.86 (dd, J = 7.6, 1.5 Hz, 1 H) 4.02 (s, 2 H) 3.33 (s, 3 H) 3.26-3.32 (m, 4 H) 3.05-3.10 (m, 2 H) 2.97 (t, J = 5.8 Hz, 2 H) 2.84 (spt, J = 6.8 Hz, 1 H) 2.20 (s, 3 H) 1.61-1.71 (m, 2 H) 1.40 (t, J = 5.8 Hz, 2 H) 1.19 (d, J = 6.8 Hz, 6 H) 0.96 (s, 6 H); MS (ESI+) m/z 487.1 (M + H)$^+$. |
| 19-T | 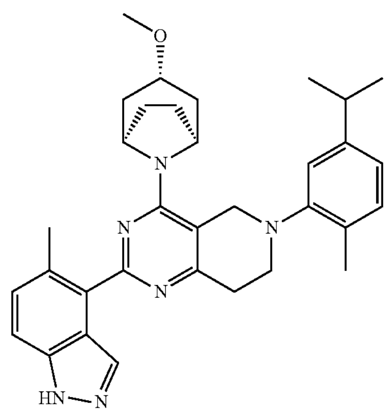 [SMILES: CO[C@H]1C[C@H]2CC[C@@H](C1)N2c1nc(-c2c(C)ccc3[nH]ncc23)nc2c1CN(c1cc(C(C)C)ccc1C)CC2] | 6-(5-isopropyl-2-methylphenyl)-4-((3-endo)-3-methoxy-8-azabicyclo[3.2.1]octan-8-yl)-2-(5-methyl-1H-indazol-4-yl)-5,6,7,8-tetrahydropyrido[4,3-d]pyrimidine. $^1$H NMR (400 MHz, CD$_2$Cl$_2$) δ ppm 8.21 (br. s., 1 H) 7.49 (d, J = 8.3 Hz, 1 H) 7.30-7.43 (m, 2 H) 7.20 (d, J = 8.3 Hz, 1 H) 7.07 (d, J = 1.5 Hz, 1 H) 6.97 (dd, J = 7.7, 1.6 Hz, 1 H) 4.59 (br. s., 2 H) 4.09 (s, 2 H) 3.53 (t, J = 4.8 Hz, 1 H) 3.40 (t, J = 5.8 Hz, 2 H) 3.32 (s, 3 H) 3.11-3.26 (m, 1 H) 2.96 (dt, J = 13.9, 7.0 Hz, 1 H) 2.66 (s, 3 H) 2.35 (s, 3 H) 2.08-2.25 (m, 4 H) 1.93-2.06 (m, 4 H) 1.31 (d, J = 6.8 Hz, 6 H); MS (ESI+) m/z 537.0 (M + H)$^+$. |
| 19-U | 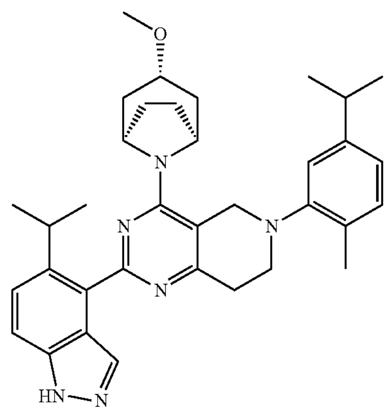 [SMILES: CO[C@H]1C[C@H]2CC[C@@H](C1)N2c1nc(-c2c(C(C)C)ccc3[nH]ncc23)nc2c1CN(c1cc(C(C)C)ccc1C)CC2] | 2-(5-isopropyl-1H-indazol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, CD$_2$Cl$_2$) δ ppm 10.24 (br. s., 1 H) 8.05 (s, 1 H) 7.51-7.56 (m, 2 H) 7.20 (d, J = 7.8 Hz, 1 H) 7.08 (d, J = 1.8 Hz, 1 H) 6.97 (dd, J = 7.8, 1.8 Hz, 1 H) 4.56 (br. s., 2 H) 4.09 (s, 2 H) 3.68 (quin, J = 6.9 Hz, 1 H) 3.52 (t, J = 4.8 Hz, 1 H) 3.41 (t, J = 5.9 Hz, 2 H) 3.31 (s, 3 H) 3.14 (t, J = 5.9 Hz, 2 H) 2.96 (quin, J = 6.9 Hz, 1 H) 2.36 (s, 3 H) 2.07-2.23 (m, 4 H) 1.92-2.04 (m, 4 H) 1.31 (d, J = 7.2 Hz, 6 H) 1.33 (d, J = 7.2 Hz, 6 H); MS (ESI+) m/z 565.1 (M + H)$^+$. |
| 19-V | 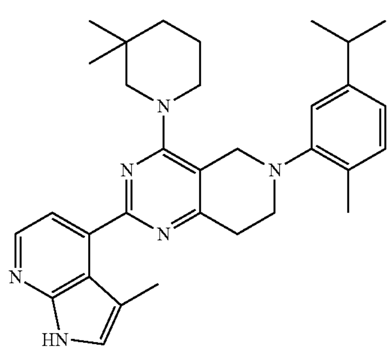 [SMILES: Cc1ccc(C(C)C)cc1N1CCc2nc(-c3ccnc4[nH]cc(C)c34)nc(N3CCCC(C)(C)C3)c2C1] | 4-(3,3-dimethylpiperidin-1-yl)-6-(5-isopropyl-2-methylphenyl)-2-(3-methyl-1H-pyrrolo[2,3-b]pyridin-4-yl)-5,6,7,8-tetrahydropyrido[4,3-d]pyrimidine. $^1$H NMR (400 MHz, CDCl$_3$) δ ppm 8.53 (br s, 1 H) 8.35 (d, J = 4.80 Hz, 1 H), 7.41 (d, J = 4.80 Hz, 1 H), 7.16 (d, J = 7.83 Hz, 1 H), 7.11-7.12 (m, 1 H), 6.96 (d, J = 1.77 Hz, 1 H), 6.92 (dd, J = 1.77, 7.58 Hz, 1 H), 4.07 (s, 2 H), 3.39 (app t, J = 6.03 Hz, 2 H), 3.34 (br t, J = 5.43 Hz, 2 H), 3.12-3.14 (m, 4 H), 2.84-2.95 (m, 1 H), 2.30 (s, 3 H), 2.21 (d, J = 1.01 Hz, 3 H), 1.69-1.75 (m, 2 H), 1.44 (t, J = 6.06 Hz, 2 H), 1.26 (d, J = 7.07 Hz, 6 H), 1.01 (s, 6 H); MS (ESI+) m/z 509.28 (M + H)$^+$. |

| | Structure | Chemical Name & Analytical Data |
|---|---|---|
| 19-W | 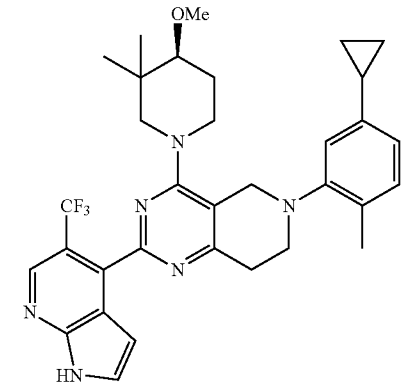 [SMILES: CO[C@H]1CCN(c2nc(-c3c(C(F)(F)F)cnc4[nH]ccc34)nc3c2CN(c2cc(C4CC4)ccc2C)CC3)CC1(C)C] | (S)-6-(5-cyclopropyl-2-methylphenyl)-4-(4-methoxy-3,3-dimethylpiperidin-1-yl)-2-(5-(trifluoromethyl)-1H-pyrrolo[2,3-b]pyridin-4-yl)-5,6,7,8-tetrahydropyrido[4,3-d]pyrimidine. $^1$H NMR (400 MHz, CD$_2$Cl$_2$) δ ppm 8.68 (s, 1 H), 7.44 (dd, J = 3.5, 2.3 Hz, 1 H), 7.10 (d, J = 7.8 Hz, 1 H), 6.85 (d, J = 1.5 Hz, 1H), 6.74 (dd, J = 7.7, 1.6 Hz, 1 H), 6.58 (dd, J = 3.5, 1.8 Hz, 1 H), 4.02 (s, 2 H), 3.70-3.76 (m, 1 H), 3.43 (d, J = 14.1 Hz, 1 H), 3.34-3.38 (m, 2 H), 3.33 (s, 3 H), 3.13 (br. s., 3 H), 2.95 (dd, J = 8.5, 3.9 Hz, 2 H), 2.27 (s, 3 H), 1.91-2.00 (m, 1 H), 1.83-1.91 (m, 1 H), 1.63-1.74 (m, 1 H), 0.98 (s, 3 H), 0.94-0.97 (m, 2 H), 0.93 (s, 3 H), 0.63-0.70 (m, 2 H); MS (ESI+) m/z 590.9 (M + H)$^+$. |
| 19-X | 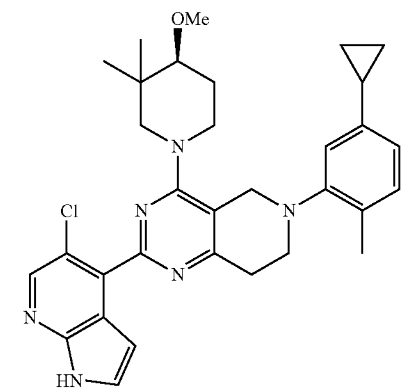 [SMILES: CO[C@H]1CCN(c2nc(-c3c(Cl)cnc4[nH]ccc34)nc3c2CN(c2cc(C4CC4)ccc2C)CC3)CC1(C)C] | (S)-2-(5-chloro-1H-pyrrolo[2,3-b]pyridin-4-yl)-6-(5-cyclopropyl-2-methylphenyl)-4-(methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 8.35 (s, 1 H), 7.39 (br. s., 1 H), 7.10 (d, J = 7.8 Hz, 1 H), 6.86 (d, J = 1.5 Hz, 1 H), 6.74 (dd, J = 7.8, 1.5 Hz, 1 H), 6.56 (br. s., 1 H), 4.00 (s, 2 H), 3.73-3.83 (m, J = 8.3 Hz, 1 H), 3.42-3.54 (m, 1 H), 3.33-3.36 (m, 6 H), 3.12-3.26 (m, 2 H), 2.92-3.03 (m, 2 H), 2.26 (s, 3 H), 1.93-2.02 (m, 1 H), 1.84-1.93 (m, 1 H), 1.66-1.77 (m, 1 H), 0.99 (s, 3 H), 0.95-0.98 (m, 2 H), 0.94 (s, 3 H), 0.64-0.69 (m, 2 H); MS (ESI+) m/z 556.9 (M + H)$^+$. |
| 19-Y | 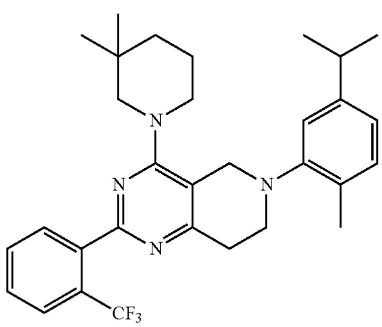 [SMILES: Cc1ccc(C(C)C)cc1N1CCc2nc(-c3ccccc3C(F)(F)F)nc(N3CCCC(C)(C)C3)c2C1] | 2-(2,5-dimethylphenyl)-4-(3,3-dimethylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 7.83 (d, J = 7.8 Hz, 1 H), 7.71-7.78 (m, 2 H), 7.61-7.70 (m, 1 H), 7.10 (d, J = 7.8 Hz, 1 H), 6.96 (s, 1 H), 6.86 (d, J = 9.1 Hz, 1 H), 4.04 (s, 2 H), 3.24-3.34 (m, 4 H), 3.08 (s, 2 H), 2.93 (app t, J = 5.9 Hz, 2 H), 2.77-2.88 (m, 1 H), 2.20 (s, 3 H), 1.58-1.70 (m, 2 H), 1.34-1.43 (m, 2 H), 1.18 (d, J = 7.1 Hz, 6 H), 0.94 (s, 6 H); MS (ESI+) m/z 523.3 (M + H)$^+$. |
| 19-Z | 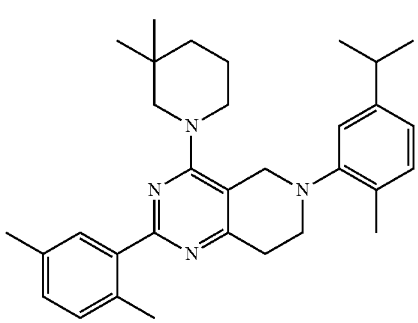 [SMILES: Cc1ccc(C)c(-c2nc3c(c(N4CCCC(C)(C)C4)n2)CN(c2cc(C(C)C)ccc2C)CC3)c1] | 2-(2,5-dimethylphenyl)-4-(3,3-dimethylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 0.99 (s, 6 H) 1.23 (d, J = 7.07 Hz, 6 H) 1.47 (m, J = 5.80, 5.80 Hz, 2 H) 1.68-1.79 (m, 2 H) 2.26 (s, 3 H) 2.35 (s, 3 H) 2.40 (s, 3 H) 2.79-2.91 (m, 1 H) 3.01 (m, J = 5.80, 5.80 Hz, 2 H) 3.12-3.19 (m, 2 H) 3.34-3.42 (m, 4 H) 4.02 (s, 2 H) 6.88 (d, J = 7.58 Hz, 1 H) 6.97 (s, 1 H) 7.05-7.19 (m, 3 H) 7.39 (s, 1 H); MS (ESI+) m/z 483.3 (M + H)$^+$. |

-continued

| | Structure | Chemical Name & Analytical Data |
|---|---|---|
| 19-AA | 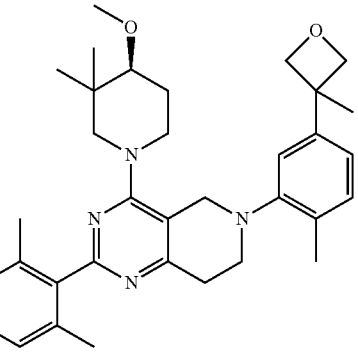 | (S)-2-(2,6-dimethylphenyl)-4-(4-methoxy-3,3-dimethylpiperidin-1-yl)-6-(2-methyl-5-(3-methyloxetan-3-yl)phenyl)-5,6,7,8-tetrahydropyrido[4,3-d]pyrimidine. $^1$H NMR (400 MHz, CD$_2$Cl$_2$) δ ppm 7.15-7.22 (m, 2 H), 7.07 (d, J = 7.6 Hz, 2 H), 6.89 (d, J = 2.0 Hz, 1 H), 6.86 (dd, J = 7.8, 1.8 Hz, 1 H), 4.91 (d, J = 5.6 Hz, 2 H), 4.58 (d, J = 5.6 Hz, 2 H), 4.03 (s, 2 H), 3.62-3.71 (m, 1 H), 3.30-3.39 (m, 6 H), 3.01-3.13 (m, 3 H), 2.94 (dd, J = 8.8, 3.8 Hz, 1 H), 2.84 (d, J = 12.6 Hz, 1 H), 2.30 (s, 3 H), 2.11 (s, 6 H), 1.91-1.99 (m, 1 H), 1.69 (s, 3 H), 1.62-1.68 (m, 1 H), 0.99 (s, 3 H), 0.94 (s, 3 H); MS (ESI+) m/z 541.1 (M + H)$^+$. |
| 19-AB | 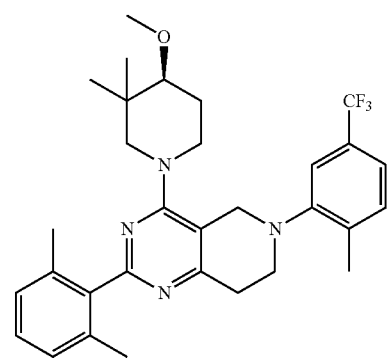 [SMILES: CO[C@H]1CCN(c2nc(-c3c(C)cccc3C)nc3c2CN(c2cc(C(F)(F)F)ccc2C)CC3)CC1(C)C] | (S)-2-(2,6-dimethylphenyl)-4-(4-methoxy-3,3-dimethylpiperidin-1-yl)-6-(2-methyl-5-(trifluoromethyl)phenyl)-5,6,7,8-tetrahydropyrido[4,3-d]pyrimidine. $^1$H NMR (400 MHz, CD$_2$Cl$_2$) δ ppm 7.35 (d, J = 7.8 Hz, 1 H), 7.28-7.31 (m, 2 H), 7.19-7.24 (m, 1 H), 7.10 (d, J = 7.6 Hz, 2 H), 4.03 (s, 2 H), 3.72 (br. s., 1 H), 3.38 (t, J = 5.8 Hz, 2 H), 3.33 (s, 3 H), 3.16 (br. s., 2 H), 2.96 (dd, J = 8.3, 3.8 Hz, 1 H), 2.38 (s, 3 H), 2.14 (br. s., 6 H), 1.91-2.01 (m, 1H), 1.63-1.75 (m, 1 H), 0.97 (s, 3 H), 0.92 (s, 3 H); MS (ESI+) m/z 539.0 (M + H)$^+$. |
| 19-AC | 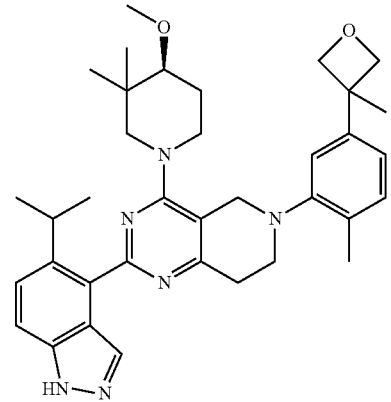 [SMILES: CO[C@H]1CCN(c2nc(-c3c(C(C)C)ccc4[nH]ncc34)nc3c2CN(c2cc(C4(C)COC4)ccc2C)CC3)CC1(C)C] | (S)-2-(5-isopropyl-1H-indazol-4-yl)-4-(4-methoxy-3,3-dimethylpiperidin-1-yl)-6-(2-methyl-5-(3-methyloxetan-3-yl)phenyl)-5,6,7,8-tetrahydropyrido[4,3-d]pyrimidine. $^1$H NMR (400 MHz, CD$_2$Cl$_2$) δ ppm 7.97 (br. s., 1 H), 7.52 (d, J = 8.3 Hz, 1 H), 7.47 (d, J = 8.8 Hz, 1 H), 7.22 (d, J = 8.1 Hz, 1 H), 6.94 (d, J = 1.5 Hz, 1 H), 6.89 (d, J = 7.6 Hz, 1 H), 4.92 (d, J = 5.6 Hz, 2 H), 4.60 (d, J = 5.6 Hz, 2 H), 4.06 (s, 2 H), 3.71 (br. s., 1 H), 3.35-3.43 (m, 3 H), 3.33 (s, 3 H), 3.14 (br. s., 2 H), 2.95 (dd, J = 8.3, 3.3 Hz, 1 H), 2.32 (s, 3 H), 1.93-2.01 (m, 1 H), 1.71 (s, 3 H), 1.64-1.70 (m, 1 H), 1.30 (d, J = 6.6 Hz, 6 H), 0.99 (s, 3 H), 0.96 (s, 3 H); MS (ESI+) m/z 595.0 (M + H)$^+$. |
| 19-AD | 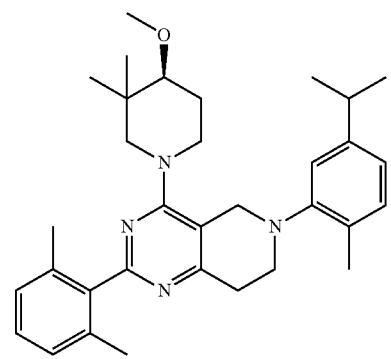 [SMILES: CO[C@H]1CCN(c2nc(-c3c(C)cccc3C)nc3c2CN(c2cc(C(C)C)ccc2C)CC3)CC1(C)C] | (S)-2-(2,6-dimethylphenyl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 7.16-7.22 (m, 1 H), 7.13 (d, J = 7.6 Hz, 1 H), 7.08 (d, J = 7.6 Hz, 2 H), 6.95 (d, J = 1.8 Hz, 1 H), 6.89 (dd, J = 7.8, 1.5 Hz, 1 H), 4.03 (s, 2 H), 3.69 (br. s., 1 H), 3.30-3.39 (m, 6 H), 3.04 (br. s., 3 H), 2.94 (dd, J = 4.8, 3.8 Hz, 1 H), 2.87 (spt, J = 6.8 Hz, 1 H), 2.28 (s, 3 H), 2.12 (s, 6 H), 1.91-1.99 (m, 1 H), 1.62-1.72 (m, 1 H), 1.24 (d, J = 7.1 Hz, 6 H), 0.99 (s, 3 H), 0.94 (s, 3 H); MS (ESI+) m/z 513.3 (M + H)$^+$. |

-continued

| | Structure | Chemical Name & Analytical Data |
|---|---|---|
| 19-AE | 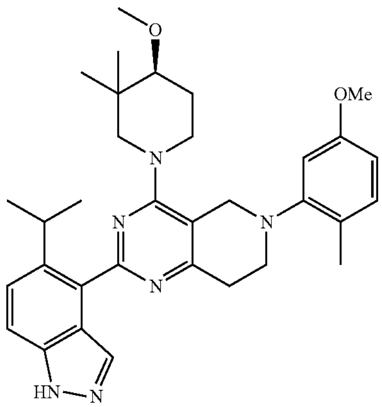 [SMILES: COc1ccc(C)c(N2CCc3nc(-c4c(C(C)C)ccc5[nH]ncc45)nc(N4CC[C@H](OC)C(C)(C)C4)c3C2)c1] | (S)-2-(5-isopropyl-1H-indazol-4-yl)-6-(5-methoxy-2-methylphenyl)-4-(4-methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 7.74 (br s., 1 H), 7.37 (br. s., 2 H) 7.15 (d, J = 7.8 Hz, 1 H), 6.72 (d, J = 2.5 Hz, 1 H), 6.63 (d, J = 7.8 Hz, 1 H), 4.03 (s, 2 H), 3.80 (s, 3 H), 3.31-3.38 (m, 6 H), 3.00 (br. s., 1 H), 2.26 (s, 3 H), 1.90-2.02 (m, 1 H), 1.73 (br. s., 1 H), 1.32 (br. s., 6 H), 0.96 (s, 3 H), 0.92 (s, 3 H); MS (ESI+) m/z 555.0 (M + H)$^+$. |
| 19-AF | 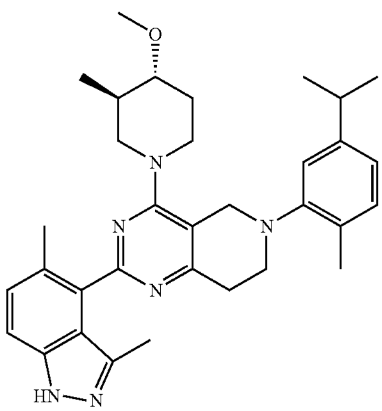 [SMILES: CO[C@@H]1CCN(c2nc(-c3c(C)ccc4[nH]nc(C)c34)nc3c2CN(c2cc(C(C)C)ccc2C)CC3)C[C@H]1C] | 2-(3,5-dimethyl-1H-indazol-4-yl)-6-(5-isopropyl-2-(methylphenyl)-4-((3R,4R)-4-methoxy-3-methylpiperidin-1-yl)-5,6,7,8-tetrahydropyrido[4,3-d]pyrimidine. $^1$H NMR (400 MHz, DMSO-d$_6$) δ ppm 12.59 (s, 1 H) 7.39 (d, J = 8.6 Hz, 1 H) 7.21 (d, J = 8.6 Hz, 1 H) 7.11 (d, J = 8.1 Hz, 1 H) 6.94 (d, J = 1.3 Hz, 1 H) 6.87 (dd, J = 7.6, 1.5 Hz, 1 H) 3.96-4.16 (m, 2 H) 3.62-3.84 (m, 2 H) 3.30-3.40 (m, 2 H) 3.26 (s, 3 H) 2.89-3.06 (m, 4 H) 2.73-2.87 (m, 2 H) 2.21 (s, 3 H) 2.19 (s, 3 H) 2.04-2.13 (m, 1 H) 1.87 (s, 3 H) 1.60-1.72 (m, 1 H) 1.29-1.42 (m, 1 H) 1.18 (d, J = 7.1 Hz, 6 H) 0.94 (d, J = 6.6 Hz, 3 H); MS (ESI+) m/z 539.4 (M + H)$^+$. |
| 19-AG | 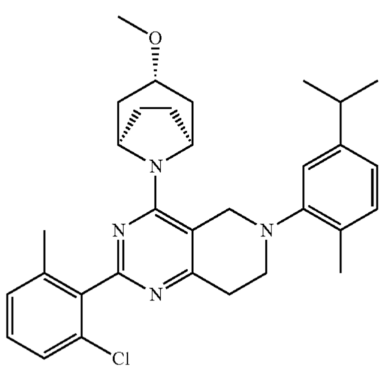 [SMILES: CO[C@H]1C[C@H]2CC[C@@H](C1)N2c1nc(-c2c(C)cccc2Cl)nc2c1CN(c1cc(C(C)C)ccc1C)CC2] | 2-(2-chloro-6-methylphenyl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, DMSO-d$_6$) δ ppm 7.22-7.37 (m, 3 H) 7.11 (d, J = 7.8 Hz, 1 H) 6.99 (d, J = 1.3 Hz, 1 H) 6.87 (dd, J = 7.6, 1.5 Hz, 1 H) 4.35-4.44 (m, 2 H) 3.98-4.05 (m, 2 H) 3.42-3.47 (m, 1 H) 3.29 (t, J = 5.9 Hz, 2 H) 3.20 (s, 3 H) 2.79-2.92 (m, 3 H) 2.22 (s, 3 H) 2.08 (s, 3 H) 1.79-2.03 (m, 8 H) 1.18 (d, J = 6.8 Hz, 6 H); MS (ESI+) m/z 531.3 (M + H)$^+$. |
| 19-AH | 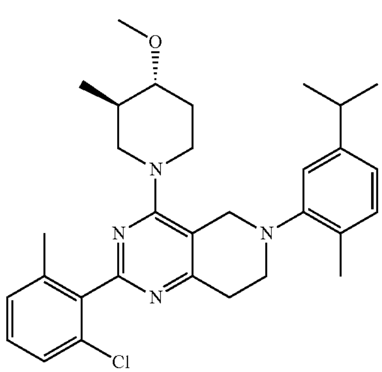 [SMILES: CO[C@@H]1CCN(c2nc(-c3c(C)cccc3Cl)nc3c2CN(c2cc(C(C)C)ccc2C)CC3)C[C@H]1C] | 2-(2-chloro-6-methylphenyl)-6-(5-isopropyl-2-methylphenyl)-4-((3R,4R)-4-methoxy-3-methylpiperidin-1-yl)-5,6,7,8-tetrahydropyrido[4,3-d]pyrimidine. $^1$H NMR (400 MHz, DMSO-d$_6$) δ ppm 7.23-7.28 (m, 3 H) 7.10 (d, J = 8.1 Hz, 1 H) 6.93 (d, J = 1.5 Hz, 1 H) 6.86 (dd, J = 7.8, 1.5 Hz, 1 H) 3.93-4.11 (m, 2 H) 3.62-3.81 (m, 2 H) 3.29-3.35 (m, 1 H) 3.26 (s, 3 H) 2.94-3.06 (m, 2 H) 2.90 (t, J = 5.8 Hz, 2 H) 2.73-2.87 (m, 2 H) 2.20 (s, 3 H) 2.08 (s, 3 H) 1.59-1.71 (m, 1 H) 1.30-1.42 (m, 1 H) 1.17-1.20 (m, 1 H) 1.17 (d, J = 6.8 Hz, 6 H) 0.95 (d, J = 6.6 Hz, 3 H); MS (ESI+) m/z 519.4 (M + H)$^+$. |

-continued

| | Structure | Chemical Name & Analytical Data |
|---|---|---|
| 19-AI | 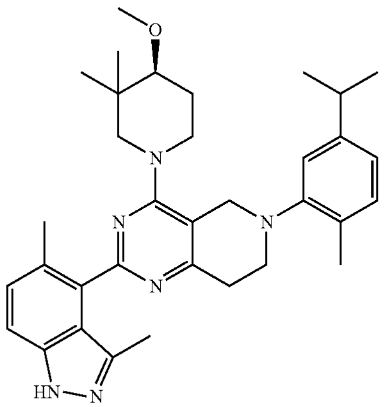 [SMILES: CO[C@H]1CCN(c2nc(-c3c(C)ccc4[nH]nc(C)c34)nc3c2CN(c2cc(C(C)C)ccc2C)CC3)CC1(C)C] | (S)-2-(3,5-dimethyl-1H-indazol-4-yl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, CD2Cl2) δ ppm 7.30 (d, J = 8.6 Hz, 1 H), 7.17 (d, J = 8.6 Hz, 1 H), 7.08 (d, J = 7.6 Hz, 1 H), 6.75-6.92 (m, 2 H), 3.98 (s, 2 H), 3.76 (br. s., 1 H), 3.32 (br. s., 3 H), 3.21-3.26 (m, 3 H), 2.91 (br. s., 1 H), 2.78 (spt, J = 6.8 Hz, 1 H), 2.31 (br. s., 2 H), 2.19 (br. s, 3 H) 2.01 (br. s., 3 H) , 1.88 (m, J = 3.5 Hz, 1 H), 1.58-1.69 (m, 1 H), 1.17 (d, J = 6.8 Hz, 6 H), 0.89 (s, 3 H), 0.84 (s, 3 H); MS (ESI+) m/z 553.1 (M + H)$^+$. |
| 19-AJ | 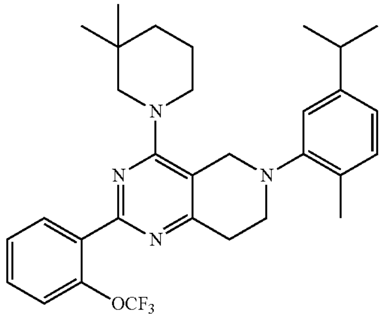 [SMILES: Cc1ccc(C(C)C)cc1N1CCc2nc(-c3ccccc3OC(F)(F)F)nc(N3CCCC(C)(C)C3)c2C1] | 4-(3,3-dimethylpiperidin-1-yl)-6-(5-isopropyl-2-methylphenyl)-2-(2-trifluoromethoxy)phenyl)-5,6,7,8-tetrahydropyrido[4,3-d]pyrimidine. $^1$H NMR (400 MHz, DMSO-d$_6$) δ ppm 0.95 (s, 6 H) 1.18 (d, J = 6.82 Hz, 6 H) 1.40 (app t, J = 5.94 Hz, 2 H) 1.65 (br. s., 2 H) 2.75-2.88 (m, 1 H) 2.94 (t, J = 5.94 Hz, 2 H) 3.10 (s, 2 H) 4.03 (s, 2 H) 6.86 (dd, J = 7.71, 1.39 Hz, 1 H) 6.96 (d, J = 1.26 Hz, 1 H) 7.10 (d, J = 7.83 Hz, 1 H) 7.45 (d, J = 8.08 Hz, 1 H) 7.48-7.54 (m, 1 H) 7.55-7.63 (m, 1 H) 7.95 (dd, J = 7.58, 177 Hz, 1 H); MS (ESI+) m/z 539.3 (M + H)$^+$. |
| 19-AK | 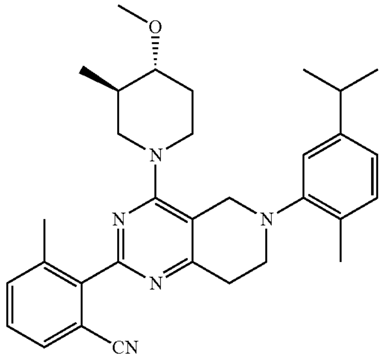 [SMILES: CO[C@@H]1CCN(c2nc(-c3c(C)cccc3C#N)nc3c2CN(c2cc(C(C)C)ccc2C)CC3)C[C@H]1C] | 2-(6-(5-isopropyl-2-methylphenyl)-4-((3R,4R)-4-methoxy-3-methylpiperidin-1-yl)-5,6,7,8-tetrahyropyrido[4,3-d]pyrimidin-2-yl)-3-methylbenzonitrile. $^1$H NMR (400 MHz, DMSO-d$_6$) δ ppm 7.75 (d, J = 7.6 Hz, 1 H) 7.64 (d, J = 7.3 Hz, 1 H) 7.52 (t, J = 7.7 Hz, 1 H) 7.10 (d, J = 8.1 Hz, 1 H) 6.98 (d, J = 1.5 Hz, 1 H) 6.87 (dd, J = 7.8, 1.5 Hz, 1 H) 3.92-4.15 (m, 2 H) 3.70-3.90 (m, 2 H) 3.28-3.32 (m, 2 H) 3.27 (s, 3 H) 3.02-3.12 (m, 1 H) 2.92-3.02 (m, 3 H) 2.75-2.89 (m, 2 H) 2.32 (s, 3 H) 2.20 (s, 3 H) 2.06-2.16 (m, 1 H) 1.61-1.74 (m, 1 H) 1.37 (d, J = 10.9 Hz, 1 H) 1.18 (d, J = 6.8 Hz, 6 H) 0.96 (d, J = 6.6 Hz, 3H). MS (ESI+) m/z 510.3 (M + H)$^+$. |
| 19-AL | 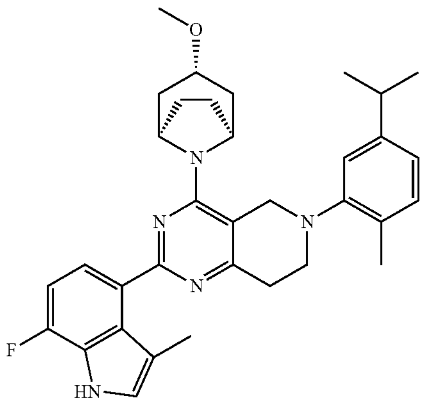 [SMILES: CO[C@H]1C[C@H]2CC[C@@H](C1)N2c1nc(-c2ccc(F)c3[nH]cc(C)c23)nc2c1CN(c1cc(C(C)C)ccc1C)CC2] | 2-(7-fluoro-3-methyl-1H-indol-4-yl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, CD$_2$Cl$_2$) δ ppm 8.40 (br. s., 1 H) 7.37 (dd, J = 8.1, 4.8 Hz, 1 H) 7.19 (d, J = 7.8 Hz, 1 H) 7.11 (s, 1 H) 7.05 (s, 1 H) 6.92-7.01 (m, 2 H) 4.56 (br. s., 2 H) 4.07 (s, 2 H) 3.52 (t, J = .7 Hz, 1 H) 3.39 (t, J = 6.0 Hz, 2 H) 3.32 (s, 3 H) 3.10 (t, J = 5.8 Hz, 2 H) 2.94 (dt, J = 13.6, 6.8 Hz, 1 H) 2.34 (s, 3 H) 2.09-2.24 (m, 7 H) 1.92-2.06 (m, 4 H) 1.31 (d, J = 6.8 Hz, 6 H); MS (ESI+) m/z 554.5 (M + H)$^+$. |

Example 20

20-A. 2-(5-Chloro-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine

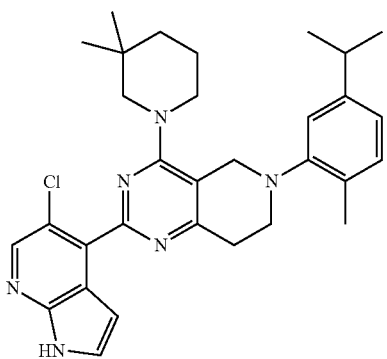 [SMILES: Cc1ccc(C(C)C)cc1N1CCc2nc(-c3c(Cl)cnc4[nH]ccc34)nc(N3CCCC(C)(C)C3)c2C1]

The title compound was prepared in a similar manner to that described in Example 19. ¹H NMR (400 MHz, DMSO-d₆) δ ppm 11.94 (br. s., 1 H), 8.30 (s, 1 H), 7.50-7.60 (m, 1 H), 7.11 (d, J=7.8 Hz, 1 H), 6.98 (d, J=1.5 Hz, 1 H), 6.87 (dd, J=7.6, 1.5 Hz, 1 H), 6.41 (d, J=5.3 Hz, 1 H), 4.08 (s, 2 H), 3.32-3.38 (m, 4 H), 3.11 (s, 2 H), 2.98 (t, J=5.8 Hz, 2 H), 2.84 (dt, J=13.7, 6.9 Hz, 1 H), 2.22 (s, 3 H), 1.65 (m, 2 H), 1.40 (t, J=5.7 Hz, 2 H), 1.19 (d, J=7.1 Hz, 6 H), 0.96 (s, 6 H); MS (ESI+) m/z 529.2 (M+H)⁺.

20-B. 2-(5-Chloro-1-tosyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine

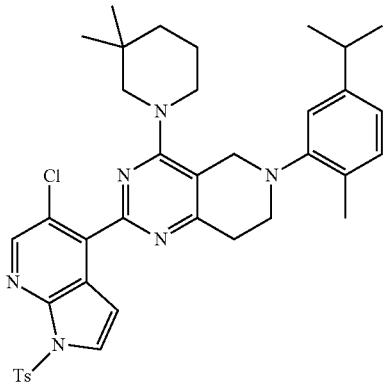 [SMILES: Cc1ccc(S(=O)(=O)n2ccc3c(-c4nc5c(c(N6CCCC(C)(C)C6)n4)CN(c4cc(C(C)C)ccc4C)CC5)c(Cl)cnc32)cc1]

To a solution of 2-(5-chloro-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine (213 mg, 0.403 mmol) in THF (2.4 mL) was added NaH 60% in oil (32 mg, 0.80 mmol) at 0° C. After 15 min, p-toluenesulfonyl-chloride (81 mg, 0.42 mmol) was added and the mixture was allowed to warmed to rt After 16 h, water was added and the aqueous phase was extracted with EtOAc (3×). The organic phases were combined, washed with brine, dried with sodium sulfate, filtered, and concentrated under reduced pressure. The residue was purified via FCC (0-20% EtOAc/heptane) to give the title compound. MS (ESI+) m/z 683.2 (M+H)⁺.

20-C. 2(5-Cyclopropyl-1-tosyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine

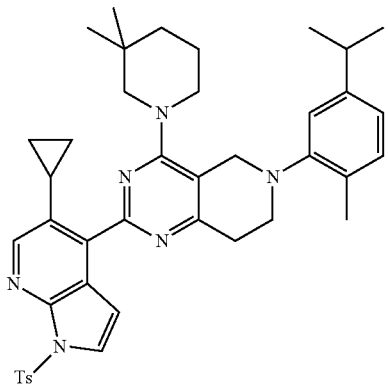 [SMILES: Cc1ccc(S(=O)(=O)n2ccc3c(-c4nc5c(c(N6CCCC(C)(C)C6)n4)CN(c4cc(C(C)C)ccc4C)CC5)c(C4CC4)cnc32)cc1]

To a mixture of 2-(5-chloro-1-tosyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine (135 mg, 0.198 mmol) in toluene (2 mL) and water (0.1 mL) was added potassium cyclopropyltrifluoroborate (58 mg, 0.39 mmol), tricyclohexylphosphine (11 mg, 0.04 mmol), Pd(OAc)₂ (4 mg, 0.02 mmol) and Cs₂CO₃ (193 mg, 0.593 mmol). The reaction mixture was heated at 100° C. for 16 h. Then the reaction mixture was filtered and the residue was purified via FCC (0-30% EtOAc/heptane) to give the title compound. MS (ESI+) m/z 689.4 (M+H)⁺.

20-D. 2-(5-Cyclopropyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine

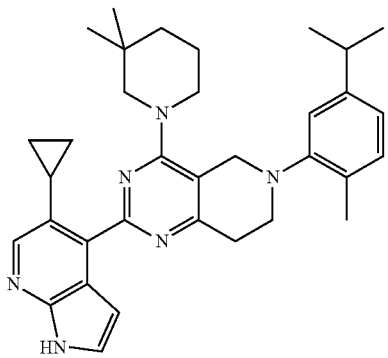 [SMILES: Cc1ccc(C(C)C)cc1N1CCc2nc(-c3c(C4CC4)cnc4[nH]ccc34)nc(N3CCCC(C)(C)C3)c2C1]

To a solution of 2-(5-cyclopropyl-1-tosyl-1H-pyrrolo[2,3-b]pyridin-4-yl)-4-(3,3-dimethylpiperidin-1-yl)-6-(5-isopropyl-2-methylphenyl)-5,6,7,8-tetrahydropyrido[4,3-d]pyrimidine (50 mg, 0.073 mmol) in EtOH (1.9 mL) was added KOH (24 mg, 0.44 mmol) and 28% aq NH₄OH (303 µL, 7.26 mmol). The mixture was heated at 100° C. for 45 min in a microwave reactor. A saturated solution of aq NH₄Cl was added and the aqueous phase was extracted with EtOAc (3×). The combined phases were washed with brine, dried with sodium sulfate, filtered and concentrated under reduced pressure. The reaction mixture was then filtered and the residue was purified via FCC (20-60% EtOAc/heptane) to give the title compound. $^1$H NMR (400 MHz, DMSO-d$_6$) δ ppm 11.53 (br. s., 1 H), 8.00 (s, 1H), 7.38-7.43 (m, 1 H), 7.11 (d, J=7.8 Hz, 1H), 6.97 (d, J=1.3 Hz, 1H), 6.86 (dd, J=7.7, 1.4 Hz, 1 H), 6.38 (dd, J=3.4, 1.9 Hz, 1 H), 4.09 (s, 2H), 3.34 (t, J=5.9 Hz, 2 H), 3.08 (s, 2 H), 2.98 (t, J=5.8 Hz, 2 H), 2.83 (dt, J=13.6, 6.8 Hz, 1 H), 2.34-2.41 (m, 1 H), 2.23 (s, 3H), 1.65 (dt, J=10.6, 5.5 Hz, 2 H), 1.40 (t, J=5.9 Hz, 2 H), 1.18 (d, J=6.8 Hz, 6 H), 0.97 (s, 6 H), 0.73-0.82 (m, 2 H), 0.55-0.63 (m, 2 H); MS (ESI+) m/z 535.4 (M+H)$^+$.

Example 21

21-A. 6-Benzyl-2-chloro-4-((2R,4R)-4-methoxy-2-methylpiperidin-1-yl)-5,6,7,8-tetrahydropyrido[4,3-d]pyrimidine

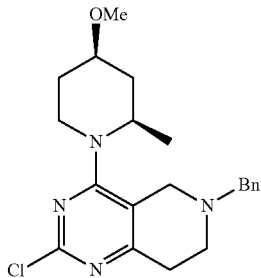 [SMILES: CO[C@@H]1CCN(c2nc(Cl)nc3c2CN(Cc2ccccc2)CC3)[C@H](C)C1]

To a solution of 6-benzyl-2,4-dichloro-5,6,7,8-tetrahydropyrido[4,3-d]pyrimidine (3.31 g, 11.2 mmol) in DMA (13 mL) was added (2R,4R)-4-methoxy-2-methylpiperidine hydrochloride (1.33 g, 8.03 mmol) and DIPEA (7.0 mL, 40 mmol). The mixture was then heated at 80° C. for 20 h. At that point water was added and the aqueous phase was extracted with a solution of EtOAc/n-heptane (4:1). The combined organic layers were washed with brine, dried over anhydrous sodium sulfate, filtered, and concentrated under reduce pressure. The residue was purified via FCC (15-30% EtOAc/heptane) to give the title compound. $^1$H NMR (400 MHz, CDCl$_3$) δ ppm 7.34-7.39 (m, 4 H), 7.32 (d, J=4.3 Hz, 1 H), 3.92-4.02 (m, 1 H), 3.75-3.82 (m, 1 H), 3.61-3.69 (m, 1 H), 3.54 (t, J=3.9 Hz, 1 H), 3.36-3.42 (m, 6 H), 2.89-2.96 (m, 2 H), 2.73-2.89 (m, 2 H), 1.75-1.83 (m, 4 H), 1.32 (d, J=6.6 Hz, 3 H); MS (ESI+) m/z 387.2 (M+H)$^+$.

21-B. 6-Benzyl-2-(2,6-dimethylphenyl)-4-((2R,4R)-4-methoxy-2-methylpiperidin-1-yl)-5,6,7,8-tetrahydropyrido[4,3-d]pyrimidine

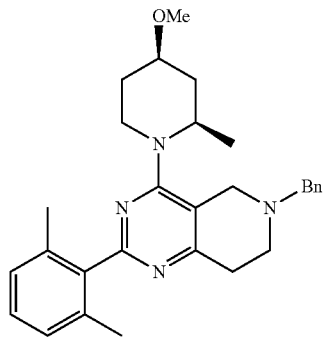 [SMILES: CO[C@@H]1CCN(c2nc(-c3c(C)cccc3C)nc3c2CN(Cc2ccccc2)CC3)[C@H](C)C1]

To a solution of 6-Benzyl-2-chloro-((2R,4R)-4-methoxy-2-methylpiperidin-1-yl)-5,6,7,8-tetrahydropyrido[4,3-d]pyrimidine (775 mg, 2.00 mmol) in DME (7 mL) was added 2,6-dimethylphenylboronic acid (601 mg, 4.01 mmol), Pd(Ph$_3$P)$_4$ (231 mg, 0.200 mmol) and a 2M solution of sodium carbonate (3.0 mL, 6.0 mmol). The reaction was heated at 130° C. in a microwave reactor for 1 h 15 min. The reaction was filtered and concentrated under reduced pressure. The residue was purified via FCC (0-30% EtOAc/heptane) to give the title compound. $^1$H NMR (400 MHz, CDCl$_3$) δ ppm 7.34-7.44 (m, 4 H), 7.30-7.33 (m, 1 H), 7.12-7.19 (m, 1 H), 7.03-7.09 (m, 2 H), 3.80-3.87 (m, 1 H), 3.73-3.77 (m, 1 H), 3.62-3.72 (m, 2 H), 3.39-3.51 (m, 2 H), 3.36 (s, 3 H), 3.21-3.31 (m, 1 H), 3.04-3.14 (m, 1 H), 2.95-3.02 (m, 2 H), 2.84-2.93 (m, 1 H), 2.75-2.84 (m, 1 H), 2.11 (s, 6 H), 1.83-1.97 (m, 2 H), 1.63-1.71 (m, 1 H), 1.60 (dd, J=13.4, 6.6 Hz, 1 H), 1.17 (d, J=6.6 Hz, 3 H); MS (ESI+) m/z 457.3 (M+H)$^+$.

21-C. 2-(2,6-Dimethylphenyl)-4-((2R,4R)-4-methoxy-2-methylpiperidin-1-yl)-5,6,7,8-tetrahydropyrido[4,3-d]pyrimidine

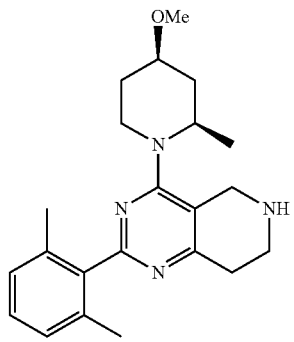 [SMILES: CO[C@@H]1CCN(c2nc(-c3c(C)cccc3C)nc3c2CNCC3)[C@H](C)C1]

To a solution of 6-benzyl-2-(2,6-dimethylphenyl)-((2R,4R)-4-methoxy-2-methylpiperidin-1-yl)-5,6,7,8-tetrahydropyrido[4,3-d]pyrimidine (549 mg, 1.20 mmol) in THF (9 mL) and water (2 mL) was added acetic acid (206 μL, 3.61 mmol) and Pd(OH)$_2$ (253 mg, 0.361 mmol). Hydrogen was bubbled through the solution for 15 min. After 1 h, a saturated solution of sodium bicarbonate was added and the solution was filtered over Celite®, washed with a solution of DCM/MeOH (4:1). The aqueous phase was extracted with DCM. The combined organic layers were washed with brine, dried over anhydrous sodium sulfate, filtered, and concentrated under reduce pressure to obtain the title compound. MS (ESI+) m/z 367.3 (M+H)$^+$.

21-D. 2-(2,6-Dimethylphenyl)-6-(5-isopropyl-2-methylphenyl)-4-((2R,4R)-4-methoxy-2-methylpiperidin-1-yl)-5,6,7,8-tetrahydropyrido[4,3-d]pyrimidine

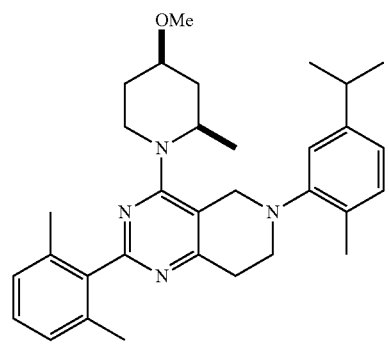 [SMILES: CO[C@@H]1CCN(c2nc(-c3c(C)cccc3C)nc3c2CN(c2cc(C(C)C)ccc2C)CC3)[C@H](C)C1]

To a solution of 2-(2,6-dimethylphenyl)-4-(2R,4R)-4-methoxy-2-methylpiperidin-1-yl)-5,6,7,8-tetrahydropyrido[4,3-d]pyrimidine (45 mg, 0.12 mmol) in dioxane (455 µL) was added 5-isopropyl-2-methylphenyl trifluoromethanesulfonate (52 mg, 0.18 mmol), $Cs_2CO_3$ (80 mg, 0.25 mmol) and Chloro(2-dicyclohexylphosphino-2'-4'-6'-triisopropyl-1,1'-biphenyl) [2-(2-aminoethyl)phenyl]palladium(II)-methyl-t-butylether adduct (14 mg, 0.020 mmol). Reaction was purged with argon and was heated at 90° C. for 16 h. The mixture was diluted with EtOAc and filtered. The residue was purified via FCC (0-30% EtOAc/heptane) to give the title compound. $^1$H NMR (400 MHz, DMSO-$d_6$) δ ppm 7.15-7.22 (m, 1 H), 7.05-7.13 (m, 3 H), 6.91 (s, 1 H), 6.86 (dd, J=7.7, 1.4 Hz, 1 H), 4.05-4.15 (m, 1 H), 3.92-4.01 (m, 1H), 3.71-3.82 (m, 1 H), 3.39-3.49 (m, 1 H), 3.31-3.36 (m, 2 H), 3.25 (s, 3 H), 3.06-3.16 (m, 1 H), 2.91 (t, J=5.7 Hz, 2 H), 2.82 (quin, J=6.8 Hz, 1 H), 2.22 (s, 3 H), 2.03 (s, 6 H), 1.86 (dt, J=13.0, 3.9 Hz, 2H), 1.54-1.67 (m, 2 H), 1.21-1.30 (m, 2 H), 1.14-1.20 (m, 9 H); MS (ESI+) m/z 499.3 (M+H)$^+$.

The following compounds were prepared in a similar manner. For the compounds containing an indazole or indole group the synthesis was carried out with the corresponding N-tosyl protected intermediates described in the other examples herein and the removal of the tosyl protecting group at the last step was done described in other examples herein.

| | Structure | Chemical Name & Analytical Data |
|---|---|---|
| 21-E | 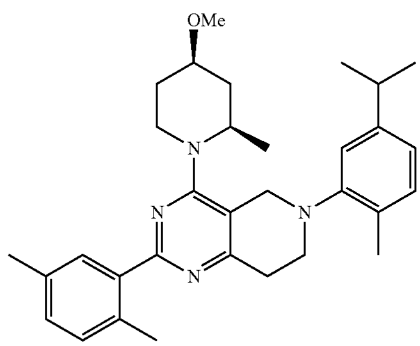 [SMILES: CO[C@@H]1CCN(c2nc(-c3cc(C)ccc3C)nc3c2CN(c2cc(C(C)C)ccc2C)CC3)[C@H](C)C1] | 2-(2,5-dimeethylphenyl)-6-(5-isopropyl-2-methylphenyl)-4-((2R,4R)-4-methoxy-2-methylpiperidin-1-yl)-5,6,7,8-tetrahydropyrido[4,3-d]pyrimidine. $^1$H (400 MHz, DMSO-$d_6$) δ ppm 7.58 (s, 1 H), 7.13-7.16 (m, 2 H), 7.08-7.13 (m, 1 H), 6.97 (d, J = 1.5 Hz, 1 H), 6.87 (dd, J = 7.6, 1.5 Hz, 1 H), 4.01-4.09 (m, 1 H), 3.87-3.96 (m, 1 H), 3.79-3.87 (m, 1 H), 3.43-3.50 (m, 1 H), 3.27 (s, 3 H), 3.13-3.21 (m, 1 H), 2.98 (t, J = 5.8 Hz, 2 H), 2.80-2.94 (m, 1 H), 2.46 (s, 3 H), 2.32 (s, 3 H), 2.20 (s, 3 H), 1.80-1.96 (m, 2 H), 1.52-1.71 (m, 2 H), 1.28 (d, J = 6.8 Hz, 3 H), 1.15-1.25 (m, 9 H); MS (ESI+) m/z 499.4 (M + H)$^+$. |
| 21-F | 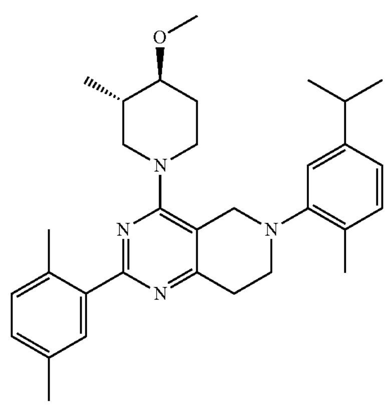 [SMILES: CO[C@H]1CCN(c2nc(-c3cc(C)ccc3C)nc3c2CN(c2cc(C(C)C)ccc2C)CC3)C[C@@H]1C] | 2-(2,5-dimethylphenyl)-6-(5-isopropyl-2-methylphenyl)-4-((3S,4S)-4-methoxy-3-methylpiperidin-1-yl)-5,6,7,8-tetrahydropyrido[4,3-d]pyrimidine. $^1$H (400 MHz, DMSO-$d_6$) δ ppm 0.97 (d, J = 6.6 Hz, 3 H) 1.19 (d, J = 6.8 Hz, 6 H) 1.30-1.43 (m, 1 H) 1.63-1.75 (m, 1 H) 2.05-2.15 (m, 1 H) 2.19 (s, 3 H) 2.32 (s, 3 H) 2.47 (s, 3 H) 2.75 (dd, J = 13.1, 9.9 Hz, 1 H) 2.85 (dt, J = 13.7, 6.9 Hz, 1 H) 2.92-3.09 (m, 4 H) 3.22-3.38 (m, 2 H), 3.27 (s, 3 H), 3.64-3.73 (m, 1 H) 3.78 (m, 1 H) 3.88-4.09 (m, 2 H) 6.86 (dd, J = 7.8, 1.5 Hz, 1 H) 6.99 (d, J = 1.3 Hz, 1 H) 7.06-7.19 (m, 3 H) 7.58 (s, 1 H); MS (ESI+) m/z 499.5 (M + H)$^+$. |
| 21-G | 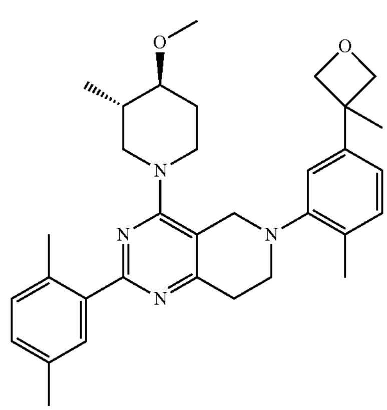 [SMILES: CO[C@H]1CCN(c2nc(-c3cc(C)ccc3C)nc3c2CN(c2cc(C4(C)COC4)ccc2C)CC3)C[C@@H]1C] | 2-(2,5-dimethylphenyl)-4-((3S,4R)-4-methoxy-3-methylpiperidin-1-yl)-6-(2-methyl-5-(3-methyloxetan-3-yl)phenyl)-5,6,7,8-tetrahydropyrido[4,3-d]pyrimidine. $^1$H (400 MHz, DMSO-$d_6$) δ ppm 0.97 (d, J = 6.6 Hz, 3 H) 1.31-1.43 (m, 1 H) 1.61 (s, 3 H) 1.65-1.75 (m, 1 H) 2.07-2.15 (m, 1 H) 2.22 (s, 3 H) 2.32 (s, 3 H) 2.46 (s, 3 H) 2.75 (dd, J = 13.1, 9.9 Hz, 1 H) 2.93-3.08 (m, 4 H) 3.28 (s, 3 H) 3.29-3.40 (m, 2 H) 3.64-3.84 (m, 2 H) 3.90-4.11 (m, 2 H) 4.52 (d, J = 5.6 Hz, 2 H) 4.78 (d, J = 5.6 Hz, 2 H) 6.87 (dd, J = 7.8, 1.8 Hz, 1 H) 6.96 (d, J = 1.8 Hz, 1 H) 7.07-7.23 (m, 3 H) 7.58 (s, 1 H); MS (ESI+) m/z 527.4 (M + H)$^+$. |

| | Structure | Chemical Name & Analytical Data |
|---|---|---|
| 21-H | 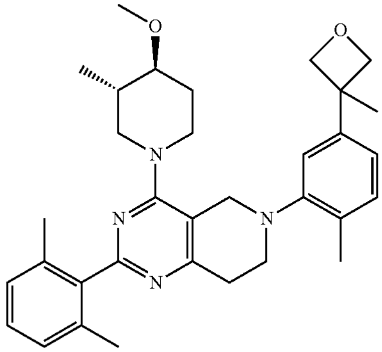 [SMILES: CO[C@H]1CCN(c2nc(-c3c(C)cccc3C)nc3c2CN(c2cc(C4(C)COC4)ccc2C)CC3)C[C@@H]1C] | 2-(2,6-dimethylphenyl)-4-((3S,4S)-4-methoxy-3-methylpiperidin-1-yl)-6-(2-methyl-5-(3-methyloxetan-3-yl)phenyl)-5,6,7,8-tetrahydropyrido[4,3-d]pyrimidine. $^1$H NMR (400 MHz, DMSO-d$_6$) δ ppm 0.95 (d, J = 6.82 Hz, 3 H) 1.31-1.42 (m, 1 H) 1.60 (s, 3 H) 1.62-1.72 (m, 1 H) 2.05 (s, 6 H) 2.06-2.12 (m, 1 H) 2.24 (s, 3 H) 2.74 (dd, J = 13.4, 9.9 Hz, 1 H) 2.87-2.93 (m, 2 H) 2.94-3.03 (m, 2 H) 3.27 (s, 3 H) 3.35 (dq, J = 12.2, 6.4 Hz, 2 H) 3.60-3.67 (m, 1 H) 3.73 (d, J = 13.9 Hz, 1 H) 3.95-4.03 (m, 1 H) 4.06-4.14 (m, 1 H) 4.50 (d, J = 5.6 Hz, 2 H) 4.76 (d, J = 5.6 Hz, 2 H) 6.83-6.92 (m, 2 H) 7.05-7.11 (m, 2 H) 7.13-7.20 (m, 2 H); MS (ESI+) m/z 527.3 (M + H)$^+$. |
| 21-I | 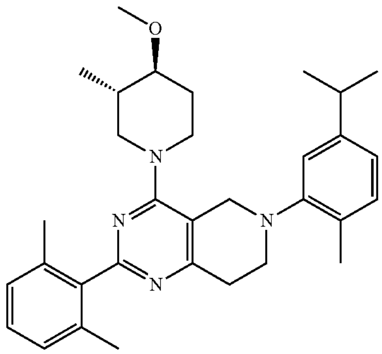 [SMILES: CO[C@H]1CCN(c2nc(-c3c(C)cccc3C)nc3c2CN(c2cc(C(C)C)ccc2C)CC3)C[C@@H]1C] | 2-(2,6-dimethylphenyl)-6-(5-isopropyl-2-methylphenyl)-4-((3S,4S)-4-methoxy-3-methylpiperidin-1-yl)-5,6,7,8-tetrahydropyrido[4,3-d]pyrimidine. $^1$H NMR (400 MHz, DMSO-d$_6$) δ ppm 0.95 (d, J = 6.57 Hz, 3 H) 1.17 (d, J = 6.8 Hz, 6 H) 1.30-1.41 (m, 1 H) 1.61-1.70 (m, 1 H) 2.05 (s, 6 H) 2.08-2.13 (m, 1 H) 2.21 (s, 3 H) 2.75 (dd, J = 13.6, 10.0 Hz, 1 H) 2.82 (dt, J = 13.7, 6.9 Hz, 1 H) 2.90 (t, J = 6.1 Hz, 2 H) 2.94-3.04 (m, 2 H) 3.27 (s, 3 H) 3.31-3.37 (m, 2 H) 3.60-3.69 (m, 1 H) 3.71-3.78 (m, 1 H) 3.95-4.02 (m, 1 H) 4.03-4.11 (m, 1 H) 6.86 (dd, J = 7.8, 1.5 Hz, 1 H) 6.92 (d, J = 1.5 Hz, 1 H) 7.04-7.12 (m, 3 H) 7.14-7.22 (m, 1 H). MS (ESI+) m/z 499.1 (M + H)$^+$. |
| 21-J | 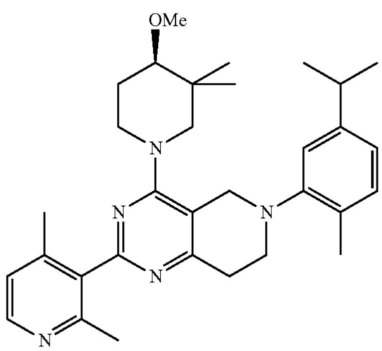 [SMILES: CO[C@@H]1CCN(c2nc(-c3c(C)ccnc3C)nc3c2CN(c2cc(C(C)C)ccc2C)CC3)CC1(C)C] | (R)-2-(2,4-dimethylpyridin-3-yl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H (400 MHz, DMSO-d$_6$) δ ppm 8.32 (d, J = 5.1 Hz, 1 H), 7.14 (d, J = 5.1 Hz, 1 H), 7.10 (d, J = 7.8 Hz, 1 H), 6.92 (s, 1 H), 6.86 (dd, J = 7.8, 1.5 Hz, 1 H), 3.99-4.14 (m, 2 H), 3.65 (dt, J = 10.2, 5.1 Hz, 1 H), 3.32-3.40 (m, 3 H), 3.28 (s, 3 H), 3.00-3.10 (m, 1 H), 2.98 (dd, J = 9.1, 4.0 Hz, 1 H), 2.91 (t, J = 5.8 Hz, 2 H), 2.74-2.88 (m, 2 H), 2.25 (s, 3 H), 2.21 (s, 3 H), 2.09 (s, 3H), 1.88-2.00 (m, 1 H), 1.47-1.62 (m, 1 H), 1.17 (d, J = 7.1 Hz, 6 H), 0.96 (s, 3 H), 0.88 (s, 3 H); MS (ESI+) m/z 514.4 (M + H)$^+$. |
| 21-K | 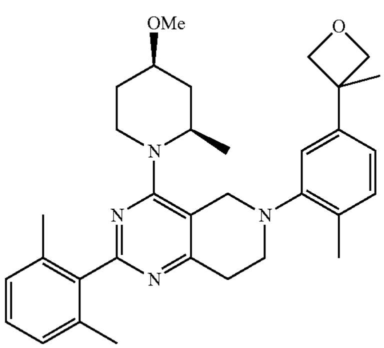 [SMILES: CO[C@@H]1CCN(c2nc(-c3c(C)cccc3C)nc3c2CN(c2cc(C4(C)COC4)ccc2C)CC3)[C@H](C)C1] | 2-(2,6-dimethylphenyl)-4-((2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine. $^1$H (400 MHz, DMSO-d$_6$) δ ppm 7.14-7.22 (m, 2 H), 7.03-7.11 (m, 2 H), 6.82-6.90 (m, 2 H), 4.76 (dd, J = 5.6, 2.8 Hz, 2 H), 4.50 (dd, J = 5.6, 1.8 Hz, 2 H), 4.08-4.17 (m, 1 H), 3.92-4.01 (m, 1 H), 3.72-3.81 (m, 1 H), 3.41-3.49 (m, 1 H), 3.33-3.39 (m, 2 H), 3.25 (s, 3 H), 3.06-3.18 (m, 1 H), 2.91 (t, J = 5.6 Hz, 2 H), 2.25 (s, 3 H), 2.03 (s, 6 H), 1.79-1.91 (m, 2 H), 1.55-1.68 (m, 5 H), 1.24 (d, J = 6.8 Hz, 1 H), 1.19 (d, J = 6.6 Hz, 3 H); MS (ESI+) m/z 527.4 (M + H)$^+$. |

| | Structure | Chemical Name & Analytical Data |
|---|---|---|
| 21-L | 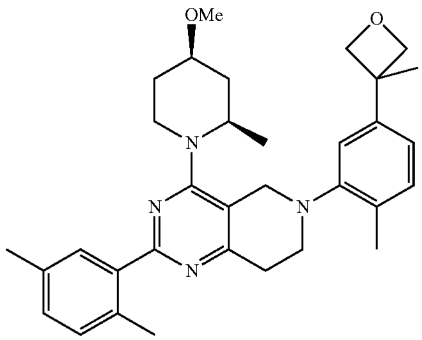 | 2-(2,5-dimethylphenyl)-4-((2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine. $^1$H (400 MHz, DMSO-d$_6$) δ ppm 7.58 (d, J = 0.5 Hz, 1 H), 7.09-7.20 (m, 3 H), 6.95 (d, J = 1.8 Hz, 1 H), 6.87 (dd, J = 7.8, 1.8 Hz, 1 H), 4.78 (dd, J = 5.6, 2.8 Hz, 2 H), 4.52 (dd, J = 5.6, 1.8 Hz, 2 H), 4.08 (d, J = 14.9 Hz, 1 H), 3.91 (d, J = 14.4 Hz, 1 H), 3.79-3.88 (m, 1 H), 3.42-3.50 (m, 1 H), 3.32-3.35 (m, 2 H), 3.27 (s, 3 H), 3.13-3.23 (m, 1 H), 2.98 (t, J = 5.9 Hz, 2 H), 2.47 (s, 3 H), 2.32 (s, 3 H), 2.23 (s, 3 H), 1.83-1.93 (m, 2 H), 1.55-1.70 (m, 6 H), 1.22 (d, J = 6.6 Hz, 3 H); MS (ESI+) m/z 527.4 (M + H)$^+$. |
| 21-M | 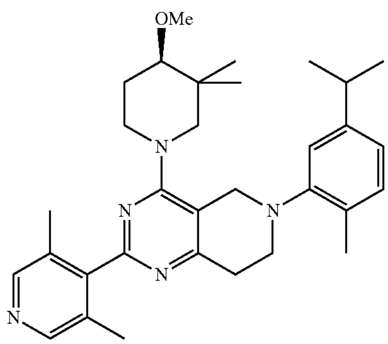 [SMILES: CO[C@@H]1CCN(c2nc(-c3c(C)cncc3C)nc3c2CN(c2cc(C(C)C)ccc2C)CC3)CC1(C)C] | (R)-2-(3,5-dimethylpyridin-4-yl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H (400 MHz, DMSO-d$_6$) δ ppm 8.34 (s, 2 H), 7.10 (d, J = 7.8 Hz, 1 H), 6.92 (d, J = 1.5 Hz, 1 H), 6.86 (dd, J = 7.7, 1.4 Hz, 1 H), 3.95-4.14 (m, 2 H), 3.56-3.76 (m, 1 H), 3.32-3.39 (m, 3 H), 3.28 (s, 3 H), 3.05 (ddd, J = 13.3, 10.1, 3.2 Hz, 1 H), 2.98 (dd, J = 9.0, 3.9 Hz, 1 H), 2.91 (t, J = 5.7 Hz, 2 H), 2.77-2.88 (m, 2 H), 2.21 (s, 3 H), 2.08 (s, 6 H), 1.89-1.97 (m, 1 H), 1.47-1.61 (m, 1 H), 1.17 (d, J = 6.8 Hz, 6 H), 0.96 (s, 3 H), 0.88 (s, 3 H); MS (ESI+) m/z 514.3 (M + H)$^+$. |
| 21-N | 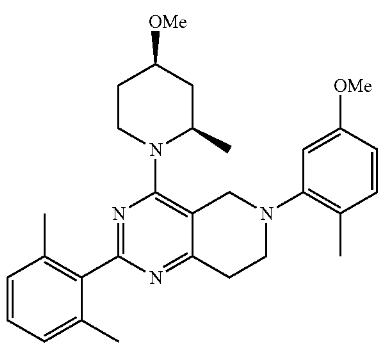 [SMILES: COc1ccc(C)c(N2CCc3nc(-c4c(C)cccc4C)nc(N4CC[C@@H](OC)C[C@H]4C)c3C2)c1] | 2-(2,6-dimethylphenyl)-6-(5-methoxy-2-methylphenyl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 7.15-7.22 (m, 1 H), 7.06-7.14 (m, 3 H), 6.68 (d, J = 2.5 Hz, 1 H), 6.60 (dd, J = 8.2, 2.4 Hz, 1 H), 4.02-4.11 (m, 1 H), 3.88-3.96 (m, 1 H), 3.74-3.79 (m, 1 H), 3.72 (s, 3 H), 3.40-3.48 (m, 1 H), 3.25 (s, 3 H), 3.06-3.16 (m, 1 H), 2.96 (t, J = 5.8 Hz, 2 H), 2.18 (s, 3 H), 2.03 (s, 6 H), 1.80-1.90 (m, 2 H), 1.54-1.67 (m, 2 H), 1.24 (d, J = 7.1 Hz, 1 H), 1.16 (d, J = 6.6 Hz, 3 H); MS (ESI+) m/z 487.3 (M + H)$^+$. |
| 21-O | 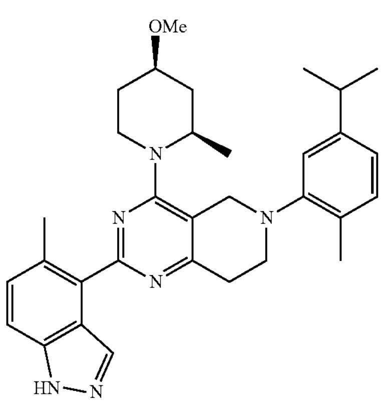 [SMILES: CO[C@@H]1CCN(c2nc(-c3c(C)ccc4[nH]ncc34)nc3c2CN(c2cc(C(C)C)ccc2C)CC3)[C@H](C)C1] | 6-(5-isopropyl-2-methylphenyl)-4-((2R,4R)-4-methoxy-2-methylpiperidin-1-yl)-2-(5-methyl-1H-indazol-4-yl)-5,6,7,8-tetrahydropyrido[4,3-d]pyrimidine. $^1$H NMR (400 MHz, DMSO-d$_6$) δ ppm 12.97 (s, 1 H), 8.08 (s, 1 H), 7.50 (d, J = 8.3 Hz, 1 H), 7.28 (d, J = 8.6 Hz, 1 H), 7.12 (d, J = 7.8 Hz, 1 H), 6.99 (s, 1 H), 6.88 (dd, J = 7.7, 1.6 Hz, 1 H), 4.06-4.16 (m, 1 H), 3.92-4.00 (m, 1 H), 3.82-3.92 (m, 1 H), 3.44-3.53 (m, 1 H), 3.32-3.39 (m, 2 H), 3.27 (s, 3 H), 3.00-3.06 (m, 2 H), 2.85 (quin, J = 6.9 Hz, 1 H), 2.55 (s, 3 H), 2.23 (s, 3 H), 1.83-1.94 (m, 2 H), 1.59-1.72 (m, 2 H), 1.23 (d, J = 6.6 Hz, 4 H), 1.19 (d, J = 7.1 Hz, 7 H); MS (ESI+) m/z 525.1 (M + H)$^+$. |

| | Structure | Chemical Name & Analytical Data |
|---|---|---|
| 21-P | 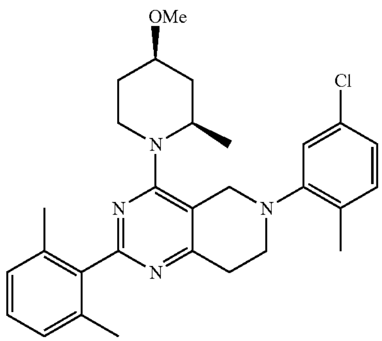 [SMILES: CO[C@@H]1CCN(c2nc(-c3c(C)cccc3C)nc3c2CN(c2cc(Cl)ccc2C)CC3)[C@H](C)C1] | 6-(5-chloro-2-methylphenyl)-2-(2,6-dimethylphenyl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 7.24 (d, J = 8.3 Hz, 1 H), 7.15-7.21 (m, 1 H), 7.13 (d, J = 2.0 Hz, 1 H), 7.02-7.11 (m, 3 H), 4.05-4.13 (m, 1 H), 3.93-4.01 (m, 1 H), 3.71-3.79 (m, 1 H), 3.39-3.47 (m, 1 H), 3.25 (s, 3 H), 3.05-3.15 (m, 1 H), 2.96 (t, J = 5.8 Hz, 2 H), 2.24 (s, 3 H), 2.03 (s, 6 H), 1.78-1.93 (m, 2 H), 1.51-1.67 (m, 2 H), 1.16 (d, J = 6.6 Hz, 3 H); MS (ESI+) m/z 491.0 (M + H)$^+$. |
| 21-Q | 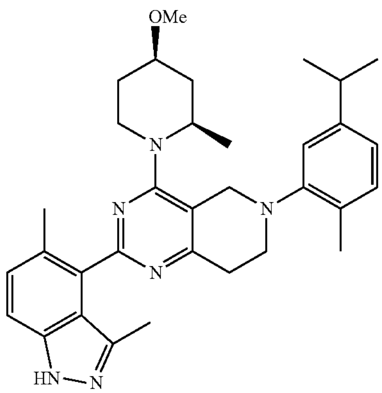 [SMILES: CO[C@@H]1CCN(c2nc(-c3c(C)ccc4[nH]nc(C)c34)nc3c2CN(c2cc(C(C)C)ccc2C)CC3)[C@H](C)C1] | (+)-2-(3,5-dimethyl-1H-indazol-4-yl)-6-(5-isopropyl-2-methylphenyl)-4-((2R,4R)-4-methoxy-2-methylpiperidijn-1-yl)-5,6,7,8-tetrahydropyrido[4,3-d]pyrimidine. $^1$H NMR (400 MHz, DMSO-d$_6$) δ ppm 12.58 (s, 1 H), 7.40 (d, J = 8.6 Hz, 1 H), 7.22 (d, J = 8.6 Hz, 1 H), 7.11 (d, J = 7.8 Hz, 1 H), 6.92 (s, 1 H), 6.87 (d, J = 7.8 Hz, 1 H), 4.07-4.19 (m, 1 H), 3.97-4.06 (m, 1 H), 3.70-3.86 (m, 1 H), 3.41-3.52 (m, 1 H), 3.34-3.40 (m, 2 H), 3.25 (s, 3 H), 3.10-3.21 (m, 1 H), 2.94 (t, J = 5.7 Hz, 2 H), 2.82 (quin, J = 6.9 Hz, 1 H), 2.23 (s, 3 H), 2.17 (s, 3 H), 1.76-1.91 (m, 5 H), 1.53-1.70 (m, 2 H), 1.09-1.27 (m, 10 H); MS (ESI+) m/z 539.4 (M + H)$^+$; [α]$^{25}_D$ +0.85 (c 1.0, MeOH). |
| 21-R | 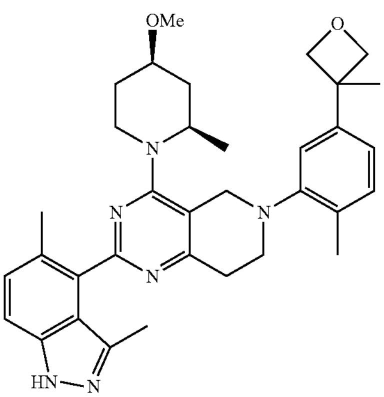 [SMILES: CO[C@@H]1CCN(c2nc(-c3c(C)ccc4[nH]nc(C)c34)nc3c2CN(c2cc(C4(C)COC4)ccc2C)CC3)[C@H](C)C1] | 2-(3,5-dimethyl-1H-indazol-4-yl)-4-((2R,4R)-4-methoxy-2-methylpiperidin-1-yl)-6-(2-methyl-5-(3-methyloxetan-3-yl)phenyl)-5,6,7,8-tetrahydropyrido[4,3-d]pyrimidine. $^1$H NMR (400 MHz, DMSO-d$_6$) δ ppm 12.58 (s, 1 H), 7.39 (d, J = 8.6 Hz, 1 H), 7.20 (dd, J = 10.7, 8.2 Hz, 2 H), 6.81-6.94 (m, 2 H), 4.78 (dd, J = 5.6, 2.5 Hz, 2 H), 4.51 (d, J = 5.6 Hz, 2 H), 4.08-4.21 (m, 1 H), 3.96-4.08 (m, 1 H), 3.71-3.85 (m, 1 H), 3.42-3.51 (m, 1 H), 3.39 (t, J = 6.1 Hz, 2 H), 3.24 (s, 3 H), 3.12-3.22 (m, 1 H), 2.95 (t, J = 5.4 Hz, 2 H), 2.43-2.47 (m, 1 H), 2.25 (s, 3 H), 2.17 (s, 3 H), 1.78-1.90 (m, 5 H), 1.54-1.67 (m, 5 H), 1.20 (d, J = 6.6 Hz, 3 H); MS (ESI+) m/z 567.3 (M + H)$^+$. |
| 21-S | 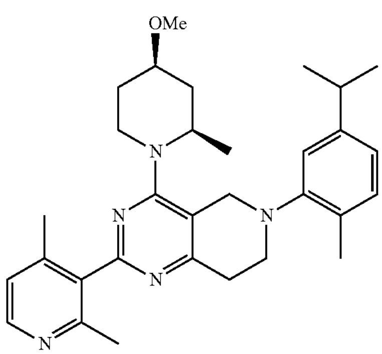 [SMILES: CO[C@@H]1CCN(c2nc(-c3c(C)ccnc3C)nc3c2CN(c2cc(C(C)C)ccc2C)CC3)[C@H](C)C1] | 2-(2,4-dimethylpyridin-3-yl)-6-(5-isopropyl-2-methylphenyl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 8.33 (d, J = 4.8 Hz, 1 H), 7.15 (d, J = 5.3 Hz, 1 H), 7.10 (d, J = 7.8 Hz, 1 H), 6.92 (s, 1 H), 6.86 (d, J = 7.8 Hz, 1 H), 4.05-4.17 (m, 1 H), 3.95 (d, J = 14.9 Hz, 1 H), 3.76-3.87 (m, 1 H), 3.42-3.51 (m, J = 3.5 Hz, 1 H), 3.32-3.37 (m, 2 H), 3.13-3.23 (m, 1 H), 2.93 (t, J = 5.7 Hz, 2 H), 2.83 (dt, J = 13.7, 6.9 Hz, 1 H), 2.18-2.29 (m, 7 H), 2.08 (s, 3 H), 1.77-1.90 (m, 2 H), 1.55-1.71 (m, 3 H), 1.19-1.24 (m, 4 H), 1.17 (d, J = 6.8 Hz, 7 H); MS (ESI+) m/z 500.3 (M + H)$^+$. |

| | Structure | Chemical Name & Analytical Data |
|---|---|---|
| 21-T | 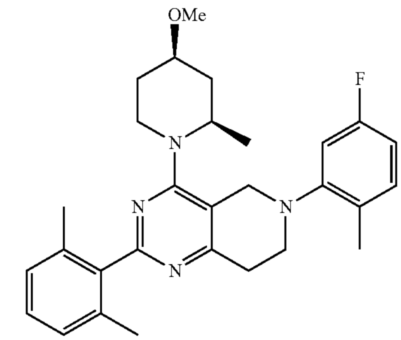 [SMILES: CO[C@@H]1CCN(c2nc(-c3c(C)cccc3C)nc3c2CN(c2cc(F)ccc2C)CC3)[C@H](C)C1] | 2-(2,6-dimethylphenyl)-6-(5-fluoro-2-methylphenyl)-4-((2R,4R)-4-mthoxy-2-methylpiperidin-1-yl)-5,6,7,8-tetrahydropyrido[4,3-d]pyrimidine. $^1$H NMR (400 MHz, DMSO-d$_6$) δ ppm 7.20-7.27 (m, 1 H), 7.18 (d, J = 8.1 Hz, 1 H), 7.05-7.12 (m, 2 H), 6.98 (dd, J = 11.4, 2.5 Hz, 1 H), 6.83 (td, J = 8.3, 2.5 Hz, 1 H), 4.03-4.12 (m, 1 H), 3.90-4.00 (m, 1 H), 3.71-3.81 (m, 1 H), 3.39-3.48 (m, 1 H), 3.25 (s, 3 H), 3.05-3.16 (m, 1 H), 2.98 (t, J = 5.7 Hz, 2 H), 2.42-2.46 (m, 1 H), 2.23 (s, 3 H), 2.03 (s, 6 H), 1.78-1.93 (m, 2 H), 1.50-1.72 (m, 3 H), 1.20-1.31 (m, 1 H), 1.16 (d, J = 6.6 Hz, 3 H); MS (ESI+) m/z 475.3 (M + H)$^+$. |
| 21-U | 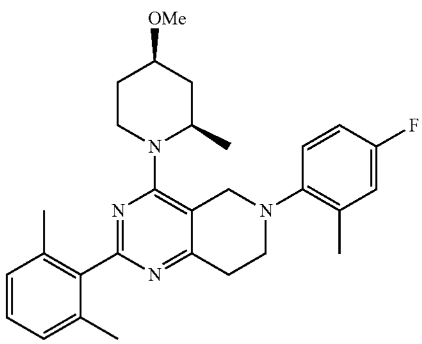 [SMILES: CO[C@@H]1CCN(c2nc(-c3c(C)cccc3C)nc3c2CN(c2ccc(F)cc2C)CC3)[C@H](C)C1] | 2-(2,6-dimethylphenyl)-6-(4-fluoro-2-methylphenyl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 7.20-7.25 (m, 1 H), 7.16-7.19 (m, 1 H), 7.06-7.11 (m, 2 H), 7.03 (td, J = 8.6, 3.0 Hz, 1 H), 3.97-4.06 (m, 1 H), 3.87-3.94 (m, 1 H), 3.74 (dt, J = 6.8, 5.5 Hz, 1 H), 3.38-3.46 (m, 1 H), 3.24 (s, 4 H), 3.04-3.13 (m, 1 H), 2.98 (t, J = 5.9 Hz, 1 H), 2.42-2.46 (m, 1 H), 2.27 (s, 2 H), 2.03 (s, 3 H), 1.78-1.91 (m, 1 H), 1.52-1.66 (m, 1 H), 1.22-1.26 (m, 0 H), 1.14 (d, J = 6.3 Hz, 2 H); MS (ESI+) m/z 475.3 (M + H)$^+$. |
| 21-V | 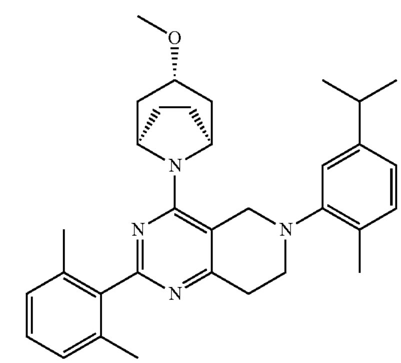 [SMILES: CO[C@H]1C[C@H]2CC[C@@H](C1)N2c1nc(-c2c(C)cccc2C)nc2c1CN(c1cc(C(C)C)ccc1C)CC2] | 2-(2,6-dimethylphenyl)-6-(5-isopropyl-2-methylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, MeOD) δ ppm 7.15-7.21 (m, 1 H) 7.05-7.14 (m, 3 H) 6.99 (d, J = 1.8 Hz, 1 H) 6.89 (dd, J = 7.7, 1.6 Hz, 1 H) 4.52 (br. s., 2 H) 4.03 (s, 2 H) 3.48 (t, J = 4.4 Hz, 1 H) 3.35 (t, J = 5.9 Hz, 2 H) 3.28 (s, 3 H) 2.93 (t, J = 5.9 Hz, 2 H) 2.85 (ddd, J = 13.8, 7.1, 7.0 Hz, 1 H) 2.27 (s, 3 H) 2.10 (s, 6 H) 2.02-2.19 (m, 4 H) 1.87-2.01 (m, 4 H) 1.23 (d, J = 7.1 Hz, 6 H); MS (ESI+) m/z 511.4 (M + H)$^+$. |
| 21-W | 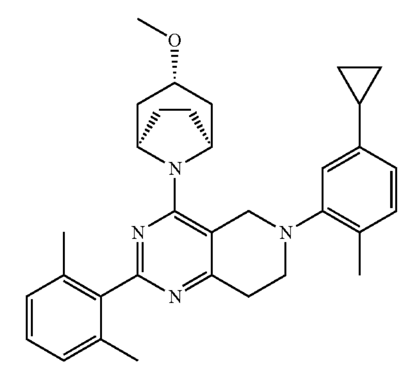 [SMILES: CO[C@H]1C[C@H]2CC[C@@H](C1)N2c1nc(-c2c(C)cccc2C)nc2c1CN(c1cc(C3CC3)ccc1C)CC2] | 6-(5-cyclopropyl-2-methylphenyl)-2-(2,6-dimethylphenyl)-4-((3-endo)-3-methoxy-8-azabicyclo[3.2.1]octan-8-yl)-5,6,7,8-tetrahydropyrido[4,3-d]pyrimidine. $^1$H NMR (400 MHz, MeOD) δ ppm 7.15-7.21 (m, 1 H) 7.04-7.11 (m, 3 H) 6.86 (d, J = 1.8 Hz, 1 H) 6.72 (dd, J = 7.6, 1.8 Hz, 1 H) 4.52 (br. s., 2 H) 4.01 (s, 2 H) 3.49 (t, J = 4.3 Hz, 1 H) 3.31-3.36 (m, 2 H) 3.28 (s, 3 H) 2.93 (t, J = 5.8 Hz, 2 H) 2.26 (s, 3 H) 2.10 (s, 6 H) 2.02-2.19 (m, 4 H) 1.82-2.00 (m, 5 H) 0.91 (dt, J = 10.6, 4.2 Hz, 2 H) 0.61 (dd, J = 5.1, 2.1 Hz, 2 H); MS (ESI+) m/z 509.1 (M + H)$^+$. |

| | Structure | Chemical Name & Analytical Data |
|---|---|---|
| 21-X | 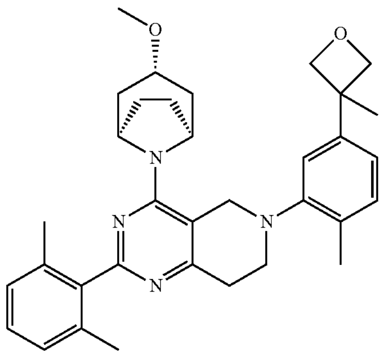 [SMILES: CO[C@H]1C[C@H]2CC[C@@H](C1)N2c1nc(-c2c(C)cccc2C)nc2c1CN(c1cc(C3(C)COC3)ccc1C)CC2] | 2-(2,6-dimethylphenyl)-4-((3-endo)-3-methoxy-8-azabicyclo[3.2.1]octan-8-yl)-6-(2-methyl-5-(3-methyloxetan-3-yl)phenyl)-5,6,7,8-tetrahydropyrido[4,3-d]pyrimidine. $^1$H NMR (400 MHz, CDCl$_3$) δ ppm 7.26 (d, J = 7.8 Hz, 1 H) 7.16-7.22 (m, 2 H) 7.1-7.14 (m, 2 H) 6.98 (d, J = 1.8 Hz, 1 H) 6.92-6.96 (m, 1 H) 5.00 (d, J = .6 Hz, 2 H) 4.68 (d, J = 5.6 Hz, 2 H) 4.49 (br. s., 2 H) 4.05 (s, 2 H) 3.48-3.55 (m, 1 H) 3.40 (t, J = 5.8 Hz, 2 H) 3.31 (s, 3 H) 3.05-3.14 (m, 2 H) 2.38 (s, 3 H) 2.20 (s, 6 H) 2.03-2.17 (m, 4 H) 1.89-2.02 (m, 4 H) 1.77 (s, 3 H); MS (ESI+) m/z 540.0 (M + H)$^+$. |
| 21-Y | 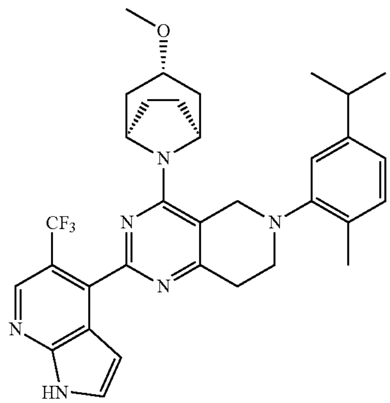 [SMILES: CO[C@H]1C[C@H]2CC[C@@H](C1)N2c1nc(-c2c(C(F)(F)F)cnc3[nH]ccc23)nc2c1CN(c1cc(C(C)C)ccc1C)CC2] | 6-(5-isopropyl-2-methylphenyl)-4-((3-endo)-3-methoxy-8-azabicyclo[3.2.1]octan-8-yl)-2-(5-(trifluoromethyl)-1H-pyrrolo[2,3-b]pyridin-4-yl)-5,6,7,8-tetrahydropyrido[4,3-d]pyrimidine. $^1$H NMR (400 MHz, CD$_2$Cl$_2$) δ ppm 8.67 (s, 1 H) 7.44 (d, J = 3.8 Hz, 1 H) 7.14 (d, J = 8.3 Hz, 1 H) 7.00 (d, J = 1.8 Hz, 1 H) 6.92 (dd, J = 7.8, 1.8 Hz, 1 H) 6.57 (d, J = 3.5 Hz, 1 H) 4.49 (br. s., 2 H) 4.04 (s, 2 H) 3.46 (t, J = 4.8 Hz, 1 H) 3.35 (t, J = 6.0 Hz, 2 H) 3.25 (s, 3 H) 3.06 (t, J = 6.0 Hz, 2 H) 2.90 (ddd, J = 13.8, 7.1, 7.0 Hz, 1 H) 2.30 (s, 3 H) 2.00-2.16 (m, 4 H) 1.83-1.96 (m, 4 H) 1.26 (d, J = 6.8 Hz, 6 H); MS (ESI+) m/z 591.0 (M + H)$^+$. |
| 21-Z | 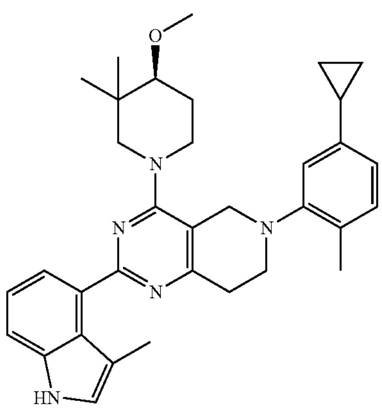 [SMILES: CO[C@H]1CCN(c2nc(-c3cccc4[nH]cc(C)c34)nc3c2CN(c2cc(C4CC4)ccc2C)CC3)CC1(C)C] | (S)-6-(5-cyclopropyl-2-methylphenyl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.22 (br. s., 1 H), 7.44 (d, J = 8.1 Hz, 1 H), 7.34 (d, J = 7.1 Hz, 1 H), 7.19-7.23 (m, 1 H), 7.01-7.13 (m, 2 H), 6.84 (s, 1 H), 6.72 (d, J = 7.8 Hz, 1 H), 4.01 (s, 2 H), 3.71 (br. s., 1 H), 3.38-3.43 (m, 1 H), 3.34 (br. s., 5 H), 3.13 (br. s., 3 H), 2.95 (dd, J = 8.7, 3.9 Hz, 2 H), 2.26 (s, 3 H), 2.09 (s, 3 H), 1.92-2.01 (m, 1 H), 1.81-1.92 (m, 1 H), 1.63-1.74 (m, 1 H), 1.00 (s, 3 H), 0.96 (br. s., 3 H), 0.91-0.95 (m, 2 H), 0.62-0.69 (m, 2 H); MS (ESI+) m/z 536.0 (M + H)$^+$. |
| 21-AA | 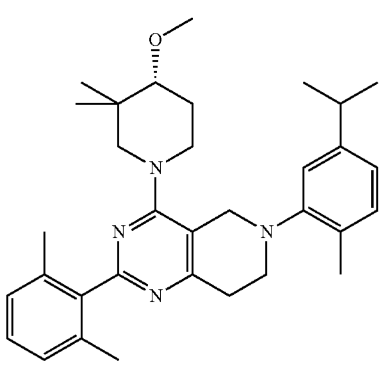 [SMILES: CO[C@@H]1CCN(c2nc(-c3c(C)cccc3C)nc3c2CN(c2cc(C(C)C)ccc2C)CC3)CC1(C)C] | (R)-2-(2,6-dimethylphenyl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 7.15-7.20 (m, 1 H) 7.06-7.12 (m, 3 H) 6.91 (d, J = 1.52 Hz, 1 H) 6.85 (dd, J = 7.83, 1.52 Hz, 1 H) 4.06 (d, J = 6.06 Hz, 2 H) 3.62 (br. s., 1 H) 3.31-3.36 (m, 3 H) 2.95-3.07 (m, 2 H) 2.86-2.92 (m, 2 H) 2.78-2.86 (m, 2 H) 2.21 (s, 3 H) 2.04 (s, 6 H) 1.89-1.98 (m, 1 H) 1.49-1.62 (m, 1 H) 1.17 (d, J = 7.07 Hz, 6 H) 0.96 (s, 3 H) 0.88 (s, 3 H); MS (ESI+) m/z 513.4 (M + H)$^+$. |

| Structure | Chemical Name & Analytical Data |
|---|---|
| 21-AB 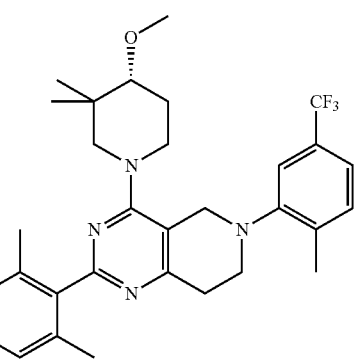 | (R)-2-(2,6-dimethylphenyl)-4-(4-methoxy-3,3-dimethylpiperidin-1-yl)-6-(2-methyl-5-(trifluoromethyl)phenyl)-5,6,7,8-tetrahydropyrido[4,3-d]pyrimidine. $^1$H NMR (400 MHz, DMSO-$d_6$) δ ppm 7.43 (d, J = 7.83 Hz, 1 H) 7.29-7.35 (m, 2 H) 7.15-7.20 (m, 1 H) 7.05-7.10 (m, 2 H) 4.13 (q, J = 14.65 Hz, 2 H) 3.64 (d, J = 12.63 Hz, 1 H) 3.40 (t, J = 6.44 Hz, 2 H) 3.33 (dd, J = 13.14, 1.26 Hz, 1 H) 3.28 (s, 3 H) 2.99-3.08 (m, 1 H) 2.97 (dd, J = 8.97, 3.92 Hz, 1 H) 2.88-2.95 (m, 2 H) 2.84 (d, J = 12.88 Hz, 1 H) 2.34 (s, 3 H) 2.04 (s, 6 H) 1.89-1.96 (m, 1 H) 1.49-1.60 (m, 1 H) 0.95 (s, 3 H) 0.86 (s, 3 H); MS (ESI+) m/z 539.3 (M + H)$^+$. |
| 21-AC 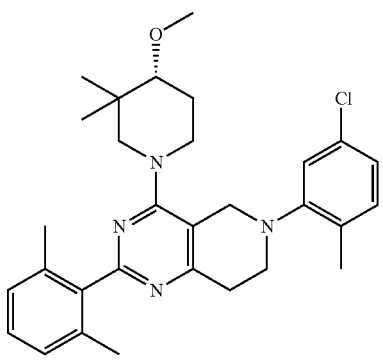 [SMILES: CO[C@@H]1CCN(c2nc(-c3c(C)cccc3C)nc3c2CN(c2cc(Cl)ccc2C)CC3)CC1(C)C] | (R)-6-(5-chloro-2-methylphenyl)-2-(2,6-dimethylphenyl)-4-(4-methoxy-3,3-dimethylpiperidin-1-yl)-5,6,7,8-tetrahydropyrido[4,3-d]pyrimidine. $^1$H NMR (400 MHz, DMSO-$d_6$) δ ppm 7.23 (d, J = 8.59 Hz, 1 H) 7.13-7.20 (m, 2 H) 7.04-7.10 (m, 3 H) 4.03-4.11 (m, 1 H) 3.95-4.03 (m, 1 H) 3.67 (d, J = 14.15 Hz, 1 H) 3.34 (d, J = 9.60 Hz, 2 H) 2.90-3.09 (m, 4 H) 2.85 (d, J = 13.14 Hz, 1 H) 2.53-2.58 (m, 1 H) 2.23 (s, 3 H) 2.04 (s, 6 H) 1.88-1.96 (m, 1 H) 1.49-1.61 (m, 1 H) 0.94 (s, 3 H) 0.84 (s, 3 H); MS (ESI+) m/z 505.3 (M + H)$^+$. |
| 21-AD 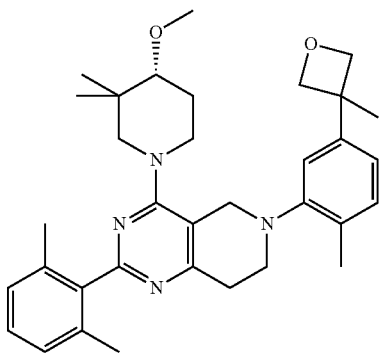 [SMILES: CO[C@@H]1CCN(c2nc(-c3c(C)cccc3C)nc3c2CN(c2cc(C4(C)COC4)ccc2C)CC3)CC1(C)C] | (R)-2-(2,6-dimethylphenyl)-4-(4-methoxy-3,3-dimethylpiperidin-1-yl)-6-(2-methyl-5-(3-methyloxetan-3-yl)phenyl)-5,6,7,8-tetrahydropyrido[4,3-d]pyrimidine. $^1$H NMR (400 MHz, CD$_2$Cl$_2$) δ ppm 7.14-7.23 (m, 2 H) 7.08 (d, J = 7.58 Hz, 2 H) 6.84-6.92 (m, 2 H) 4.90 (d, J = 5.56 Hz, 2 H) 4.58 (d, J = 5.56 Hz, 2 H) 4.04 (s, 2 H) 3.67 (d, J = 15.92 Hz, 1 H) 3.29-3.40 (m, 6 H) 3.05 (br. s., 3 H) 2.94 (dd, J = 8.84, 3.79 Hz, 1 H) 2.84 (d, J = 14.40 Hz, 1 H) 2.31 (s, 3 H) 2.12 (s, 6 H) 1.90-2.01 (m, 1 H) 1.61-1.73 (m, 4 H) 0.97 (d, J = 16.93 Hz, 6 H); MS (ESI+) m/z 541.3 (M + H)$^+$. |
| 21-AE 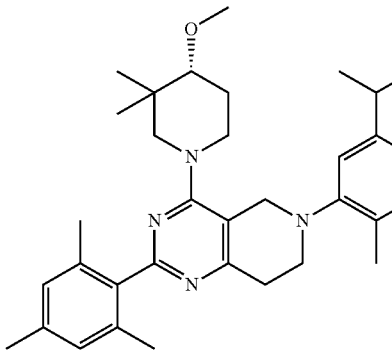 | (R)-6-(5-isopropyl-2-methylphenyl)-2-mesityl-4-(4-methoxy-3,3-dimethylpiperidin-1-yl)-5,6,7,8-tetrahydropyrido[4,3-d]pyrimidine. $^1$H NMR (400 MHz, DMSO-$d_6$) δ ppm 7.09 (d, J = 7.83 Hz, 1 H) 6.91 (s, 1 H) 6.89 (s, 2 H) 6.85 (dd, J = 7.71, 1.39 Hz, 1 H) 3.99-4.11 (m, 2 H) 3.58-3.68 (m, 1 H) 3.33 (d, J = 6.06 Hz, 3 H) 3.28 (s, 3 H) 2.95-3.06 (m, 2 H) 2.86-2.91 (m, 2 H) 2.77-2.85 (m, 2 H) 2.27 (s, 3 H) 2.21 (s, 3 H) 2.02 (s, 6 H) 1.93 (dd, J = 13.14, 3.79 Hz, 1 H) 1.49-1.61 (m, 1 H) 1.16 (d, J = 6.82 Hz, 6 H) 0.96 (s, 3 H) 0.88 (s, 3 H). MS (ESI+) m/z 527.4 (M + H)$^+$. |

-continued

| | Structure | Chemical Name & Analytical Data |
|---|---|---|
| 21-AF | 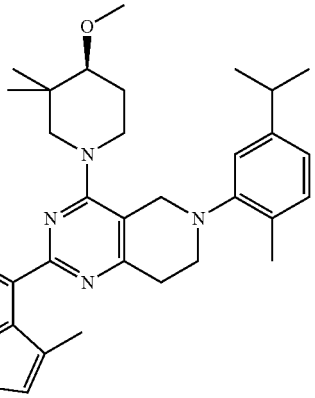 | (S)-2-(7-fluoro-3-methyl-1H-indol-4-yl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 8.25 (br. s., 1 H) 7.22 (dd, J = 8.1, 4.8 Hz, 1 H) 7.03 (d, J = 7.8 Hz, 1 H) 6.98 (d, J = 1.0 Hz, 1 H) 6.88 (d, J = 1.5 Hz, 1 H) 6.76-6.86 (m, 2 H) 3.95 (s, 2 H) 3.50-3.67 (m, 1 H) 3.19-3.36 (m, 6 H) 2.94-3.06 (m, 3 H) 2.69-2.91 (m, 3 H) 2.18 (s, 3 H) 2.03 (s, 3 H) 1.82-1.95 (m, 1 H) 1.51-1.68 (m, 1 H) 1.16 (d, J = 6.8 Hz, 6 H) 0.92 (s, 3 H) 0.89 (s, 3 H); MS (ESI+) m/z 556.4 (M + H)$^+$. |
| 21-AG | 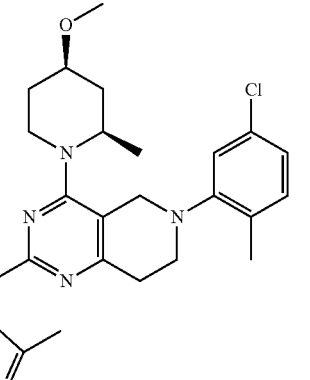 | 6-(5-chloro-2-methylphenyl)-2-(3,5-dimethyl-1H-indazol-4-yl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 12.58 (s, 1 H), 7.39 (d, J = 8.3 Hz, 1 H), 7.23 (t, J = 8.1 Hz, 2 H) 7.10 (d, J = 2.0 Hz, 1 H), 7.06 (dd, J = 8.1, 1.8 Hz, 1 H), 4.07-4.17 (m, 1 H), 3.99-4.07 (m, 1 H), 3.74-3.84 (m, 1 H), 3.42-3.49 (m, ,1 H), 3.34-3.39 (m, 2 H), 3.25 (s, 3 H), 3.11-3.21 (m, 1 H), 2.96 (t, J = 5.9 Hz, 2 H), 2.25 (s, 3 H), 2.17 (s, 3 H), 1.86-1.90 (m, 1 H), 1.84 (s, 3 H), 1.56-1.69 (m, 2 H), 1.24 (br. s., 1 H), 1.18 (d, J = 6.6 Hz, 3 H); MS (ESI+) m/z 531.2 (M + H)$^+$. |
| 21-AH | 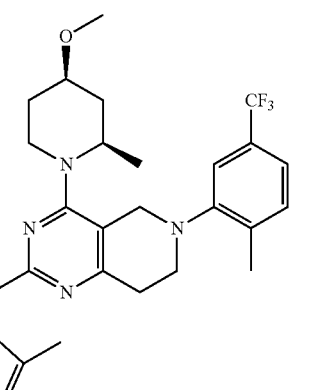 | 2-(3,5-dimethyl-1H-indazol-4-yl)-4-((2R,4R)-4-methoxy-2-methylpiperidin-1-yl)-6-(2-methyl-5-(trifluoromethyl)phenyl)-5,6,7,8-tetrahydropyrido[4,3-d]pyrimidine. $^1$H NMR (400 MHz, DMSO-d$_6$) δ ppm 12.58 (s, 1 H), 7.45 (d, J = 7.8 Hz, 1 H), 7.39 (d, J = 8.6 Hz, 1 H), 7.34 (d, J = 8.3 Hz, 1 H), 7.28 (s, 1 H), 7.22 (d, J = 8.6 Hz, 1 H), 4.16-4.24 (m, 1 H), 4.06-4.15 (m, 1 H), 3.75-3.82 (m, 1 H), 3.44 (t, J = 5.7 Hz, 2 H), 3.25 (s, 3 H), 3.11-3.20 (m, 1 H), 2.95 (t, J = 6.3 Hz, 2 H), 2.44-2.47 (m, 1 H), 2.36 (s, 3 H), 2.17 (s, 3 H), 1.86-1.90 (m, 2 H), 1.83 (s, 3 H), 1.56-1.66 (m, 2 H), 1.24 (d, J = 3.0 Hz, 1 H), 1.19 (d, J = 6.6 Hz, 3 H); MS (ESI+) 565.3 m/z (M + H)$^+$. |

-continued

| | Structure | Chemical Name & Analytical Data |
|---|---|---|
| 21-AI | 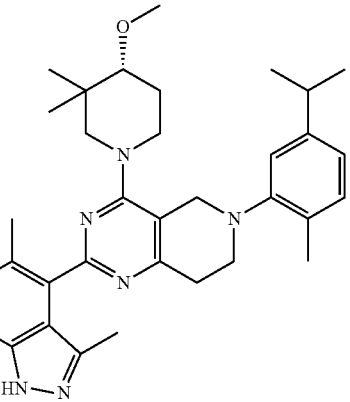 | (R)-2-(3,5-dimethyl-1H-indazol-4-yl)-6-(5-isopropyl-2-methylphenyl)-4-(4-methoxy-3,3-dimethylpiperidin-1-yl)-5,6,7,8-tetrahydropyrido[4,3-d]pyrimidine. $^1$H NMR (400 MHz, DMSO-d6) δ ppm 12.57 (s, 1 H) 7.39 (d, J = 8.34 Hz, 1 H) 7.21 (d, J = 8.84 Hz, 1 H) 7.11 (d, J = 7.83 Hz, 1 H) 6.93 (s, 1 H) 6.84-6.89 (m, 1 H) 4.02-4.17 (m, 2 H) 3.65 (d, J = 13.14 Hz, 1 H) 3.33-3.41 (m, 3 H) 3.27 (s, 3 H) 3.00-3.13 (m, 1 H) 2.98 (dd, J = 8.97, 3.92 Hz, 1 H) 2.89-2.95 (m, 2 H) 2.77-2.87 (m, 2 H) 2.22 (s, 3 H) 2.19 (s, 3 H) 1.89-1.97 (m, 1 H) 1.87 (s, 3 H) 1.49-1.61 (m, 1 H) 1.18 (d, J = 6.82 Hz, 6 H) 0.96 (s, 3 H) 0.89 (s, 3 H); MS (ESI+) m/z 553.3 (M + H)$^+$. |
| 21-AJ | 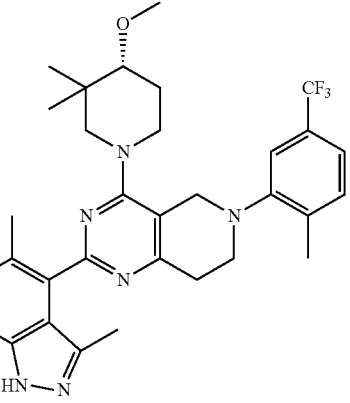 | (R)-2-(3,5-dimethyl-1H-indazol-4-yl)-4-(4-methoxy-3,3-dimethylpiperidin-1-yl)-6-(2-methyl-5-(trifluoromethyl)phenyl)-5,6,7,8-tetrahydropyrido[4,3-d]pyrimidine. $^1$H NMR (400 MHz, DMSO-d6) δ ppm 12.57 (s, 1 H) 7.44 (d, J = 8.08 Hz, 1 H) 7.39 (d, J = 8.34 Hz, 1 H) 7.27-7.36 (m, 2 H) 7.21 (d, J = 8.59 Hz, 1 H) 4.10-4.25 (m, 2 H) 3.62-3.70 (m, 1 H) 3.44 (t, J = 6.19 Hz, 2 H) 3.36 (d, J = 13.64 Hz, 1 H) 3.27 (s, 3 H) 3.01-3.10 (m, 1 H) 2.98 (dd, J = 9.09, 3.79 Hz, 1 H) 2.93 (t, J = 6.32 Hz, 2 H) 2.85 (d, J = 13.14 Hz, 1 H) 2.35 (s, 3 H) 2.18 (s, 3 H) 1.93 (dd, J = 13.64, 4.04 Hz, 1 H) 1.85 (s, 3 H) 1.49-1.61 (m, 1 H) 0.95 (s, 3 H) 0.87 (s, 3 H); MS (ESI+) m/z 579.3 (M + H)$^+$. |
| 21-AK | 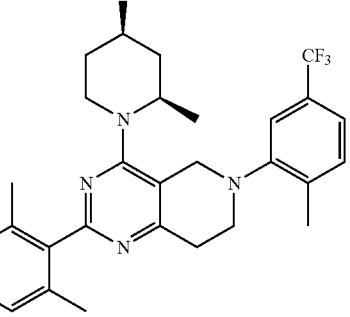 | 2-(2,6-dimethylphenyl)-4-((2R,4R)-4-methoxy-2-methylpiperidin-1-yl)-6-(2-methyl-5-(trifluoromethyl)phenyl)-5,6,7,8-tetrahydropyrido[4,3-d]pyrimidine. $^1$H NMR (400 MHz, DMSO-d$_6$) δ ppm 7.44 (d, J = 7.8 Hz, 1 H), 7.34 (d, J = 8.6 Hz, 1 H), 7.29 (s, 1 H), 7.15-7.22 (m, 1 H), 7.05-7.12 (m, 2 H), 4.11-4.21 (m, 1 H), 4.00-4.09 (m, 1 H), 3.71-3.81 (m, 1 H), 3.42-3.48 (m, 1 H), 3.40 (t, J = 6.1 Hz, 2 H), 3.25 (s, 3 H), 3.11 (ddd, J = 13.8, 6.6, 4.3 Hz, 1 H), 2.94 (t, J = 5.9 Hz, 2 H), 2.35 (s, 3 H), 2.03 (s, 6 H), 1.80-1.91 (m, 2 H), 1.54-1.67 (m, 2 H), 1.18 (d, J = 6.6 Hz, 3 H); MS (ESI+) m/z 525.2 (M + H)$^+$. |
| 21-AL | 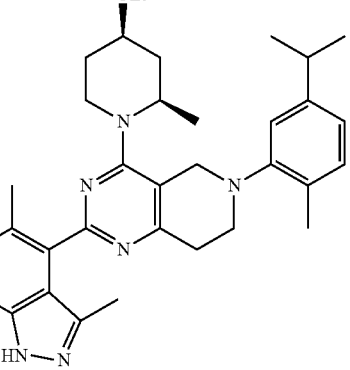 | 2-(3,5-dimethyl-1H-indazol-4-yl)-4-((2R,4R)-4-ethoxy-2-methylpiperidin-1-yl)-6-(5-isopropyl-2-methylphenyl)-5,6,7,8-tetrahydropyrido[4,3-d]pyrimidine. $^1$H NMR (400 MHz, DMSO-d$_6$) δ ppm 12.58 (s, 1 H), 7.39 (d, J = 8.3 Hz, 1 H), 7.22 (d, J = 8.6 Hz, 1 H), 7.11 (d, J = 7.6 Hz, 1 H), 6.92 (s, 1 H), 6.87 (dd, J = 7.7, 1.4 Hz, 1 H), 4.08-4.18 (m, 1 H), 3.96-4.05 (m, 1 H), 3.74-3.84 (m, 1 H), 3.55 (t, J = 5.7 Hz, 1 H), 3.40-3.49 (m, 2 H), 3.34-3.40 (m, 3 H), 3.11-3.21 (m, 1 H), 2.94 (t, J = 5.7 Hz, 2 H), 2.82 (dt, J = 13.6, 6.8 Hz, 1 H), 2.23 (s, 3 H), 2.17 (s, 3 H), 1.77-1.90 (m, 5 H), 1.55-1.66 (m, 2 H), 1.15-1.23 (m, 9 H), 1.10 (t, J = 6.9 Hz, 3 H); MS (ESI+) m/z 553.5 (M + H)$^+$. |

| | Structure | Chemical Name & Analytical Data |
|---|---|---|
| 21-AM | 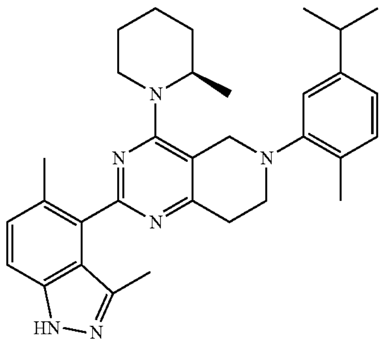 [SMILES: Cc1ccc(C(C)C)cc1N1CCc2nc(-c3c(C)ccc4[nH]nc(C)c34)nc(N3CCCC[C@H]3C)c2C1] | (R)-2-(3,5-dimethyl-1H-indazol-4-yl)-6-(5-isopropyl-2-methylphenyl)-4-(2-methylpiperidin-1-yl)-5,6,7,8-tetrahydropyrido[4,3-d]pyrimidine. $^1$H NMR (400 MHz, DMSO-$d_6$) δ ppm 12.59 (s, 1 H), 7.39 (d, J = 8.6 Hz, 1 H), 7.21 (d, J = 8.6 Hz, 1 H), 7.11 (d, J = 8.1 Hz, 1 H), 6.93 (d, J = 1.5 Hz, 1 H), 6.86 (dd, J = 7.6, 1.5 Hz, 1 H), 3.88-4.17 (m, 3 H), 3.43-3.57 (m, 1 H), 3.11-3.24 (m, 1 H), 2.89-3.00 (m, 2 H), 2.77-2.88 (m, 1 H), 2.22 (s, 3 H), 2.17 (br. s., 3 H), 1.84-1.90 (m, 3 H), 1.59-1.75 (m, 3 H), 1.52 (d, J = 4.8 Hz, 3 H), 1.13-1.21 (m, 9 H); MS (ESI+) m/z 509.4 (M + H)$^+$. |
| 21-AN | 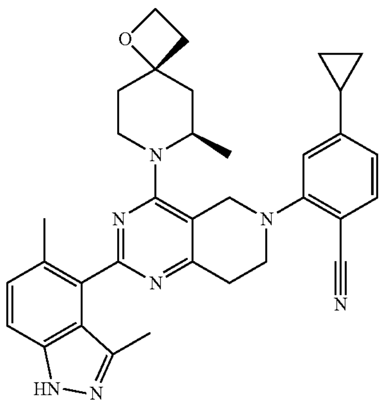 [SMILES: Cc1ccc2[nH]nc(C)c2c1-c1nc2c(c(N3CC[C@@]4(CCO4)C[C@H]3C)n1)CN(c1cc(C3CC3)ccc1C#N)CC2] | 4-Cyclopropyl-2-(2-(3,5-dimethyl-1H-indazol-4-yl)-4-((4S,6R)-6-methyl-1-oxa-7-azaspiro[3.5]nonan-7-yl)-7,8-dihydropyrido[4,3-d]pyrimidin-6(5H)-yl)benzonitrile. $^1$H NMR (400 MHz, CD$_2$Cl$_2$) δ ppm 9.76 (br. s., 1H), 7.40 (d, J = 7.83 Hz, 1H), 7.28 (d, J = 8.34 Hz, 1H), 7.17 (d, J = 8.84 Hz, 1H), 6.54-6.67 (m, 2H), 4.36-4.50 (m, 2H), 4.31 (d, J = 15.16 Hz, 1H), 4.20 (d, J = 15.16 Hz, 1H), 3.91-4.02 (m, 1H), 3.71-3.81 (m, 1H), 3.61-3.71 (m, 1H), 3.44 (td, J = 4.71, 13.83 Hz, 1H), 3.12 (ddd, J = 3.03, 10.04, 13.45 Hz, 1H), 2.98-3.05 (m, 2H), 2.45-2.57 (m, 1H), 2.34-2.45 (m, 1H), 2.15 (s, 3H), 1.97-2.08 (m, 1H), 1.86-1.94 (m, 2H), 1.84 (s, 3H), 1.76-1.83 (m, 2H), 1.11 (d, J = 6.82 Hz, 3H), 0.94-1.02 (m, 2H), 0.61-0.68 (m, 2H). MS (ESI+) m/z 560.3 (M + H)$^+$. |

Example 22

22-A. 6-Benzyl-4-((2R,4R)-4-methoxy-2-methylpiperidin-1-yl)-2-(5-(trifluoromethyl)-1H-pyrrolo[2,3-b]pyridin-4-yl)-5,6,7,8-tetrahydropyrido[4,3-d]pyrimidine

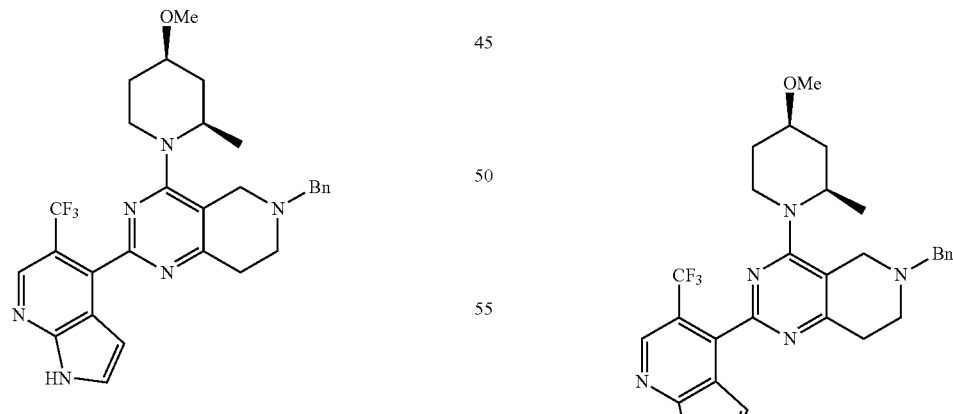

The product was prepared as in a similar manner as described in Example 21-b by using 6-benzyl-2-chloro-((2R,4R)-4-methoxy-2-methylpiperidin-1-yl)-5,6,7,8-tetrahydropyrido[4,3-d]pyrimidine (190 mg, 0.491 mmol), 4-(4,4,5,5-tetramethyl-1,3,2-dioxaborolan-2-yl)-5-(trifluoromethyl)-1-(triisopropylsilyl)-1H-pyrrolo[2,3-b]pyridine (460 mg, 0.982 mmol) Pd(PPh$_3$)$_4$ (57 mg, 0.049 mmol) and a 2 M solution of NaHCO$_3$ (737 μL, 1.47 mmol). The residue was purified via FCC (0 to 5% MeOH/DCM (1% NH$_4$OH)) to give the title compound. MS (ESI+) m/z 537.0 (M+H)$^+$.

22-B. 6-Benzyl-4-((2R,4R)-4-methoxy-2-methylpiperidin-1-yl)-2-(1-tosyl-5-(trifluoromethyl)-1H-pyrrolo[2,3-b]pyridin-4-yl)-5,6,7,8-tetrahydropyrido[4,3-d]pyrimidine To a solution of 6-benzyl-((2R,4R)-4-methoxy-2-methylpiperidin-1-yl)-2-(5-(trifluoromethyl)-1H-pyrrolo[2,3-b]

pyridin-4-yl)-5,6,7,8-tetrahydropyrido[4,3-d]pyrimidine (214 mg, 0.399 mmol) in THF (4 mL) was added NaH 60% in oil (32 mg, 0.80 mmol) at 0° C. After 20 min, p-toluenesulfonyl chloride (91 mg, 0.48 mmol) was added and the reaction was allowed to warm to room temperature. After 2 h, the reaction was quenched with a saturated solution of $NH_4Cl$. The mixture was extracted with EtOAc. The organic layer was washed with brine, dried over anhydrous sodium sulfate, filtered, and concentrated under reduced pressure. The resulting residue was purified via FCC (0-70% EtOAc/heptane) to give the title compound. MS (ESI+) m/z 691.1 $(M+H)^+$.

22-C. 6-(5-Isopropyl-2-methylphenyl)-4-((2R,4R)-4-methoxy-2-methylpiperidin-1-yl)-2-(5-(trifluoromethyl)-1H-pyrrolo[2,3-b]pyridin-4-yl)-5,6,7,8-tetrahydropyrido[4,3-d]pyrimidine

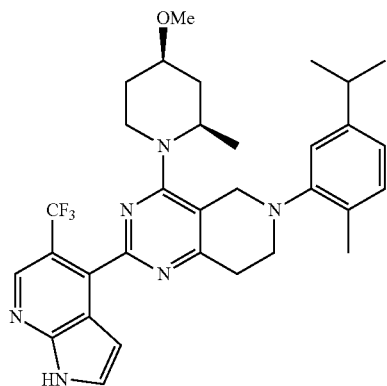 [SMILES: CO[C@@H]1CCN(c2nc(-c3c(C(F)(F)F)cnc4[nH]ccc34)nc3c2CN(c2cc(C(C)C)ccc2C)CC3)[C@H](C)C1]

To a solution of 6-(5-isopropyl-2-methylphenyl)-((2R,4R)-4-methoxy-2-methylpiperidin-1-yl)-2-(1-tosyl-5-(trifluoromethyl)-1H-pyrrolo[2,3-b]pyridin-4-yl)-5,6,7,8-tetrahydropyrido[4,3-d]pyrimidine (25 mg, 0.034 mmol), prepared as described in Examples 21-c and 21-d, in EtOH (898 µL) was added KOH (17.2 mg, 0.307 mmol) and $NH_4OH$ (202 µL, 5.12 mmol). The reaction was heated at 100° C. for 40 min in a microwave reactor. The reaction was then concentrated and the residue was dissolved in EtOAc and a saturated solution of $NH_4Cl$. The layers were separated and the aqueous phase was extracted with EtOAc (2×). The organic phases were combined, washed with brine, dried with sodium sulfate, filtered and concentrated under reduced pressure. The resulting residue was purified via FCC (0-60% EtOAc/heptane) to give the title compound. $^1$H NMR (400 MHz, DMSO-$d_6$) δ ppm 12.24 (br. s., 1 H), 8.64 (s, 1 H), 7.65-7.70 (m, 1 H), 7.11 (d, J=7.8 Hz, 1 H), 6.94 (s, 1 H), 6.87 (dd, J=7.7, 1.6 Hz, 1 H), 6.41 (dd, J=3.5, 1.8 Hz, 1 H), 4.13 (d, J=15.4 Hz, 1 H), 3.94-4.03 (m, 1 H), 3.86-3.94 (m, 1 H), 3.44-3.50 (m, 1 H), 3.33-3.38 (m, 2 H), 3.25 (s, 3 H), 2.92-3.01 (m, 2 H), 2.84 (dt, J=13.7, 6.9 Hz, 1 H), 2.43-2.47 (m, 1 H), 2.23 (s, 3 H), 1.75-1.89 (m, 2 H), 1.61-1.72 (m, 2 H), 1.22 (d, J=6.8 Hz, 4 H), 1.18 (d, J=6.8 Hz, 6 H); MS (ESI+) m/z 579.1 $(M+H)^+$.

Example 23

23-A. (S)-2-(2,6-Dimethylphenyl)-6-(3-isopropyl-1-methyl-1H-pyrazol-5-yl)-4-(4-methoxy-3,3-dimethylpiperidin-1-yl)-5,6,7,8-tetrahydropyrido[4,3-d]pyrimidine

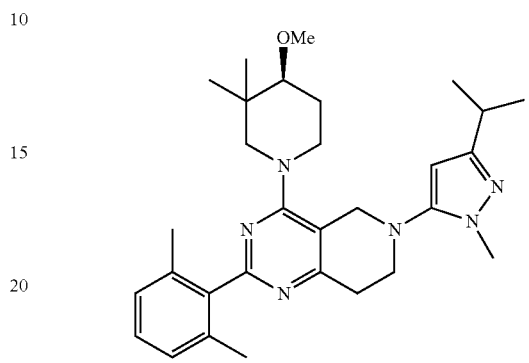

In a microwave reaction vial (S)-2-(2,6-dimethylphenyl)-4-(4-methoxy-3,3-dimethylpiperidin-1-yl)-5,6,7,8-tetrahydropyrido[4,3-d]pyrimidine (115 mg, 0.302 mmol), prepared by a method similar to that described by Examples 21-c and 21-d, was combined with methyl isobutyryl acetate (65 mg, 0.45 mmol), toluene (2 mL) and DMAP (7 mg, 0.060 mmol). The vial was heated in a microwave reactor at 150° C. for 30 min. The reaction mixture was then diluted with DCM and water. The layers were separated and the aqueous phase was extracted twice with DCM. The combined organic layers were washed with brine, dried over $Na_2SO_4$, filtered, and concentrated. The resulting residue was purified by silica gel flash column chromatography (0-100% 10:1 EtOAc:MeOH/heptanes) to provide (S)-1-(2-(2,6-dimethylphenyl)-4-(4-methoxy-3,3-dimethylpiperidin-1-yl)-7,8-dihydropyrido[4,3-d]pyrimidin-6(5H)-yl)-4-methylpentane-1,3-dione. MS (ESI+) m/z 493.0 $(M+H)^+$ To a solution of Lawesson's Reagent (61 mg, 0.15 mmol) in THF (1 mL) was added pyridine (0.050 mL) followed by methyl hydrazine (9.9 µl, 0.19 mmol). The reaction mixture was stirred for 35 minutes at room temperature. A solution of (S)-1-(2-(2,6-dimethylphenyl)-4-(4-methoxy-3,3-dimethylpiperidin-1-yl)-7,8-dihydropyrido[4,3-d]pyrimidin-6(5H)-yl)-4-methylpentane-1,3-dione (62 mg, 0.13 mmol) in THF (1 mL) was added and the reaction was immediately sealed and heated by microwave irradiation for 12 minutes at 125° C. The reaction mixture was concentrated and the resulting residue was purified by flash column chromatography on silica gel (0-5% 10:1 MeOH:$NH_4OH$/DCM to provide (S)-2-(2,6-dimethylphenyl)-6-(3-isopropyl-1-methyl-1H-pyrazol-5-yl)-4-(4-methoxy-3,3-dimethylpiperidin-1-yl)-5,6,7,8-tetrahydropyrido[4,3-d]pyrimidine. $^1$H NMR (400 MHz, $CD_2Cl_2$) δ ppm 7.20 (br. s., 1 H), 7.09 (d, J=7.1 Hz, 2 H), 5.66 (s, 1 H), 3.98 (d, J=2.3 Hz, 2 H), 3.68-3.76 (m, 1 H), 3.66 (s, 3 H), 3.34 (s, 3 H), 3.31 (t, J=6.1 Hz, 2 H), 3.07 (br. s., 1 H), 2.93-3.00 (m, 1 H), 2.84 (spt, J=6.6 Hz, 1 H), 2.13 (br. s., 6 H), 1.92-2.00 (m, 1 H), 1.64-1.74 (m, 1 H), 1.21 (d, J=7.1 Hz, 6 H), 0.96 (s, 3 H), 0.90 (s, 3 H); MS (ESI+) m/z 503.2 $(M+H)^+$.

The following compounds were prepared in a similar manner. For the compounds containing an indazole or indole group the synthesis was carried out with the corresponding N-tosyl protected intermediates described in the other examples herein and the removal of the tosyl protecting group at the last step was done described in other examples herein.

| | Structure | Chemical Name & Analytical Data |
|---|---|---|
| 23-B | 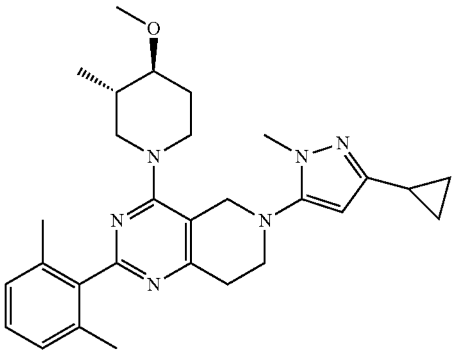 [SMILES: CO[C@H]1CCN(c2nc(-c3c(C)cccc3C)nc3c2CN(c2cc(C4CC4)nn2C)CC3)C[C@@H]1C] | 6-(3-cyclopropyl-1-methyl-1H-pyrazol-5-yl)-2-(2,6-dimethylphenyl)-4-((3S,4S)-4-methoxy-3-methylpiperidin-1-yl)-5,6,7,8-tetrahydropyrido[4,3-d]pyrimidine. $^1$H NMR (400 MHz, DMSO-$d_6$) δ ppm 0.51-0.63 (m, 2 H) 0.74-0.83 (m, 2 H) 0.93 (d, J = 6.6 Hz, 3 H) 1.29-1.42 (m, 1 H) 1.58-1.69 (m, 1 H) 1.70-1.81 (m, 1 H) 2.01-2.10 (m, 1 H) 2.04 (s, 6 H) 2.74 (dd, J = 13.4, 9.9 Hz, 1 H) 2.88-3.06 (m, 4 H) 3.25-3.29 (m, 2 H) 3.27 (s, 3 H) 3.56 (s, 3 H) 3.58-3.65 (m, 1 H) 3.72 (d, J = 12.6 Hz, 1 H) 3.96 (s, 2 H) 5.59 (s, 1 H) 7.03-7.11 (m, 2 H) 7.12-7.22 (m, 1 H); MS (ESI+) m/z 487.1 (M + H)$^+$. |
| 23-C | 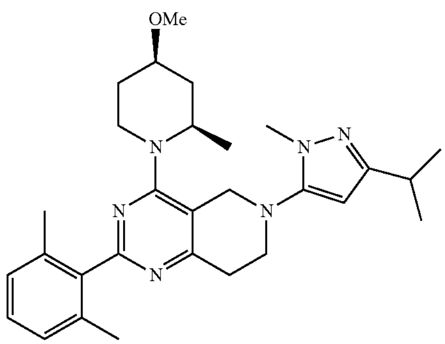 [SMILES: CO[C@@H]1CCN(c2nc(-c3c(C)cccc3C)nc3c2CN(c2cc(C(C)C)nn2C)CC3)[C@H](C)C1] | 2-(2,6-dimethylphenyl)-6-(3-isopropyl-1-methyl-1H-pyrazol-5-yl)-4-((2R,4R)-4-methoxy-2-methylpiperidin-1-yl)-5,6,7,8-tetrahydropyrido[4,3-d]pyrimidine. $^1$H NMR (400 MHz, DMSO-$d_6$) δ ppm 7.14-7.23 (m, 1 H), 7.04-7.11 (m, 2 H), 5.68 (s, 1 H), 4.00-4.12 (m, 1 H), 3.89-4.00 (m, 1 H), 3.67-3.77 (m, 1 H), 3.60 (s, 3 H), 3.37-3.48 (m, 1 H), 3.25 (s, 3 H), 3.02-3.13 (m, 1 H), 2.95 (t, J = 5.8 Hz, 2 H), 2.76 (dt, J = 13.8, 6.9 Hz, 1 H), 2.02 (s, 5 H), 1.78-1.91 (m, 2 H), 1.52-1.70 (m, 2 H), 1.11-1.19 ppm (m, 9H); MS (ESI+) m/z 489.3 (M + H)$^+$. |
| 23-D | 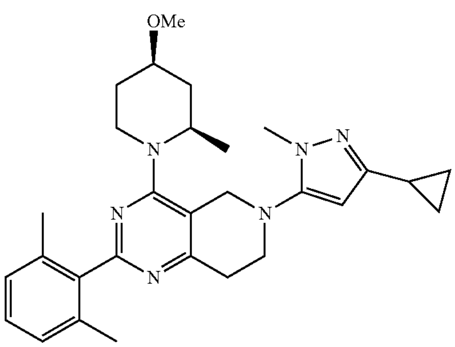 [SMILES: CO[C@@H]1CCN(c2nc(-c3c(C)cccc3C)nc3c2CN(c2cc(C4CC4)nn2C)CC3)[C@H](C)C1] | 6-(3-cyclopropyl-1-methyl-1H-pyrazol-5-yl)-2-(2,6-dimethylphenyl)-4-((2R,4R)-4-methoxy-2-methylpiperidin-1-yl)-5,6,7,8-tetrahydropyrido[4,3-d]pyrimidine. $^1$H NMR (400 MHz, DMSO-$d_6$) δ ppm 7.14-7.23 (m, 1 H), 7.03-7.12 (m, 2 H), 5.59 (s, 1 H), 3.98-4.08 (m, 1 H), 3.86-3.96 (m, 1 H), 3.68-3.80 (m, 1 H), 3.57 (s, 3 H), 3.39-3.49 (m, 1 H), 3.25 (s, 4 H), 3.02-3.13 (m, 1 H), 2.90-2.99 (m, 2 H), 2.02 (s, 6 H), 1.80-1.92 (m, 2 H), 1.71-1.80 (m, 1 H), 1.52-1.68 (m, 2 H), 1.15 (d, J = 6.6 Hz, 3 H), 0.73-0.83 (m, 2 H), 0.53-0.61 (m, 2 H); MS (ESI+) m/z 487.3 (M + H)$^+$. |
| 23-E | 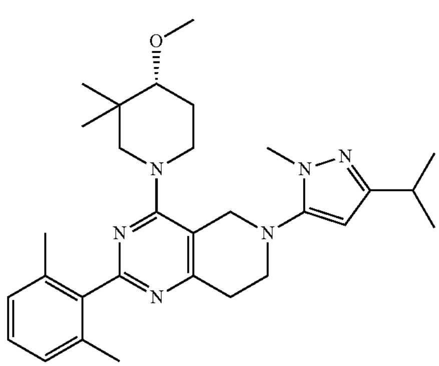 [SMILES: CO[C@@H]1CCN(c2nc(-c3c(C)cccc3C)nc3c2CN(c2cc(C(C)C)nn2C)CC3)CC1(C)C] | (R)-2-(2,6-dimethylphenyl)-6-(3-isopropyl-1-methyl-1H-pyrazol-5-yl)-4-(4-methoxy-3,3-dimethylpiperidin-1-yl)-5,6,7,8-tetrahydropyrido[4,3-d]pyrimidine; $^1$H NMR (400 MHz, CD$_2$Cl$_2$) δ ppm 7.14-7.23 (m, 1 H) 7.07 (d, J = 7.58 Hz, 2 H) 5.65 (s, 1 H) 3.93-4.04 (m, 2 H) 3.70 (d, J = 8.34 Hz, 1 H) 3.66 (s, 3 H) 3.28-3.37 (m, 6 H) 3.12 (br. s., 1 H) 3.04 (br. s., 2 H) 2.95 (dd, J = 8.59, 3.79 Hz, 1 H) 2.85 (dq, J = 13.86, 6.92 Hz, 2 H) 2.11 (s, 6 H) 1.92-2.01 (m, 1 H) 1.63-1.75 (m, 1 H) 1.22 (s, 3 H) 1.20 (s, 3 H) 0.97 (s, 3 H) 0.91 (s, 3 H); MS (ESI+) m/z 503.4 (M + H)$^+$. |

| | Structure | Chemical Name & Analytical Data |
|---|---|---|
| 23-F | 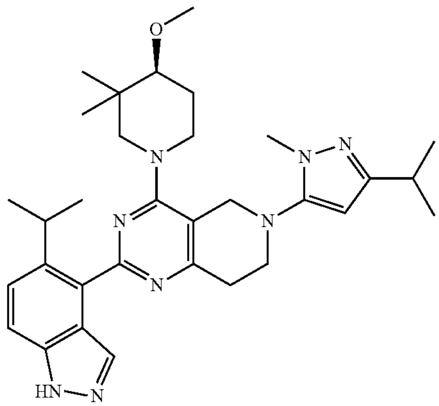 [SMILES: CO[C@H]1CCN(c2nc(-c3c(C(C)C)ccc4[nH]ncc34)nc3c2CN(c2cc(C(C)C)nn2C)CC3)CC1(C)C] | (S)-6-(3-isopropyl-1-methyl-1H-pyrazol-5-yl)-2-(5-isopropyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, CD$_2$Cl$_2$) δ ppm 7.95 (br. s., 1 H), 7.53 (d, J = 8.8 Hz, 1 H), 7.47 (d, J = 8.8 Hz, 1 H), 5.73 (s, 1 H), 4.02 (s, 2 H), 3.68 (m, 4 H), 3.42 (s, 2 H), 3.31-3.37 (m, 5 H), 3.14 (br. s., 2 H), 2.96 (dd, J = 8.2, 3.4 Hz, 1 H), 2.86 (spt, J = 6.8 Hz, 1 H), 1.93-2.02 (m, 1 H), 1.65-1.76 (m, 1 H), 1.29 (d, J = 6.8 Hz, 6 H), 1.23 (d, J = 6.8 Hz, 6 H), 0.98 (s, 3 H), 0.94 (s, 3 H); MS (ESI+) m/z 557.1 (M + H)$^+$. |
| 23-G | 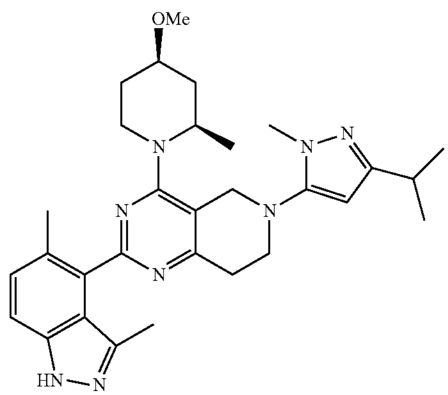 [SMILES: CO[C@@H]1CCN(c2nc(-c3c(C)ccc4[nH]nc(C)c34)nc3c2CN(c2cc(C(C)C)nn2C)CC3)[C@H](C)C1] | 2-(3,5-dimethyl-1H-indazol-4-yl)-6-(3-isopropyl-1-methyl-1H-pyrazol-5-yl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 12.58 (s, 1 H), 7.39 (d, J = 8.6 Hz, 1 H), 7.22 (d, J = 8.3 Hz, 1 H), 5.63 (s, 1 H), 4.07-4.14 (m, 1 H), 3.97-4.05 (m, 1 H), 3.75 (q, J = 6.0 Hz, 1 H), 3.61 (s, 3 H), 3.41-3.48 (m, 1 H), 3.33-3.38 (m, 2 H), 3.25 (s, 3 H), 3.08-3.18 (m, 1 H), 2.95 (t, J = 5.7 Hz, 2 H), 2.76 (dt, J = 13.8, 6.9 Hz, 1H), 2.16 (s, 3 H), 1.81-1.89 (m, 5 H), 1.54-1.71 (m, 2 H), 1.12-1.19 (m, 9 H); MS (ESI+) m/z 529.4 (M + H)$^+$. |
| 23-H | 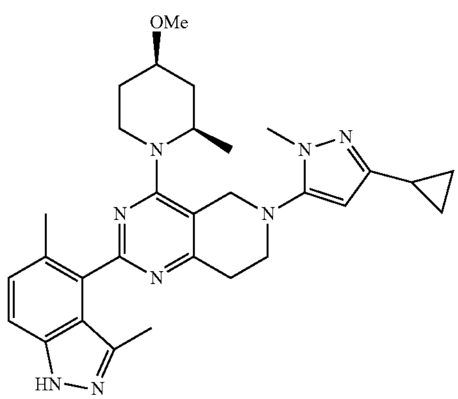 [SMILES: CO[C@@H]1CCN(c2nc(-c3c(C)ccc4[nH]nc(C)c34)nc3c2CN(c2cc(C4CC4)nn2C)CC3)[C@H](C)C1] | 6-(3-cyclopropyl-1-methyl-1H-pyrazol-5-yl)-2-(3,5-dimethyl-1H-indazol-4-yl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 12.58 (s, 1 H), 7.39 (d, J = 8.6 Hz, 1 H), 7.21 (d, J = 8.6 Hz, 1 H), 5.55 (s, 1 H), 4.04-4.15 (m, 1 H), 3.92-4.04 (m, 1 H), 3.70-3.81 (m, 2 H), 3.58 (s, 3 H), 3.41-3.50 (m, 2 H), 3.25 (s, 3 H), 3.07-3.20 (m, 1 H), 2.95 (t, J = 5.8 Hz, 2 H), 2.16 (s, 3 H), 1.85 (s, 6 H), 1.70-1.79 (m, 1 H), 1.55-1.70 (m, 2 H), 1.17 (d, J = 6.6 Hz, 3 H), 0.73-0.85 (m, 2 H), 0.50-0.64 (m, 2 H); MS (ESI+) m/z 527.4 (M + H)$^+$. |
| 23-I | 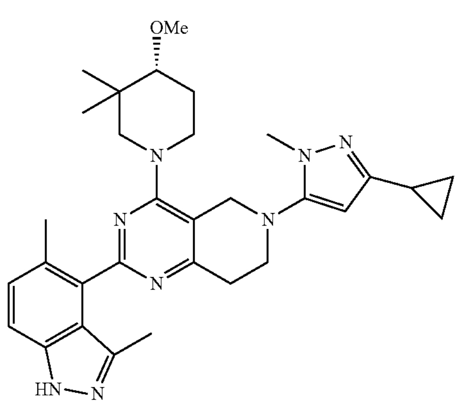 [SMILES: CO[C@@H]1CCN(c2nc(-c3c(C)ccc4[nH]nc(C)c34)nc3c2CN(c2cc(C4CC4)nn2C)CC3)CC1(C)C] | (R)-6-(3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.57 (s, 1 H) 7.38 (d, J = 8.59 Hz, 1 H) 7.21 (d, J = 8.59 Hz, 1 H) 5.52 (s, 1 H) 4.07-4.14 (m, 1 H) 3.96-4.03 (m, 1 H) 3.67 (d, J = 12.38 Hz, 1 H) 3.57 (s, 3 H) 3.33 (br. s., 2 H) 3.27 (s, 3 H) 3.01-3.11 (m, 1 H) 2.98 (dd, J = 8.97, 3.92 Hz, 1 H) 2.92 (t, J = 6.06 Hz, 2 H) 2.86 (d, J = 13.14 Hz, 1 H) 2.55 (br. s., 1 H) 2.18 (s, 3 H) 1.94 (d, J = 3.28 Hz, 1 H) 1.87 (s, 3 H) 1.70-1.80 (m, 1 H) 1.49-1.62 (m, 1 H) 0.94 (s, 3 H) 0.84 (s, 3 H) 0.76-0.82 (m, 2H) 0.53-0.58 (m, 2H); MS (ESI+) m/z 541.3 (M + H)$^+$. |

| | Structure | Chemical Name & Analytical Data |
|---|---|---|
| 23-J | 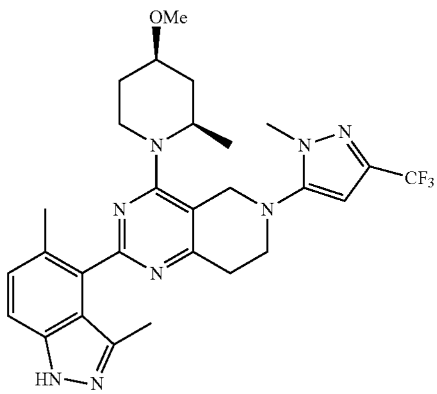 [SMILES: CO[C@@H]1CCN(c2nc(-c3c(C)ccc4[nH]nc(C)c34)nc3c2CN(c2cc(C(F)(F)F)nn2C)CC3)[C@H](C)C1] | 2-(3,5-dimethyl-1H-indazol-4-yl)-4-((2R,4R)-4-methoxy-2-methylpiperidin-1-yl)-6-(1-methyl-3-(trifluoromethyl)-1H-pyrazol-5-yl)-5,6,7,8-tetrahydropyrido[4,3-d]pyrimidine. $^1$H NMR (400 MHz, DMSO-d$_6$) δ ppm 12.61 (s, 1 H), 7.40 (d, J = 8.6 Hz, 1 H), 7.22 (d, J = 8.6 Hz, 1 H), 6.35 (s, 1 H), 4.13-4.26 (m, 1 H), 4.02-4.14 (m, 1 H), 3.73-3.89 (m, 4 H), 3.37-3.51 (m, 2 H), 3.25 (s, 3 H), 3.14-3.19 (m, , 1 H), 2.98-3.00 (m, 2 H), 2.89 (s, 1 H), 2.73 (s, 1 H), 2.16 (s, 3 H), 1.75-1.92 (m, 5 H), 1.52-1.75 (m, 2 H), 1.18 (d, J = 6.6 Hz, 3 H); MS (ESI+) m/z 555.5(M + H)$^+$. |
| 23-K | 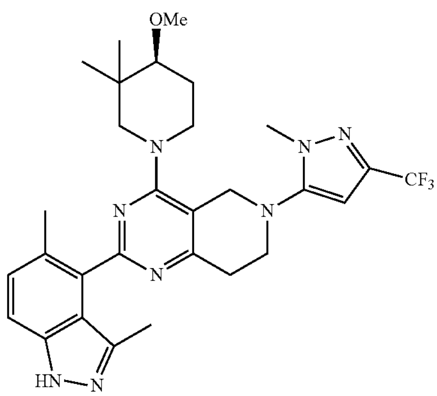 [SMILES: CO[C@H]1CCN(c2nc(-c3c(C)ccc4[nH]nc(C)c34)nc3c2CN(c2cc(C(F)(F)F)nn2C)CC3)CC1(C)C] | (S)-2-(3,5-dimethyl-1H-indazol-4-yl)-4-(4-methoxy-3,3-dimethylpiperidin-1-yl)-6-(1-methyl-3-(trifluoromethyl)-1H-pyrazol-5-yl)-5,6,7,8-tetrahydropyrido[4,3-d]pyrimidine. 1H NMR (400 MHz, DICHLOROMETHANE-d$_6$) δ ppm 7.36-7.42 (m, 1 H), 7.24-7.29 (m, 1 H), 6.12 (s, 1 H), 4.02-4.13 (m, 2 H), 3.81 (s, 3 H), 3.67-3.76 (m, 1 H), 3.37-3.44 (m, 2 H), 3.33 (s, 4 H), 3.02-3.23 (br. m, 3 H), 2.87-3.01 (m, 2 H), 2.29 (s, 3 H), 1.91-2.04 (m, 5 H), 1.63-1.76 (m, 1 H), 0.97 (s, 3 H), 0.91 (s, 3 H); MS (ESI+) m/z 569.4 (M + H)$^+$. |
| 23-L | 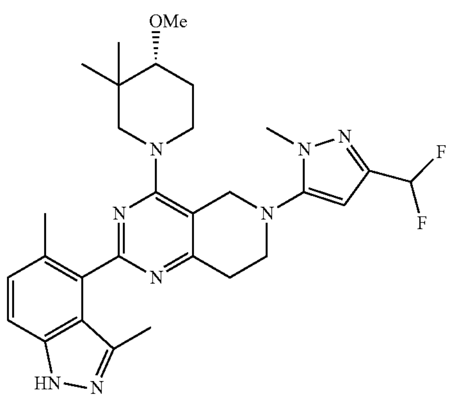 [SMILES: CO[C@@H]1CCN(c2nc(-c3c(C)ccc4[nH]nc(C)c34)nc3c2CN(c2cc(C(F)F)nn2C)CC3)CC1(C)C] | (R)-6-(3-(difluoromethyl)-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.60 (s, 1 H), 7.39 (d, J = 8.3 Hz, 1 H), 7.21 (d, J = 8.6 Hz, 1 H), 6.85 (t, J = 54.8 Hz, 1 H), 6.11 (s, 1 H), 4.21 (d, J = 14.9 Hz, 1 H), 4.08 (d, J = 14.9 Hz, 1 H), 3.73 (s, 3 H), 3.66-3.71 (m, 1 H), 3.37-3.44 (m, 2 H), 3.27 (s, 3 H), 3.02-3.10 (m, 1 H), 2.92-3.01 (m, 3 H), 2.87 (d, J = 13.1 Hz, 1 H), 2.18 (s, 3 H), 1.88-1.96 (m, 1 H), 1.86 (s, 3 H), 1.50-1.62 (m, 1 H), 0.94 (s, 3 H), 0.83 (s, 3 H); MS (ESI+) m/z 551.5 (M + H)$^+$. |
| 23-M | 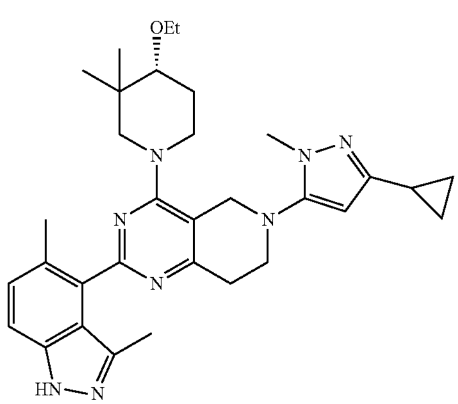 [SMILES: CCO[C@@H]1CCN(c2nc(-c3c(C)ccc4[nH]nc(C)c34)nc3c2CN(c2cc(C4CC4)nn2C)CC3)CC1(C)C] | (R)-6-(3-cyclopropyl-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine. $^1$H NMR (400 MHz, DMSO-d$_6$) δ ppm 12.60 (s, 1 H), 7.39 (d, J = 8.3 Hz, 1 H), 7.21 (d, J = 8.6 Hz, 1 H), 5.52 (s, 1 H), 4.08 (s, 1 H), 4.00 (s, 1 H), 3.64-3.74 (m, 1 H), 3.59-3.64 (m, 1 H), 3.57 (s, 3 H), 3.00-3.11 (m, 2 H), 2.92 (t, J = 5.8 Hz, 2 H), 2.85 (d, J = 13.1 Hz, 1 H), 2.17 (s, 3 H), 1.82-1.92 (m, 4 H), 1.74 (tt, J = 8.4, 5.0 Hz, 1 H), 1.51-1.56 (m, 1 H), 1.09 (t, J = 6.9 Hz, 3 H), 0.93 (s, 3 H), 0.84 (s, 3 H), 0.75-0.81 (m, 2 H), 0.49-0.60 (m, 2 H); MS (ESI+) m/z 555.5(M + H)$^+$. |

| | Structure | Chemical Name & Analytical Data |
|---|---|---|
| 23-N | 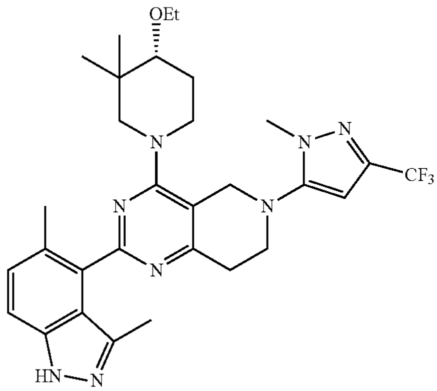 [SMILES: CCO[C@@H]1CCN(c2nc(-c3c(C)ccc4[nH]nc(C)c34)nc3c2CN(c2cc(C(F)(F)F)nn2C)CC3)CC1(C)C] | (R)-2-(3,5-dimethyl-1H-indazol-4-yl)-4-(4-ethoxy-3,3-dimethylpiperidin-1-yl)-6-(1-methyl-3-(trifluoromethyl)-1H-pyrazol-5-yl)-5,6,7,8-tetrahydropyrido[4,3-d]pyrimidine. 1H NMR (400 MHz, DMSO-$d_6$) δ ppm 12.60 (s, 1 H), 7.39 (d, J = 8.3 Hz, 1 H), 7.21 (d, J = 8.6 Hz, 1 H), 6.31 (s, 1 H), 4.15-4.32 (m, 1 H), 4.01-4.14 (m, 1 H), 3.78 (s, 3 H), 3.70 (d, J = 13.1 Hz, 1 H), 3.54-3.65 (m, 1 H), 3.42 (app q, J = 6.1 Hz, 2 H), 3.38 (t, J = 4.0 Hz, 1 H), 3.01-3.13 (m, 2 H), 2.96 (br. s., 2 H), 2.88 (d, J = 13.1 Hz, 1 H), 2.12-2.23 (m, 3 H), 1.85 (s, 4 H), 1.47-1.66 (m, 1 H), 1.03-1.17 (m, 3 H), 0.93 (s, 3 H), 0.75-0.87 (m, 3 H); MS (ESI+) m/z 583.4 (M + H)+. |
| 23-O | 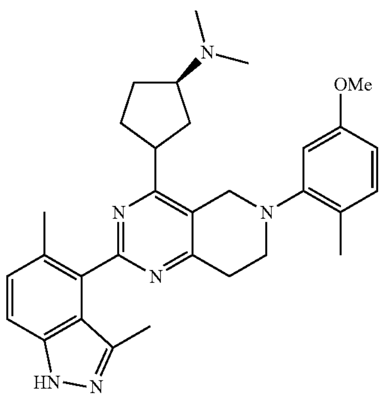 [SMILES: COc1ccc(C)c(N2CCc3nc(-c4c(C)ccc5[nH]nc(C)c45)nc(C4CC[C@@H](N(C)C)C4)c3C2)c1] | (R)-1-(2-(3,5-dimethyl-1H-indazol-4-yl)-6-(5-methoxy-2-methylphenyl)-5,6,7,8-tetrahydropyrido[4,3-d]pyrimidin-4-yl)-N,N-dimethylpyrrolidin-3-amine. $^1$H NMR (400 MHz, DMSO-$d_6$) δ ppm 12.55 (s, 1 H), 7.36 (d, J = 8.3 Hz, 1 H), 7.19 (d, J = 8.6 Hz, 1 H), 7.11 (d, J = 8.6 Hz, 1 H), 6.68 (d, J = 2.5 Hz, 1 H), 6.60 (dd, J = 8.3, 2.5 Hz, 1 H), 4.39 (d, J = 14.7 Hz, 1 H), 4.18 (d, J = 14.7 Hz, 1 H), 3.83 (dd, J = 10.2, 6.7 Hz, 1 H), 3.73-3.79 (m, 1 H), 3.72 (s, 3 H), 3.59-3.68 (m, 1 H), 3.38 (dd, J = 10.0, 8.5 Hz, 1 H), 3.26-3.29 (m, 1 H), 3.13-3.22 (m, 1 H), 2.76-2.97 (m, 2 H), 2.62-2.66 (m, 1 H), 2.21 (s, 3 H), 2.20 (s, 3 H), 2.15 (s, 6 H), 2.00-2.09 (m, 1 H), 1.91 (s, 3 H), 1.64-1.76 (m, 1 H); MS (ESI+) m/z 512.3 (M + H)+. |

Example 24

24-A. (R)-tert-Butyl-4-(2-(2,5-dimethylphenyl)-6-(5-isopropyl-2-methylphenyl)-5,6,7,8-tetrahydropyrido[4,3-d]pyrimidin-4-yl)-3-methylpiperazine-1-carboxylate

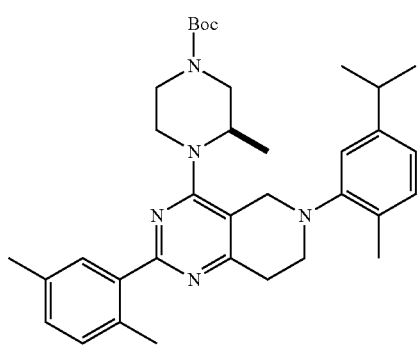 [SMILES: Cc1ccc(C)c(-c2nc3c(c(N4CCN(C(=O)OC(C)(C)C)C[C@H]4C)n2)CN(c2cc(C(C)C)ccc2C)CC3)c1]

The title compound was prepared in a similar manner to that described in Example 21. MS (ESI+) m/z 570.4 (M+H)+.

24-B. (R)-2-(2,5-Dimethylphenyl)-6-(5-isopropyl-2-methylphenyl)-4-(2-methylpiperazin-1-yl)-5,6,7,8-tetrahydropyrido[4,3-d]pyrimidine

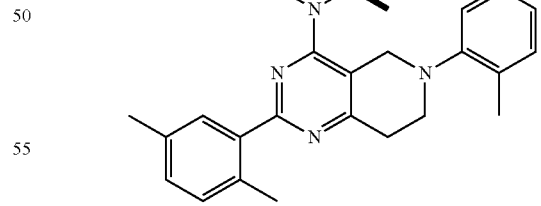

(R)-tert-Butyl 4-(2-(2,5-dimethylphenyl)-6-(5-isopropyl-2-methylphenyl)-5,6,7,8-tetrahydropyrido[4,3-d]pyrimidin-4-yl)-3-methylpiperazine-1-carboxylate (60 mg, 0.105 mmol) in DCM (1 mL) was treated with TFA (1 mL, 13.0 mmol) at rt for 15 min. The mixture was then concentrated to provide (R)-2-(2,5-Dimethylphenyl)-6-(5-isopropyl-2-methylphenyl)-4-(2-methylpiperazin-1-yl)-5,6,7,8-tetrahydropyrido[4,3-d]pyrimidine, which was taken on without need further purification. MS (ESI+) m/z 470.4 (M+H)+.

24-C. (R)-2-(4-(2-(2,5-Dimethylphenyl)-6-(5-isopropyl-2-methylphenyl)-5,6,7,8-tetrahydropyrido[4,3-d]pyrimidin-4-yl)-3-methylpiperazin-1-yl)acetamide

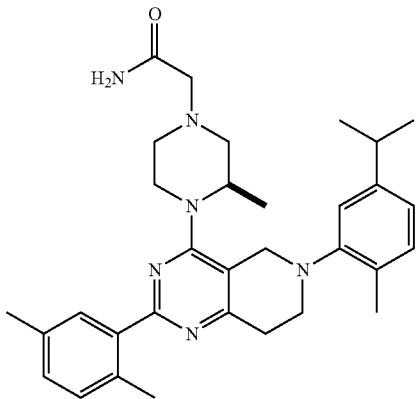 [SMILES: Cc1ccc(C)c(-c2nc3c(c(N4CCN(CC(N)=O)C[C@H]4C)n2)CN(c2cc(C(C)C)ccc2C)CC3)c1]

A mixture of (R)-2-(2,5-dimethylphenyl)-6-(5-isopropyl-2-methylphenyl)-4-(2-methylpiperazin-1-yl)-5,6,7,8-tetrahydropyrido[4,3-d]pyrimidine (43 mg, 0.053 mmol), 2-bromoacetamide (14.6 mg, 0.106 mmol) and DIEA (0.074 mL, 0.424 mmol) in DCM (2 mL) was stirred at rt for 16 h. The reaction was then diluted with EtOAc, and washed successively with sat aq NaHCO$_3$, and brine. The organic layer was then dried over anhydrous sodium sulfate, filtered, and concentrated under reduced pressure. The resulting residue was purified by HPLC(C18, 15-85% acetonitrile in H$_2$O with 0.1% NH$_4$OH) to provide (R)-2-(4-(2-(2,5-dimethylphenyl)-6-(5-isopropyl-2-methylphenyl)-5,6,7,8-tetrahydropyrido[4,3-d]pyrimidin-4-yl)-3-methylpiperazin-1-yl)acetamide. $^1$H NMR (400 MHz, DMSO-d$_6$, at 120° C.) δ ppm 7.58 (s, 1 H) 7.08-7.18 (m, 5 H) 6.99 (d, J=1.64 Hz, 1 H) 6.87 (dd, J=7.71, 1.64 Hz, 1 H) 4.01-4.09 (m, 1 H) 3.89-4.01 (m, 2 H) 3.48-3.58 (m, 1 H) 3.37-3.47 (m, 1 H) 2.97 (t, J=5.87 Hz, 2 H) 2.81-2.90 (m, 3 H) 2.78 (d, J=10.36 Hz, 1 H) 2.61 (dd, J=11.62, 1.77 Hz, 1 H) 2.47 (s, 3 H) 2.40 (dd, J=11.31, 3.35 Hz, 1 H) 2.23-2.34 (m, 4 H) 2.20 (s, 3 H) 1.28 (d, J=6.44 Hz, 3 H) 1.19 (dd, J=6.95, 1.52 Hz, 6 H); MS (ESI+) m/z 527.4 (M+H)$^+$.

The following compounds were prepared in a similar manner.

| | Structure | Chemical Name & Analytical Data |
|---|---|---|
| 24-D | 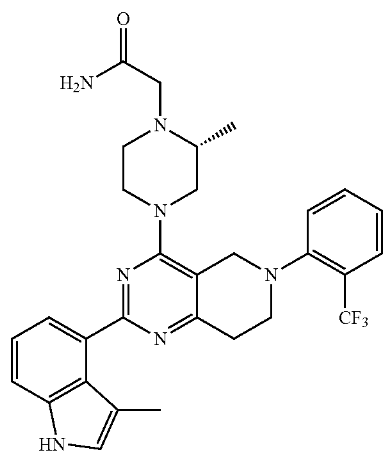 [SMILES: Cc1c[nH]c2cccc(-c3nc4c(c(N5CCN(CC(N)=O)[C@H](C)C5)n3)CN(c3ccccc3C(F)(F)F)CC4)c12] | (R)-2-(2-methyl-4-(2-(3-methyl-1H-indol-4-yl)-6-(2-(trifluoromethyl)phenyl)-5,6,7,8 tetrahydropyrido[4,3-d]pyrimidin-4-yl)piperazin-1-yl)acetamide. $^1$H NMR (400 MHz, DMSO-d$_6$) δ ppm 10.93 (br. s., 1H) 7.68-7.82 (m, 3H) 7.37-7.48 (m, 2H) 7.19-7.30 (m, 2H) 7.05-7.18 (m, 3H) 4.04 (s, 2H) 3.59 (t, J = 8.84 Hz, 2H) 3.05-3.24 (m, 3H) 2.97 (t, J = 5.56 Hz, 2H) 2.88 (dd, J = 12.63, 8.84 Hz, 1H) 2.72-2.82 (m, 2H) 2.52-2.64 (m, 2H) 2.40-2.47 (m, 1H) 2.02 (s, 3H) 0.98 (d, J = 6.06 Hz, 3H); MS (ESI+) m/z 564.4 (M + H)$^+$. |
| 24-E | 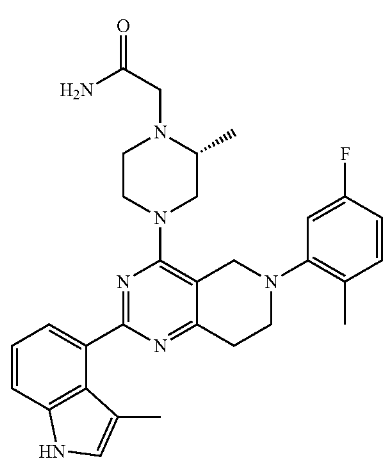 [SMILES: Cc1ccc(F)cc1N1CCc2nc(-c3cccc4[nH]cc(C)c34)nc(N3CCN(CC(N)=O)[C@H](C)C3)c2C1] | (R)-2-(4-(6-(5-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide. $^1$H NMR (400 MHz, DMSO-d$_6$) δ ppm 10.92 (d, J = 1.77 Hz, 1H) 7.41 (dd, J = 8.08, 1.01 Hz, 1H) 7.19-7.30 (m, 3H) 7.08-7.16 (m, 3H) 7.02 (dd, J = 11.24, 2.65 Hz, 1H) 6.83 (td, J = 8.34, 2.53 Hz, 1H) 4.01 (s, 2H) 3.62 (t, J = 11.62 Hz, 2H) 3.27-3.30 (m, 2H) 3.21 (t, J = 10.11 Hz, 2H) 3.13 (d, J = 16.17 Hz, 1H) 2.89-3.02 (m, 3H) 2.77-2.85 (m, 2H) 2.59-2.65 (m, 1H) 2.22 (s, 3H) 2.02 (s, 3H) 1.02 (d, J = 6.32 Hz, 3H); MS (ESI+) m/z 528.4 (M + H)$^+$. |

| | Structure | Chemical Name & Analytical Data |
|---|---|---|
| 24-F | 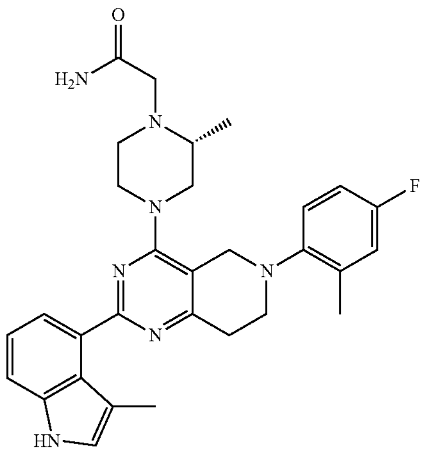 [SMILES: Cc1cc(F)ccc1N1CCc2nc(-c3cccc4[nH]cc(C)c34)nc(N3CCN(CC(N)=O)[C@H](C)C3)c2C1] | (R)-2-(4-(6-(4-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide. ¹H NMR (400 MHz, DMSO-d₆) δ ppm 10.93 (br. s., 1H) 7.42 (d, J = 7.83 Hz, 1H) 7.19-7.31 (m, 3H) 7.00-7.18 (m, 5H) 3.97 (br. s., 2H) 3.61 (br. s., 2H) 3.17-3.29 (m, 4H) 3.13 (d, J = 16.42 Hz, 1H) 2.99 (br. s., 3H) 2.80 (d, J = 14.15 Hz, 2H) 2.60 (d, J = 1.77 Hz, 1H) 2.27 (s, 3H) 2.03 (s, 3H) 1.02 (br. s., 3H); MS (ESI+) m/z 528.4 (M + H)⁺. |
| 24-G | 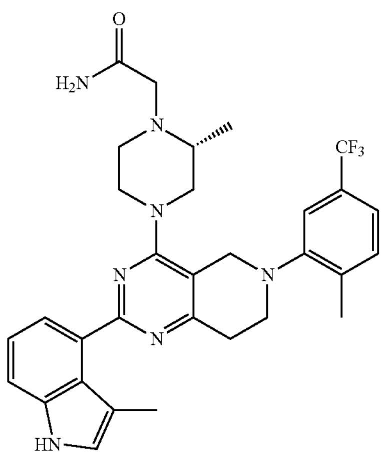 | (R)-2-(2-methyl-4-(2-(3-methyl-1H-indol-4-yl)-6-(2-methyl-5-(trifluoromethyl)phenyl)-5,6,7,8-tetrahydropyrido[4,3-d]pyrimidin-4-yl)piperazin-1-yl)acetamide. ¹H NMR(400 MHz, DMSO-d₆) δ ppm 10.93 (br. s., 1H) 7.31-7.50 (m, 4H) 7.28 (br. s., 1H) 7.21 (d, J = 7.07 Hz, 1H) 7.06-7.18 (m, 3H) 4.02-4.17 (m, 2H) 3.61 (t, J = 11.37 Hz, 2H) 3.17-3.30 (m, 3H) 3.11 (d, J = 16.17 Hz, 1H) 2.88-3.04 (m, 3H) 2.81 (d, J = 15.92 Hz, 2H) 2.60-2.70 (m, 1H) 2.42-2.47 (m, 1H) 2.34 (s, 3H) 2.02 (s, 3H) 1.03 (d, J = 6.06 Hz, 3H); MS (ESI+) m/z 578.4 (M + H)⁺. |
| 24-H | 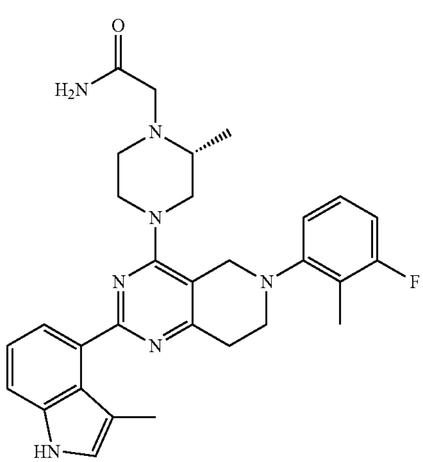 [SMILES: Cc1c(F)cccc1N1CCc2nc(-c3cccc4[nH]cc(C)c34)nc(N3CCN(CC(N)=O)[C@H](C)C3)c2C1] | (R)-2-(4-(6-(3-fluoro-2-methylphenyl)-2-(3-methyl-1H-indol-4-yl)-5,6,7,8-tetrahydropyrido[4,3-d]pyrimidin-4-yl)-2-methylpiperazin-1-yl)acetamide. ¹H NMR (400 MHz, DMSO-d₆) δ ppm 10.90 (d, J = 2.02 Hz, 1H) 7.39-7.44 (m, 1H) 7.19-7.28 (m, 3H) 7.07-7.17 (m, 3H) 7.02 (d, J = 8.08 Hz, 1H) 6.90 (t, J = 8.84 Hz, 1H) 4.04 (s, 2H) 3.58-3.66 (m, 2H) 3.33-3.36 (m, 1H) 3.28 (s, 2H) 3.17-3.25 (m, 1H) 3.13 (d, J = 16.17 Hz, 1H) 2.97-3.03 (m, 2H) 2.92 (dd, J = 12.76, 8.72 Hz, 1H) 2.77-2.86 (m, 2H) 2.58-2.66 (m, 1H) 2.16 (d, J = 2.27 Hz, 3H) 2.03 (s, 3H) 1.02 (d, J = 6.06 Hz, 3H); MS (ESI+) m/z 528.4 (M + H)⁺. |

-continued

| | Structure | Chemical Name & Analytical Data |
|---|---|---|
| 24-I | 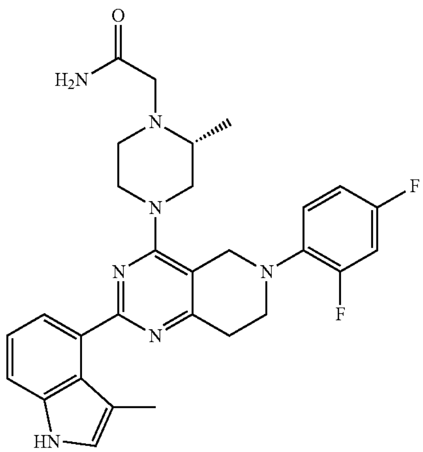 [SMILES: Cc1c[nH]c2cccc(-c3nc4c(c(N5CCN(CC(N)=O)[C@H](C)C5)n3)CN(c3ccc(F)cc3F)CC4)c12] | (R)-2-(4-(6-(2,4-difluorophenyl)-2-(3-methyl-1H-indol-4-yl)-5,6,7,8-tetrahydropyrido[4,3-d]pyrimidin-4-yl)-2-methylpiperazin-1-yl)acetamide. $^1$H NMR (400 MHz, DMSO-$d_6$) δ ppm 10.90 (s, 1H) 7.41 (dd, J = 8.08, 1.01 Hz, 1H) 7.01-7.30 (m, 8H) 4.13 (s, 2H) 3.61 (t, J = 1.62 Hz, 2H) 3.47 (t, J = 6.19 Hz, 2H) 3.36 (br. s., 1H) 3.18-3.25 (m, 1H) 3.14 (d, J = 16.17 Hz, 1H) 2.89-2.99 (m, 3H) 2.78-2.85 (m, 2H) 2.65 (br. s., 1H) 2.00 (s, 3H) 1.03 (d, J = 6.32 Hz, 3H); MS (ESI+) m/z 532.4 (M + H)$^+$. |
| 24-J | 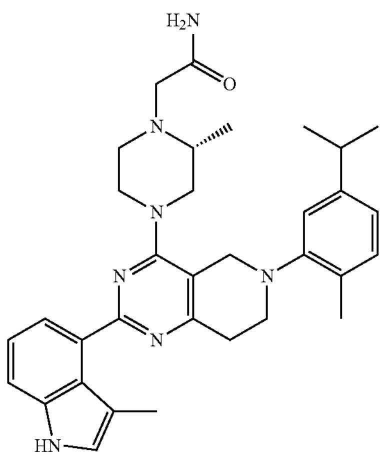 [SMILES: Cc1ccc(C(C)C)cc1N1CCc2nc(-c3cccc4[nH]cc(C)c34)nc(N3CCN(CC(N)=O)[C@H](C)C3)c2C1] | (R)-2-(4-(6-(5-isopropyl-2-methylphenyl)-2-(3-methyl-1H-indol-4-yl)-5,6,7,8-tetrahydropyrido[4,3-d]pyrimidin-4-yl)-2-methylpiperazin-1-yl)acetamide. $^1$H NMR (400 MHz, CD$_2$Cl$_2$) δ ppm 8.30 (br. s., 1H) 7.46 (d, J = 7.83 Hz, 1H) 7.35-7.42 (m, 1H) 7.22 (t, J = 7.71 Hz, 1H) 7.15 (d, J = 7.58 Hz, 1H) 7.08 (s, 1H) 6.98 (d, J = 1.52 Hz, 1H) 6.92 (dd, J = 7.58, 1.52 Hz, 1H) 5.36 (d, J = 7.07 Hz, 2H) 3.97-4.08 (m, 2H) 3.79 (br. s., 2H) 3.37 (t, J = 5.43 Hz, 3H) 3.21 (br. s., 2H) 3.03-3.15 (m, 1H) 2.81-3.03 (m, 3H) 2.72 (br. s., 1H) 2.60 (br. s., 1H) 2.28 (s, 3H) 2.11 (s, 3H) 1.25 (m, 7H) 1.14 (d, J = 9.35 Hz, 3H); MS (ESI+) m/z 552.4 (M + H)$^+$. |
| 24-K | 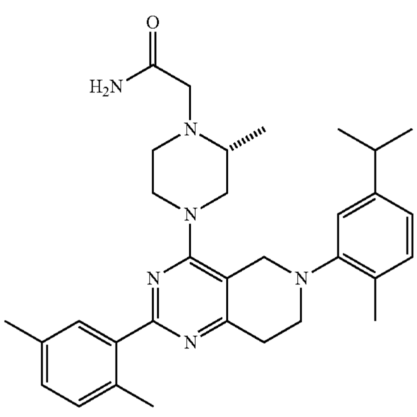 [SMILES: Cc1ccc(C)c(-c2nc3c(c(N4CCN(CC(N)=O)[C@H](C)C4)n2)CN(c2cc(C(C)C)ccc2C)CC3)c1] | (R)-2-(4-(2-(2,5-dimethylphenyl)-6-(5-isopropyl-2-methylphenyl)-5,6,7,8-tetrahydropyrido[4,3-d]pyrimidin-4-yl)-2-methylpiperazin-1-yl)acetamide. $^1$H NMR (400 MHz, CD$_3$CN) δ ppm 7.59(s, 1H) 7.10-7.19 (m, 3H) 7.03 (d, J = 1.77 Hz, 2H) 6.91 (dd, J = 7.71, 1.64 Hz, 1H) 5.77 (br. s., 1H) 3.93-4.04 (m, 2H) 3.64 (dd, J = 12.63, 2.53 Hz, 2H) 3.23-3.37 (m, 3H) 3.20 (d, J = 16.67 Hz, 1H) 3.02 (t, J = 6.06 Hz, 2H) 2.92-2.99 (m, 1H) 2.83-2.91 (m, 2H) 2.78 (d, J = 16.67 Hz, 1H) 2.61-2.69 (m, 1H) 2.45-2.54 (m, 4H) 2.35 (s, 3H) 2.24 (s, 3H) 1.22 (d, J = 6.82 Hz, 6H) 1.07 (d, J = 6.32 Hz, 3H); MS (ESI+) m/z 527.4 (M + H)$^+$. |

| | Structure | Chemical Name & Analytical Data |
|---|---|---|
| 24-L | 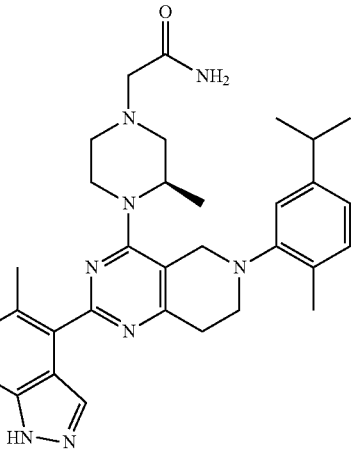 | (R)-2-(4-(6-(5-isopropyl-2-methylphenyl)-2-(5-methyl-1H-indazol-4-yl)-5,6,7,8-tetrahydropyrido[4,3-d]pyrimidin-4-yl)-3-methylpiperazin-1-yl)acetamide. $^1$H NMR (400 MHz, DMSO-$d_6$) δ ppm 8.09 (s, 1H) 7.50 (d, J = 8.34 Hz, 1H) 7.28 (d, J = 8.59 Hz, 1H) 7.10-7.18 (m, 2H) 6.99 (s, 1H) 6.88 (d, J = 7.58 Hz, 1H) 4.07-4.15 (m, 1H) 3.96-4.05 (m, 2H) 3.52-3.60 (m, 1H) 3.45 (t, J = 11.12 Hz, 1H) 3.32-3.37 (m, 2H) 3.02 (t, J = 5.31 Hz, 2H) 2.75-2.91 (m, 4H) 2.63 (d, J = 10.36 Hz, 1H) 2.55 (s, 3H) 2.38-2.46 (m, 1H) 2.24-2.31 (m, 1H) 2.23 (s, 3H) 1.31 (d, J = 6.57 Hz, 3H) 1.19 (dd, J = 6.95, 1.64 Hz, 6H); MS (ESI+) m/z 553.4 (M + H)$^+$. |

Example 25

25-A. (R)-1-(4-(6-(5-Isopropyl-2-methylphenyl)-2-(3-methyl-1H-indol-4-yl)-5,6,7,8-tetrahydropyrido[4,3-d]pyrimidin-4-yl)-3-methylpiperazin-1-yl)ethanone

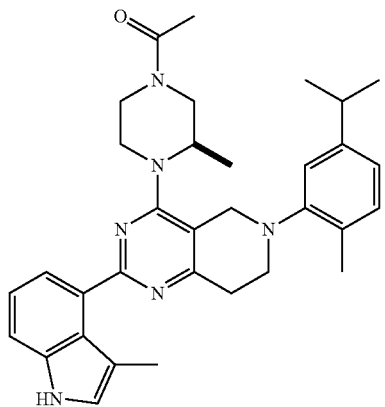 [SMILES: CC(=O)N1CCN(c2nc(-c3cccc4[nH]cc(C)c34)nc3c2CN(c2cc(C(C)C)ccc2C)CC3)[C@H](C)C1]

To a solution of (R)-tert-butyl 4-(6-(5-isopropyl-2-methylphenyl)-2-(3-methyl-1-tosyl-1H-indol-4-yl)-5,6,7,8-tetrahydropyrido[4,3-d]pyrimidin-4-yl)-3-methylpiperazine-1-carboxylate (143 mg, 0.191 mmol), prepared as described in Example 17, in DCM (3 mL), was added TFA (2 mL) and the solution was stirred at rt for 30 min. The reaction was concentrated to give the TFA salt of (R)-6-(5-isopropyl-2-methylphenyl)-2-(3-methyl-1-tosyl-1H-indol-4-yl)-4-(2-methylpiperazin-1-yl)-5,6,7,8-tetrahydropyrido[4,3-d]pyrimidine. MS (ESI+) m/z 649.4 (M+H)$^+$.

The TFA salt of (R)-6-(5-isopropyl-2-methylphenyl)-2-(3-methyl-1-tosyl-1H-indol-4-yl)-4-(2-methylpiperazin-1-yl)-5,6,7,8-tetrahydropyrido[4,3-d]pyrimidine (62 mg, 0.095 mmol) was dissolved in DCM (5 mL) and acetic anhydride (0.014 mL, 0.143 mmol) and DIEA (0.133 mL, 0.764 mmol) were added. The reaction was stirred at rt for 45 min and diluted with EtOAc, and washed successively with sat NaHCO$_3$ and brine. The organic layer was then dried over Na$_2$SO$_4$ and filtered. After concentration, the resulting residue was purified by FCC (60-90% EtOAc/heptane) to provide (R)-1-(4-(6-(5-isopropyl-2-methylphenyl)-2-(3-methyl-1-tosyl-1H-indol-4-yl)-5,6,7,8-tetrahydropyrido[4,3-d]pyrimidin-4-yl)-3-methylpiperazin-1-yl)ethanone. MS (ESI+) m/z 691.4 (M+H)$^+$.

(R)-1-(4-(6-(5-Isopropyl-2-methylphenyl)-2-(3-methyl-1-tosyl-1H-indol-4-yl)-5,6,7,8-tetrahydropyrido[4,3-d]pyrimidin-4-yl)-3-methylpiperazin-1-yl)ethanone was dissolved in EtOH (2 mL), then NH$_4$OH (0.54 mL, 13.7 mmol) was added followed by KOH (46 mg, 0.821 mmol). The mixture was heated in a microwave reactor at 100° C. for 1 h. The reaction was then diluted with EtOAc and washed with brine. After concentration, the resulting residue was purified by HPLC (C18, 15-85% acetonitrile in H$_2$O with 0.1% NH$_4$OH) to provide (R)-1-(4-(6-(5-isopropyl-2-methylphenyl)-2-(3-methyl-1H-indol-4-yl)-5,6,7,8-tetrahydropyrido[4,3-d]pyrimidin-4-yl)-3-methylpiperazin-1-yl)ethanone. $^1$H NMR (400 MHz, CD$_3$CN) δ ppm 9.15 (br. s., 1 H) 7.46 (d, J=8.08 Hz, 1 H) 7.26 (d, J=7.33 Hz, 1 H) 7.16 (dd, J=16.29, 7.96 Hz, 2 H) 7.06 (d, J=13.64 Hz, 2 H) 6.91 (dd, J=7.58, 1.52 Hz, 1 H) 3.98-4.16 (m, 4 H) 3.46-3.67 (m, 2 H) 3.26-3.46 (m, 4 H) 2.84-3.13 (m, 4 H) 2.26 (s, 3 H) 2.00-2.06 (m, 6 H) 1.23 (d, J=6.82 Hz, 6H) 1.11-1.21 (m, 3 H); MS (ESI+) m/z 537.4 (M+H)$^+$.

The following compounds were prepared in a similar manner.

| | Structure | Chemical Name & Analytical Data |
|---|---|---|
| 25-B | 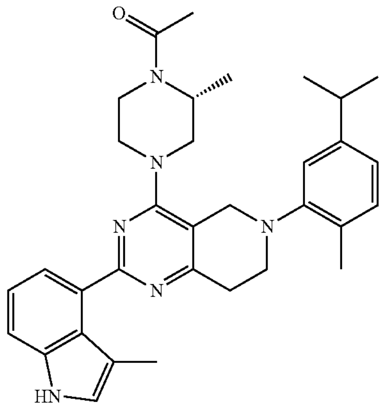 [SMILES: CC(=O)N1CCN(c2nc(-c3cccc4[nH]cc(C)c34)nc3c2CN(c2cc(C(C)C)ccc2C)CC3)C[C@H]1C] | (R)-1-(4-(6-(5-isopropyl-2-methylphenyl)-2-(3-methyl-1H-indol-4-yl)-5,6,7,8-tetrahydropyrido[4,3-d]pyrimidin-4-yl)-2-methylpiperazin-1-yl)ethanone. $^1$H NMR (400 MHz, DMSO-d$_6$) δ ppm 10.91 (s, 1H) 7.40-7.43 (m, 1H) 7.24 (d, J = 6.57 Hz, 1H) 7.09-7.16 (m, 3H) 7.03 (br. s., 1H) 6.87 (dd, J = 7.71, 1.39 Hz, 1H) 4.24-4.70 (m, 1H) 4.03-4.22 (m, 2H) 3.70-3.86 (m, 3H) 3.33-3.49 (m, 2H) 3.04-3.17 (m, 1H) 2.78-3.04 (m, 5H) 2.23 (s, 3H) 1.96-2.05 (m, 6H) 1.31 (d, J = 7.07 Hz, 1H) 1.20 (m 8H); MS (ESI+) m/z 537.4 (M + H)$^+$. |
| 25-C | 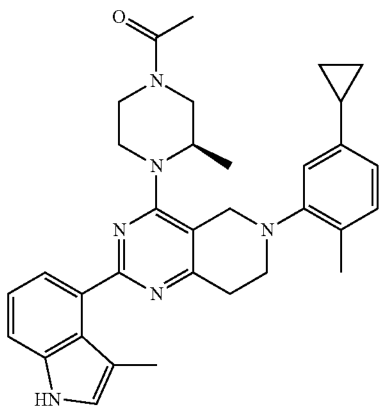 [SMILES: CC(=O)N1CCN(c2nc(-c3cccc4[nH]cc(C)c34)nc3c2CN(c2cc(C4CC4)ccc2C)CC3)[C@H](C)C1] | (R)-1-(4-(6-(5-cyclopropyl-2-methylphenyl)-2-(3-methyl-1H-indol-4-yl)-5,6,7,8-tetrahydropyrido[4,3-d]pyrimidin-4-yl)-3-methylpiperazin-1-yl)ethanone. $^1$H NMR (400 MHz, DMSO-d$_6$) δ ppm 10.90 (s, 1H) 7.41 (dd, J = 7.96, 1.14 Hz, 1H) 7.22 (d, J = 6.57 Hz, 1H) 7.05-7.16 (m, 3H) 6.86 (d, J = 1.52 Hz, 1H) 6.69 (dd, J = 7.83, 1.52 Hz, 1H) 3.98-4.22 (m, 4H) 3.70-3.83 (m, 1H) 3.45-3.70 (m, 2H) 3.32-3.43 (m, 2H) 3.20-3.27 (m, 1H) 2.88-3.07 (m, 3H) 2.20 (s, 3H) 1.98-2.06 (m, 6H) 1.83-1.93 (m, 1H) 1.06-1.20 (m, 3H) 0.88-0.95 (m, 2H) 0.59-0.65 (m, 2H); MS (ESI+) m/z 535.4 (M + H)$^+$. |
| 25-D | 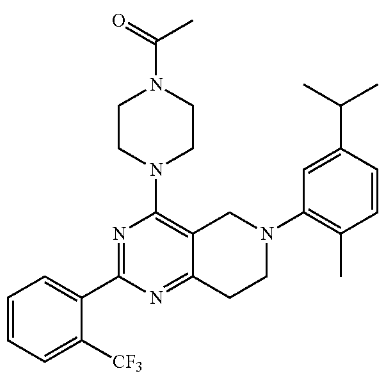 [SMILES: CC(=O)N1CCN(c2nc(-c3ccccc3C(F)(F)F)nc3c2CN(c2cc(C(C)C)ccc2C)CC3)CC1] | 1-(4-(6-(5-isopropyl-2-methylphenyl)-2-(2-(trifluoromethyl)phenyl)-5,6,7,8-tetrahydropyrido[4,3-d]pyrimidin-4-yl)piperazin-1-yl)ethanone. $^1$H NMR (400 MHz, DMSO-d$_6$) δ ppm 7.84 (d, J = 7.83 Hz, 1H) 7.73-7.79 (m, 2H) 7.64-7.70 (m, 1H) 7.10 (d, J = 7.83 Hz, 1H) 7.00 (d, J = 1.26 Hz, 1H) 6.88 (dd, J = 7.58, 1.52 Hz, 1H) 4.01 (s, 2H) 3.54 (dd, J = 6.32, 3.28 Hz, 4H) 3.42-3.48 (m, 2H) 3.38 (d, J = 6.06 Hz, 2H) 2.97 (t, J = 5.81 Hz, 2H) 2.85 (dt, J = 13.83, 6.85 Hz, 1H) 2.20 (s, 3H) 2.01 (s, 3H) 1.19 (d, J = 6.82 Hz, 6H); MS (ESI+) m/z 538.1 (M + H)$^+$. |
| 25-E | 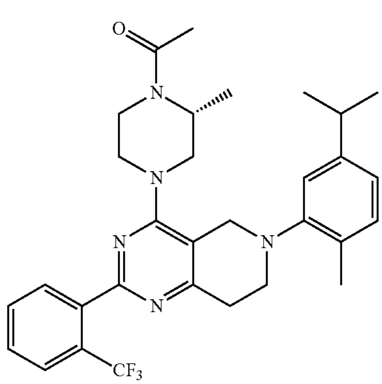 [SMILES: CC(=O)N1CCN(c2nc(-c3ccccc3C(F)(F)F)nc3c2CN(c2cc(C(C)C)ccc2C)CC3)C[C@H]1C] | (R)-1-(4-(6-(5-isopropyl-2-methylphenyl)-2-(2-(trifluoromethyl)phenyl)-5,6,7,8-tetrahydropyrido[4,3-d]pyrimidin-4-yl)-2-methylpiperazin-1-yl)ethanone. $^1$H NMR (400 MHz, CD$_2$Cl$_2$) δ ppm 7.79 (d, J = 7.58 Hz, 2H) 7.67 (t, J = 7.45 Hz, 1H) 7.59 (t, J = 7.58 Hz, 1H) 7.14 (d, J = 7.58 Hz, 1H) 6.97 (s, 1H) 6.92 (dd, J = 7.83, 1.52 Hz, 1H) 3.93-4.15 (m, 3H) 3.59-3.82 (m, 2H) 3.43-3.59 (m, 1H) 3.25-3.43 (m, 3H) 3.16 (br. s., 2H) 2.97-3.11 (m, 1H) 2.84-2.97 (m, 1H) 2.28 (s, 3H) 2.06 (d, J = 8.84 Hz, 3H) 1.20-1.35 (m, 10 H); MS (ESI+) m/z 552.2 (M + H)$^+$. |

| | Structure | Chemical Name & Analytical Data |
|---|---|---|
| 25-F | 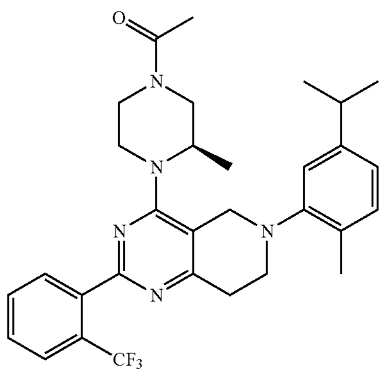 [SMILES: CC(=O)N1CCN(c2nc(-c3ccccc3C(F)(F)F)nc3c2CN(c2cc(C(C)C)ccc2C)CC3)[C@H](C)C1] | (R)-1-(4-(6-(5-isopropyl-2-methylphenyl)-2-(2-(trifluoromethyl)phenyl)-5,6,7,8-tetrahydropyrido[4,3-d]pyrimidin-4-yl)-3-methylpiperazin-1-yl)ethanone. $^1$H NMR (400 MHz, DMSO-d$_6$) δ ppm 7.84 (d, J = 7.83 Hz, 1H) 7.72-7.79 (m, 2H) 7.64-7.71 (m. 1H) 7.10 (d, J = 7.83 Hz, 1H) 6.98 (s, 1H) 6.87 (dd, J = 7.71, 1.39 Hz, 1H) 3.94-4.18 (m, 4H) 3.52-3.70 (m, 2H) 3.43 (dd, J = 13.14, 3.79 Hz, 1H) 3.37 (br. s., 1H) 3.17-3.27 (m, 1H) 2.90-3.03 (m, 3H) 2.78-2.90 (m, 2H) 2.20 (s, 3H) 1.96-2.07 (m, 3H) 1.05-1.22 (m, 9H); MS (ESI+) m/z 552.3 (M + H)$^+$. |
| 25-G | 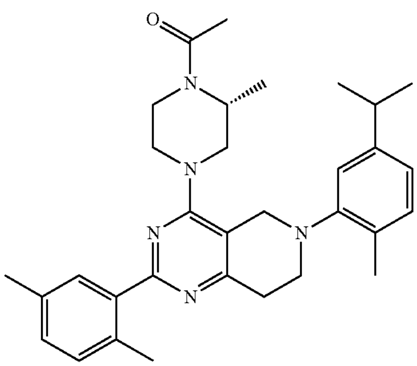 [SMILES: CC(=O)N1CCN(c2nc(-c3cc(C)ccc3C)nc3c2CN(c2cc(C(C)C)ccc2C)CC3)C[C@H]1C] | (R)-1-(4-(2-(2,5-dimethylphenyl)-6-(5-isopropyl-2-methylphenyl)-5,6,7,8-tetrahydropyrido[4,3-d]pyrimidin-4-yl)-2-methylpiperazin-1-yl)ethanone. $^1$H NMR (400 MHz, DMSO-d$_6$, at 100° C.) δ ppm 7.63 (s, 1H) 7.09-7.17 (m, 3H) 7.00 (s, 1H) 6.87 (d, J = 8.08 Hz, 1H) 4.46 (br. s., 1H) 3.94-4.15 (m, 3H) 3.83 (d, J = 12.76 Hz, 1H) 3.70 (d, J = 13.64 Hz, 1H) 3.24-3.43 (m, 3H) 3.18 (dd, J = 13.20, 3.47 Hz, 1H) 3.04 (d, J = 1.77 Hz, 1H) 2.79-2.92 (m, 2H) 2.34 (s, 3H) 2.24 (s, 3H) 2.02 (s, 3H) 1.16-1.31 (m, 9H); MS (ESI+) m/z 512.4 (M + H)$^+$. |
| 25-H | 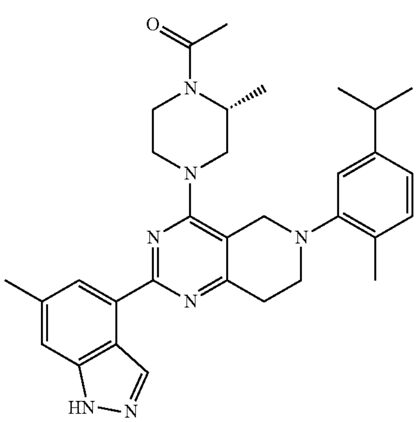 [SMILES: CC(=O)N1CCN(c2nc(-c3cc(C)cc4[nH]ncc34)nc3c2CN(c2cc(C(C)C)ccc2C)CC3)C[C@H]1C] | (R)-1-(4-(6-(5-isopropyl-2-methylphenyl)-2-(5-methyl-1H-indazol-4-yl)-5,6,7,8-tetrahydropyrido[4,3-d]pyrimidin-4-yl)-2-methylpiperazin-1-yl)ethanone. $^1$H NMR (400 MHz, DMSO-d$_6$) δ ppm 13.02 (br. s., 1H) 8.13 (s, 1H) 7.52 (d, J = 7.07 Hz, 1H) 7.30 (d, J = 8.34 Hz, 1H) 6.99-7.21 (m, 2H) 6.88 (d, J = 7.58 Hz, 1H) 4.17 (d, J = 14.91 Hz, 3H) 3.85 (br. s., 1H) 3.77 (d, J = 12.13 Hz, 2H) 3.39-3.53 (m, 1H) 3.27 (br. s., 2H) 3.12 (br. s., 1H) 3.05 (br. s., 2H) 2.93-3.02 (m, 1H) 2.87 (dt, J = 13.64, 6.82 Hz, 1H) 2.55 (s, 3H) 2.24 (s, 3H) 2.03 (d, J = 17.68 Hz, 3H) 1.31 (d, J = 5.31 Hz, 1H) 1.09-1.26 (m, 8H); MS (ESI+) m/z 538.4 (M + H)$^+$. |
| 25-I | 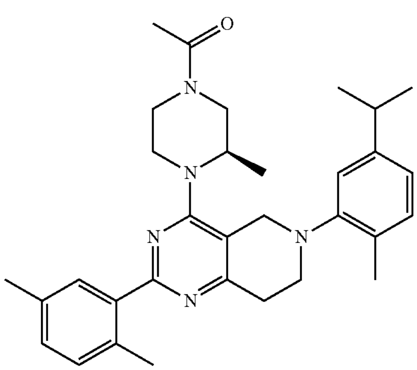 [SMILES: CC(=O)N1CCN(c2nc(-c3cc(C)ccc3C)nc3c2CN(c2cc(C(C)C)ccc2C)CC3)[C@H](C)C1] | (R)-1-(4-(2-(2,5-dimethylphenyl)-6-(5-isopropyl-2-methylphenyl)-5,6,7,8-tetrahydropyrido[4,3-d]pyrimidin-4-yl)-3-methylpiperazin-1-yl)ethanone $^1$H NMR (400 MHz, DMSO-d$_6$, at 120° C.) δ ppm 7.62 (s, 1H) 7.09-7.17 (m, 3H) 6.98 (d, J = 1.89 Hz, 1H) 6.88 (dd, J = 7.64, 1.83 Hz, 1H) 4.00-4.21 (m, 3H) 3.93 (br. s., 1H) 3.76 (br. s., 1H) 3.51-3.59 (m, 1H) 3.32-3.42 (m, 4H) 3.24 (br. s., 1H) 3.01 (t, J = 6.19 Hz, 2H) 2.85-2.95 (m, 4H) 2.34 (s, 3H) 2.25 (s, 3H) 2.03 (s, 3H) 1.22 (d, J = 6.95 Hz, 6H) 1.17 (d, J = 6.44 Hz, 3H); MS (ESI+) m/z 512.4 (M + H)$^+$. |

Example 26

26-A. (R)-1-(4-(6-Benzyl-2-(3-methyl-1-tosyl-1H-indol-4-yl)-5,6,7,8-tetrahydropyrido[4,3-d]pyrimidin-4-yl)-3-methylpiperazin-1-yl)ethanone

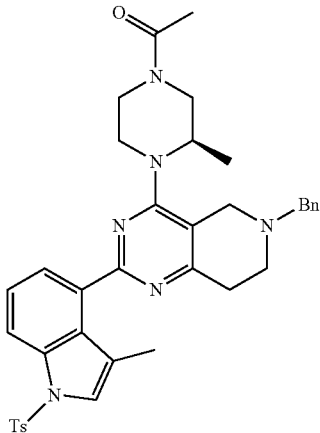 [SMILES: CC(=O)N1CCN(c2nc(-c3cccc4c3c(C)cn4S(=O)(=O)c3ccc(C)cc3)nc3c2CN(Cc2ccccc2)CC3)[C@H](C)C1]

A mixture of 6-benzyl-2,4-dichloro-5,6,7,8-tetrahydropyrido[4,3-d]pyrimidine (0.655 g, 1.89 mmol), (R)-1-(3-methylpiperazin-1-yl)ethanone 2,2,2-trifluoroacetate (1 g, 2.84 mmol) and DIEA (2.65 mL, 15.2 mmol) in i-PrOH (25 mL) was heated to 80° C. for 48 h. The reaction mixture was then diluted with EtOAc, and washed successively with sat aq NaHCO₃ and brine. The organic layer was then dried over Na₂SO₄, filtered and concentrated. The resulting residue was diluted with DCM and filtered to remove solid. The filtrate was concentrated and purified by FCC (0-5% MeOH in DCM) to provide (R)-1-(4-(6-benzyl-2-chloro-5,6,7,8-tetrahydropyrido[4,3-d]pyrimidin-4-yl)-3-methylpiperazin-1-yl)ethanone. MS (ESI+) m/z 400.3 (M+H)⁺.

A mixture of (R)-1-(4-(6-benzyl-2-chloro-5,6,7,8-tetrahydropyrido[4,3-d]pyrimidin-4-yl)-3-methylpiperazin-1-yl)ethanone (0.27 g, 0.675 mmol), 3-methyl-4-(4,4,5,5-tetramethyl-1,3,2-dioxaborolan-2-yl)-1-tosyl-1H-indole (0.305 g, 0.743 mmol) and 2 M aq Na₂CO₃ (1.1 mL, 2.19 mmol) in DME (3 mL) was degassed by sparging with argon. Pd(PPh₃)₄ (0.117 g, 0.101 mmol) was then added and the mixture was heated in a microwave reactor at 140° C. for 1.5 h. The reaction was filtered and diluted with EtOAc, washed successively with sat aq Na₂CO₃ and, brine, and then dried over Na₂SO₄. After concentration the residue was purified by FCC (5-70% EtOAc/heptane) to provide (R)-1-(4-(6-benzyl-2-(3-methyl-1-tosyl-1H-indol-4-yl)-5,6,7,8-tetrahydropyrido[4,3-d]pyrimidin-4-yl)-3-methylpiperazin-1-yl)ethanone. MS (ESI+) m/z 649.3 (M+H)⁺.

26-B. (R)-1-(3-Methyl-4-(2-(3-methyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)ethanone

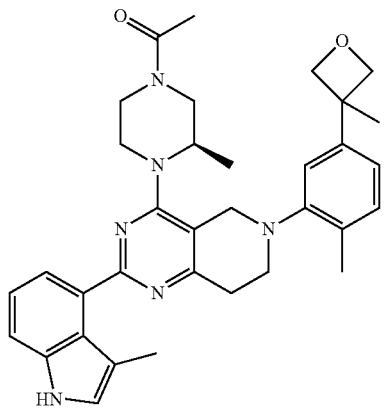 [SMILES: CC(=O)N1CCN(c2nc(-c3cccc4[nH]cc(C)c34)nc3c2CN(c2cc(C4(C)COC4)ccc2C)CC3)[C@H](C)C1]

A mixture of (R)-1-(4-(6-benzyl-2-(3-methyl-1-tosyl-1H-indol-4-yl)-5,6,7,8-tetrahydropyrido[4,3-d]pyrimidin-4-yl)-3-methylpiperazin-1-yl)ethanone (0.35 g, 0.539 mmol), acetic acid (0.154 mL, 2.70 mmol), THF (9 mL) and H₂O (3 mL) was degassed via vacuum and recharged with nitrogen gas (2×). Then 20 mol % Pd(OH)₂/carbon (0.114 g, 0.162 mmol) was added and the mixture was degassed via vacuum and placed under an atmosphere of hydrogen. The mixture was stirred at rt under H₂ atmosphere via balloon for 2 h and then filtered. The solution was then diluted with EtOAc and washed with sat aq NaHCO₃. The organic layer was washed with brine, dried over Na₂SO₄, filtered and concentrated to provide (R)-1-(3-methyl-4-(2-(3-methyl-1-tosyl-1H-indol-4-yl)-5,6,7,8-tetrahydropyrido[4,3-d]pyrimidin-4-yl)piperazin-1-yl)ethanone, which was used without the need for further purification. MS (ESI+) m/z 559.3 (M+H)⁺.

A mixture of (R)-1-(3-methyl-4-(2-(3-methyl-1-tosyl-1H-indol-4-yl)-5,6,7,8-tetrahydropyrido[4,3-d]pyrimidin-4-yl)piperazin-1-yl)ethanone (0.155 g, 0.278 mmol), 2-methyl-5-(3-methyloxetan-3-yl)phenyl trifluoromethanesulfonate (0.086 g, 0.278 mmol) prepared as described in Example 13, cesium carbonate (0.272 g, 0.834 mmol) and chloro(2-dicyclohexylphosphino-2'-4'-6'-triisopropyl-1,1'-biphenyl)[2-(2-aminoethyl)phenyl]palladium(II)-methyl-t-butylether adduct (CAS#1028276-56-5) (0.031 g, 0.042 mmol) in THF (4 mL) was heated in a microwave reactor at 140° C. for 3 h. The reaction was then filtered and concentrated, the resulting residue was purified by FCC (60-100% EtOAc/DCM) to provide (R)-1-(3-methyl-4-(2-(3-methyl-1-tosyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)ethanone. MS (ESI+) m/z 719.3 (M+H)⁺.

A mixture of (R)-1-(3-methyl-4-(2-(3-methyl-1-tosyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)ethanone (0.104 g, 0.145 mmol), 30% ammonium hydroxide (0.854 mL, 21.70 mmol) and KOH (0.073 g, 1.302 mmol) in EtOH (4 mL) was heated in a microwave reactor at 100° C. for 30 min. The mixture was concentrated and partially purified by FCC (0-6% MeOH in DCM). Further purification with HPLC (C18, 15-85% CH₃CN in H₂O with 0.1% NH₄OH) provided (R)-1-(3-methyl-4-(2-(3-methyl-1H-indol-4-yl)-6-(2-methyl-5-(3-methyloxetan-3-yl)phenyl)-5,6,7,8-tetrahydropyrido[4,3-d]pyrimidin-4-yl)piperazin-1-yl)ethanone. ¹H NMR (400 MHz, DMSO-d₆ at 120° C.) δ ppm 10.50 (br. s., 1 H) 7.42 (d, J=8.08 Hz, 1 H) 7.25 (d, J=7.20 Hz, 1 H) 7.19 (d, J=7.83 Hz, 1 H) 7.07-7.15 (m, 2 H) 6.97 (s, 1 H) 6.90 (d, J=7.96 Hz, 1 H) 4.79 (d, J=5.43 Hz, 2 H) 4.53 (d, J=5.05 Hz, 2 H) 4.05-4.19 (m, 3 H) 3.91 (br. s., 1 H) 3.75 (br. s., 1 H) 3.56 (d, J=13.26 Hz, 1 H) 3.22-3.48 (m, 5 H) 3.00 (t, J=5.62 Hz, 2 H) 2.29 (s, 3 H) 2.07 (s, 3 H) 1.99-2.04 (m, 3 H) 1.65 (s, 3 H) 1.17 (d, J=6.44 Hz, 3 H); MS (ESI+) m/z 565.4 (M+H)⁺.

EXAMPLE 27

27-A. Racemic tert-Butyl 4-(6-benzyl-2-chloro-5,6,7,8-tetrahydropyrido[4,3-d]pyrimidin-4-yl)-(trans)-2,5-dimethylpiperazine-1-carboxylate

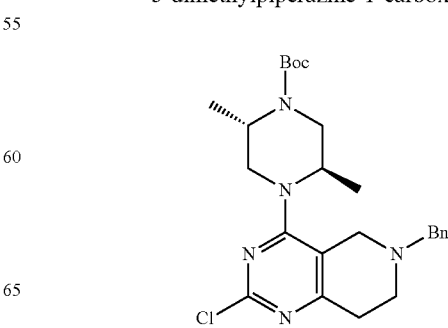

A mixture of 6-benzyl-2,4-dichloro-5,6,7,8-tetrahydropyrido[4,3-d]pyrimidine (2.0 g, 6.80 mmol), (trans)-2,5-dimethylpiperazine dihydrochloride (7.63 g, 40.8 mmol), DIEA (15.4 mL, 88 mmol) and iPrOH (180 mL) was heated at 80° C. for 3.5 days. At that time the reaction was diluted with diethyl ether and the solid was removed by filtration. The filtrate was then washed with brine and the organic layer was dried ($Na_2SO_4$), filtered and concentrated to provide crude racemic 6-benzyl-2-chloro-4-(trans)-2,5-dimethylpiperazin-1-yl)-5,6,7,8-tetrahydropyrido[4,3-d]pyrimidine, which was then carried to the next step without further purification. MS (ESI+) m/z 372.2 $(M+H)^+$ A solution of racemic 6-benzyl-2-chloro-4-(trans)-2,5-dimethylpiperazin-1-yl)-5,6,7,8-tetrahydropyrido[4,3-d]pyrimidine (2.53 g, 6.80 mmol), $Boc_2O$ (2.26 g, 10.2 mmol), DIEA (3.6 mL, 20.4 mmol) and DCM (30 mL) was stirred at rt for 30 min. At that point the reaction was diluted with DCM and washed with sat aq $NaHCO_3$ and brine. The organic layer was dried ($Na_2SO_4$), filtered and concentrated. The residue was then purified by FCC (10-50% EtOAc/heptane) to give racemic tert-butyl 4-(6-benzyl-2-chloro-5,6,7,8-tetrahydropyrido[4,3-d]pyrimidin-4-yl)-(trans)-2,5-dimethylpiperazine-1-carboxylate. MS (ESI+) m/z 472.2 $(M+H)^+$.

27-B. Racemic tert-Butyl 4-(6-benzyl-2-(2,6-dimethylphenyl)-5,6,7,8-tetrahydropyrido[4,3-d]pyrimidin-4-yl)-(trans)-2,5-dimethylpiperazine-1-carboxylate

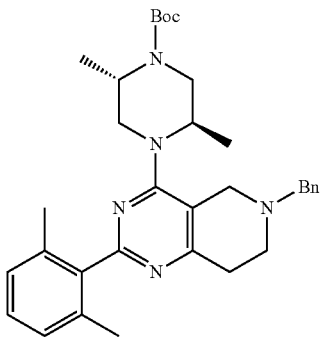 [SMILES: Cc1cccc(C)c1-c1nc2c(c(N3C[C@H](C)N(C(=O)OC(C)(C)C)C[C@H]3C)n1)CN(Cc1ccccc1)CC2]

To a solution of racemic tert-butyl 4-(6-benzyl-2-chloro-5,6,7,8-tetrahydropyrido[4,3-d]pyrimidin-4-yl)-(trans)-2,5-dimethylpiperazine-1-carboxylate (0.54 g, 1.14 mmol) in DME (9 mL) was added 2,6-dimethylphenylboronic acid (0.257 g, 1.72 mmol), $Pd(Ph_3P)_4$ (0.198 g, 0.172 mmol) and a 2 M aq solution of sodium carbonate (1.9 mL). The reaction was heated at 140° C. in a microwave reactor for 1.75 h. The reaction was filtered and diluted with EtOAc and brine. The organic layer was separated and then dried ($Na_2SO_4$), filtered and concentrated. The residue was then purified by FCC (55-80% EtOAc/heptane) to give the title compound. MS (ESI+) m/z 542.5 $(M+H)^+$.

27-C. Racemic tert-Butyl 4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazine-1-carboxylate

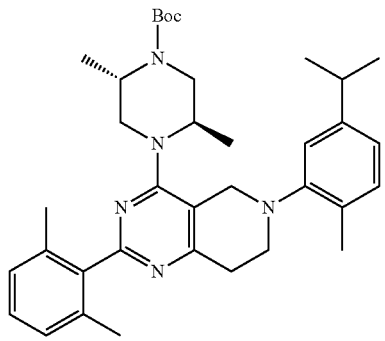 [SMILES: Cc1ccc(C(C)C)cc1N1CCc2nc(-c3c(C)cccc3C)nc(N3C[C@H](C)N(C(=O)OC(C)(C)C)C[C@H]3C)c2C1]

To a solution of racemic tert-butyl 4-(6-benzyl-2-(2,6-dimethylphenyl)-5,6,7,8-tetrahydropyrido[4,3-d]pyrimidin-4-yl)-(trans)-2,5-dimethylpiperazine-1-carboxylate (0.43 g, 0.794 mmol) in THF (9 mL) and water (3 mL) was added acetic acid (227 μL, 3.97 mmol) and 20% $Pd(OH)_2$ on carbon (50% wet) (0.167 g, 0.238 mmol). The flask was evacuated and purged with hydrogen gas and then placed under a hydrogen atmosphere. After stirring at rt for 1 h the mixture was filtered over Celite®, and the Celite® pad was washed with EtOAc. The filtrate was washed with sat aq $NaHCO_3$ and then the organic layer was dried over anhydrous sodium sulfate, filtered, and concentrated under reduced pressure to obtain racemic tert-butyl 4-(2-(2,6-dimethylphenyl)-5,6,7,8-tetrahydropyrido[4,3-d]pyrimidin-4-yl)-(trans)-2,5-dimethylpiperazine-1-carboxylate. MS (ESI+) m/z 452.3 $(M+H)^+$.

To a solution of racemic tert-butyl 4-(2-(2,6-dimethylphenyl)-5,6,7,8-tetrahydropyrido[4,3-d]pyrimidin-4-yl)-(trans)-2,5-dimethylpiperazine-1-carboxylate (0.187 g, 0.414 mmol) in THF (4 mL) was added 5-isopropyl-2-methylphenyl trifluoromethanesulfonate (0.175 g, 0.620 mmol) prepared as described in Example 15, $Cs_2CO_3$ (0.404 g, 1.24 mmol) and chloro(2-dicyclohexylphosphino-2'-4'-6'-triisopropyl-1,1'-biphenyl)[2-(2-aminoethyl)phenyl]palladium(II)-methyl-t-butylether adduct (0.046 mg, 0.062 mmol). The reaction was purged with argon and was heated at 130° C. for 3 h in a microwave reactor. The mixture was then concentrated and the residue was purified via FCC (10-35% EtOAc/heptane) to give racemic tert-butyl 4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazine-1-carboxylate. MS (ESI+) m/z 584.4 $(M+H)^+$.

27-D. Racemic 1-(4-(2-(2,6-Dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)ethanone

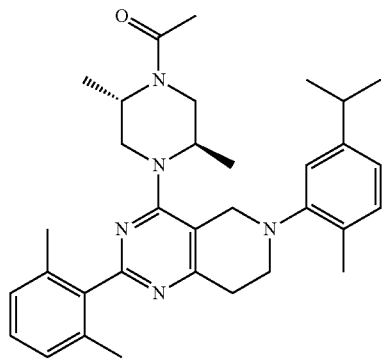 [SMILES: CC(=O)N1C[C@@H](C)N(c2nc(-c3c(C)cccc3C)nc3c2CN(c2cc(C(C)C)ccc2C)CC3)C[C@@H]1C]

To a solution of racemic tert-butyl 4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazine-1-carboxylate (0.227 g, 0.389 mmol) and DCM (3 mL) at rt was added TFA (1 mL). After 20 min an additional 0.5 mL aliquot of TFA was added. After 1 h more the reaction was concentrated under reduced pressure to give 2-(2,6-dimethylphenyl)-4-((trans)-2,5-dimethylpiperazin-1-yl)-6-(5-isopropyl-2-methylphenyl)-5,6,7,8-tetrahydropyrido[4,3-d]pyrimidine as a TFA salt. MS (ESI+) m/z 484.4 $(M+H)^+$ To a solution of the TFA salt of 2-(2,6-dimethylphenyl)-4-((trans)-2,5-dimethylpiperazin-1-yl)-6-(5-isopropyl-2-methylphenyl)-5,6,7,8-tetrahydropyrido[4,3-d]pyrimidine TFA salt (0.113 g, 0.233 mmol), DIEA (0.33 mL, 1.87 mmol) and DCM (5 mL) was added Ac$_2$O (0.044 mL, 0.467 mmol). The reaction was stirred at rt for 1 h before being diluted with EtOAc. The solution was washed with sat aq NaHCO$_3$ and then brine before the organic layers were separated and then dried (Na$_2$SO$_4$), filtered and concentrated. The residue was then purified by FCC (35-45% EtOAc/heptane) to give racemic-1-(4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)ethanone. $^1$H NMR (400 MHz, DMSO-d$_6$, at 100° C.) δ ppm 7.14-7.19 (m, 1 H) 7.05-7.12 (m, 3 H) 6.91 (d, J=1.39 Hz, 1 H) 6.86 (dd, J=7.71, 1.52 Hz, 1 H) 4.29 (dt, J=6.22, 3.27 Hz, 1 H) 4.12-4.18 (m, 1 H) 4.00-4.07 (m, 1 H) 3.50-3.58 (m, 1 H) 3.41-3.47 (m, 1 H) 3.39 (t, J=6.19 Hz, 2 H) 2.93 (br. s., 4 H) 2.84 (dt, J=13.80, 6.93 Hz, 1 H) 2.52 (br. s., 1 H) 2.25 (s, 3 H) 2.08 (s, 6 H) 2.01 (s, 3 H) 1.19 (dd, J=6.95, 2.40 Hz, 6 H) 1.10-1.17 (m, 6 H); MS (ESI+) m/z 526.4 (M+H)$^+$.

The racemic-1-(4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)ethanone was then separated by chiral HPLC (WhelkO column; 40% EtOH/heptanes; 1.2 mL/min to give the following two compounds:

27-E. Enantiomer-1

R$_t$ 9.78 min, (WhelkO1 20×250 mm column, 50% EtOH in heptane). $^1$H NMR (400 MHz, DMSO-d$_6$, at 120° C.) δ ppm 7.14-7.19 (m, 1 H) 7.05-7.12 (m, 3 H) 6.92 (d, J=1.52 Hz, 1 H) 6.87 (dd, J=7.77, 1.58 Hz, 1 H) 4.40 (br. s., 1 H) 4.27-4.34 (m, 1 H) 4.10-4.19 (m, 1 H) 4.01-4.10 (m, 1 H) 3.52-3.58 (m, 1 H) 3.37-3.48 (m, 4 H) 2.94 (t, J=6.25 Hz, 2 H) 2.86-2.89 (m, 1 H) 2.82 (br. s., 1H) 2.25 (s, 3 H) 2.09 (s, 6 H) 2.01 (s, 3 H) 1.20 (dd, J=6.95, 2.02 Hz, 6 H) 1.15 (dd, J=12.82, 6.63 Hz, 6H); MS (ESI+) m/z 526.4 (M+H)$^+$ 27-F. Enantiomer-2

R$_t$ 14.69 min, (WhelkO1 20×250 mm column, 50% EtOH in heptane). $^1$H NMR (400 MHz, DMSO-d$_6$, 120° C.) δ ppm 7.14-7.19 (m, 1 H), 7.05-7.12 (m, 3 H) 6.92 (s, 1 H) 6.87 (dd, J=7.77, 1.45 Hz, 1 H) 4.34-4.49 (m, 1 H) 4.30 (dt, J=6.76, 3.44 Hz, 1 H) 4.10-4.19 (m, 1 H) 4.01-4.10 (m, 1 H) 3.52-3.58 (m, 1 H) 3.37-3.48 (m, 4 H) 2.94 (t, J=6.13 Hz, 2 H) 2.81-2.84 (m, 2 H) 2.26 (s, 3H) 2.09 (s, 6 H) 2.01 (s, 3 H) 1.20 (dd, J=6.88, 1.96 Hz, 6 H) 1.15 (dd, J=12.82, 6.63 Hz, 6 H); MS (ESI+) m/z 526.4 (M+H)$^+$ The following compound was prepared in a similar manner.

27-G. Racemic 1-((trans)-4-(6-(5-Isopropyl-2-methylphenyl)-2-(3-methyl-1H-indol-4-yl)-5,6,7,8-tetrahydropyrido[4,3-d]pyrimidin-4-yl)-2,5-dimethylpiperazin-1-yl)ethanone

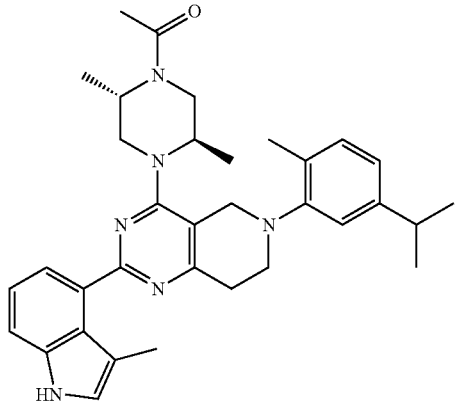 [SMILES: CC(=O)N1C[C@@H](C)N(c2nc(-c3cccc4[nH]cc(C)c34)nc3c2CN(c2cc(C(C)C)ccc2C)CC3)C[C@@H]1C]

$^1$H NMR (400 MHz, DMSO-d$_6$, 100° C.) δ ppm 10.58 (br. s., 1 H) 7.41 (d, J=8.21 Hz, 1 H) 7.23-7.25 (m, 1 H) 7.08-7.13 (m, 3 H) 6.97 (s, 1 H) 6.87 (dd, J=8.08, 1.26 Hz, 1 H) 4.33 (d, J=4.67 Hz, 1 H) 4.09-4.17 (m, 1 H) 4.00-4.09 (m, 1 H) 3.54 (br. s., 2 H) 3.39 (t, J=6.51 Hz, 2 H) 2.97-3.02 (m, 5 H) 2.81-2.90 (m, 1 H) 2.25 (s, 3 H) 1.99-2.08 (m, 6 H) 1.14-1.23 (m, 12 H). MS (ESI+) m/z 551.4 (M+H)$^+$.

Example 28

28-A. Racemic-2-(-4-(2-(2,6-Dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)acetamide

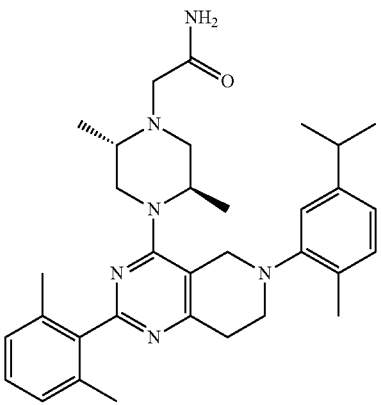 [SMILES: Cc1ccc(C(C)C)cc1N1CCc2nc(-c3c(C)cccc3C)nc(N3C[C@H](C)N(CC(N)=O)C[C@H]3C)c2C1]

The title compound was prepared in a similar manner to those described in Examples 24 and 28 above. MS (ESI+) m/z 541.3 (M+H)$^+$. Racemic-2+4-(2-(2,6-dimethylphenyl)-6-(5-isopropyl-2-methylphenyl)-5,6,7,8-tetrahydropyrido[4,3-d]pyrimidin-4-yl)-(trans)-2,5-dimethylpiperazin-1-yl)acetamide was then separated by chiral HPLC (Cel-LUX2 column; 30% EtOH/heptanes; 1.2 mL/min) to give the two corresponding enantiomers:

28-B. Enantiomer-1

R$_t$ 11.83 min, (Cel-LUX2 20×250 mm column, 30% EtOH in heptane). $^1$H NMR (400 MHz, DMSO-d$_6$) δ ppm 7.14-7.21 (m, 2 H) 7.10 (t, J=7.83 Hz, 4 H) 6.83-6.91 (m, 2 H) 4.01-4.13 (m, 2 H) 3.88 (br. s., 1 H) 3.32-3.42 (m, 3 H) 2.95-3.02 (m, 1 H) 2.91 (d, J=9.09 Hz, 4 H) 2.83 (dt, J=12.88, 6.19 Hz, 3 H) 2.24-2.30 (m, 1 H) 2.22 (s, 3 H) 2.03 (s, 6 H) 1.16 (dd, J=6.82, 3.28 Hz, 6 H) 1.11 (d, J=6.32 Hz, 3 H) 0.96 (d, J=6.32 Hz, 3 H); MS (ESI+) m/z 541.4 (M+H)$^+$.

28-C. Enantiomer-2

R$_t$ 16.10 min, (Cel-LUX2 20×250 mm column, 30% EtOH in heptane). $^1$H NMR (400 MHz, DMSO-d$_6$) δ ppm 7.15-7.21 (m, 2 H) 7.10 (t, J=7.83 Hz, 4 H) 6.84-6.90 (m, 2 H) 4.01-4.12 (m, 2 H) 3.88 (br. s., 1 H) 3.33-3.42 (m, 3 H) 2.95-3.01 (m, 1 H) 2.91 (d, J=9.09 Hz, 4 H) 2.79-2.86 (m, 3 H) 2.27 (dd, J=11.37, 5.81 Hz, 1 H) 2.22 (s, 3 H) 2.03 (s, 6 H) 1.16 (dd, J=6.82, 3.28 Hz, 6 H) 1.11 (d, J=6.32 Hz, 3 H) 0.96 (d, J=6.32 Hz, 3 H); MS (ESI+) m/z 541.4 (M+H)$^+$.

The following compound was prepared in a similar manner.

28-D. Racemic-2-(4-(6-(5-Isopropyl-2-methylphenyl)-2-(3-methyl-1H-indol-4-yl)-5,6,7,8-tetrahydropyrido[4,3-d]pyrimidin-4-yl)-(trans)-2,5-dimethylpiperazin-1-yl)acetamide

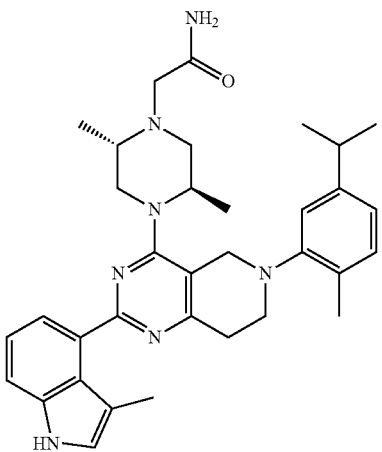 [SMILES: Cc1ccc(C(C)C)cc1N1CCc2nc(-c3cccc4[nH]cc(C)c34)nc(N3C[C@H](C)N(CC(N)=O)C[C@H]3C)c2C1]

¹H NMR (400 MHz, DMSO-d₆) δ ppm 10.90 (s, 1 H) 7.42 (dd, J=8.08, 1.01 Hz, 1 H) 7.20-7.23 (m, 1 H) 7.10-7.19 (m, 5 H) 6.94 (d, J=1.52 Hz, 1 H) 6.87 (dd, J=7.83, 1.52 Hz, 1 H) 3.99-4.12 (m, 2 H) 3.89-3.97 (m, 1 H) 3.34-3.44 (m, 3 H) 3.00-3.10 (m, 1 H) 2.89-3.00 (m, 4 H) 2.79-2.88 (m, 3 H) 2.28 (dd, J=11.75, 5.68 Hz, 1 H) 2.22 (s, 3 H) 2.03 (s, 3 H) 1.18 (dd, J=6.82, 3.03 Hz, 6 H) 1.14 (d, J=6.32 Hz, 3H) 0.98 (d, J=6.32 Hz, 3 H). MS (ESI+) m/z 566.4 (M+H)⁺.

Example 29

(R)-6-(5-isopropyl-2-methylphenyl)-2-(3-methyl-1H-indol-4-yl)-4-(3-methyl-4-(methylsulfonyl)piperazin-1-yl)-5,6,7,8-tetrahydropyrido[4,3-d]pyrimidine

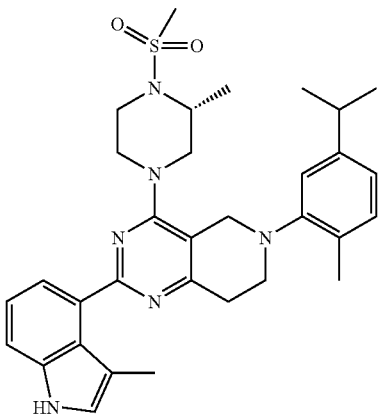 [SMILES: Cc1ccc(C(C)C)cc1N1CCc2nc(-c3cccc4[nH]cc(C)c34)nc(N3CCN(S(C)(=O)=O)[C@H](C)C3)c2C1]

A mixture of (R)-6-(5-isopropyl-2-methylphenyl)-2-(3-methyl-1-tosyl-1H-indol-4-yl)-4-(3-methylpiperazin-1-yl)-5,6,7,8-tetrahydropyrido[4,3-d]pyrimidine (52 mg, 0.080 mmol), prepared in a manner similar to that described in Example 25, methanesulfonyl chloride (0.01 mL, 0.096 mmol) and DIEA (0.042 mL, 0.240 mmol) in DCM (3 mL) was stirred at rt for 30 min. The reaction mixture was diluted with EtOAc, washed successively with sat NaHCO₃, and brine, dried over Na₂SO₄ and concentrated. The resulting residue was purified via FCC (5-50% EtOAc/heptane) to provide (R)-6-(5-isopropyl-2-methylphenyl)-2-(3-methyl-1-tosyl-1H-indol-4-yl)-4-(3-methyl-4-(methylsulfonyl)piperazin-1-yl)-5,6,7,8-tetrahydropyrido[4,3-d]pyrimidine. MS (ESI+) m/z 727.4 (M+H)⁺. To a solution of (R)-6-(5-isopropyl-2-methylphenyl)-2-(3-methyl-1-tosyl-1H-indol-4-yl)-4-(3-methyl-4-(methylsulfonyl)piperazin-1-yl)-5,6,7,8-tetrahydropyrido[4,3-d]pyrimidine (40 mg, 0.055 mmol) in MeOH (4 mL), NH₄OH (0.325 mL, 8.25 mmol) and KOH (27.8 mg, 0.495 mmol) was added. The mixture was heated in a microwave reactor 100° C. for 1 h. The mixture was then filtered and concentrated. The resulting residue was purified via FCC (0-45% EtOAc/heptane) to provide (R)-6-(5-isopropyl-2-methylphenyl)-2-(3-methyl-1H-indol-4-yl)-4-(3-methyl-4-(methylsulfonyl)piperazin-1-yl)-5,6,7,8-tetrahydropyrido[4,3-d]pyrimidine. ¹H NMR (400 MHz, DMSO-d₆) δ ppm 10.91 (d, J=2.02 Hz, 1 H) 7.40-7.43 (m, 1 H) 7.24 (dd, J=7.33, 1.01 Hz, 1 H) 7.09-7.16 (m, 3 H) 7.02 (d, J=1.26 Hz, 1 H) 6.87 (dd, J=7.83, 1.26 Hz, 1 H) 4.03-4.16 (m, 3 H) 3.70-3.84 (m, 2 H) 3.56 (d, J=12.88 Hz, 1 H) 3.33-3.42 (m, 2 H) 3.23-3.28 (m, 1 H) 3.14 (dd, J=12.88, 3.54 Hz, 1 H) 2.92-3.06 (m, 6 H) 2.79-2.90 (m, 1H) 2.22 (s, 3 H) 2.03 (s, 3 H) 1.32 (d, J=6.82 Hz, 3 H) 1.19 (dd, J=6.95, 1.89 Hz, 6 H); MS (ESI+) m/z 573.4 (M+H)⁺.

Example 30

30-A. (R)-6-(5-Isopropyl-2-methylphenyl)-2-(3-methyl-1H-indol-4-yl)-4-(3-methyl-4-(oxetan-3-yl)piperazin-1-yl)-5,6,7,8-tetrahydropyrido[4,3-d]pyrimidine

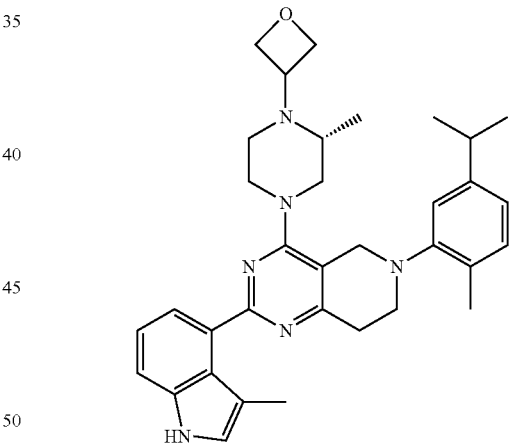

A mixture of (R)-6-(5-isopropyl-2-methylphenyl)-2-(3-methyl-1-tosyl-1H-indol-4-yl)-4-(3-methylpiperazin-1-yl)-5,6,7,8-tetrahydropyrido[4,3-d]pyrimidine (53 mg, 0.082 mmol), oxetan-3-one (17.6 mg, 0.245 mmol) and Na(AcO)₃BH (51.9 mg, 0.245 mmol) in DCM (3 mL) was stirred at rt for 3 h. At that point starting material remained so additional oxetan-3-one (17.7 mg, 0.245 mmol) and Na(AcO)₃BH (51.9 mg, 0.245 mmol) were added and the reaction stirred for 16 h. The mixture was then diluted with EtOAc, washed with sat NaHCO₃ and brine. The organic layer was then dried over Na₂SO₄, filtered and concentrated. The residue was purified by FCC (5-65% EtOAc/heptane) to provide (R)-6-(5-isopropyl-2-methylphenyl)-2-(3-methyl-1-tosyl-1H-indol-4-yl)-4-(3-methyl-4-(oxetan-3-yl)piperazin-1-yl)-5,6,7,8-tetrahydropyrido[4,3-d]pyrimidine. MS (ESI+) m/z 705.5 (M+H)⁺.

The crude product was then dissolved product in MeOH (4 mL). NH₄OH (0.50 mL, 12.8 mmol) and KOH (43.0 mg, 0.766 mmol) were added. The mixture was then heated in a microwave reactor at 100° C. for 45 min before being filtered and concentrated. The residue was then and purified by FCC (0-45% EtOAc/heptane) to provide (R)-6-(5-isopropyl-2-methylphenyl)-2-(3-methyl-1H-indol-4-yl)-4-(3-methyl-4-(oxetan-3-yl)piperazin-1-yl)-5,6,7,8-tetrahydropyrido[4,3-d]pyrimidine. ¹H NMR (400 MHz, DMSO-d₆) δ ppm 10.90 (d, J=1.52 Hz, 1 H) 7.41 (dd, J=8.08, 1.01 Hz, 1 H) 7.22 (dd, J=7.33, 1.01 Hz, 1 H) 7.09-7.16 (m, 3 H) 6.98 (d, J=1.26 Hz, 1 H) 6.87 (dd, J=7.71, 1.39 Hz, 1 H) 4.45-4.56 (m, 4 H) 3.96-4.07 (m, 2 H) 3.71 (quin, J=6.88 Hz, 1 H) 3.42-3.57 (m, 2 H) 3.36 (s, 1 H) 3.20-3.27 (m, 1 H) 3.00-3.10 (m, 1 H) 2.96 (t, J=5.81 Hz, 2 H) 2.79-2.88 (m, 1 H) 2.67-2.73 (m, 1 H) 2.55 (d, J=3.79 Hz, 1 H) 2.43-2.48 (m, 1 H) 2.16-2.25 (m, 4 H) 2.03 (s, 3 H) 1.18 (d, J=6.82 Hz, 6 H) 0.90 (d, J=6.32 Hz, 3 H; MS (ESI+) m/z 551.4 (M+H)⁺.

The following compounds were prepared in a similar manner.

30-B. (R)-6-(5-Chloro-2-methylphenyl)-4-(4-ethyl-3-methylpiperazin-1-yl)-2-(3-methyl-1H-indol-4-yl)-5,6,7,8-tetrahydropyrido[4,3-d]pyrimidine

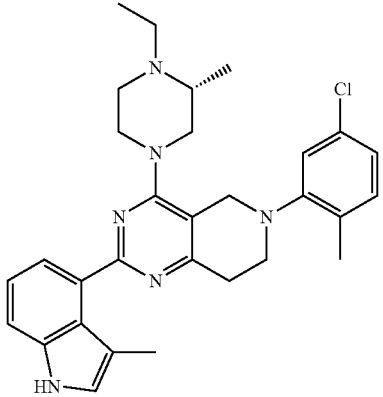 [SMILES: CCN1CCN(c2nc(-c3cccc4[nH]cc(C)c34)nc3c2CN(c2cc(Cl)ccc2C)CC3)C[C@H]1C]

¹H NMR (400 MHz, DMSO-d₆) δ ppm 10.90 (s, 1 H) 7.41 (dd, J=8.08, 1.01 Hz, 1 H) 7.17-7.25 (m, 3 H) 7.04-7.16 (m, 3 H) 4.03 (s, 2 H) 3.58-3.66 (m, 1 H) 3.55 (d, J=12.63 Hz, 1 H) 3.31-3.36 (m, 3 H) 3.12-3.22 (m, 1 H) 2.87-3.02 (m, 3 H) 2.77-2.86 (m, 1 H) 2.68-2.77 (m, 1 H) 2.31-2.36 (m, 2 H) 2.23 (s, 3 H) 2.02 (s, 3 H) 1.02 (d, J=6.32 Hz, 3 H) 0.96 (t, J=7.20 Hz, 3 H); MS (ESI+) m/z 515.3/517.4 (M+H)⁺.

30-C. (R)-6-(5-Chloro-2-methylphenyl)-2-(3-methyl-1H-indol-4-yl)-4-(3-methyl-4-(oxetan-3-yl)piperazin-1-yl)-5,6,7,8-tetrahydropyrido[4,3-d]pyrimidine

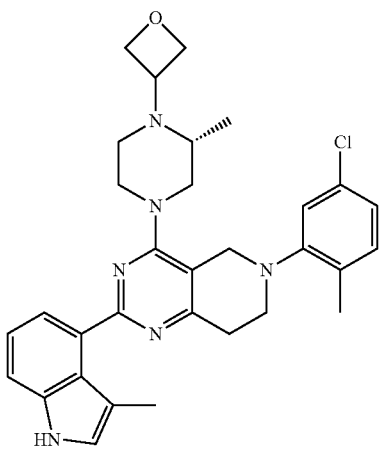 [SMILES: Cc1ccc(Cl)cc1N1CCc2nc(-c3cccc4[nH]cc(C)c34)nc(N3CCN(C4COC4)[C@H](C)C3)c2C1]

¹H NMR (400 MHz, DMSO-d₆) δ ppm 10.90 (s, 1 H) 7.39-7.42 (m, 1 H) 7.17-7.25 (m, 3 H) 7.04-7.16 (m, 3 H) 4.44-4.57 (m, 4 H) 4.02 (s, 2 H) 3.71 (t, J=6.95 Hz, 1 H) 3.52-3.58 (m, 1 H) 3.47 (dd, J=12.00, 1.39 Hz, 1 H) 3.31-3.36 (m, 1 H) 3.21-3.27 (m, 1 H) 2.95-3.08 (m, 3 H) 2.67-2.70 (m, 1 H) 2.45 (dd, J=3.54, 1.52 Hz, 1 H) 2.14-2.26 (m, 5 H) 2.03 (d, J=0.76 Hz, 3 H) 0.88 (d, J=6.32 Hz, 3 H); MS (ESI+) m/z 543.3/545.3 (M+H)⁺.

Example 31

31-A. 6-Benzyl-4-methoxy-2-(5-methyl-1H-indazol-4-yl)-5,6,7,8-tetrahydropyrido[4,3-d]pyrimidine

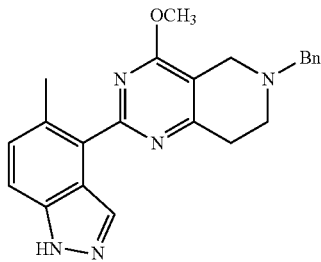 [SMILES: COc1nc(-c2c(C)ccc3[nH]ncc23)nc2c1CN(Cc1ccccc1)CC2]

A mixture of 6-benzyl-2-chloro-4-methoxy-5,6,7,8-tetrahydropyrido[4,3-d]pyrimidine (1.09 g, 3.75 mmol), (5-methyl-1H-indazol-4-yl)boronic acid (600 mg, 3.41 mmol), Pd(PPh₃)₄ (197 mg, 0.170 mmol), and Na₂CO₃ (2 M, 5.97 mL, 11.9 mmol) in DME (11 mL) was heated in a microwave reactor at 140° C. for 1.5 h. The reaction mixture was partitioned between EtOAc and water. The aqueous layer was extracted with EtOAc. The combined organics were washed with brine, dried (Na₂SO₄), and concentrated. The residue was purified by silica gel chromatography (20-100% EtOAc/heptane) to provide 6-benzyl-4-methoxy-2-(5-methyl-1H-indazol-4-yl)-5,6,7,8-tetrahydropyrido[4,3-d]pyrimidine. MS (ESI+) m/z 386.2 (M+H)⁺.

31-B. 6-benzyl-4-methoxy-2-(5-methyl-1-tosyl-1H-indazol-4-yl)-5,6,7,8-tetrahydropyrido[4,3-d]pyrimidine

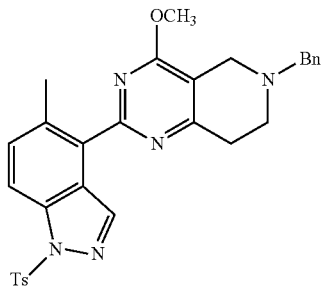 [SMILES: COc1nc(-c2c(C)ccc3c2cnn3S(=O)(=O)c2ccc(C)cc2)nc2c1CN(Cc1ccccc1)CC2]

6-Benzyl-4-methoxy-2-(5-methyl-1H-indazol-4-yl)-5,6,7,8-tetrahydropyrido[4,3-d]pyrimidine (2.00 g, 5.19 mmol) was added to a suspension of NaH (60% dispersion in mineral oil, 415 mg, 10.4 mmol) in THF (50 mL) at 0° C. After 20 min, TsCl (1.19 g, 6.23 mmol) was added. The reaction mixture was stirred for 20 min and sat aq NH₄Cl solution was added to quench excess base. The resulting mixture was extracted with EtOAc (3×). The combined organics were dried (Na₂SO₄) and concentrated. The residue was purified by silica gel chromatography (0-100% EtOAc/heptane) to provide 6-benzyl-4-methoxy-2-(5-methyl-1-tosyl-1H-indazol-4-yl)-5,6,7,8-tetrahydropyrido[4,3-d]pyrimidine. MS (ESI+) m/z 540.2 (M+H)⁺.

31-C. 4-Methoxy-2-(5-methyl-1-tosyl-1H-indazol-4-yl)-5,6,7,8-tetrahydropyrido[4,3-d]pyrimidine

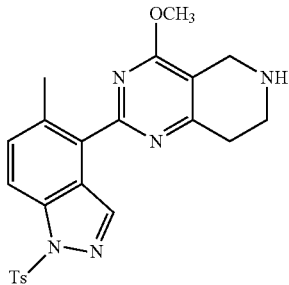 [SMILES: COc1nc(-c2c(C)ccc3c2cnn3S(=O)(=O)c2ccc(C)cc2)nc2c1CNCC2]

A mixture of 6-benzyl-4-methoxy-2-(5-methyl-1-tosyl-1H-indazol-4-yl)-5,6,7,8-tetrahydropyrido[4,3-d]pyrimidine (1.85 g, 3.43 mmol) and Pd(OH)$_2$ on carbon (wet) (10%, 0.722 g, 1.03 mmol) in water (7.5 mL) and acetic acid (0.59 mL) was stirred under 1 atm of hydrogen at room temperature for 2.5 h. The reaction mixture was filtered through Celite® and the solids were washed with EtOAc. The combined filtrates were washed with saturated NaHCO$_3$ solution. The layers were separated and the aqueous layer was extracted with EtOAc. The combined organics were washed with brine, dried (Na$_2$SO$_4$) and concentrated. The residue was purified by silica gel chromatography (0-10% MeOH (10% NH$_4$OH)/DCM) to provide 4-methoxy-2-(5-methyl-1-tosyl-1H-indazol-4-yl)-5,6,7,8-tetrahydropyrido[4,3-d]pyrimidine. MS (ESI+) m/z 450.1 (M+H)$^+$.

31-D. 6-(5-Isopropyl-2-methylphenyl)-4-methoxy-2-(5-methyl-1-tosyl-1H-indazol-4-yl)-5,6,7,8-tetrahydropyrido[4,3-d]pyrimidine

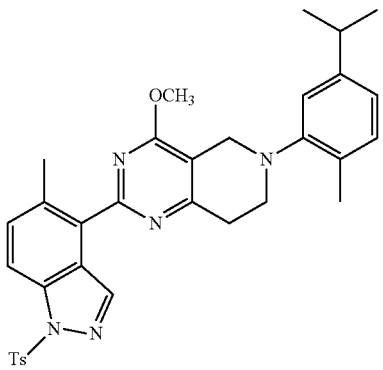 [SMILES: COc1nc(-c2c(C)ccc3c2cnn3S(=O)(=O)c2ccc(C)cc2)nc2c1CN(c1cc(C(C)C)ccc1C)CC2]

A mixture of 4-methoxy-2-(5-methyl-1-tosyl-1H-indazol-4-yl)-5,6,7,8-tetrahydropyrido[4,3-d]pyrimidine (250 mg, 0.556 mmol), 5-isopropyl-2-methylphenyl trifluoromethanesulfonate (235 mg, 0.834 mmol), X-Phos (53.0 mg, 0.111 mmol), Pd$_2$(dba)$_3$ (50.9 mg, 0.056 mmol), and Cs$_2$CO$_3$ (362 mg, 1.11 mmol) in THF (3 mL) was heated in a microwave reactor at 140° C. for 60 min. The reaction mixture was partitioned between EtOAc and water. The organic layer was washed with brine, dried (Na$_2$SO$_4$) and concentrated. The residue was purified by silica gel chromatography (0-50% EtOAc/heptane) to provide 6-(5-isopropyl-2-methylphenyl)-4-methoxy-2-(5-methyl-1-tosyl-1H-indazol-4-yl)-5,6,7,8-tetrahydropyrido[4,3-d]pyrimidine. MS (ESI+) m/z 582.1 (M+H)$^+$.

31-E. 6-(5-Isopropyl-2-methylphenyl)-4-methoxy-2-(5-methyl-1H-indazol-4-yl)-5,6,7,8-tetrahydropyrido[4,3-d]pyrimidine

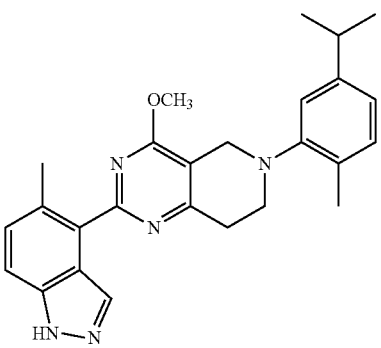 [SMILES: COc1nc(-c2c(C)ccc3[nH]ncc23)nc2c1CN(c1cc(C(C)C)ccc1C)CC2]

A mixture of 6-(5-isopropyl-2-methylphenyl)-4-methoxy-2-(5-methyl-1-tosyl-1H-indazol-4-yl)-5,6,7,8-tetrahydropyrido[4,3-d]pyrimidine (200 mg, 0.344 mmol), KOH (80 mg, 1.43 mmol) and concentrated aq NH$_4$OH solution (4 mL) in MeOH (8 mL) was heated in a microwave reactor at 80° C. for 30 min. The reaction mixture was partitioned between EtOAc and water. The aqueous layer was extracted with EtOAc (3×). The combined organics were washed with brine, dried (Na$_2$SO$_4$) and concentrated. The residue was purified by silica gel chromatography (0-100% EtOAc/heptanes) to provide 6-(5-isopropyl-2-methylphenyl)-4-methoxy-2-(5-methyl-1H-indazol-4-yl)-5,6,7,8-tetrahydropyrido[4,3-d]pyrimidine as a white solid. $^1$H NMR (400 MHz, CD$_2$Cl$_2$) δ ppm 8.31 (s, 1 H) 7.52 (d, J=8.34 Hz, 1 H) 7.40 (d, J=8.59 Hz, 1 H) 7.21 (d, J=7.83 Hz, 1 H) 7.11 (d, J=1.52 Hz, 1 H) 6.97 (dd, J=7.71, 1.64 Hz, 1 H) 4.04-4.20 (m, 5 H) 3.37 (t, J=5.68 Hz, 2 H) 3.19 (t, J=5.56 Hz, 2 H) 2.88-3.01 (m, 1 H) 2.70 (s, 3 H) 2.37 (s, 3 H) 1.31 (d, J=6.82 Hz, 6 H); MS (ESI+) m/z 428.1 (M+H)$^+$.

The following compounds were prepared in a similar manner.

| | Structure | Chemical Name & Analytical Data |
|---|---|---|
| 31-F | 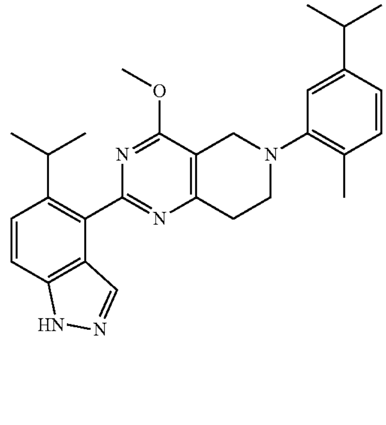 [SMILES: COc1nc(-c2c(C(C)C)ccc3[nH]ncc23)nc2c1CN(c1cc(C(C)C)ccc1C)CC2] | 2-(5-isopropyl-1H-indazol-4-yl)-6-(5-isopropyl-2-methylphenyl)-4-methoxy-5,6,7,8-tetrahydropyrido[4,3-d]pyrimidine. $^1$H NMR (400 MHz, CD$_2$Cl$_2$) δ ppm 7.94 (s, 1H) 7.40-7.46 (m, 2H) 7.06 (d, J = 8.1 Hz, 1H) 6.97 (d, J = 1.5 Hz, 1H) 6.83 (dd, J = 7.6, 1.8 Hz, 1H) 3.99 (s, 2H) 3.94 (s, 3H) 3.48 (quin, J = 6.9 Hz, 1H) 3.23 (t, J = 5.68 Hz, 2H) 3.04 (t, J = 5.68 Hz, 2H) 2.81 (quin, J = 6.9 Hz, 1H) 2.24 (s, 3H) 1.22 (d, J = 6.8 Hz, 6H) 1.17 (d, J = 7.1 Hz, 6H); MS (ESI+) m/z 456.1 (M + H)$^+$. |

| Structure | Chemical Name & Analytical Data |
|---|---|
| 31-G 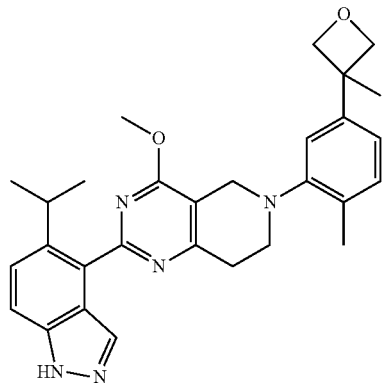 [SMILES: COc1nc(-c2c(C(C)C)ccc3[nH]ncc23)nc2c1CN(c1cc(C3(C)COC3)ccc1C)CC2] | 2-(5-isopropyl-1H-indazol-4-yl)-4-methoxy-6-(2-methyl-5-(3-methyloxetan-3-yl)phenyl)-5,6,7,8-tetrahydropyrido[4,3-d]pyrimidine. $^1$H NMR (400 MHz, CDCl$_3$) δ ppm 8.13 (br. s., 1H) 7.44-7.70 (m, 2H) 7.27 (d, J = 8.3 Hz, 1H) 7.08 (d, J = 1.8 Hz, 1H) 6.94 (dd, J = 7.7, 1.9 Hz, 1H) 5.04 (d, J = 5.6 Hz, 2H) 4.70 (d, J = 5.8 Hz, 2H) 4.15 (s, 2H) 4.09 (s, 3H) 3.60 (quin, J = 6.9 Hz, 1H) 3.39 (t, J = 5.7 Hz, 2H) 3.23 (t, J = 5.3 Hz, 2H) 2.42 (s, 3H) 1.80 (s, 3H) 1.37 (d, J = 6.8 Hz, 6H); MS (ESI+) m/z 484.0 (M + H)$^+$. |
| 31-H 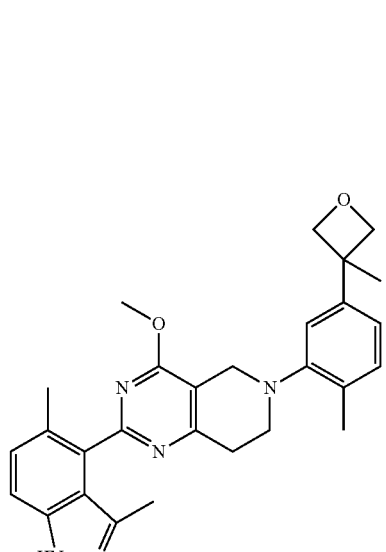 | 2-(3,5-dimethyl-1H-indazol-4-yl)-4-methoxy-6-(2-methyl-5-(3-methyloxetan-3-yl)phenyl)-5,6,7,8-tetrahydropyrido[4,3-d]pyrimidine. 1H NMR (400 MHz, CD$_2$Cl$_2$) δ ppm 9.88 (br. s., 1H) 7.45 (d, J = 8.3 Hz, 1H) 7.33 (d, J = 8.3 Hz, 1H) 7.27 (d, J = 7.8 Hz, 1H) 7.06 (d, J = 1.8 Hz, 1H) 6.93 (dd, J = 7.7, 1.9 Hz, 1H) 4.99 (d, J = 5.3 Hz, 2H) 4.66 (d, J = 5.3 Hz, 2H) 4.15 (s, 2H) 4.05 (s, 3H) 3.38 (t, J = 5.7 Hz, 2H) 3.14 (t, J = 5.7 Hz, 2H) 2.40 (s, 3H) 2.34 (s, 3H) 2.05 (s, 3H) 1.77 (s, 3H); MS (ESI+) m/z 470.3 (M + H)$^+$. |
| 31-I 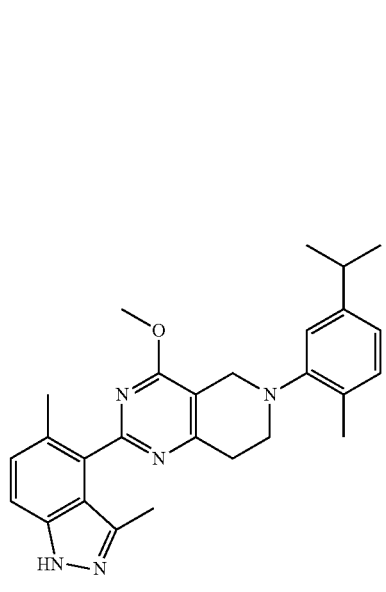 [SMILES: COc1nc(-c2c(C)ccc3[nH]nc(C)c23)nc2c1CN(c1cc(C(C)C)ccc1C)CC2] | 2-(3,5-dimethyl-1H-indazol-4-yl)-6-(5-isopropyl-2-methylphenyl)-4-methoxy-5,6,7,8-tetrahydropyrido[4,3-d]pyrimidine. 1H NMR (400 MHz, CD$_2$Cl$_2$) δ ppm 7.39-7.48 (m, 1H) 7.29-7.37 (m, 1H) 7.21 (d, J = 7.8 Hz, 1H) 7.10 (d, J = 1.5 Hz, 1H) 6.97 (dd, J = 7.6, 1.8 Hz, 1H) 4.15 (s, 2H) 4.05 (s, 3H) 3.37 (t, J = 5.7 Hz, 2H) 3.13 (t, J = 5.6 Hz, 2H) 2.87-3.02 (m, 1H) 2.38 (s, 3H) 2.35 (s, 3H) 2.08 (s, 3H) 1.31 (d, J = 7.1 Hz, 6H); MS (ESI+) m/z 442.3 (M + H)$^+$. |

Example 32

32-A. 2-(3-Chloro-5-methyl-1H-indazol-4-yl)-6-(5-isopropyl-2-methylphenyl)-4-methoxy-5,6,7,8 tetrahydropyrido[4,3-d]pyrimidine

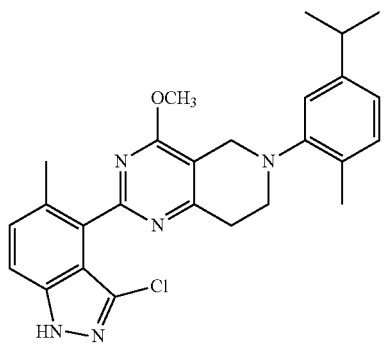 [SMILES: COc1nc(-c2c(C)ccc3[nH]nc(Cl)c23)nc2c1CN(c1cc(C(C)C)ccc1C)CC2]

Elite® bleach (5.25% sodium hypochlorite) was added dropwise to a solution of 6-(5-isopropyl-2-methylphenyl)-4-methoxy-2-(5-methyl-1H-indazol-4-yl)-5,6,7,8-tetrahydropyrido[4,3-d]pyrimidine (40 mg, 0.094 mmol) in EtOH (4 mL) at 0° C. The reaction was monitored by LC-MS. After all the starting material was consumed, the reaction mixture was directly loaded onto reverse phase HPLC and purified (CH$_3$CN-water 0-100%) to provide 2-(3-chloro-5-methyl-1H-indazol-4-yl)-6-(5-isopropyl-2-methylphenyl)-4-methyl-5,6,7,8-tetrahydro-1,6-naphthyridine. $^1$H NMR (400 MHz, CD$_3$CN) δ ppm 11.23 (br. s., 1 H) 7.55 (d, J=8.59 Hz, 1 H) 7.41 (d, J=8.59 Hz, 1 H) 7.18 (d, J=7.58 Hz, 1 H) 7.10 (d, J=2.02 Hz, 1 H) 6.95 (dd, J=7.71, 1.89 Hz, 1 H) 4.11 (s, 2 H) 3.97 (s, 3 H) 3.32 (t, J=5.68 Hz, 2 H) 3.01-3.06 (m, 2 H) 2.92 (ddd, J=13.83, 6.88, 6.82 Hz, 1 H) 2.33 (s, 3 H) 2.31 (s, 3 H) 1.26 (d, J=6.82 Hz, 6 H); MS (ESI+) m/z 462.1 (M+H)$^+$.

The following compounds were prepared in a similar manner.

32-B. (S)-2-(3-Chloro-5-methyl-1H-indazol-4-yl)-6-(5-isopropyl-2-methylphenyl)-4-(4-methoxy-3,3-dimethylpiperidin-1-yl)-5,6,7,8-tetrahydropyrido[4,3-d]pyrimidine

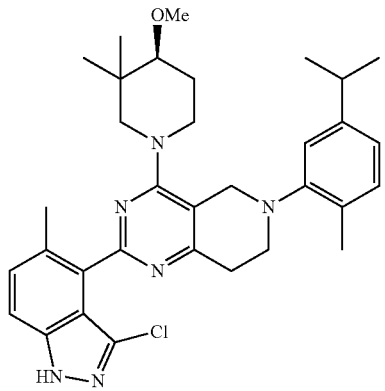 [SMILES: CO[C@H]1CCN(c2nc(-c3c(C)ccc4[nH]nc(Cl)c34)nc3c2CN(c2cc(C(C)C)ccc2C)CC3)CC1(C)C]

$^1$H NMR (400 MHz, CD$_3$CN) δ ppm 7.50 (d, J=8.6 Hz, 1 H), 7.36 (d, J=8.6 Hz, 1 H), 7.13 (d, J=7.8 Hz, 1 H), 7.01 (d, J=1.5 Hz, 1 H), 6.90 (dd, J=7.7, 1.6 Hz, 1 H), 4.02-4.14 (m, 2 H), 3.65-3.70 (m, 1 H), 3.33-3.40 (m, 3 H), 3.30 (s, 3 H), 3.05 (ddd, J=13.1, 10.0, 3.2 Hz, 1 H), 2.95-2.99 (m, 3 H), 2.82-2.91 (m, 2 H), 2.25 (s, 6 H), 1.57-1.66 (m, 1 H), 1.23 (d, J=6.6 Hz, 6 H), 0.97 (s, 3 H), 0.91 (s, 3 H); MS (ESI+) m/z 573.0 (M+H)$^+$.

32-C. 2-(3-Chloro-5-methyl-1H-indazol-4-yl)-6-(5-isopropyl-2-methylphenyl)-4-methyl-5,6,7,8-tetrahydro-1,6-naphthyridine

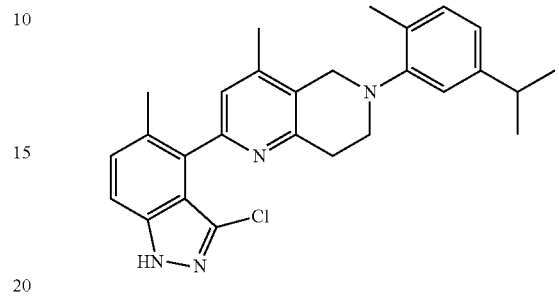

$^1$H NMR (400 MHz, DICHLOROMETHANE-d$_2$) δ ppm 10.32 (br. s., 1 H) 7.38 (s, 2 H) 7.21 (d, J=7.58 Hz, 1 H) 7.08-7.13 (m, 2 H) 6.97 (dd, J=7.58, 1.77 Hz, 1 H) 4.21 (s, 2 H) 3.37-3.42 (m, 2 H) 3.20-3.26 (m, 2 H) 2.95 (dt, J=13.83, 6.85 Hz, 1 H) 2.40 (s, 3 H) 2.35 (s, 3 H) 2.30 (s, 3 H) 1.31 (d, J=6.82 Hz, 6 H); MS (ESI+) m/z 445.0 (M+H)$^+$.

Example 33

33-A. (S)-2,4-Dichloro-6-(1-phenylethyl)-5,6,7,8-tetrahydropyrido[4,3-d]pyrimidine

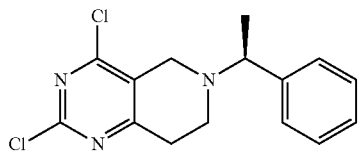 [SMILES: C[C@@H](c1ccccc1)N1CCc2nc(Cl)nc(Cl)c2C1]

A mixture of eerie ammoniumnitrate (22.6 g, 41.3 mmol), (S)-phenyl-ethylamine (25 g, 207 mmol), and THF (100 mL) was cooled to 10° C. and then ethylacrylate (51.6 g, 516 mmol) was added dropwise. The reaction mixture was then brought to rt and then warmed to 60° C. and heated for 15 h. The mixture was diluted with water and EtOAc and the organic layer was then separated, dried (Na$_2$SO$_4$), filtered and concentrated. The residue was purified by FCC (30% EtOAc/hexanes) to give (S)-diethyl 3,3'-((1-phenylethyl)azanediyl)dipropanoate. MS (ESI+) m/z 322 (M+H)$^+$.

A suspension of NaH (2.24 g, 93.4 mmol) in THF (20 mL) was cooled to 0° C. and as solution of (S)-diethyl 3,3'-((1-phenylethyl)azanediyl)dipropanoate (15 g, 46.7 mmol) in THF was then added dropwise. The reaction mixture was allowed to warm to rt and then warmed to 60° C. and heated for 3 h. The mixture was diluted with water and EtOAc and the organic layer was then separated, dried (Na$_2$SO$_4$), filtered and concentrated. The residue was purified by FCC (5-7% EtOAc/hexanes) to give (5)-ethyl 4-oxo-1-((S)-1-phenylethyl)piperidine-3-carboxylate.

A combination of urea (0.37 g, 15.6 mmol), sodium methoxide (1.47 g, 27.2 mmol) and MeOH (50 mL) was cooled to 0° C. and then a solution of (S)-ethyl 4-oxo-1-((S)-1-phenylethyl)piperidine-3-carboxylate (9.0 g, 7.8 mmol) in THF was added. The reaction mixture was allowed to warm to rt and then warmed to 60° C. and heated for 3 h. The mixture was diluted with water and EtOAc and the organic layer was then separated, dried (Na₂SO₄), filtered and concentrated. The residue was purified by FCC (8-10% MeOH/CH₂Cl₂) to give (S)-6-(1-phenylethyl)-5,6,7,8-tetrahydropyrido[4,3-d]pyrimidine-2,4-diol.

A combination of POCl₃ (10 mL) and DIEA (2.0 mL) was cooled to 0° C. and then (S)-6-(1-phenylethyl)-5,6,7,8-tetrahydropyrido[4,3-d]pyrimidine-2,4-diol (2.0 g, 7.38) in THF was added The reaction mixture was allowed to warm to rt and then warmed to 60° C. and heated for 3 h. The mixture was diluted with water and EtOAc and the organic layer was then separated, dried (Na₂SO₄), filtered and concentrated. The residue was purified by FCC (10% EtOAc/hexanes) to give (S)-2,4-dichloro-6-(1-phenylethyl)-5,6,7,8-tetrahydropyrido[4,3-d]pyrimidine. MS (ESI+) m/z 310 (M+2).

33-B. (±)-2-Chloro-4-(4-methoxy-3,3-dimethylpiperidin-1-yl)-6-((S)-1-phenylethyl)-5,6,7,8-tetrahydropyrido[4,3-d]pyrimidine

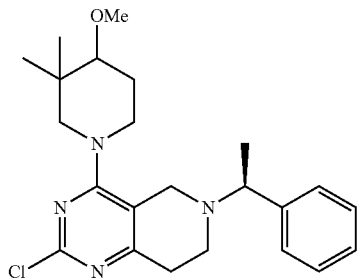 [SMILES: COC1CCN(c2nc(Cl)nc3c2CN([C@@H](C)c2ccccc2)CC3)CC1(C)C]

A mixture of racemic 4-methoxy-3,3-dimethylpiperidine (0.30 g, 1.95 mmol), (S)-2,4-dichloro-6-(1-phenylethyl)-5,6,7,8-tetrahydropyrido[4,3-d]pyrimidine (0.40 g, 1.30 mmol), DIEA (0.50 g, 3.90 mmol), and isopropanol (10 mL) was heated at 60° C. for 24 h. The mixture was diluted with water and EtOAc and the organic layer was then separated, dried (Na₂SO₄), filtered and concentrated. The residue was taken to the next step without further purification. MS (ESI+) m/z 415.2 (M+H)⁺.

33-C. (±)-2-(2,6-Dimethylphenyl)-4-(4-methoxy-3,3-dimethylpiperidin-1-yl)-6-((S)-1-phenylethyl)-5,6,7,8-tetrahydropyrido[4,3-d]pyrimidine

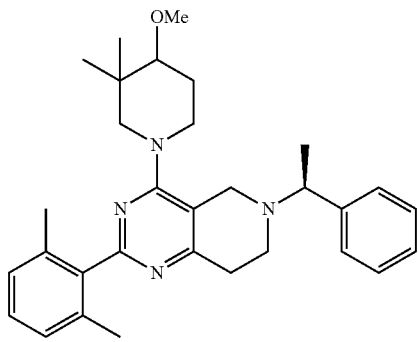 [SMILES: COC1CCN(c2nc(-c3c(C)cccc3C)nc3c2CN([C@@H](C)c2ccccc2)CC3)CC1(C)C]

A mixture of 2,6-dimethylphenyl boronic acid (0.081 g, 0.54 mmol), (±)-2-chloro-4-(4-methoxy-3,3-dimethylpiperidin-1-yl)-6-((S)-1-phenylethyl)-5,6,7,8-tetrahydropyrido[4,3-d]pyrimidine (0.15 g, 0.36 mmol), Pd(PPh₃)₄ (0.041 g, 0.036 mmol), sat aq Na₂CO₃ (2.0 mL), and DMF (5 mL) was placed under a nitrogen atmosphere and heated to 120° C. in a microwave reactor for 0.5 h. The mixture was diluted with water and EtOAc and the organic layer was then separated, dried (Na₂SO₄), filtered and concentrated. The residue was then purified by semi-prep HPLC (Column: ZORBAX, XDB, C-18; A: 10 mM NH₄OAc in water; B: MeCN; Flow Rate: 20 mL/min; Gradient: 0.0 min, 70.0% MeCN, 2.0 min, 80.0% MeCN, 6.0 min, 90.0% MeCN). After lyophilization, the mixture was dissolved in DCM and washed with water to remove NH₄OAc, dried over Na₂SO₄ and solvents were removed under reduced pressure. MS (ESI+) m/z 485.3 (M+H)⁺.

The following compounds were prepared in a similar manner.

33-B. (±)-2-(2,6-Dimethylphenyl)-4-(4-methoxy-3,3-dimethylpiperidin-1-yl)-6-4R)-1-phenylethyl)-5,6,7,8-tetrahydropyrido[4,3-d]pyrimidine

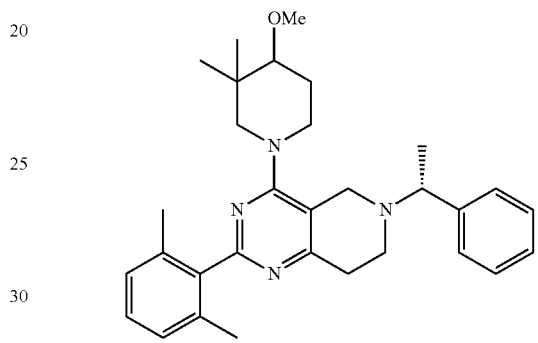

MS (ESI+) m/z 485.4 (M+H)⁺.

Example 34

34-A. 1-(4-Methoxy-2-(3-methyl-1-tosyl-1H-indol-4-yl)-7,8-dihydropyrido[4,3-d]pyrimidin-6(5H)-yl)-4-methylpentane-1,3-dione

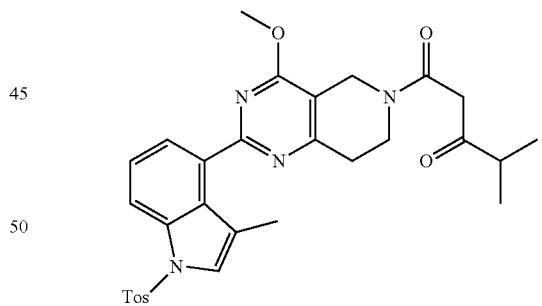

To a solution of 4-methoxy-2-(3-methyl-1-tosyl-1H-indol-4-yl)-5,6,7,8-tetrahydropyrido[4,3-d]pyrimidine, prepared as described in Example 17, (300 mg, 0.67 mmol) in toluene (3 mL), in a 2-5 mL microwave vial, was added methyl 4-methyl-3-oxopentanoate (0.28 mL, 2 mmol) followed by DMAP (25 mg, 0.2 mmol). The reaction vessel was then sealed and heated via microwave irradiation at 150° C. for 35 min. The reaction mixture was then cooled to room temperature and diluted with dichloromethane and water. The layers were separated and the organic layer was dried by passing through a phase separator and then concentrated. The resulting residue was purified via silica gel flash chromatography (45-90% ethyl acetate/heptanes) to furnish 1-(4-methoxy-2-

(3-methyl-1-tosyl-1H-indol-4-yl)-7,8-dihydropyrido[4,3-d]pyrimidin-6(5H)-yl)-4-methylpentane-1,3-dione. MS (ESI+) m/z 561.3 (M+H)+.

34-B. 6-(3-Isopropyl-1-methyl-1H-pyrazol-5-yl)-4-methoxy-2-(3-methyl-1-tosyl-1H-indol-4-yl)-5,6,7,8-tetrahydropyrido[4,3-d]pyrimidine

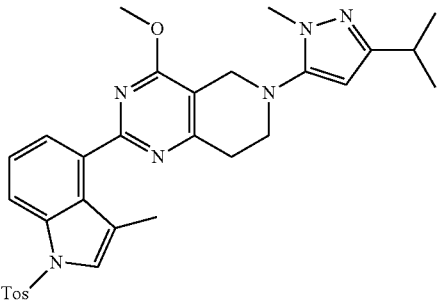

To a solution of 1-(4-methoxy-2-(3-methyl-1-tosyl-1H-indol-4-yl)-7,8-dihydropyrido[4,3-d]pyrimidin-6(5H)-yl)-4-methylpentane-1,3-dione (350 mg, 0.624 mmol) in THF (3.3 mL), in a 2-5 mL microwave vial, was added Lawesson's reagent (278 mg, 0.687 mmol) and methyl hydrazine (0.049 mL, 0.94 mmol). The vessel was immediately sealed and heated via microwave irradiation at 120° C. for 10 minutes. The reaction was then cooled to room temperature and diluted with dichloromethane and water. The layers were separated and the aqueous layer was extracted two additional times with dichloromethane. The organic layers were combined, dried over Na₂SO₄, filtered, and concentrated. The resulting residue was purified via silica gel flash chromatography (45-67% ethyl acetate/heptanes) to provide 6-(3-isopropyl-1-methyl-1H-pyrazol-5-yl)-4-methoxy-2-(3-methyl-1-tosyl-1H-indol-4-yl)-5,6,7,8-tetrahydropyrido[4,3-d]pyrimidine. MS (ESI+) m/z 571.4 (M+H)+.

34-C. 4-Chloro-6-(3-isopropyl-1-methyl-1H-pyrazol-5-yl)-2-(3-methyl-1-tosyl-1H-indol-4-yl)-5,6,7,8-tetrahydropyrido[4,3-d]pyrimidine

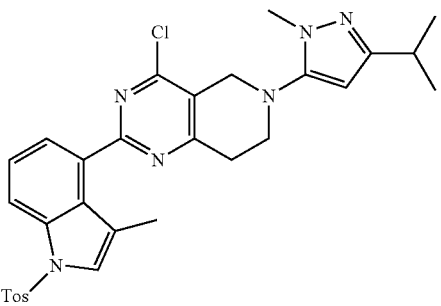

Ethanol (1.8 mL) was added to 6-(3-isopropyl-1-methyl-1H-pyrazol-5-yl)-4-methoxy-2-(3-methyl-1-tosyl-1H-indol-4-yl)-5,6,7,8-tetrahydropyrido[4,3-d]pyrimidine (195 mg, 0.342 mmol) followed by 12 N aqueous hydrochloric acid (1.8 mL, 21.8 mmol). The mixture was then heated to 87° C. for ca. 15 hours. The mixture was then cooled to room temperature, diluted with dichloromethane, and slowly neutralized with saturated aqueous sodium bicarbonate. The resulting layers were separated and the aqueous layers were extracted an additional time with dichloromethane. The organic layers were combined and dried by passing through a phase separator and then concentrated. The resulting residue was diluted with 1,2-dichloroethane (3.5 mL) and place at 0° C. Then N-chloromethylene-N,N-dimethyl ammonium chloride (Vilsmeier reagent) (85 mg, 067 mmol) was added. The resulting mixture was then heated to 35° C. After 5 minutes at 35° C. the mixture was diluted with dichloromethane, and slowly neutralized with saturated aqueous sodium bicarbonate. The resulting layers were separated and the aqueous layers were extracted an additional time with dichloromethane. The organic layers were combined and dried over Na₂SO₄, filtered and concentrated to furnish 4-chloro-6-(3-isopropyl-1-methyl-1H-pyrazol-5-yl)-2-(3-methyl-1-tosyl-1H-indol-4-yl)-5,6,7,8-tetrahydropyrido[4,3-d]pyrimidine without the need for further purification. MS (ESI+) m/z 575.3 (M+H)+.

34-D. 4-Chloro-6-(4-chloro-3-isopropyl-1-methyl-1H-pyrazol-5-yl)-2-(3-methyl-1-tosyl-1H-indol-4-yl)-5,6,7,8-tetrahydropyrido[4,3-d]pyrimidine

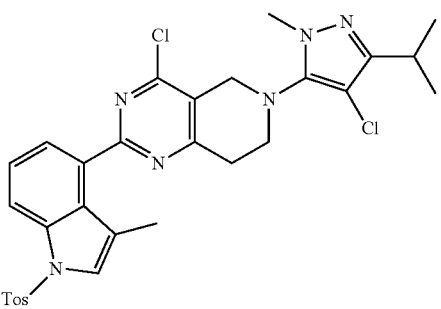

To a solution of 4-chloro-6-(3-isopropyl-1-methyl-1H-pyrazol-5-yl)-2-(3-methyl-1-tosyl-1H-indol-4-yl)-5,6,7,8-tetrahydropyrido[4,3-d]pyrimidine (90 mg, 0.156 mmol) in MeCN (2.0 mL) at 0° C. was added N-chlorosuccinimide (21 mg, 0.156 mmol). The reaction was permitted to stir for 2.5 h at 0° C., and then was diluted with diethyl ether and saturated aqueous sodium bicarbonate. The layers were separated and the organic layer was washed once with brine, dried over MgSO₄, filtered and concentrated to furnish 4-chloro-6-(4-chloro-3-isopropyl-1-methyl-1H-pyrazol-5-yl)-2-(3-methyl-1-tosyl-1H-indol-4-yl)-5,6,7,8-tetrahydropyrido[4,3-d]pyrimidine without the need for further purification. MS (ESI+) m/z 609.2 (M+H)+.

34-E. 6-(4-Chloro-3-isopropyl-1-methyl-1H-pyrazol-5-yl)-4-(3,3-dimethylpiperidin-1-yl)-2-(3-methyl-1-tosyl-1H-indol-4-yl)-5,6,7,8-tetrahydropyrido[4,3-d]pyrimidine

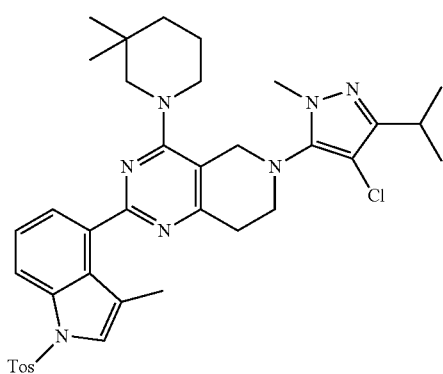

Isopropanol (2.2 mL) was added to 4-chloro-6-(4-chloro-3-isopropyl-1-methyl-1H-pyrazol-5-yl)-2-(3-methyl-1-tosyl-1H-indol-4-yl)-5,6,7,8-tetrahydropyrido[4,3-d]pyrimidine (85 mg, 0.139 mmol) in a microwave vial. Then diisopropylethylamine (0.1 mL, 0.573 mmol) was added followed by the HCl salt of 3,3-dimethylpiperidine (25 mg, 0.167 mmol). The vessel was sealed and heated via microwave irradiation at 120° C. for 2.5 h then cooled to room temperature and diluted with dichloromethane and brine. The layers were separated and the organic layer was dried over $Na_2SO_4$, filtered, and concentrated. The resulting residue was purified via silica gel flash chromatography (25-55% ethyl acetate/heptanes) to provide 6-(4-chloro-3-isopropyl-1-methyl-1H-pyrazol-5-yl)-4-(3,3-dimethylpiperidin-1-yl)-2-(3-methyl-1-tosyl-1H-indol-4-yl)-5,6,7,8-tetrahydropyrido[4,3-d]pyrimidine. MS (ESI+) m/z 686.4 $(M+H)^+$.

34-F. 6-(4-Chloro-3-isopropyl-1-methyl-1H-pyrazol-5-yl)-4-(3,3-dimethylpiperidin-1-yl)-2-(3-methyl-1H-indol-4-yl)-5,6,7,8-tetrahydropyrido[4,3-d]pyrimidine

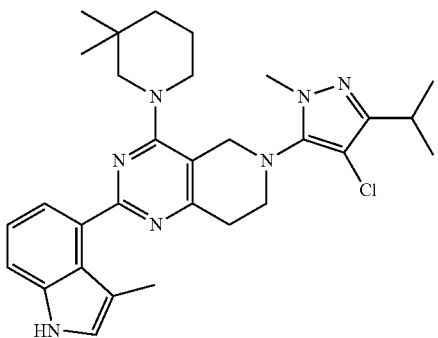 [SMILES: Cc1c[nH]c2cccc(-c3nc4c(c(N5CCCC(C)(C)C5)n3)CN(c3c(Cl)c(C(C)C)nn3C)CC4)c12]

Ethanol (1.8 mL) was added to 6-(4-chloro-3-isopropyl-1-methyl-1H-pyrazol-5-yl)-4-(3,3-dimethylpiperidin-1-yl)-2-(3-methyl-1-tosyl-1H-indol-4-yl)-5,6,7,8-tetrahydropyrido[4,3-d]pyrimidine (74 mg, 0.108 mmol) in a microwave vial. Next, KOH (61 mg, 1.08 mmol) was added followed by 28% aqueous ammonium hydroxide (0.6 mL, 4.35 mmol). The vessel was sealed and heated via microwave irradiation at 100° C. for 75 minutes. The reaction mixture was cooled to room temperature and diluted with dichloromethane and water. The layers were separated and the organic layer was dried by passing through a phase separator. The eluent was concentrated and the resulting residue was purified by reverse phase HPLC (20-55% MeCN/Water (0.1% TFA)). The eluent from the HPLC was neutralized with saturated aqueous sodium bicarbonate and extracted with dichloromethane. The organic extract was dried by passing through a phase separator and concentrating to provide 6-(4-chloro-3-isopropyl-1-methyl-1H-pyrazol-5-yl)-4-(3,3-dimethylpiperidin-1-yl)-2-(3-methyl-1H-indol-4-yl)-5,6,7,8-tetrahydropyrido[4,3-d]pyrimidine.

$^1$H NMR (400 MHz, $CD_2Cl_2$) δ ppm 0.97 (s, 6 H) 1.26 (d, J=7.1 Hz, 6 H) 1.39-1.46 (m, 2 H) 1.66-1.77 (m, 2 H) 2.09 (s, 3 H) 2.99 (dt, J=13.9, 7.0 Hz, 1 H) 3.04-3.12 (m, 4 H) 3.25-3.34 (m, 2 H) 3.53-3.59 (m, 2 H) 3.63 (s, 3 H) 4.30 (s, 2 H) 7.04 (br. s., 1 H) 7.20 (t, J=7.7 Hz, 1 H) 7.32 (d, J=6.3 Hz, 1 H) 7.41 (d, 1 H) 8.22 (br. s., 1 H); MS (ESI+) m/z 532.4 $(M+H)^+$.

Example 35

35-A. (R)-6-Benzyl-2-chloro-4-(3-methyl-4-((2-nitrophenyl)sulfonyl)piperazin-1-yl)-5,6,7,8-tetrahydropyrido[4,3-d]pyrimidine

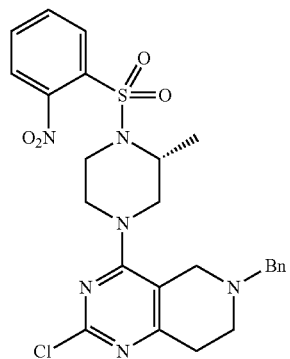 [SMILES: C[C@@H]1CN(c2nc(Cl)nc3c2CN(Cc2ccccc2)CC3)CCN1S(=O)(=O)c1ccccc1[N+](=O)[O-]]

Isopropanol (80 mL) was added to 6-benzyl-2,4-dichloro-5,6,7,8-tetrahydropyrido[4,3-d]pyrimidine (CAS#778574-06-4 2.5 g, 8.50 mmol) followed by triethylamine (3.55 mL, 25.5 mmol) and (R)-2-methylpiperazine (1.28 g, 12.8 mmol). The mixture was heated at 50° C. for 6.5 hours and then cooled to room temperature and diluted with dichloromethane and water. The layers were separated and the aqueous layer was extracted one additional time with dichloromethane. The organic layers were combined dried over $Na_2SO_4$, filtered, and concentrated. A portion of the resulting residue (1.3 g) was then dissolved in dichloromethane (25 mL) and charged with triethylamine (1.2 mL, 8.7 mmol). The mixture was placed at 0° C. and then 2-nitrobenzene-1-sulfonyl chloride (0.97 g, 4.4 mmol) was added. The mixture was stirred at 0° C. for 30 minutes then warmed to room temperature and stirred an additional 1 hour. The mixture was then quenched with saturated aqueous sodium bicarbonate and stirred for 1 hour. The mixture was then further diluted with dichloromethane and saturated aqueous sodium bicarbonate and the layers separated. The aqueous layer was extracted one additional time with dichloromethane. The organic layers were combined dried over $Na_2SO_4$, filtered, and concentrated. The resulting residue was purified by silica gel flash chromatography (50-85% ethyl acetate/heptanes) to afford: (R)-6-benzyl-2-chloro-4-(3-methyl-4-((2-nitrophenyl)sulfonyl)piperazin-1-yl)-5,6,7,8-tetrahydropyrido[4,3-d]pyrimidine. MS (ESI+) m/z 686.4 $(M+H)^+$.

35-B. (R)-6-Benzyl-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine

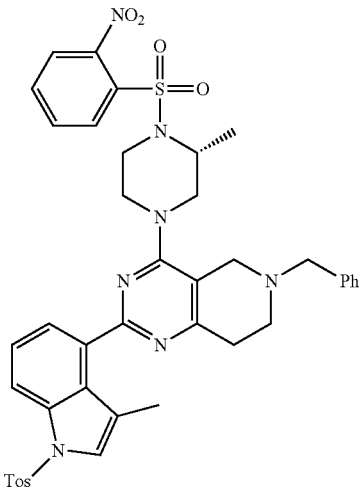

1,2-Dimethoxyethane (6.75 mL) was added to a 20 mL microwave vial containing a mixture of (R)-6-benzyl-2-chloro-4-(3-methyl-4-((2-nitrophenyl)sulfonyl)piperazin-1-yl)-5,6,7,8-tetrahydropyrido[4,3-d]pyrimidine (1.1 g, 2.03 mmol) and 3-methyl-4-(4,4,5,5-tetramethyl-1,3,2-dioxaborolan-2-yl)-1-tosyl-1H-indole (0.92 g, 2.23 mmol). Then 2M aqueous Na$_2$CO$_3$ was added and the reaction mixture was degassed via three argon/vacuum cycles, then charged with Pd(Ph$_3$P)$_4$ (0.234 g, 0.203 mmol). The vial was sealed and heated via microwave irradiation at 140° C. for 90 minutes. The mixture was then cooled to room temperature and diluted with Et$_2$O and water. The layers were separated and the aqueous layer was extracted two additional times with dichloromethane. The organic layers were combined dried over MgSO$_4$, filtered and concentrated. The resulting residue was purified by silica gel flash chromatography [55-75% ethyl acetate (containing 2% EtOH)/heptanes] to afford (R)-6-benzyl-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine. MS (ESI+) m/z 792.5 (M+H)$^+$.

35-C. (R)-2-(3-Methyl-1-tosyl-1H-indol-4-yl)-4-(3-methyl-4-β2-nitrophenyl)sulfonyl)piperazin-1-yl)-5,6,7,8-tetrahydropyrido[4,3-d]pyrimidine

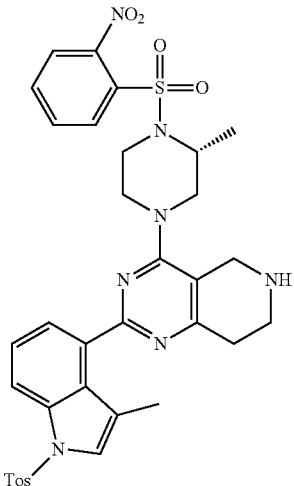

To a solution of (R)-6-benzyl-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine (1.17 g, 1.47 mmol) in MeCN (15 mL) was added 1-chloroethyl carbonochloridate (0.18 mL, 1.62 mmol), and the mixture was stirred for 15 minutes at which time the mixture was concentrated in vacuo. The resulting residue was dissolved in a 2:1 mixture of dichloromethane:methanol (15 mL) and heated at 40° C. for 1 hour and then placed at room temperature for ca. 15 h. The mixture was then diluted with dichloromethane and saturated aqueous sodium bicarbonate. The layers were separated and the aqueous layer was extracted two additional times with dichloromethane. The organic layers were combined dried over Na$_2$SO$_4$, filtered and concentrated. The resulting residue was purified by silica gel flash chromatography (3-12% MeOH/DCM) to provide (R)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine. MS (ESI+) m/z 702.3 (M+H)$^+$.

35-D. (R)-4-Methyl-1-(2-(3-methyl-1-tosyl-1H-indol-4-yl)-4-(3-methyl-4-((2-nitrophenyl)sulfonyl)piperazin-1-yl)-7,8-dihydropyrido[4,3-d]pyrimidin-6(5H)-yl)pentane-1,3-dione

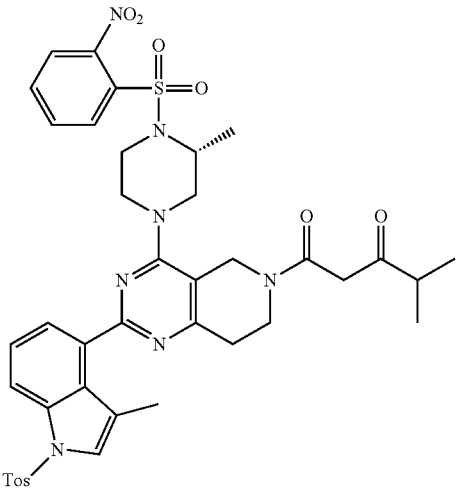

The title compound was prepared from (R)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine following the procedure described in Example 34. MS (ESI+) m/z 814.3 (M+H)$^+$.

35-E. (R)-6-(3-Isopropyl-1-methyl-1H-pyrazol-5-yl)-2-(3-methyl-1-tosyl-1H-indol-4-yl)-4-(3-methyl-44(2-nitrophenyl)sulfonyl)piperazin-1-yl)-5,6,7,8-tetrahydropyrido[4,3-d]pyrimidine

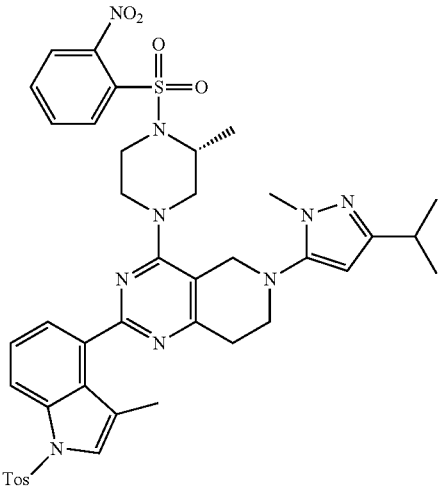

The title compound was prepared from (R)-4-methyl-1-(2-(3-methyl-1-tosyl-1H-indol-4-yl)-4-(3-methyl-4-((2-nitrophenyl)sulfonyl)piperazin-1-yl)-7,8-dihydropyrido[4,3-d]pyrimidin-6(5H)-yl)pentane-1,3-dione following the procedure described in Example 34. MS (ESI+) m/z 824.4 (M+H)⁺.

35-F. (R)-6-(3-Isopropyl-1-methyl-1H-pyrazol-5-yl)-2-(3-methyl-1-tosyl-1H-indol-4-yl)-4-(3-methylpiperazin-1-yl)-5,6,7,8-tetrahydropyrido[4,3-d]pyrimidine

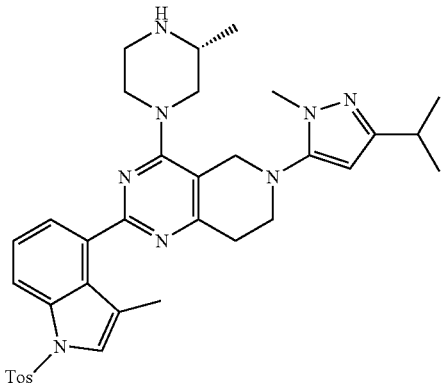

To a solution of (R)-6-(3-isopropyl-1-methyl-1H-pyrazol-5-yl)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine (105 mg, 0.127 mmol) in DMF (3 mL) was added DBU (0.1 mL, 0.64 mmol) followed by 2-mercaptoacetic acid (0.018 mL, 0.255 mmol). The mixture was stirred for 3 hours and then diluted with water and dichloromethane. The layers were separated and the aqueous layer was extracted three additional times with dichloromethane. The organic layers were combined, dried over Na₂SO₄, filtered and concentrated. The resulting residue was purified via silica gel flash chromatography [4-25% (2 M NH₃ in MeOH)/DCM] to provide (R)-6-(3-isopropyl-1-methyl-1H-pyrazol-5-yl)-2-(3-methyl-1-tosyl-1H-indol-4-yl)-4-(3-methylpiperazin-1-yl)-5,6,7,8-tetrahydropyrido[4,3-d]pyrimidine. MS (ESI+) m/z 639.4 (M+H)⁺.

35-G. (R)-2-(4-(6-(3-Isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperazin-1-yl)acetamide

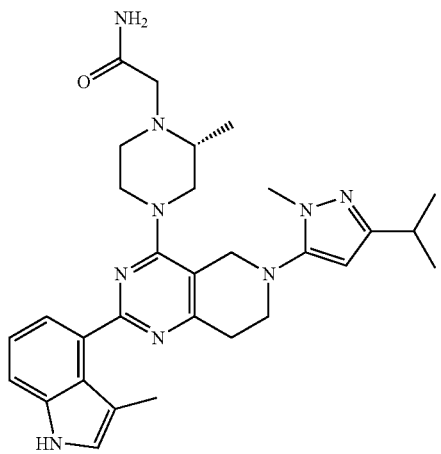 [SMILES: Cc1c[nH]c2cccc(-c3nc4c(c(N5CCN(CC(N)=O)[C@H](C)C5)n3)CN(c3cc(C(C)C)nn3C)CC4)c12]

To a solution of (R)-6-(3-isopropyl-1-methyl-1H-pyrazol-5-yl)-2-(3-methyl-1-tosyl-1H-indol-4-yl)-4-(3-methylpiperazin-1-yl)-5,6,7,8-tetrahydropyrido[4,3-d]pyrimidine (78 mg, 0.122 mmol) in MeCN (2 mL) was added diisopropylethylamine (0.064 mL, 0.37 mmol) followed by 2-bromoacetamide (20 mg, 0.146 mmol). The mixture was heated to 55° C. and stirred for 105 minutes, then cooled to room temperature quenched with saturated aqueous NH₄Cl. The mixture was diluted with dichloromethane and saturated aqueous sodium bicarbonate and the layers were separated. The aqueous layer was extracted two additional times with dichloromethane and the organic layers were then combined, dried over Na₂SO₄, filtered and concentrated. The resulting residue was then dissolved in ethanol (2.1 mL) and placed in a microwave vial. The vial was charged with KOH (69 mg, 1.24 mmol) and 28% aqueous ammonium hydroxide (0.7 mL, 5.1 mmol), sealed and heated via microwave irradiation at 100° C. for 70 minutes. The mixture was then cooled to room temperature, diluted with dichloromethane and water and then neutralized with 1M aqueous NaHSO₄. The resulting layers were separated and the organic layer was dried by passing through a phase separator. The eluent was concentrated and purified by reverse phase HPLC [10-55% MeCN/(0.1% NH₄OH)water] to furnish (R)-2-(4-(6-(3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperazin-1-yl)acetamide. ¹H NMR (400 MHz, DMSO-d₆) δ ppm 1.02 (d, J=6.3 Hz, 3 H) 1.16 (d, J=6.8 Hz, 6 H) 2.02 (s, 3 H) 2.59-2.66 (m, 1 H) 2.72-2.85 (m, 3 H) 2.89-3.00 (m, 3 H) 3.13 (d, J=16.2 Hz, 1 H) 3.20-3.26 (m, 1 H) 3.27-3.30 (m, 3 H) 3.56-3.64 (m, 5 H) 4.01 (s, 2 H) 5.73 (s, 1 H) 7.08-7.13 (m, 2 H) 7.13-7.16 (m, 1 H) 7.18-7.22 (m, 1 H) 7.26 (d, J=2.8 Hz, 1 H) 7.41 (dd, J=8.1, 1.0 Hz, 1 H) 10.90 (s, 1H); MS (ESI+) m/z 542.4 (M+H)⁺.

Example 36

(R)-2-(4-(2-(2,6-Dimethylphenyl)-6-(3-isopropyl-1-methyl-1H-pyrazol-5-yl)-5,6,7,8-tetrahydropyrido[4,3-d]pyrimidin-4-yl)-2-methylpiperazin-1-yl)acetamide

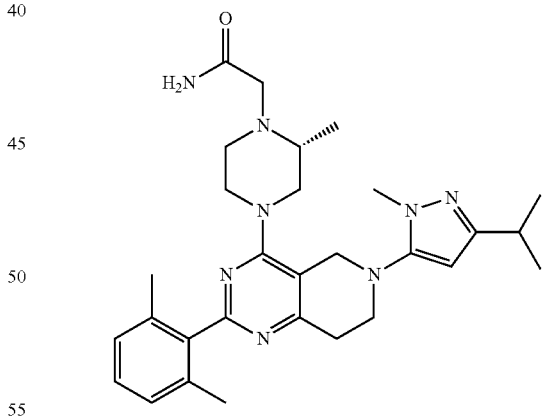

MeCN (2 mL) was added to 4-chloro-2-(2,6-dimethylphenyl)-6-(3-isopropyl-1-methyl-1H-pyrazol-5-yl)-5,6,7,8-tetrahydropyrido[4,3-d]pyrimidine, prepared as described in Example 16, (110 mg, 0.278 mmol) in a microwave vial. The vial was then charged with diisopropylethylamine (0.24 mL, 1.38 mmol) and (R)-2-methylpiperazine (56 mg, 0.556 mmol). The vial was sealed and heated via microwave irradiation at 100° C. for 45 minutes. The mixture was cooled to room temperature and then charged with 2-bromoacetamide (115 mg, 0.833 mmol), re-sealed and heated via microwave irradiation at 100° C. for 10 minutes. The reaction was then cooled to room temperature and adsorbed in vacuo onto silica and loaded onto a silica gel flash chromatography column for purification [0-10% (10% NH₄OH)MeOH/DCM]. The material was then further purified by additional silica gel flash chromatography {0-35% [10% MeOH (containing 1% NH₄OH)/EtOAc]/DCM} to furnish (R)-2-(4-(2-(2,6-dimethylphenyl)-6-(3-isopropyl-1-methyl-1H-pyrazol-5-yl)-5,6,7,8-tetrahydropyrido[4,3-d]pyrimidin-4-yl)-2-methylpiperazin-1-yl)acetamide. ¹H NMR (400 MHz, DMSO-d₆) δ ppm 7.27 (br. s., 1 H) 7.17 (d, J=7.58 Hz, 1 H) 7.13 (br. s., 1 H) 7.08 (d, J=7.58 Hz, 2 H) 5.72 (s, 1 H) 3.98 (s, 2 H) 3.59 (s, 3 H) 3.51-3.58 (m, 2 H) 3.25-3.32 (m, 3 H) 3.16-3.24 (m, 1 H) 3.11 (d, J=16.17 Hz, 1 H) 2.94 (br. s., 3 H) 2.71-2.85 (m, 3 H) 2.56-2.65 (m, 1 H) 2.05 (s, 6 H) 1.11-1.19 (m, 6 H) 1.00 (d, J=6.06 Hz, 3 H); MS (ESI+) m/z 517.34 (M+H)⁺.

Example 37

37-A. (R)-6-(4-Chloro-3-isopropyl-1-methyl-1H-pyrazol-5-yl)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine

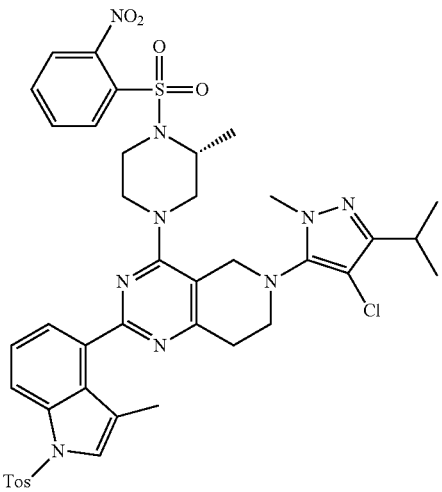

The title compound was prepared from (R)-6-(3-isopropyl-1-methyl-1H-pyrazol-5-yl)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine following the procedure described in Example 34. MS (ESI+) m/z 858.4 (M+H)⁺.

37-B. (R)-2-(4-(6-(4-Chloro-3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperazin-1-yl)acetamide

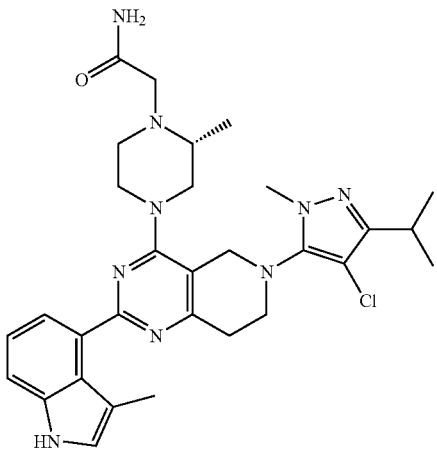 [SMILES: Cc1c[nH]c2cccc(-c3nc4c(c(N5CCN(CC(N)=O)[C@H](C)C5)n3)CN(c3c(Cl)c(C(C)C)nn3C)CC4)c12]

The title compound was prepared from (R)-6-(4-chloro-3-isopropyl-1-methyl-1H-pyrazol-5-yl)-2-(3-methyl-1-tosyl-1H-indol-4-yl)-4-(3-methyl-4-((2-nitrophenyl)sulfonyl)piperazin-1-yl)-5,6,7,8-tetrahydropyrido[4,3-d]pyrimidine by following the procedures described in Examples 35. ¹H NMR (400 MHz, DMSO-d₆) δ ppm 1.00 (d, J=6.3 Hz, 3 H) 1.20 (d, J=6.8 Hz, 6 H) 2.03 (s, 3 H) 2.58-2.65 (m, 1 H) 2.76-3.00 (m, 6 H) 3.10-3.23 (m, 2 H) 3.27-3.30 (m, 1 H) 3.52 (t, J=6.1 Hz, 2 H) 3.55-3.64 (m, 5 H) 4.21-4.34 (m, 2 H) 7.07-7.13 (m, 2 H) 7.13-7.16 (m, 1 H) 7.21 (dd, J=7.3, 1.0 Hz, 1 H) 7.23-7.27 (m, 1 H) 7.41 (dd, J=8.0, 0.9 Hz, 1 H) 10.90 (s, 1 H); MS (ESI+) m/z 576.5 (M+H)⁺.

Example 38

38-A. 6-(3-Isopropyl-1-methyl-1H-pyrazol-5-yl)-2-(3-methyl-1-tosyl-1H-indol-4-yl)-5,6,7,8-tetrahydropyrido[4,3-d]pyrimidin-4-ol

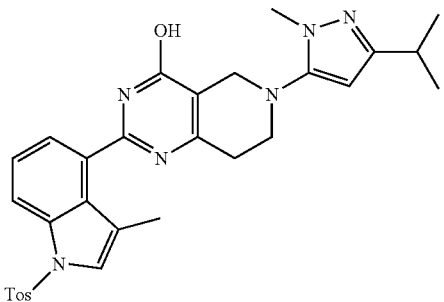

To a solution of 6-(3-isopropyl-1-methyl-1H-pyrazol-5-yl)-4-methoxy-2-(3-methyl-1-tosyl-1H-indol-4-yl)-5,6,7,8-tetrahydropyrido[4,3-d]pyrimidine (1.8 g, 3.15 mmol), prepared as described in Example 16, in ethanol (10 mL) in a 150 mL sealed tube, was added concentrated hydrochloride (10 mL). After the tube was sealed, the reaction was stirred and heated to 85° C. for 18 h. The reaction mixture wascooled to 0° C. and poured into ice water. Solid NaHCO₃ was added to neutralize the reaction mixture, then the mixture was extracted with DCM twice and the combined organic layers were dried over Na₂SO₄. The resulting residue was purified via silica gel FCC (0-100% EtOAc/heptane) to provide 6-(3-isopropyl-1-methyl-1H-pyrazol-5-yl)-2-(3-methyl-1-tosyl-1H-indol-4-yl)-5,6,7,8-tetrahydropyrido[4,3-d]pyrimidin-4-ol. MS (ESI+) m/z 557.2 (M+H)⁺.

38-B. 4-Chloro-6-(3-isopropyl-1-methyl-1H-pyrazol-5-yl)-2-(3-methyl-1H-indol-4-yl)-5,6,7,8-tetrahydropyrido[4,3-d]pyrimidine

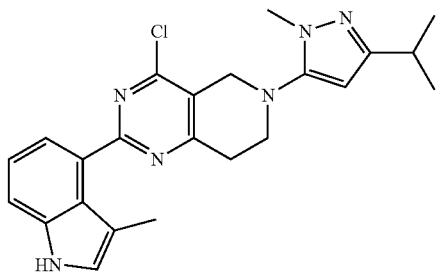 [SMILES: Cc1c[nH]c2cccc(-c3nc(Cl)c4c(n3)CCN(c3cc(C(C)C)nn3C)C4)c12]

To a solution of 6-(3-isopropyl-1-methyl-1H-pyrazol-5-yl)-2-(3-methyl-1-tosyl-1H-indol-4-yl)-5,6,7,8-tetrahydropyrido[4,3-d]pyrimidin-4-ol (550 mg, 0.988 mmol) in methanol (5 mL) in a microwave vial, was added potassium hydroxide (554 mg, 9.88 mmol) and then 28% ammonium hydroxide (1 mL, 0.988 mmol). The reaction was heated at 80° C. via microwave irradiation for 45 min. The reaction mixture was poured into iced water, then 4 N aq HCl was added to acidify the reaction mixture to pH=1, then NaHCO$_3$ solid was added to neutralize reaction mixture to pH=7-8. The mixture was extracted twice with a solution of 5% trifluoroethanol in DCM. The combined organic layers were washed with brine, dried over Na$_2$SO$_4$, filtered and concentrated. The resulting residue was dissolved in dichloroethane (3 mL), and the reaction flask was charged with phosphorus oxychloride (3.67 mL, 39.5 mmol). The reaction flask was capped and then heated to 80° C. for 1 h. The reaction mixture was cooled to r.t. and poured into ice water and diluted with acetone (10 mL). The reaction mixture was stirred for 30 min to provide a clear solution. At that point, NaHCO$_3$ solid was added to neutralize the reaction, and the mixture was extracted twice with DCM. The resulting residue was purified via silica gel FCC (0-100% EtOAc/heptane) to provide 4-chloro-6-(3-isopropyl-1-methyl-1H-pyrazol-5-yl)-2-(3-methyl-1H-indol-4-yl)-5,6,7,8-tetrahydropyrido[4,3-d]pyrimidine. MS (ESI+) m/z 421.2 (M+H)$^+$.

38-C. (S)-6-(3-Isopropyl-1-methyl-1H-pyrazol-5-yl)-2-(3-methyl-1H-indol-4-yl)-4-(2-methylpiperidin-1-yl)-5,6,7,8-tetrahydropyrido[4,3-d]pyrimidine

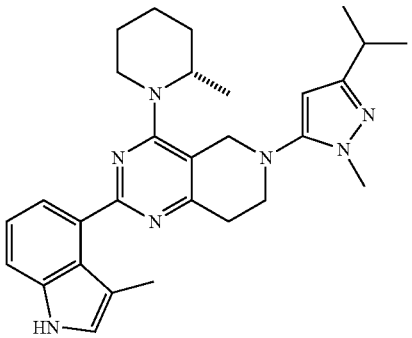 [SMILES: Cc1c[nH]c2cccc(-c3nc4c(c(N5CCCC[C@@H]5C)n3)CN(c3cc(C(C)C)nn3C)CC4)c12]

To a solution of 4-chloro-6-(3-isopropyl-1-methyl-1H-pyrazol-5-yl)-2-(3-methyl-1H-indol-4-yl)-5,6,7,8-tetrahydropyrido[4,3-d]pyrimidine (50 mg, 0.123 mmol) in N,N-dimethylacetamide (1.5 mL), was added diisopropylethylamine (0.15 mL, 0.86 mmol) and (S)-2-methylpiperidine (37 mg, 0.37 mmol). The reaction was stirred and heated to 125° C. for 24 h. After cooling, the mixture was directly purified via HPLC ((0.1% ammonium hydroxide in acetonitrile)/water=35%-100%). $^1$H NMR (400 MHz, CD$_2$Cl$_2$) δ ppm 8.23 (br. s., 1 H), 7.42 (d, J=8.1 Hz, 1 H), 7.33 (d, J=8.1 Hz, 1 H), 7.16-7.26 (m, 1 H), 7.04 (s, 1 H), 5.69 (s, 1 H), 4.06-4.16 (m, 1 H), 3.90-4.06 (m, 2 H), 3.67 (s, 3 H), 3.53 (d, J=13.4 Hz, 1 H), 3.29-3.40 (m, 2 H), 3.16-3.29 (m, 1 H), 3.10 (d, J=4.5 Hz, 2 H), 2.85 (dt, J=13.8, 6.9 Hz, 1 H), 2.10 (s, 3 H), 1.74-1.91 (m, 2 H), 1.65-1.74 (m, 2 H), 1.48-1.65 (m, 2 H), 1.22 (d, J=6.8 Hz, 6 H); MS (ESI+) m/z 484.4 (M+H)$^+$.

The following compounds were prepared in a similar manner.

| | Structure | Chemical Name & Analytical Data |
|---|---|---|
| 38-D | 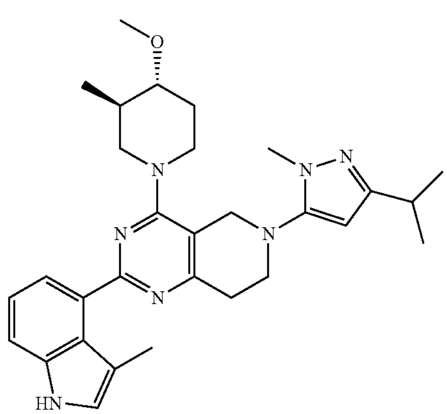 [SMILES: CO[C@@H]1CCN(c2nc(-c3cccc4[nH]cc(C)c34)nc3c2CN(c2cc(C(C)C)nn2C)CC3)C[C@H]1C] | (6-(3-isopropyl-1-methyl-1H-pyrazol-5-yl)-4-((3R,4R)-4-methoxy-3-methylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.22 (br. s., 1H), 7.43 (d, J = 7.8 Hz, 1H), 7.34 (d, J = 7.3 Hz, 1H), 7.16-7.24 (m, 1H), 7.05 (s, 1H), 5.68 (s, 1H), 4.01 (s, 2H), 3.84 (d, J = 13.4 Hz, 1H), 3.73 (d, J = 14.4 Hz, 1H), 3.66 (s, 3H), 3.35 (s, 3H), 3.31-3.35 (m, 2H), 3.10 (t, J = 4.9 Hz, 2H), 2.98-3.07 (m, 1H), 2.94 (td, J = 9.2,4.3 Hz, 1H), 2.81-2.89 (m, 1H), 2.76 (dd, J = 12.9, 10.4 Hz, 1H), 2.10-2.19 (m, 1H), 2.09 (s, 3H), 1.71-1.84 (m, 1H), 1.45-1.60 (m, 1H), 1.22 (d, J = 6.8 Hz, 6H), 1.01 (d, J = 6.6 Hz, 3H); MS (ESI+) m/z 514.4 (M + H)$^+$. |

| Structure | Chemical Name & Analytical Data |
|---|---|
| 38-E | (S)-6-(3-isopropyl-1-methyl-1H-pyrazol-5-yl)-4-(4-methoxy-3,3-dimethylpiperidin-1-yl)-2-(3-methyl-1H-indol-4-yl)-5,6,7,8-tetrahydropyrido[4,3-d]pyrimidine. $^1$H NMR (400 MHz, CD$_2$Cl$_2$) δ ppm 8.28 (br. s., 1H), 7.44 (d, J = 8.1 Hz, 1H), 7.35 (d, J = 7.1 Hz, 1H), 7.15-7.25 (m, 1H), 7.06 (s, 1H), 5.67 (s, 1H), 4.03 (s, 2H), 3.73 (d, J = 1.6 Hz, 1H), 3.66 (s, 3H), 3.42 (d, J = 11.4 Hz, 1H), 3.35 (s, 3H), 3.31-3.35 (m, 2H), 3.04-3.27 (m, 3H), 2.97 (dd, J = 8.5, 3.9 Hz, 2H), 2.78-2.91 (m, 1H), 2.09 (s, 3H), 1.91-2.04 (m, 1H), 1.65-1.78 (m, 1H), 1.21 (d, J = 6.8 Hz, 6H), 0.99 (s, 3H), 0.97 (s, 3H); MS (ESI+) m/z 528.4 (M + H)$^+$. |
| 38-F | (±)-1-(6-(3-isopropyl-1-methyl-1H-pyrazol-5-yl)-2-(3-methyl-1H-indol-4-yl)-5,6,7,8-tetrahydropyrido[4,3-d]pyrimidin-4-yl)-2-methylpiperidin-4-ol. $^1$H NMR (400 MHz, CD$_2$Cl$_2$) δ ppm 8.25 (br. s., 1H), 7.43 (d, J = 8.1 Hz, 1H), 7.34 (d, J = 8.1 Hz, 1H), 7.21 (t, J = 7.7 Hz, 1H), 7.06 (s, 1H), 5.70 (s, 1H), 4.17 (d, J = 15.2 Hz, 1H), 3.96 (d, J = 15.4 Hz, 1H), 3.84-3.93 (m, 1H), 3.70-3.77 (m, 1H), 3.68 (s, 3H), 3.32-3.40 (m, 1H), 3.22-3.32 (m, 1H), 3.06-3.13 (m, 2H), 2.95-3.05 (m, 2H), 2.80-2.90 (m, 1H), 2.51 (br. s., 1H), 2.09 (s, 3H), 1.90-2.06 (m, 2H), 1.56-1.70 (m, 1H), 1.42-1.55 (m, 1H), 1.22 (d, J = 7.1 Hz, 6H), 1.18 (d, J = 6.1 Hz, 3H); MS (ESI+) m/z 500.3 (M + H)$^+$. |

Example 39

39-A. 6-Benzyl-2-chloro-4-(3-methoxypropoxy)-5,6,7,8-tetrahydropyrido[4,3-d]pyrimidine

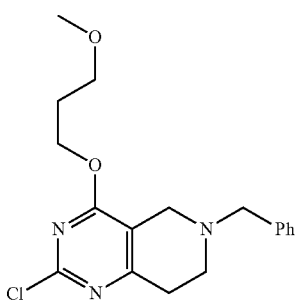 [SMILES: COCCCOc1nc(Cl)nc2c1CN(Cc1ccccc1)CC2]

To a solution of 3-methoxypropan-1-ol (0.500 mL, 5.23 mmol) in t-butanol (5 mL) was added a 60% dispersion of NaH in oil (70 mg, 1.75 mmol). The resulting suspension was permitted to stir for 30 minutes at which time the reaction was placed at 0° C. and charged with 6-benzyl-2,4-dichloro-5,6,7,8-tetrahydropyrido[4,3-d]pyrimidine (CAS#778574-06-4, 300 mg, 1.02 mmol) as a solution in THF (1.5 mL). After 20 minutes the mixture was quenched with saturated aqueous NH$_4$Cl, and diluted with ethyl acetate and water. The layers were then separated and the organic layer was washed with brine and dried over Na$_2$SO$_4$, filtered and concentrated. The resulting residue was purified via silica gel flash chromatography to provide 6-benzyl-2-chloro-4-(3-methoxypropoxy)-5,6,7,8-tetrahydropyrido[4,3-d]pyrimidine. MS (ESI+) m/z 348.1 (M+H)$^+$.

39-B. 6-Benzyl-2-(2,6-dimethylphenyl)-4-(3-methoxypropoxy)-5,6,7,8-tetrahydropyrido[4,3-d]pyrimidine

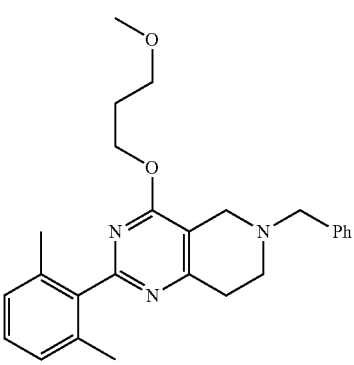 [SMILES: COCCCOc1nc(-c2c(C)cccc2C)nc2c1CN(Cc1ccccc1)CC2]

The title compound was prepared from provide 6-benzyl-2-chloro-4-(3-methoxypropoxy)-5,6,7,8-tetrahydropyrido[4,3-d]pyrimidine following the procedure described in Example 16. MS (ESI+) m/z 418.1 (M+H)$^+$.

39-C. 2-(2,6-Dimethylphenyl)-4-(3-methoxypropoxy)-5,6,7,8-tetrahydropyrido[4,3-d]pyrimidine

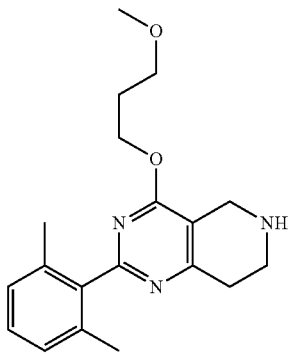 [SMILES: COCCCOc1nc(-c2c(C)cccc2C)nc2c1CNCC2]

To a solution of 6-benzyl-2-(2,6-dimethylphenyl)-4-(3-methoxypropoxy)-5,6,7,8-tetrahydropyrido[4,3-d]pyrimidine (170 mg, 0.41 mmol) in THF (3.5 mL) was added water (0.5 mL) and acetic acid (0.070 mL, 1.22 mmol). The reaction mixture was placed under argon and then charged with 20 mol % Pd(OH)$_2$/C (50% wet, 114 mg, 0.081 mmol). The atmosphere was then replaced with hydrogen gas via a balloon and was permitted to stir for 5 hours. The mixture was then neutralized with saturated aqueous sodium bicarbonate, diluted with dichloromethane and filtered through a pad of Celite®. The eluent was further diluted with dichloromethane and saturated aqueous sodium bicarbonate and the layers were separated. The aqueous layer was extracted two additional times with dichloromethane. The organic layers were combined, dried over Na$_2$SO$_4$, filtered and concentrated. The resulting residue was purified by silica gel flash chromatography [7-20% (2 M NH$_3$ in MeOH)/DCM] to furnish 2-(2,6-dimethylphenyl)-4-(3-methoxypropoxy)-5,6,7,8-tetrahydropyrido[4,3-d]pyrimidine. MS (ESI+) m/z 328.3 (M+H)$^+$.

39-D. 2-(2,6-Dimethylphenyl)-6-(5-isopropyl-2-methylphenyl)-4-(3-methoxypropoxy)-5,6,7,8-tetrahydropyrido[4,3-d]pyrimidine

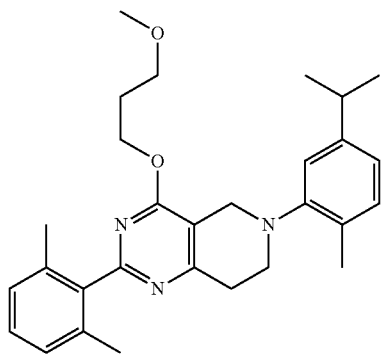 [SMILES: COCCCOc1nc(-c2c(C)cccc2C)nc2c1CN(c1cc(C(C)C)ccc1C)CC2]

To 5-isopropyl-2-methylphenyl trifluoromethanesulfonate, prepared as described in Example 15 (153 mg, 0.541 mmol) in a microwave vial was added a solution of 2-(2,6-dimethylphenyl)-4-(3-methoxypropoxy)-5,6,7,8-tetrahydropyrido[4,3-d]pyrimidine in THF (4 mL). Next, Cs$_2$CO$_3$ (235 mg, 0.721 mmol) was added and the reaction mixture was degassed via a series of argon/vacuum cycles. The reaction mixture was then charged with chloro(2-dicyclohexylphosphino-2',4',6'-triisopropyl-1,1'-biphenyl)-[2-(2-aminoethyl)phenyl)]-palladium(II) (CAS#1028206-56-5, 26.6 mg, 0.036 mmol). The vessel was then sealed and heated via microwave irradiation at 140° C. for 90 minutes. The reaction was then cooled to room temperature and diluted with ethyl acetate and water. The layers were separated and the aqueous layer was extracted once with ethyl acetate. The organic layers were combined, dried over Na$_2$SO$_4$ filtered and concentrated. The resulting residue was purified by silica gel flash chromatography (5-50% ethyl acetate/heptanes) to provide 2-(2,6-dimethylphenyl)-6-(5-isopropyl-2-methylphenyl)-4-(3-methoxypropoxy)-5,6,7,8-tetrahydropyrido[4,3-d]pyrimidine. $^1$H NMR (400 MHz, CD$_2$Cl$_2$) δ ppm 1.25 (d, J=7.1 Hz, 6 H) 2.08 (quin, J=6.3 Hz, 2 H) 2.28 (s, 6 H) 2.49 (s, 3 H) 2.92 (dt, J=13.8, 6.9 Hz, 1 H) 3.28 (s, 3 H) 3.49 (t, J=5.9 Hz, 2 H) 3.58 (t, J=5.7 Hz, 2 H) 3.81 (t, J=5.6 Hz, 2 H) 4.37 (s, 2 H) 4.71 (t, J=6.4 Hz, 2 H) 7.12 (dd, J=7.7, 1.4 Hz, 1 H) 7.17 (s, 1 H) 7.20-7.27 (m, 3 H) 7.36-7.41 (m, 1 H); MS (ESI+) m/z 460.4 (M+H)$^+$.

Example 40

40-A. Methyl 2-chloro-4-methyl-6-(3-methyl-1-tosyl-1H-indol-4-yl)nicotinate

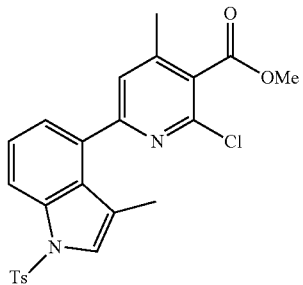 [SMILES: COC(=O)c1c(C)cc(-c2cccc3c2c(C)cn3S(=O)(=O)c2ccc(C)cc2)nc1Cl]

A mixture of methyl 2,6-dichloro-4-methylnicotinate (0.250 g, 1.14 mmol), 3-methyl-4-(4,4,5,5-tetramethyl-1,3,2-dioxaborolan-2-yl)-1-tosyl-1H-indole (Example 6) (0.514 g, 1.25 mmol), Pd(Ph$_3$P)$_4$ (0.131 g, 0.114 mmol), and CsF (0.345 g, 2.27 mmol), in DMF (5 mL) was heated at 110° C. for 6 h. At that time the vessel was removed from the oil bath and allowed to cool to rt. The mixture was diluted with brine (50 mL) and EtOAc (50 mL). The layers were mixed and then separated. The aqueous layer was further extracted with EtOAc (50 mL) and the combined organic layers were dried (Na$_2$SO$_4$), filtered, and concentrated. The residue was then purified via FCC (0-10% EtOAc/heptane) to give the title compound. MS ESI m/z 469.0 & 470.9 (M+H)$^+$.

40-B. Methyl 4-methyl-6-(3-methyl-1-tosyl-1H-indol-4-yl)-2-vinylnicotinate

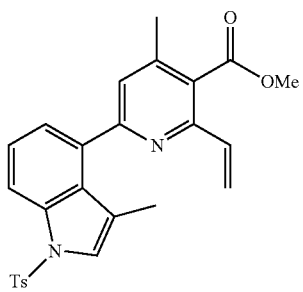 [SMILES: C=Cc1nc(-c2cccc3c2c(C)cn3S(=O)(=O)c2ccc(C)cc2)cc(C)c1C(=O)OC]

A solution of methyl 2-chloro-4-methyl-6-(3-methyl-1-tosyl-1H-indol-4-yl)nicotinate (0.348 g, 0.742 mmol) in DMF (5 mL) was sparged with argon for 10 min before trans-Pd(PPh$_3$)$_2$Cl$_2$ (0.052 g, 0.074 mmol), tri-n-butyl(vinyl)tin (0.353 g, 1.11 mmol), and BHT (0.016 g, 0.074 mmol) were added. The resulting suspension was sparged with argon for 5 min and the vessel was sealed and heated at 60° C. After 24 h the reaction was allowed to cool to rt and 50% KF on Celite® was added. The resulting slurry was then filtered over Celite® eluting with EtOAc. The organic was then washed with 10% KF in water and then dried (Na$_2$SO$_4$), filtered and concentrated. The residue was then purified by FCC (5-40% EtOAc/heptane) to give the title compound. MS ESI m/z 461.1 (M+H)$^+$.

40-C. 6-(5-Isopropyl-2-methylphenyl)-4-methyl-2-(3-methyl-1-tosyl-1H-indol-4-yl)-7,8-dihydro-1,6-naphthyridin-5(6H)-one

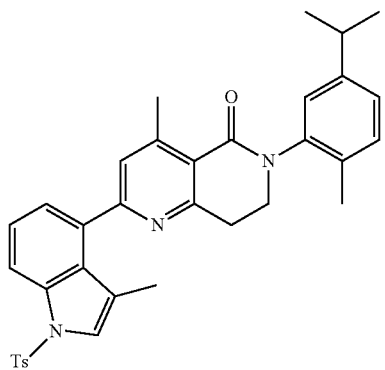 [SMILES: Cc1ccc(S(=O)(=O)n2cc(C)c3c(-c4cc(C)c5c(n4)CCN(c4cc(C(C)C)ccc4C)C5=O)cccc32)cc1]

A solution of methyl 4-methyl-6-(3-methyl-1-tosyl-1H-indol-4-yl)-2-vinylnicotinate (0.19 g, 0.413 mmol), and 5-isopropyl-2-methylaniline (0.074 g, 0.495 mmol) in AcOH (5 mL) was heated to 110° C. for 18 h. At that point, the reaction was concentrated under reduced pressure. The residue was then taken up in DCM (25 mL) and washed with 1 M aq NaOH (25 mL). The aqueous layer was further extracted with DCM (2×25 mL) and the combined organic layers were then dried (Na$_2$SO$_4$), filtered and concentrated. The residue was then purified by FCC (20-65% EtOAc/heptane) to give the title compound. MS ESI m/z 578.3 (M+H)$^+$.

40-D. 6-(5-Isopropyl-2-methylphenyl)-4-methyl-2-(3-methyl-1H-indol-4-yl)-5,6,7,8-tetrahydro-1,6-naphthyridine

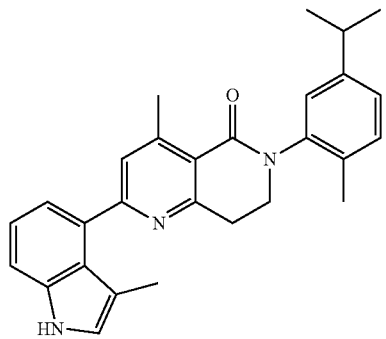 [SMILES: Cc1ccc(C(C)C)cc1N1CCc2nc(-c3cccc4[nH]cc(C)c34)cc(C)c2C1=O]

To a solution of 6-(5-isopropyl-2-methylphenyl)-4-methyl-2-(3-methyl-1-tosyl-1H-indol-4-yl)-7,8-dihydro-1,6-naphthyridin-5(6H)-one (0.156 g, 0.270 mmol) in THF (5 mL) at rt was added LiAlH$_4$ (5.40 mL, 1 M in THF). The reaction mixture was left to stir at rt until conversion was deemed complete as judged by LCMS. The reaction was quenched with water and then 1 M aq NaOH. The mixture was then extracted with DCM. The organic layer was then dried (Na$_2$SO$_4$), filtered and concentrated. The residue was then purified by FCC (10-60% EtOAc/heptane) to give the title compound. $^1$H NMR (400 MHz, DMSO-d$_6$) δ ppm 10.88 (br. s., 1 H), 7.38 (d, J=8.1 Hz, 1 H), 7.21 (s, 1 H), 7.05-7.17 (m, 4 H), 6.96 (d, J=6.3 Hz, 1 H), 6.90 (d, J=8.8 Hz, 1 H), 4.10 (s, 2 H), 3.21-3.37 (m, 2 H), 3.01-3.09 (m, 2 H), 2.81-2.92 (m, 1 H), 2.30 (s, 3 H), 2.28 (s, 3 H), 1.89 (s, 3 H), 1.21 (d, J=7.1 Hz, 6 H); MS ESI m/z 410.4 (M+H)$^+$.

For the preparation of deuterated compounds LiAlD$_4$ was used in a similar method in place of LiAlH$_4$. The following compounds were prepared in a similar manner.

| | Structure | Chemical Name & Analytical Data MS (ESI) m/z (M + H)$^+$ |
|---|---|---|
| 40-E | 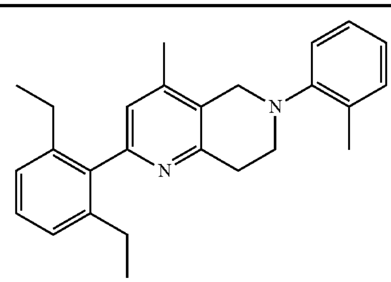 | 2-(2,6-diethylphenyl)-4-methyl-6-(o-tolyl)-5,6,7,8-tetrahydro-1,6-naphthyridine. TFA salt. $^1$H NMR (400 MHz, CDCl$_3$) δ ppm 7.39-7.41 (m, 1H), 7.25-7.29 (m, 3H), 7.18-7.21 (m, 3H), 7.09-7.13 (m, 1H), 4.18 (s, 2H), 3.56 (br t, J = 5.68 Hz, 2H), 3.34 (br t, J = 5.68 Hz, 2H), 2.52-2.41 (m, 5H), 2.37 (s, 3H), 2.18-2.28 (m, 2H), 1.11 (t, J = 7.58 Hz, 6H); MS (ESI+) m/z 371.17 (M + H)$^+$. |
| 40-G | 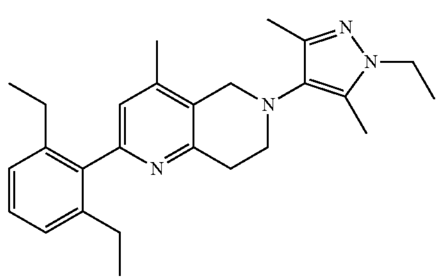 [SMILES: CCc1cccc(CC)c1-c1cc(C)c2c(n1)CCN(c1c(C)nn(CC)c1C)C2] | 2-(2,6-diethylphenyl)-6-(1-ethyl-3,5-dimethyl-1H-pyrazol-4-yl)-4-methyl-5,6,7,8-tetrahydro-1,6-naphthyridine. 2-(2,6-diethylphenyl)-6-(1-ethyl-3,5-dimethyl-1H-pyrazol-4-yl)-4-methyl-5,6,7,8-tetrahydro-1,6-naphthyridine. $^1$H NMR (400 MHz, DMSO-d$_6$) δ ppm 7.24-7.31 (m, 1H) 7.12 (d, J = 7.58 Hz, 2H) 6.96 (s, 1H) 4.06 (s, 2H) 3.93 (q, J = 7.16 Hz, 2H) 3.29 (obs, 2H) 2.93 (t, J = 5.56 Hz, 2H) 2.25 (q, J = 7.41 Hz, 4H) 2.19 (s, 6H) 2.16 (s, 3H) 1.26 (t, J = 7.20 Hz, 3H) 0.98 (t, J = 7.45 Hz, 6H); MS (ESI+) m/z 403.3 (M + H)$^+$. |

| | Chemical Name & Analytical Data MS (ESI) m/z (M + H)+ |
|---|---|
| 40-H | 2-(2,6-diethylphenyl)-6-(1,3-dimethyl-1H-pyrazol-5-yl)-4-methyl-5,6,7,8-tetrahydro-1,6-naphthyridine. $^1$H NMR (400 MHz, DMSO-d$_6$) δ ppm 7.24-7.30 (m, 1H) 7.12 (d, J = 7.58 Hz, 2H) 7.00 (s, 1H) 5.81 (s, 1H) 4.08 (s, 2H) 3.63 (s, 3H) 3.23 (t, J = 5.81 Hz, 2H) 3.03 (t, J = 5.68 Hz, 2H) 2.22-2.28 (m, 7H) 2.10 (s, 3H) 0.98 (t, J = 7.45 Hz, 6H); MS (ESI+) m/z 375.4 (M + H)+. |
| 40-I | 2-(2,6-diethylphenyl)-6-(5-methoxy-2-methylphenyl)-4-methyl-5,6,7,8-tetrahydro-1,6-naphthyridine. $^1$H NMR (400 MHz, DMSO-d$_6$) δ ppm 7.25-7.29 (m, 1H) 7.13 (d, J = 7.58 Hz, 3H) 6.99 (s, 1H) 6.80 (d, J = 2.53 Hz, 1H) 6.61 (dd, J = 8.34, 2.53 Hz, 1H) 4.09 (s, 2H) 3.74 (s, 3H) 3.23 (t, J = 5.68 Hz, 2H) 3.01 (t, J = 5.56 Hz, 2H) 2.22-2.30 (m, 10 H) 0.99 (t, J = 7.58 Hz, 6H); MS (ESI+) m/z 401.3 (M + H)+. |
| 40-J | 2-(2,6-diethyphenyl)-6-(2,5-dimethylphenyl)-4-methyl-5,6,7,8-tetrahydro-1,6-naphthyridine. $^1$H NMR (400 MHz, DMSO-d$_6$) δ ppm 7.25-7.30 (m, 1H) 7.05-7.15 (m, 4H) 6.99 (s, 1H) 6.83 (d, J = 7.58 Hz, 1H) 4.09 (s, 2H) 3.21 (t, J = 5.68 Hz, 2H) 3.02 (t, J = 5.43 Hz, 2H) 2.23-2.31 (m, 13H) 0.99 (t, J = 7.58 Hz, 6H); MS (ESI+) m/z 385.4 (M + H)+. |
| 40-K | 2-(2,6-diethylphenyl)-6-(1-ethyl-3-methyl-1H-pyrazol-5-yl)-4-methyl-5,6,7,8-tetrahydro-1,6-naphthyridine. $^1$H NMR (400 MHz, DMSO-d$_6$) δ ppm 7.24-7.30 (m, 1H) 7.12 (d, J = 7.58 Hz, 2H) 7.00 (s, 1H) 5.83 (s, 1H) 4.07 (s, 2H) 3.96 (q, J = 7.33 Hz, 2H) 3.21 (t, J = 5.68 Hz, 2H) 3.02 (t, J = 5.81 Hz, 2H) 2.19-2.29 (m, 7H) 2.12 (s, 3H) 1.33 (t, J = 7.20 Hz, 3H) 0.98 (t, J = 7.45 Hz, 6H); MS (ESI+) m/z 389.4 (M + H)+. |
| 40-L | 2-(2,6-diethylphenyl)-6-(2,4-dimethylphenyl)-4-methyl-5,6,7,8-tetrahydro-1,6-naphthyridine. $^1$H NMR (400 MHz, DMSO-d$_6$) δ ppm 7.24-7.30 (m, 1H) 7.10-7.19 (m, 3H) 6.97-7.07 (m, 3H) 4.05 (s, 2H) 3.19 (t, J = 5.68 Hz, 2H) 3.01 (t, J = 5.56 Hz, 2H) 2.22-2.31 (m, 13H) 0.99 (t, J = 7.58 Hz, 6H); MS (ESI+) m/z 385.4 (M + H)+. |

| Structure | Chemical Name & Analytical Data MS (ESI) m/z (M + H)+ |
|---|---|
| 40-M 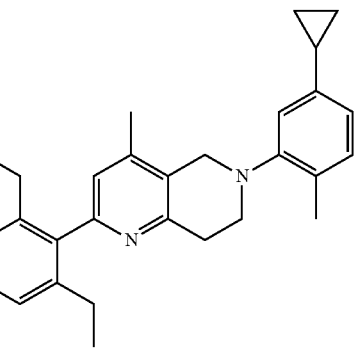 | 6-(5-cyclopropyl-2-methylphenyl)-2-(2,6-diethylphenyl)-4-methyl-5,6,7,8-tetrahydro-1,6-naphthyridine. $^1$H NMR (400 MHz, DMSO-d$_6$) δ ppm 7.25-7.30 (m, 1H) 7.07-7.16 (m, 3H) 6.96-7.01 (m, 2H) 6.69 (dd, J = 7.71. 1.64 Hz, 1H) 4.10 (s, 2H) 3.23 (t, J = 5.68 Hz, 2H) 2.99 (t, J = 5.56 Hz, 2H) 2.22-2.31 (m, 10 H) 1.89 (tt, J = 8.37, 5.02 Hz, 1H) 0.99 (t, J = 7.58 Hz, 6H) 0.87-0.94 (m, 2H) 0.60-0.66 (m, 2H); MS (ESI+) m/z 411.4 (M + H)+. |
| 40-N 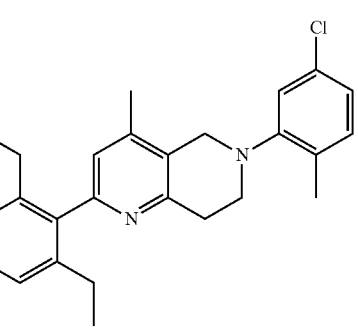 | 6-(5-chloro-2-methylphenyl)-2-(2,6-diethylphenyl)-4-methyl-5,6,7,8-tetrahydro-1,6-naphthyridine. $^1$H NMR (400 MHz, DMSO-d$_6$) δ ppm 7.23-7.30 (m, 3H) 7.13 (d, J = 7.58 Hz, 2H) 7.07 (dd, J = 8.08, 2.27 Hz, 1H) 7.00 (s, 1H) 4.14 (s, 2H) 3.24 (t, J = 5.81 Hz, 2H) 3.03 (t, J = 5.56 Hz, 2H) 2.23-2.31 (m, 10 H) 0.99 (t, J = 7.45 Hz, 6H); MS (ESI+) m/z 405.2 (M + H)+. |
| 40-O 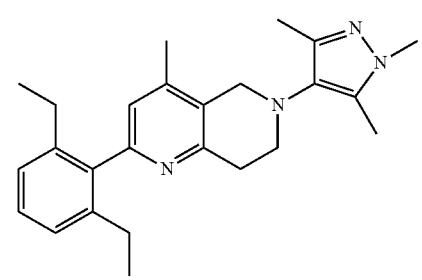 [SMILES: CCc1cccc(CC)c1-c1cc(C)c2c(n1)CCN(c1c(C)nn(C)c1C)C2] | 2-(2,6-diethylphenyl)-4-methyl-6-(1,3,5-trimethyl-1H-pyrazol-4-yl)-5,6,7,8-tetrahydro-1,6-naphthyridine. $^1$H NMR (400 MHz, DMSO-d$_6$) δ ppm 7.24-7.29 (m, 1H) 7.12 (d, J = 7.58 Hz, 2H) 6.96 (s, 1H) 4.06 (s, 2H) 3.60 (s, 3H) 3.29 (s, 2H) 2.93 (t, J = 5.56 Hz, 2H) 2.25 (q, J = 7.58 Hz, 4H) 2.19 (d, J = 4.29 Hz, 6H) 2.14 (s, 3H) 0.98 (t, J = 7.58 Hz, 6H); MS (ESI+) m/z 389.4 (M + H)+. |
| 40-P 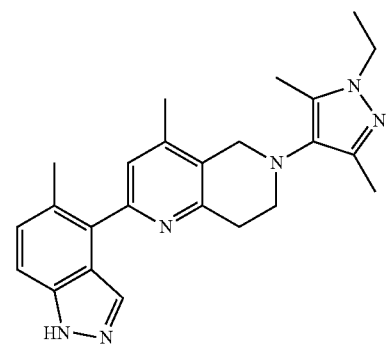 [SMILES: CCn1nc(C)c(N2CCc3nc(-c4c(C)ccc5[nH]ncc45)cc(C)c3C2)c1C] | 6-(1-ethyl-3,5-dimethyl-1H-pyrazol-4-yl)-4-methyl-2-(5-methyl-1H-indazol-4-yl)-5,6,7,8-tetrahydro-1,6-naphthyridine. $^1$H NMR (400 MHz, DMSO-d$_6$) δ ppm 12.97 (br. s., 1H) 7.76 (s, 1H) 7.46 (d, J = 8.34 Hz, 1H) 7.28 (d, J = 8.59 Hz, 1H) 7.23 (s, 1H) 4.08 (s, 2H) 3.94 (q, J = 7.07 Hz, 2H) 3.33-3.36 (m, 2H) 3.02 (t, J = 5.43 Hz, 2H) 2.36 (s, 3H) 2.24 (s, 3H) 2.20 (s, 3H) 2.18 (s, 3H) 1.27 (t, J = 7.20 Hz, 3H); MS (ESI+) m/z 401.3 (M + H)+. |
| 40-Q 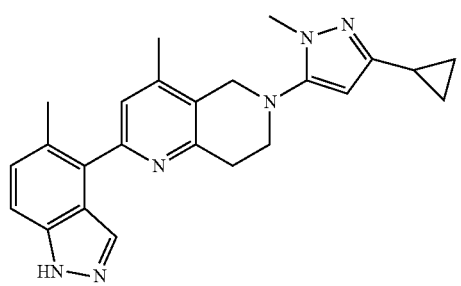 [SMILES: Cc1cc(-c2c(C)ccc3[nH]ncc23)nc2c1CN(c1cc(C3CC3)nn1C)CC2] | 6-(3-cyclopropyl-1-methyl-1H-pyrazol-5-yl)-4-methyl-2-(5-methyl-1H-indazol-4-yl)-5,6,7,8-tetrahydro-1,6-naphthyridine. $^1$H NMR (400 MHz, DMSO-d$_6$) δ ppm 12.99 (s, 1H) 7.76 (s, 1H) 7.47 (d, J = 8.34 Hz, 1H) 7.25-7.31 (m, 2H) 5.76 (s, 1H) 4.09 (s, 2H) 3.62 (s, 3H) 3.25 (t, J = 5.81 Hz, 2H) 3.10 (t, J = 5.56 Hz, 2H) 2.36 (s, 3H) 2.29 (s, 3H) 1.74-1.83 (m, 1H) 0.77-0.84 (m, 2H) 0.59-0.65 (m, 2H); MS (ESI+) m/z 399.3 (M + H)+. |

| Structure | Chemical Name & Analytical Data MS (ESI) m/z (M + H)+ |
|---|---|
| 40-R 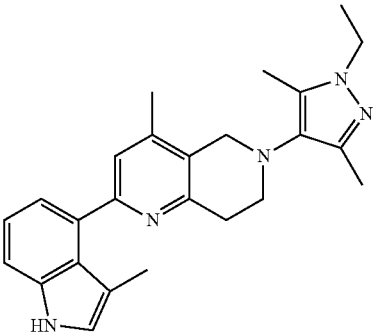 [SMILES: CCn1nc(C)c(N2CCc3nc(-c4cccc5[nH]cc(C)c45)cc(C)c3C2)c1C] | 6-(1-ethyl-3,5-dimethyl-1H-pyrazol-4-yl)-4-methyl-2-(3-methyl-1H-indol-4-yl)-5,6,7,8-tetrahydro-1,6-naphthyridine. $^1$H NMR (400 MHz, DMSO-$d_6$) δ ppm 10.88 (br. s., 1H) 7.38 (d, J = 8.08 Hz, 1H) 7.18 (s, 1H) 7.08-7.13 (m, 2H) 6.92-6.96 (m, 1H) 4.06 (s, 2H) 3.93 (q, J = 7.07 Hz, 2H) 3.31-3.35 (m, 2H) 2.98 (t, J = 5.31 Hz, 2H) 2.22 (s, 3H) 2.19 (s, 3H) 2.16 (s, 3H) 1.89 (s, 3H) 1.27 (t, J = 7.33 Hz, 3H); MS (ESI+) m/z 400.4 (M + H)+. |
| 40-S 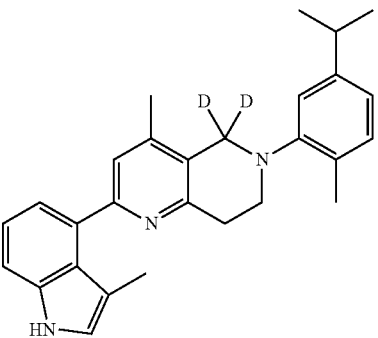 [SMILES: [2H]C1([2H])c2c(C)cc(-c3cccc4[nH]cc(C)c34)nc2CCN1c1cc(C(C)C)ccc1C] | $^1$H NMR (400 MHz, DMSO-$d_6$) δ ppm 10.89 (br. s., 1H), 7.38 (d, J = 7.8 Hz, 1H), 7.21 (s, 1H), 7.12 (t, J = 6.9 Hz, 2H), 7.08 (s, 2H), 6.96 (d, J = 7. 1 Hz, 1H), 6.89 (d, J = 7.6 Hz, 1H), 3.26 (t, J = 5.6 Hz, 2H), 3.04 (t, J = 5.4 Hz, 2H), 2.86 (dt, J = 13.8, 6.9 Hz, 1H), 2.30 (s, 3H), 2.27 (s, 3H), 1.89 (s, 3H), 1.21 (d, J = 6.8 Hz, 6H); MS (ESI+) m/z 412.3 (M + H)+. |

Example 41

41-A. 6-Benzyl-2-chloro-4-methyl-5,6,7,8-tetrahydro-1,6-naphthyridine

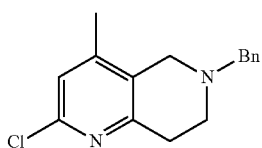 [SMILES: Cc1cc(Cl)nc2c1CN(Cc1ccccc1)CC2]

A mixture of 1-benzyl-4-piperidone (19.6 mL, 106 mmol), acetoacetamide (11.7 g, 116 mmol) in Eaton's reagent (40 mL) was allowed to stir at 110° C. After stirring for 18 h, the reaction mixture was cooled to rt, and then slowly poured into stirred aq NaHCO$_3$ (150 g of NaHCO$_3$ in 1000 mL of water. The mixture was diluted with DCM (1000 mL) and H$_2$O (50 mL), and the two phases were separated. The products were extracted once with DCM (500 mL) from the aqueous layer. The combined organic layer was washed with brine (500 mL), dried over Na$_2$SO$_4$, filtered, and concentrated under reduced pressure. The brown residue was triturated with acetone (200 mL). The precipitated solid was collected on a funnel, washed with acetone (100 mL), and dried under reduced pressure to give 6-benzyl-4-methyl-5,6,7,8-tetrahydro-1,6-naphthyridin-2-ol. $^1$H NMR (400 MHz, CDCl$_3$) δ ppm 12.71 (br s, 1 H), 7.26-7.35 (m, 5 H), 6.22 (s, 1 H), 3.71 (s, 2 H), 3.34 (s, 2 H), 2.70-2.73 (m, 2 H), 2.77-2.79 (m, 2 H), 2.03 (s, 3 H); MS (ESI+) m/z 255.42 (M+H)+.

A solution of 6-benzyl-4-methyl-5,6,7,8-tetrahydro-1,6-naphthyridin-2-ol (13.6 g, 53.5 mmol), benzyltriethylammonium chloride (24.4 g, 107 mmol) and POCl$_3$ (100 mL, 1069 mmol) was allowed to stir at 105° C. After stirring for 18 h, the mixture was cooled to rt, and diluted with EtOAc (100 mL). The precipitate was collected on a funnel, washed with EtOAc (200 mL), and then dried under reduced pressure to give benzyl-2-chloro-4-methyl-5,6,7,8-tetrahydro-1,6-naphthyridine as a dihydrochloride salt.

$^1$H NMR (400 MHz, DMSO-$d_6$) δ ppm 12.02 (br s, 1 H), 7.71-7.73 9m, 2 H), 7.48-7.49 (m, 3 H), 7.34 (s, 1 H), 4.21-4.57 (m, 4 H), 3.60-3.62 (m, 1 H), 3.28-3.37 (m, 2 H), 3.02-3.05 (m, 1 H), 2.19 (s, 3H); MS (ESI+) m/z 273.33 (M+H)+.

41-B. 2-Chloro-4-methyl-5,6,7,8-tetrahydro-1,6-naphthyridine hydrochloride

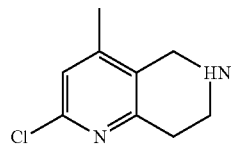

To a suspension of crude benzyl-2-chloro-4-methyl-5,6,7,8-tetrahydro-1,6-naphthyridine dihydrochloride (8.00 g, 23.1 mmol) in DCM (100 mL), 2 M Na$_2$CO$_3$aq (50 mL) was added. The mixture was stirred for 20 min, and then diluted with brine. The products were extracted twice with DCM, and the combined organic layer was washed with brine, dried over Na$_2$SO$_4$, filtered, and concentrated to give crude (6.14 g). A solution of the residue and ACECl (5.05 mL, 46.3 mmol) in DCE (100 mL) was allowed to stir at 70° C. for 1.5 h under nitrogen. MeOH (50 mL) was added and the mixture was stirred at the same temperature for 1 h. The mixture was cooled to rt and concentrated. The residue was triturated with MeOH (10 mL) and EtOAc (400 mL), and the white solid was collected on a funnel, washed with EtOAc (200 mL), and dried under reduced pressure to give 2-chloro-4-methyl-5,6,7,8-tetrahydro-1,6-naphthyridine hydrochloride (4.54 g): $^1$H NMR (400 MHz, DMSO-d$_6$) δ ppm 9.54 (br s, 2 H), 7.33 (s, 1 H), 4.21-4.24 (app t, 2 H), 3.41-3.43 (m, 2 H), 3.05 (t, J=6.57 Hz, 2 H), 2.24 (s, 3 H); MS (ESI+) m/z 183.44 (M+H)$^+$.

41-C. 2-Chloro-6-(5-isopropyl-2-methylphenyl)-4-methyl-5,6,7,8-tetrahydro-1,6-naphthyridine

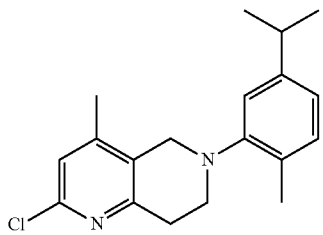 [SMILES: Cc1ccc(C(C)C)cc1N1CCc2nc(Cl)cc(C)c2C1]

To a suspension of 2-chloro-4-methyl-5,6,7,8-tetrahydro-1,6-naphthyridine hydrochloride (4.03 g, 18.39 mmol) in DCM (100 mL), 2 M aq Na$_2$CO$_3$ (100 mL) was added. After stirring for 30 min, the mixture was diluted with brine (200 mL). The products were extracted twice with DCM. The combined organic layer was washed with brine, dried over Na$_2$SO$_4$, filtered, and concentrated. A suspension of the residue (3.25 g), 5-isopropyl-2-methylphenyl trifluoromethanesulfonate (11.42 g, 40.5 mmol), Pd$_2$(dba)$_3$.CHCl$_3$ adduct (0.762 g, 0.736 mmol), rac-BINAP (0.945 g, 1.471 mmol) and Cs$_2$CO$_3$ (17.98 g, 55.2 mmol) in toluene (17 mL) and t-butanol (3 mL) was allowed to stir at 90° C. for 23 h under argon. The reaction was cooled to rt, and diluted with EtOAc and brine. The products were extracted three times with EtOAc. The combined organic layer was dried over Na$_2$SO$_4$, and filtered. The filtrate was added to 60 g of silica gel and then concentrated. The residue was washed with EtOAc on a funnel, and then the filtrate was concentrated. The residue was purified by flash column chromatography on 330 g of silica gel (with 25 g pre-column; eluent: heptane/EtOAc=100:0 to 80:20) to give the desired product along with 18 mol % of Carvacrol (2.97 g). The mixture was purified by flash column chromatography on 55 g of NH-modified silica gel (with 20 g of aminopropyl-modified silca gel as pre-column; eluent: heptane/EtOAc=100:0 to 90:10) to give 2-chloro-6-(5-isopropyl-2-methylphenyl)-4-methyl-5,6,7,8-tetrahydro-1,6-naphthyridine (2.50 g) as a yellow oil: $^1$H NMR (400 MHz, CDCl$_3$) δ ppm 7.16 (d, J=7.83 Hz, 1 H), 6.99-7.00 (m, 2 H), 6.92-6.95 (m, 1 H), 3.98 (s, 2 H), 3.28 (t, J=5.81 Hz, 2 H), 3.12 (br t, J=5.68 Hz, 2 H), 2.84-2.94 (m, 1 H), 2.29 (s, 3 H), 2.20 (s, 3 H), 1.26 (d, J=6.82 Hz, 6 H); MS (ESI+) m/z 315.34 (M+H)$^+$.

41-D. 6-(5-Isopropyl-2-methylphenyl)-4-methyl-2-(5-methyl-1H-indazol-4-yl)-5,6,7,8-tetrahydro-1,6-naphthyridine

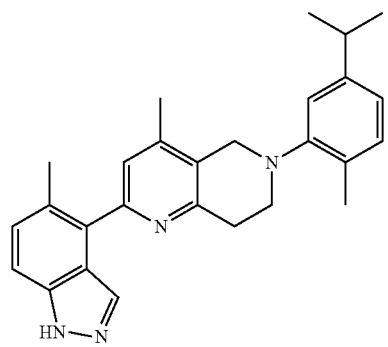 [SMILES: Cc1ccc(C(C)C)cc1N1CCc2nc(-c3c(C)ccc4[nH]ncc34)cc(C)c2C1]

A mixture of 2-chloro-6-(5-isopropyl-2-methylphenyl)-4-methyl-5,6,7,8-tetrahydro-1,6-naphthyridine (2.50 g, 7.94 mmol), 5-methyl-1H-indazol-4-ylboronic acid (1.817 g, 10.32 mmol), Pd(PPh$_3$)$_4$ (0.918 g, 0.794 mmol) and K$_3$PO$_4$ (3.37 g, 15.88 mmol) in 1,4-dioxane (30 mL) and H$_2$O (3 mL) was heated at 130° C. for 1 h under nitrogen in a microwave reactor. The mixture was concentrated and diluted with EtOAc and brine. The products were extracted twice with EtOAc. The combined organic layer was dried over Na$_2$SO$_4$, filtered, and concentrated. The residue was purified twice by flash column chromatography on 120 g of silica gel (with 25 g of silica gel pre-column; eluent: heptane/EtOAc=75:25 to 30:70) to give a yellow solid. The yellow solid was suspended with 25 g of aminopropyl-modified silica gel in DCM, and the suspension was concentrated. The residue was loaded on 55 g of NH-silica gel and purified by flash column chromatography (eluent: heptane/EtOAc=75:25 to 25:75) to give the desired product (2.50 g). The product was triturated in CH$_3$CN/H$_2$O, collected on a funnel and dried under reduced pressure to give 6-(5-isopropyl-2-methylphenyl)-4-methyl-2-(5-methyl-1H-indazol-4-yl)-5,6,7,8-tetrahydro-1,6-naphthyridine (2.23 g) as a white solid: $^1$H NMR (400 MHz, CDCl$_3$) δ ppm 10.03 (br s, 1 H), 7.90 (d, J=0.67 Hz, 1 H), 7.40 (dd, J=0.67, 8.50 Hz, 1 H), 7.32 (d, J=8.50 Hz, 1 H), 7.19 (d, J=7.75 Hz, 1 H), 7.16 (s, 1 H), 7.08 (d, J=1.60 Hz, 1 H), 6.94-6.97 (dd, J=1.60, 7.75 Hz, 1 H), 4.14 (s, 2 H), 3.38 (br t, J=5.68 Hz, 2 H), 3.26 (br t, J=5.69 Hz, 2 H), 2.87-2.98 (m, 1 H), 2.44 (s, 3 H), 2.37 (s, 3 H), 2.31 (s, 3 H), 1.29 (d, J=6.82 Hz, 6 H); MS (ESI+) m/z 411.33 (M+H)$^+$.

The following compounds were prepared in a similar manner.

| Structure | Chemical Name & Analytical Data MS (ESI) m/z (M + H)+ |
|---|---|
| 41-E 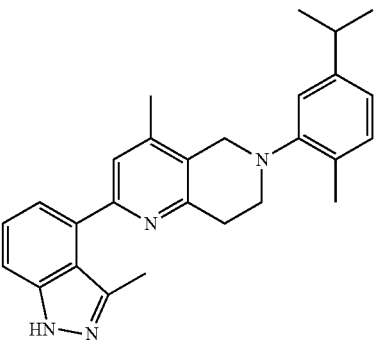 [SMILES: Cc1ccc(C(C)C)cc1N1CCc2nc(-c3cccc4[nH]nc(C)c34)cc(C)c2C1] | 6-(5-isopropyl-2-methylphenyl)-4-methyl-2-(3-methyl-1H-indazol-4-yl)-5,6,7,8-tetrahydro-1,6-naphthyridine. TFA salt $^1$H NMR (400 MHz, CDCl$_3$) δ ppm 7.32-7.42 (m, 4H), 7.22 (d, J = 7.83 Hz, 1H), 7.06 (d, J = 1.77 Hz, 1H), 7.00-7.02 (m, 1H), 4.19 (s, 2H), 3.66 (app t, 2H), 3.41 (br t, J = 5.68 Hz, 2H), 2.88-2.98 (m, 1H), 2.49 (s, 3H), 2.35 (s, 3H), 2.22 (s, 3H), 1.29 (d, J = 6.82 Hz, 6H); MS (ESI+) m/z 411.26 (M + H)+. |
| 41-F 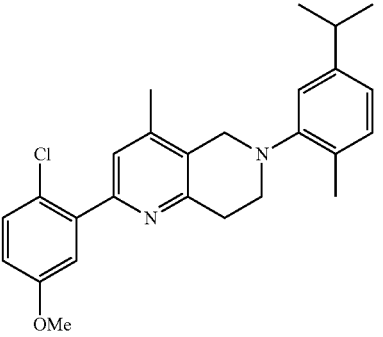 [SMILES: COc1ccc(Cl)c(-c2cc(C)c3c(n2)CCN(c2cc(C(C)C)ccc2C)C3)c1] | 2-(2-chloro-5-methoxyphenyl)-6-(5-isopropyl-2-methylphenyl)-4-methyl-5,6,7,8-tetrahydro-1,6-naphthyridine. $^1$H NMR (400 MHz, CDCl$_3$) δ ppm 7.35 (d, J = 8.84 Hz, 1H), 7.28 (s, 1H), 7.18 (d, J = 7.83 Hz, 1H), 7.10 (d, J = 3.28 Hz, 1H), 7.05 (d, J = 1.77 Hz, 1H), 6.94 (dd, J = 1.77, 7.83 Hz, 1H), 6.86 (dd, J = 3.28, 8.84 Hz, 1H), 4.09 (s, 2H), 3.83 (s, 3H), 3.34 (br t, J = 5.68 Hz, 2H), 3.24 (br t, J =5.68 Hz, 2H), 2.89-2.97 (m, 1H), 2.34 (s, 3H), 2.28 (s, 3H), 1.28 (d, J = 6.82 Hz, 6H); MS (ESI+) m/z 421.30 (M + H)+. |
| 41-G 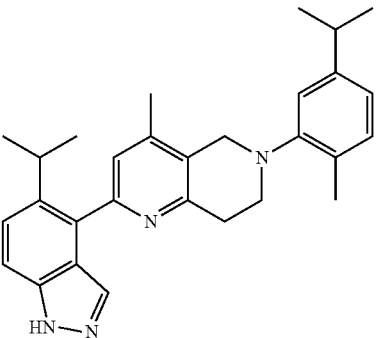 [SMILES: Cc1ccc(C(C)C)cc1N1CCc2nc(-c3c(C(C)C)ccc4[nH]ncc34)cc(C)c2C1] | 2-(5-isopropyl-1H-indazol-4-yl)-6-(5-isopropyl-2-methylphenyl)-4-methyl-5,6,7,8-tetrahydro-1,6-naphthyridine. $^1$H NMR (400 MHz, CDCl$_3$) δ ppm 7.79 (s, 1H), 7.45-7.50 (m, 2H), 7.20 (d, J = 7.75 Hz, 1H), 7.11 (s, 1H), 7.08 (d, J = 1.60 Hz, 1H), 6.96 (dd, J = 1.60, 7.75 Hz, 1H), 4.15 (s, 2H), 3.38 (br t, J = 5.68 Hz, 2H), 3.18-3.26 (m, 3H), 2.88-2.98 (m, 1H), 2.38 (s, 3H), 2.31 (s, 3H), 1.29 (d, J = 6.82 Hz, 6H), 1.26 (d, J = 6.82 Hz, 6H); MS (ESI+) m/z 439.3 (M + H)+. |
| 41-H 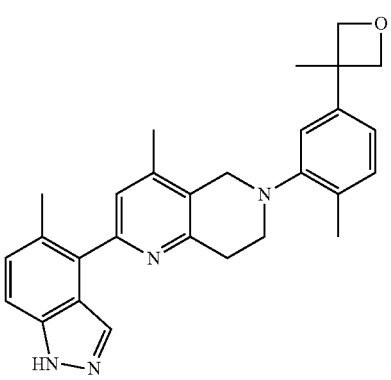 [SMILES: Cc1ccc(C2(C)COC2)cc1N1CCc2nc(-c3c(C)ccc4[nH]ncc34)cc(C)c2C1] | 4-methyl-2-(5-methyl-1H-indazol-4-yl)-6-(2-methyl-5-(3-methyloxetan-3-yl)phenyl)-5,6,7,8-tetrahydro-1,6-naphthyridine. $^1$H NMR (400 MHz, DMSO-d$_6$) δ ppm 13.01 (br s, 1H), 7.78 (app t, 1H), 7.47(dd, J = 1.01,8.51 Hz, 1H), 7.29 (d, J = 8.51 Hz, 1H),7.27(s, 1H),7.21 (d, J = 7.83 Hz, 1H), 7.08 (d, J = 1.94 Hz, 1H), 6.89 (dd, J = 1.94, 7.83 Hz, 1H), 4.83 (d, J = 5.56 Hz, 2H), 4.55 (d, J = 5.56 Hz, 2H), 4.13 (s, 2H), 3.30 (br , J = 5.81 Hz, 2H), 3.10 (br t, J = 5.56 Hz, 2H), 2.37 (s, 3H), 2.32 (s, 3H), 2.31 (s, 3H), 1.65 (s, 3H); MS (ESI+) m/z 439.44 (M + H)+. |

| Structure | Chemical Name & Analytical Data MS (ESI) m/z (M + H)+ |
|---|---|
| 41-I 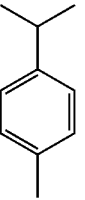 | 6-(5-isopropyl-2-methylphenyl)-2-(5-methyl-1H-indazol-4-yl)-5,6,7,8-tetrahydro-1,6-naphthyridine. ¹H NMR (400 MHz, CDCl₃) δ ppm 9.98 (br s, 1H), 7.91 (d, J = 1.26 Hz, 1H), 7.53 (d, J = 7.83 Hz, 1H), 7.42 (dd, J = 1.01, 8.59 Hz, 1H), 7.30-7.34 (m, 2H), 7.18 (d, J = 7.66 Hz, 1H), 7.03 (d, J = 1.94 Hz, 1H), 6.94 (dd, J = 1.94, 7.66 Hz, 1H), 4.24 (s, 2H), 3.39 (br t, J = 5.94 Hz, 2H), 3.27 (br t, J = 5.68 Hz, 2H), 2.86-2.96 (m, 1H), 2.44 (s, 3H), 2.37 (s, 3H), 1.28 (d, J = 6.82 Hz, 6H); MS (ESI+) m/z 397.3 (M + H)+. |
| 41-J 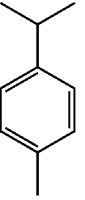 | 2-(2,6-diethylphenyl)-6-(5-isopropyl-2-methylphenyl)-4-methyl-5,6,7,8-tetrahydro-1,6-naphthyridine. ¹H NMR (400 MHz, DMSO-d₆) δ ppm 7.24-7.31 (m, 1H) 7.10-7.16 (m, 3H) 7.07 (d, J = 1.52 Hz, 1H) 7.00 (s, 1H) 6.89 (dd, J = 7.58, 1.52 Hz, 1H) 4.11 (s, 2H) 3.21-3.28 (m, 2H) 2.99 (app t, J = 5.56 Hz, 2H) 2.86 (spt, J = 6.86 Hz, 1H) 2.27 (s, 6H) 2.22-2.31 (obs m, 4H) 1.20 (d, J = 6.82 Hz, 6H) 0.99 (t, J = 7.45 Hz, 6H) MS (ESI+) m/z 413.3 (M + H)+. |
| 41-K 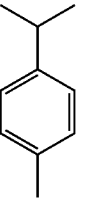 | 2-(3,5-dimethyl-1H-indazol-4-yl)-6-(5-isopropyl-2-methylphenyl)-4-methyl-5,6,7,8-tetrahydro-1,6-naphthyridine. ¹H NMR (400 MHz, DMSO-d₆) δ ppm 12.55 (br. s., 1H) 7.38 (d, J = 8.34 Hz, 1H) 7.23 (d, J = 8.34 Hz, 1H) 7.08-7.17 (m, 3H) 6.90 (d, J = 7.83 Hz, 1H) 4.14 (s, 2H) 3.25-3.30 (m, 2H) 3.00-3.07 (m, 2H) 2.82-2.90 (m, 1H) 2.31 (s, 3H) 2.28 (s, 3H) 2.16 (s, 3H) 1.78 (s, 3H) 1.21 (d, J = 6.82 Hz, 6H); MS (ESI+) m/z 426.4 (M + H)+. |

Example 42

42-A. (E)-Methyl 6-(2,6-diethylphenyl)-4-methyl-2-(prop-1-en-1-yl)nicotinate

The title compound was prepared by similar method to that described in Example 41 using (E)-prop-1-en-1-ylboronic acid. MS (ESI+) m/z 324.3 (M+H)+.

42-B. 2-(2,6-Diethylphenyl)-4,7-dimethyl-7,8-dihydro-5H-pyrano[4,3-b]pyridin-5-one

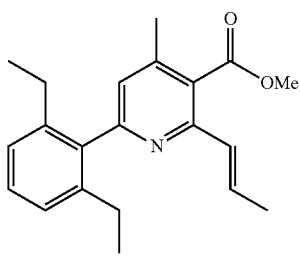 [SMILES: C/C=C/c1nc(-c2c(CC)cccc2CC)cc(C)c1C(=O)OC]

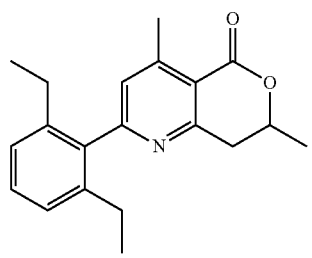 [SMILES: CCc1cccc(CC)c1-c1cc(C)c2c(n1)CC(C)OC2=O]

A mixture of (E)-methyl 6-(2,6-diethylphenyl)-4-methyl-2-(prop-1-enyl)nicotinate (150 mg, 0.464 mmol), H₂O (0.17 mL, 9.28 mmol) and TFA (2.9 mL, 37.1 mmol) was heated in a microwave reactor at 160° C. for 30 min. Starting material was observed. Additional TFA (0.5 mL) and H₂O (0.05 mL) were added and heating continued at 160° C. for 45 min and then at 140° C. for 2 h. The reaction was then poured into sat NaHCO₃ and extracted with EtOAc. The organic layer was washed with brine and then dried over Na₂SO₄ and concentrated. The residue was then purified with FCC (0-50% EtOAc/heptane) to provide 2-(2,6-diethylphenyl)-4,7-dimethyl-7,8-dihydro-5H-pyrano[4,3-b]pyridin-5-one. MS (ESI+) m/z 310.3 (M+H)⁺.

42-C. 1-(6-(2,6-Diethylphenyl)-3-(hydroxy(²H₂) methyl)-4-methylpyridin-2-yl)propan-2-ol

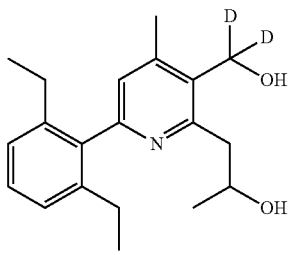 [SMILES: [2H]C([2H])(O)c1c(C)cc(-c2c(CC)cccc2CC)nc1CC(C)O]

A mixture of 2-[2,6-d]ethylphenyl)-4,7-dimethyl-7,8-dihydro-5H-pyrano[4,3-b]pyridin-5-one (118 mg, 0.381 mmol), sodium borodeuteride (63.9 mg, 1.53 mmol) in THF/EtOH (2:1) (6 mL) was heated to 60° C. for 3 h. The reaction was diluted with EtOAc and filtered. The filtrate was concentrated and purified with FCC (5-60% EtOAc/heptane) to provide 1-(6-(2,6-diethylphenyl)-3-(hydroxyl(²H₂)methyl)-4-methylpyridin-2-yl)propan-2-ol. MS (ESI+) m/z 316.4 (M+H)⁺.

42-D. 3-(Chloro(²H₂)methyl)-2-(2-chloropropyl)-6-(2,6-diethylphenyl)-4-methylpyridine

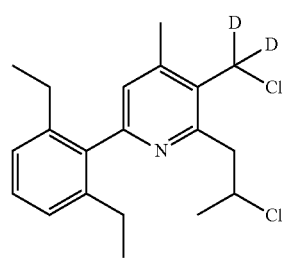 [SMILES: [2H]C([2H])(Cl)c1c(C)cc(-c2c(CC)cccc2CC)nc1CC(C)Cl]

A mixture of 1-(6-(2,6-diethylphenyl)-3-(hydroxy(²H₂)methyl)-4-methylpyridin-2-yl)propan-2-ol (99 mg, 0.314 mmol) and SOCl₂ (0.14 mL, 1.88 mmol) in DCM (5 mL) was stirred at rt for 3 h. The reaction was poured into sat aq NaHCO₃ carefully and diluted with EtOAc. The layers were mixed and then separated. The organic layer was washed with brine, dried over Na₂SO₄, and filtered. The residue, following concentration, provided crude 3-(chloro(²H₂)methyl)-2-(2-chloropropyl)-6-(2,6-diethylphenyl)-4-methylpyridine. MS (ESI+) m/z 352.2 (M+H)⁺.

42-E. N-((2-(2-Chloropropyl)-6-(2,6-diethylphenyl)-4-methylpyridin-3-yl)(²H₂)methyl)-3-cyclopropyl-1-methyl-1H-pyrazol-5-amine

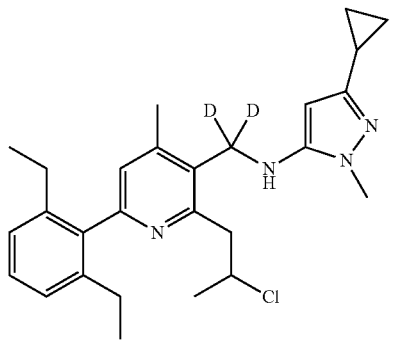 [SMILES: [2H]C([2H])(Nc1cc(C2CC2)nn1C)c1c(C)cc(-c2c(CC)cccc2CC)nc1CC(C)Cl]

A mixture of 3-(chloro(²H₂)methyl)-2-(2-chloropropyl)-6-(2,6-diethylphenyl)-4-methylpyridine (29.6 mg, 0.084 mmol), 3-cyclopropyl-1-methyl-1H-pyrazol-5-amine (57.6 mg, 0.420 mmol), NaI (37.8 mg, 0.252 mmol) and DIEA (0.044 mL, 0.252 mmol) in THF (3 mL) was stirred at rt for 1 h. Then the reaction mixture was heated to 60° C. for 4 h. The reaction was then diluted with EtOAc, washed with sat aq NaHCO₃, and brine. The organic layer was dried over Na₂SO₄, filtered and concentrated. The residue was purified by FCC (5-100% EtOAc/heptane followed by 0-10% MeOH/DCM) to provide N-((2-(2-chloropropyl)-6-(2,6-diethylphenyl)-4-methylpyridin-3-yl)(²H₂)methyl)-3-cyclopropyl-1-methyl-1H-pyrazol-5-amine. MS (ESI+) m/z 453.3 (M+H)⁺.

42-F. 6-(3-Cyclopropyl-1-methyl-1H-pyrazol-5-yl)-2-(2,6-diethylphenyl)-4,7-dimethyl-5,6,7,8-tetrahydro(5,5-²H₂)-1,6-naphthyridine

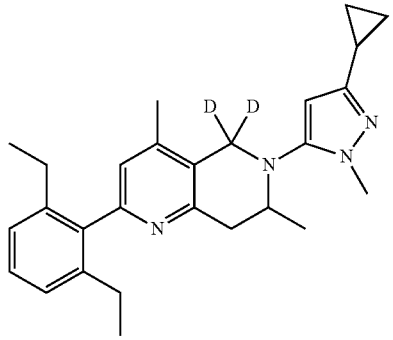 [SMILES: [2H]C1([2H])c2c(C)cc(-c3c(CC)cccc3CC)nc2CC(C)N1c1cc(C2CC2)nn1C]

To a solution of N-((2-(2-chloropropyl)-6-(2,6-diethylphenyl)-4-methylpyridin-3-yl)(²H₂)methyl)-3-cyclopropyl-1-methyl-1H-pyrazol-5-amine (14.2 mg, 0.031 mmol) in acetonitrile (2 mL), DIEA (0.016 mL, 0.094 mmol) was added followed by NaI (9.4 mg, 0.063 mmol). The mixture was heated in a microwave reactor at 160° C. for 30 min. At that point the reaction was diluted with EtOAc and washed with sat aq NaHCO₃ and then brine. The organic layer was then dried over Na₂SO₄, filtered and concentrated. The residue was then purified with FCC (5-50% EtOAc/heptane) to provide racemic 6-(3-cyclopropyl-1-methyl-1H-pyrazol-5-yl)-2-(2,6-diethylphenyl)-4,7-dimethyl-5,6,7,8-tetrahydro(5,5-$^2$H$_2$)-1,6-naphthyridine. $^1$H NMR (400 MHz, CD$_2$Cl$_2$) δ ppm 7.23-7.32 (m, 1 H) 7.13 (d, J=7.58 Hz, 2 H) 6.91 (s, 1 H) 5.67 (s, 1 H) 3.68 (s, 3 H) 3.41-3.53 (m, 1 H) 3.15-3.29 (m, 1 H) 2.87 (dd, J=17.05, 6.44 Hz, 1H) 2.33 (q, J=7.49 Hz, 4 H) 2.22 (s, 3 H) 1.84 (tt, J=8.46, 5.05 Hz, 1 H) 1.01-1.08 (m, 9 H) 0.82-0.89 (m, 2 H) 0.63-0.69 (m, 2 H). MS (ESI+) m/z 417.4 (M+H)$^+$. Two enantiomers were obtained by chiral separation (OD 4.6×250 mm column, 5% EtOH in heptane). 42-G enanatiomer 1: R, 9.26 min, MS (ESI+) m/z 417.3 (M+H)$^+$; 42-H enanatiomer 1: R, 12.62 min, MS (ESI+) m/z 417.3 (M+H)$^+$.

The following compounds were prepared in a similar manner.

(3.06 g, 14.0 mmol) and DIPEA (3.34 mL, 19.1 mmol) in DCM (30 mL) was allowed to stir at rt for 45 min. The mixture was diluted with 5% aqueous citric acid and DCM. The organic layer was separated in a separatory funnel, and concentrated. The residue was purified by flash column chromatography on 80 g of silica gel (with 25 g silica gel pre-column; eluent: heptane/EtOAc=100:0 to 50:50) to give tert-butyl 2-chloro-4-methyl-7,8-dihydro-1,6-naphthyridine-6(5H)-carboxylate. $^1$H NMR (400 MHz, CDCl$_3$) δ ppm 7.02 (s, 1 H), 4.47 (s, 2 H), 3.71 (t, J=5.81 Hz, 2 H), 2.95 (br t, J=5.68 Hz, 2 H), 2.23 (s, 3 H), 1.50 (s, 9 H); MS (ESI+) m/z 283.30 (M+H)$^+$.

To a suspension of ruthenium trichloride (0.141 g, 0.681 mmol) and NaIO4 (8.32 g, 38.9 mmol) in H$_2$O (30 mL) at 0° C., a solution of tert-butyl 2-chloro-4-methyl-7,8-dihydro-1,6-naphthyridine-6(5H)-carboxylate (2.75 g, 9.73 mmol) in

| | Structure | Chemical Name & Analytical Data |
|---|---|---|
| 42-I | 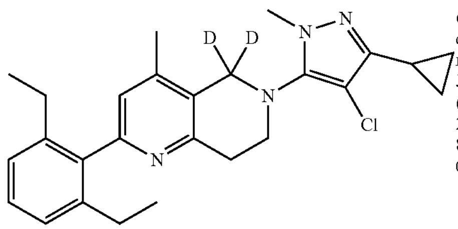 [SMILES: [2H]C1([2H])c2c(C)cc(-c3c(CC)cccc3CC)nc2CCN1c1c(Cl)c(C2CC2)nn1C] | 6-(4-chloro-3-cyclopropyl-1-methyl-1H-pyrazol-5-yl)-2-(2,6-diethylphenyl)-4-methyl-5,6,7,8-tetrahydro(5,5-$^2$H$_2$)-1,6-naphthyridine. $^1$H NMR (400 MHz, CD$_2$Cl$_2$) δ ppm 7.45 (t, J = 7.71 Hz, 1H) 7.37 (s, 1H) 7.23 (d, J = 7.83 Hz, 2H) 3.67 (s, 3H) 3.53-3.60 (m, 2H) 3.48 (t, J = 5.56 Hz, 2H) 2.37-2.50 (m, 5H) 2.18-2.31 (m, 2H) 1.79-1.91 (m, J = 8.15, 8.15, 5.43, 5.31 Hz, 1H) 1.10 (t, J = 7.45 Hz, 6H) 0.84-0.93 (m, 4H). MS (ESI+) m/z 437.3 (M + H)$^+$. |
| 42-J | 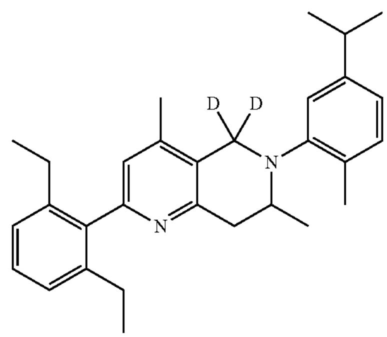 | 43-J racemic-2-(2,6-diethylphenyl)-6-(5-isopropyl-2-methylphenyl)-4,7-dimethyl-5,6,7,8-tetrahydro(5,5-$^2$H$_2$)-1,6-naphthyridine. $^1$H NMR (400 MHz, DMSO-d$_6$) δ ppm 7.24-7.30 (m, 1H) 7.09-7.17 (m, 4H) 6.99 (s, 1H) 6.91 (dd, J = 7.71, 1.64 Hz, 1H) 3.53-3.60 (m, 1H) 3.13 (dd, J = 16.93,4.80 Hz, 1H) 2.85 (dt, J = 13.71, 6.92 Hz, 1H) 2.67-2.75 (m, 1H) 2.22-2.32 (m, 10 H) 1.16-1.23 (m, 6H) 0.93-1.03 (m, 9H); MS (ESI+) m/z 429.4 (M + H)$^+$.<br>43-K ent-1 R,5.38 min, (OD 4.6 × 250 mm column, 5% EtOH in heptane). MS (ESI+) m/z 429.4 (M + H)$^+$<br>43-L ent-2 R,6.50 min, OD 4.6 × 250 mm column, 5% EtOH in heptane). MS (ESI+) m/z 429.4 (M + H) |

Example 43

43-A. 6-(5-Isopropyl-2-methylphenyl)-4-methyl-2-(5-methyl-1H-indazol-4-yl)-5,6,7,8-tetrahydro(5,5-$^2$H$_2$)-1,6-naphthyridine

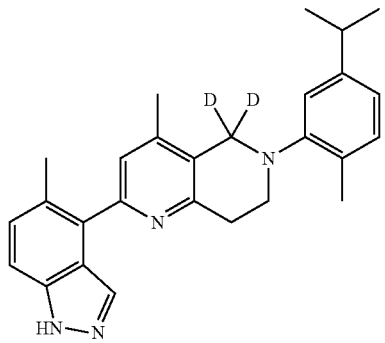 [SMILES: [2H]C1([2H])c2c(C)cc(-c3c(C)ccc4[nH]ncc34)nc2CCN1c1cc(C(C)C)ccc1C]

A solution of 2-Chloro-4-methyl-5,6,7,8-tetrahydro-1,6-naphthyridine hydrochloride (3.10 g, 12.7 mmol), Boc$_2$O EtOAc (30 mL) was added. After stirring for 5 min., the reaction mixture was warmed up to rt and stirred. After stirring for 21.5 h, the mixture was diluted with EtOAc and brine. The organic layer was separated, dried over Na$_2$SO$_4$, filtered, and concentrated. The crude was purified by flash column chromatography on 80 g of silica gel (with 25 g pre-column of silica gel; eluent: heptane/EtOAc=100:0 to 70:30) to give tert-butyl 2-chloro-4-methyl-5-oxo-7,8-dihydro-1,6-naphthyridine-6(5H)-carboxylate (2.10 g) as a white solid: $^1$H NMR (400 MHz, CDCl$_3$) δ ppm 7.15 (s, 1H), 3.98 (t, J=6.32 Hz, 2 H), 3.13 (t, J=6.32 Hz, 2 H), 2.70 (s, 3 H), 1.58 (s, 9 H).

A solution of tert-butyl 2-chloro-4-methyl-5-oxo-7,8-dihydro-1,6-naphthyridine-6(5H)-carboxylate (2.08 g, 7.01 mmol) and borane-d$_3$-THF complex solution (21.0 mL, 21.0 mmol) was allowed to stir at 60° C. for 17 h under nitrogen. The reaction mixture was cooled to rt, and quenched with MeOH (2 mL). The mixture was diluted with saturated aqueous NH$_4$Cl, brine and EtOAc. The products were extracted twice with EtOAc. The combined organic layer was washed with brine, dried over MgSO$_4$, filtered, and concentrated to give tert-butyl 2-chloro-4-methyl-5,6,7,8-tetrahydro(5,5-$^2$H$_2$)-1,6-naphthyridine-6-carboxylate along with an impurity as colorless oil (94% deuterium incorporation). The obtained material was used without further purification: MS (ESI+) m/z 285.30 (M+H)$^+$.

To a solution of give tert-butyl 2-chloro-4-methyl-5,6,7,8-tetrahydro(5,5-$^2$H$_2$)-1,6-naphthyridine-6-carboxylate (1.59 g, 5.58 mmol) in EtOAc (8 mL), 4 M HCl in 1,4-dioxane (6.98 mL, 27.9 mmol) was added and a white solid precipitated. After stirring for 1 h, additional 4 M HCl in 1,4-dioxane (6.98 mL, 27.9 mmol) was added. After stirring for further 1 h, MeOH (10 mL) was added to the reaction mixture, followed by the addition of EtOAc (400 mL). The precipitated solid was collected on a funnel, washed with EtOAc (100 mL), and dried under reduced pressure to give the desired product as a hydrochloride salt (1.29 g). The solid was neutralized with 2 M Na$_2$CO$_3$aq (10 mL) in DCM (10 mL). The mixture was allowed to stir for 1 h. The mixture was diluted with brine and DCM. The organic layer was separated and concentrated to give 2-chloro-4-methyl-5,6,7,8-tetrahydro(5,5-$^2$H$_2$)-1,6-naphthyridine (93% D): $^1$H NMR (400 MHz, CDCl$_3$) δ ppm 6.96 (s, 1 H), 3.17 (t, J=5.94 Hz, 2 H), 2.91 (t, J=5.94 Hz, 2 H), 2.17 (s, 3 H).

A suspension of 2-chloro-4-methyl-5,6,7,8-tetrahydro(5,5-$^2$H$_2$)-1,6-naphthyridine (0.92 g, 4.98 mmol), 5-isopropyl-2-methylphenyl trifluoromethanesulfonate (4.22 g, 14.95 mmol), Pd$_2$(dba)$_3$·CHCl$_3$ adduct (0.206 g, 0.199 mmol), rac-BINAP (0.248 g, 0.399 mmol) and Cs$_2$CO$_3$ (4.87 g, 14.95 mmol) in toluene (4 mL) and tent-Butanol (0.7 mL) was allowed to stir at 90° C. for 17 h under nitrogen. The reaction mixture was cooled to rt and diluted with EtOAc and brine. The products were extracted three times with EtOAc. The organic layer was dried over Na$_2$SO$_4$, and filtered. The residue was purified by flash column chromatography on 80 g of silica gel (with 15 g pre-column of silica gel; eluent: heptane/EtOAc=100:0 to 80:20), followed by flash column chromatography on 20 g of NH-modified silica gel (with 15 g pre-column of NH-modified silica gel; eluent: heptane/EtOAc=100:0 to 90:10) to give 2-chloro-6-(5-isopropyl-2-methylphenyl)-4-methyl-5,6,7,8-tetrahydro(5,5-$^2$H$_2$)-1,6-naphthyridine (94% D) as a pale orange solid: $^1$H NMR (400 MHz, CDCl$_3$) δ ppm 7.16 (d, J=7.83 Hz, 1 H), 6.99-7.00 (m, 2 H), 6.92-6.95 (m, 1 H), 3.28 (t, J=5.81 Hz, 2 H), 3.12 (t, J=5.81 Hz, 2 H), 2.84-2.94 (m, 1 H), 2.29 (s, 3 H), 2.20 (s, 3 H), 1.26 (d, J=6.82 Hz, 6 H); MS (ESI+) m/z 317.40 (M+H)$^+$.

A mixture of 2-chloro-6-(5-isopropyl-2-methylphenyl)-4-methyl-5,6,7,8-tetrahydro(5,5-$^2$H$_2$)-1,6-naphthyridine (120 mg, 0.379 mmol), 5-methyl-1H-indazol-4-ylboronic acid (87 mg, 0.492 mmol), Pd(PPh$_3$)$_4$ (43.8 mg, 0.038 mmol) and K$_3$PO$_4$ (161 mg, 0.757 mmol) in 1,4-dioxane (1.3 mL) and H$_2$O (0.13 mL) at 130° C. for 1 h under nitrogen in a microwave reactor. The mixture was concentrated and diluted with EtOAc and brine. The products were extracted twice with EtOAc, and the combined organic layer was dried over Na$_2$SO$_4$, filtered, and concentrated. The residue was purified twice by flash column chromatography on 12 g of silica gel (eluent: heptane/EtOAc=75:25 to 30:70), followed by flash column chromatography on 12 g of NH-modified silica gel (eluent: heptane/EtOAc=75:25 to 25:75) to give 6-(5-isopropyl-2-methylphenyl)-4-methyl-2-(5-methyl-1H-indazol-4-yl)-5,6,7,8-tetrahydro(5,5-$^2$H$_2$)-1,6-naphthyridine. $^1$H NMR (400 MHz, CDCl$_3$) δ ppm 10.06 (br s, 1 H), 7.90 (d, J=1.01 Hz, 1 H), 7.37-7.40 (m, 1 H), 7.31 (d, J=8.59 Hz, 1H), 7.19 (d, J=7.66 Hz, 1H), 7.16 (s, 1 H), 7.07 (d, J=1.85 Hz, 1 H), 6.95 (dd, J=1.85, 7.66 Hz, 1 H), 3.37 (br t, J=5.81 Hz, 2 H), 3.26 (br t, J=5.81 Hz, 2 H), 2.87-2.97 (m, 1 H), 2.44 (s, 3 H), 2.37 (s, 3 H), 2.31 (s, 3 H), 1.28 (d, J=6.82 Hz, 6 H); MS (ESI+) m/z 413.27 (M+H)$^+$.

The following compounds were prepared in a similar manner.

| | Structure | Chemical Name & Analytical Data MS (ESI) m/z (M + H)$^+$ |
|---|---|---|
| 43-B | 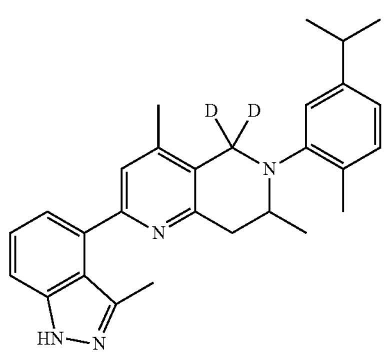 | 6-(5-isopropyl-2-methylphenyl)-4-methyl-2-(3-methyl-1H-indazol-4-yl)-5,6,7,8-tetrahydro(5,5-$^2$H$_2$)-1,6-naphthyridine. $^1$H NMR(400 MHz, DMSO-d$_6$) δ ppm 12.78 (br s, 1H), 7.51 (d, J = 7.83 Hz, 1H), 7.35-7.39 (m, 1H), 7.34 (s, 1H), 7.10-7.15 (m, 2H), 7.09 (d, J = 1.94 Hz, 1H), 6.90 (dd, J = 1.94, 7.58 Hz, 1H), 3.27 (br t, J = 5.68 Hz, 2H), 3.07 (br t, J = 5.68 Hz, 2H), 2.82-2.92 (m, 1H), 2.32 (s, 3H), 2.27 (s, 3H), 2.23 (s, 3H), 1.21 (d, J = 6.82 Hz, 6H); MS (ESI+) m/z 413.4 (M + H)$^+$. |
| 43-C | 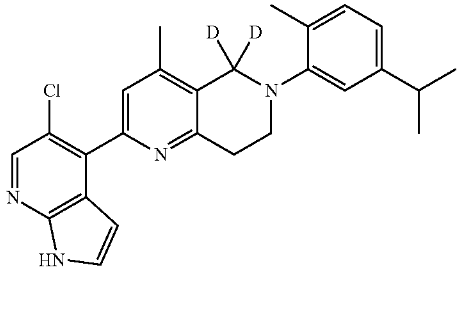 | 2-(5-chloro-1H-pyrrolo[2,3-b]pyridin-4-yl)-6-(5-isopropyl-2-methylphenyl)-4-methyl-5,6,7,8-tetrahydro(5,5-$^2$H$_2$)-1,6-naphthyridine. $^1$H NMR (400 MHz, DMSO-d$_6$) δ ppm 11.95 (br s, 1H), 8.32 (s, 1H), 7.55 (d, J = 3.54 Hz, 1H), 7.35 (s, 1H), 7.14 (d, J = 7.66 Hz, 1H), 7.10 (d, J = 1.60 Hz, 1H), 6.89 (dd, J = 1.60, 7.66 Hz, 1H), 6.30 (d, J = 3.54 Hz, 1H), 3.27 (br t, J = 5.68 Hz, 2H), 3.09 (br t, J = 5.68 Hz, 2H), 2.83-2.93 (m, 1H), 2.32 (s, 3H), 2.28 (s, 3H), 1.22 (d, J = 6.82 Hz, 6H); MS (ESI+) m/z 433.13 (M + H)$^+$. |

| | Structure | Chemical Name & Analytical Data MS (ESI) m/z (M + H)⁺ |
|---|---|---|
| 43-D | 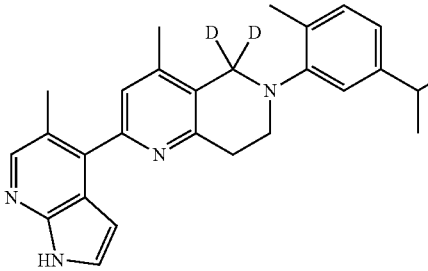 | 6-(5-isopropyl-2-methylphenyl)-4-methyl-2-(5-methyl-1H-pyrrolo[2,3-b]pyridin-4-yl)-5,6,7,8-tetrahydro(5,5-$^2$H$_2$)-1,6-naphthyridine. $^1$H NMR (400 MHz, DMSO-d$_6$) δ ppm 11.55 (br s, 1H), 8.15 (s, 1H), 7.40-7.41 (m, 1H), 7.27 (m, 1H), 7.14 (d, J = 7.83 Hz, 1H), 7.10-7.10 (m, 1H), 6.89-6.91 (m, 1H), 6.22-6.23 (m, 1H), 3.27 (br t, J = 5.81 Hz, 2H), 3.08 (br t, J = 5.68 Hz, 2H), 2.84-2.91 (m, 1H), 2.33 (s, 3H), 2.32 (s, 3H), 2.28 (s, 3H), 1.22 (d, J = 6.82 Hz, 6H); MS (ESI+) m/z 413.3 (M + H)⁺. |

Example 44

44-A. (E)-Methyl 6-(2,6-diethylphenyl)-2-(2-methoxyvinyl)-4-methylnicotinate

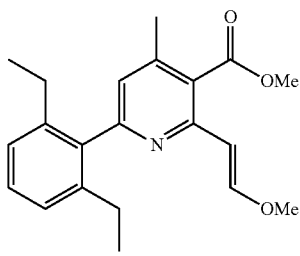 [SMILES: CCc1cccc(CC)c1-c1cc(C)c(C(=O)OC)c(/C=C/OC)n1]

The title compound was prepared with in a similar manner to that described in Example 41. MS (ESI+) m/z 354.4 (M+H)⁺.

44-B. 2-(2,6-Diethylphenyl)-6-(2,4-dimethylpyridin-3-yl)-4-methyl-1,6-naphthyridin-5(6H)-one

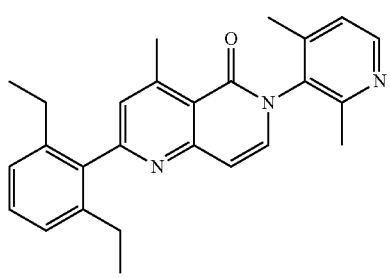 [SMILES: CCc1cccc(CC)c1-c1cc(C)c2c(=O)n(-c3c(C)ccnc3C)ccc2n1]

To a solution of (E)-methyl 6-(2,6-diethylphenyl)-2-(2-methoxyvinyl)-4-methylnicotinate (82 mg, 0.23 mmol) in toluene (2.8 mL) and acetic acid (1.9 mL) was added 2,4-dimethylpyridin-3-amine (425 mg, 3.48 mmol). Reaction was heated at 115° C. for 6 h. The mixture was concentrated under reduce pressure. The residue was purified via FCC (40-80% EtOAc/heptane) to give the title compound. $^1$H NMR (400 MHz, DMSO-d$_6$) δ ppm 8.43 (d, J=4.8 Hz, 1 H), 7.58 (d, J=7.6 Hz, 1 H), 7.31-7.36 (m, 3 H), 7.19 (d, J=7.6 Hz, 2 H), 6.78 (d, J=7.6 Hz, 1 H), 2.84 (s, 3 H), 2.24-2.35 (m, 7 H), 2.11 (s, 3 H), 1.02 (t, J=7.6 Hz, 6 H); MS (ESI+) m/z 398.3 (M+H)⁺.

44-C. 2-(2,6-Diethylphenyl)-6-(2,4-dimethylpyridin-3-yl)-4-methyl-7,8-dihydro-1,6-naphthyridin-5(6H)-one

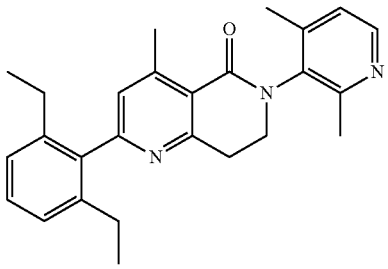 [SMILES: CCc1cccc(CC)c1-c1cc(C)c2c(n1)CCN(c1c(C)ccnc1C)C2=O]

To a solution of 2-(2,6-diethylphenyl)-6-(2,4-dimethylpyridin-3-yl)-4-methyl-1,6-naphthyridin-5(6H)-one (44 mg, 0.11 mmol) and ammonium formate (70 mg, 1.1 mmol) was added Pd/C (118 mg, 5%). Reaction was sealed and was heated at 80° C. for 2 h. Reaction was filtered. The residue was purified via FCC (40-80% EtOAc/heptane) to give the title compound. MS (ESI+) m/z 400.4 (M+H)⁺.

44-D. 2-(2,6-Diethylphenyl)-6-(2,4-dimethylpyridin-3-yl)-4-methyl-5,6,7,8-tetrahydro(5,5-$^2$H$_2$)-1,6-naphthyridine

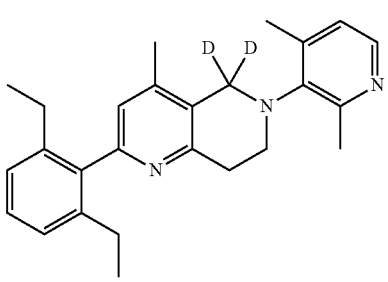 [SMILES: [2H]C1([2H])c2c(C)cc(-c3c(CC)cccc3CC)nc2CCN1c1c(C)ccnc1C]

To 2-(2,6-diethylphenyl)-6-(2,4-dimethylpyridin-3-yl)-4-methyl-7,8-dihydro-1,6-naphthyridin-5(6H)-one (32 mg, 0.08 mmol) was added a 1M solution of lithium aluminum deuteride (1.60 mL). After 16 h, solution was cooled down to 0° C. and sodium sulfate hydrate was added slowly. The mixture was filtered and concentrated under reduced pressure. The residue was purified via FCC (0-70% EtOAc/heptane) to give the title compound. $^1$H NMR (400 MHz, DMSO-$d_6$) δ ppm 8.13 (d, 1 H), 7.24-7.30 (m, 1 H), 7.13 (d, J=7.6 Hz, 2 H), 7.06-7.11 (m, 1 H), 6.96-7.01 (m, 1 H), 3.41 (t, J=5.6 Hz, 2 H), 2.99 (t, J=5.4 Hz, 2 H), 2.34 (s, 3 H), 2.27 (q, J=7.6 Hz, 4 H), 2.21 (s, 3 H), 1.00 (t, 6 H); MS (ESI+) m/z 388.3 (M+H)$^+$.

The following compounds were prepared in a similar manner.

44-B. 6-(2,6-dimethylphenyl)-4-methyl-2-(3-methyl-1H-indol-4-yl)-5,6,7,8-(5,5-$^2$H$_2$)tetrahydro-1,6-naphthyridine

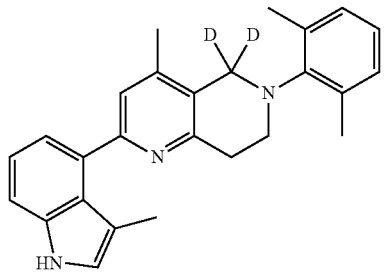 [SMILES: [2H]C1([2H])c2c(C)cc(-c3cccc4[nH]cc(C)c34)nc2CCN1c1c(C)cccc1C]

$^1$H NMR (400 MHz, DMSO-$d_6$) δ ppm 10.88 (br. s., 1 H), 7.38 (dd, J=7.9, 0.9 Hz, 1 H), 7.20 (s, 1 H), 7.12 (s, 1 H), 7.10 (d, J=8.1 Hz, 1 H), 7.03-7.08 (m, 2 H), 6.99-7.03 (m, 1 H), 6.94-6.99 (m, 1 H), 3.44 (t, J=5.6 Hz, 2 H), 3.02 (t, J=5.4 Hz, 2 H), 2.31 (s, 6 H), 2.23 (s, 3 H), 1.90 (s, 3 H); MS (ESI+) m/z 384.3 (M+H)$^+$.

Example 45

6-(5-Methoxy-2-methylphenyl)-4-methyl-2-(5-methyl-1H-indazol-4-yl)-5,6,7,8-tetrahydro(5,5-$^2$H$_2$)-1,6-naphthyridine

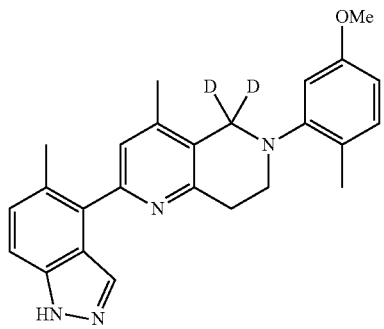 [SMILES: [2H]C1([2H])c2c(C)cc(-c3c(C)ccc4[nH]ncc34)nc2CCN1c1cc(OC)ccc1C]

To a solution of 6-(5-methoxy-2-methylphenyl)-4-methyl-2-(5-methyl-1H-indazol-4-yl)-7,8-dihydro-1,6-naphthyridin-5(6H)-one (48 mg, 0.085 mmol), prepared as in Example 40, in THF (170 μL) was added a 1M solution of lithium aluminum deuteride (424 μL). After 2.5 h, solution was cooled down to 0° C. and sodium sulfate hydrate was added slowly. The mixture was filtered and concentrated under reduce pressure. The residue was purified via FCC (50-80% EtOAc/heptane) to give the title compound. $^1$H NMR (400 MHz, DMSO-$d_6$) δ ppm 12.99 (s, 1 H), 7.77 (s, 1 H), 7.47 (d, J=8.6 Hz, 1 H), 7.20-7.35 (m, 2 H), 7.14 (d, J=8.3 Hz, 1 H), 6.80 (d, J=2.5 Hz, 1 H), 6.62 (dd, J=8.2, 2.7 Hz, 1 H), 3.75 (s, 3 H), 3.21-3.29 (m, 2 H), 3.09 (t, J=5.8 Hz, 2 H), 2.37 (s, 3 H), 2.32 (s, 3 H), 2.25 (s, 3 H); MS (ESI+) m/z 401.3 (M+H)$^+$.

Example 46

46-A. 6-(3-Cyclopropyl-1-methyl-1H-pyrazol-5-yl)-2-(5-isopropyl-1H-indazol-4-yl)-4-methyl-5,6,7,8-tetrahydro-1,6-naphthyridine

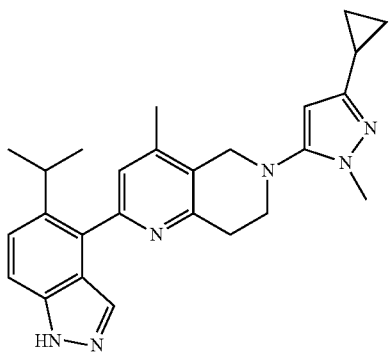 [SMILES: Cc1cc(-c2c(C(C)C)ccc3[nH]ncc23)nc2c1CN(c1cc(C3CC3)nn1C)CC2]

Microwave was used to irradiated a suspension of 2-chloro-4-methyl-5,6,7,8-tetrahydro-1,6-naphthyridine hydrochloride (1.00 g, 4.56 mmol), methyl 3-cyclopropyl-3-oxopropanoate (1.298 g, 9.13 mmol), 4-pyrrolidinopyridine (0.068 g, 0.456 mmol) and DIPEA (1.20 mL, 6.85 mmol) in toluene (10 mL) at 150° C. for 45 min. The mixture was cooled to rt and diluted with 1 M HClaq (10 mL) and EtOAc. The products were extracted twice with EtOAc. The combined organic layer was washed with a mixed solution of 1M HClaq/brine (1 mL/2 mL), dried over Na$_2$SO$_4$, filtered, and concentrated to give crude. The residue was purified by flash column chromatography on 12 g of silica gel (eluent: DCM/EtOAc=90:10 to 0:100) to give crude 1-(2-chloro-4-methyl-7,8-dihydro-1,6-naphthyridin-6(5H)-yl)-3-cyclopropylpropane-1,3-dione (0.70 g): MS (ESI+) m/z 293.31 (M+H)$^+$. The obtained material was used without further purification.

Microwave was used to irradiated a solution of crude give crude 1-(2-chloro-4-methyl-7,8-dihydro-1,6-naphthyridin-6(5H)-yl)-3-cyclopropylpropane-1,3-dione (0.70 g), pyridine (1.5 mL, 19.1 mmol), Lawesson's reagent (1.064 g, 2.63 mmol) and methyl hydrazine (0.151 mL, 2.87 mmol) in THF (9 mL) at 120° C. for 20 min. The mixture was diluted with EtOAc and brine. The organic layer was extracted with EtOAc, washed with brine, dried over Na$_2$SO$_4$, filtered, and concentrated. The residue was purified by flash column chromatography on 80 g of silica gel (eluent: heptane/EtOAc=80:20 to 0:100) to give 2-chloro-6-(3-cyclopropyl-1-methyl-1H-pyrazol-5-yl)-4-methyl-5,6,7,8-tetrahydro-1,6-naphthyridine (110 mg): $^1$H NMR (400 MHz, CDCl$_3$) δ ppm 7.02 (s, 1 H), 5.56 (s, 1 H), 3.96 (s, 2 H), 3.69 (s, 3 H), 3.08-3.23 (m, 4 H), 2.19 (s, 3 H), 1.83-1.90 (m, 1 H), 0.86-0.91 (m, 2 H), 0.68-0.72 (m, 2 H); MS (ESI+) m/z 303.28 (M+H)$^+$.

Microwave was used to irradiated a solution of 2-chloro-6-(3-cyclopropyl-1-methyl-1H-pyrazol-5-yl)-4-methyl-5,6,7,8-tetrahydro-1,6-naphthyridine (30 mg, 0.099 mmol), crude 5-isopropyl-4-(4,4,5,5-tetramethyl-1,3,2-dioxaborolan-2-yl)-1H-indazole (38.2 mg, 0.119 mmol), Pd(PPh$_3$)$_4$ (11.45 mg, 9.91 μmol) and K$_3$PO$_4$ (42.1 mg, 0.198 mmol) in 1,4-dioxane (0.5 mL) and H$_2$O (0.05 mL) at 130° C. for 1 h under nitrogen. Additional Pd(PPh$_3$)$_4$ (22.90 mg, 0.020 mmol) was added to the mixture. Microwave was irradiated to the mixture at 130° C. for further 2 h under nitrogen. The mixture was diluted with brine and EtOAc. The organic layer was separated, dried over Na$_2$SO$_4$, filtered, and concentrated. The residue was purified by flash column chromatography on 12 g of silica gel (eluent: DCM/MeOH=100:0 to 10:1) to give 6-(3-cyclopropyl-1-methyl-1H-pyrazol-5-yl)-2-(5-isopropyl-1H-indazol-4-yl)-4-methyl-5,6,7,8-tetrahydro-1,6-naphthyridine: $^1$H NMR (400 MHz, CDCl$_3$) δ ppm 9.98 (br s, 1 H), 7.76 (d, J=0.76 Hz, 1H), 7.45-7.51 (m, 2 H), 7.12 (s, 1 H), 5.65 (s, 1 H), 4.11 (s, 2 H), 3.75 (s, 3 H), 3.30-3.33 (app t, 2 H), 3.15-3.24 (m, 3 H), 2.30 (s, 3 H), 1.87-1.94 (m, 1 H), 1.25 (d, J=7.07 Hz, 6 H), 0.89-0.94 (m, 2 H), 0.72-0.76 (m, 2 H); MS (ESI+) m/z 427.33 (M+H)$^+$.

46-B. 6-(4-Chloro-3-cyclopropyl-1-methyl-1H-pyrazol-5-yl)-2-(5-isopropyl-1H-indazol-4-yl)-4-methyl-5,6,7,8-tetrahydro-1,6-naphthyridine

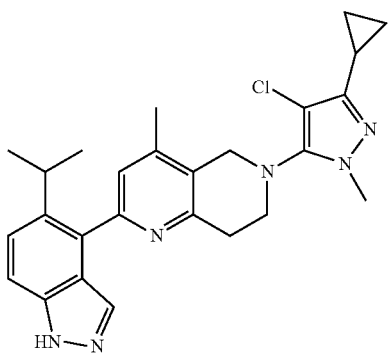 [SMILES: Cc1cc(-c2c(C(C)C)ccc3[nH]ncc23)nc2c1CN(c1c(Cl)c(C3CC3)nn1C)CC2]

To a solution of 6-(3-cyclopropyl-1-methyl-1H-pyrazol-5-yl)-2-(5-isopropyl-1H-indazol-4-yl)-4-methyl-5,6,7,8-tetrahydro-1,6-naphthyridine (20 mg, 0.047 mmol) in THF (0.5 mL), NCS (6.26 mg, 0.047 mmol) was added at rt. After stirring for 2.5 h, the reaction mixture was diluted with H$_2$O and DCM. The organic layer was separated and concentrated. The residue was purified by flash column chromatography on 12 g of NH-modified silica gel (eluent: DCM/MeOH=100:0 to 10:1) to give the desired product along with a small amount of pinacol (10 mg). The crude was purified by HPLC (C18, H$_2$O (0.1% NH$_4$OH)/CH$_3$CN) to give 6-(4-chloro-3-cyclopropyl-1-methyl-1H-pyrazol-5-yl)-2-(5-isopropyl-1H-indazol-4-yl)-4-methyl-5,6,7,8-tetrahydro-1,6-naphthyridine (2.6 mg) as a pink solid: $^1$H NMR (400 MHz, CDCl$_3$) δ ppm 10.02 (br s, 1 H), 7.77 (s, 1 H), 7.46-7.51 (m, 2 H), 7.13 (s, 1 H), 4.36 (s, 2 H), 3.72 (s, 3 H), 3.58 (t, J=5.81 Hz, 2 H), 3.16-3.23 (m, 3 H), 2.28 (s, 3 H), 1.85-1.92 (m, 1 H), 1.26 (d, J=6.82 Hz, 6 H), 0.93 (s, 2 H), 0.90-0.92 (m, 2 H); MS (ESI+) m/z 461.14 (M+H)$^+$.

Example 47

47-A. 2-(2,6-Diethylphenyl)-6-(1-ethyl-3,5-dimethyl-1H-pyrazol-4-yl)-4-methyl-5,6,7,8-tetrahydro(5, 5-2H$_2$)-1,6-naphthyridine

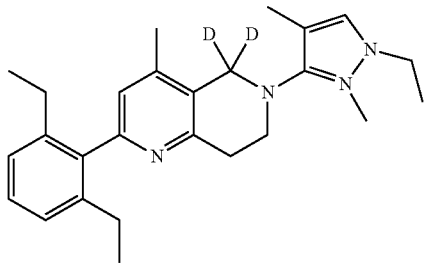

A mixture of 2-(2,6-diethylphenyl)-6-(1-ethyl-3,5-dimethyl-1H-pyrazol-4-yl)-4-methyl-7,8-dihydro-1,6-naphthyridin-5(6H)-one (88 mg, 0.211 mmol), prepared with similar method to that described in Example 41, and 1M lithium aluminun deuteride (2.11 mL, 2.11 mmol) was stirred at rt for 1 h. The reaction was then quenched with Na$_2$SO$_4$:10H$_2$O and then diluted with THF and filtered. The filtrate was concentrated and the resulting residue was purified by HLPC (XB C18 15-85% acetonitrile in H$_2$O with 0.1% NH$_4$OH) to provide 2-(2,6-diethylphenyl)-6-(1-ethyl-3,5-dimethyl-1H-pyrazol-4-yl)-4-methyl-5,6,7,8-tetrahydro(5,5-$^2$H$_2$)-1,6-naphthyridine, $^1$H NMR (400 MHz, DMSO-d$_6$) δ ppm 7.24-7.30 (m, 1H) 7.12 (d, J=7.83 Hz, 2 H) 6.96 (s, 1 H) 3.93 (q, J=7.07 Hz, 2 H) 3.29 (d, J=5.56 Hz, 2 H) 2.93 (t, J=5.56 Hz, 2 H) 2.25 (q, J=7.49 Hz, 4 H) 2.17 (d, J=13.89 Hz, 9 H) 1.26 (t, J=7.20 Hz, 3 H) 0.98 (t, J=7.58 Hz, 6 H). MS (ESI+) m/z 405.3 (M+H)$^+$.

The following compounds were prepared in a similar manner.

47-B. 6-(1-Ethyl-3,5-dimethyl-1H-pyrazol-4-yl)-4-methyl-2-(3-methyl-1H-indol-4-yl)-5,6,7,8-tetrahydro(5,5-$^2$H$_2$)-1,6-naphthyridine

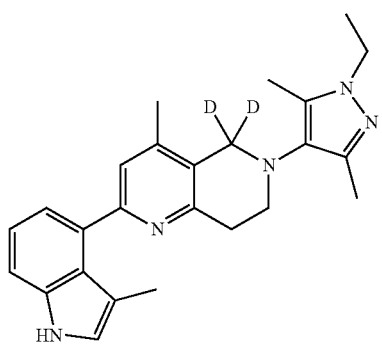 [SMILES: [2H]C1([2H])c2c(C)cc(-c3cccc4[nH]cc(C)c34)nc2CCN1c1c(C)nn(CC)c1C]

$^1$H NMR (400 MHz, DMSO-d$_6$) δ ppm 10.88 (br. s., 1 H) 7.38 (d, J=7.33 Hz, 1 H) 7.18 (s, 1 H) 7.07-7.14 (m, 2 H) 6.94 (d, J=6.32 Hz, 1 H) 3.93 (q, J=7.33 Hz, 2 H) 3.33 (br. s., 1 H) 3.28 (s, 1 H) 2.98 (t, J=5.68 Hz, 2 H) 2.12-2.25 (m, 9 H) 1.89 (s, 3 H) 1.27 (t, J=7.20 Hz, 3 H); MS (ESI+) m/z 402.3 (M+H)$^+$.

Example 48

2-(2,6-Diethylphenyl)-4-methyl-6-(1-methyl-1H-tetrazol-5-yl)-5,6,7,8-tetrahydro-1,6-naphthyridine

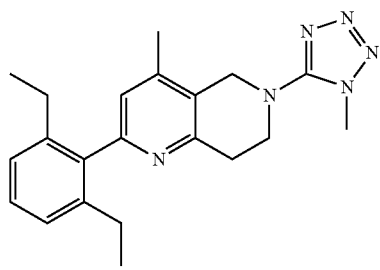 [SMILES: CCc1cccc(CC)c1-c1cc(C)c2c(n1)CCN(c1nnnn1C)C2]

A solution of methyl 6-(2,6-diethylphenyl)-4-methyl-2-vinylnicotinate (0.50 g, 1.62 mmol) and ammonium acetate (1.25 g, 16.2 mmol) in AcOH (9 mL) was allowed to stir at 120° C. in a sealed tube. After stirring for 14 h, the reaction mixture was cooled to rt, and concentrated. The residue was partitioned between DCM and aq 2 M $Na_2CO_3$, and extracted with DCM. The separated organic layer was concentrated. The residue was purified by flash column chromatography on 40 g of silica gel (eluent: DCM/EtOAc=80:20 to 0:100) to give 2-(2,6-diethylphenyl)-4-methyl-7,8-dihydro-1,6-naphthyridin-5(6H)-one. $^1$H NMR (400 MHz, $CDCl_3$) δ ppm 7.29 (t, J=7.75 Hz, 1 H), 7.14 (d, J=7.75 Hz, 1 H), 7.06 (s, 1 H), 6.01 (br s, 1 H), 3.58-3.62 (m, 2 H), 3.20 (t, J=6.57 Hz, 2 H), 2.76 (s, 3 H), 2.31-2.37 (m, 4 H), 1.06 (t, J=7.58 Hz, 2 H); MS (ESI+) m/z 295.32 (M+H)$^+$.

In a flask where 2-(2,6-diethylphenyl)-4-methyl-7,8-dihydro-1,6-naphthyridin-5(6H)-one (299 mg, 1.016 mmol) was placed, LAH in THF (5.0 mL, 5.08 mmol) was added. After stirring for 45 min, additional LAH in THF (5.0 mL, 5.08 mmol) was added. After stirring for further 2.5 h, the reaction mixture was diluted with $H_2O$ and then with aq 1 M NaOH. The products were extracted with DCM. The separated organic solution was concentrated to give crude. The crude was dissolved in 1.25 M HCl/MeOH (3 mL), and stirred for 5 min. The solution was concentrated to give crude as yellow oil. The crude was dissolved in isopropyl acetate, and concentrated to give the desired product as its hydrochloride salt. $^1$H NMR (400 MHz, $CDCl_3$) δ ppm 7.25-7.27 (m, 1 H), 7.13 (d, J=7.83 Hz, 1 H), 6.96 (s, 1 H), 4.27 (s, 2 H), 3.50 (br t, J=6.06 Hz 2 H), 3.25 (br t, J=6.06 Hz, 2 H), 2.30-2.35 (m, 4 H), 2.27 (s, 3 H), 1.05 (t, J=7.58 Hz, 2 H); MS (ESI+) m/z 281.35 (M+H)$^+$.

To a solution of 2-(2,6-diethylphenyl)-4-methyl-5,6,7,8-tetrahydro-1,6-naphthyridine dihydrochloride (21.7 mg, 0.061 mmol) in THF (0.5 mL), 1.6 M n-BuLi in hexanes (0.119 mL, 0.190 mmol) was added at −78° C. under nitrogen. After stirring for 10 min. at the same temperature, 1-methyl-5-(methylsulfonyl)-1H-tetrazole (24.90 mg, 0.154 mmol) was added. The mixture was warmed up to rt and stirred for 19 h. The mixture was diluted with brine and EtOAc. The products were extracted with EtOAc, and the organic layer was concentrated. The crude was purified by RP-HPLC (X-Bridge Phenyl®, $H_2O$ (0.1% $NH_4OH$)/$CH_3CN$), then the fractions including the desired product were lyophilized to give the desired product. $^1$H NMR (400 MHz, $CDCl_3$) δ ppm 7.26-7.30 (m, 2 H), 7.14 (d, J=7.58 Hz, 1 H), 6.98 (s, 1 H), 4.58 (s, 2 H), 4.01 (s, 3 H), 3.68 (t, J=5.94 Hz, 2 H), 3.25 (br t, J=5.94 Hz, 2 H), 2.30-2.37 (m, 7 H), 1.06 (t, J=7.58 Hz, 6 H); MS (ESI+) m/z 363.27 (M+H)$^+$.

Example 49

49-A. Methyl 2,6-dichloro-4-methoxynicotinate

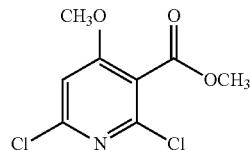

To a solution of methyl 2,4,6-trichloronicotinate [(5.04 g, 20.96 mmol), prepared as described in WO2010/31589] in methanol (52 mL) was added the sodium methoxide (25 wt % in methanol, 5.04 mL, 22.0 mmol) at room temperature. The cloudy white mixture was stirred for 17 h, then partitioned between EtOAc and water. The layers were separated and the aqueous layer was further extracted with EtOAc (2×). The combined organic layers were dried over sodium sulfate, filtered, and concentrated. The residue was purified by FCC (0-20% EtOAc:heptane) to provide methyl 2,6-dichloro-4-methoxynicotinate. MS (ESI+) m/z 236.1 (M+H)$^+$.

Methyl 2,6-dichloro-4-methoxynicotinate was also prepared using the alternative method described below:

A 1.0 M solution of TMPMgCl.LiCl in THF and toluene [(15.6 mL, 15.6 mmol) was added to 2,6-dichloro-4-methoxypyridine (2.32 g, 13.0 mmol), prepared as described in WO2007/21710] and the clear orange-brown reaction mixture stirred at room temperature. After 20 min, the resulting Grignard solution was added dropwise to a solution of methyl chloroformate (3.08 mL, 39.1 mmol) in toluene (52 mL). After stirring for 15 min, the reaction mixture was partitioned between EtOAc and saturated aqueous sodium bicarbonate solution. The aqueous layer was extracted with EtOAc (2×) and the combined organic layers were washed with brine, then dried over sodium sulfate, filtered, and concentrated. The residue was purified by FCC (0-25% EtOAc:heptanes) to provide methyl 2,6-dichloro-4-methoxynicotinate.

49-B. Methyl 6-(2,6-dimethylphenyl)-4-methoxy-2-vinylnicotinate

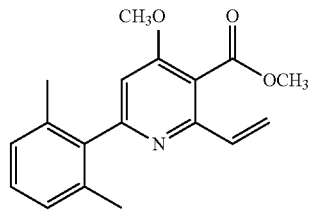

A mixture of methyl 2,6-dichloro-4-methoxynicotinate (2.3 g, 9.74 mmol), 2,6-dimethylphenylboronic acid (1.75 g, 11.7 mmol), Pd(PPh$_3$)$_4$ (1.13 g, 0.974 mmol), and 2.0 M aqueous sodium carbonate solution (14.6 mL, 29.2 mmol) in DMF (97 mL) was degassed by evacuation and backfilling with nitrogen (5 cycles). The reaction mixture was then heated to 110° C. and stirred at that temperature. After 16.5 h, 4,4,5,5-tetramethyl-2-vinyl-1,3,2-dioxaborolane (4.17 mL, 24.36 mmol) was added to the reaction mixture, followed by Pd(PPh$_3$)$_4$ (500 mg, 0.417 mmol) and 2.0 M aqueous sodium carbonate solution (7 mL, 13.98 mmol). The resulting mixture was further stirred at 110° C.

After 4.5 h, the reaction mixture was hot filtered, rinsing with EtOAc, and the filtrate was concentrated on the rotovap to remove a portion of the DMF. The residual concentrate was partitioned between EtOAc and water with brine. The aqueous layer was extracted with EtOAc (2×), and the combined organic layers were washed with brine (3×), then dried over sodium sulfate, filtered, and concentrated. The residue was purified by FCC (0-25% EtOAc/heptane) to provide methyl 6-(2,6-dimethylphenyl)-4-methoxy-2-vinylnicotinate. MS (ESI+) m/z 298.2 (M+H)$^+$.

49-C. 2-(2,6-Dimethylphenyl)-6-(5-isopropyl-2-methylphenyl)-4-methoxy-7,8-dihydro-1,6-naphthyridin-5(6H)-one

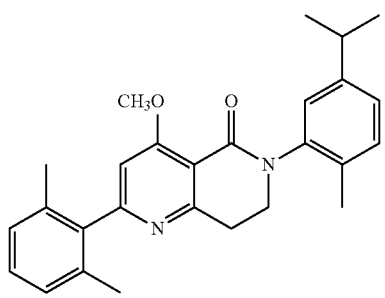

A solution of 6-(2,6-dimethylphenyl)-4-methoxy-2-vinylnicotinate (1.77 g, 5.95 mmol) and 5-isopropyl-2-methylaniline (4.44 g, 29.8 mmol) in toluene (26.5 mL) and acetic acid (13.2 mL) was heated to 110° C. and stirred at that temperature. After 12 h, the reaction mixture was removed from the heat and concentrated on the rotovap to remove the bulk of the solvent. The residue was partitioned between EtOAc and aqueous 1 N sodium hydroxide solution with added brine. The layers were separated and the aqueous layer was extracted with EtOAc (3×). The combined organic layers were washed with brine, then dried over sodium sulfate, filtered, and concentrated. The residue was purified by FCC (0-15% EtOAc/DCM) to provide 2-(2,6-dimethylphenyl)-6-(5-isopropyl-2-methylphenyl)-4-methoxy-7,8-dihydro-1,6-naphthyridin-5(6H)-one. The product contained some 5-isopropyl-2-methylaniline and was used in the next step without further purification. MS (ESI+) m/z 415.2 (M+H)$^+$.

49-D. 2-(2,6-Dimethylphenyl)-6-(5-isopropyl-2-methylphenyl)-4-methoxy 5,6,7,8-tetrahydro-1,6-naphthyridine

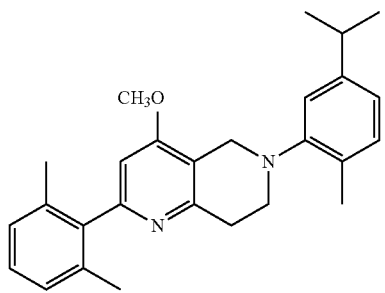

A 1.0 M solution of lithium aluminum hydride in THF (405 μL, 0.405 mmol) was added to a vessel containing 2-(2,6-dimethylphenyl)-6-(5-isopropyl-2-methylphenyl)-4-methoxy-7,8-dihydro-1,6-naphthyridin-5(6H)-one (42 mg, 0.101 mmol). The reaction mixture, which bubbled and turned clear orange, was stirred at room temperature. After 1 h, the reaction mixture was diluted with 1 mL of THF and cooled to 0° C. with an ice bath. 150 μL of a 9:1 THF/H$_2$O mixture was added dropwise, followed by the slow addition of 100 μL of 1 N aqueous NaOH. After stirring for 5 min, the ice bath was removed and 100 μL of H$_2$O and 1 mL of THF were added in sequence. The mixture was stirred for 10 min, then 150 mg of magnesium sulfate were added and the flask was stirred and shaken gently. The mixture was then filtered over Celite® and the filter cake washed with EtOAc. The filtrate was concentrated and the residue purified by FCC (0-20% EtOAc/heptane) to provide 2-(2,6-dimethylphenyl)-6-(5-isopropyl-2-methylphenyl)-4-methoxy-5,6,7,8-tetrahydro-1,6-naphthyridine. $^1$H NMR (400 MHz, DMSO-d$_6$) δ ppm 7.19 (dd, J=8.4, 6.8 Hz, 1 H) 7.09-7.14 (m, 3 H) 7.03 (d, J=1.5 Hz, 1 H) 6.89 (dd, J=7.7, 1.6 Hz, 1 H) 6.81 (s, 1 H) 4.00-4.03 (m, 2 H) 3.86 (s, 3 H) 3.22 (t, J=5.7 Hz, 2 H) 2.97 (t, J=5.6 Hz, 2 H) 2.86 (spt, J=6.8 Hz, 1 H) 2.25 (s, 3 H) 2.03 (s, 6 H) 1.19 (d, J=7.1 Hz, 6 H); MS (ESI+) m/z 401.3 (M+H)$^+$.

The following compounds were prepared in a similar manner.

49-E. 2-(2,6-Dimethylphenyl)-6-(5-isopropyl-2-methylphenyl)-4-methoxy 5,6,7,8-tetrahydro(5,5-$^2$H$_2$)-1,6-naphthyridine

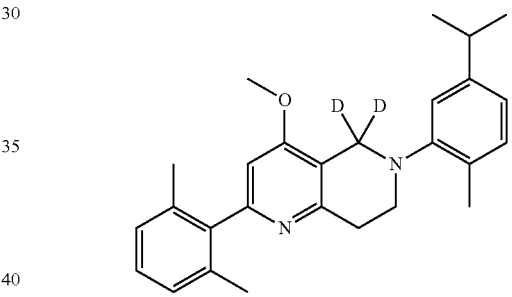

$^1$H NMR (400 MHz, DMSO-d$_6$) δ ppm 7.16-7.22 (m, 1 H) 7.08-7.14 (m, 3 H) 7.02 (d, J=1.8 Hz, 1 H) 6.88 (dd, J=7.7, 1.6 Hz, 1 H) 6.81 (s, 1 H) 3.86 (s, 3 H) 3.21 (t, J=5.7 Hz, 2 H) 2.96 (t, J=5.7 Hz, 2 H) 2.85 (spt, J=6.9 Hz, 1 H) 2.24 (s, 3 H) 2.03 (s, 6 H) 1.19 (d, J=7.1 Hz, 6 H); MS (ESI+) m/z 403.3 (M+H)$^+$.

Example 50

50-A. 4-Chloro-2-(2,6-dimethylphenyl)-6-(5-isopropyl-2-methylphenyl)-7,8-dihydro-1,6-naphthyridin-5(6H)-one

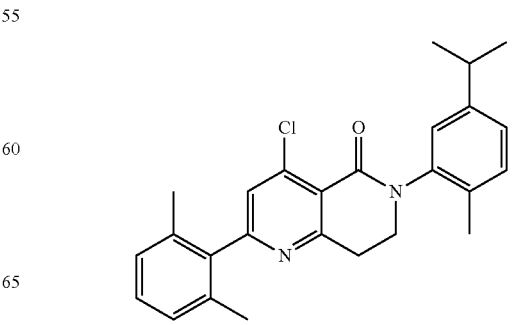

To a solution of 2-(2,6-dimethylphenyl)-6-(5-isopropyl-2-methylphenyl)-4-methoxy-7,8-dihydro-1,6-naphthyridin-5(6H)-one (1.49 g, 3.59 mmol) in dioxane (23.96 mL) was added potassium trimethylsilanolate (2.306 g, 17.97 mmol) as a solid in one portion. The 75-mL pressure vessel was sealed and the reaction mixture heated to 140° C. for 3 h. The reaction mixture was allowed to cool to room temperature before opening the vessel. The reaction mixture was then poured into water and DCM and the aqueous pH adjusted to pH 7 with 1 N HCl. The aqueous layers was further extracted with DCM (2×) and the combined organic layers washed with brine, dried over sodium sulfate, filtered, and concentrated. The crude 2-(2,6-dimethylphenyl)-4-hydroxy-6-(5-isopropyl-2-methylphenyl)-7,8-dihydro-1,6-naphthyridin-5(6H)-one was used directly in the next step without further purification.

To a solution of crude 2-(2,6-dimethylphenyl)-4-hydroxy-6-(5-isopropyl-2-methylphenyl)-7,8-dihydro-1,6-naphthyridin-5(6H)-one (1.4 g, 3.50 mmol) in DCM (35.0 mL) was added Vilsmeier's reagent (0.895 g, 6.99 mmol) as a solid in one portion and the reaction mixture stirred at room temperature. After 2 h 500 mg of Vilsmeier's reagent was added and stirring continued. After 35 min an additional portion of 200 mg of Vilsmeier's reagent was added and stirring continued. After 15 min the reaction mixture was diluted with DCM and poured into saturated aqueous sodium bicarbonate solution containing 1 N NaOH. The layers were separated and the aqueous layer was extracted with DCM (2×). The combined organic layers were dried over sodium sulfate, filtered, and concentrated. The residue was purified by FCC (0-20% EtOAc/heptane) to provide 4-chloro-2-(2,6-dimethylphenyl)-6-(5-isopropyl-2-methylphenyl)-7,8-dihydro-1,6-naphthyridin-5(6H)-one. MS (ESI+) m/z 419.2 (M+H)+.

50-B. (S)-2-(2,6-Dimethylphenyl)-6-(5-isopropyl-2-methylphenyl)-4-(4-methoxy-3,3-dimethylpiperidin-1-yl)-7,8-dihydro-1,6-naphthyridin-5(6H)-one

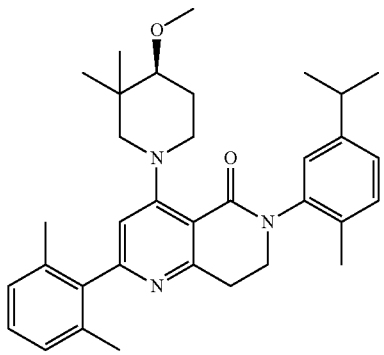 [SMILES: CO[C@H]1CCN(c2cc(-c3c(C)cccc3C)nc3c2C(=O)N(c2cc(C(C)C)ccc2C)CC3)CC1(C)C]

A 10-mL reaction flask containing an orange solution of 4-chloro-2-(2,6-dimethylphenyl)-6-(5-isopropyl-2-methylphenyl)-7,8-dihydro-1,6-naphthyridin-5(6H)-one (100 mg, 0.239 mmol), (S)-4-methoxy-3,3-dimethylpiperidine HCl salt (129 mg, 0.716 mmol), and DIEA (208 µL, 1.193 mmol) in DMA (1.2 mL) was placed in a sand bath preheated to 110° C. and stirred at that temperature. After 4 h the reaction mixture was allowed to cool to room temperature, then diluted with DCM and poured into mixture of saturated aqueous sodium bicarbonate solution and brine. The aqueous layer was extracted with DCM (3×), and the combined organic layers were washed with brine, then dried over sodium sulfate, filtered, and concentrated. The residue was purified by FCC (0-100% EtOAc/heptane) to provide (S)-2-(2,6-dimethylphenyl)-6-(5-isopropyl-2-methylphenyl)-4-(4-methoxy-3,3-dimethylpiperidin-1-yl)-7,8-dihydro-1,6-naphthyridin-5(6H)-one. $^1$H NMR (400 MHz, DMSO-$d_6$) δ ppm 7.07-7.25 (m, 6 H) 6.73 (s, 1 H) 3.80-3.96 (m, 1 H) 3.63-3.79 (m, 1 H) 3.27 (s, 3 H) 3.09-3.24 (m, 2 H) 2.93-3.07 (m, 3 H) 2.79-2.92 (m, 2 H) 2.18-2.22 (m, 3 H) 2.06 (s, 6 H) 1.79-1.94 (m, 1 H) 1.48-1.65 (m, 1 H) 1.21 (d, J=6.8 Hz, 6 H) 1.14-1.19 (m, 1 H) 0.90 (s, 3 H) 0.83 (s, 1 H)* 0.78 (s, 2 H)*; MS (ESI+) m/z 526.3 (M+H)+. (*indicates one methyl group appearing as two peaks due to restricted rotation).

The following compounds were prepared in a similar manner.

| | Structure | Chemical Name & Analytical Data |
|---|---|---|
| 50-C | 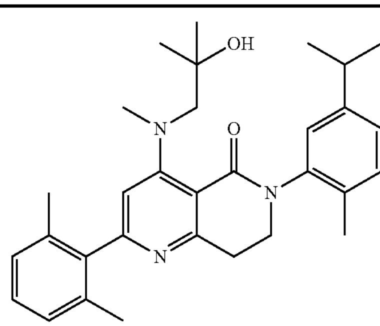 | 2-(2,6-dimethylphenyl)-4-((2-hydroxy-2-methylpropyl)(methyl)amino)-6-(5-isopropyl-2-methylphenyl)-7,8-dihydro-1,6-naphthyridin-5(6H)-one. $^1$H NMR (400 MHz, DMSO-$d_6$) δ ppm 7.05-7.26 (m, 6H) 6.91 (s, 1H) 4.32 (s, 1H) 3.86-4.00 (m, 1H) 3.63-3.75 (m, 2H) 3.17-3.29 (m, 2H) 3.03 (s, 3H) 2.94-3.02 (m, 1H) 2.88 (quin, J = 6.9 Hz, 1H) 2.19 (s, 3H) 2.04 (s, 6H) 1.21 (d, J = 6.8 Hz, 6H) 1.04 (s, 6H); MS (ESI+) m/z 486.3 (M + H)+. |

| | Structure | Chemical Name & Analytical Data |
|---|---|---|
| 50-D | 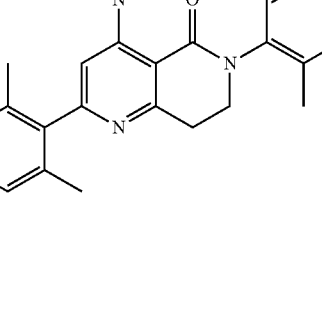 | 4-((cyclopropylmethyl)(propyl)amino)-2-(2,6-dimethylphenyl)-6-(5-isopropyl-2-methylphenyl)-7,8-dihydro-1,6-naphthyridin-5(6H)-one. $^1$H NMR (400 MHz, DMSO-$d_6$) δ ppm 7.06-7.26 (m, 6H) 6.68 (s, 1H) 3.82-3.93 (m, 1H) 3.63-3.73 (m, 1H) 3.35-3.51 (m, 2H) 3.07-3.31 (m, 3H) 2.93-3.04 (m, 1H) 2.87 (dt, J = 13.7, 6.9 Hz, 1H) 2.20 (s, 3H) 2.06 (s, 6H) 1.49-1.59 (m, 2H) 1.21 (d, J = 6.8 Hz, 6H) 1.01-1.08 (m, 1H) 0.82 (t, J = 7.3 Hz, 3H) 0.43-0.50 (m, 2H) 0.10-0.16 (m, 2H); MS (ESI+) m/z 496.3 (M + H)$^+$. |
| 50-E | 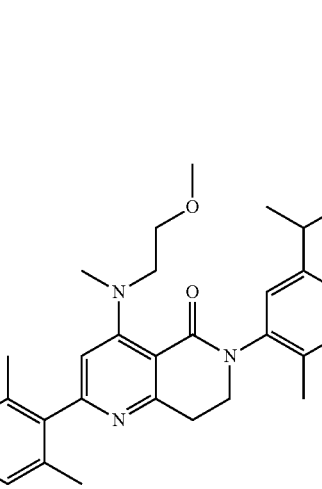 | 2-(2,6-dimethylphenyl)-6-(5-isopropyl-2-methylphenyl)-4-((2-methoxyethyl)(methyl)amino)-7,8-dihydro-1,6-naphthyridin-5(6H)-one. $^1$H NMR (400 MHz, DMSO-$d_6$) δ ppm 7.07-7.24 (m, 6H) 6.67 (s, 1H) 3.83-3.93 (m, 1H) 3.67-3.77 (m, 1H) 3.53-3.56 (m, 2H) 3.47-3.53 (m, 2H) 3.23 (dd, J = 9.5,4.2 Hz, 1H) 3.20 (s, 3H) 2.95-3.05 (m, 1H) 2.93 (s, 3H) 2.87 (dt, J = 13.9, 6.9 Hz, 1H) 2.18 (s, 3H) 2.06 (s, 6H) 1.20 (d, J = 6.8 Hz, 6H); MS (ESI+) m/z 472.3 (M + H)$^+$. |
| 50-F | 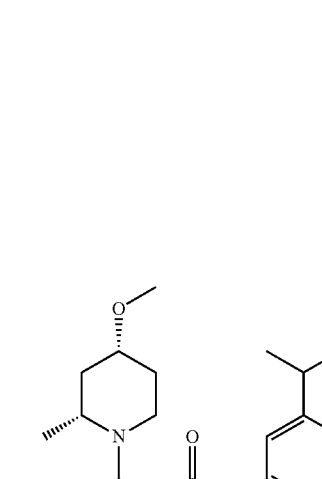 | 2-(2,6-dimethylphenyl)-6-(5-isopropyl-2-methylphenyl)-4-((2R,4R)-4-methoxy-2-methylpiperidin-1-yl)-7,8-dihydro-1,6-naphthyridin-5(6H)-one. $^1$H NMR (400 MHz, DMSO-$d_6$) δ ppm 7.08-7.24 (m, 6H) 6.69 (s, 0.5H)* 6.64 (s, 0.5H)* 3.87-3.99 (m, 2H) 3.65-3.85 (m, 1H) 3.52 (qd, 1H) 3.35-3.44 (m, 1H) 3.24 (d, J = 1.8 Hz, 3H) 3.11-3.22(m, 1H) 2.94-3.10 (m, 1H) 2.88 (quin, J = 6.9 Hz, 1H) 2.18 (d, J = 4.3 Hz, 3H) 2.06 (s, 6H) 1.65-1.96 (m, 4H) 1.25 (d, J = 6.8 Hz, 2H)* 1.21 (d, J = 7.1 Hz, 6H) 1.18 (d, J = 6.8 Hz, 1H)*, MS (ESI+) m/z 512.3 (M + H)$^+$. |

*indicates additional peaks due to restricted rotation;

Example 51

51-A. (S)-2-(2,6-Dimethylphenyl)-6-(5-isopropyl-2-methylphenyl)-4-(4-methoxy-3,3-dimethylpiperidin-1-yl)-5,6,7,8-tetrahydro-1,6-naphthyridine

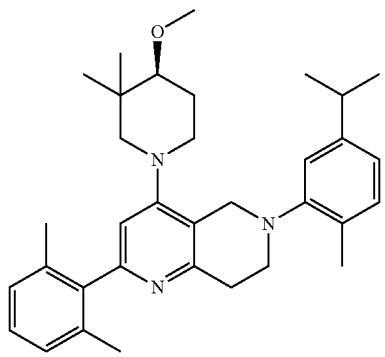 [SMILES: CO[C@H]1CCN(c2cc(-c3c(C)cccc3C)nc3c2CN(c2cc(C(C)C)ccc2C)CC3)CC1(C)C]

A 1.0 M solution of lithium aluminum hydride in THF (23.0 mL, 3.00 mmol) was added to a vessel containing (S)-2-(2,6-dimethylphenyl)-6-(5-isopropyl-2-methylphenyl)-4-(4-methoxy-3,3-dimethylpiperidin-1-yl)-7,8-dihydro-1,6-naphthyridin-5(6H)-one (63 mg, 0.120 mmol). The reaction flask was then capped and the pink reaction mixture was heated to 55° C. and stirred at that temperature. After 1.5 h the oil bath was removed, the reaction mixture was diluted with 6 mL of THF, and the reaction flask cooled to 0° C. Then 0.9 mL of a 9:1 THF/H$_2$O mixture was added dropwise, followed by 3 mL of THF, and 0.3 mL of 2 N NaOH was slowly added. After stirring for 5 min, the ice bath was removed and 600 µL of H$_2$O and 6 mL of THF were added. The mixture was stirred for 10 min, then 900 mg of magnesium sulfate were added and the mixture further stirred. The mixture was then filtered over Celite® and the filter cake washed with EtOAc. The filtrate was concentrated and the residue was purified by FCC (0-50% EtOAc/heptanes) to provide (S)-2-(2,6-dimethylphenyl)-6-(5-isopropyl-2-methylphenyl)-4-(4-methoxy-3,3-dimethylpiperidin-1-yl)-5,6,7,8-tetrahydro-1,6-naphthyridine. $^1$H NMR (400 MHz, DMSO-d$_6$) δ ppm 7.14-7.19 (m, 1 H) 7.06-7.12 (m, 3 H) 6.94 (d, J=1.5 Hz, 1 H) 6.83 (dd, J=7.8, 1.5 Hz, 1 H) 6.68 (s, 1 H) 4.10-4.22 (m, 2 H) 3.28 (s, 3 H) 3.07-3.18 (m, 1 H) 2.73-3.04 (m, 6 H) 2.23 (s, 3 H) 2.00 (s, 6 H) 1.91-2.03 (m, 2 H) 1.58 (d, J=9.3 Hz, 1 H) 1.20-1.28 (m, 1 H) 1.16 (d, J=6.8 Hz, 6 H) 1.01 (d, J=10.4 Hz, 6 H); MS (ESI+) m/z 512.4 (M+H)$^+$.

The following compounds were prepared in a similar manner.

| | Structure | Chemical Name & Analytical Data<br>MS (ESI) m/z (M + H)$^+$ |
|---|---|---|
| 51-B | 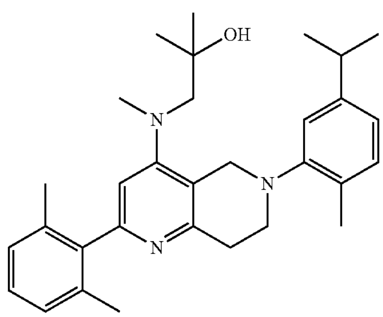 | 1-((2-(2,6-dimethylphenyl)-6-(5-isopropyl-2-methylphenyl)-5,6,7,8-tetrahydro-1,6-naphthyridin-4-yl)(methyl)amino)-2-methylpropan-2-ol. $^1$H NMR (400 MHz, DMSO-d$_6$) δ ppm 7.13-7.19 (m, 1H) 7.06-7.12 (m, 3H) 6.92 (d, J = 1.5 Hz, 1H) 6.86 (dd, J = 7.7, 1.6 Hz, 1H) 6.75 (s, 1H) 4.37 (s, 1H) 4.05-4.10 (m, 2H) 3.11 (s, 2H) 2.91 (s, 3H) 2.89-2.96 (m, 2H) 2.80 (dt, J = 13.6, 6.8 Hz, 0H) 2.23 (s, 3H) 2.01 (s, 6H) 1.16 (d, J = 6.8 Hz, 6H) 1.06 (s, 6H); MS (ESI+) m/z 472.3 (M + H)$^+$. |
| 51-C | 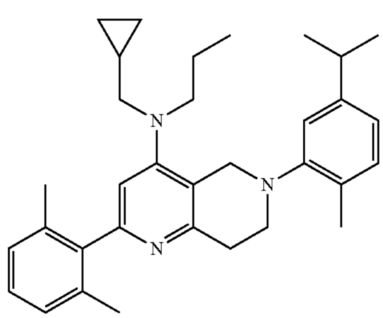 | N-(cyclopropylmethyl)-2-(2,6-dimethylphenyl)-6-(5-isopropyl-2-methylphenyl)-N-propyl-5,6,7,8-tetrahydro-1,6-naphthyridin-4-amine. $^1$H NMR (400 MHz, DMSO-d$_6$) δ ppm 7.14-7.22 (m, 1H) 7.07-7.12 (m, 3H) 6.90 (d, J = 1.5 Hz, 1H) 6.85 (dd, J = 7.6, 1.5 Hz, 1H) 6.79 (s, 1H) 4.03-4.09 (m, 2H) 3.14 (t, J = 7.1 Hz, 2H) 2.89-2.98 (m, 4H) 2.80 (dt, J = 13.8, 6.9 Hz, 1H) 2.23 (s, 3H) 2.01 (s, 6H) 1.45 (m, 2H) 1.15 (d, J = 6.8 Hz, 6H) 0.87-0.94 (m, 1H) 0.83 (t, J = 7.3 Hz, 3H) 0.35-0.42 (m, 2H) 0.04-0.10 (m, 2H); MS (ESI+) m/z 482.3 (M + H)$^+$. |

| | Chemical Name & Analytical Data |
| Structure | MS (ESI) m/z (M + H)+ |
|---|---|
| 51-D 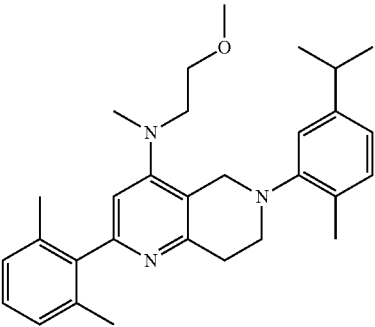 | 2-(2,6-dimethylphenyl)-6-(5-isopropyl-2-methylphenyl)-N-(2-methoxyethyl)-N-methyl-5,6,7,8-tetrahydro-1,6-naphthyridin-4-amine. ¹H NMR (400 MHz, DMSO-d₆) δ ppm 7.13-7.19 (m, 1H) 7.06-7.12 (m, 3H) 6.95 (d, J = 1.5 Hz, 1H) 6.85 (dd, J = 7.7, 1.6 Hz, 1H) 6.68 (s, 1H) 4.04-4.08 (m, 2H) 3.52 (t, J = 5.6 Hz, 2H) 3.29 (t, J = 6.2 Hz, 2H) 3.20 (s, 3H) 3.19-3.24 (m, 2H) 2.96 (t, J = 5.9 Hz, 2H) 2.75-2.88 (m, 4H) 2.23 (s, 3H) 2.02 (s, 6H) 1.18 (d, J = 6.8 Hz, 6H); MS (ESI+) m/z 458.3 (M + H)+. |
| 51-E 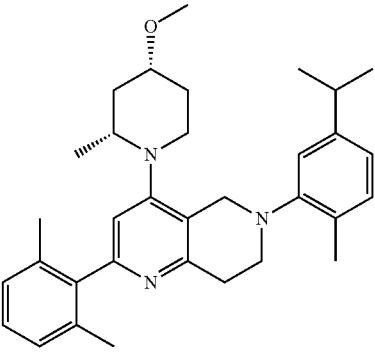 | 2-(2,6-dimethylphenyl)-6-(5-isopropyl-2-methylphenyl)-4-((2R,4R)-4-methoxy-2-methylpiperidin-1-yl)-5,6,7,8-tetrahydro-1,6-naphthyridine. ¹H NMR (400 MHz, DMSO-d₆) δ ppm 7.15-7.21 (m, 1H) 7.08-7.13 (m, 3H) 6.90-6.94 (m, 2H) 6.86 (dd, J = 7.7, 1.6 Hz, 1H) 4.23 (d, J = 15.7 Hz, 1H) 4.02 (d, J = 15.7 Hz, 1H) 3.34-3.42 (m, 1H) 3.26-3.30 (m, 2H) 3.25 (s, 3H) 3.15-3.22 (m, 1H) 2.89-3.09 (m, 3H) 2.82 (dt, J = 13.7, 6.9 Hz, 1H) 2.24 (s, 3H) 2.00 (s, 6H) 1.97-2.11 (m, 2H) 1.34-1.44 (m, 1H) 1.19-1.25 (m, 1H) 1.17 (d, J = 6.8, Hz, 3H)* 1.15 (d, J = 6.8, Hz, 3H)* 0.91 (d, 3H), MS (ESI+) m/z 498.4 (M + H)+. |

*indicates additional peaks due to restricted rotation;

Example 52

52-A. (R)-tert-Butyl 4-(6-(5-isopropyl-2-methylphenyl)-2-(3-methyl-1-tosyl-1H-indol-4-yl)-5,6,7,8-tetrahydropyrido[4,3-d]pyrimidin-4-yl)-3-methylpiperazine-1-carboxylate

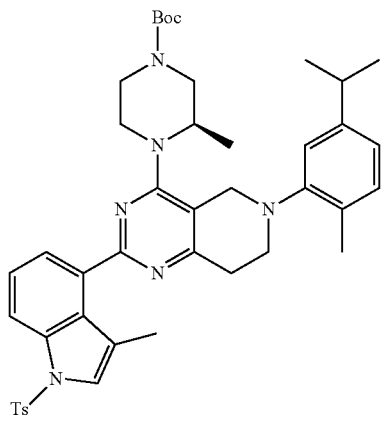 [SMILES: Cc1ccc(S(=O)(=O)n2cc(C)c3c(-c4nc5c(c(N6CCN(C(=O)OC(C)(C)C)C[C@H]6C)n4)CN(c4cc(C(C)C)ccc4C)CC5)cccc32)cc1]

A mixture of 4-chloro-6-(5-isopropyl-2-methylphenyl)-2-(3-methyl-1-tosyl-1H-indol-4-yl)-5,6,7,8-tetrahydropyrido[4,3-d]pyrimidine (Example 17-E) (0.274 g, 0.468 mmol), (R)-tert-butyl 3-methylpiperazine-1-carboxylate (0.375 g, 1.87 mmol) and DIEA (0.33 mL, 1.87 mmol) in N,N-dimethylacetamide (3 mL) was heated at 125° C. for 15 h. Reaction mixture was diluted with EtOAc, washed with sat aq NaHCO₃ and brine. The organic layer was then dried over Na₂SO₄, concentrated, purified via FCC (0-40% EtOAc/heptane) to provide the title compound. MS (ESI+) m/z 749.4 (M+H)+.

52-B. (R)-2-(4-(6-(5-Isopropyl-2-methylphenyl)-2-(3-methyl-1-tosyl-1H-indol-4-yl)-5,6,7,8-tetrahydropyrido[4,341]pyrimidin-4-yl)-3-methylpiperazin-1-yl)acetamide

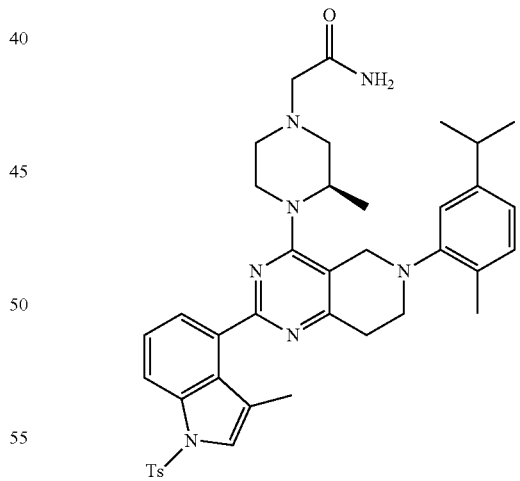

A solution of (R)-tert-butyl 4-(6-(5-isopropyl-2-methylphenyl)-2-(3-methyl-1-tosyl-1H-indol-4-yl)-5,6,7,8-tetrahydropyrido[4,3-d]pyrimidin-4-yl)-3-methylpiperazine-1-carboxylate (0.143 g, 0.191 mmol), TFA (2 mL) and DCM (3 mL) was stirred at rt for 30 min before being concentrated. To the resulting residue in DCM (3 mL) were added DIEA (0.133 mL, 0.764 mmol), 2-bromoacetamide (0.040 g, 0.287 mmol) and sodium iodide (0.043 g, 0.287 mmol). The mixture was stirred at rt for 20 h and then diluted with EtOAc. The mixture was washed with sat aq NaHCO₃ and then brine. The organic layer was then dried over Na₂SO₄. After concentration, the residue was purified via FCC (60-90% EtOAc/heptane) to provide the title compound. MS (ESI+) m/z 706.4 (M+H)⁺.

52-C. (R)-2-(4-(6-(5-Isopropyl-2-methylphenyl)-2-(3-methyl-1H-indol-4-yl)-5,6,7,8-tetrahydropyrido[4,3-d]pyrimidin-4-yl)-3-methylpiperazin-1-yl)acetamide

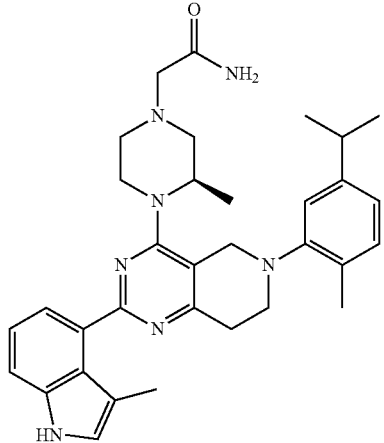 [SMILES: Cc1ccc(C(C)C)cc1N1CCc2nc(-c3cccc4[nH]cc(C)c34)nc(N3CCN(CC(N)=O)C[C@H]3C)c2C1]

A mixture of (R)-2-(4-(6-(5-isopropyl-2-methylphenyl)-2-(3-methyl-1-tosyl-1H-indol-4-yl)-5,6,7,8-tetrahydropyrido[4,3-d]pyrimidin-4-yl)-3-methylpiperazin-1-yl)acetamide (0.075 mg, 0.106 mmol), 30% ammonium hydroxide (0.63 mL 15.94 mmol) and potassium hydroxide (0.054 g, 0.956 mmol) in ethanol (3 mL) was heated in a microwave reactor at 100° C. for 1 h. The reaction mixture was concentrated and then filtered before being purified via HPLC (RP C18, 15-85% CH₃CN in H₂O with 0.1% NH₄OH to provide the title compound. ¹H NMR (400 MHz, CD₃CN) δ ppm 9.16 (br. s., 1 H) 7.45 (d, J=8.08 Hz, 1H) 7.25 (dd, J=7.20, 1.14 Hz, 1 H) 7.15 (dd, J=15.28, 7.71 Hz, 2 H) 7.01-7.09 (m, 2 H) 6.82-6.94 (m, 2 H) 5.80 (br. s., 1 H) 3.94-4.13 (m, 3 H) 3.51-3.60 (m, 1 H) 3.41-3.50 (m, 1 H) 3.28-3.41 (m, 2 H) 2.95-3.12 (m, 2 H) 2.82-2.95 (m, 3 H) 2.78 (d, J=10.86 Hz, 1 H) 2.57-2.66 (m, 1 H) 2.47-2.56 (m, 1 H) 2.37 (td, J=10.74, 3.03 Hz, 1 H) 2.26 (s, 3 H) 2.05 (s, 3 H) 1.30 (d, J=6.82 Hz, 3 H) 1.23 (dd, J=6.82, 1.01 Hz, 6 H); MS (ESI+) m/z 552.4 (M+H)⁺.

The following compounds were prepared in a similar manner.

| Structure | Chemical Name & Analytical Data MS (ESI) m/z (M + H)⁺ |
|---|---|
| 52-D | (R)-2-(4-(6-(5-isopropyl-2-methylphenyl)-2-(2-(trifluoromethyl)phenyl)-5,6,7,8-tetrahydropyrido[4,3-d]pyrimidin-4-yl)-2-methylpiperazin-1-yl)acetamide. ¹H NMR (400 MHz, CD₂Cl₂) δ ppm 7.75-7.80 (m, 2 H) 7.65 (t, J = 7.45 Hz, 1 H) 7.56 (t, J = 7.71 Hz, 1 H) 7.14 (d, J = 7.58 Hz, 1 H) 7.06 (br. s., 1 H) 6.96 (d, J = 1.52 Hz, 1 H) 6.91 (dd, J = 7.71, 1.64 Hz, 1 H) 3.92-4.04 (m, 2 H) 3.67 (d, J = 12.38 Hz, 2 H) 3.21-3.40 (m, 4 H) 3.08 (t, J = 5.81 Hz, 2 H) 2.77-2.98 (m, 4 H) 2.60-2.74 (m, 1 H) 2.47-2.60 (m, 1 H) 2.27 (s, 3 H) 1.24 (d, J = 6.82 Hz, 6 H) 1.09 (d, J 5.81 Hz, 3 H); MS (ESI+) m/z 567.4 (M + H)⁺. |
| 52-E | (R)-2-(4-(2-(2,6-dimethylphenyl)-6-(o-tolyl)-5,6,7,8-tetrahydropyrido[4,3-d]pyrimidin-4-yl)-2-methylpiperazin-1-yl)acetamide. ¹H NMR (400 MHz, DMSO-d₆) δ ppm 7.14-7.27 (m, 4 H), 7.05-7.12 (m, 2 H), 6.97-7.04 (m, 1 H), 3.98 (s, 2 H), 3.57 (t, J = 12.4 Hz, 2 H), 3.24-3.29 (m, 2 H), 3.15-3.23 (m, 1 H), 3.11 (app. d, J = 16.2 Hz, 1 H), 2.96 (t, J = 5.7 Hz, 2 H), 2.90 (dd, J = 12.8, 8.7 Hz, 1 H), 2.81 (s, 1 H), 2.75-2.79 (m, 1 H), 2.59 (t, J = 6.1 Hz, 1 H), 2.43-2.48 (m, 1 H), 2.26 (s, 3 H), 2.06 (s, 6 H), 1.00 (d, J = 6.3 Hz, 3 H); MS (ESI+) m/z 485.2 (M + H)⁺. |

| Structure | Chemical Name & Analytical Data MS (ESI) m/z (M + H)+ |
|---|---|
| 52-F 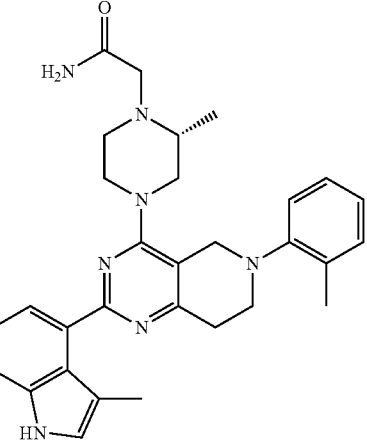 | (R)-2-(2-methyl-4-(2-(3-methyl-1H-indol-4-yl)-6-(o-tolyl)-5,6,7,8-tetrahydropyrido[4,3-d]pyrimidin-4-yl)piperazin-1-yl)acetamide. $^1$H NMR (400 MHz, CD$_2$Cl$_2$) δ ppm 8.23 (br. s., 1 H), 7.44 (dd, J = 8.1, 1.0 Hz, 1 H), 7.35 (dd, J = 7.2, 0.9 Hz, 1 H), 7.19-7.25 (m, 3 H), 7.11-7.15 (m, 1 H), 7.05-7.08 (m, 1 H), 7.03 (dd, J = 7.3, 1.3 Hz, 1 H), 4.01 (s, 2 H), 3.68 (d, J = 12.1 Hz, 2 H), 3.23-3.39 (m, 4 H), 3.13 (t, J = 5.7 Hz, 2 H), 2.89-3.02 (m, 2 H), 2.84 (app. d, J = 16.9 Hz, 1 H), 2.64-2.73 (m, 1 H), 2.59 (t, J = 9.9 Hz, 1 H), 2.33 (s, 3 H), 2.10 (d, J = 1.0 Hz, 3 H), 1.11 (d, J = 6.1 Hz, 3 H); MS (ESI+) m/z 510.3 (M + H)+. |
| 52-G 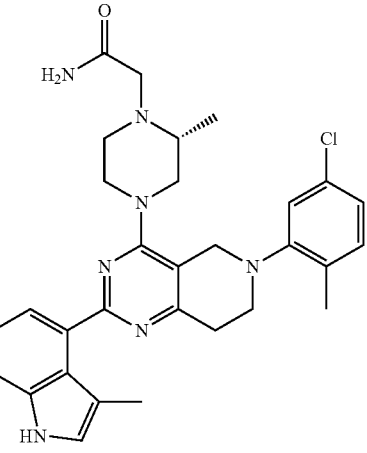 | (R)-2-(4-(6-(5-chloro-2-methylphenyl)-2-(3-methyl-1H-indol-4-yl)-5,6,7,8-tetrahydropyrido[4,3-d]pyrimidin-4-yl)-2-methylpiperazin-1-yl)acetamide. $^1$H NMR (400 MHz, CD$_2$Cl$_2$) δ ppm 8.25 (br. s., 1 H), 7.44 (dd, J = 8.1, 1.0 Hz, 1 H), 7.35 (dd, J = 7.3, 1.0 Hz, 1 H), 7.19-7.24 (m, 1 H), 7.17 (dd, J = 8.1, 0.5 Hz, 1 H), 7.10 (d, J = 2.3 Hz, 1 H), 7.05-7.07 (m, 1 H), 7.03 (dd, J = 8.1, 2.0 Hz, 1 H), 3.98 (s, 2 H), 3.66 (app. d, J = 11.9 Hz, 2 H), 3.24-3.38 (m, 4 H), 3.14 (t, J = 5.9 Hz, 2 H), 2.90-3.03 (m, 2 H), 2.85 (app. d, J = 16.9 Hz, 1 H), 2.64-2.75 (m, 1 H), 2.60 (t, J = 9.9 Hz, 1 H), 2.29 (s, 3 H), 2.10 (d, J = 0.8 Hz, 3 H), 1.11 (d, J = 6.3 Hz, 3 H); MS (ESI+) m/z 544.3 (M + H)+. |
| 52-H 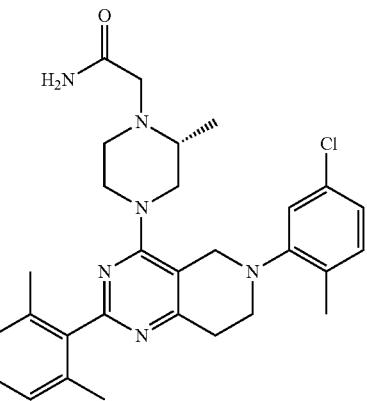 | (R)-2-(4-(6-(5-chloro-2-methylphenyl)-2-(2,6-dimethylphenyl)-5,6,7,8-tetrahydropyrido[4,3-d]pyrimidin-4-yl)-2-methylpiperazin-1-yl)acetamide. $^1$H NMR (400 MHz, DMSO-d$_6$) δ ppm 7.26 (d, J = 2.8 Hz, 1 H), 7.23 (d, J = 8.3 Hz, 1 H), 7.15-7.20 (m, 2 H), 7.12 (d, J = 2.8 Hz, 1 H), 7.09 (s, 1 H), 7.07 (m, J = 1.8 Hz, 1 H), 7.05 (d, J = 2.0 Hz, 1 H), 4.01 (br. s., 2 H), 3.53-3.62 (m, 2 H), 3.31 (br. s, 2 H), 3.26-3.29 (m, 1 H), 3.17-3.25 (m, 1 H), 3.11 (app. d, J = 16.2 Hz, 1 H), 2.88-2.99 (m, 3 H), 2.76-2.82 (m, 2 H), 2.57-2.65 (m, 1 H), 2.23 (s, 3 H), 2.05 (s, 6 H), 1.01 (d, J = 6.3 Hz, 3 H); MS (ESI+) m/z 519.2 (M + H)+. |

| Structure | Chemical Name & Analytical Data MS (ESI) m/z (M + H)+ |
|---|---|
| 52-I 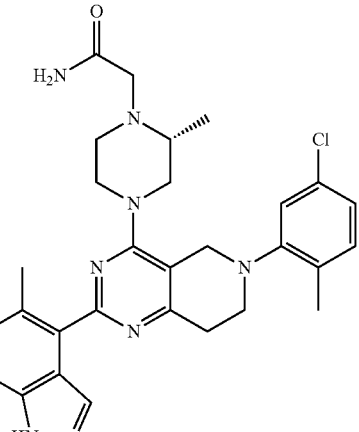 | (R)-2-(4-(6-(5-chloro-2-methylphenyl)-2-(5-methyl-1H-indazol-4-yl)-5,6,7,8-tetrahydropyrido[4,3-d]pyrimidin-4-yl)-2-methylpiperazin-1-yl)acetamide. $^1$H NMR (400 MHz, DMSO-$d_6$) δ ppm 8.13 (s, 1 H), 7.50 (d, J = 7.8 Hz, 1 H), 7.22-7.31 (m, 3 H), 7.11-7.15 (m, 1 H), 7.08 (dd, J = 7.8, 1.8 Hz, 1 H), 3.97-4.08 (m, 2 H), 3.60-3.68 (m, 2 H), 3.13 (app. d, J = 16.2 Hz, 1 H), 3.06 (t, J = 5.7 Hz, 1 H), 2.92-3.00 (m, 1 H), 2.77-2.86 (m, 2 H), 2.54-2.57 (m, 3 H), 2.23-2.26 (m, 3 H), 1.03 (d, J = 6.3 Hz, 3 H); MS (ESI+) m/z 545.2 (M + H)+. |

Example 53

1-(7-(6-(5-Isopropyl-2-methylphenyl)-2-(3-methyl-1H-indol-4-yl)-5,6,7,8-tetrahydropyrido[4,3-d]pyrimidin-4-yl)-4,7-diazaspiro[2.5]octan-4-yl)ethanone

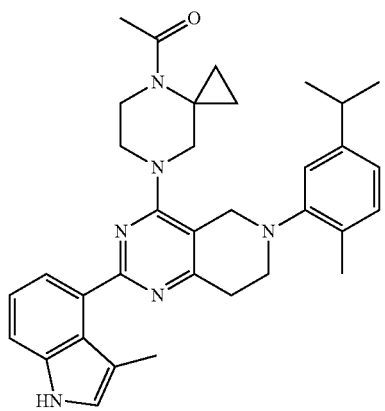 [SMILES: CC(=O)N1CCN(c2nc(-c3cccc4[nH]cc(C)c34)nc3c2CN(c2cc(C(C)C)ccc2C)CC3)CC12CC2]

Prepared in a similar manner to that described in Example 52 using 4,7-diazaspiro[2.5]octane dihydrochloride. $^1$H NMR (400 MHz, DMSO-$d_6$) δ ppm 10.89 (s, 1 H) 7.41 (dd, J=7.83, 1.01 Hz, 1 H) 7.21 (dd, J=7.33, 1.01 Hz, 1 H) 7.07-7.16 (m, 3 H) 6.99 (d, J=1.26 Hz, 1 H) 6.87 (dd, J=7.71, 1.39 Hz, 1 H) 4.01 (s, 2 H) 3.61-3.83 (m, 2 H) 3.36-3.52 (m, 2 H) 3.32 (br. s., 4 H) 2.97 (t, J=5.81 Hz, 2 H) 2.85 (quin, J=6.82 Hz, 1 H) 2.21 (s, 3 H) 2.12 (s, 3 H) 2.01 (s, 3 H) 1.20 (d, J=7.07 Hz, 6 H) 0.94-1.09 (m, 4 H); MS (ESI+) m/z 549.4 (M+H)+.

Example 54

54-A. 6-(4-Chloro-3-isopropyl-1-methyl-1H-pyrazol-5-yl)-2-(3,5-dimethyl-1-tosyl-1H-indazol-4-yl)-4-((2R,4R)-4-methoxy-2-methylpiperidin-1-yl)-5,6,7,8-tetrahydropyrido[4,3-d]pyrimidine

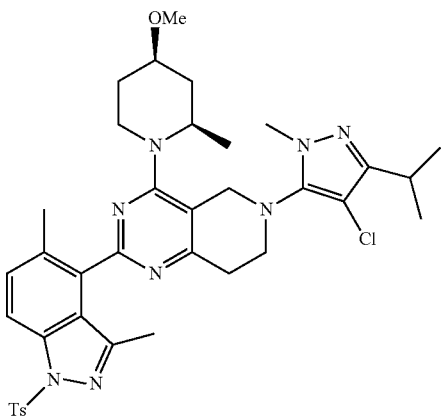 [SMILES: CO[C@@H]1CCN(c2nc(-c3c(C)ccc4c3c(C)nn4S(=O)(=O)c3ccc(C)cc3)nc3c2CN(c2c(Cl)c(C(C)C)nn2C)CC3)[C@H](C)C1]

The title compound was prepared in a similar manner to that described in Example 34-D using 2-(3,5-dimethyl-1-tosyl-1H-indazol-4-yl)-6-(3-isopropyl-1-methyl-1H-pyrazol-5-yl)-((2R,4R)-4-methoxy-2-methylpiperidin-1-yl)-5,6,7,8-tetrahydropyrido[4,3-d]pyrimidine. MS (ESI+) m/z 717.3 (M+H)+.

54-B. 6-(4-Chloro-3-isopropyl-1-methyl-1H-pyrazol-5-yl)-2-(3,5-dimethyl-1H-indazol-4-yl)-4-((2R,4R)-4-methoxy-2-methylpiperidin-1-yl)-5,6,7,8-tetrahydropyrido[4,3-d]pyrimidine

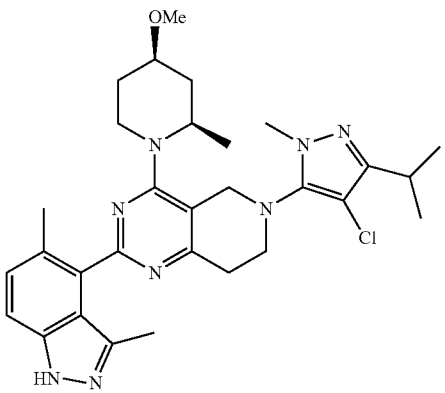 [SMILES: CO[C@@H]1CCN(c2nc(-c3c(C)ccc4[nH]nc(C)c34)nc3c2CN(c2c(Cl)c(C(C)C)nn2C)CC3)[C@H](C)C1]

The title compound was prepared in a similar manner to that described in Example 19-F using 6-(4-chloro-3-isopropyl-1-methyl-1H-pyrazol-5-yl)-2-(3,5-dimethyl-1-tosyl-1H-indazol-4-yl)-((2R,4R)-4-methoxy-2-methylpiperidin-1-yl)-5,6,7,8-tetrahydropyrido[4,3-d]pyrimidine. $^1$H NMR (400 MHz, DMSO-$d_6$) δ ppm 12.58 (s, 1 H), 7.40 (d, J=8.6 Hz, 1 H), 7.22 (d, J=8.6 Hz, 1 H), 4.23-4.39 (m, 2 H), 3.62 (s, 3 H), 3.46-3.58 (m, 1 H), 3.38-3.46 (m, 1 H), 3.02-3.12 (m, 1 H), 2.92-2.99 (m, 4 H), 2.84-2.92 (m, 1 H), 2.16 (s, 3 H), 1.96 (s, 1 H), 1.89 (br. s., 1 H), 1.85 (s, 6 H), 1.49-1.67 (m, 3 H), 1.20 (d, J=6.8 Hz, 6 H), 1.14 (d, J=6.3 Hz, 3 H); MS (ESI+) m/z 563.3 (M+H)$^+$.

The following compound was prepared in a similar manner.

54-B. 6-(4-Chloro-3-cyclopropyl-1-methyl-1H-pyrazol-5-yl)-2-(3,5-dimethyl-1H-indazol-4-yl)-4-methoxy-5,6,7,8-tetrahydropyrido[4,3-d]pyrimidine

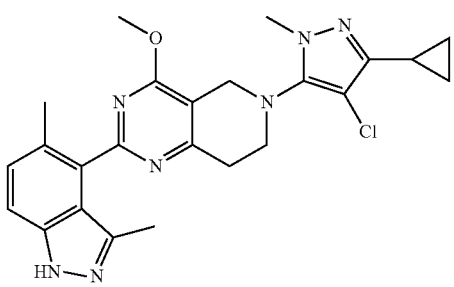 [SMILES: COc1nc(-c2c(C)ccc3[nH]nc(C)c23)nc2c1CN(c1c(Cl)c(C3CC3)nn1C)CC2]

$^1$H NMR (400 MHz, CD$_2$Cl$_2$) δ ppm 9.85 (br. s., 1 H) 7.39-7.52 (m, 1 H) 7.33 (d, J=8.3 Hz, 1 H) 4.33 (s, 2 H) 4.04 (s, 3 H) 3.70 (s, 3 H) 3.59 (t, J=5.8 Hz, 2 H) 3.08 (t, J=5.7 Hz, 2 H) 2.33 (s, 3 H) 2.059 (s, 3 H) 1.89 (quin, J=6.8 Hz, 1H) 0.83-0.97 (m, 4 H); MS (ESI+) m/z 464.2 (M+H)$^+$.

Example 55

55-A. (R)-6-Benzyl-2-chloro-4-(4-methoxy-3,3-dimethylpiperidin-1-yl)-5,6,7,8-tetrahydropyrido[4,3-d]pyrimidine

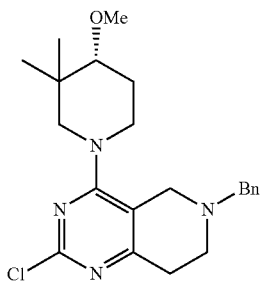 [SMILES: CO[C@@H]1CCN(c2nc(Cl)nc3c2CN(Cc2ccccc2)CC3)CC1(C)C]

To a solution of 6-benzyl-2,4-dichloro-5,6,7,8-tetrahydropyrido[4,3-d]pyrimidine (5.55 g, 18.8 mmol) in iPrOH (170 mL) was added (R)-4-methoxy-3,3-dimethylpiperidin-1-ium chloride, Example 7-D (3.08 g, 17.1 mmol) and TEA (7.2 mL, 51.4 mmol). The reaction mixture was then heated overnight at 50° C. At that point the solvent was removed in vacuo and the residue was purified via FCC (0-50% EtOAc/heptane) to give the title compound. MS (ESI+) m/z 401.3 (M+H)$^+$.

55-B. (R)-6-Benzyl-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine

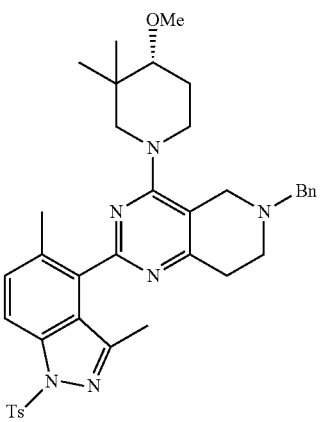 [SMILES: CO[C@@H]1CCN(c2nc(-c3c(C)ccc4c3c(C)nn4S(=O)(=O)c3ccc(C)cc3)nc3c2CN(Cc2ccccc2)CC3)CC1(C)C]

To a solution of (R)-6-benzyl-2-chloro-4-(4-methoxy-3,3-dimethylpiperidin-1-yl)-5,6,7,8-tetrahydropyrido[4,3-d]pyrimidine (5.04 g, 12.6 mmol) in 1,4-dioxane (100 mL) was added 3,5-dimethyl-4-(4,4,5,5-tetramethyl-1,3,2-dioxaborolan-2-yl)-1-tosyl-1H-indazole, Example 3, (6.16 g, 12.6 mmol), Pd(Ph$_3$P)$_4$ (2.18 g, 1.89 mmol) and a 2 M solution of sodium carbonate (18.9 mL, 37.7 mmol). The reaction mixture was heated at 100° C. under a nitrogen atmosphere for 16 h. The reaction mixture was then allowed to cool to rt and was diluted with EtOAc and water. The layers were mixed and then separated. The organic layer was washed with water and then brine. The separated organic layer was then dried over sodium sulfate, filtered and concentrated. The residue was then purified via FCC (0-70% EtOAc/heptane) to give the title compound. MS (ESI+) m/z 665.6 (M+H)$^+$.

55-C. (R)-2-(3,5-Dimethyl-1-tosyl-1H-indazol-4-yl)-4-(4-methoxy-3,3-dimethylpiperidin-1-yl)-5,6,7,8-tetrahydropyrido[4,3-d]pyrimidine

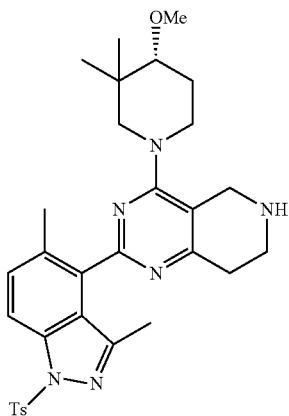 [SMILES: CO[C@@H]1CCN(c2nc(-c3c(C)ccc4c3c(C)nn4S(=O)(=O)c3ccc(C)cc3)nc3c2CNCC3)CC1(C)C]

To a solution of (R)-6-benzyl-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine (3.0 g, 4.51 mmol) in THF (24 mL) and water (6 mL) was added acetic acid (1.30 mL, 22.6 mmol). The solution was warmed to 40° C. and Pd(OH)$_2$ 20% on carbon (0.792 mg, 1.13 mmol) was added. The mixture was then stirred under a hydrogen atmosphere for 2.25 h. The mixture was then allowed to cool to rt and was filtered over Celite®, washing with EtOAc and MeOH. The filtrate was then basified with aqueous 1 N NaOH and extracted with EtOAc (3×). The combined organic layers were dried over anhydrous sodium sulfate, filtered, and concentrated under reduce pressure. The residue was then purified via FCC (0-15% MeOH/DCM; with 10% NH$_4$OH in DCM) to obtain the title compound. MS (ESI+) m/z 575.5 (M+H)$^+$.

55-D. (R)-1-Cyclopropyl-3-(2-(3,5-dimethyl-1-tosyl-1H-indazol-4-yl)-4-(4-methoxy-3,3-dimethylpiperidin-1-yl)-7,8-dihydropyrido[4,3-d]pyrimidin-6(5H)-Apropane-1,3-dione

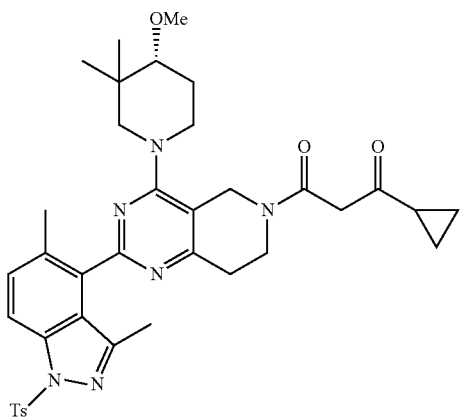 [SMILES: CO[C@@H]1CCN(c2nc(-c3c(C)ccc4c3c(C)nn4S(=O)(=O)c3ccc(C)cc3)nc3c2CN(C(=O)CC(=O)C2CC2)CC3)CC1(C)C]

A solution of (R)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine (0.200 g, 0.35 mmol), 4-DMAP (0.013 g, 0.10 mmol) and methyl 3-cyclopropyl-3-oxopropanoate (0.13 mL, 1.04 mmol) in toluene (3 mL) was heated at 150° C. in a microwave reactor for 35 min. The reaction was then diluted with EtOAc and water. The aqueous phase was extracted further with EtOAc (3×) and the combined organic layers were dried over anhydrous sodium sulfate, filtered, and concentrated under reduce pressure. The residue was then purified via FCC (0-10% MeOH/DCM) to obtain the title compound. MS (ESI+) m/z 685.6 (M+H)$^+$.

55-E. (R)-6-(3-Cyclopropyl-1-methyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine

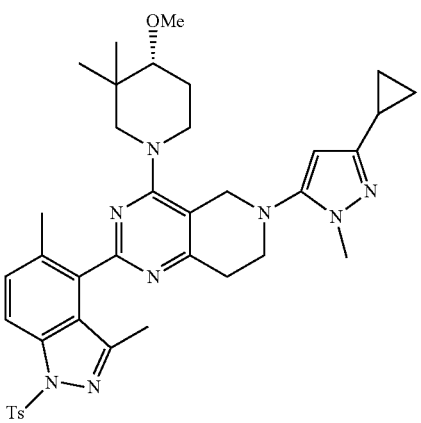 [SMILES: CO[C@@H]1CCN(c2nc(-c3c(C)ccc4c3c(C)nn4S(=O)(=O)c3ccc(C)cc3)nc3c2CN(c2cc(C4CC4)nn2C)CC3)CC1(C)C]

A microwave vial was charged with (R)-1-cyclopropyl-3-(2-(3,5-dimethyl-1-tosyl-1H-indazol-4-yl)-4-(4-methoxy-3,3-dimethylpiperidin-1-yl)-7,8-dihydropyrido[4,3-d]pyrimidin-6(5H)-yl)propane-1,3-dione (0.563 g, 0.82 mmol) and THF (5 mL) and placed under a nitrogen atmosphere. Methyl hydrazine (87 μL, 1.64 mmol), pyridine (0.25 mL) and Lawesson's reagent (0.366 g, 0.90 mmol) were then added in sequence. The vessel was sealed and heated at 125° C. in a microwave reactor for 12 min. At that point the reaction mixture was concentrated and the residue was purified via FCC (0-10% MeOH/DCM; 10% NH$_4$OH in DCM) to obtain the title compound. $^1$H NMR (400 MHz, DMSO-d$_6$) δ ppm 8.56-8.61 (m, 1H), 8.05 (d, J=8.6 Hz, 1 H), 7.79 (d, J=8.3 Hz, 2 H), 7.56 (d, J=8.8 Hz, 1 H), 7.38 (d, J=8.6 Hz, 2 H), 5.52 (s, 1 H), 4.08 (d, J=13.4 Hz, 1 H), 3.96 (d, J=15.4 Hz, 1 H), 3.61-3.69 (m, 1 H), 3.55 (s, 3 H), 3.28-3.31 (m, 2 H), 3.26 (s, 3 H), 3.04 (t, J=10.2 Hz, 1 H), 2.94-2.99 (m, 1 H), 2.82-2.92 (m, 2 H), 2.33 (s, 3 H), 2.19 (s, 3 H), 1.86-1.94 (m, 1 H), 1.83 (s, 3 H), 1.67-1.78 (m, 1 H), 1.45-1.58 (m, 1 H), 0.91 (s, 3 H), 0.74-0.83 (m, 5H), 0.50-0.58 (m, 2 H); MS (ESI+) m/z 695.6 (M+H)$^+$.

55-F. (R)-6-(4-Chloro-3-cyclopropyl-1-methyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine 55-G. (R)-6-(4-Chloro-3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine

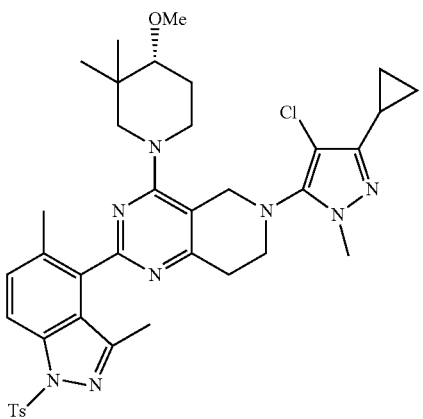 [SMILES: CO[C@@H]1CCN(c2nc(-c3c(C)ccc4c3c(C)nn4S(=O)(=O)c3ccc(C)cc3)nc3c2CN(c2c(Cl)c(C4CC4)nn2C)CC3)CC1(C)C]

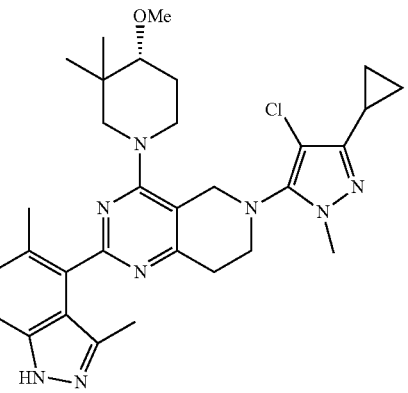

To a solution of (R)-6-(3-cyclopropyl-1-methyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine (0.062 g, 0.089 mmol) in DCM (2 mL) under an atmosphere of nitrogen was added N-chlorosuccinimide (0.012 g, 0.089 mmol). The mixture was left to stir for 1 h at rt. The reaction mixture was then directly purified by FCC (40-75% EtOAc/heptanes) to give the title compound. $^1$H NMR (400 MHz, DICHLOROMETHANE-$d_2$) δ ppm 8.08 (d, J=8.3 Hz, 1 H), 7.79 (d, J=8.3 Hz, 2 H), 7.45 (d, J=8.8 Hz, 1 H), 7.25 (d, J=8.3 Hz, 2 H), 4.32 (d, J=14.7 Hz, 1 H), 4.22 (d, J=14.4 Hz, 1 H), 3.67 (d, J=11.6 Hz, 1 H), 3.58 (s, 3 H), 3.52 (dq, J=12.8, 6.3 Hz, 2 H), 3.28-3.36 (m, 4 H), 3.09 (br. s., 1 H), 2.99 (br. s., 2 H), 2.92 (dd, J=8.6, 3.8 Hz, 1 H), 2.86 (d, J=11.6 Hz, 1 H), 2.72 (s, 2 H), 2.36 (s, 3 H), 2.25 (s, 3 H), 1.88-1.96 (m, 4 H), 1.78-1.88 (m, 1 H), 1.52-1.69 (m, 3 H), 0.94 (s, 3 H), 0.81-0.90 (m, 8 H); MS (ESI+) m/z 729.4 (M+H)$^+$.

To a solution of (R)-6-(4-chloro-3-cyclopropyl-1-methyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine (0.050 g, 0.068 mmol) in MeOH (3 mL) was added $K_2CO_3$ (0.057 g, 0.410 mmol). The mixture was heated at 55 C. under a nitrogen atmosphere for 2 h. At that point the mixture was diluted with EtOAc and washed with sat aq $NH_4Cl$ and then brine. The organic layer was dried over sodium sulfate, filtered and concentrated. The residue was purified by FCC (0-10% MeOH/DCM) to give the title compound. $^1$H NMR (400 MHz, DMSO-$d_6$) δ ppm 12.59 (s, 1 H), 7.39 (d, J=8.3 Hz, 1 H), 7.21 (d, J=8.8 Hz, 1 H), 4.39 (d, J=14.9 Hz, 1 H), 4.25 (d, J=14.7 Hz, 1 H), 3.62-3.78 (m, 1 H), 3.56 (s, 3 H), 3.46-3.55 (m, 2 H), 3.30 (d, J=3.5 Hz, 1 H), 3.26 (s, 3 H), 2.99-3.08 (m, 1 H), 2.97 (dd, J=9.1, 4.0 Hz, 1 H), 2.92 (app. t, J=5.9 Hz, 2 H), 2.85 (d, J=12.9 Hz, 1 H), 2.18 (s, 3 H), 1.85-1.96 (m, 4 H), 1.74-1.82 (m, 1 H), 1.49-1.60 (m, 1 H), 0.92 (s, 3 H), (overlapped m, 2 H), 0.81 (s, 3H), 0.72-0.77 (m, 2 H); MS (ESI+) m/z 575.5 (M+H)$^+$.

The following compounds were prepared in a similar manner.

| Structure | Chemical Name & Analytical Data |
|---|---|
| 55-H ![structure] | (R)-6-(4-chloro-3-cyclopropyl-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine $^1$H NMR (400 MHz, DMSO-$d_6$) δ ppm 12.59 (s, 1 H), 7.39 (d, J = 8.6 Hz, 1 H), 7.08-7.30 (m, 1 H), 4.33-4.48 (m, 1 H), 4.16-4.31 (m, 1 H), 3.64-3.75 (m, 1 H), 3.58-3.63 (m, 1 H), 3.54-3.57 (m, 3 H), 3.46-3.54 (m, 2 H), 2.99-3.10 (m, 2 H), 2.92 (t, J = 5.8 Hz, 2 H), 2.84 (d, J = 13.1 Hz, 1 H), 2.15-2.22 (m, 3 H), 1.83-1.91 (m, 4H), 1.74-1.82 (m, 1 H), 1.50-1.63 (m, 1 H), 1.09 (t, J = 6.9 Hz, 3 H), 0.90-0.94 (m, 3 H), 0.82-0.88 (m, 5 H), 0.71-0.77 (m, 2 H); MS (ESI+) m/z 590.4 (M + H)$^+$ |

| Structure | Chemical Name & Analytical Data |
|---|---|
| 55-I 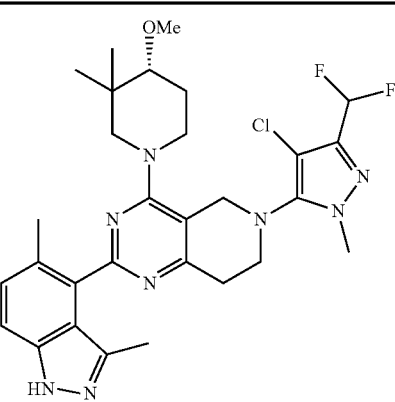 | (R)-6-(4-chloro-3-(difluoromethyl)-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d6) δ ppm 12.60 (s, 1 H), 7.39 (d, J = 8.6 Hz, 1 H), 7.21 (d, J = 8.8 Hz, 1 H), 6.93 (t, J = 53.1 Hz, 1 H), 4.45 (d, J = 14.7 Hz, 1 H), 4.31 (d, J = 14.9 Hz, 1 H), 3.71 (s, 3 H), 3.64-3.69 (m, 1 H), 3.53-3.62 (m, 2 H), 3.26 (s, 3 H), 3.00-3.09 (m, 1 H), 2.91-3.00 (m, 3 H), 2.85 (d, J = 13.1 Hz, 1 H), 2.18 (s, 3 H), 1.85-1.97 (m, 4 H), 1.50-1.63 (m, 1 H), 0.92 (s, 3 H), 0.83 (s, 3 H); MS (ESI+) m/z 585.5 (M + H)$^+$. |
| 55-J 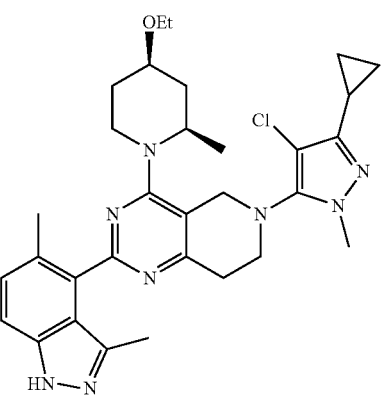 [SMILES: CCO[C@@H]1CCN(c2nc(-c3c(C)ccc4[nH]nc(C)c34)nc3c2CN(c2c(Cl)c(C4CC4)nn2C)CC3)[C@H](C)C1] | 6-(4-chloro-3-cyclopropyl-1-methyl-1H-pyrazol-5-yl)-2-(3,5-dimethyl-1H-indazol-4-yl)-4-((2R,4R)-4-ethoxy-2-methylpiperidin-1-yl)-5,6,7,8-tetrahydropyrido[4,3-d]pyrimidine. $^1$H NMR (400 MHz, DMSO-d6) δ ppm 12.61 (s, 1 H) 7.40 (d, J = 8.34 Hz, 1 H) 7.22 (d, J = 8.59 Hz, 1 H) 4.31-4.38 (m, 1 H) 4.23-4.31 (m, 1 H) 3.65-3.78 (m, 1 H) 3.58 (s, 3 H) 3.48-3.56 (m, 3 H) 3.39-3.48 (m, 2 H) 3.24-3.29 (m, 1 H) 3.03-3.15 (m, 1 H) 2.93 (t, J = 5.81 Hz, 2 H) 2.16 (s, 3 H) 1.82-1.92 (m, 5 H) 1.78 (tt, J = 8.34, 5.05 Hz, 1 H) 1.50-1.65 (m, 2 H) 1.15 (d, J = 6.32 Hz, 3 H) 1.10 (t, J = 6.95 Hz, 3 H) 0.82-0.88 (m, 2 H) 0.71-0.77 (m, 2 H); MS (ESI+) m/z 575.4 (M + H)$^+$. |
| 55-K 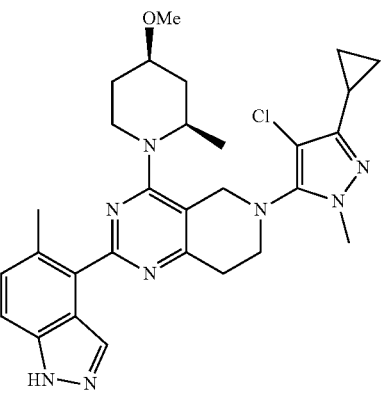 [SMILES: CO[C@@H]1CCN(c2nc(-c3c(C)ccc4[nH]ncc34)nc3c2CN(c2c(Cl)c(C4CC4)nn2C)CC3)[C@H](C)C1] | 6-(4-chloro-3-cyclopropyl-1-methyl-1H-pyrazol-5-yl)-4-((2R,4R)-4-methoxy-2-methylpiperidin-1-yl)-2-(5-methyl-1H-indazol-4-yl)-5,6,7,8-tetrahydropyrido[4,3-d]pyrimidine. $^1$H NMR (400 MHz, DMSO-d6) δ ppm 13.00 (s, 1 H), 8.06-8.10 (m, 1 H), 7.51 (dd, J = 8.5, 0.6 Hz, 1 H), 7.29 (d, J = 8.6 Hz, 1 H), 4.20-4.41 (m, 2 H), 3.72-3.87 (m, 1 H), 3.58 (s, 3 H), 3.49-3.56 (m, 2 H), 3.42-3.49 (m, 1 H), 3.26 (s, 3 H), 3.11-3.19 (m, 1 H), 3.03 (app. t, J = 5.7 Hz, 2 H), 2.54 (s, 3 H), 1.84-1.97 (m, 2 H), 1.79 (tt, J = 8.3, 5.1 Hz, 1 H), 1.56-1.71 (m, 2 H), 1.19 (d, J = 6.6 Hz, 3 H), 0.82-0.89 (m, 2 H), 0.72-0.77 (m, 2 H); MS (ESI+) m/z 547.5 (M + H)$^+$. |
| 55-L 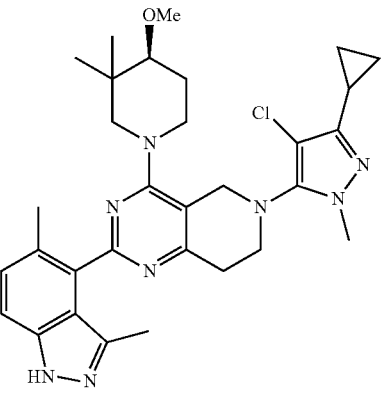 [SMILES: CO[C@H]1CCN(c2nc(-c3c(C)ccc4[nH]nc(C)c34)nc3c2CN(c2c(Cl)c(C4CC4)nn2C)CC3)CC1(C)C] | (S)-6-(4-Chloro-3-cyclopropyl-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, Acetone-d6) δ ppm 11.71 (br. s., 1 H), 7.42 (d, J = 8.3 Hz, 1 H), 7.23 (d, J = 8.6 Hz, 1 H), 4.48 (d, J = 14.9 Hz, 1 H), 4.39 (d, J = 14.9 Hz, 1 H), 3.72-3.81 (m, 1 H), 3.53-3.67 (m, 5 H), 3.41 (dd, J = 13.1, 1.8 Hz, 1 H), 3.32 (s, 3 H), 3.10-3.19 (m, 1 H), 2.98-3.07 (m, 3 H), 2.92 (d, J = 12.9 Hz, 1 H), 2.78-2.81 (m, 2 H), 2.26 (s, 3 H), 1.96-1.98 (m, 3 H), 1.79-1.88 (m, 1 H), 1.62-1.73 (m, 1 H), 0.98 (s, 3 H), 0.92 (s, 3 H), 0.71-0.90 (m, 5 H); MS (ESI+) m/z 575.4 (M + H)$^+$. |

| Structure | Chemical Name & Analytical Data |
|---|---|
| 55-M 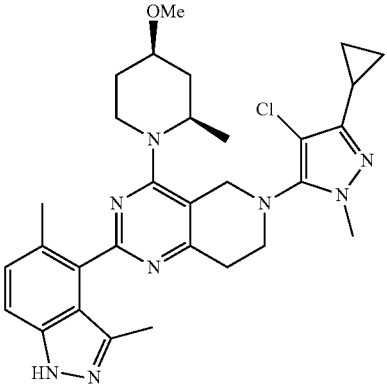 [SMILES: CO[C@@H]1CCN(c2nc(-c3c(C)ccc4[nH]nc(C)c34)nc3c2CN(c2c(Cl)c(C4CC4)nn2C)CC3)[C@H](C)C1] | 6-(4-chloro-3-cyclopropyl-1-methyl-1H-pyrazol-5-yl)-2-(3,5-dimethyl-1H-indazol-4-yl)-4-((2R,4R)-4-methoxy-2-methylpiperidin-1-yl)-5,6,7,8-tetrahydropyrido[4,3-d]pyrimidine. $^1$H NMR (400 MHz, DMSO-d$_6$) δ ppm 12.58 (s, 1 H), 7.40 (d, J = 8.3 Hz, 1 H), 7.22 (d, J = 8.6 Hz, 1 H), 4.21-4.41 (m, 2 H), 3.65-3.76 (m, 1 H), 3.58 (s, 3 H), 3.47-3.56 (m, 2 H), 3.37-3.45 (m, 1 H), 3.20-3.26 (m, 3 H), 3.02-3.14 (m, 1 H), 2.94 (t, J = 6.1 Hz, 2 H), 2.16 (s, 3 H), 1.83-1.92 (m, 5 H), 1.73-1.82 (m, 1 H), 1.51-1.66 (m, 2 H), 1.14 (d, J = 6.3 Hz, 3 H), 0.81-0.90 (m, 2 H), 0.70-0.78 (m, 2 H); MS (ESI+) m/z 561.3 (M + H)$^+$. |
| 55-N 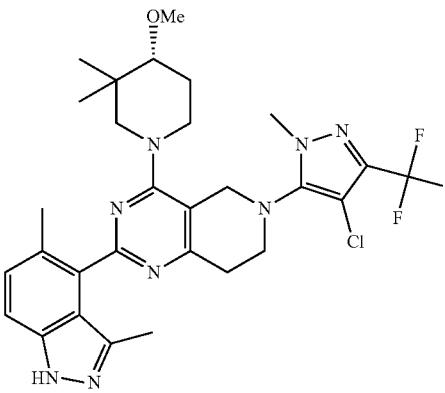 | (R)-6-(4-chloro-1-methyl-3-(trifluoromethyl)-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d6) δ ppm 12.60 (s, 1 H), 7.39 (d, J = 8.1 Hz, 1 H), 7.21 (d, J = 8.6 Hz, 1 H), 4.47 (d, J = 15.2 Hz, 1 H), 4.33 (d, J = 14.9 Hz, 1 H), 3.76 (s, 3 H), 3.63-3.72 (m, 1 H), 3.57-3.63 (m, 2 H), 3.26 (s, 3 H), 3.00-3.09 (m, 1 H), 2.91-3.00 (m, 3 H), 2.86 (d, J = 13.1 Hz, 1 H), 2.18 (s, 3 H), 1.90-1.96 (m, 1 H), 1.88 (s, 3 H), 1.51 - 1.62 (m, 1 H), 0.92 (s, 3 H), 0.83 (s, 3 H); MS (ESI+) m/z 603.5 (M + H)$^+$. |

Example 56

56-A. 6-(3-Cyclopropyl-4-fluoro-1-methyl-1H-pyrazol-5-yl)-2-(3,5-dimethyl-1-tosyl-1H-indazol-4-yl)-4-((3-endo)-3-methoxy-8-azabicyclo[3.2.1]octan-8-yl)-5,6,7,8-tetrahydropyrido[4,3-d]pyrimidine

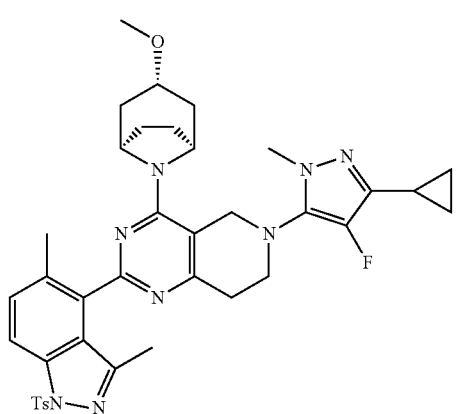 [SMILES: CO[C@H]1C[C@H]2CC[C@@H](C1)N2c1nc(-c2c(C)ccc3c2c(C)nn3S(=O)(=O)c2ccc(C)cc2)nc2c1CN(c1c(F)c(C3CC3)nn1C)CC2]

To a solution of 6-(3-cyclopropyl-1-methyl-1H-pyrazol-5-yl)-2-(3,5-dimethyl-1-tosyl-1H-indazol-4-yl)-4-((3-endo)-3-methoxy-8-azabicyclo[3.2.1]octan-8-yl)-5,6,7,8-tetrahydropyrido[4,3-d]pyrimidine (45 mg, 0.13 mmol), prepared in a similar method as described in Example 55-E, in acetonitrile (1 mL) was added Selectfluor® (88 mg, 0.13 mmol), and the reaction mixture was stirred at rt overnight. The reaction mixture was concentrated and the residue purified by silica gel flash chromatography (0-100% ethyl acetate/heptanes) to afford 6-(3-cyclopropyl-4-fluoro-1-methyl-1H-pyrazol-5-yl)-2-(3,5-dimethyl-1-tosyl-1H-indazol-4-yl)-4-((3-endo)-3-methoxy-8-azabicyclo[3.2.1]octan-8-yl)-5,6,7,8-tetrahydropyrido[4,3-d]pyrimidine. MS (ESI+) m/z 711.7 (M+H)$^+$.

56-B. 6-(3-cyclopropyl-4-fluoro-1-methyl-1H-pyrazol-5-yl)-2-(3,5-dimethyl-1H-indazol-4-yl)-4-β3-endo)-3-methoxy-8-azabicyclo[3.2.1]octan-8-yl)-5,6,7,8-tetrahydropyrido[4,3-d]pyrimidine

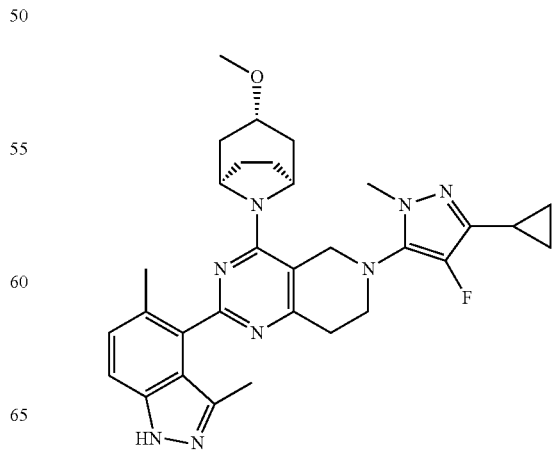

6-(3-cyclopropyl-4-fluoro-1-methyl-1H-pyrazol-5-yl)-2-(3,5-dimethyl-1H-indazol-4-yl)-4-(3-endo)-3-methoxy-8-azabicyclo[3.2.1]octan-8-yl)-5,6,7,8-tetrahydropyrido[4,3-d]pyrimidine was prepared in a similar method as described in Example 55-G. $^1$H NMR (400 MHz, DMSO-d$_6$) δ ppm 12.57 (s, 1 H), 7.37 (d, J=8.3 Hz, 1 H), 7.20 (d, J=8.6 Hz, 1 H), 4.37 (br. s., 2 H), 4.21 (s, 2 H), 3.55 (s, 3 H), 3.40-3.46 (m, 4 H), 3.20 (s, 3 H), 2.89 (t, J=5.8 Hz, 2 H), 2.18 (s, 3 H), 1.93-2.04 (m, 4 H), 1.82-1.88 (m, 6 H), 1.74-1.81 (m, 1 H), 0.80-0.87 (m, 2 H), 0.70-0.75 (m, 2 H); MS (ESI+) m/z 557.6 (M+H)$^+$.

The following compounds were prepared with similar method.

| Structure | Chemical Name & Analytical Data |
|---|---|
| 56-C 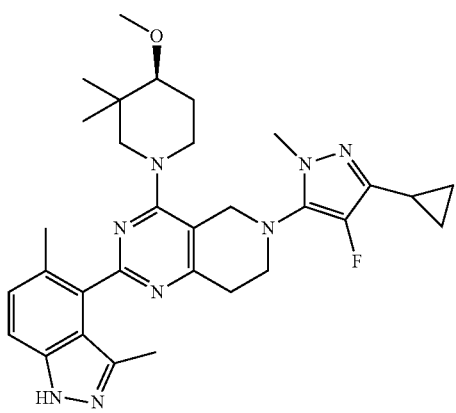 [SMILES: CO[C@H]1CCN(c2nc(-c3c(C)ccc4[nH]nc(C)c34)nc3c2CN(c2c(F)c(C4CC4)nn2C)CC3)CC1(C)C] | (S)-6-(3-cyclopropyl-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.59 (br. s., 1 H), 7.39 (d, J = 8.3 Hz, 1 H), 7.21 (d, J = 8.3 Hz, 1 H), 4.29 (d, J = 13.4 Hz, 1 H), 4.17 (d, J = 14.1 Hz, 1 H), 3.64-3.74 (m, 1 H), 3.54 (s, 3 H), 3.42-3.50 (m, 2 H), 3.27 (s, 3 H), 2.95- 3.10 (m, 2 H), 2.89-2.96 (m, 2 H), 2.80-2.89 (m, 1 H), 2.58-2.63 (m, 1 H), 2.18 (s, 3 H), 1.83-1.96 (m, 4 H), 1.71-1.81 (m, 1 H), 1.49-1.60 (m, 1 H), 0.92 (s, 3 H), 0.78-0.87 (m, 5 H), 0.66-0.75 (m, 2 H); MS (ESI+) m/z 559.4 (M + H)$^+$. |
| 56-D 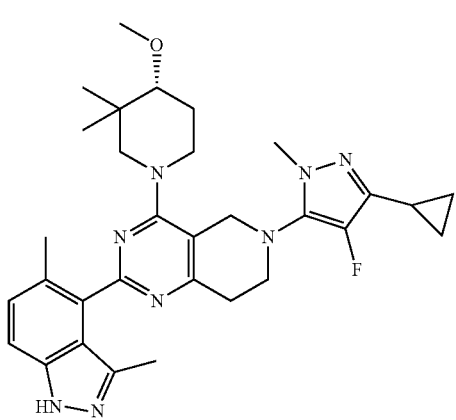 [SMILES: CO[C@@H]1CCN(c2nc(-c3c(C)ccc4[nH]nc(C)c34)nc3c2CN(c2c(F)c(C4CC4)nn2C)CC3)CC1(C)C] | (R)-6-(3-cyclopropyl-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.59 (s, 1 H), 7.39 (d, J = 8.6 Hz, 1 H), 7.21 (d, J = 8.6 Hz, 1 H), 4.29 (d, J = 14.9 Hz, 1 H), 4.16 (d, J = 15.2 Hz, 1 H), 3.64-3.72 (m, 1 H), 3.53 (s, 3 H), 3.46 (t, J = 6.2 Hz, 2 H), 3.27 (s, 3 H), 3.00-3.08 (m, 1 H), 2.97 (dd, J = 9.0, 3.9 Hz, 1 H), 2.91 (app. t, J = 6.1 Hz, 2 H), 2.84 (d, J = 12.9 Hz, 1 H), 2.18 (s, 3 H), 1.88-1.95 (m, 1 H), 1.87 (s, 3 H), 1.72-1.81 (m, 1 H), 1.49-1.60 (m, 1 H), 0.92 (s, 3 H), 0.80-0.86 (m, 5 H), 0.68-0.74 (m, 2 H); MS (ESI+) m/z 559.5 (M + H)$^+$. |
| 56-E 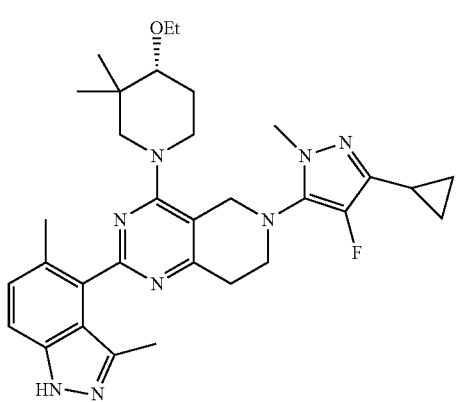 [SMILES: CCO[C@@H]1CCN(c2nc(-c3c(C)ccc4[nH]nc(C)c34)nc3c2CN(c2c(F)c(C4CC4)nn2C)CC3)CC1(C)C] | (R)-6-(3-cyclopropyl-4-fluoro-1-methyl-1H-pyrazol-5-yl)-2-(3,5-dimethyl-1H-indazol-4-yl)-4-(4-ethoxy-3,3-dimethylpiperidin-1-yl)-5,6,7,8-tetrahydropyrido[4,3-d]pyrimidine. 1H NMR (400 MHz, DMSO-d$_6$) δ ppm 12.59 (s, 1 H), 7.39 (d, J = 8.3 Hz, 1 H), 7.21 (d, J = 8.6 Hz, 1 H), 4.22-4.34 (m, 1 H), 4.10-4.20 (m, 1 H), 3.65-3.75 (m, 1 H), 3.55-3.64 (m, 1 H), 3.53 (s, 3 H), 3.46 (t, J = 6.1 Hz, 2 H), 2.99-3.10 (m, 2 H), 2.88-2.95 (m, 2 H), 2.84 (d, J = 12.9 Hz, 1 H), 2.18 (s, 3 H), 2.00 (s, 1 H), 1.87 (s, 4 H), 1.72-1.81 (m, 1 H), 1.55 (d, J = 10.1 Hz, 1 H), 1.23 (s, 1 H), 1.09 (t, J = 6.9 Hz, 3 H), 0.91 (s, 3 H), 0.79-0.87 (m, 5 H), 0.67-0.74 (m, 2 H); MS (ESI+) m/z 573.5 (M + H)$^+$. |

| Structure | Chemical Name & Analytical Data |
|---|---|
| 56-F 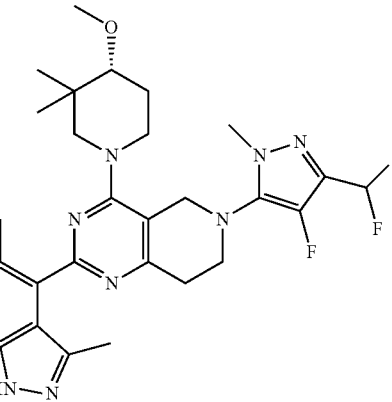 | (R)-6-(3-(difluoromethyl)-4-fluoro-1-methyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.59 (s, 1 H), 7.39 (d, J = 8.1 Hz, 1 H), 7.21 (d, J = 8.6 Hz, 1 H), 6.95 (t, J = 53.3 Hz, 1 H), 4.36 (d, J = 14.7 Hz, 1 H), 4.23 (d, J = 15.2 Hz, 1 H), 3.63-3.75 (m, 4 H), 3.53 (t, J = 6.2 Hz, 2 H), 3.27 (s, 3 H), 3.01-3.10 (m, 1 H), 2.90-3.00 (m, 3 H), 2.86 (d, J = 13.1 Hz, 1 H), 2.18 (s, 3 H), 1.88-1.96 (m, 1 H), 1.87 (s, 3 H), 1.50-1.61 (m, 1 H), 0.92 (s, 3 H), 0.82 (s, 3 H); MS (ESI+) m/z 569.6 (M + H)$^+$. |
| 56-G 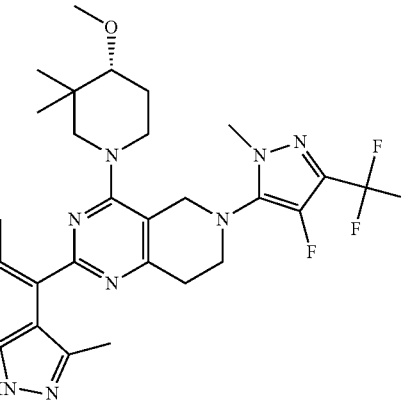 | (R)-2-(3,5-dimethyl-1H-indazol-4-yl)-6-(4-fluoro-1-methyl-3-(trifluoromethyl)-1H-pyrazol-5-yl)-4-(4-methoxy-3,3-dimethylpiperidin-1-yl)-5,6,7,8-tetrahydropyrido[4,3-d]pyrimidine. $^1$H NMR (400 MHz, DMSO-d$_6$) δ ppm 12.59 (s, 1 H), 7.39 (d, J = 8.3 Hz, 1 H), 7.21 (d, J = 8.8 Hz, 1 H), 4.40 (d, J = 15.2 Hz, 1 H), 4.25 (d, J = 15.2 Hz, 1 H), 3.75 (s, 3 H), 3.65-3.72 (m, 1 H), 3.55 (t, J = 6.3 Hz, 2 H), 3.27 (s, 3 H), 3.01-3.10 (m, 1 H), 2.91-3.00 (m, 3 H), 2.86 (d, J = 13.1 Hz, 1 H), 2.18 (s, 3 H), 1.88-1.95 (m, 1 H), 1.86 (s, 3 H), 1.50-1.62 (m, 1 H), 0.92 (s, 3 H), 0.82 (s, 3 H); MS (ESI+) m/z 587.5 (M + H)$^+$. |

Example 57

57-A. Racemic (trans)-tert-butyl 3-(dimethylamino)-4-hydroxypyrrolidine-1-carboxylate

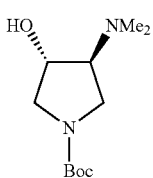 [SMILES: CN(C)[C@H]1CN(C(=O)OC(C)(C)C)C[C@@H]1O]

To a solution of racemic (trans)-4-(dimethylamino)pyrrolidin-3-ol dihydrochloride (0.87 g, 4.28 mmol) in DCM (10 mL) was added triethylamine (2.39 mL, 17.1 mmol) and di-tert-butyl dicarbonate (0.99 mL, 4.28 mmol). The reaction mixture was stirred at room temperature for 18 h. The reaction mixture was then diluted with water and extracted three times with EtOAc. The combined organic extracts were washed with brine, dried over Na$_2$SO$_4$, filtered, and concentrated to provide racemic (trans)-tert-butyl 3-(dimethylamino)-4-hydroxypyrrolidine-1-carboxylate. $^1$H NMR (400 MHz, DMSO-d$_6$) δ ppm 5.09 (d, J=4.8 Hz, 1 H), 4.09 (br. s., 1 H), 3.42 (m, 2 H), 3.08-3.18 (m, 1 H), 2.95-3.04 (m, 1 H), 2.17 (s, 6 H), 1.39 (s, 9 H).

57-B. Racemic (trans)-tert-butyl-3-(dimethylamino)-4-methoxypyrrolidine-1-carboxylate

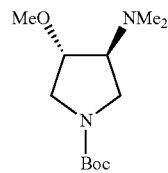 [SMILES: CO[C@H]1CN(C(=O)OC(C)(C)C)C[C@@H]1N(C)C]

To a solution of racemic (trans)-tert-butyl 3-(dimethylamino)-4-hydroxypyrrolidine-1-carboxylate (0.96 g, 4.17 mmol) in THF (40 mL) at 0° C. was added NaH (0.25 g, 6.25 mmol, 60% dispersion in mineral oil), and the reaction mixture was stirred at 0° C. for 10 min. Then, iodomethane (0.29 mL, 4.6 mmol) was added dropwise and the resulting mixture was stirred at room temperature for 18 h. The reaction mixture was quenched with sat aq NH$_4$Cl and extracted three times with EtOAc. The combined organic extracts were washed with brine, dried over Na$_2$SO$_4$, filtered, and concentrated to provide racemic-(trans)-tert-butyl-3-(dimethylamino)-4-methoxypyrrolidine-1-carboxylate. $^1$H NMR (400 MHz, DMSO-d$_6$) δ ppm 3.84 (br. s., 1 H), 3.46-3.54 (m, 1 H), 3.25 (s, 3 H), 3.12-3.22 (obs m, 3 H), 2.72 (br. s., 1 H), 2.16 (s, 6 H), 1.39 (s, 9 H).

57-C. Racemic (trans)-3-(dimethylamino)-4-methoxypyrrolidin-1-ium 2,2,2-trifluoroacetate

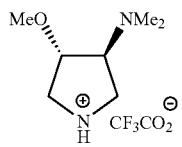

To a solution of racemic (trans)-tert-butyl-3-(dimethylamino)-4-methoxypyrrolidine-1-carboxylate (0.68 g, 2.8 mmol) in DCM (4.0 mL) was added TFA (2.1 mL, 28 mmol), and the reaction mixture was stirred at room temperature for 18 h. Then, the reaction mixture was concentrated under reduced pressure to provide racemic (trans)-3-(dimethylamino)-4-methoxypyrrolidin-1-ium 2,2,2-trifluoroacetate. $^1$H NMR (400 MHz, DEUTERIUM OXIDE) δ ppm 4.42-4.48 (m, 1 H), 3.96-4.05 (m, 2 H), 3.60 (d, J=5.4 Hz, 2 H), 3.48-3.55 (m, 1 H), 3.39 (s, 3 H), 2.97 (s, 6 H).

Example 58

58-A. Racemic-(2R*,3R*)-3-(benzhydrylamino)butane-1,2-diol

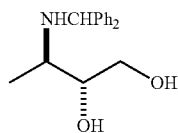

To a stirred suspension of (E)-but-2-en-1-ol (825 µL, 9.32 mmol) in DCM (23 mL) was added m-CPBA (2.19 g, 9.79 mmol) at 0° C. The reaction was allowed to warm to room temperature and was stirred for 16 h. Then the reaction mixture was cooled down to 0° C. and the solution was filtered and the solid was rinsed with cold DCM. The filtrate was concentrated and carried over to the next step.

To a solution of 3-(methyloxiran-2-yl)methanol (0.826 g, 9.38 mmol) in DCM was added α-aminodiphenylmethane (1.50 mL, 8.44 mmol) and titanium(IV) isopropoxide (5.5 mL, 18.7 mmol), and the reaction mixture was heated at 60° C. for 16 h. A saturated aqueous solution of Rochelle's salt was added to the mixture followed by a solution of 3 N NaOH. The reaction miture was stirred overnight. The aqueous phase was then extracted with DCM (3×). The combined organic layers were washed with brine, dried with sodium sulfate, filtered and concentrated under reduced pressure. The residue was purified via FCC (30-60% EtOAc/heptanes) to give the title compound. MS (ESI+) m/z 272.4 (M+H)$^+$.

58-B. Racemic-(trans)-1-benzhydryl-2-methylazetidin-3-ol

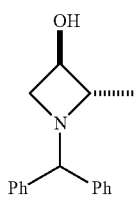 [SMILES: C[C@H]1[C@H](O)CN1C(c1ccccc1)c1ccccc1]

Preparation of racemic-(trans)-1-benzhydryl-2-methylazetidin-3-ol was done as described in *Tetrahedron Letters*, 1991, 32, 6935-6938; in this instance the starting material used was racemic. $^1$H NMR (400 MHz, CDCl$_3$) δ ppm 7.47-7.38 (m, 5 H), 7.35-7.24 (m, 5 H), 4.36 (s, 1 H), 3.95 (quin, J=6.4 Hz, 1 H), 3.69 (ddd, J=1.0, 6.4, 7.7 Hz, 1 H), 3.03 (quin, J=6.1 Hz, 1 H), 2.61-2.54 (m, 1 H), 1.79-1.71 (m, 1 H), 0.77 (d, J=6.3 Hz, 3 H).

58-C. Racemic-(trans)-3-hydroxy-2-methylazetidin-1-ium chloride

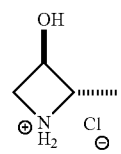

To a solution of racemic-(trans)-1-benzhydryl-2-methylazetidin-3-ol (0.137 g, 0.541 mmol) in MeOH (5.41 mL) was added 10% Pd/C (57 mg, 0.027 mmol) and 4 M HCl in dioxane (406 µL, 1.62 mmol). H$_2$ was bubbled through the solution for 15 min, and the reaction mixture was stirred overnight. The mixture was filtered through a pad of Celite® and rinsed with DCM. The filtrate was concentrated to give the title compound.

Example 59

59-A. Racemic-(trans)-1-benzhydryl-3-methoxy-2-methylazetidine

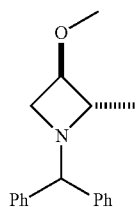

To a solution of racemic-(trans)-1-benzhydryl-2-methylazetidin-3-ol (0.198 g, 0.782 mmol) in THF (16 mL) was added iodomethane (98 µL, 1.6 mmol) and sodium hydride (0.035 g, 0.86 mmol, 60% in mineral oil). After 1.5 h, water was added and the mixture was extracted with EtOAc (3×). The combined organic phases were washed with brine, dried with sodium sulfate, filtered and concentrated under reduced pressure. The residue was purified via FCC (0-15% EtOAc/n-heptanes) to give the title compound. MS (ESI+) m/z 268.2 (M+H)$^+$.

59-B. Racemic-(trans)-3-methoxy-2-methylazetidin-1-ium chloride

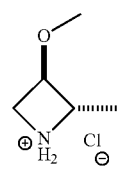

Preparation of racemic-(trans)-3-methoxy-2-methylazetidin-1-ium chloride was done as described in Example 58-C.

Example 60

60-A. Racemic (cis)-3-benzyl-7-oxa-3-azabicyclo[4.2.0]octane

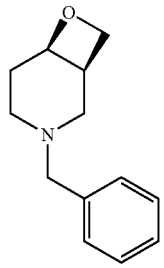 [SMILES: c1ccc(CN2CC[C@H]3OC[C@H]3C2)cc1]

Step 1: To a solution of ethyl 1-benzyl-4-oxopiperidine-3-carboxylate hydrochloride salt (5.2 g, 17.5 mmol) in EtOH (80 mL) was added NaBH$_4$ (5.29 g, 140 mmol). The reaction mixture was stirred at room temperature for 4 h, then filtered through celite and concentrated under reduced pressure. The residue was dissolved in DCM, washed with water, dried over Na$_2$SO$_4$, filtered and concentrated to afford a mixture of cis and trans diastereomers of 1-benzyl-3-(hydroxymethyl)piperidin-4-ol, which was used for the next step without further purification.

Step 2: To a solution of above crude cis and trans mixture of 1-benzyl-3-(hydroxymethyl)piperidin-4-ol (2.69 g, 12.16 mmol) in DCM (60 mL) was added DIPEA (3.39 mL, 24.31 mmol) and MsCl (0.947 mL, 12.2 mmol) dropwise at 0° C. The reaction mixture was further stirred for 1.5 h at 0-5° C. and then quenched with saturated aqueous NaHCO$_3$. The aqueous phase was extracted with DCM. The combined organic phases were dried over Na$_2$SO$_4$, filtered and concentrated to afford a mixture of mono- and bi-mesylated compounds. The crude was then dissolved in THF (250 mL) and added NaH (1.05 g, 43.8 mmol, 60% in mineral oil) portionwise at room temperature. After being stirred for 40 min at room temperature, the reaction mixture was then heated to 65° C. for 4.5 h. The reaction mixture was cooled to room temperature, then quenched with water and concentrated in vacuo. The residue was dissolved in EtOAc, washed with saturated aqueous NH$_4$Cl, dried over Na$_2$SO$_4$, filtered and concentrated. The resulting residue was purified by silica gel flash chromatography (0-100% EtOAc/heptanes) to provide racemic (cis)-3-benzyl-7-oxa-3-azabicyclo[4.2.0]octane as a colorless oil. $^1$H NMR (400 MHz, CD$_2$Cl$_2$) δ ppm 7.32-7.41 (m, 5H), 4.97 (ddd, J=3.03, 4.42, 6.19 Hz, 1H), 4.68 (t, J=5.68 Hz, 1H), 4.07-4.13 (m, 1H), 3.53-3.60 (m, 2H), 2.90-2.98 (m, 1H), 2.82-2.90 (m, 1H), 2.52-2.59 (m, 2H), 2.49 (dd, J=6.32, 11.37 Hz, 1H), 1.83-1.87 (m, 2H).

60-B. Racemic (cis)-7-oxa-3-azabicyclo[4.2.0]octane

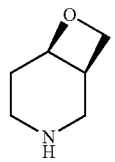

To a solution of racemic (cis)-3-benzyl-7-oxa-3-azabicyclo[4.2.0]octane (440 mg, 2.165 mmol) and HOAc (200 μL, 3.49 mmol) in MeOH (40 mL) was added Pd/C (5%, 461 mg, 0.216 mmol) at room temperature under nitrogen atmosphere. The vessel was evacuated and backfilled with hydrogen 3 times and then left to stir under hydrogen atmosphere for 3 h. The mixture was then filtered through celite and the celite was washed with MeOH and EtOAc. The filtrates were combined and concentrated under reduced pressure (bath temperature <30° C.) to provide racemic (cis)-7-oxa-3-azabicyclo[4.2.0]octane as an acetic acid salt. $^1$H NMR (400 MHz, CD$_3$OD) δ ppm 5.11 (td, J=3.32, 6.76 Hz, 1H), 4.84 (t, J=6.57 Hz, 1H), 4.24 (dd, J=3.92, 6.44 Hz, 1H), 3.46 (dd, J=6.95, 13.52 Hz, 1H), 3.33-3.40 (m, 1H), 3.04-3.14 (m, 3H), 1.95-2.02 (m, 2H).

Example 61

61-A. Ethyl 1-benzyl-3-methyl-4-oxopiperidine-3-carboxylate

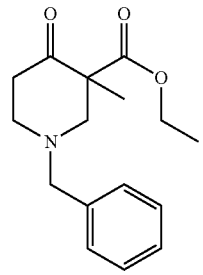 [SMILES: CCOC(=O)C1(C)CN(Cc2ccccc2)CCC1=O]

To a suspension of ethyl 1-benzyl-4-oxopiperidine-3-carboxylate hydrochloride (20 g, 67.2 mmol) in THF (130 mL)/DMF (130 mL) was added KOH (powder, 7.64 g, 136 mmol) at room temperature. The reaction mixture was stirred for 5-10 min, then added iodomethane (4.62 mL, 73.9 mmol) dropwise. The reaction mixture was further stirred for 3 h at room temperature and then quenched with water. The aqueous phase was extracted with diethyl ether twice. The organic phases were combined and washed with water, dried over Na$_2$SO$_4$, filtered and concentrated. The resulting residue was purified by silica gel flash chromatography (0-20% EtOAc/heptanes) to provide ethyl 1-benzyl-3-methyl-4-oxopiperidine-3-carboxylate. $^1$H NMR (400 MHz, DMSO-d$_6$) δ ppm 7.15-7.45 (m, 5H), 4.00-4.21 (m, 2H), 3.66 (d, J=13.39 Hz, 1H), 3.47 (d, J=13.39 Hz, 1H), 3.30 (dd, J=2.78, 11.62 Hz, 1H), 2.96-3.08 (m, 1H), 2.77 (ddd, J=6.69, 11.68, 14.46 Hz, 1H), 2.36-2.45 (m, 1H), 2.27-2.35 (m, 1H), 2.14 (d, J=11.37 Hz, 1H), 1.15 (t, J=7.07 Hz, 3H), 1.09 (s, 3H).

61-B. Racemic (cis)-3-benzyl-1-methyl-7-oxa-3-azabicyclo[4.2.0]octane

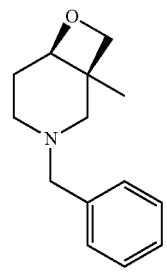 [SMILES: C[C@@]12CO[C@@H]1CCN(Cc1ccccc1)C2]

The above compound was synthesized in a similar manner as Example 60-A to provide racemic (cis)-3-benzyl-1-methyl-7-oxa-3-azabicyclo[4.2.0]octane. $^1$H NMR (400 MHz, CDCl$_2$) δ ppm 7.17-7.47 (m, 5H), 4.49-4.65 (m, 1H), 4.27 (d, J=5.05 Hz, 1H), 4.12 (d, J=5.05 Hz, 1H), 3.57 (br. s., 2H), 2.47-2.62 (m, 4H), 1.73-1.95 (m, 2H), 1.17 (s, 3H).

61-C. Racemic (cis)-1-methyl-7-oxa-3-azabicyclo[4.2.0]octane

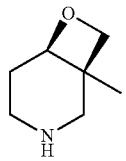

The above compound was synthesized in a similar manner as Example 60-B to provide racemic (cis)-1-methyl-7-oxa-3-azabicyclo[4.2.0]octane as an acetic acid salt. $^1$H NMR (400 MHz, CD$_3$OD) δ ppm 4.74 (t, J=2.91 Hz, 1H), 4.44 (d, J=6.32 Hz, 1H), 4.39 (d, J=6.57 Hz, 1H), 3.32-3.39 (m, 1H), 3.18-3.29 (m, 2H), 3.10 (d, J=13.39 Hz, 1H), 1.95-2.10 (m, 2H), 1.28 (s, 3H).

Example 62

62-A. (4S,6R)-6-Methyl-7-((R)-1-phenylethyl)-1-oxa-7-azaspiro[3.5]nonane

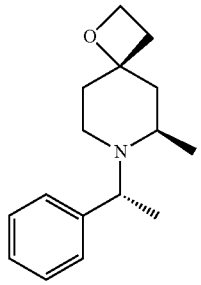 [SMILES: C[C@@H]1C[C@]2(CCO2)CCN1[C@H](C)c1ccccc1]

To a solution of trimethylsulfoxonium iodide (10.1 g, 46.0 mmol) in t-BuOH (anhydrous, 10 mL) was added tBuOK (1M in t-BuOH, 36.8 mL, 36.8 mmol) and the resulting mixture was stirred at 60° C. for 1 h. Then a solution of (R)-2-methyl-1-((R)-1-phenylethyl)piperidin-4-one (2 g, 9.20 mmol) in t-BuOH (6 mL) was added slowly. The reaction mixture was heated at 60° C. for 72 h, then cooled to room temperature and poured into water. The aqueous phase was extracted with EtOAc (2×). The organic phases were combined, washed with brine, dried over Na$_2$SO$_4$, filtered and concentrated. The resulting residue was purified by silica gel flash chromatography (0-30% EtOAc/heptanes) to provide the desired isomer (4S,6R)-6-methyl-7-((R)-1-phenylethyl)-1-oxa-7-azaspiro[3.5]nonane as a colorless oil (0.67 g, 30%). $^1$H NMR (400 MHz, CD$_2$Cl$_2$) δ ppm 7.48 (d, J=7.83 Hz, 2H), 7.34 (t, J=7.58 Hz, 2H), 7.24 (t, J=6.82 Hz, 1H), 4.39-4.51 (m, 2H), 4.25 (q, J=6.74 Hz, 1H), 2.78-3.01 (m, 1H), 2.30-2.45 (m, 3H), 2.21-2.30 (m, 1H), 2.13 (td, J=2.56, 13.07 Hz, 1H), 1.85-1.95 (m, 1H), 1.44-1.62 (m, 2H), 1.28 (d, J=6.82 Hz, 3H), 1.20 (d, J=6.32 Hz, 3H).

62-B. (4S,6R)-6-Methyl-1-oxa-7-azaspiro[3.5]nonane

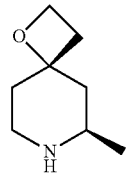

The above compound was synthesized in a similar manner as Example 60-B to provide (4S,6R)-6-methyl-1-oxa-7-azaspiro[3.5]nonane as an acetic acid salt. $^1$H NMR (400 MHz, CD$_2$Cl$_2$) δ ppm 4.53 (t, J=7.83 Hz, 2H), 3.19-3.30 (m, 2H), 3.01 (dt, J=3.03, 13.14 Hz, 1H), 2.45 (dt, J=1.26, 7.83 Hz, 2H), 2.15-2.28 (m, 2H), 1.93 (dt, J=4.80, 13.77 Hz, 1H), 1.77 (dd, J=12.51, 13.77 Hz, 1H), 1.34 (d, J=6.57 Hz, 3H).

Example 63

63-A. 2-(3,5-Dimethyl-1H-indazol-4-yl)-6-(5-isopropyl-2-methylphenyl)-5,6,7,8-tetrahydropyrido[4,3-d]pyrimidin-4-ol

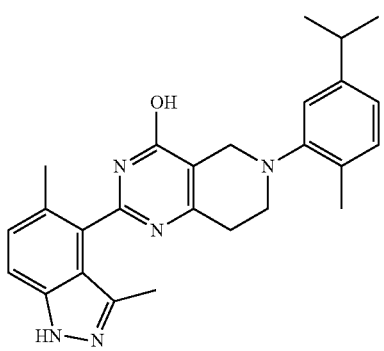 [SMILES: Cc1ccc(C(C)C)cc1N1CCc2nc(-c3c(C)ccc4[nH]nc(C)c34)nc(O)c2C1]

Ethanol (12 mL) was added to 2-(3,5-dimethyl-1H-indazol-4-yl)-6-(5-isopropyl-2-methylphenyl)-4-methoxy-5,6,7,8-tetrahydropyrido[4,3-d]pyrimidine (2.07 g, 3.47 mmol), followed by 12 N aqueous hydrochloric acid (12 mL). The mixture was then heated at 85° C. for 18 h. The mixture was cooled to room temperature, diluted with dichloromethane and slowly neutralized with saturated aqueous sodium bicarbonate. The resulting layers were separated and the aqueous layers were extracted with dichloromethane. The organic layers were combined. The combined organics were dried and concentrated. The residue was purified by FCC (0-100% EtOAc/heptane) to provide 2-(3,5-dimethyl-1H-indazol-4-yl)-6-(5-isopropyl-2-methylphenyl)-5,6,7,8-tetrahydropyrido[4,3-d]pyrimidin-4-ol. MS (ESI$^+$) m/z 428.3 (M+H)$^+$.

63-B. 4-Chloro-2-(3,5-dimethyl-1H-indazol-4-yl)-6-(5-isopropyl-2-methylphenyl)-5,6,7,8-tetrahydropyrido[4,3-d]pyrimidine and 63-C. 4-(4-Chloro-6-(5-isopropyl-2-methylphenyl)-5,6,7,8-tetrahydropyrido[4,3-d]pyrimidin-2-yl)-3,5-dimethyl-1H-indazole-1-carbaldehyde

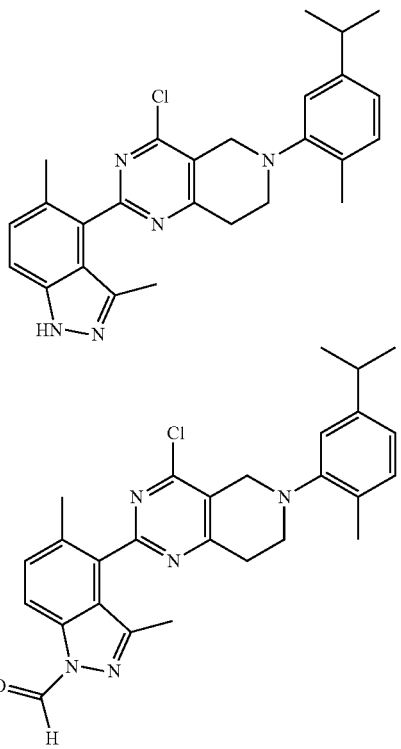

To a suspension of 2-(3,5-dimethyl-1H-indazol-4-yl)-6-(5-isopropyl-2-methylphenyl)-5,6,7,8-tetrahydropyrido[4,3-d]pyrimidin-4-ol (1.3 g, 3.04 mmol) in DCE (50 mL) was added Vilsmeier reagent (1.95 g, 15.2 mmol). The mixture was heated at 50° C. for 2 h. LC-MS showed reaction complete. The reaction mixture was poured into water, and the layers were separated. The aqueous layer was extracted with DCM. The organics were combined and concentrated. The residue was purified by FCC (0-100% EtOAc/heptane) to provide 4-chloro-2-(3,5-dimethyl-1H-indazol-4-yl)-6-(5-isopropyl-2-methylphenyl)-5,6,7,8-tetrahydropyrido[4,3-d]pyrimidine MS (ESI$^+$) m/z 446.3 (M+H)$^+$ and 4-(4-chloro-6-(5-isopropyl-2-methylphenyl)-5,6,7,8-tetrahydropyrido[4,3-d]pyrimidin-2-yl)-3,5-dimethyl-1H-indazole-1-carbaldehyde MS (ESE) m/z 474.3 (M+H)$^+$.

63-D. 2-(3,5-Dimethyl-1H-indazol-4-yl)-4-(2-fluoroethoxy)-6-(5-isopropyl-2-methylphenyl)-5,6,7,8-tetrahydropyrido[4,3-d]pyrimidine

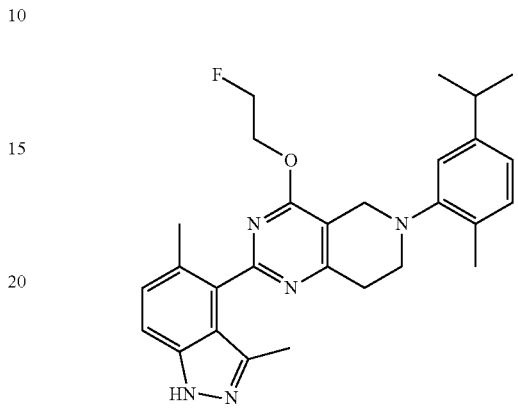

To a solution of 4-(4-chloro-6-(5-isopropyl-2-methylphenyl)-5,6,7,8-tetrahydropyrido[4,3-d]pyrimidin-2-yl)-3,5-dimethyl-1H-indazole-1-carbaldehyde (30 mg, 0.063 mmol) in THF (3 mL) was added 2-fluoroethanol (16.2 mg, 0.25 mmol) and NaH (15.1 mg, 0.63 mmol, 60% in mineral oil). The mixture was stirred at room temperature for 4 h. LC-MS showed reaction complete. The reaction mixture was concentrated and the residue was partitioned between saturated aqueous NH$_4$Cl solution and DCM. The layers were separated and the aqueous layer was extracted further with DCM. The organics were combined and concentrated. The residue was purified by FCC (0-100% EtOAc/heptane) to provide 2-(3,5-dimethyl-1H-indazol-4-yl)-4-(2-fluoroethoxy)-6-(5-isopropyl-2-methylphenyl)-5,6,7,8-tetrahydropyrido[4,3-d]pyrimidine. $^1$H NMR (400 MHz, METHANOL-d$_4$) δ ppm 7.47 (d, J=8.59 Hz, 1H), 7.34 (s, 1H), 7.15 (d, J=7.71 Hz, 1H), 7.06 (d, J=1.39 Hz, 1H), 6.92 (dd, J=1.52, 7.71 Hz, 1H), 4.71-4.81 (m, 2H), 4.67 (s, 2H), 4.13 (s, 2H), 3.33-3.39 (m, 2H), 3.05 (t, J=5.56 Hz, 2H), 2.88 (td, J=6.93, 13.80 Hz, 1H), 2.32 (s, 3H), 2.27 (s, 3H), 1.98 (s, 3H), 1.25 (d, J=6.82 Hz, 6H); MS (ESE) m/z 474.4 (M+H)$^+$.

The following compounds were prepared in a similar manner.

| | Structure | Chemical Name & Analytical Data |
|---|---|---|
| 63-E | 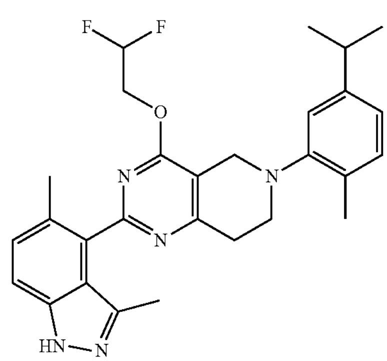 [SMILES: Cc1ccc(C(C)C)cc1N1CCc2nc(-c3c(C)ccc4[nH]nc(C)c34)nc(OCC(F)F)c2C1] | 4-(2,2-difluoroethoxy)-2-(3,5-dimethyl-1H-indazol-4-yl)-6-(5-isopropyl-2-methylphenyl)-5,6,7,8-tetrahydropyrido[4,3-d]pyrimidine. $^1$H NMR (400 MHz, METHANOL-d$_4$) δ ppm 7.47 (d, J = 8.59 Hz, 1 H), 7.33 (d, J = 8.59 Hz, 1 H), 7.14 (d, J = 7.71 Hz, 1 H), 7.06 (d, J = 1.52 Hz, 1 H), 6.92 (dd, J = 1.52, 7.71 Hz, 1 H), 6.03-6.38 (m, 1 H), 4.71 (dt, J = 3.66, 14.21 Hz, 2 H), 4.14 (s, 2 H), 3.36 (t, J = 5.68 Hz, 2 H), 3.07 (t, J = 5.62 Hz, 2 H), 2.88 (td, J = 6.93, 13.80 Hz, 1 H), 2.32 (s, 1 H), 2.28 (s, 3 H), 1.98 (s, 3 H), 1.25 (d, J = 6.82 Hz, 6 H); MS (ESI$^+$) m/z 492.5 (M + H)$^+$. |

| Structure | Chemical Name & Analytical Data |
|---|---|
| 63-F 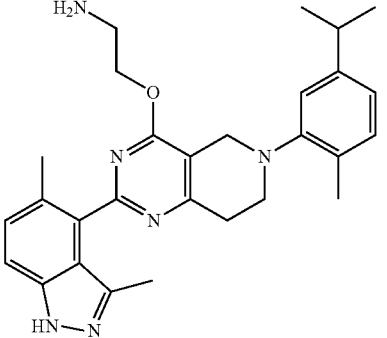 [SMILES: Cc1ccc(C(C)C)cc1N1CCc2nc(-c3c(C)ccc4[nH]nc(C)c34)nc(OCCN)c2C1] | 2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)ethanamine. $^1$H NMR (400 MHz, METHANOL-d$_4$) δ ppm 7.46 (d, J = 8.59 Hz, 1 H), 7.32 (d, J = 8.84 Hz, 1 H), 7.14 (d, J = 7.83 Hz, 1 H), 7.08 (d, J = 1.64 Hz, 1 H), 6.92 (dd, J = 1.71, 7.77 Hz, 1 H), 4.44-4.52 (m, 2 H), 4.16 (s, 2 H), 3.33-3.37 (m, 2 H), 2.99-3.09 (m, 4 H), 2.88 (td, J = 6.90, 13.86 Hz, 1 H), 2.32 (s, 3 H), 2.27 (s, 3 H), 1.99 (s, 3 H), 1.25 (d, J = 6.95 Hz, 6 H); MS (ESI$^+$) m/z 471.5 (M + H)$^+$. |
| 63-G 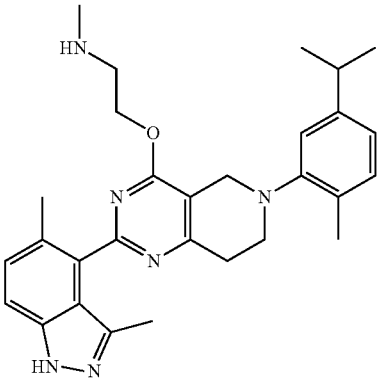 [SMILES: CNCCOc1nc(-c2c(C)ccc3[nH]nc(C)c23)nc2c1CN(c1cc(C(C)C)ccc1C)CC2] | 2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)-N-methylethanamine. $^1$H NMR (400 MHz, METHANOL-d$_4$) δ ppm 7.46 (d, J = 8.59 Hz, 1 H), 7.32 (d, J = 8.59 Hz, 1 H), 7.14 (d, J = 7.96 Hz, 1 H), 7.08 (d, J = 1.64 Hz, 1 H), 6.92 (dd, J = 1.64, 7.71 Hz, 1 H), 4.52 - 4.59 (m, 2 H), 4.15 (s, 2 H), 3.32-3.37 (m, 2 H), 3.04 (t, J = 5.62 Hz, 2 H), 2.93-2.99 (m, 2 H), 2.88 (td, J = 6.90, 13.86 Hz, 1 H), 2.40 (s, 3 H), 2.32 (s, 3 H), 2.27 (s, 3 H), 1.98 (s, 3 H), 1.25 (d, J = 6.95 Hz, 6 H); MS (ESI$^+$) m/z 485.6 (M + H)$^+$. |
| 63-H 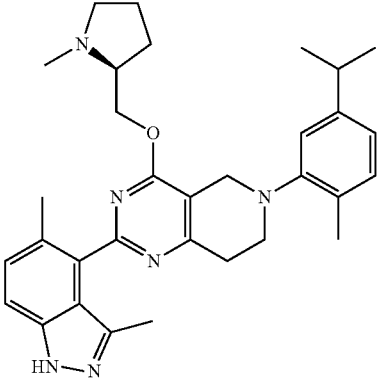 [SMILES: Cc1ccc(C(C)C)cc1N1CCc2nc(-c3c(C)ccc4[nH]nc(C)c34)nc(OC[C@@H]3CCCN3C)c2C1] | (S)-2-(3,5-dimethyl-1H-indazol-4-yl)-6-(5-isopropyl-2-methylphenyl)-4-((1-methylpyrrolidin-2-yl)methoxy)-5,6,7,8-tetrahydropyrido[4,3-d]pyrimidine. $^1$H NMR (400 MHz, METHANOL-d$_4$) δ ppm 7.46 (d, J = 8.46 Hz, 1 H), 7.32 (d, J = 8.59 Hz, 1 H), 7.14 (d, J = 7.96 Hz, 1 H), 7.05 (d, J = 1.52 Hz, 1 H), 6.91 (dd, J = 1.71, 7.77 Hz, 1 H), 4.47-4.55 (m, 1 H), 4.40 (dd, J = 6.32, 11.24 Hz, 1 H), 4.07-4.20 (m, 2 H), 3.33-3.39 (m, 2 H), 3.00-3.09 (m, 3 H), 2.87 (td, J = 6.93, 13.80 Hz, 1 H), 2.76 (dtd, J = 4.55, 6.62, 8.61 Hz, 1 H), 2.44 (s, 3 H), 2.29-2.38 (m, 4 H), 2.27 (s, 3 H), 2.00-2.10 (m, 1 H), 1.99 (s, 3 H), 1.73-1.83 (m, 2 H), 1.62-1.73 (m, 1 H), 1.20-1.28 (m, 6 H); MS (ESI$^+$) m/z 525.5 (M + H)$^+$. |
| 63-I 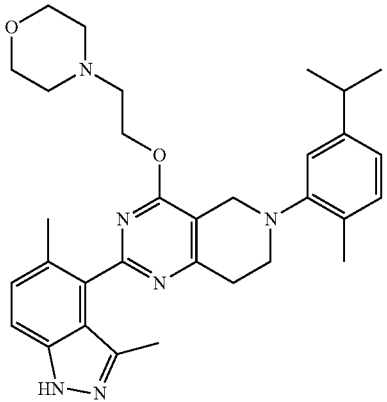 [SMILES: Cc1ccc(C(C)C)cc1N1CCc2nc(-c3c(C)ccc4[nH]nc(C)c34)nc(OCCN3CCOCC3)c2C1] | 4-(2-((2-(3,5-dimethyl-1H-indazol-4-yl)-6-(5-isopropyl-2-methylphenyl)-5,6,7,8-tetrahydropyrido[4,3-d]pyrimidin-4-yl)oxy)ethyl)morpholine. $^1$H NMR (400 MHz, METHANOL-d$_4$) δ ppm 7.46 (d, J = 8.46 Hz, 1 H), 7.32 (d, J = 8.59 Hz, 1 H), 7.14 (d, J = 7.83 Hz, 1 H), 7.05 (d, J = 1.64 Hz, 1 H), 6.92 (dd, J = 1.71, 7.77 Hz, 1 H), 4.62 (t, J = 5.56 Hz, 2 H), 4.12 (s, 2 H), 3.60-3.68 (m, 4 H), 3.35 (t, J = 5.68 Hz, 2 H), 3.04 (t, J = 5.62 Hz, 2 H), 2.83-2.93 (m, 1 H), 2.81 (t, J = 5.62 Hz, 2 H), 2.50-2.59 (m, 4 H), 2.32 (s, 3 H), 2.27 (s, 3 H), 1.99 (s, 3 H), 1.25 (d, J = 6.95 Hz, 6 H); MS (ESI$^+$) m/z 541.5 (M + H)$^+$. |

| Structure | Chemical Name & Analytical Data |
|---|---|
| 63-J | (S)-4-((2,2-dimethyl-1,3-dioxolan-4-yl)methoxy)-2-(3,5-dimethyl-1H-indazol-4-yl)-6-(5-isopropyl-2-methylphenyl)-5,6,7,8-tetrahydropyrido[4,3-d]pyrimidine. MS (ESI$^+$) m/z 542.5 (M + H)$^+$. |

Example 64

(R)-3-((2-(3,5-Dimethyl-1H-indazol-4-yl)-6-(5-isopropyl-2-methylphenyl)-5,6,7,8-tetrahydropyrido[4,3-d]pyrimidin-4-yl) oxy) propane-1,2-diol

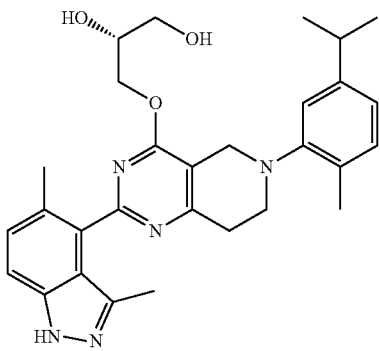 [SMILES: Cc1ccc(C(C)C)cc1N1CCc2nc(-c3c(C)ccc4[nH]nc(C)c34)nc(OC[C@H](O)CO)c2C1]

A solution of (S)-4-((2,2-dimethyl-1,3-dioxolan-4-yl)methoxy)-2-(3,5-dimethyl-1H-indazol-4-yl)-6-(5-isopropyl-2-methylphenyl)-5,6,7,8-tetrahydropyrido[4,3-d]pyrimidine (20 mg, 0.037 mmol) in TFA (0.9 mL) and H$_2$O (0.1 mL) was stirred at room temperature for 16 h. The reaction mixture was concentrated and the residue was partitioned between DCM and saturated aqueous NaHCO$_3$. The layers were separated and the aqueous layer was extracted with DCM. The organics were combined and concentrated. The residue was purified by reverse phase HPLC (C18, 10-100% acetonitrile in H$_2$O with 0.1% NH$_4$OH) to give (R)-3-((2-(3,5-dimethyl-1H-indazol-4-yl)-6-(5-isopropyl-2-methylphenyl)-5,6,7,8-tetrahydropyrido[4,3-d]pyrimidin-4-yl)oxy) propane-1,2-diol. $^1$H NMR (400 MHz, CD$_2$Cl$_2$) δ ppm 7.33 (d, J=8.46 Hz, 1H), 7.21 (d, J=8.59 Hz, 1H), 7.08 (d, J=7.96 Hz, 1H), 6.97 (d, J=1.52 Hz, 1H), 6.86 (dd, J=1.71, 7.77 Hz, 1H), 4.36-4.47 (m, 2H), 4.06 (s, 2H), 3.88-3.95 (m, 1H), 3.53-3.60 (m, 1H), 3.46-3.52 (m, 1H), 3.26 (t, J=5.68 Hz, 2H), 3.02-3.10 (m, 2H), 2.76-2.86 (m, 1H), 2.26 (s, 3H), 2.20 (s, 3H), 1.92 (s, 3H), 1.17 (d, J=6.95 Hz, 6H); MS (ESL) m/z 502.5 (M+H)$^+$.

Example 65

65-A. 1-(2-(3,5-Dimethyl-1H-indazol-4-yl)-6-(5-isopropyl-2-methylphenyl)-5,6,7,8-tetrahydropyrido[4,3-d]pyrimidin-4-yl)-N,N-dimethylazetidin-3-amine

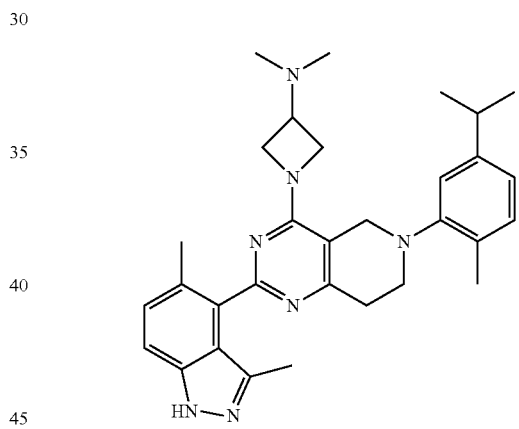

A solution of 4-chloro-2-(3,5-dimethyl-1H-indazol-4-yl)-6-(5-isopropyl-2-methylphenyl)-5,6,7,8-tetrahydropyrido[4,3-d]pyrimidine (30 mg, 0.07 mmol), N,N-dimethylazetidin-3-amine bistrifluoroacetate salt (20.0 mg, 0.2 mmol) and DIEA (0.06 mL, 0.35 mmol) in DMA (1.5 mL) was heated to 180° C. for 3 min in a microwave reactor. The reaction mixture was filtered through a 0.45 μM PTFE filter and the filtrate was purified by reverse phase HPLC (C18, 10-100% acetonitrile-H$_2$O with 0.1% NH$_4$OH) to afford 1-(2-(3,5-dimethyl-1H-indazol-4-yl)-6-(5-isopropyl-2-methylphenyl)-5,6,7,8-tetrahydropyrido[4,3-d]pyrimidin-4-yl)-N,N-dimethylazetidin-3-amine $^1$H NMR (400 MHz, METHANOL-d$_4$) δ ppm 7.43 (d, J=8.46 Hz, 1H), 7.30 (d, J=8.59 Hz, 1H), 7.13 (d, J=7.83 Hz, 1H), 7.04 (d, J=1.39 Hz, 1H), 6.91 (dd, J=1.52, 7.71 Hz, 1H), 4.36 (t, J=8.21 Hz, 2H), 4.08-4.20 (m, 4H), 3.32-3.38 (m, 2H), 3.18-3.27 (m, 1H), 2.79-2.97 (m, 3H), 2.31 (s, 3H), 2.27 (s, 3H), 2.18 (s, 6H), 2.04 (s, 3H), 1.24 (d, J=6.95 Hz, 6H); MS (ESL) m/z 510.5 (M+H)$^+$.

The following compounds were prepared in a similar manner.

| Structure | Chemical Name & Analytical Data |
|---|---|
| 65-B 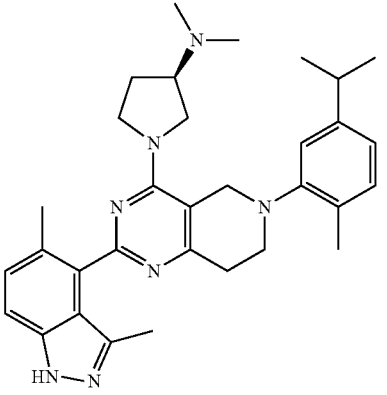 [SMILES: Cc1ccc(C(C)C)cc1N1CCc2nc(-c3c(C)ccc4[nH]nc(C)c34)nc(N3CC[C@@H](N(C)C)C3)c2C1] | (R)-1-(2-(3,5-dimethyl-1H-indazol-4-yl)-6-(5-isopropyl-2-methylphenyl)-5,6,7,8-tetrahydropyrido[4,3-d]pyrimidin-4-yl)-N,N-dimethylpyrrolidin-3-amine. $^1$H NMR (400 MHz, METHANOL-d$_4$) δ ppm 7.42 (d, J = 8.46 Hz, 1 H), 7.30 (d, J = 8.72 Hz, 1 H), 7.13 (d, J = 7.96 Hz, 1 H), 7.04 (d, J = 1.52 Hz, 1 H), 6.90 (dd, J = 1.58, 7.77 Hz, 1 H), 4.36-4.45 (m, 1 H), 4.24 (d, J = 14.6 Hz, 1 H), 3.88-4.01 (m, 2 H), 3.76 (dt, J = 6.57, 10.55 Hz, 1 H), 3.54 (dd, J = 8.59, 10.61 Hz, 1 H), 3.41-3.25 (m, 2 H overlap with solvent), 2.96-3.08 (m, 1 H), 2.78-2.95 (m, 3 H), 2.29 (m, 12 H), 2.15-2.26 (m, 1 H), 2.03 (s, 3 H), 1.83 (quin, J = 10.26 Hz, 1 H), 1.24 (d, J = 6.95 Hz, 6 H); MS (ESI$^+$) m/z 524.5 (M + H)$^+$. |
| 65-C 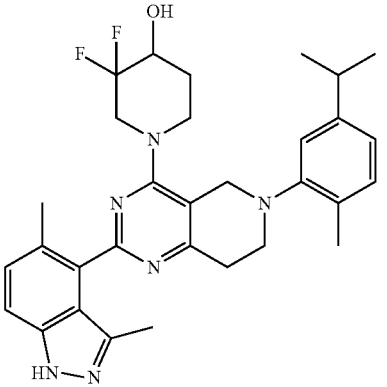 [SMILES: Cc1ccc(C(C)C)cc1N1CCc2nc(-c3c(C)ccc4[nH]nc(C)c34)nc(N3CCC(O)C(F)(F)C3)c2C1] | 1-(2-(3,5-dimethyl-1H-indazol-4-yl)-6-(5-isopropyl-2-methylphenyl)-5,6,7,8-tetrahydropyrido[4,3-d]pyrimidin-4-yl)-3,3-difluoropiperidin-4-ol. $^1$H NMR (400 MHz, DICHLOROMETHANE-d$_2$) δ ppm 7.39 (d, J = 8.3 Hz, 1 H), 7.27 (d, J = 8.6 Hz, 1 H), 7.14 (d, J = 7.8 Hz, 1 H), 6.98 (d, J = 1.5 Hz, 1 H), 6.92 (dd, J = 7.7, 1.6 Hz, 1 H), 3.93-4.13 (m, 3 H), 3.71-3.91 (m, 1 H), 3.49-3.68 (m, 2 H), 3.40 (td, J = 6.1, 1.5 Hz, 3 H), 3.12 (t, J = 5.7 Hz, 2 H), 2.89 (spt, J = 6.8 Hz, 1 H), 2.28 (s, 6 H), 2.04-2.19 (m, 1 H), 1.98 (s, 3 H), 1.86-1.96 (m, 1 H), 1.25 (d, J = 6.8 Hz, 6 H); MS (ESI+) m/z 547.5 (M + H)+. |
| 65-D 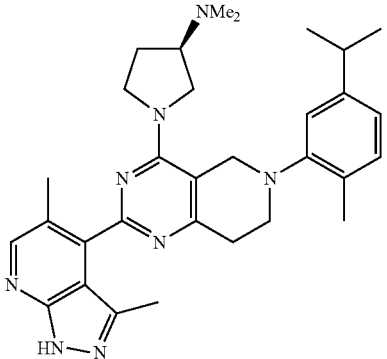 [SMILES: Cc1ccc(C(C)C)cc1N1CCc2nc(-c3c(C)cnc4[nH]nc(C)c34)nc(N3CC[C@@H](N(C)C)C3)c2C1] | (R)-1-(2-(3,5-dimethyl-1H-pyrazolo[3,4-b]pyridin-4-yl)-6-(5-isopropyl-2-methylphenyl)-5,6,7,8-tetrahydropyrido[4,3-d]pyrimidin-4-yl)-N,N-dimethylpyrrolidin-3-amine. $^1$H NMR (400 MHz, DMSO-d$_6$) δ ppm 13.14 (s, 1 H), 8.41 (s, 1 H), 7.12 (d, J = 7.8 Hz, 1 H), 7.01 (d, J = 1.5 Hz, 1 H), 6.88 (dd, J = 7.6, 1.5 Hz, 1 H), 4.43 (d, J = 15.2 Hz, 1 H), 4.20 (d, J = 14.9 Hz, 1 H), 3.89 (dd, J = 10.4, 7.1 Hz, 1 H), 3.74-3.82 (m, 1 H), 3.58-3.69 (m, 1 H), 3.38-3.45 (m, 1 H), 3.13-3.23 (m, 1 H), 2.90-3.00 (m, 1 H), 2.79-2.88 (m, 2 H), 2.28 (s, 3 H), 2.23 (s, 3 H), 2.16 (s, 6 H), 2.05-2.09 (m, 1 H), 2.04 (s, 3 H), 1.64-1.76 (m, 1 H), 1.19 (d, J = 6.8 Hz, 6 H); MS (ESI+) m/z 525.3 (M + H)$^+$. |

| Structure | Chemical Name & Analytical Data |
|---|---|
| 65-E<br>65-F<br>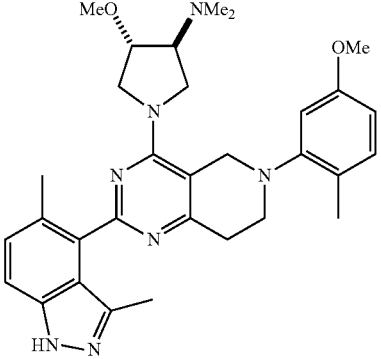 [SMILES: COc1ccc(C)c(N2CCc3nc(-c4c(C)ccc5[nH]nc(C)c45)nc(N4C[C@H](OC)[C@@H](N(C)C)C4)c3C2)c1] | The racemic (trans)-1-(2-(3,5-dimethyl-1H-indazol-4-yl)-6-(5-methoxy-2-methylphenyl)-5,6,7,8-tetrahydropyrido[4,3-d]pyrimidin-4-yl)-4-methoxy-N,N-dimethylpyrrolidin-3-amine was separated by chiral HPLC (AD-H column; 20% IPA (5 mM NH$_4$OH) in CO$_2$; 75 g/min) to give the following two compounds: Enantiomer-1 (65-E): [α]$_D^{20}$ −6.8; R$_t$ 5.4 min, (AD-H 20 × 250 mm column; 20% IPA (5 mM NH$_4$OH) in CO$_2$; 75 g/min). $^1$H NMR (400 MHz, DMSO-d$_6$) δ ppm 12.56 (s, 1 H), 7.37 (d, J = 8.3 Hz, 1 H), 7.20 (d, J = 8.6 Hz, 1 H), 7.11 (d, J = 8.8 Hz, 1 H), 6.71 (d, J = 2.5 Hz, 1 H), 6.60 (dd, J = 8.2, 2.7 Hz, 1 H), 4.31 (d, J = 14.9 Hz, 1 H), 4.25 (d, J = 14.7 Hz, 1 H), 3.89-3.96 (m, 2 H), 3.71-3.78 (m, 4 H), 3.54-3.65 (m, 2 H), 3.23-3.29 (m, 5 H), 2.84-2.90 (m, 2 H), 2.75-2.82 (m, 1 H), 2.21 (s, 3 H), 2.20 (s, 3 H), 2.19 (s, 6 H), 1.90 (s, 3 H); MS (ESI+) m/z 542.3 (M + H)$^+$. Enantiomer-2 (65-F): [α]$_D^{20}$ +4.6; R$_t$ 6.8 min, (AD-H 20 × 250 mm column; 20% IPA (5 mM NH$_4$OH) in CO$_2$; 75 g/min). $^1$H NMR (400 MHz, DMSO-d$_6$) δ ppm 12.56 (s, 1 H), 7.37 (d, J = 8.3 Hz, 1 H), 7.20 (d, J = 8.6 Hz, 1 H), 7.11 (d, J = 8.3 Hz, 1 H), 6.71 (d, J = 2.5 Hz, 1 H), 6.60 (dd, J = 8.2, 2.7 Hz, 1 H), 4.31 (d, J = 14.7 Hz, 1 H), 4.25 (d, J = 14.7 Hz, 1 H), 3.90-3.95 (m, 2 H), 3.71-3.79 (m, 4 H), 3.54-3.63 (m, 2 H), 3.23-3.28 (m, 5 H), 2.87 (t, J = 5.8 Hz, 2 H), 2.76-2.81 (m, 1 H), 2.21 (s, 3 H), 2.20 (s, 3 H), 2.19 (s, 6 H), 1.90 (s, 3 H); MS (ESI+) m/z 542.3 (M + H)$^+$. |
| 65-G<br>65-H<br>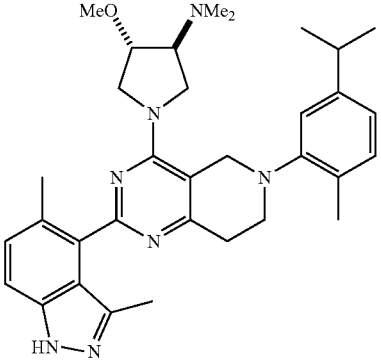 [SMILES: CO[C@H]1CN(c2nc(-c3c(C)ccc4[nH]nc(C)c34)nc3c2CN(c2cc(C(C)C)ccc2C)CC3)C[C@@H]1N(C)C] | The racemic (trans)-1-(2-(3,5-dimethyl-1H-indazol-4-yl)-6-(5-isopropyl-2-methylphenyl)-5,6,7,8-tetrahydropyrido[4,3-d]pyrimidin-4-yl)-4-methoxy-N,N-dimethylpyrrolidin-3-amine was separated by chiral HPLC (AD-H column; 20% IPA (5 mM NH$_4$OH) in CO$_2$; 80 g/min) to give the following two compounds: Enantiomer-1 (65-G): [α]$_D^{20}$ +8.0; R$_t$ 3.5 min, (AD-H column 20 × 250 mm column; 20% IPA (5 mM NH$_4$OH) in CO$_2$; 80 g/min). $^1$H NMR (400 MHz, DMSO-d$_6$) δ ppm 12.56 (s, 1 H), 7.37 (d, J = 8.3 Hz, 1 H), 7.20 (d, J = 8.6 Hz, 1 H), 7.12 (d, J = 8.1 Hz, 1 H), 6.99-7.02 (m, 1 H), 6.88 (dd, J = 7.7, 1.6 Hz, 1 H), 4.29 (s, 2 H), 3.89-3.96 (m, 2 H), 3.73-3.81 (m, 1 H), 3.53-3.64 (m, 2 H), 3.26-3.28 (m, 4H), 2.77-2.91 (m, 2 H), 2.23 (s, 3 H), 2.22 (s, 3 H), 2.19 (s, 6 H), 1.91 (s, 3 H), 1.19 (d, J = 6.8 Hz, 6 H); MS (ESI+) m/z 554.4 (M + H)$^+$. Enantiomer-2 (65-H): [α]$_D^{20}$ −10.5; R$_t$ 4.5 min (AD-H column 20 × 250 mm column; 20% IPA (5 mM NH$_4$OH) in CO$_2$; 80 g/min). $^1$H NMR (400 MHz, DMSO-d$_6$) δ ppm 12.57 (br. s, 1 H), 7.38 (d, J = 8.3 Hz, 1 H), 7.21 (d, J = 8.6 Hz, 1 H), 7.12 (d, J = 7.8 Hz, 1 H), 7.01 (br. s, 1 H), 6.89 (d, J = 7.8 Hz, 1 H), 4.29 (br. s., 2 H), 3.92 (br. s., 2 H), 3.71-3.82 (m, 1 H), 3.58 (br. s., 2 H), 3.25-3.30 (m, 4 H), 2.78-2.93 (m, 4 H), 2.23 (s, 3 H), 2.22 (s, 3 H), 2.19 (br. s., 6 H), 1.91 (s, 3 H), 1.19 (d, J = 7.1 Hz, 6 H); MS (ESI+) m/z 554.4 (M + H)$^+$. |
| 65-I<br>65-J<br>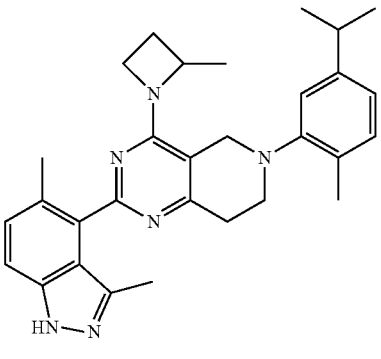 [SMILES: Cc1ccc(C(C)C)cc1N1CCc2nc(-c3c(C)ccc4[nH]nc(C)c34)nc(N3CCC3C)c2C1] | The racemic 2-(3,5-dimethyl-1H-indazol-4-yl)-6-(5-isopropyl-2-methylphenyl)-4-(2-methylazetidin-1-yl)-5,6,7,8-tetrahydropyrido[4,3-d]pyrimidine was separated by chiral HPLC (IB column; 40% IPA (10 mM NH40H) in CO2; 75 g/min) to give the following two compounds: Enantiomer-1 (65-I): R$_t$ 2.1 min, (IB column 20 × 250 mm column; 40% IPA (10 mM NH$_4$OH) in CO$_2$; 75 g/min). $^1$H NMR (400 MHz, DMSO-d$_6$) δ ppm 12.56 (s, 1 H), 7.37 (d, J = 8.6 Hz, 1 H), 7.20 (d, J = 8.3 Hz, 1 H), 7.12 (d, J = 7.8 Hz, 1 H), 6.99 (s, 1 H), 6.88 (dd, J = 7.8, 1.5 Hz, 1 H), 4.47-4.59 (m, 1 H), 4.25-4.33 (m, 1 H), 4.12-4.25 (m, 2 H), 3.95 (d, J = 15.2 Hz, 1 H), 3.24-3.29 (m, 1 H), 3.15-3.23 (m, 1 H), 2.74-2.92 (m, 3 H), 2.35-2.43 (obs m, 1 H), 2.25 (s, 3 H), 2.20 (s, 3 H), 1.91 (s, 3 H), 1.87-1.98 (obs m, 1 H), 1.34 (d, J = 6.1 Hz, 3 H), 1.20 (d, J = 1.0 Hz, 3 H), 1.18 (d, J = 0.8 Hz, 3 H); MS (ESI+) m/z 481.4 (M + H)$^+$. Enantiomer-2 (65-J): R$_t$ 2.5 min (IB column 20 × 250 mm column; 40% IPA (10 mM NH$_4$OH) in CO$_2$; 75 g/min). $^1$H NMR (400 MHz, DMSO-d$_6$) δ ppm 12.56 (s, 1 H), 7.37 (d, J = 8.3 Hz, 1 H), 7.20 (d, J = 8.6 Hz, 1 H), 7.12 (d, J = 8.1 Hz, 1 H), 6.99 (s, 1 H), 6.88 (dd, J = 7.7, 1.6 Hz, 1 H), 4.47-4.61 (m, 1 H), 4.25-4.34 (m, 1 H), 4.11-4.25 (m, 2 H), 3.95 (d, J = 15.4 Hz, 1 H), 3.24-3.29 (m, 1 H), 3.15-3.24 (m, 1 H), 2.76-2.91 (m, 3 H), 2.36-2.43 (obs m, 1 H), 2.25 (s, 3 H), 2.20 (s, 3 H), 1.91 (s, 3 H), 1.87-1.98 (obs m, 1 H), 1.34 (d, J = 6.1 Hz, 3 H), 1.20 (d, J = 1.0 Hz, 3 H), 1.18 (d, J = 1.0 Hz, 3 H); MS (ESI+) m/z 481.4 (M + H)$^+$. |

-continued

| Structure | Chemical Name & Analytical Data |
|---|---|
| 65-K 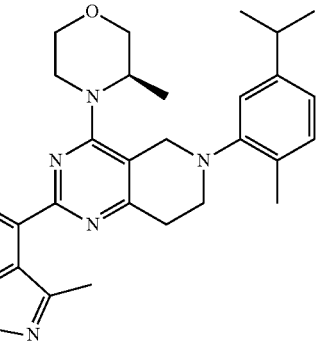 | (R)-4-(2-(3,5-dimethyl-1H-indazol-4-yl)-6-(5-isopropyl-2-methylphenyl)-5,6,7,8-tetrahydropyrido[4,3-d]pyrimidin-4-yl)-3-methylmorpholine. $^1$H NMR (400 MHz, DMSO-d$_6$) δ ppm 12.60 (s, 1 H), 7.39 (d, J = 8.3 Hz, 1 H), 7.22 (d, J = 8.8 Hz, 1 H), 7.11 (d, J = 8.1 Hz, 1 H), 6.95 (d, J = 1.5 Hz, 1 H), 6.87 (dd, J = 7.6, 1.5 Hz, 1 H), 4.04 (s, 2 H), 3.86-3.97 (m, 1 H), 3.80 (d, J = 11.1 Hz, 1 H), 3.62-3.71 (m, 1 H), 3.48-3.61 (m, 2 H), 3.35-3.41 (m, , 4 H), 2.95 (t, J = 5.8 Hz, 2 H), 2.76-2.89 (m, 1 H), 2.22 (s, 3 H), 2.18 (s, 3 H), 1.88 (s, 3 H), 1.17-1.19 (m, 9 H); MS (ESI+) m/z 511.5 (M + H); MS (ESI+) m/z 511.5 (M + H)$^+$. |
| 65-L 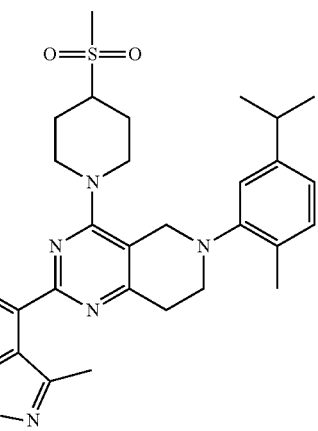 | 2-(3,5-dimethyl-1H-indazol-4-yl)-6-(5-isopropyl-2-methylphenyl)-4-(4-(methylsulfonyl)piperidin-1-yl)-5,6,7,8-tetrahydropyrido[4,3-d]pyrimidine. $^1$H NMR (400 MHz, DMSO-d$_6$) δ ppm 12.6 (s, 1H), 7.39 (d, J = 8.3 Hz, 1 H), 7.22 (d, J = 8.8 Hz, 1 H), 7.11 (d, J = 8.1 Hz, 1 H), 6.96 (d, J = 1.5 Hz, 1 H), 6.88 (dd, J = 7.7, 1.6 Hz, 1 H), 4.05 (s, 2 H), 3.99 (d, J = 13.4 Hz, 2 H), 3.37 (t, J = 5.9 Hz, 2 H), 2.98-3.05 (m, 2H), 2.92 (s, 3 H), 2.79-2.88 (m, 1 H), 2.78 (s, 2 H), 2.20 (d, J = 9.3 Hz, 6 H), 2.06 (d, J = 12.1 Hz, 2 H), 1.87 (s, 3 H), 1.67 (qd, J = 12.4, 3.7 Hz, 2 H), 1.19 (d, J = 6.8 Hz, 6 H); MS (ESI+) m/z 573.3 (M + H)$^+$. |

Example 66

66-A. 6-(3-Cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine

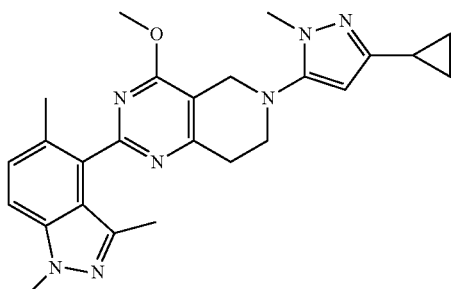

This compound was prepared in a similar manner as described in Example 34-B. MS (ESL) m/z 584.4 (M+H)$^+$.

66-B. 4-Chloro-6-(3-cyclopropyl-1-methyl-1H-pyrazol-5-yl)-2-(3,5-dimethyl-1H-indazol-4-yl)-5,6,7,8-tetrahydropyrido[4,3-d]pyrimidine

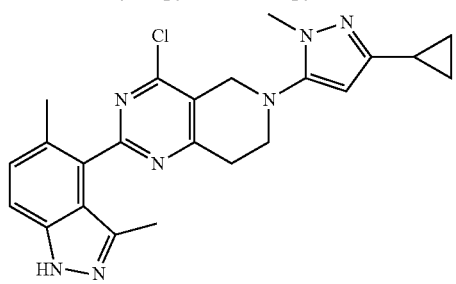 [SMILES: Cc1ccc2[nH]nc(C)c2c1-c1nc(Cl)c2c(n1)CCN(c1cc(C3CC3)nn1C)C2]

This compound was prepared in a similar manner as described in Example 63 from 6-(3-cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine. MS (ESI$^+$) m/z 434.3 (M+H)$^+$.

Example 67

67-A. 6-(3-Cyclopropyl-1-methyl-1H-pyrazol-5-yl)-4-(2,2-difluoroethoxy)-2-(3,5-dimethyl-1H-indazol-4-yl)-5,6,7,8-tetrahydropyrido[4,3-d]pyrimidine

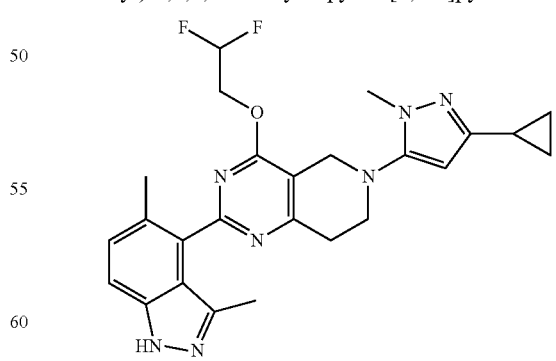

Title compound was prepared in a similar manner as described in Example 63-D from 4-chloro-6-(3-cyclopropyl-1-methyl-1H-pyrazol-5-yl)-2-(3,5-dimethyl-1H-indazol-4-yl)-5,6,7,8-tetrahydropyrido[4,3-d]pyrimidine. MS (ESI$^+$) m/z 480.3 (M+H)$^+$.

67-B. 6-(4-Chloro-3-cyclopropyl-1-methyl-1H-pyrazol-5-yl)-4-(2,2-difluoroethoxy)-2-(3,5-dimethyl-1H-indazol-4-yl)-5,6,7,8-tetrahydropyrido[4,3-d]pyrimidine

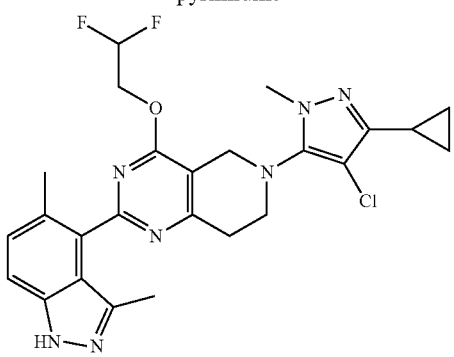

Title compound was prepared in a similar manner as described in Example 68-B from 6-(3-cyclopropyl-1-methyl-1H-pyrazol-5-yl)-4-(2,2-difluoroethoxy)-2-(3,5-dimethyl-1H-indazol-4-yl)-5,6,7,8-tetrahydropyrido[4,3-d]pyrimidine. $^1$H NMR (400 MHz, METHANOL-$d_4$) δ ppm 7.47 (d, J=8.59 Hz, 1H), 7.33 (d, J=8.72 Hz, 1H), 6.02-6.36 (m, 1H), 4.69 (dt, J=3.66, 14.21 Hz, 2H), 4.38 (s, 2H), 3.68 (s, 3H), 3.59 (t, J=5.68 Hz, 2H), 3.03 (t, J=5.68 Hz, 2H), 2.26 (s, 3H), 1.97 (s, 3H), 1.80-1.91 (m, 1H), 0.80-0.94 (m, 4H); MS (ESI$^+$) m/z 514.4 (M+H)$^+$.

Example 68

68-A. 6-(3-Cyclopropyl-1-methyl-1H-pyrazol-5-yl)-2-(3,5-dimethyl-1H-indazol-4-yl)-4-(3-ethoxyazetidin-1-yl)-5,6,7,8-tetrahydropyrido[4,3-d]pyrimidine

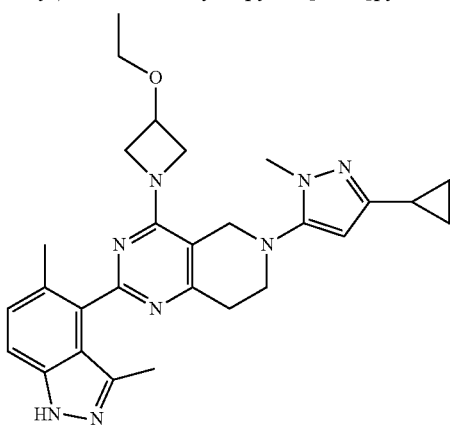

This compound was prepared in a similar manner as described in Example 65-A from 4-chloro-6-(3-cyclopropyl-1-methyl-1H-pyrazol-5-yl)-2-(3,5-dimethyl-1H-indazol-4-yl)-5,6,7,8-tetrahydropyrido[4,3-d]pyrimidine. MS (ESI$^+$) m/z 499.5 (M+H)$^+$.

68-B. 6-(4-Chloro-3-cyclopropyl-1-methyl-1H-pyrazol-5-yl)-2-(3,5-dimethyl-1H-indazol-4-yl)-4-(3-ethoxyazetidin-1-yl)-5,6,7,8-tetrahydropyrido[4,3-d]pyrimidine

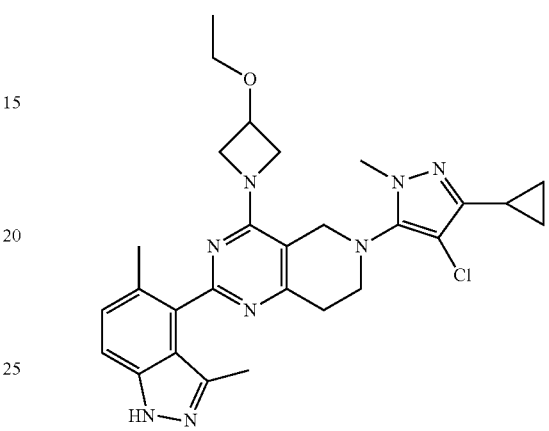

To a solution of 6-(3-cyclopropyl-1-methyl-1H-pyrazol-5-yl)-2-(3,5-dimethyl-1H-indazol-4-yl)-4-(3-ethoxyazetidin-1-yl)-5,6,7,8-tetrahydropyrido[4,3-d]pyrimidine (30 mg, 0.060 mmol) in DCM (2 mL) was added N-chlorosuccinimide (9.64 mg, 0.072 mmol) at room temperature. The mixture was stirred for 30 min then concentrated. The residue was purified by reverse phase HPLC (C18, 10-100% acetonitrile-H$_2$O with 0.1% NH$_4$OH) to give 6-(4-chloro-3-cyclopropyl-1-methyl-1H-pyrazol-5-yl)-2-(3,5-dimethyl-1H-indazol-4-yl)-4-(3-ethoxyazetidin-1-yl)-5,6,7,8-tetrahydropyrido[4,3-d]pyrimidine. $^1$H NMR (400 MHz, METHANOL-$d_4$) δ ppm 7.43 (d, J=8.46 Hz, 1H), 7.30 (d, J=8.59 Hz, 1H), 4.49 (dd, J=6.63, 9.41 Hz, 2H), 4.35-4.45 (m, 3H), 4.14 (dd, J=4.04, 10.36 Hz, 2H), 3.66 (s, 3H), 3.46-3.55 (m, 4H), 2.89 (t, J=5.68 Hz, 2H), 2.27 (s, 3H), 2.04 (s, 3H), 1.81-1.88 (m, 1H), 1.19 (t, J=7.01 Hz, 3H), 0.76-0.93 (m, 4H); MS (ESI$^+$) m/z 533.4 (M+H)$^+$.

The following compounds were prepared in a similar manner.

| Structure | Chemical Name & Analytical Data |
|---|---|
| 68-C <br>  | (R)-1-(6-(4-chloro-3-cyclopropyl-1-methyl-1H-pyrazol-5-yll)-2-(3,5-dimethyl-1H-indazol-4-yl)-5,6,7,8-tetrahydropyrido[4,3-d]pyrimidin-4-yl)-N,N-dimethylpyrrolidin-3-amine. $^1$H NMR (400 MHz, METHANOL-$d_4$) δ ppm 7.42 (d, J = 8.59 Hz, 1 H), 7.29 (d, J = 8.59 Hz, 1 H), 4.42 (d, J = 14.91 Hz, 1 H), 3.86-3.98 (m, 2 H), 3.75 (dt, J = 6.69, 10.55 Hz, 1 H), 3.65 (s, 3 H), 3.43-3.64 (m, 4 H), 2.94-3.06 (m, 1 H), 2.78-2.94 (m, 2 H), 2.30 (s, 6 H), 2.27 (s, 3 H), 2.16-2.25 (m, 1 H), 2.04 (s, 3 H), 1.77-1.91 (m, 2 H), 0.78-0.92 (m, 4 H); MS (ESI$^+$) m/z 546.5 (M + H)$^+$. |

Example 69

69-A. 6-(4-Chloro-3-cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine

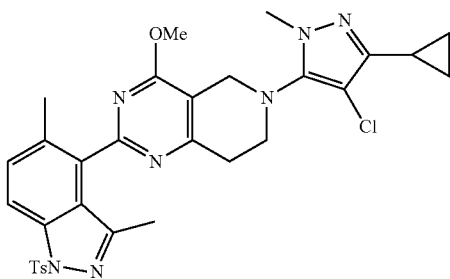 [SMILES: COc1nc(-c2c(C)ccc3c2c(C)nn3S(=O)(=O)c2ccc(C)cc2)nc2c1CN(c1c(Cl)c(C3CC3)nn1C)CC2]

To a solution of 6-(3-cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine (7.0 g, 11.99 mmol) in DCM (120 mL) was added N-chlorosuccinimide (1.76 g, 13.19 mmol) at room temperature, and the reaction mixture was stirred overnight. The mixture was then concentrated and the residue was directly purified by FCC (20-100% EtOAc/heptane) to provide 6-(4-chloro-3-cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine. MS (ESI⁺) m/z 619.9 (M+H)⁺.

69-B. 4-Chloro-6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidine and 65-C. 4-(4-Chloro-6-(4-chloro-3-cyclopropyl-1-methyl-1H-pyrazol-5-yl)-5,6,7,8-tetrahydropyrido[4,3-d]pyrimidin-2-yl)-3,5-dimethyl-1H-indazole-1-carbaldehyde

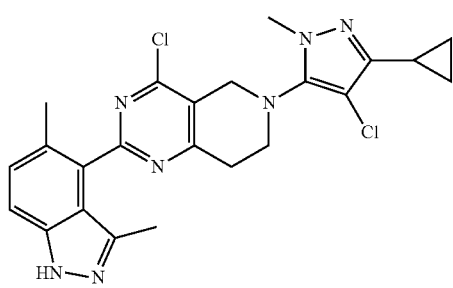

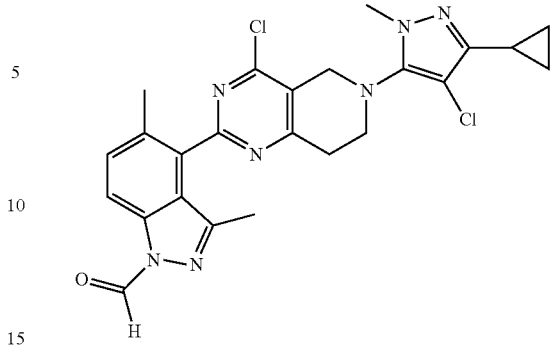

To a solution of 6-(4-chloro-3-cyclopropyl-1-methyl-1H-pyrazol-5-yl)-2-(3,5-dimethyl-1-tosyl-1H-indazol-4-yl)-4-methoxy-5,6,7,8-tetrahydropyrido[4,3-d]pyrimidine (5.4 g, 8.74 mmol) in EtOH (50 mL) was added concentrated HCl (21.2 mL, 699 mmol) at room temperature, and the reaction mixture was then heated to 100° C. for 24 h. The mixture was then cooled to room temperature and 200 mL of water was added. Then, solid NaOH was added until the pH of the solution reached pH 10. EtOAc was added to the reaction mixture and the resulting layers were separated and the aqueous layers were extracted with EtOAc (3×). The organic layers were combined and the combined organics were dried (Na₂SO₄), filtered and concentrated to a light yellow solid and used without further purification. The yellow solid (2.47 g, 5.49 mmol) was dissolved in DMF (55 mL) and Vilsmeier reagent (3.51 g, 27.4 mmol) was added to the mixture at room temperature, and the reaction mixture was stirred for 15 min. Then, the reaction mixture was poured into water, and Et₂O added. The layers were separated and the aqueous layer was extracted with Et₂O. The organics were combined and washed with 5% aqueous LiCl. The organics were then dried (Na₂SO₄), filtered and concentrated to a yellow oil. The residue was purified by FCC (20-100% EtOAc/heptane) to provide 4-chloro-6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidine and 4-(4-chloro-6-(4-chloro-3-cyclopropyl-1-methyl-1H-pyrazol-5-yl)-5,6,7,8-tetrahydropyrido[4,3-d]pyrimidin-2-yl)-3,5-dimethyl-1H-indazole-1-carbaldehyde, MS (ESI⁺) m/z 468.1 (M+H)⁺ and MS (ESI⁺) m/z 496.1 (M+H)⁺, respectively.

The following compounds were prepared from 4-chloro-6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidine or 4-(4-chloro-6-(4-chloro-3-cyclopropyl-1-methyl-1H-pyrazol-5-yl)-5,6,7,8-tetrahydropyrido[4,3-d]pyrimidin-2-yl)-3,5-dimethyl-1H-indazole-1-carbaldehyde in a similar manner to Example 65-A.

69-D
69-E

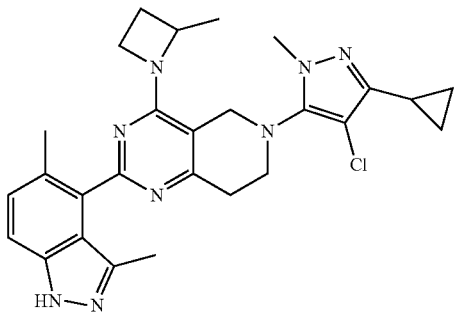 [SMILES: Cc1ccc2[nH]nc(C)c2c1-c1nc2c(c(N3CCC3C)n1)CN(c1c(Cl)c(C3CC3)nn1C)CC2]

The racemic 6-(4-chloro-3-cyclopropyl-1-methyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine was separated by chiral HPLC (LUX-2 column; 30% EtOH/heptanes; 1.0 mL/min) to give the following two compounds: Enantiomer-1 (69-D): $R_t$ 11.52 min, (LUX-2 4.6 × 250 mm column, 30% EtOH in heptane). $^1$H NMR (400 MHz, DMSO-$d_6$) δ ppm 12.54 (s, 1 H), 7.36 (d, 7 = 8.5 Hz, 1 H), 7.19 (d, J = 8.8 Hz, 1 H), 4.49-4.58 (m, 1 H), 4.45 (d, J = 15.4 Hz, 1 H), 4.22-4.31 (m, 1 H), 4.09-4.22 (m, 2 H), 3.60 (s, 3 H), 3.43-3.52 (m, 1 H), 2.74-2.91 (m, 2 H), 2.34-2.44 (m, 1 H), 2.19 (s, 3 H), 1.92 (s, 3 H), 1.85-1.90 (m, 1 H), 1.74-1.83 (m, 1 H), 1.33 (d, J = 6.2 Hz, 3 H), 0.82-0.90 (m, 2 H), 0.72-0.78 (m, 2 H); MS (ESI+) m/z 503.3 (M + H)$^+$. Enantiomer-2 (69-E): $R_t$ 15.86 min, (LUX-2 4.6 × 250 mm column, 30% EtOH in heptane). $^1$H NMR (400 MHz, DMSO-$d_6$) δ ppm 12.53 (s, 1 H), 7.36 (d, J = 8.5 Hz, 1 H), 7.19 (d, J = 8.6 Hz, 1 H), 4.49-4.57 (m, 1 H), 4.45 (d, J = 15.0 Hz, 1 H), 4.23-4.30 (m, 1 H), 4.10-4.22 (m, 2 H), 3.60 (s, 3 H), 3.43-3.52 (m, 1 H), 3.34-3.41 (m, 1 H), 2.75-2.90 (m, 2 H), 2.35-2.44 (m, 1 H), 2.19 (s, 3 H), 1.92 (s, 3 H), 1.84-1.90 (m, 1 H), 1.74-1.82 (m, 1 H), 1.33 (d, J = 6.1 Hz, 3 H), 0.81-0.88 (m, 2 H), 0.72-0.78 (m, 2 H); MS (ESI+) m/z 503.3 (M + H)$^+$

69-F
69-G

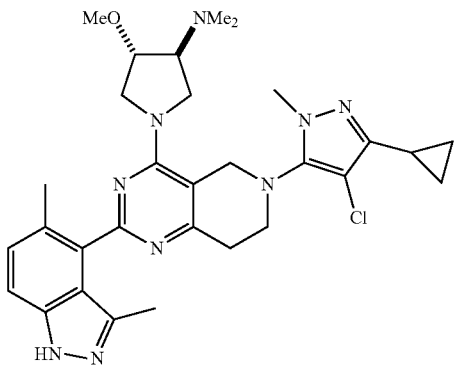 [SMILES: CO[C@H]1CN(c2nc(-c3c(C)ccc4[nH]nc(C)c34)nc3c2CN(c2c(Cl)c(C4CC4)nn2C)CC3)C[C@@H]1N(C)C]

The racemic (trans)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-4-methoxy-N,N-dimethylpyrrolidin-3-amine was separated by chiral HPLC (WhelkOD-H column; 15% EtOH (DEA)/heptanes; 1.0 mL/min) to give the following two compounds: Enantiomer-1 (69-F): $R_t$ 10.05 min, (WhelkOD-H 4.6 × 250 mm column, 15% EtOH (DEA) in heptane). $^1$H NMR (400 MHz, DMSO-$d_6$) δ ppm 12.56 (s, 1 H), 7.37 (d, J = 8.3 Hz, 1 H), 7.20 (d, J = 8.8 Hz, 1 H), 4.49-4.61 (m, 2 H), 3.87-3.94 (m, 2 H), 3.69-3.76 (m, 1 H), 3.52-3.63 (m, 5 H), 3.41-3.49 (m, 2 H), 3.26 (s, 3 H), 2.86 (t, J = 5.4 Hz, 2 H), 2.74-2.81 (m, 1 H), 2.20 (s, 3 H), 2.18 (s, 6 H), 1.92 (s, 3 H), 1.74-1.83 (m, 1 H), 0.82-0.88 (m, 2 H), 0.73-0.78 (m, 2 H); MS (ESI+) m/z 576.3 (M + H)$^+$. Enantiomer-2 (69-G): $R_t$ 14.69 min, (WhelkOD-H 4.6 × 250 mm column, 15% EtOH (DEA) in heptane). $^1$H NMR (400 MHz, DMSO-$d_6$) δ ppm 12.56 (s, 1 H), 7.37 (d, J = 8.3 Hz, 1 H), 7.20 (d, J = 8.6 Hz, 1 H), 4.48-4.59 (m, 2 H), 3.87-3.94 (m, 2 H), 3.69-3.76 (m, 1 H), 3.53-3.63 (m, 5 H), 3.42-3.48 (m, 2 H), 3.26 (s, 3 H), 2.83-2.90 (m, 2 H), 2.74-2.81 (m, 1 H), 2.20 (s, 3 H), 2.18 (s, 6 H), 1.92 (s, 3 H), 1.73-1.83 (m, 1 H), 0.81-0.89 (m, 1 H), 0.70-0.78 (m, 1 H); MS (ESI+) m/z 576.3 (M + H)$^+$.

69-H

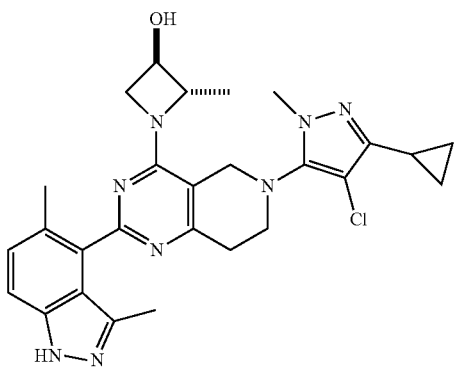 [SMILES: Cc1ccc2[nH]nc(C)c2c1-c1nc2c(c(N3C[C@@H](O)[C@@H]3C)n1)CN(c1c(Cl)c(C3CC3)nn1C)CC2]

racemic (trans)-1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-2-methylazetidin-3-ol. $^1$H NMR (400 MHz, DMSO-$d_6$) δ ppm 12.57 (s, 1 H), 7.38 (d, J = 8.3 Hz, 1 H), 7.20 (d, J = 8.6 Hz, 1 H), 5.64 (d, J = 6.3 Hz, 1 H), 4.51-4.39 (m, 2 H), 4.20-3.99 (m, 3 H), 3.84 (dd, J = 5.3, 8.1 Hz, 1 H), 3.60 (s, 3 H), 3.53-3.42 (m, 1 H), 3.41-3.35 (m, 1 H), 2.92-2.74 (m, 2 H), 2.19 (s, 3 H), 1.91 (s, 3 H), 1.83-1.73 (m, 1 H), 1.29 (d, J = 6.3 Hz, 3 H), 0.89-0.81 (m, 2 H), 0.78-0.71 (m, 2 H); MS (ESI+) m/z 519.1 (M + H)$^+$.

| | | |
|---|---|---|
| 69-I | 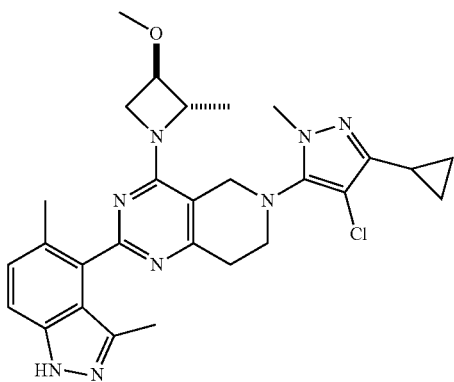 [SMILES: CO[C@@H]1CN(c2nc(-c3c(C)ccc4[nH]nc(C)c34)nc3c2CN(c2c(Cl)c(C4CC4)nn2C)CC3)[C@H]1C] | racemic 6-(4-chloro-3-cyclopropyl-1-methyl-1H-pyrazol-5-yl)-2-(3,5-dimethyl-1H-indazol-4-yl)-4-((trans)-methoxy-2-methylazetidin-1-yl)-5,6,7,8-tetrahydropyrido[4,3-d]pyrimidine. $^1$H NMR (400 MHz, DMSO-$d_6$) δ ppm 12.57 (s, 1 H), 7.37 (d, J = 8.3 Hz, 1 H), 7.20 (d, J = 8.6 Hz, 1 H), 4.52-4.41 (m, 2 H), 4.31-4.22 (m, 1 H), 4.10 (d, J = 15.2 Hz, 1 H), 3.96 (dd, J = 4.7, 8.5 Hz, 1 H), 3.84 (td, J = 4.5, 6.2 Hz, 1 H), 3.60 (s, 3 H), 3.53-3.44 (m, 1 H), 3.43-3.36 (m, 1 H), 3.23-3.18 (s, 3 H), 2.92-2.75 (m, 2 H), 2.19 (s, 3 H), 1.90 (s, 3 H), 1.75-1.82 (m, 1 H), 1.34 (d, J = 6.3 Hz, 3 H), 0.89-0.82 (m, 2 H), 0.78-0.71 (m, 2 H); MS (ESI+) m/z 533.1 (M + H). |
| 69-J | 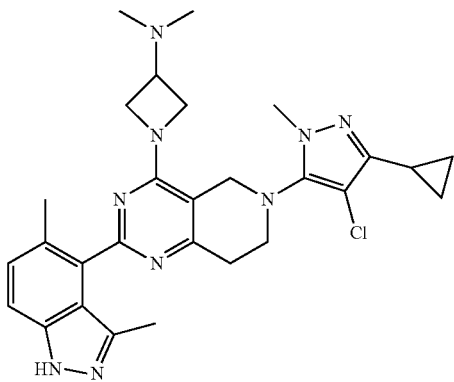 [SMILES: Cc1ccc2[nH]nc(C)c2c1-c1nc2c(c(N3CC(N(C)C)C3)n1)CN(c1c(Cl)c(C3CC3)nn1C)CC2] | 1-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-N,N-dimethylazetidin-3-amine. $^1$H NMR (400 MHz, DMSO-$d_6$) δ ppm 12.56 (s, 1 H) 7.37 (d, J = 8.59 Hz, 1 H) 7.19 (d, J = 8.59 Hz, 1 H) 4.33 (s, 2 H) 4.18 (t, J = 7.96 Hz, 2 H) 3.98 (dd, J = 8.84, 5.31 Hz, 2 H) 3.60 (s, 3 H) 3.40-3.49 (m, 2 H) 3.00-3.13 (m, 1 H) 2.81 (t, J = 5.43 Hz, 2 H) 2.19 (s, 3 H) 2.05 (s, 6 H) 1.92 (s, 3 H) 1.78 (tt, J = 8.34, 5.05 Hz, 1 H) 0.82-0.90 (m, 2 H) 0.72-0.79 (m, 2 H), MH (ESI+) m/z 532.5 (M + H)$^+$. |
| 69-K | 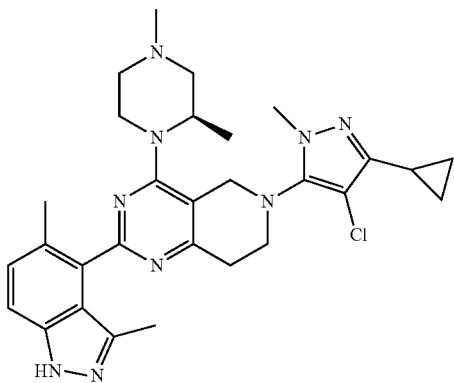 [SMILES: Cc1ccc2[nH]nc(C)c2c1-c1nc2c(c(N3CCN(C)C[C@H]3C)n1)CN(c1c(Cl)c(C3CC3)nn1C)CC2] | (R)-6-(4-chloro-3-cyclopropyl-1-methyl-1H-pyrazol-5-yl)-2-(3,5-dimethyl-1H-indazol-4-yl)-4-(2,4-dimethylpiperazin-1-yl)-5,6,7,8-tetrahydropyrido[4,3-d]pyrimidine. $^1$H NMR (400 MHz, DMSO-$d_6$) δ ppm 12.60 (s, 1 H), 7.39 (d, J = 8.34 Hz, 1 H), 7.21 (d, J = 8.59 Hz, 1 H), 4.27-4.36 (m, 1 H), 4.17-4.27 (m, 1 H), 3.95 (d, J = 6.32 Hz, 1 H), 3.57 (s, 3 H), 3.45-3.55 (m, 2 H), 3.39-3.44 (m, 1 H), 3.21-3.30 (m, 2 H), 2.93 (t, J = 5.94 Hz, 2 H), 2.18-2.25 (m, 2 H), 2.17 (s, 3 H), 2.14 (s, 3 H), 2.02-2.09 (m, 1 H), 1.89 (s, 3 H), 1.73-1.82 (m, 1 H), 1.18 (d, J = 6.57 Hz, 3 H), 0.82-0.88 (m, 2 H), 0.72-0.77 (m, 2 H); MS (ESI+) m/z 546.5 (M + H). |
| 69-L | 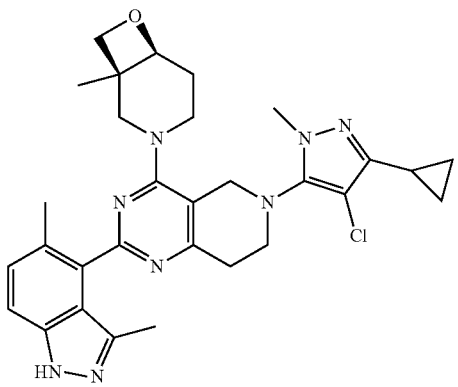 [SMILES: Cc1ccc2[nH]nc(C)c2c1-c1nc2c(c(N3CC[C@@H]4OC[C@]4(C)C3)n1)CN(c1c(Cl)c(C3CC3)nn1C)CC2] | racemic (1S*,6S*)-3-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-1-methyl-7-oxa-3-azabicyclo[4.2.0]octane. $^1$H NMR (400 MHz, CD$_3$CN) δ ppm 10.72 (br. S., 1 H), 7.40 (d, J = 8.34 Hz, 1 H), 7.24 (d, J = 8.59 Hz, 1 H), 4.59 (t, J = 3.16 Hz, 1 H), 4.55 (d, J = 14.91 Hz, 1 H), 4.44 (d, J = 6.06 Hz, 1 H), 4.28 (d, J = 14.91 Hz, 1 H), 4.23 (d, J = 5.81 Hz, 1 H), 3.92 (td, J = 11.81, 4.42 Hz, 1 H), 3.65 (d, J = 13.64 Hz, 1 H), 3.57-3.63 (m, 4 H), 3.57 (s, 3 H), 3.45-3.53 (m, 2 H), 3.30 (d, J = 13.39 Hz, 1 H), 2.89-3.06 (m, 2 H), 2.24 (s, 3 H), 1.98-2.06 (m, 1 H), 1.80-1.87 (m, 2 H), 1.21 (s, 3 H), 0.83-0.89 (m, 2 H), 0.75-0.80 (m, 2 H). MS (ESI+) m/z 559.5 (M + H)$^+$. |

| | | |
|---|---|---|
| 69-M | 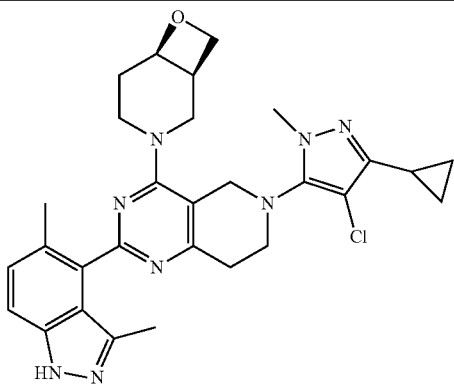 | racemic (cis)-3-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-7-oxa-3-azabicyclo[4.2.0]octane. $^1$H NMR (400 MHz, CD$_2$Cl$_2$) δ ppm 9.48 (br. s, 1 H), 7.26 (d, J = 8.59 Hz, 1 H), 7.16 (d, J = 9.09 Hz, 1 H), 4.93-5.00 (m, 1 H), 4.63 (dd, J = 6.32, 7.58 Hz, 1 H), 4.47 (d, J = 14.65 Hz, 1 H), 4.35 (t, J = 5.68 Hz, 1 H), 4.14 (d, J = 14.65 Hz, 1 H), 3.91-4.01 (m, 1 H), 3.54-3.71 (m, 3 H), 3.52 (s, 3 H), 3.47-3.51 (m, 1 H), 3.35-3.44 (m, 1 H), 3.07-3.17 (m, 1 H), 2.85-3.07 (m, 2 H), 2.20 (s, 3 H), 1.92 (s, 3 H), 1.86-1.91 (m, 2 H), 1.75 (tt, J = 5.34, 8.18 Hz, 1 H), 0.73-0.80 (m, 4 H); MS (ESI+) m/z 545.3 (M + H)$^+$. |

Example 70

70-A. N-((4-Chloro-2,6-dimethoxypyrimidin-5-yl)methyl)-3-cyclopropyl-1-ethyl-1H-pyrazol-5-amine

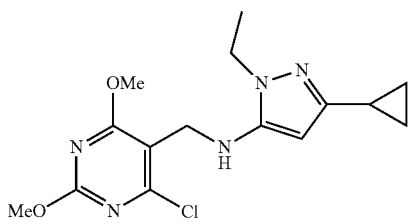 [SMILES: CCn1nc(C2CC2)cc1NCc1c(Cl)nc(OC)nc1OC]

To a precooled (−78° C.) solution of 4-chloro-2,6-dimethoxypyrimidine (7.0 g, 40.1 mmol) in THF (125 mL) under a nitrogen atmosphere was added n-BuLi (17.6 mL, 44.1 mmol, 2.5 M in heptane). The resulting solution was maintained at −78° C. for 0.5 h before DMF (7.45 mL, 96 mmol) was added. The resulting solution was stirred at −78° C. for 20 min and then removed from the dry ice bath and allowed to stir for 30 min. At that point the solution was returned to the dry ice bath and stirred for 20 min before being quenched by the slow addition of 30 mL of 6 N HCl. The flask was removed from the dry ice bath and allowed to warm to rt where it was left stirring for 2 h. The mixture was partially concentrated under reduced pressure and then was diluted with EtOAc and washed with saturated aqueous NaHCO$_3$. The aqueous layer was extracted further with EtOAc (2×300 mL) and the combined organic layers were then dried over sodium sulfate, filtered and concentrated. After drying on high vacuum the product 4-chloro-2,6-dimethoxypyrimidine-5-carbaldehyde was taken to the next step without further purification. MS (ESI$^+$) m/z 202.9 (M+H)$^+$.

A solution of 4-chloro-2,6-dimethoxypyrimidine-5-carbaldehyde (2.4 g, 11.8 mmol), and 3-cyclopropyl-1-ethyl-1H-pyrazol-5-amine (2.15 g, 14.2 mmol) in THF was heated at 50° C. for 3 h. The flask was then removed from the heating bath and cooled in an ice bath and EtOH (13 mL) was added followed by NaBH$_4$ (0.896 g, 23.7 mmol). The resulting mixture was left to gradually warm to rt and stir for 18 h. The excess NaBH$_4$ was quenched slowly with saturated aqueous NH$_4$Cl and diluted with EtOAc. The aqueous layer was further extracted with EtOAc (2×250 mL) and the combined organic layers were dried over sodium sulfate, filtered and concentrated. The residue was then purified via FCC (20-75% EtOAc/heptane) to give the title compound N-((4-chloro-2,6-dimethoxypyrimidin-5-yl)methyl)-3-cyclopropyl-1-ethyl-1H-pyrazol-5-amine. MS (ESI$^+$) m/z 338.0 (M+H)$^+$.

70-B. 6-(3-Cyclopropyl-1-ethyl-1H-pyrazol-5-yl)-2,4-dimethoxy-5,6,7,8-tetrahydropyrido[4,3-d]pyrimidine

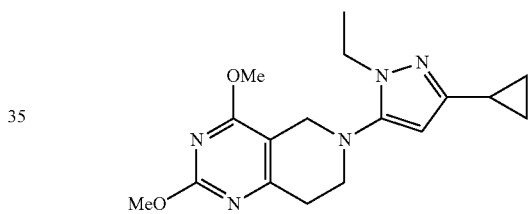

To a solution of N-((4-chloro-2,6-dimethoxypyrimidin-5-yl)methyl)-3-cyclopropyl-1-ethyl-1H-pyrazol-5-amine (2.42 g, 7.16 mmol) in DME (50 mL) and water (15 mL) was added 4,4,5,5-tetramethyl-2-vinyl-1,3,2-dioxaborolane (2.5 mL, 14.3 mmol), Pd(Ph$_3$P)$_4$ (0.828 g, 0.716 mmol) and sodium carbonate (2.47 g, 23.3 mmol). The mixture was sparged with argon for 15 min and then heated at reflux for 18 h. The mixture was then absorbed onto silica gel and dried under reduced pressure. After dry loading, the product was purified by FCC (10-75% EtOAc/heptane) to give 3-cyclopropyl-N-((2,4-dimethoxy-6-vinylpyrimidin-5-yl)methyl)-1-ethyl-1H-pyrazol-5-amine. MS (ESI$^+$) m/z 330.1 (M+H)$^+$.

3-Cyclopropyl-N-((2,4-dimethoxy-6-vinylpyrimidin-5-yl)methyl)-1-ethyl-1H-pyrazol-5-amine (2.10 g, 6.38 mmol) was taken up in AcOH (40 mL) and heated at 100° C. for 5 h. The solvent was removed under reduced pressure and the residue was taken up in EtOAc (150 mL) and washed with saturated aqueous NaHCO$_3$ (150 mL). The aqueous layer was further extracted with EtOAc (3×150 mL) and the combined organic layers were then dried over sodium sulfate, filtered and concentrated. The residue was then purified by FCC (40-80% EtOAc/heptane) to give the title compound 6-(3-cyclopropyl-1-ethyl-1H-pyrazol-5-yl)-2,4-dimethoxy-5,6,7,8-tetrahydropyrido[4,3-d]pyrimidine. MS (ESI$^+$) m/z 330.2 (M+H)$^+$.

70-C. 2,4-Dichloro-6-(3-cyclopropyl-1-ethyl-1H-pyrazol-5-yl)-5,6,7,8-tetrahydropyrido[4,3-d]pyrimidine

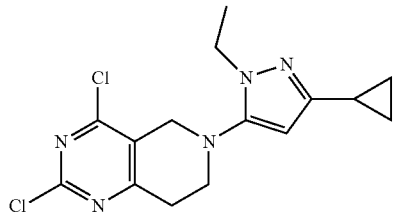 [SMILES: CCn1nc(C2CC2)cc1N1CCc2nc(Cl)nc(Cl)c2C1]

A solution of 6-(3-cyclopropyl-1-ethyl-1H-pyrazol-5-yl)-2,4-dimethoxy-5,6,7,8-tetrahydropyrido[4,3-d]pyrimidine (1.20 g, 3.64 mmol) in 12 N HCl (15 mL) and EtOH (15 mL) was heated at reflux for 8 h. The solvent was then removed under reduced pressure and the product 6-(3-cyclopropyl-1-ethyl-1H-pyrazol-5-yl)-5,6,7,8-tetrahydropyrido[4,3-d]pyrimidine-2,4-diol taken to the next step without further purification. MS (ESI$^+$) m/z 302.1 (M+H)$^+$.

To 6-(3-cyclopropyl-1-ethyl-1H-pyrazol-5-yl)-5,6,7,8-tetrahydropyrido[4,3-d]pyrimidine-2,4-diol (1.10 g, 3.64 mmol) was added POCl$_3$ (11.4 mL) and this mixture was heated to reflux. After 3.5 h the excess POCl$_3$ was removed by distillation. The residue was cooled to 0° C. and added slowly to a solution of MeOH (50 mL) and Et$_3$N (12 mL). The solution was stirred at rt for 15 min and evaporated. The residue was dissolved in DCM and washed with a solution of saturated aqueous NaHCO$_3$. The aqueous layer was further extracted with DCM (2×). The combined organic layers were dried with sodium sulfate, filtered and concentrated. The residue was purified by FCC (0-50% EtOAc/heptane) to provide the title compound 2,4-dichloro-6-(3-cyclopropyl-1-ethyl-1H-pyrazol-5-yl)-5,6,7,8-tetrahydropyrido[4,3-d]pyrimidine. MS (ESL) m/z 338.0 (M+H)$^+$.

70-D. (R)-4-(2-Chloro-6-(3-cyclopropyl-1-ethyl-1H-pyrazol-5-yl)-5,6,7,8-tetrahydropyrido[4,3-d]pyrimidin-4-yl)-3-methylmorpholine

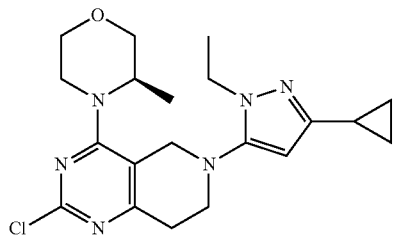 [SMILES: CCn1nc(C2CC2)cc1N1CCc2nc(Cl)nc(N3CCOC[C@H]3C)c2C1]

To a solution of 2,4-dichloro-6-(3-cyclopropyl-1-methyl-1H-pyrazol-5-yl)-5,6,7,8-tetrahydropyrido[4,3-d]pyrimidine (0.110 g, 0.325 mmol) in DMA (2.2 mL) was added (R)-3-methylmorpholine (49.3 mg, 0.488 mmol) and DIPEA (284 μL, 1.63 mmol). The mixture was heated at 110° C. for 2 h. Water was added and the aqueous phase was extracted with EtOAc (3×). The organic phases were combined, washed with brine (3×), dried with sodium sulfate, filtered and concentrated under reduce pressure. Purification by FCC (0-60% EtOAc/heptane) provided the title compound (R)-4-(2-chloro-6-(3-cyclopropyl-1-ethyl-1H-pyrazol-5-yl)-5,6,7,8-tetrahydropyrido[4,3-d]pyrimidin-4-yl)-3-methylmorpholine. MS (ESI$^+$) m/z 403.1 (M+H)$^+$.

70-E. (R)-4-(6-(3-Cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine

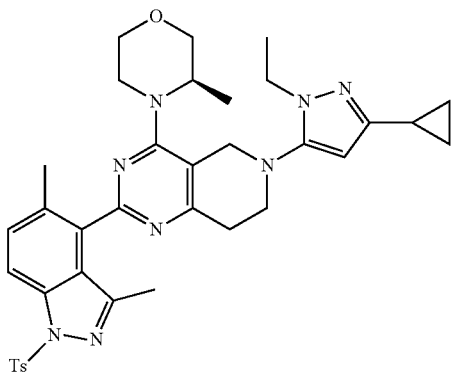 [SMILES: CCn1nc(C2CC2)cc1N1CCc2nc(-c3c(C)ccc4c3c(C)nn4S(=O)(=O)c3ccc(C)cc3)nc(N3CCOC[C@H]3C)c2C1]

To a solution of (R)-4-(2-chloro-6-(3-cyclopropyl-1-ethyl-1H-pyrazol-5-yl)-5,6,7,8-tetrahydropyrido[4,3-d]pyrimidin-4-yl)-3-methylmorpholine (0.116 g, 0.288 mmol) in DME (1.4 mL) was added 3,5-dimethyl-4-(4,4,5,5-tetramethyl-1,3,2-dioxaborolan-2-yl)-1-tosyl-1H-indazole (0.129 g, 0.302 mmol), Pd(Ph$_3$P)$_4$ (0.033 g, 0.029 mmol) and aqueous Na$_2$CO$_3$ (0.43 mL, 2 M). The mixture was sparged with argon and heated in a microwave reactor at 130° C. for 1 h 20 min. The mixture was filtered and concentrated under reduced pressure. Purification by FCC (40-100% EtOAc/heptane) provided the title compound (R)-4-(6-(3-cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine. MS (ESI$^+$) m/z 667.2 (M+H)$^+$.

70-F. (R)-4-(6-(4-Chloro-3-cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine

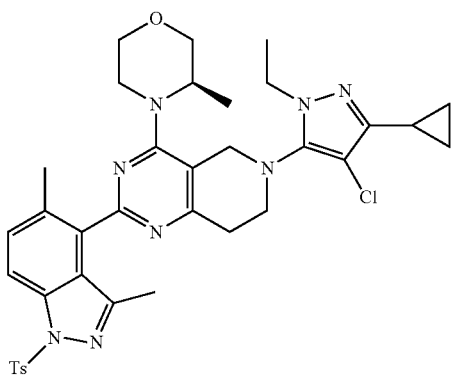 [SMILES: CCn1nc(C2CC2)c(Cl)c1N1CCc2nc(-c3c(C)ccc4c3c(C)nn4S(=O)(=O)c3ccc(C)cc3)nc(N3CCOC[C@H]3C)c2C1]

To a solution of (R)-4-(6-(3-cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine (0.075 g, 0.112 mmol) in DCM (2.2 mL) was added NCS (0.016 g, 0.124 mmol). After 1 h the solvent was removed under reduced pressure and the residue purified directly by FCC (20-80% EtOAc/heptanes) to provide the title compound (R)-4-(6-(4-chloro-3-cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine. MS (ESI$^+$) m/z 701.1 (M+H)$^+$.

70-G. (R)-4-(6-(4-Chloro-3-cyclopropyl-1-ethyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine

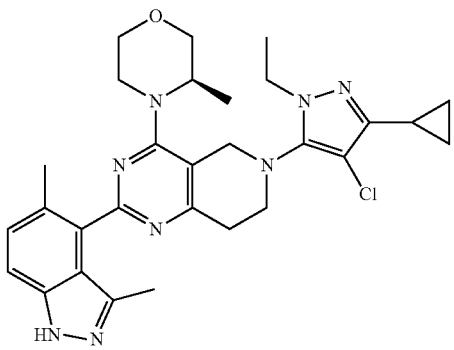 [SMILES: CCn1nc(C2CC2)c(Cl)c1N1CCc2nc(-c3c(C)ccc4[nH]nc(C)c34)nc(N3CCOC[C@H]3C)c2C1]

To a solution of (R)-4-(6-(4-chloro-3-cyclopropyl-1-ethyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine (0.081 g, 0.116 mmol) in MeOH (3 mL) was added $K_2CO_3$ (0.080 g, 0.578 mmol). The mixture was heated at 55° C. for 1 h 30 min. The methanol was removed under reduced pressure and the residue was taken up in water and the aqueous phase was neutralized to pH=6 (with 3 N HCl) and then extracted with EtOAc (3×). The combined organic phases were washed with brine, dried with sodium sulfate, filtered and concentrated under reduce pressure. Purification by FCC (0-4% MeOH/DCM) provided the title compound. $^1$H NMR (400 MHz, DMSO-$d_6$) δ ppm 12.58 (s, 1H), 7.39 (d, J=8.4 Hz, 1H), 7.21 (d, J=8.5 Hz, 1H), 4.33 (d, J=14.9 Hz, 1H), 4.18 (d, J=15.0 Hz, 1H), 3.90 (q, J=7.2 Hz, 2H), 3.87-3.82 (m, 1H), 3.81-3.74 (m, 1H), 3.67 (dd, J=11.2, 2.9 Hz, 1H), 3.63-3.42 (m, 4H), 3.39-3.31 (m, 1H), 3.00-2.93 (m, 2H), 2.18 (s, 3H), 1.88 (s, 3H), 1.84-1.73 (m, 1H), 1.29-1.21 (m, 3H), 1.14 (d, J=6.6 Hz, 3H), 0.89-0.81 (m, 4H), 0.80-0.73 (m, 1H); MS (ESI+) m/z 547.2 (M+H)$^+$.

The following compounds were prepared in a similar manner.

| | Structure | Chemical Name & Analytical Data |
|---|---|---|
| 70-H 70-I | (structure shown) | The racemic 6-(4-chloro-3-cyclopropyl-1-ethyl-1H-pyrazol-5-yl)-2-(3,5-dimethyl-1H-indazol-4-yl)-4-(2-methylazetidin-1-yl)-5,6,7,8-tetrahydropyrido[4,3-d]pyrimidine was separated by SFC MS-100; mobile phase: 5-55% MeOH + 5 mM NH$_4$OH in CO$_2$, 5 ml/min; column: CelLUX2, 5 μm, 4.6 × 100 mm) to provide the corresponding enantiomers. Enantiomer-1 (70-H): $^1$H NMR (400 MHz, DMSO-$d_6$) δ ppm 12.54 (s, 1 H) 7.36 (d, J = 8.46 Hz, 1 H) 7.19 (d, J = 8.59 Hz, 1 H) 4.48-4.56 (m, 1 H) 4.45 (d, J = 15.41 Hz, 1 H) 4.22-4.28 (m, 1 H) 4.17 (q, J = 7.58 Hz, 1 H) 4.09 (d, J = 15.41 Hz, 1 H) 3.91-3.98 (m, 2 H) 3.42-3.52 (m, 1 H) 3.36 (d, J = 7.20 Hz, 1 H) 2.75-2.92 (m, 2 H) 2.35-2.41 (m, 1 H) 2.19 (s, 3 H) 1.92 (s, 3 H) 1.84-1.90 (m, 1 H) 1.80 (tt, J = 8.32, 5.07 Hz, 1 H) 1.33 (d, J = 6.06 Hz, 3 H) 1.26 (t, J = 7.20 Hz, 3 H) 0.83-0.88 (m, 2 H) 0.74-0.79 (m, 2 H); MS (ESI$^+$) m/z 517.5 (M + H)$^+$; 98.6% ee (R$_t$ 3.67 min, instrument: SFC MS-100; mobile phase: 5-55% MeOH + 5 mM NH$_4$OH in CO$_2$, 5 ml/min; column: CelLUX2, 5 μm, 4.6 × 100 mm) Enantiomer-2 (70-1): $^1$H NMR (400 MHz, DMSO-$d_6$) δ ppm 12.54 (s, 1 H) 7.36 (d, J = 8.46 Hz, 1 H) 7.19 (d, J = 8.46 Hz, 1 H) 4.42-4.55 (m, 2 H) 4.22-4.29 (m, 1 H) 4.16 (q, J = 7.87 Hz, 1 H) 4.09 (d, J = 15.16 Hz, 1 H) 3.90-3.99 (m, 2 H) 3.43-3.51 (m, 1 H) 3.33-3.39 (m, 1 H) 2.74-2.92 (m, 2 H) 2.35-2.43 (m, 1 H) 2.19 (s, 3 H) 1.92 (s, 3 H) 1.85-1.90 (m, 1 H) 1.74-1.85 (m, 1 H) 1.33 (d, J = 6.19 Hz, 3 H) 1.26 (t, J = 7.20 Hz, 3 H) 0.82-0.90 (m, 2 H) 0.73-0.80 (m, 2 H); MS (ESI$^+$) m/z 517.4 (M + H)$^+$; 98% ee (R$_t$ 3.97 min, instrument: SFC MS-100; mobile phase: 5-55% MeOH + 5 mM NH$_4$OH in CO$_2$, 5 ml/min; column: CelLUX2, 5 μm, 4.6 × 100 mm) |
| 70-J | (structure shown) | (R-4-(6-(4-chloro-3-cyclopropyl-1-methyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine. $^1$H NMR (400 MHz, DMSO-$d_6$) δ ppm 12.61 (br. s., 1 H), 7.46-7.33 (m, 1 H), 7.22 (d, J = 8.6 Hz, 1 H), 4.42-4.29 (m, 1 H), 4.29-4.13 (m, 1 H), 3.85 (br. s., 1 H), 3.79 (d, J = 11.1 Hz, 1 H), 3.72-3.64 (m, 1 H), 3.62-3.52 (m, 6 H), 3.53-3.46 (m, 2 H), 2.95 (br. s., 2 H), 2.18 (s, 3 H), 1.89 (s, 3 H), 1.83-1.69 (m, 1 H), 1.15 (d, J = 6.3 Hz, 3 H), 0.90-0.81 (m, 2 H), 0.78-0.67 (m, 2 H); MS (ESI+) m/z 533.2 (M + H)$^+$. |

| Structure | Chemical Name & Analytical Data |
|---|---|
| 70-K 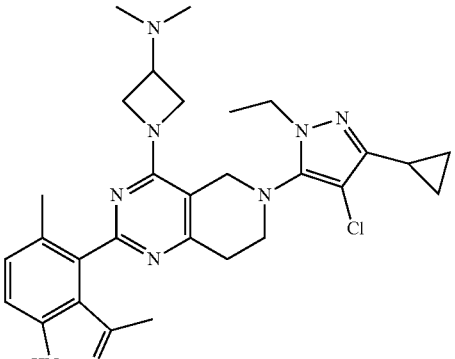 | 1-(6-(4-chloro-3-cyclopropyl-1-ethyl-1H-pyrazol-5-yl)-2-(3,5-dimethyl-1H-indazol-4-yl)-5,6,7,8-tetrahydropyrido[4,3-d]pyrimidin-4-yl)-N,N-dimethylazetidin-3-amine. $^1$H NMR (400 MHz, DMSO-d$_6$) δ ppm 12.56 (s, 1 H), 7.37 (d, J = 8.3 Hz, 1 H), 7.19 (d, J = 8.6 Hz, 1 H), 4.32 (s, 2 H), 4.18 (t, J = 8.0 Hz, 2 H), 4.03-3.88 (m, 4 H), 3.42 (t, J = 5.6 Hz, 2 H), 3.13-2.98 (m, 1 H), 2.82 (t, J = 5.4 Hz, 2 H), 2.19 (s, 3 H), 2.11-2.00 (m, 6 H), 1.92 (s, 3 H), 1.80 (tt, J = 5.1, 8.3 Hz, 1 H), 1.27 (t, J = 7.2 Hz, 3 H), 0.91-0.81 (m, 2 H), 0.81-0.70 (m, 2 H); MS (ESI+) m/z 546.2 (M + H)$^+$. |

Example 71

71-A. (R)-6-(3-Cyclopropyl-1-ethyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine

71-B. (R)-6-(3-Cyclopropyl-1-ethyl-4-fluoro-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine

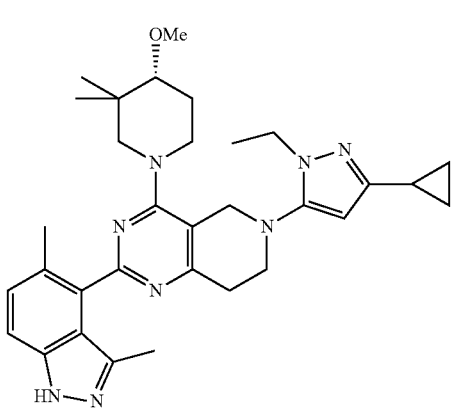 [SMILES: CCn1nc(C2CC2)cc1N1CCc2nc(-c3c(C)ccc4[nH]nc(C)c34)nc(N3CC[C@@H](OC)C(C)(C)C3)c2C1]

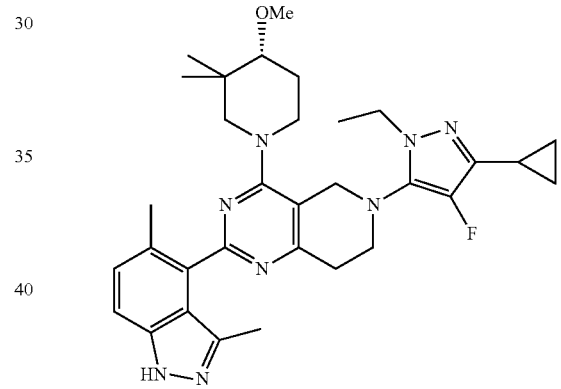

(R)-6-(3-Cyclopropyl-1-ethyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine, prepared in a similar method as described in Example 70-E, was treated in a similar method as described in Example 70-G. The residue was purified by FCC (3-6% MeOH/DCM) to give the title compound. $^1$H NMR (400 MHz, DMSO-d$_6$) δ ppm 12.60 (s, 1 H), 7.39 (d, J=8.3 Hz, 1 H), 7.21 (d, J=8.6 Hz, 1 H), 5.54 (s, 1 H), 4.16-4.04 (m, 1 H), 4.00-3.94 (m, 1 H), 3.89 (q, J=7.1 Hz, 2 H), 3.66 (d, J=13.6 Hz, 1 H), 3.27 (s, 3 H), 3.11-2.76 (m, 5 H), 2.18 (s, 3 H), 1.91 (dd, J=4.5, 9.1 Hz, 1 H), 1.87 (s, 3 H), 1.77 (tt, J=5.0, 8.4 Hz, 1 H), 1.54 (q, J=9.3 Hz, 1 H), 1.30 (t, J=7.2 Hz, 3 H), 0.93 (s, 3 H), 0.83 (s, 3 H), 0.82-0.77 (m, 2 H), 0.59-0.52 (m, 2 H); MS (ESI+) m/z 555.2 (M+H)$^+$.

(R)-6-(3-Cyclopropyl-1-ethyl-4-fluoro-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine was prepared in a similar method as described in Example 56-A. The residue was purified by FCC (3-6% MeOH/DCM) to give the title compound. $^1$H NMR (400 MHz, DMSO-d$_6$) δ ppm 12.59 (s, 1 H), 7.39 (d, J=8.6 Hz, 1 H), 7.21 (d, J=8.6 Hz, 1 H), 4.32-4.20 (m, 1 H), 4.19-4.07 (m, 1 H), 3.85 (q, J=7.1 Hz, 2 H), 3.67 (d, J=13.9 Hz, 1 H), 3.54-3.39 (m, 2 H), 3.28 (br. s., 3 H), 3.11-2.89 (m, 3 H), 2.84 (d, J=13.1 Hz, 1 H), 2.63-2.54 (m, 1 H), 2.23-2.13 (m, 3 H), 1.96-1.84 (m, 1 H), 1.83-1.72 (m, 1 H), 1.53 (d, J=9.6 Hz, 1 H), 1.25 (t, J=7.2 Hz, 3 H), 0.91 (s, 3 H), 0.87-0.82 (m, 2H), 0.82 (s, 3H), 0.76-0.68 (m, 2 H); MS (ESI+) m/z 573.5 (M+H)$^+$.

Example 72

(R)-6-(4-Chloro-3-cyclopropyl-1-ethyl-1H-pyrazol-5-yl)-2-(3,5-dimethyl-1H-indazol-4-yl)-4-(4-methoxy-3,3-dimethylpiperidin-1-yl)-5,6,7,8-tetrahydropyrido[4,3-d]pyrimidine

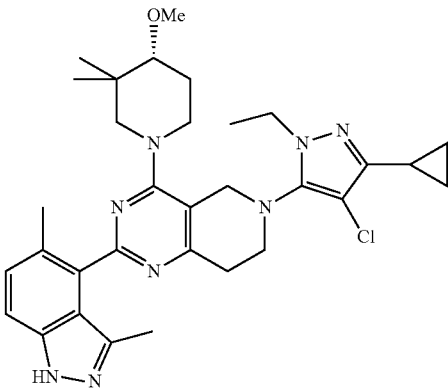 [SMILES: CCn1nc(C2CC2)c(Cl)c1N1CCc2nc(-c3c(C)ccc4[nH]nc(C)c34)nc(N3CC[C@@H](OC)C(C)(C)C3)c2C1]

The title compound was prepared from (R)-6-(3-cyclopropyl-1-ethyl-1H-pyrazol-5-yl)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine by removal of the tosyl protecting group as in Example 70-G followed by chlorination of the pyrazole in a similar manner as described in Example 70-F. The residue was purified by FCC (2-6% MeOH/DCM) to give the title compound. $^1$H NMR (400 MHz, DMSO-$d_6$) δ ppm 12.59 (s, 1 H), 7.39 (d, J=8.3 Hz, 1 H), 7.21 (d, J=8.8 Hz, 1 H), 4.44-4.30 (m, 1 H), 4.21 (d, J=14.7 Hz, 1 H), 3.89 (q, J=7.1 Hz, 2 H), 3.67 (d, J=12.9 Hz, 1 H), 3.58-3.40 (m, 2 H), 3.28 (br. s., 3 H), 3.13-2.78 (m, 5 H), 2.18 (s, 3 H), 1.89-1.93 (obs m. 1 H), 1.87 (s, 3 H), 1.76-1.83 (m, 1 H), 1.48-1.58 (m, 1 H), 1.23 (t, J=7.2 Hz, 3 H), 0.91 (s, 3 H), 0.89-0.83 (m, 2 H), 0.82 (s, 3 H), 0.80-0.71 (m, 2 H); MS (ESI+) m/z 589.2 (M+H).

Example 73

73-A. (R)-3-(Difluoromethyl)-5-(2-(3,5-dimethyl-1-tosyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbaldehyde

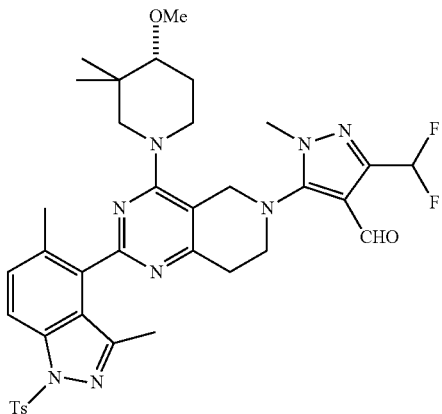 [SMILES: CO[C@@H]1CCN(c2nc(-c3c(C)ccc4c3c(C)nn4S(=O)(=O)c3ccc(C)cc3)nc3c2CN(c2c(C=O)c(C(F)F)nn2C)CC3)CC1(C)C]

A mixture of (R)-2-(3,5-dimethyl-1-tosyl-1H-indazol-4-yl)-4-(4-methoxy-3,3-dimethylpiperidin-1-yl)-5,6,7,8-tetrahydropyrido[4,3-d]pyrimidine (320 mg, 0.557 mmol), 5-chloro-3-(difluoromethyl)-1-methyl-1H-pyrazole-4-carbaldehyde (217 mg, 1.114 mmol) and cesium fluoride (169 mg, 1.114 mmol) in DMA (2.2 mL) was heated at 140° C. for 1.5 h. The reaction mixture was then partitioned between EtOAc and water. The aqueous layer was extracted with EtOAc (2×). The combined organics were washed with brine, dried over sodium sulfate, filtered, and concentrated. The residue was purified by FCC (EtOAc-heptane 10-100%) to provide (R)-3-(difluoromethyl)-5-(2-(3,5-dimethyl-1-tosyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbaldehyde. MS (ESI+) m/z 733.4 (M+H)$^+$.

The following compound was prepared in a similar manner.

73-B. 3-(Difluoromethyl)-5-(2-(3,5-dimethyl-1-tosyl-1H-indazol-4-yl)-4-methoxy-7,8-dihydropyrido[4,3-d]pyrimidin-6(5H)-yl)-1-methyl-1H-pyrazole-4-carbaldehyde

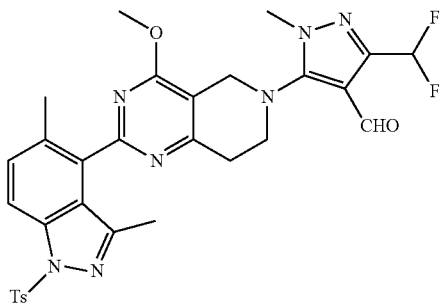 [SMILES: COc1nc(-c2c(C)ccc3c2c(C)nn3S(=O)(=O)c2ccc(C)cc2)nc2c1CN(c1c(C=O)c(C(F)F)nn1C)CC2]

MS (ESI+) m/z 622.2 (H+ H)$^+$.

Example 74

74-A. (R)-3-(Difluoromethyl)-5-(2-(3,5-dimethyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbonitrile

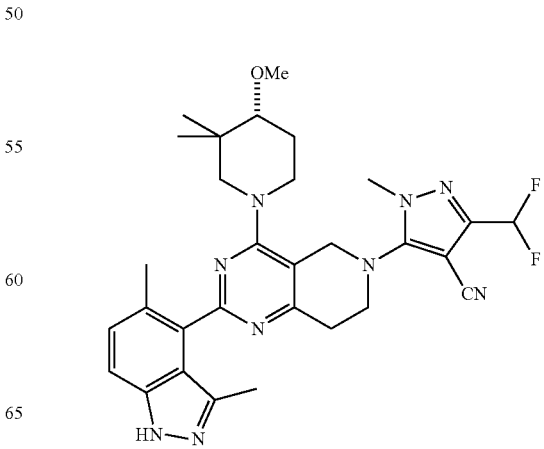

321

A vessel was charged with (R)-3-(difluoromethyl)-5-(2-(3,5-dimethyl-1-tosyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbaldehyde (54 mg, 0.074 mmol), hydroxylamine hydrochloride (77 mg, 1.105 mmol), and DMSO (491 μL). The vessel was capped and placed in a sand bath preheated to 100° C. and the reaction mixture was stirred at that temperature. After 2 h the mixture was diluted with methanol and transferred to a round-bottomed flask. Potassium carbonate was added, and the mixture stirred for 2 h at 60° C., then allowed to cool to room temperature. The mixture was then filtered through Celite and concentrated, redissolved in methanol, filtered through a syringe filter, and purified by HPLC (15-100% CH$_3$CN in water with 0.1% NH$_4$OH) to provide (R)-3-(difluoromethyl)-5-(2-(3,5-dimethyl-1H-indazol-4-yl)-4-(4-methoxy-3,3-dimethylpiperidin-1-yl)-7,8-dihydropyrido[4,3-d]pyrimidin-6(5H)-yl)-1-methyl-1H-pyrazole-4-carbonitrile. $^1$H NMR (400 MHz, CD$_3$OD) δ ppm 7.44 (d, J=8.6 Hz, 1 H), 7.31 (d, J=8.6 Hz, 1 H), 6.54-6.92 (m, 1 H), 4.64 (d, J=14.8 Hz, 1 H), 4.53 (d, J=14.8 Hz, 1 H), 3.85-3.95 (m, 1 H), 3.80 (s, 3 H), 3.67-3.75 (m, 2 H), 3.52 (dd, J=13.4, 1.3 Hz, 1 H), 3.37 (s, 3 H), 3.01-3.10 (m, 4 H), 2.26 (s, 3 H), 2.01 (s, 3 H), 1.97-2.06 (m, 1 H), 1.67-1.79 (m, 1 H), 1.01 (s, 3 H), 0.93 (s, 3 H); MS (ESI+) m/z 576.4 (M+H)$^+$.

Example 75

75-A. 6-(3-(Difluoromethyl)-1-methyl-1H-pyrazol-5-yl)-2-(3,5-dimethyl-1H-indazol-4-yl)-5,6,7,8-tetrahydropyrido[4,3-d]pyrimidin-4-ol

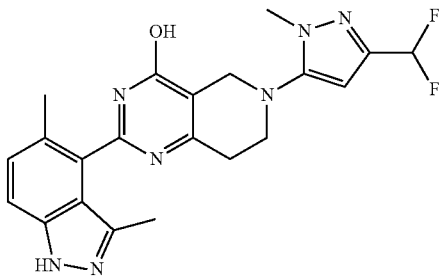 [SMILES: Cc1ccc2[nH]nc(C)c2c1-c1nc(O)c2c(n1)CCN(c1cc(C(F)F)nn1C)C2]

To a solution of 3-(difluoromethyl)-5-(2-(3,5-dimethyl-1-tosyl-1H-indazol-4-yl)-4-methoxy-7,8-dihydropyrido[4,3-d]pyrimidin-6(5H)-yl)-1-methyl-1H-pyrazole-4-carbaldehyde (0.8 g, 1.287 mmol) in ethanol (10.7 mL) was added concentrated HCl (2.1 mL). The microwave vessel was sealed and the mixture was irradiated at 125° C. for 1 h 20 min. The reaction mixture was then cooled to 0° C. and poured into ice water. Solid sodium bicarbonate was slowly added to neutralize the reaction mixture to pH=7, then the crude product was extracted with DCM (3×) and the combined organic layers were dried over sodium sulfate to provide 6-(3-(difluoromethyl)-1-methyl-1H-pyrazol-5-yl)-2-(3,5-dimethyl-1H-indazol-4-yl)-5,6,7,8-tetrahydropyrido[4,3-d]pyrimidin-4-ol, MS (ESI+) m/z 426.4 (M+H)$^+$.

322

75-B. 4-(4-Chloro-6-(3-(difluoromethyl)-1-methyl-1H-pyrazol-5-yl)-5,6,7,8-tetrahydropyrido[4,3-d]pyrimidin-2-yl)-3,5-dimethyl-1H-indazole-1-carbaldehyde

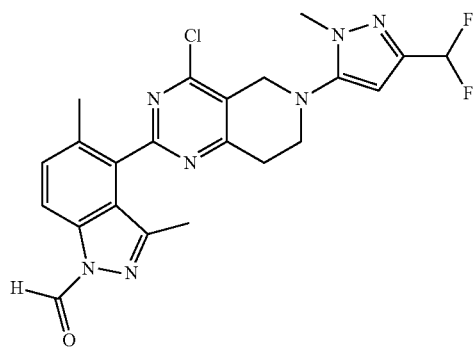 [SMILES: Cc1ccc2c(c(C)nn2C=O)c1-c1nc(Cl)c2c(n1)CCN(c1cc(C(F)F)nn1C)C2]

This compound was prepared in a similar manner to Example 69-C. MS (ESI+) m/z 472.1 (M+H)$^+$.

75-C. Racemic (1S*,6S*)-3-(6-(3-(Difluoromethyl)-1-methyl-1H-pyrazol-5-yl)-2-(3,5-dimethyl-1H-indazol-4-yl)-5,6,7,8-tetrahydropyrido[4,3-d]pyrimidin-4-yl)-1-methyl-7-oxa-3-azabicyclo[4.2.0]octane

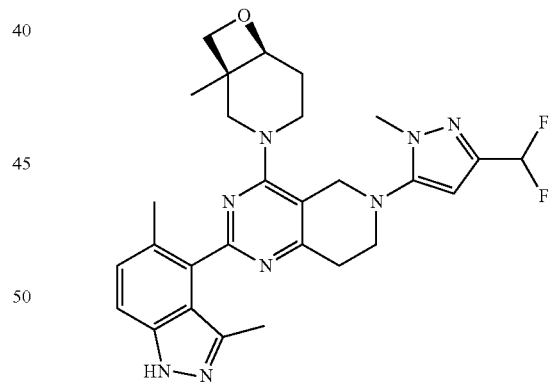

This compound was prepared in a similar manner to Example 65-A. $^1$H NMR (400 MHz, DMSO-d$_6$) δ ppm 12.58 (s, 1 H), 7.38 (d, J=8.59 Hz, 1 H), 7.20 (d, J=8.84 Hz, 1 H), 6.85 (t, J=55.00 Hz, 1 H), 6.17 (s, 1 H), 4.57 (t, J=3.03 Hz, 1 H), 4.30-4.39 (m, 2 H), 4.14-4.22 (m, 2 H), 3.92 (td, J=12.00, 4.29 Hz, 1 H), 3.73 (s, 3 H), 3.67 (d, J=13.39 Hz, 1 H), 3.49-3.57 (m, 1 H), 3.38-3.46 (m, 1 H), 3.29-3.36 (m, 2 H), 2.86-3.05 (m, 2 H), 2.19 (s, 3 H), 1.96-2.07 (m, 1 H), 1.89 (s, 3 H), 1.85-1.92 (m, 1 H), 1.20 (s, 3 H); MS (ESI+) m/z 535.2 (M+H)$^+$.

Example 76

76-A. (R)-4-(6-(3-Cyclopropyl-1-methyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine

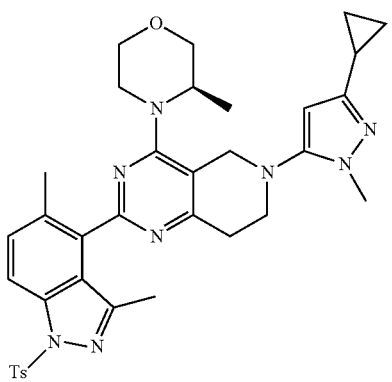 [SMILES: Cc1ccc(S(=O)(=O)n2nc(C)c3c(-c4nc5c(c(N6CCOC[C@H]6C)n4)CN(c4cc(C6CC6)nn4C)CC5)c(C)ccc32)cc1]

The title compound was prepared from (R)-4-(2-chloro-6-(3-cyclopropyl-1-methyl-1H-pyrazol-5-yl)-5,6,7,8-tetrahydropyrido[4,3-d]pyrimidin-4-yl)-3-methylmorpholine in a similar manner to Example 70-E. MS (ESI+) m/z 653.4 (M+H)+.

76-B. (R)-4-(6-(3-Cyclopropyl-4-fluoro-1-methyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine

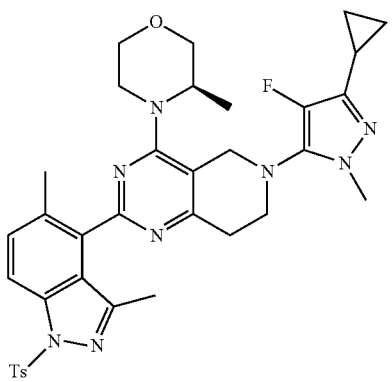 [SMILES: Cc1ccc(S(=O)(=O)n2nc(C)c3c(-c4nc5c(c(N6CCOC[C@H]6C)n4)CN(c4c(F)c(C6CC6)nn4C)CC5)c(C)ccc32)cc1]

The title compound was prepared from (R)-4-(6-(3-cyclopropyl-1-methyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine as described in Example 56-A. MS (ESI+) m/z 671.2 (M+H)+.

76-C. (R)-4-(6-(3-Cyclopropyl-4-fluoro-1-methyl-1H-pyrazol-5-yl)-2-(3,5-dimethyl-1H-indazol-4-yl)-5,6,7,8-tetrahydropyrido[4,3-d]pyrimidin-4-yl)-3-methylmorpholine

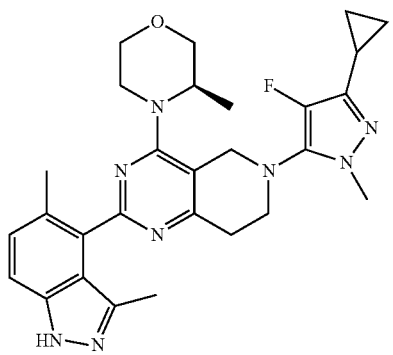 [SMILES: Cc1ccc2[nH]nc(C)c2c1-c1nc2c(c(N3CCOC[C@H]3C)n1)CN(c1c(F)c(C3CC3)nn1C)CC2]

The title compound was prepared from (R)-4-(6-(3-cyclopropyl-4-fluoro-1-methyl-1H-pyrazol-5-yl)-2-(3,5-dimethyl-1-tosyl-1H-indazol-4-yl)-5,6,7,8-tetrahydropyrido[4,3-d]pyrimidin-4-yl)-3-methylmorpholine as described in Example 55-G. $^1$H NMR (400 MHz, CD$_2$Cl$_2$) δ ppm 9.70 (br. s., 1H), 7.29 (d, J=8.59 Hz, 1H), 7.18 (d, J=8.34 Hz, 1H), 4.08 (td, J=13.89, 15.41 Hz, 2H), 3.71-3.82 (m, 2H), 3.67 (dd, J=2.91, 11.24 Hz, 1H), 3.52-3.60 (m, 2H), 3.51 (s, 3H), 3.25-3.47 (m, 4H), 2.87-3.12 (m, 2H), 2.15 (br. s., 3H), 1.87 (br. s., 3H), 1.72 (tt, J=5.40, 8.24 Hz, 1H), 1.15 (d, J=6.57 Hz, 3H), 0.63-0.85 (m, 4H). MS (ESI+) m/z 517.3 (M+H)+.

Example 77

77-A. (R)-6-(3-Cyclopropyl-1-methyl-1H-pyrazol-5-yl)-2-(3,5-dimethyl-1H-indazol-4-yl)-4-(2-methylpiperidin-1-yl)-5,6,7,8-tetrahydropyrido[4,3-d]pyrimidine

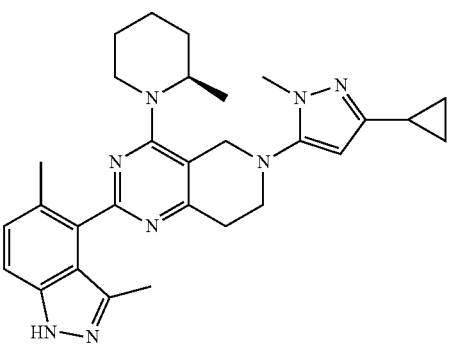 [SMILES: Cc1ccc2[nH]nc(C)c2c1-c1nc2c(c(N3CCCC[C@H]3C)n1)CN(c1cc(C3CC3)nn1C)CC2]

(R)-6-(3-Cyclopropyl-1-methyl-1H-pyrazol-5-yl)-2-(3,5-dimethyl-1-tosyl-1H-indazol-4-yl)-4-(2-methylpiperidin-1-yl)-5,6,7,8-tetrahydropyrido[4,3-d]pyrimidine, prepared in a similar method as described in Example 55-E, was treated in a similar method as described in Example 55-G. The residue was purified by FCC (1-7% MeOH/DCM) to give the title compound. $^1$H NMR (400 MHz, DMSO-d$_6$) δ ppm 12.59 (s, 1 H), 7.45-7.31 (m, 1 H), 7.21 (d, J=8.8 Hz, 1 H), 5.55 (s, 1 H), 4.10-3.88 (m, 3 H), 3.57 (s, 3 H), 3.51-3.40 (m, 1 H), 3.14 (t, J=11.2 Hz, 1 H), 2.93 (t, J=5.9 Hz, 2 H), 2.17 (s, 3 H), 1.87 (s, 3 H), 1.80-1.45 (m, 8 H), 1.16 (d, J=6.8 Hz, 3 H), 0.84-0.73 (m, 2 H), 0.61-0.50 (m, 2 H)); MS (ESI+) m/z 497.3 (M+H).

77-B. (R)-6-(4-Chloro-3-cyclopropyl-1-methyl-1H-pyrazol-5-yl)-2-(3,5-dimethyl-1H-indazol-4-yl)-4-(2-methylpiperidin-1-yl)-5,6,7,8-tetrahydropyrido[4,3-d]pyrimidine

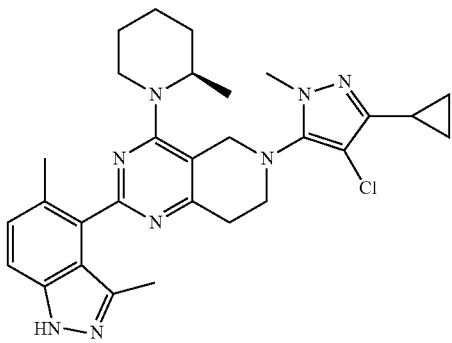 [SMILES: Cc1ccc2[nH]nc(C)c2c1-c1nc2c(c(N3CCCC[C@H]3C)n1)CN(c1c(Cl)c(C3CC3)nn1C)CC2]

(R)-6-(4-Chloro-3-cyclopropyl-1-methyl-1H-pyrazol-5-yl)-2-(3,5-dimethyl-1H-indazol-4-yl)-4-(2-methylpiperidin-1-yl)-5,6,7,8-tetrahydropyrido[4,3-d]pyrimidine was prepared in a similar method as described in Example 55-F. The residue was purified by FCC (1-7% MeOH/DCM) to give the title compound. $^1$H NMR (400 MHz, DMSO-$d_6$) δ ppm 12.59 (s, 1 H), 7.39 (d, J=8.6 Hz, 1 H), 7.21 (d, J=8.6 Hz, 1 H), 4.38-4.16 (m, 2 H), 3.99 (d, J=6.6 Hz, 1 H), 3.57 (s, 3 H), 3.54-3.49 (m, 2 H), 3.45-3.37 (m, 1 H), 3.14 (t, J=10.7 Hz, 1 H), 2.93 (t, J=5.8 Hz, 2 H), 2.17 (s, 3 H), 1.89 (s, 3 H), 1.83-1.74 (m, 1 H), 1.44-1.73 (m, 6 H), 1.15 (d, J=6.6 Hz, 3 H), 0.88-0.82 (m, 2 H), 0.78-0.72 (m, 2 H); MS (ESI+) m/z 531.3 (M+H).

Example 78

Alternate synthesis of Example 55-G

General Synthetic Scheme:

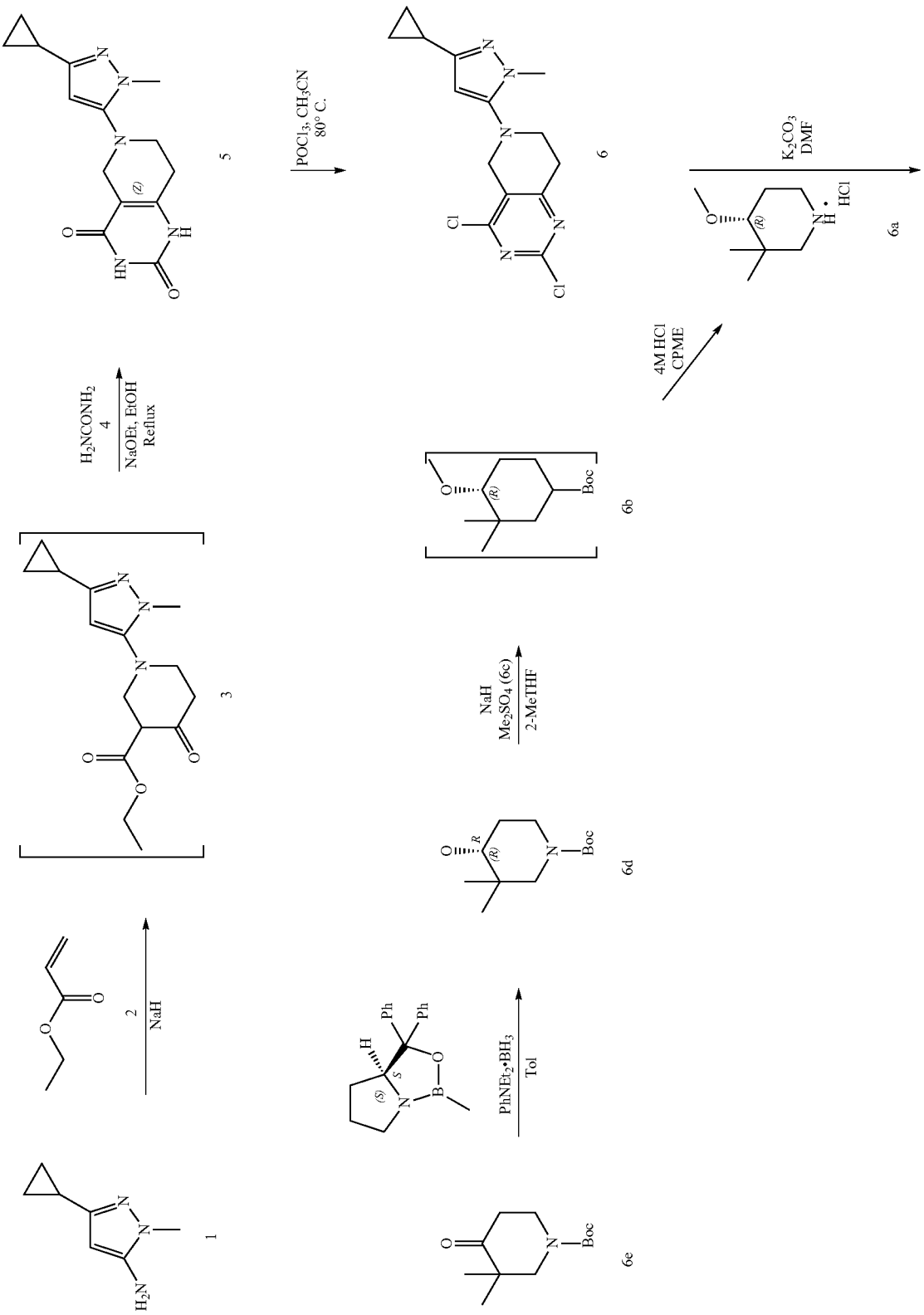

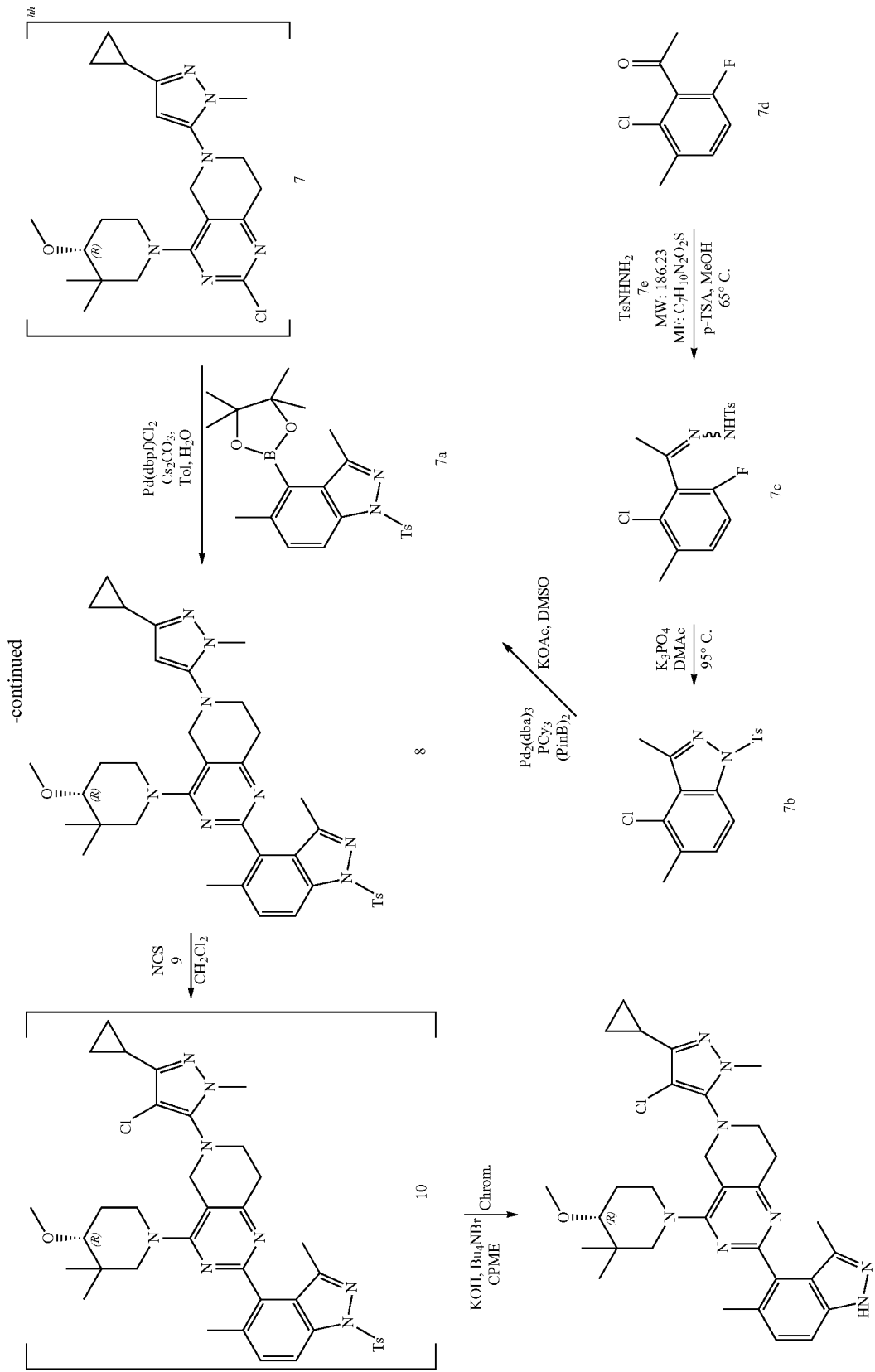

Step 1+2→[3]

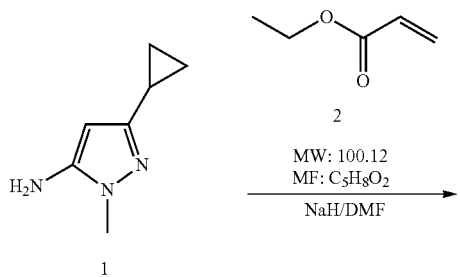

Into a nitrogen-purged 22 L 4-necked RBF, 500 g of 5-aminopyrazol 1, 3500 mL of DMF was added and cooled to 2° C. 160 g of 60% NaH in mineral oil (1.1 eq) was added in portions. The reaction was stirred at 0-5° C. for 60 min and a suspension formed. 870 mL of ethylacrylate (2.2 eq) at 5-20° C. was added to the reaction over 20 minutes. The reaction was stirred at 0-20° C. for 1.5 h followed by addition of 260 g of HOAc, 5000 mL of EtOAc, 5000 mL 5% $Na_2CO_3$ solution, and 5000 mL of water. Two layers formed, were separated and the aqueous layer was extracted twice with 2000 mL of EtOAc. All of the EtOAc layers were combined and held at room temperature overnight. The combined EtOAc layers were passed through a silica gel pad and washed with 1500 mL EtOAc. The filtrate and wash were combined, concentrated to minimal volume as a brown oily residue and purged with nitrogen at room temperature overnight. 1268 g of thick oil product was obtained with HPLC purity (254 nm): 35.08%. Yield: 119.7% (no purity correction).

Step [3]+4→5

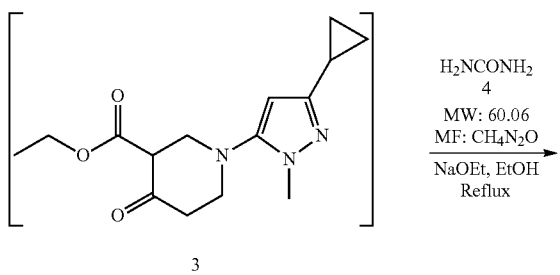

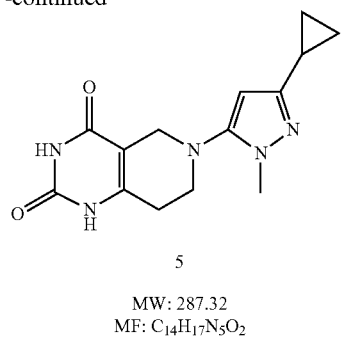

Into a 22 L 4-necked RBF 498 g of urea 4, 1268 g of crude ketoester 3, 5000 mL of absolute EtOH and 3800 g of 21% NaOEt/EtOH solution was added. The mixture was heated to 80° C. and stirred at 80° C. for 30 h. The mixture was then allowed to cool to room temperature and stirred overnight. The mixture was then cooled to 0-5° C. and 733 g of HOAc was added via addition funnel over 40 min at 0-10° C. The mixture was then split into 4 equal parts. Each part was concentrated at 50° C./30 mbar to a thick slurry. To each part 1000 mL of water and 500 mL DCM was added. The four parts were recombined the pH of the aqueous layer was adjusted to 8.8 by adding 50% NaOH solution. Solids formed and 2.0 L of water and 1.0 L of DCM were added. The whole batch was filtered and washed with 500 mL EtOAc. The filtered material was dried at 55° C./30 mbar over the weekend. 65.3 g of beige solid was obtained. HPLC purity (254 nm): 95.58%. $^1$H NMR (DMSO-$d_6$): consistent with the molecular structure. LC-MS: ES+288.0.

The filtrate was filtered again, washed with water and the aqueous layer was discarded. 3.0 g of beige solid was isolate on the filter. The DCM filtrate and EtOAc wash was concentrated under vacuum, and the residue was dissolved in 1.2 L of 2.0 M HCl solution. 1.0 L TBME was added and the pH was adjusted to 8.8 by adding 200 g of 50% NaOH solution. The mixture was allowed to stir for 60 minutes at 38° C. and then filtered. The pH of the aqueous layer was adjusted to 3.0 by adding concentrated HCl solution. The pH was adjusted to −0.24 with concentrated HCl solution and 500 mL TBME was added. The layers were separated and the aqueous layer was washed with 1.0 L TBME. The pH was adjusted to 7.5 with 50% NaOH solution and held at room temperature overnight. The aqueous layer (pH 7.0-7.5) was then extracted three times with 1.0 L of 2-Me THF. The aqueous layer was discarded and the 2-Me THF layers were combined and then concentrated at 40° C./30 mbar. The 2-Me THF is azeotropically removed with iPOAc. Bottom is thick, supernatant has negligible amount of product. Decant the supernatant and rinse the residue with iPOAc. Discard the iPOAc supernatant. Into the residue, add 500 mL THF. Heat, a suspension is formed. Add 500 mL iPOAc. Concentrate to 800 mL. Cool to rt and stir at rt for overnight. Filter, wash with iPOAc. Dry at 65° C./30 mbar overnight. 58.0 g of beige solid was obtained. HPLC (254 nm): 95.1%. $^1$H NMR (DMSO-$d_6$): consistent with the molecular structure. Combined yield from amine 1 (two crops): 12.6%.

Step 5→6

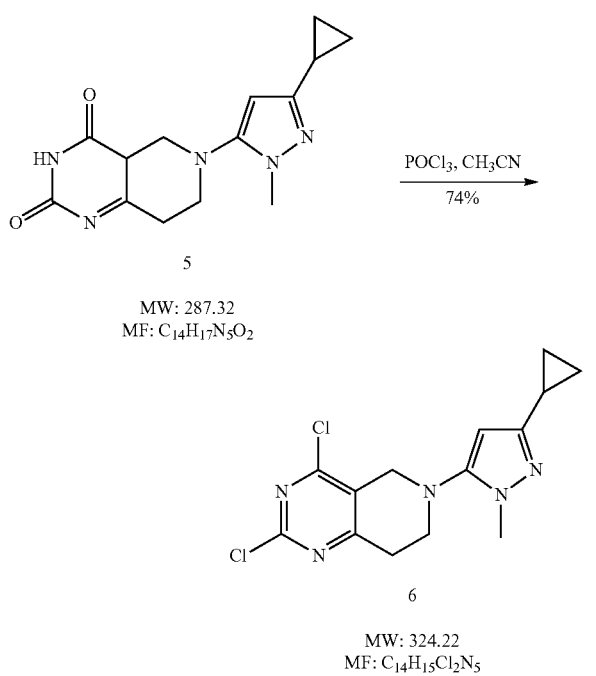

POCl₃ (176 mL) was slowly added to a suspension of 5 (200 g, 97.7% purity) and MeCN (1.05 L) in a 5-L flask at 77 to 80° C. over 30 min (slightly exothermic reaction, HCl gas evolution). The contents were gently refluxed at 80-81° C. for 16 h to obtain an orange-brown suspension and then PSC was checked (by HPLC, <2% S.M.). H₂O (600 mL) was added slowly into flask at 5-10° C. over 30 min (exothermic reaction) and then the contents were stirred at 5-10° C. for 2 h. i-PrOAc (3.47 L) was added into pot over 2 min, and a solution of Na₂CO₃ (504 g) in H₂O (6.2 L) was then added slowly into the mixture at 5-10° C. over 1 h (CO₂ gas evolution). The mixture was maintained at 10 to 20° C. overnight (final pH 5.5-6.0). The bottom aqueous layer was discarded. The top organic layer was washed once with H₂O (1.2 L) and once with saturated NaCl solution (1.2 L), dried over anhydrous MgSO₄, filtered, and then concentrated (55° C., 35 mbar) to a thick suspension. TBME (800 mL) was added into flask and the suspension was heated at 45° C. for 30 min and heptanes (800 mL) were then added. The contents were cooled to 15° C. over 30 min and then the solids were filtered (fast filtration). The filter cake was dried in a vacuum oven (55-60° C., 35 mbar) for 16 h to give 6 (164 g) as a yellow solid. HPLC Purity (254 nm) of 6: 99.53% ¹H NMR Analysis (CDCl₃): Consistent with the structure. Theoretical Yield= [(200×0.977)/287.32]×324.22=220.6 g. Actual Yield=(164× 0.9953)/220.6=74.0%

Step 6e→6d

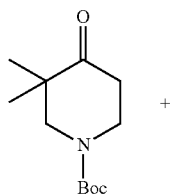

+

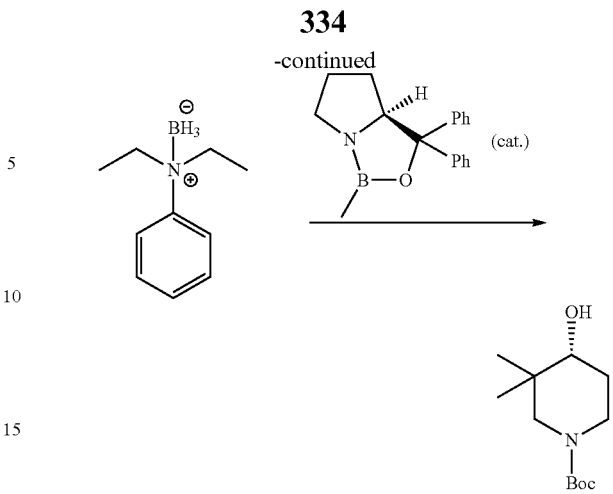

Into a nitrogen-purged 4-necked 12 L RBF 38.9 g of S-Me CBS catalyst 2.35 L of anhydrous toluene and 471 g of BH₃.diethylaniline (DEAB) complex was added. A solution of 649.2 g of ketone in 3.90 L of anhydrous toluene was prepared in a 5 L RBF by stirring at rt. The mixture in the 12 L RBF was heated to 35° C. and the ketone solution was added at 35-42° C. in 55 min. The mixture was stirred for 30 minutes at 40-30° C. The clear mixture is cooled to 10-15° C. and 4.06 L of 1.0 M HCl solution was added over 10 minutes while controlling temp at 15-25° C. The mixture is stirred for 30 minutes at 20° C. for 30 min. The layers are separated and the organic phase is washed with 4.0 L of 1.0 M HCl solution, 2.0 L 1.0 N NaHCO₃ solution and twice with 2.0 L of water. The combined organic layers were concentrated at 50° C./30 mbar to yield 657 g of an oily product. Into the 657 g of crude oily product 1.0 L of heptane was added at 50° C. The mixture was cooled to 0-10° C., seeded and stirred at 0-10° C. for 1 h. The mixture was filtered and washed with 500 mL cold heptane. The isolated solids were dried at 35° C./30 mbar over the weekend. 542.1 g of white solid was obtained. HPLC purity (210 nm): 94.7%. Chiral HPLC (205 nm): 99.8% ee. ¹H NMR (DMSO-d₆): clean and consistent with the molecular structure. ML Chiral HPLC (205 nm): 90.8% ee.

The mother liquor was concentrated to remove all volatiles at 50° C./30 mbar. 350 g of heptane was added and the mixture was cooled to 0-5° C., seeded and stirred at 0-5° C. for 2 h. The mixture was filtered and the solids were washed with cold heptane. The collected solids were dried at 35° C./30 mbar overnight. 39.8 g of white solid was obtained. HPLC purity (210 nm): 96.4%. Chiral HPLC (205 nm): 98.8% ee. ¹H NMR (DMSO-d₆): clean and consistent with the molecular structure.

Discard the ML Chiral HPLC (205 nm): 73.6% ee. Overall yield: 90.4%

Step 6d+6c→[6b]

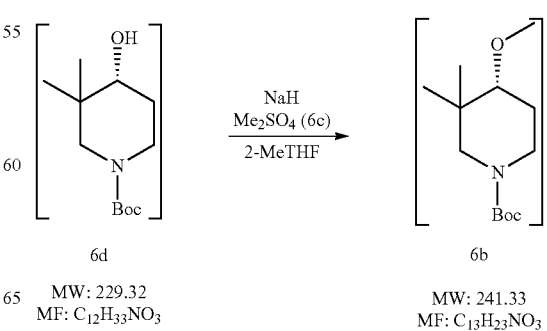

To a 12 L nitrogen purged RBF was added 572 g of chiral alcohol 6d and 4900 mL of 2-Me THF. The mixture was cooled to 0-10° C. and 199.5 g of 60% NaH in mineral oil was added in portions. The mixture was stirred at 0-10° C. for 30 minutes and 566.3 g of $Me_2SO_4$ was added in portions at 0-10° C. 5.3 mL of water was added and the suspension was stirred at 5-20° C. for 16 hours. The mixture was cooled to 0-5° C. and 570 mL of water and 1140 mL 20% $K_2CO_3$ solution were added dropwise. Stir at rt for 2 h. Upon standing the layers were separated and the organic layer was washed twice with 1100 mL 20% NaCl solution and once with 1000 mL water. The organic layer was concentrated at 50° C./30 mbar yielding 858.7 g of an oily residue. Overall yield: 121%.

Step [6b]→6a

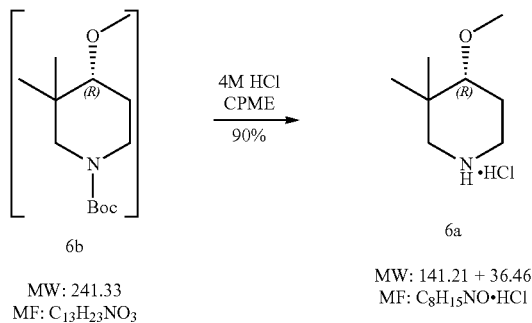

6b
MW: 241.33
MF: $C_{13}H_{23}NO_3$

6a
MW: 141.21 + 36.46
MF: $C_8H_{15}NO$•HCl

To a 12 L nitrogen purged RBF was added 848.7 g of crude Boc-amine 6b and 800 mL CPME. At room temperature 2.66 L 4.0 M HCl/CPME was added and the mixture was allowed to stir at room temperature for 18 hours. 4000 mL of heptane was added and the mixture was allowed to stir at room temperature for 2 hours. The mixture was filtered and washed with 1000 mL heptanes. The isolated solid was dried at 35° C./30 mbar over the weekend. 514.6 g of white solid 6a was obtained. Yield: 82.1%.

$^1$H NMR ($D_2O$): consistent with the molecular structure.

Step 6+6a→[7]

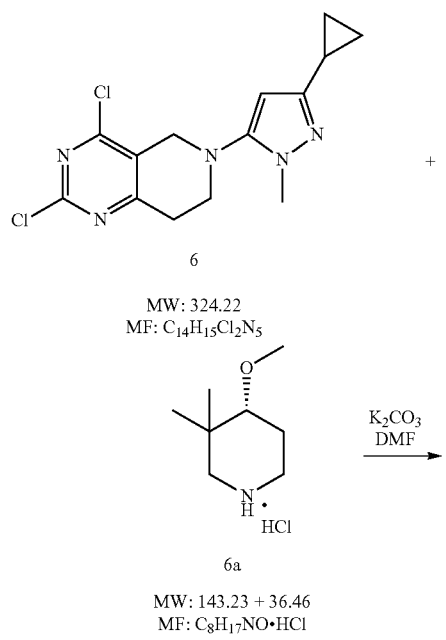

6
MW: 324.22
MF: $C_{14}H_{15}Cl_2N_5$

6a
MW: 143.23 + 36.46
MF: $C_8H_{17}NO$•HCl

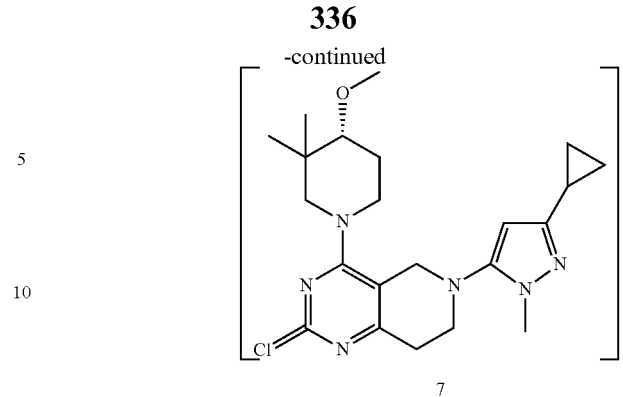

7
MW: 430.99
MF: $C_{22}H_{31}ClN_6O$

A 12-L 4-necked RBF, was charged with 6 (404.4 g, 1.247 mol), 6a (261.9 g, 1.457 mol) and DMF (2.5 L) at room temperature. Stirred to give a slurry. Cooled to 0-5° C. Added $K_2CO_3$ (518.6 g, 3.752 mol) portion wise in 30 minutes while maintaining the temperature at 0-5° C. Stirred the resulting good slurry at 0-5° C. for 6 hours. Slowly warmed to room temperature. After 8 hours (from finishing addition of $K_2CO_3$), stop stirring and let it stand over night. Stirred at room temperature and added MTBE (3.0 L) to a slurry. Added $H_2O$ (3.0 L), exothermic (Tmax~31° C.). A bi-phasic solution with small amount of solids. Transferred the reaction mixture to a 22-L flask with bottom valve. Rinsed the 12-L RBF with MTBE (4.09 L) and $H_2O$ (2.67 L), and transferred into the 22-L flask. Stirred at RT for ~1 h. Let it settle. Still small amount of solids between the layers. Added MTBE (0.79 L, total 7.88 L) and $H_2O$ (0.63 L, total 6.30 L). Still some solids did not dissolve (solids soluble in $H_2O$). Separated the aqueous layer. The rag layer with some solids was kept with organic layer. Washed the organic layer with $H_2O$ (250 mL) to dissolve the solids. Removed the aqueous layer. Extracted the 250 mL aqueous layer with MTBE (1.0 L). Saved the MTBE layer and discarded the aqueous layer. Extracted the 1st aqueous layer with the 1.0 L MTBE layer and 1.66 L of fresh MTBE (total: 2.66 L). Separated the MTBE layer (HPLC indicated no 7 in the aqueous layer, discarded). The MTBE layer was combined into the 1st organic layer. Extracted with $H_2O$ (1.77 L), followed by 20% brine (1.77 L). Separated the organic layer. Concentrated on rotovapor to a foaming oil residue to afford 7. Weight: 605 g. Stand on bench at room temperature over night. HPLC: 91.03%, 6: n.d., regio-isomer of 7: 6.11% (254 nm). LC-MS (M+1: 431.0, 432.8) confirmed the structure. Added toluene (500 mL). Concentrated on rotovapor to a foaming oil residue. Added toluene (500 mL). Concentrated on rotovapor to a foaming oil residue. Weight: 661.2 g. Used directly in the next step.

Step [7]+7a→[8]

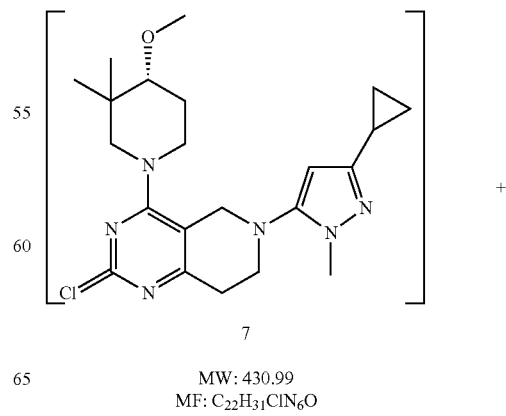

7
MW: 430.99
MF: $C_{22}H_{31}ClN_6O$

-continued

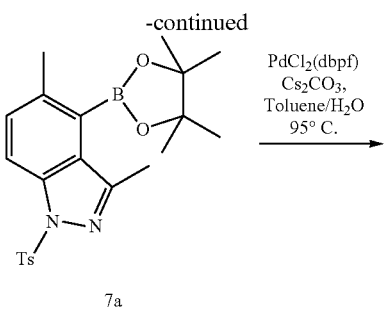

7a

MW: 426.35
MF: C$_{22}$H$_{27}$BN$_2$O$_4$S

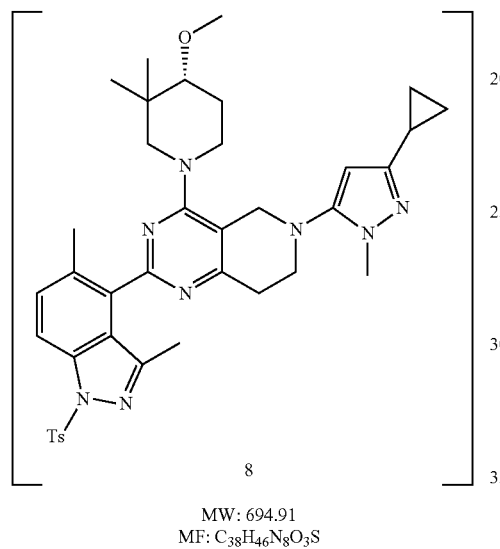

8

MW: 694.91
MF: C$_{38}$H$_{46}$N$_8$O$_3$S

A nitrogen purged 12 L 4-necked RBF was charged with 584.1 g of the crude 7/toluene solution, 273.3 g of 7a, 30.8 g of Pd(dbpf)Cl$_2$, and 3.3 L of toluene. Nitrogen was bubbled through the mixture for 30 min and then heated to 60° C. while bubbling with nitrogen was continued. In a 1000 mL Erlenmyer flask 520.8 g of cesium carbonate and 374 mL of water was charged. Nitrogen was bubbled through the solution at 60° C. for 30 minutes. At 60° C., the cesium carbonate solution was charged to the mixture. The mixture was then refluxed at 93-95° C. for 17.5 h and then cooled. At 30° C. 2.5 L of water was added and 2 dark layers formed. The organic layer was isolated and filtered through a celite bed. The organic layer was extracted with 1.9 L 2.0 M HCl solution twice. The aqueous layers were combined and washed with 1.9 L of toluene. 446 mL of 50% NaOH solution and 3.9 L EtOAc at 40° C. were added to the aqueous layer and 100 mL 4.0 N NaOH solution was used to adjust pH to 9. The layers were separated and the organic layer was held at room temperature overnight. The organic layer was washed with 3.9 L 20% NaCl solution. The organic layer was concentrated yielding 600 g of a residue. The residue was taken up in 1000 mL MTBE at 40° C. and 22 g of pica 120 was added and mixed. The mixture was filtered through a silica gel pad with 1.0 L TBME at room temperature by gravity overnight. The TBME solution was charged to a 22 L RBF and 500 mL 5-6 N HCl in iPA was added and stirred at room temperature for 40 minutes. The mixture was filtered and the filter cake was washed three time with 1.0 L EtOAc. The wet filter cake was transferred to a 22 L RBF using 6.0 L 5% Na$_2$CO$_3$ solution and 6.0 L EtOAc. The layers were separated and the organic layer was washed with 2.0 L 20% NaCL solution. The organic layer was held at room temperature overnight and then concentrated to dryness at 40° C./30 mbar. The residue was taken up in 1.0 L DCM at 30-40° C. and filtered through a celite bed in a sintered-glass funnel washed with 500 mL DCM and concentrated at 40° C./30 mbar to dryness. Use another 1000 mL DCM to dissolve the residue and concentrate at 40° C./30 mar again to dryness. 538.1 g of black foaming solid was obtained. $^1$H NMR (CDCl$_3$): consistent. HPLC (210 nm): 95.8% product. LC-MS: ES+695.2. Overall yield: 95.1% from dichloropyrimidine (no purity correction).

Step [8]+9→[10]

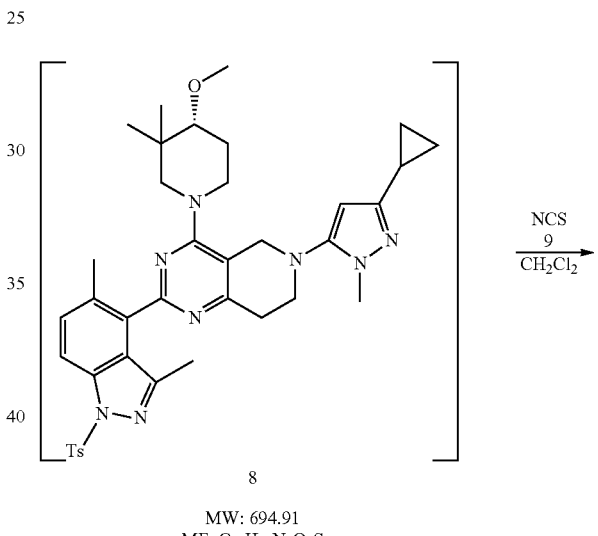

8

MW: 694.91
MF: C$_{38}$H$_{46}$N$_8$O$_3$S

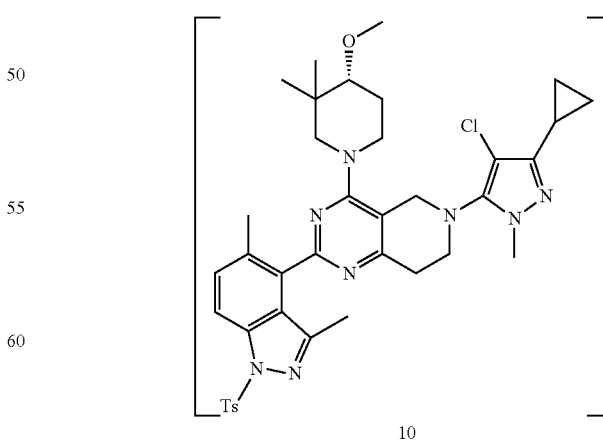

10

MW: 729.35
MF: C$_{38}$H$_{45}$ClN$_8$O$_3$S 8 (534 g, 768.5 mmol) was dissolved in CH$_2$Cl$_2$ (2.00 L). A little bit of solids and tiny amount of H$_2$O was observed. Added 60 g of anhydrous MgSO$_4$. Filtered and rinsed with CH$_2$Cl$_2$ (1.0 L) (filtration was slow) and added into the reaction mixture. Charged into a 12-L, 4 necked RBF at RT under N$_2$. Rinsed with CH$_2$Cl$_2$ (0.5 L) and added into the reaction mixture. Charged NCS (102.6 g, 768.5 mmol) at room temperature in 5-10 min (slightly exothermic, Tr from 14° C. to 20° C.). Rinsed with CH$_2$Cl$_2$ (0.5 L, total 4.0 L) and added into the reaction mixture (20° C.). A brown solution. Stirred at room temperature under N$_2$ overnight.

Added H$_2$O (2.00 L) and stirred at room temperature for 30-60 min. Let it settle for 2 h. Separated the organic layer and washed it with H$_2$O (2.00 L). Separated the organic layer and washed it with saturated aqueous NaHCO$_3$ (2.00 L). Separated the organic layer, dried with anhydrous MgSO$_4$ (100 g) and let the mixture stand at room temperature overnight. Filtered off MgSO$_4$ and concentrated the reaction mixture was concentrated on rotovapor under vacuum to dryness to a foaming oil residue (weight: 470 g). Added CPME (350 mL) and concentrated under vacuum to dryness to a foaming oil residue. Repeated two more times to obtain 10 as an foaming oil residue. Weight: 470 g (crude yield: 83%). HPLC: 91.6%, 11: 1.26%, 7.2 min impurity: 4.67% and several other small impurities (210 nm). LC-MS (M+1: 729.1, 731.1) confirmed the structure.

Step 10→11

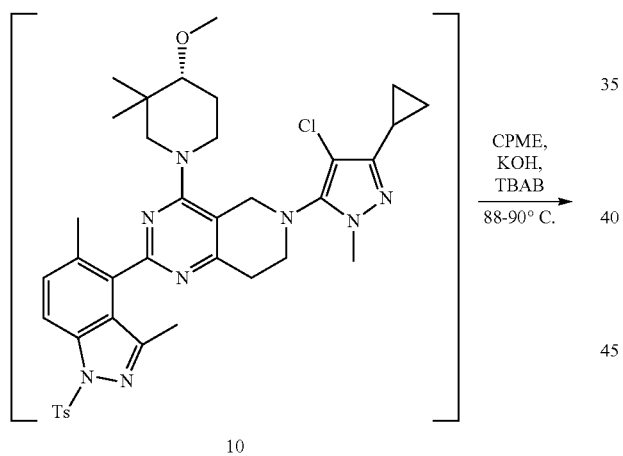

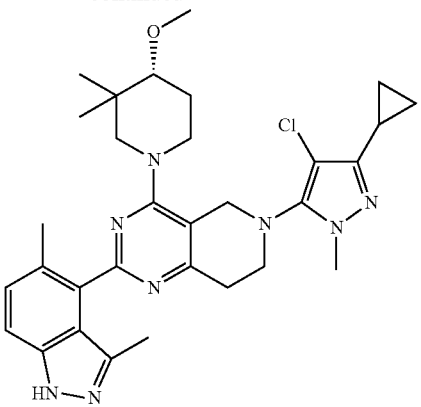

Charge a 5-L flask with 235 g of crude compound 10, 2300 mL of CPME, and 36 g of KOH. Heat to 90 oC, add 23.5 g of TBAB. Hold at 90.6° C. for 3 h. Cool to 20° C., add 600 mL of water, stir for 30 min. Separated two layers. Wash the organic layer with 400 mL of water twice and 500 mL of brine. Concentrate the organic layer to dryness to give 175 g of the desired product in 95% yield. Purified the product via column chromatography. Charge a 5-L flask with 1600 mL of water, then slowly add a solution of 170 g of the product in 400 mL of methanol. Stir at 20° C. for 1 h after addition. Filter the solids and washed the wet cake with 20% MeOH in water. Dry at 45° C. for 16 h to give 160 g of the desired product in 94% yield. LC-MS and NMR confirmed the structure. HPLC: 98.6%; residual solvents met specs.

EXAMPLE 79

Alternate synthesis of Example 19-F

General Synthetic Scheme:

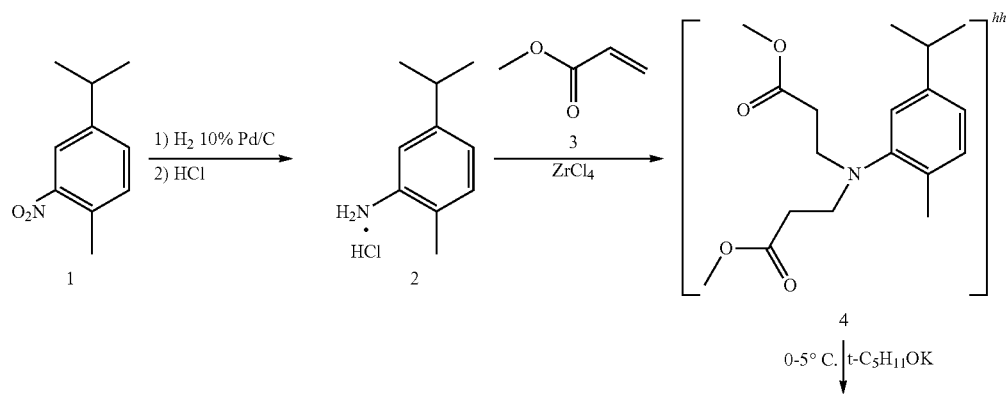

-continued

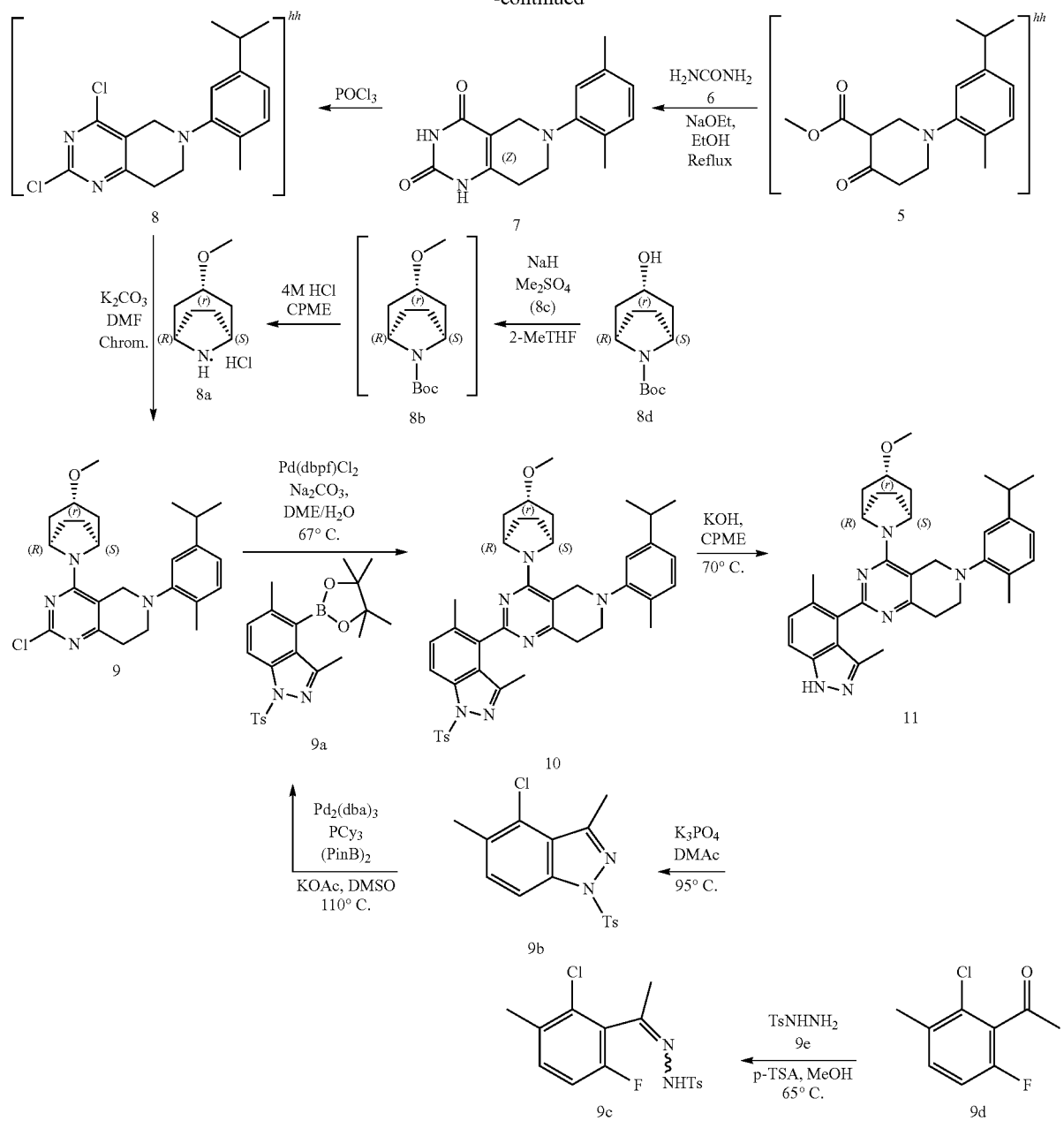

Step 1→2

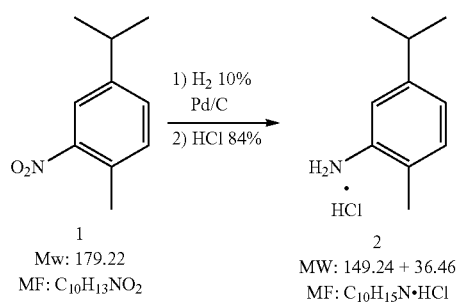

To a 5-L hydrogenator was charged 10% Pd/C (50% wet, 12.0 g) and purged with N₂ 5 times. Charged EtOH (2.0 L), then 1 (426.6 g). Rinsed with EtOH (1.2 L, total 3.2 L) and added into the reaction mixture. Purged with N₂ 5 times, then H₂ 5 times. Hydrogenated at 15 pisg of H₂, 325 rpm stirring and 25° C. for 6 h. No H₂ uptake after 3.5 h. The reaction mixture was stored in the reactor at RT under N₂ over night. The reaction mixture was filtered through a celite pad. Rinsed the reactor with EtOH (110 g). Rinsed the celite pad with the EtOH rinse, then with fresh EtOH (150 mL). Combined the reaction mixture and rinses to afford a dark blue solution. Concentrated it on rotovapor to dryness to obtain crude 2 free base as a dark blue liquid. Weight: 360 g. HPLC: 81.3% (254 nm). $^1$H and $^{13}$C-NMR confirmed the structure with some impurities.

Crude 2 free base was added with CPME (150 mL) to give a solution. Concentrated to dryness (weight: 408 g) on rotovapor. The residue was dissolved in CPME (2.0 L) to give a dark blue solution. Added 4M HCl in CPME (650 mL) slowly (1 h). Solids started to form after 200 mL of HCl was added. Rinsed with CPME (850 mL, total 3.55 L, including from residue 2) and added into the reaction mixture. A good pinkish slurry (T 36° C.). Slowly cooled to room temperature. Stirred at room temperature over night. The solids were filtered through a polypropylene pad and washed with CPME (3.0 L). Dried the solid in the vacuum oven at 40° C. for over weekend (not much change after a few hours) to afford a pink solid. Weight: 374.5 g (wet: 419.6 g), yield: 84.7%. HPLC: 99.0% (254 nm). HPLC: 94.2%, ~1% regio-isomer (210 nm, 254 nm), ~3.8% des-isopropyl 2 (254 nm). NMR and LC-MS (M+1: 150.1) confirmed the structure.

Step 2+3→[4]

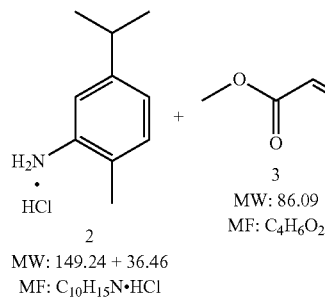

2
MW: 149.24 + 36.46
MF: C$_{10}$H$_{15}$N·HCl

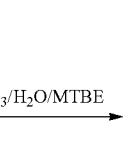

3
MW: 86.09
MF: C$_4$H$_6$O$_2$

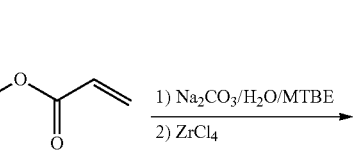

1) Na$_2$CO$_3$/H$_2$O/MTBE
2) ZrCl$_4$

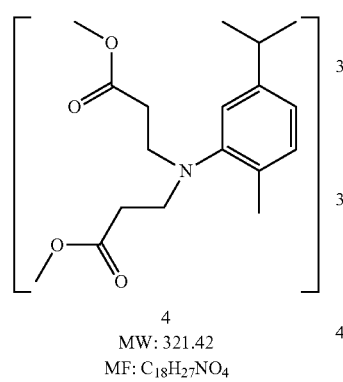

4
MW: 321.42
MF: C$_{18}$H$_{27}$NO$_4$

Mix 4.1 L of 10% Na$_2$CO$_3$ solution, 370 g of aniline HCl salt (2), and 4.0 L TBME at ambient temperature for 30 min. Two clear layers formed. Separate, and wash the organic phase twice with 1.0 L 20% NaCl solution. HPLC of the organic layer (210 nm): 93.7% aniline (5.34 m), 5.66% 2.7 min, 0.6% 5.2 min. Dry the organic layer with 80 g of anhydrous magnesium sulfate. Filter off the solids, wash with TBME. Concentrate the combined TBME solution at 45° C./30 mbar to dryness. Purge with nitrogen for 2 h. 295 g of oily aniline free base was obtained. HPLC (210 nm): 94.4% aniline (5.34 m), 5.2% 2.7 min, 0.4% 5.2 min. $^1$H NMR (DMSO-d$_6$): consistent with the molecular structure.

Mix the 295 g of aniline free base and 700 g (700 mL) of acrylate (3). Cool the batch to 0-5° C. with an ice/water bath. Then add through a solid addition funnel 69.1 g of ZrCl$_4$ powder over 2 h at 6±3° C. Stir at 0-5° C. for 30 minutes. Remove the ice bath, allow the batch to warm up to room temperature. Stir at 10-20° C. for 3 h. HPLC: 79.3% product 4 (8.89 min), 1.3% mono-addition product (7.93 min), 5.6% 6.71 min, 7.5% 14.1 min out of total except acrylate.

At ambient temperature, add into the batch 2.0 L toluene and 1.36 L of 10% Na$_2$CO$_3$ solution while controlling batch temperature at room temperature. Filter the batch through a celite bed and wash with 300 mL toluene. Separate, and wash the toluene layer with 500 mL 1.0 M NaHCO$_3$ solution (aq pH 10) and wash twice with 500 mL 20% NaCl solution (aq pH 8, 6.5). Dry the organic layer with 50 g of MgSO$_4$. Filter off the solid and wash with toluene. Concentrate the combined toluene filtrate at 45° C./30 mbar, then at 60° C./30 mbar to dryness. Purge the product 4 with nitrogen over weekend. 644.9 g of orange liquid was obtained. This oily product 4 was directly used in the next step without further purification. Yield: 100.7% (no purity correction). HPLC purity (210 nm): 81.7%. Major impurities: 5.0% 6.7 min, 1.4% mono-addition product (7.9 min), 0.6% 9.4 min, 1.2% 11.0 min, 6.8% 14.1 min. $^1$H NMR (DMSO-d$_6$): consistent with the molecular structure.

Step [4]→[5]

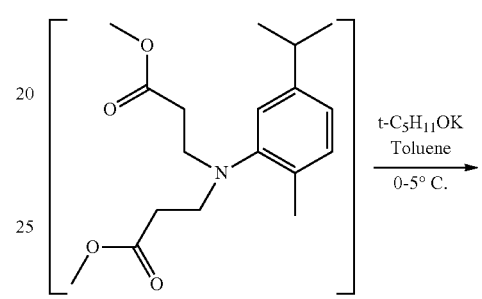

4
MW: 321.42
MF: C$_{18}$H$_{27}$NO$_4$ t-C$_5$H$_{11}$OK
Toluene
0-5° C.

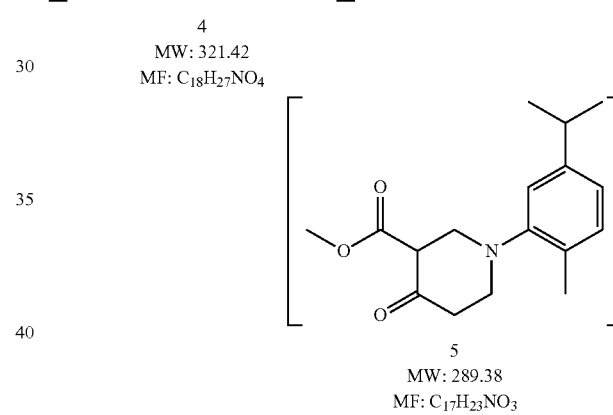

5
MW: 289.38
MF: C$_{17}$H$_{23}$NO$_3$

Into a solution of 630.7 g of diester in 6.3 L of toluene pre-cooled to 0-5° C. with an ice/water bath, was added through an addition funnel 2.475 kg of 25% potassium amylate solution in toluene at 0-5° C. dropwise over 60 min. The batch became a yellow suspension at the end of addition. Stir the batch at 0-5° C. for 30 min. At 0-15° C., add 294.6 g of HOAc dropwise in 15 min and 5.5 L of 1.0 M NaHCO$_3$ solution. Mix the batch at ambient temperature and separate the aqueous layer. Wash the organic phase twice with 2 L 20% NaCl solution. Dry the organic layer with 100 g of anhydrous MgSO$_4$. Filter off the solid, wash with toluene. Hold the combined toluene solution at ambient temperature overnight. Concentrate the toluene solution at 55° C./30 mbar to dryness and purge with nitrogen for 2 h. 622.1 g of yellow oil was obtained. This oily product was directly used in the next step without further purification. Yield: 101.8%. HPLC (210 nm): 41.2% 11.3 min, 49.6% 12.5 min (probably keto-enol tautomerization), major impurities: 2.3% 7.6 min, 0.7% 15.6 min. $^1$H NMR (DMSO-d$_6$): consistent with the molecular structure.

Step [5]+6→7

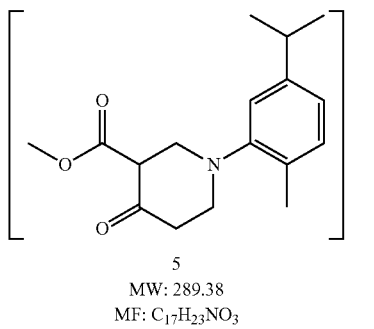

5
MW: 289.38
MF: C₁₇H₂₃NO₃

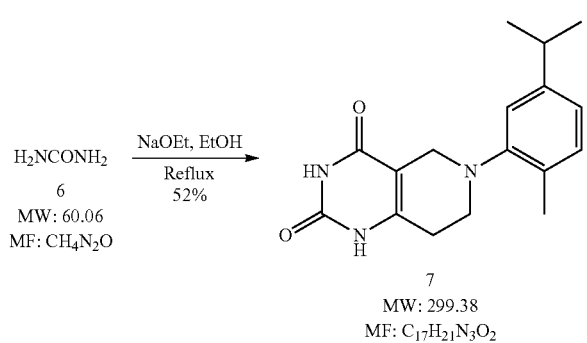

Into a mixture of 271.1 g of urea (6) and 622.1 g of ketoester (5) in 3.75 L of EtOH (fresh), was added 2.117 kg of 21% NaOEt/EtOH in portions at 15° C. Stir and heat the batch to 80° C. for 20 h under even agitation. Allow the batch to cool down to ambient temperature over night. Cool the batch to 12° C. with an ice bath, add 392.3 g of HOAc into the batch slowly at 12-16° C. over 20 min. Concentrate the batch in 1.5 L portions at 50° C./30 mbar to nearly dryness. Stir the solid residue in 6.0 L of water at ambient temperature for 1 h. Filter and wash the cake with 1.0 L of water. Stir the wet filter cake with 1.7 L of i-POAc, and heat to reflux. Stir and cool to ambient temperature, and stir over night. Filter the batch and wash the cake with 600 mL of i-POAc. Dry the filter cake at 60° C./30 mbar over night to obtain 335.7 g of 7 as beige powder. Yield: 52.2%. HPLC (210 nm): 95.5% ¹1-1 NMR (DMSO-d₆): consistent with the molecular structure.

Step 7→[8]

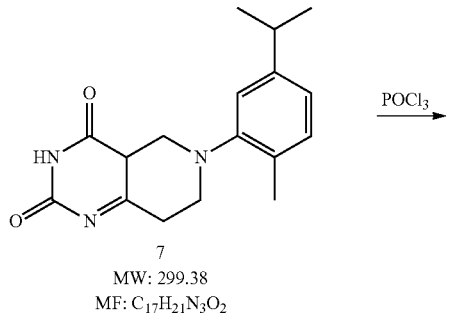

7
MW: 299.38
MF: C₁₇H₂₁N₃O₂

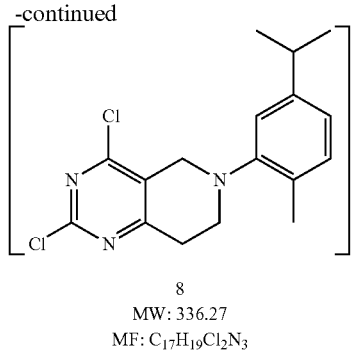

8
MW: 336.27
MF: C₁₇H₁₉Cl₂N₃

To a 3-necked, 5-L round-bottomed flask, equipped with a mechanical stirrer, a thermometer, a reflux condenser, a heating mantle, and a nitrogen inlet is charged at ambient temperature, 106 g (354 mmol) of the starting material, uracil, 7 and 1.0 L of toluene. Stir the beige yellow slurry at 23° C. for 10 min. Add in one portion, 1.040 kg (6.78mol) of phosphorous oxychloride. Heat the mixture to an internal temperature at 105° C. over 30 min. Maintain at this temperature for 6 h. The reaction mixture over time will turn into a clear dark solution, which is an indication that the chlorination reaction is complete. HPLC shows no more uracil, 7 is left. The solution is cooled to 23° C. and is held overnight.

The excess phosphorous oxychloride is distilled off under vacuum, while maintaining the batch temperature at below 45° C. The remaining POCl₃ is azeotropically removed by the addition of two 300 mL additions of toluene. Dilute the reaction mixture in 1.0 L of toluene. Cool the dark solution to an internal temperature at 15° C. Basify the toluene solution with an aqueous solution of 200 g of sodium carbonate in 1.5 L of water. Make sure the final pH is 9. Stir the resulting tan suspension at ambient temperature for 1 h. Separate layers. Extract the aqueous layer with 500 mL of toluene. Wash the combined organic layers with 400 mL of brine and 100 mL of water. Separate layers. Concentrate the organic layer to a constant weight of, T: 156 g of 8 as a dark oil in >100% yield. HPLC, TLC and ¹H-NMR: consistent with the molecular structure.

Step 8d+8c→[8b]

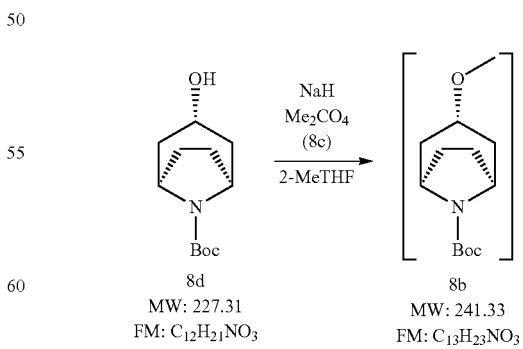

8d
MW: 227.31
FM: C₁₂H₂₁NO₃

8b
MW: 241.33
FM: C₁₃H₂₃NO₃

N-BOC-Nortropin 8d (106.5 g) was stirred with 2-MeTHF (450 mL) at RT to give a slurry. Cooled to 12° C. Added with NaH (60% in mineral oil, 37.48 g) at this temperature and rinsed with 2-MeTHF (50 mL). Some bubbles were observed at beginning, but not much exothermic. Stirred at 10° C. for 30 minutes to obtain a slurry. Added (CH$_3$)$_2$SO$_4$ (106.4 g). Rinsed with 2-MeTHF (100 mL, total 600 mL) and added into the reaction mixture to obtain a slurry. Added H$_2$O (1 mL). Slowly warm to RT (slowly exothermic, temperature rose to ~30° C., then cooled down). Stirred at RT for over night. Cooled the reaction mixture to ~10° C. Added H$_2$O (100 mL). Added 20% K$_2$CO$_3$ aqueous solution (200 mL) to give a bi-phasic solution (pH 14). Stirred at RT for 2 hours. Transferred to a separatory funnel Rinsed with TBME (300 mL) and added into the reaction mixture. Separated the aqueous layer and discarded. The organic layer was extracted with H$_2$O (300 mL each) twice. The organic layer was concentrated to dryness on rotovapor. Added CPME (100 mL) and concentrated to dryness on rotovapor to obtain 8b as an oil residue. Weight: 139.3 g. Used directly in the next step without further purification.

Step [8b]→8a

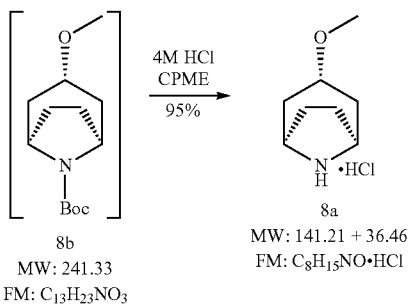

8b (139.3 g, from 468.53 mmol of BOC-nortropin) was transferred to a 2-L, 4-necked RBF. Rinsed with CPME (50 mL) and added into the reaction mixture. Cooled to 5-10° C. Still a solution. Added with 4M HCl in CPME (340 mL) at this temperature. Stirred and slowly warmed to room temperature. Stirred at room temperature over night to obtain a slurry. Added heptanes (400 mL) to obtain a white slurry. Stirred at RT for 2 h. The solids were filtered through a polypropylene pad and washed with heptanes (50 mL) under N$_2$ flow. Dried the solid in the vacuum oven at 40° C. for over weekend to afford a white solid. Weight: 81.3 g (wet: 84.2 g), yield: 97.6% (from 8d). NMR (D$_2$O) confirmed the structure.

Step [8]+8a→9

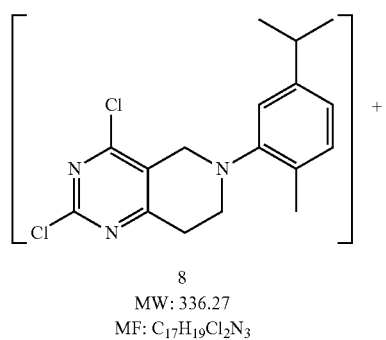

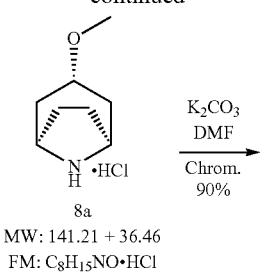

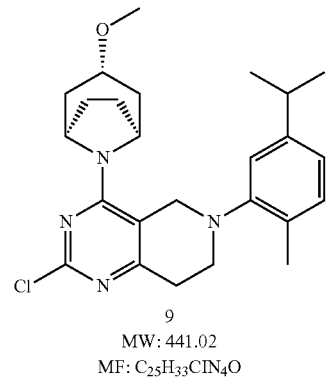

To a 3-necked, 3-L, round-bottomed flask, equipped with a mechanical stirrer, a thermometer, a nitrogen inlet and an addition funnel, and a cooling bath, was charged at 20° C., 105 g (760 mmol) of potassium carbonate, 66 g (372 mmol) of HCl salt of 8a and 5 g (35 mmol) of free base form of 8a and 500 mL of DMF. Mechanically stir the suspension at 20° C. for 10 min and cool to an internal temperature at below 5° C. over 30 min. Add to the cold suspension, a solution of 112 g (333 mmol) (containing 18% of toluene) of the dichloride, 8 in 300 mL of DMF over 15 min via an addition funnel. Rinse the funnel twice with 50 mL of DMF. Maintain at this temperature for 10 h. Warm the reaction mixture gradually to ambient temperature overnight. Cool the reaction mixture to an internal temperature at 15° C. Dilute with 800 mL of ethyl acetate. Dilute with 1.02 L of water in portions, while maintaining the internal temperature at below 22° C. Stir the orange solution with precipitates at 20° C. for 30 min Separate layers. Check the pH of the aqueous layer and ensure it is 10. Wash the dark organic layer with 750 mL of water. Wash with 500 mL of a 10% citric acid solution. Check the pH to be 2. Finally, wash the organic layer with 400 mL of brine. Concentrate down the organic layer at a bath temperature at 45° C. to a constant weight of, T: 164 g of 9 as a tan oil in >100% yield, which solidifies into a waxy yellow solid upon standing. HPLC indicates no signs of solvent DMF. TLC shows only trace amount of the starting material dichloride, 8.

The crude product, 9 passed through a silica gel pad to eliminate the 4% des-isopropyl adduct. Simply, dissolve 182 g of crude nortropine adduct, 9 in 50 mL of dichloromethane and 200 mL of toluene. Load the solution onto a 328 g silica gel (60-230 mesh) bed. [1.8 g of silica to 1 g of crude 9]. Elute with 100% toluene. The desired product, 9 elutes first, leaving all others including the des-isopropyl by-product behind. After combining fractions and concentrating down to constant weight, the yield is 148 g of a pale yellow oil, which solidifies over time into a bright light yellow solid of 9. The purity is ~98% by HPLC at 210 nm.

Step 9d+9e→9c

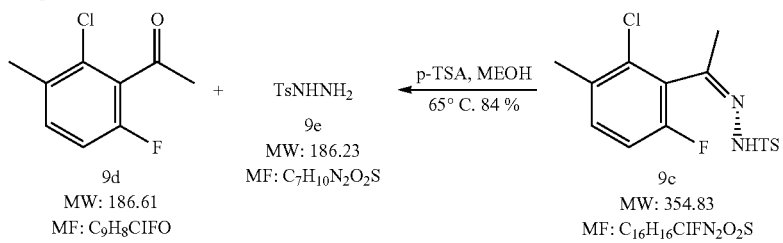

To a 5-L 4-necked RBF, charged 9d (498.3 g), 9e (621.6 g, 1.25 eq), p-TSA monohydrate (50.8 g, 0.1 eq) and MeOH (2.5 L) to afford a white slurry. Stirred at room temperature. Warmed the reaction mixture to 65° C. in 45 min. Stirred the reaction mixture at 65° C. for ~8 h. The reaction mixture was cooled down slowly to room temperature and stirred at room temperature overnight to obtain a white slurry. The reaction mixture was further cooled to 5° C. and stirred for 3-4 h. The solids were filtered through a polypropylene pad and washed three times with cold MeOH (333 mL). Dried the solid in the vacuum oven at 50° C. for over night to afford a white solid. Weight: 824 g (wet: 873.6 g), yield: 87%. HPLC (E/Z mixture): 100% (210 nm), 99.61% (254 nm). NMR (E/Z isomer ratio: ~4.6/1.0) and LC-MS (M+1: 354.9, 356.7) confirmed the structure.

Step 9c→9b

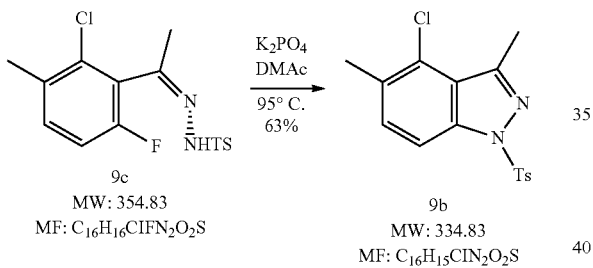

To a 12-L 4-necked RBF, charged 9c (819 g), K$_3$PO$_4$ (979.9 g, 2.0 eq) and DMAc (3.28 L) at room temperature to afford a white slurry. Warmed the reaction mixture to 95±3° C. in 45 min. Stirred at 95±3° C. for 10 hours. Cooled down slowly to room temperature and stirred at room temperature for over night. Added H$_2$O (6.56 L) in 1.5 h while maintaining temperature <35° C. with ice bath. Cooled the reaction mixture to 20° C. and stirred for 1 h. The solids were filtered through a polypropylene pad and washed with H$_2$O (4 L). Dried the solid in the vacuum oven at 50-60° C. for over night to 593 g. Continued drying at 50-60° C. for over weekend to afford a light brown solid. Weight: 583.1 g (wet: 698.4 g), yield: 75.4%. HPLC: 97.0% (254 nm).

To a 5-L 4-necked RBF, charged 9b (402.0 g) and 2-propanol (4.02 L) to obtain a slurry. Stirred the reaction mixture at RT. Warmed to 82° C. in 45 min. Stirred the reaction mixture at 82° C. for 1 h. Cooled to room temperature. The reaction mixture was cooled down slowly to 5° C. and stirred at this temperature for 1 h. The solids were filtered through a polypropylene pad and washed with cold 2-propanol (1.35 L). Dried the solid in the vacuum oven at 50-60° C. for over night to afford a creamy colored sandy solid. Weight: 339.9 g (wet: 341.7 g), yield: 84.6% (total 63.7%). HPLC: 99.0% (254 nm). NMR and LC-MS (M+1: 334.9, 336.8) confirmed the structure.

Step 9b→9a

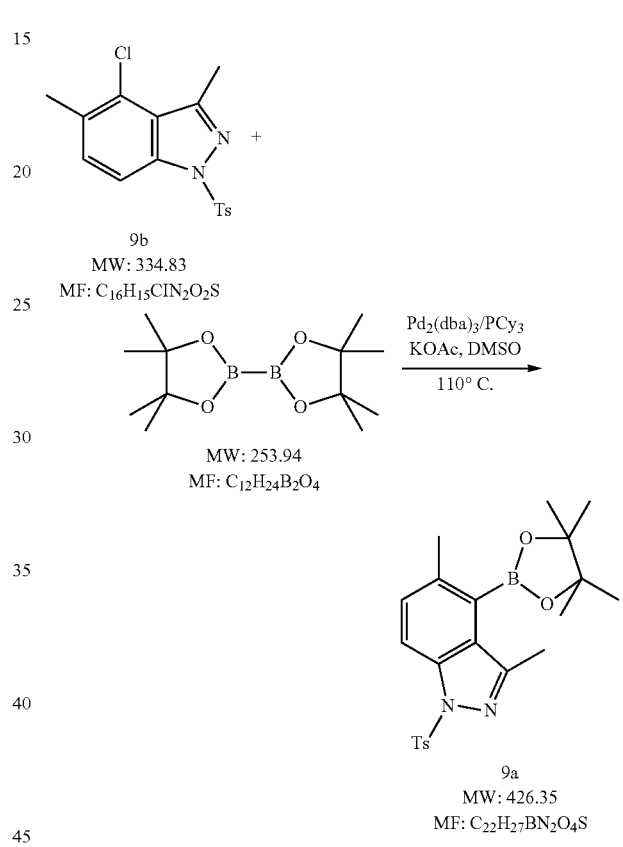

Into a nitrogen-purged 5-L 4-necked RBF, add 45.1 g Pd$_2$(dba)$_3$, 66.4 g of PCy$_3$, and 1.0 L nitrogen-bubbled DMSO. Stir at room temperature while bubbling nitrogen for 60 min in a 12-L 4-necked RBF with nitrogen for 30 min, then add 660.2 g of tosyl indazole, 1,502 g of pinacol diboron (3.0 eq), 580.6 g of KOAc (3.0 eq), and 5.5 L of DMSO. Bubble nitrogen through and purge the head space of the batch for 10 min, then heat to 70° C. in 60 min while maintaining nitrogen bubbling and purging. At 70° C., add all preformed catalyst/DMSO thin suspension as prepared above. Heat the batch to 110° C. and stir at 110° C. for 15 h while maintaining nitrogen bubbling and purging. Cool the batch to room temperature and hold over weekend. Heat the batch to 50° C. to make the batch from a thick suspension to a flow-flowing suspension, transfer all contents into a 22-L 4-necked RBF with 5,500 mL 2-MeTHF, 5,000 mL water, and 160 g of celite. Stir the batch at 40-50° C. for 30 min. Separate the organic layer. Back-extract the aqueous layer with 1.0 L of 2-MeTHF and 1.5 L water. Filter the combined organic layer and aqueous layer containing celite through a celite pad, wash with 2,000 mL of 2-MeTHF. Separate the organic layer. Hold the solution at room temperature overnight. Wash the organic layer with 3.0 L of 20% NaCl solution, and 4.0 L 6% NaCl solution. Divide the organic layer into 3 parts, concentrate each at 40° C./30 mbar to nearly dryness, add each 600 mL heptane, concentrate at 40° C./30 mbar to nearly dryness. Add into each 600 mL heptane. Stir at 45° C. to make a free-flowing suspension. Combine into a 12-L RBF, add 5.3 L more heptane. Stir at 45° C. for 2 h, cool to room temperature and stir overnight. Filter the batch, wash the cake with 2.0 L of heptane. Dry the wet cake at 55° C./30 mbar over night. 596.8 g of light pink solid was obtained. Yield: 71.0%. HPLC purity (254 nm): 98.2%. LC-MS: ES+426.9. NMR (CDCl$_3$): consistent with the molecular structure.

Step 9+9a→10

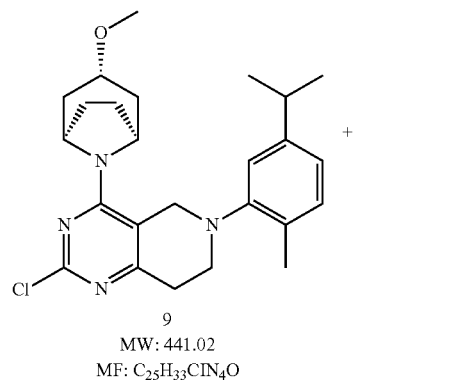

9
MW: 441.02
MF: C$_{25}$H$_{33}$ClN$_4$O

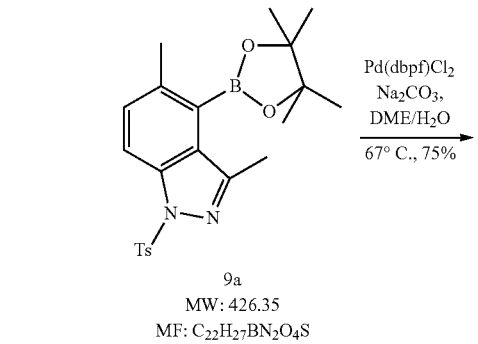

9a
MW: 426.35
MF: C$_{22}$H$_{27}$BN$_2$O$_4$S

To a 3-necked, 2-L round-bottomed flask, equipped with a mechanical stirrer, a reflux condenser, a heating mantle, a thermometer and a nitrogen inlet is charged at 20° C., 40 g (90.7 mmol) of nortropine adduct, 9, 46.3 g (108.6 mmol) of the indazole boronate, 9a and 600 mL of dimethoxyethane to give a clear light brown solution. Stir vigorously at 20° C. for 10 min to ensure visually that all chunks of solids have dissolved. Add an aqueous solution of 30 g (283 mmol) of sodium carbonate in 330 mL of water. Add 2.0 g (3.07 mmol) of the Pd catalyst (3.4 mol %) and rinse with 50 mL of dimethoxyethane. Heat the solution-like mixture to an internal temperature at 67° C. quickly in less than 15 min. Stir and maintain at this temperature for 2 h. Cool to ambient temperature. The reaction mixture, a tan slurry is filtered through a Buchner funnel under house vacuum over a polypropylene pad. Wash the filter cake twice with 100 mL of MTBE, twice with 100 mL of water and once with 50 mL of dimethoxyethane. Dry the filter cake at an oven temperature at 48° C. under house vacuum with a slight nitrogen bleed for 20 h to obtain T: 61 g of the desired crude Suzuki product 10 in ~95% yield.

Dissolve 161 g of crude Suzuki product in 650 mL of dichloromethane. Wash the clear pale yellow solution twice with 160 mL of water and 276 g of brine. Pass the organic solution through a short 228 g pad of silica gel (60-230 mesh). Eluted with 100% dichloromethane and followed by 30% ethyl acetate/dichloromethane. The fractions are combined and concentrated down. Residual dichloromethane is chased off with 400 mL of MTBE to obtain 360 g of a wet cake. The wet cake of 10 is mechanically stirred in 1.4 L of MTBE at an internal temperature at 45° C. The slurry is stirred at ambient temperature overnight and is filtered under house vacuum over a Buchner funnel over a polypropylene pad. Wash the filtered cake with MTBE and air-dried at ambient temperature for 30 min. The solids are then dried at an oven temperature at 48° C. under house vacuum with a slight nitrogen bleed for 18 h to afford: 135 g of purified Suzuki product, 10 in ~84% recovery. The purity is >99% by HPLC at 210 nm. The structure is consistent by $^1$H-NMR and LC/MS (MH$^+$=705).

Step 10→11

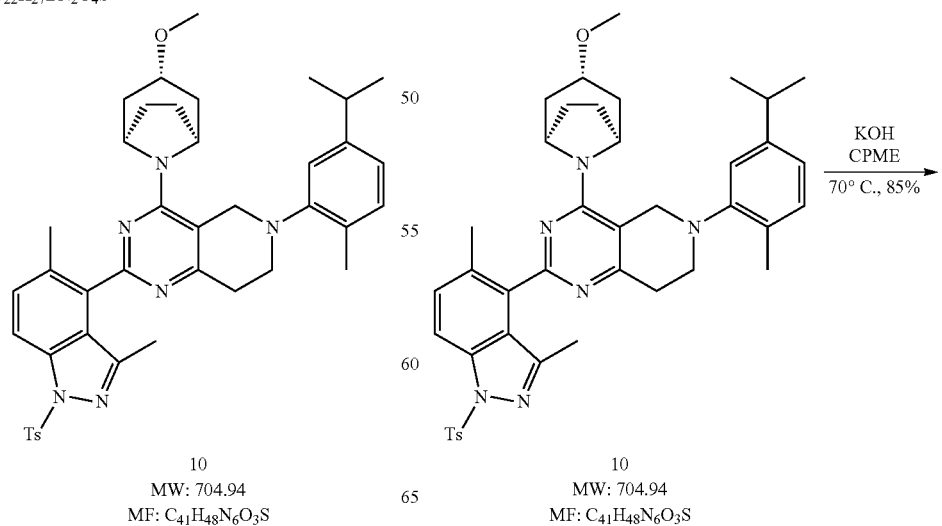

10
MW: 704.94
MF: C$_{41}$H$_{48}$N$_6$O$_3$S

10
MW: 704.94
MF: C$_{41}$H$_{48}$N$_6$O$_3$S

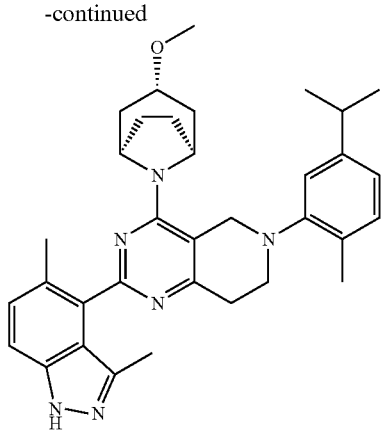

11
MW: 550.75
MF: $C_{34}H_{42}N_6O$

To a 3-necked, 3-L round-bottomed flask, equipped with a mechanical stirrer, a heating mantle, a reflux condenser, and a nitrogen inlet, was charged at 20° C., 100 g (142 mmol) of 10, 20 g (357 mmol) of powderized potassium hydroxide and 1 L of cyclopentyl methyl ether. Stir mechanically the slurry at 20° C. for 10 min. Heat gradually to an internal temperature at 68° C. Stir and maintain at this temperature for 7 h. Cool the reaction mixture to 20° C. Stir overnight. Add 500 mL of water, 500 mL of cyclopentyl methyl ether and 500 mL of brine. Separate layers. Wash the organic layer with 500 mL of water and 500 mL of brine. Separate layers. Dilute the organic layer with 500 mL of isopropyl acetate. Wash the organic layer with 700 mL of water. Separate layers. Pass the organic layer through a coarse sintered glass funnel under house vacuum over a fiber glass filtered paper. Concentrate the organic layer at a bath temperature at 40° C. to constant weight to obtain T: 221 g of crude 11 as a gummy oil.

The crude product of 11, the free base form of the drug substance, LKP581 will have to be solidify out. Initially, solids of 11 can be obtained by scratching it from heptane. However, as much as 2% of solvent retention based on $^1$H-NMR made this process unacceptable. After much process development efforts and inputs from the crystallization group, a feasible condition is devised, allowing the delivery of the CSP batch of LKP581 as a solid, with the right purity level and yield. Hence, met the AUDD. Simply, dissolve the crude oil of 11 in methanol. Carefully, add it into water. Filter and dry.

EXAMPLE 80

MTBE Solvate of Example 19-F

To 100 mg of the amorphous free form of Example 19-F, 100 µL of MTBE was added. On stirring a clear solution is formed. The solution was stirred at −20° C. and over approx. 60 minutes a precipitate was formed. The resulting solid was collected by filtration and dried at 40° C. under vacuum for 72 hours. The solid form is crystalline by XRPD, with a melting point of 102.8° C. and a concurrent 4.9% weight loss. The XRPD is shown in FIG. 1. The DSC and TGA are shown in FIG. 2.

Powder X-Ray Diffraction Peaks of Example 19-F from MTBE

| Angle 2θ | d value Å | Relative Intensity % |
|---|---|---|
| 3.433 | 25.74 | 29.9 |
| 6.369 | 13.88 | 40.3 |
| 7.058 | 12.52 | 50.3 |
| 9.306 | 9.50 | 49.6 |
| 10.522 | 8.41 | 42.5 |
| 11.908 | 7.43 | 54.2 |
| 12.511 | 7.08 | 36.7 |
| 13.434 | 6.59 | 69.3 |
| 15.527 | 5.71 | 54.8 |
| 16.385 | 5.41 | 60.6 |
| 17.39 | 5.10 | 100 |
| 18.883 | 4.70 | 78.1 |
| 20.285 | 4.38 | 52.9 |
| 22.351 | 3.98 | 34.1 |
| 23.297 | 3.82 | 38.5 |

EXAMPLE 81

Me-THF Solvate of Example 19-F

To 100 mg of the amorphous free form, 100 µL (or 200 µL) of Me-THF was added. On stirring a clear solution is formed. The solution was stirred at −20° C. and over approx. 2 hours a precipitate was formed. The resulting solid was collected by filtration and dried at 40° C. under vacuum for 72 hours. Material collected and analyzed without drying was found to have a different XRPD pattern than the dried material suggesting a conversion of crystalline forms. Conversion could be followed by XPRD over ~30 minutes under ambient conditions.

Figure 5:
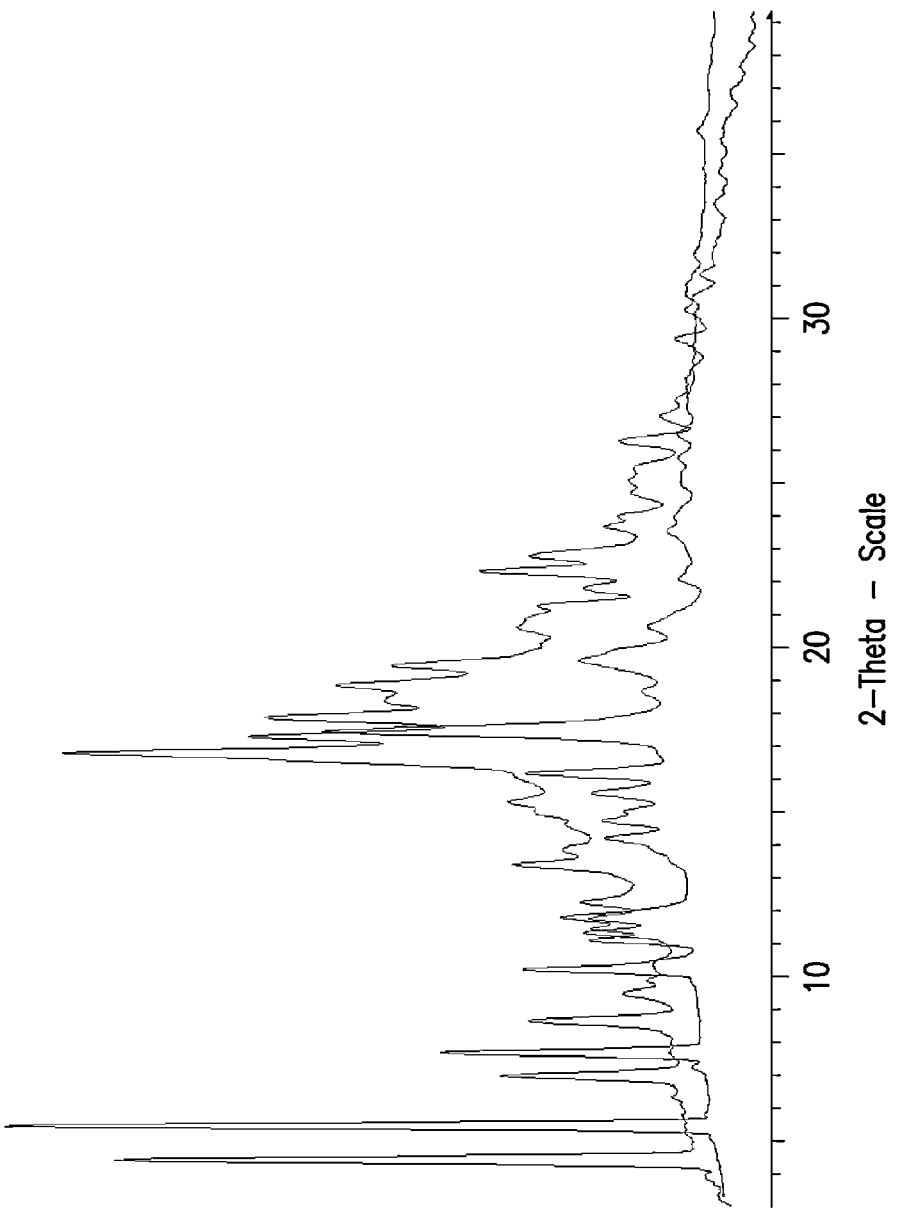
FIG. 5. illustrates the x-ray powder diffraction patterns of Example 19-F of the initial precipitate (upper pattern) and dried material (lower pattern) from Me-THF.

The solid form is crystalline by XRPD, with a melting point of 126.8° C. and a concurrent 1.5% weight loss. The XRPD is shown in FIG. 3 and FIG. 5. The DSC and TGA are shown in FIG. 4.

Powder X-Ray Diffraction Peaks of Example 19-F Initial Precipitate from Me-THF

| Angle 2θ | d value Å | Relative Intensity % |
|---|---|---|
| 4.394 | 20.11 | 93.1 |
| 6.959 | 12.70 | 41.8 |
| 8.629 | 10.24 | 38.1 |
| 11.31 | 7.82 | 30.8 |
| 13.387 | 6.61 | 40.3 |
| 16.778 | 5.28 | 100 |
| 17.287 | 5.12 | 75.3 |
| 17.865 | 4.96 | 73.2 |
| 18.849 | 4.70 | 63.7 |
| 19.452 | 4.56 | 56.4 |
| 22.353 | 3.97 | 44.6 |
| 22.83 | 3.89 | 38 |
| 26.312 | 3.38 | 26.2 |

Powder X-Ray Diffraction Peaks of Example 19-F Dried Material from Me-THF

| Angle 2θ | d value Å | Relative Intensity % |
|---|---|---|
| 5.148 | 17.16 | 100 |
| 7.37 | 11.99 | 40.2 |
| 9.908 | 8.92 | 29.1 |
| 10.807 | 8.18 | 20 |
| 11.489 | 7.70 | 24 |
| 13.904 | 6.36 | 17.9 |
| 14.434 | 6.13 | 18.3 |
| 15.273 | 5.80 | 19.7 |
| 15.879 | 5.58 | 28.6 |
| 17.164 | 5.16 | 56.6 |
| 19.318 | 4.59 | 21.4 |

EXAMPLE 82

Toluene Solvate of Example 19-F

To 100 mg of the amorphous free form, 150 μL of toluene was added. On stirring a clear solution is formed. The solution was stirred at −20° C. and over approx. 12 hours a precipitate was formed. The resulting solid was collected by filtration and dried at 40° C. under vacuum for 72 hours. The solid form is crystalline by XRPD, with a melting point of 117.4° C. and a concurrent 3.2% weight loss. The XRPD is shown in FIG. 6. The DSC and TGA are shown in FIG. 7.

Powder X-Ray Diffraction Peaks of Example 19-F from Toluene

| Angle 2θ | d value Å | Relative Intensity % |
|---|---|---|
| 5.134 | 17.21 | 35.9 |
| 7.431 | 11.90 | 35.9 |
| 9.97 | 8.87 | 35.8 |
| 10.975 | 8.06 | 37.2 |
| 11.562 | 7.65 | 33.4 |
| 12.209 | 7.25 | 26.4 |
| 13.632 | 6.50 | 28.8 |
| 14.448 | 6.13 | 46.1 |
| 15.032 | 5.89 | 32.5 |
| 15.865 | 5.59 | 37.3 |
| 16.974 | 5.22 | 100 |
| 17.28 | 5.13 | 68.2 |
| 18.829 | 4.71 | 65.6 |
| 22.402 | 3.97 | 25 |
| 23.165 | 3.84 | 29.4 |

EXAMPLE 83

EtOAc Solvate of Example 19-F

To 100 mg of the amorphous free form, 150 μL of EtOAc was added. On stirring a clear solution is formed. The solution was stirred at −20° C. and over approx. 4 hours a precipitate was formed. The resulting solid was collected by filtration and dried at 40° C. under vacuum for 72 hours.

The solid form is crystalline by XRPD, with a melting point of 117.4° C. and a concurrent 3.2% weight loss. The XRPD is shown in FIG. 8. The DSC and TGA are shown in FIG. 9.

Powder X-Ray Diffraction Peaks of Example 19-F from EtOAc

| Angle 2θ | d value Å | Relative Intensity % |
|---|---|---|
| 5.188 | 17.03 | 64.2 |
| 7.43 | 11.90 | 70.2 |
| 9.171 | 9.64 | 18.7 |
| 10.048 | 8.80 | 42.2 |
| 11.07 | 7.99 | 61.8 |
| 11.555 | 7.66 | 66 |
| 12.318 | 7.19 | 27.1 |
| 13.778 | 6.43 | 33.8 |
| 14.49 | 6.11 | 52.1 |
| 15.972 | 5.55 | 37.9 |
| 17.394 | 5.10 | 100 |
| 19.025 | 4.66 | 68.4 |
| 23.283 | 3.82 | 38.3 |

EXAMPLE 84

Example 19-F Hydrochloride Form A

Example 19-F hydrochloride Form A was prepared on a 100 mg scale. To the Example 19-F free base material, a solution of 0.1N HCl in IPA was added at a 1:1.1 molar ratio creating a slight excess of HCl. Upon addition of the acid, the solution became transparent after <1 min of stirring. The solution was protected from light and allowed to stir at room temperature. Opacity is observed after a few hours but the reaction mixture is allowed to stir for 48 hrs. Material was collected by vacuum filtration, rinsed with IPA, and dried by pulling air through the sample on in vacuum filtration set-up for 1 hour. The yield was approximately 85%.

By elemental analysis and Karl-Fisher, Example 19-F Hydrochloride was determined to be a monochloride salt without a stoichiometric hydrate. It is crystalline and experiences a loss of water at 127° C. (broad DSC endotherm) followed by a melt at 190° C. Mass loss is observed in a stepwise manner by TGA: 5.4% wt by 138° C. and an additional 2.8% wt by 186° C. The XRPD is shown in FIG. 11. The TGA is shown in FIG. 12. The non-hermetic DSC is shown in FIG. 13. The hermetic DSC is shown in FIG. 14.

XRPD Peaks of Example 19-F Hydrochloride Form A

| Angle 2θ | d value Å | Relative Intensity % |
|---|---|---|
| 4.666 | 18.94 | 28.9 |
| 6.928 | 12.76 | 32.5 |
| 7.63 | 11.59 | 100 |
| 9.394 | 9.41 | 55.6 |
| 10.875 | 8.14 | 21.1 |
| 12.252 | 7.22 | 21.7 |
| 14.263 | 6.21 | 26.2 |
| 15.378 | 5.76 | 41 |
| 17.227 | 5.15 | 31.1 |
| 18.146 | 4.89 | 54.6 |
| 19.187 | 4.63 | 52.4 |
| 26.521 | 3.36 | 29.8 |

EXAMPLE 85

Example 19-F Hydrochloride Form B

Example 19-F Hydrochloride Form B was on a 500 mg scale. Its synthesis is similar to that of Form A except that additional drying time is used. To the Example 19-F free base material, a solution of 0.1N HCl in IPA was added at a 1:1.1 molar ratio creating a slight excess of HCl. Upon addition of the acid, the solution became transparent after <1 min of stirring. The solution was protected from light and allowed to stir at room temperature. Opacity is observed after a few hours but the reaction mixture is allowed to stir for 48 hrs. Material was collected by vacuum filtration, rinsed with IPA, dried by pulling air through the sample on in vacuum filtration set-up for 1 hour and then placed in a vacuum oven (40° C.) for 72 hrs. Form B resulted after this period. The yield was approximately 85%.

Aqueous suspensions of Example 19-F Hydrochloride Form A and Example 19-F Hydrochloride Form B were prepared. Form A became amorphous in 24 hrs; Form B appears to retain a small amount of Form B crystallinity but becomes significantly amorphous By ion chromatography, Example 19-F Hydrochloride Form B was determined to be a monochloride salt. It is crystalline and experiences a loss of water at 127° C. (broad DSC endotherm) followed by a melt at 199° C. By 167° C., 5.5% wt. is lost by TGA. The XRPD is shown in FIG. 15. The TGA is shown in FIG. 16. The non-hermetic DSC is shown in FIG. 17.

XRPD Peaks of Example 19-F Hydrochloride Form B

| Angle 2θ | d value Å | Relative Intensity % |
|---|---|---|
| 4.916 | 17.98 | 27.1 |
| 7.407 | 11.94 | 44.1 |
| 8.041 | 11.00 | 85 |
| 8.368 | 10.57 | 100 |
| 9.681 | 9.14 | 41.3 |
| 9.983 | 8.86 | 39.7 |
| 13.252 | 6.68 | 30.2 |
| 15.006 | 5.90 | 45 |
| 15.554 | 5.70 | 39.2 |
| 19.271 | 4.61 | 47.2 |
| 20.137 | 4.41 | 35.4 |

EXAMPLE 86

Example 19-F Phosphate Form A

Example 19-F Phosphate Form A was produced on a 25 mg scale. Example 19-f free base was dissolved in acetone at 42 mg/mL. Next a solution of 0.1M phosphoric acid in acetone was added at a 1:1.5 molar ratio generating an excess of acid. The solution concentration of free base was thus 19.6 mg/mL. Some immediate haziness was observed. The solution was allowed to stir over 48 hrs at room temperature yielding an opaque suspension. The material was collected by vacuum filtration, washed with acetone and dried in a vacuum oven (40° C.) for 24 hrs.

Example 19-F Phosphate Form A is crystalline and melts at 128° C. The XRPD is shown in FIG. 18. The hermetic DSC is shown in FIG. 19.

XRPD peaks of Example 19-F Phosphate Form A

| Angle 2θ | d value Å | Relative Intensity % |
|---|---|---|
| 4.73 | 18.68 | 100 |
| 7.956 | 11.11 | 12 |
| 9.584 | 9.23 | 19 |
| 10.644 | 8.31 | 15.1 |
| 13.588 | 6.52 | 13.1 |
| 14.548 | 6.09 | 15.5 |
| 16.287 | 5.44 | 25.9 |
| 17.266 | 5.14 | 21.1 |
| 11.835 | 7.48 | 14 |
| 18.948 | 4.68 | 19.1 |

EXAMPLE 87

Example 19-F Phosphate Form B

Example 19-F Phosphate Form B was produced on a 25 mg scale. Example 19-F free base material was dissolved in acetone at 9.2 mg/mL. Next, a solution of 0.1M phosphoric acid in acetone was added at a 1:1.4 molar ratio generating an excess of acid. The solution concentration of the free base was thus 7.45 mg/mL. The solution was clear upon addition of the phosphoric acid. The solution was allowed to stir over 72 hrs at room temperature yielding an opaque suspension. The material was collected by vacuum filtration, washed with acetone and dried by pulling air through the vacuum filtration apparatus approximately 30 minutes.

By ion chromatography, Example 19-F Phosphate Form B was determined to be a monophosphate salt. It is crystalline and has several endotherms as determined by hermetic DSC: 119° C., 131° C. and 164° C. The XRPD is shown in FIG. 20. The hermetic DSC is shown in FIG. 21.

XRPD Peaks of Example 19-F Phosphate Form B

| Angle 2θ | d value Å | Relative Intensity % |
|---|---|---|
| 4.428 | 19.95 | 100 |
| 5.873 | 15.05 | 16.4 |
| 7.086 | 12.47 | 20.8 |
| 7.993 | 11.06 | 57.6 |
| 10.188 | 8.68 | 23.1 |
| 11.865 | 7.46 | 25.8 |
| 13.382 | 6.62 | 54.8 |
| 14.434 | 6.14 | 29.6 |
| 16.946 | 5.23 | 32.1 |
| 18.742 | 4.73 | 58.7 |
| 20.709 | 4.29 | 29.3 |
| 21.718 | 4.09 | 29.1 |
| 22.728 | 3.91 | 38.7 |

EXAMPLE 88

Example 19-F Phosphate Form C

After 2 DVS cycles from 0-85% RH, Example 19-F Phosphate Form B was found to convert to Example 19-F Phosphate Form C.

By elemental analysis and Karl-Fisher, Example 19-F Form C was determined to be a monophosphate salt with a stoichiometric dihydrate. It is crystalline and experiences a loss of water at 70° C. (broad DSC endotherm) followed by a melt at 165° C. By 119° C., 1.2% wt. is lost by TGA. The XRPD is shown in FIG. 22. The non-hermetic DSC is shown in FIG. 23. TGA is shown in FIG. 24.

XRPD peaks of Example 19-F Phosphate Form C

| Angle 2θ | d value Å | Relative Intensity % |
|---|---|---|
| 4.50 | 19.65 | 100 |
| 7.93 | 11.15 | 11.6 |
| 8.65 | 10.22 | 13.9 |
| 10.63 | 8.32 | 10.3 |
| 12.00 | 7.38 | 15.8 |
| 13.85 | 6.39 | 21.9 |
| 15.35 | 5.77 | 14 |
| 16.06 | 5.52 | 15.4 |
| 17.65 | 5.03 | 18 |
| 18.82 | 4.72 | 18.7 |

EXAMPLE 89

Solubility of Example 19-F, Example 19-F Hydrochloride Form A, and Example 19-F Phosphate Form C

| | 24 hr Equilibrium Solubility (mg/mL) [pH] | | |
|---|---|---|---|
| | Example 19-F | Example 19-F Hydrochloride Form A | Example 19-F Phosphate Form C |
| Physical Form | Amorphous | Crystalline | Crystalline |
| pH 1 | <0.0005 [1.32] | 0.14 [1.41] | 0.83 [1.22] |
| pH 4.5 | <0.0005 [4.28] | <0.001 [4.54] | 0.006 [3.70] |
| pH 6.8 | <0.0005 [6.62] | <0.001 [6.86] | 0.001 [5.83] |
| SGF | <0.0005 [1.3] | 0.13 [2.20] | 0.55 [1.84] |
| SIF | * | <0.001 [6.60] | 0.001 [6.56] |
| FeSSIF pH 5.5 | <0.0005 [7] | 1.01 [5.78] | 0.65 [5.22] |
| FaSSIF pH 6.5 | <0.0005 [6.47] | 0.01 [6.58] | 0.02 [6.09] |
| Water | <0.0005 [6.09] | <0.001 [4.68] | 0.04 [3.33] |
| Capmul MCM | >26.5 | 24.97 | 4.21 |
| Corn oil glyceride | >26.1 | 23.08 | 13.14 |
| 20% HPbCD | 0.003 | 0.03 | 0.77 |
| PG | 3.426 | 13.89 | 15.48 |
| PEG300 | 8.260 | 10.19 | 13.89 |
| 50% PEG300 | 0.016 | 8.01 | 5.23 |
| 10% Solutol | 0.078 | 7.77 | 8.96 |
| 10% Cremophor | * | 5.14 | 8.76 |
| 1% Tween80 | 0.006 | 0.52 | 0.71 |
| 1% SLS | 0.005 | 0.48 | 0.53 |
| MEPC5 | * | 16.45 | 22.07 |
| MEPC4 | * | 11.57 | 25.96 |

* Data not available

EXAMPLE 90

Key in vivo Data Demonstrating Advanced Biopharmaceutical Performance

Figure 25:
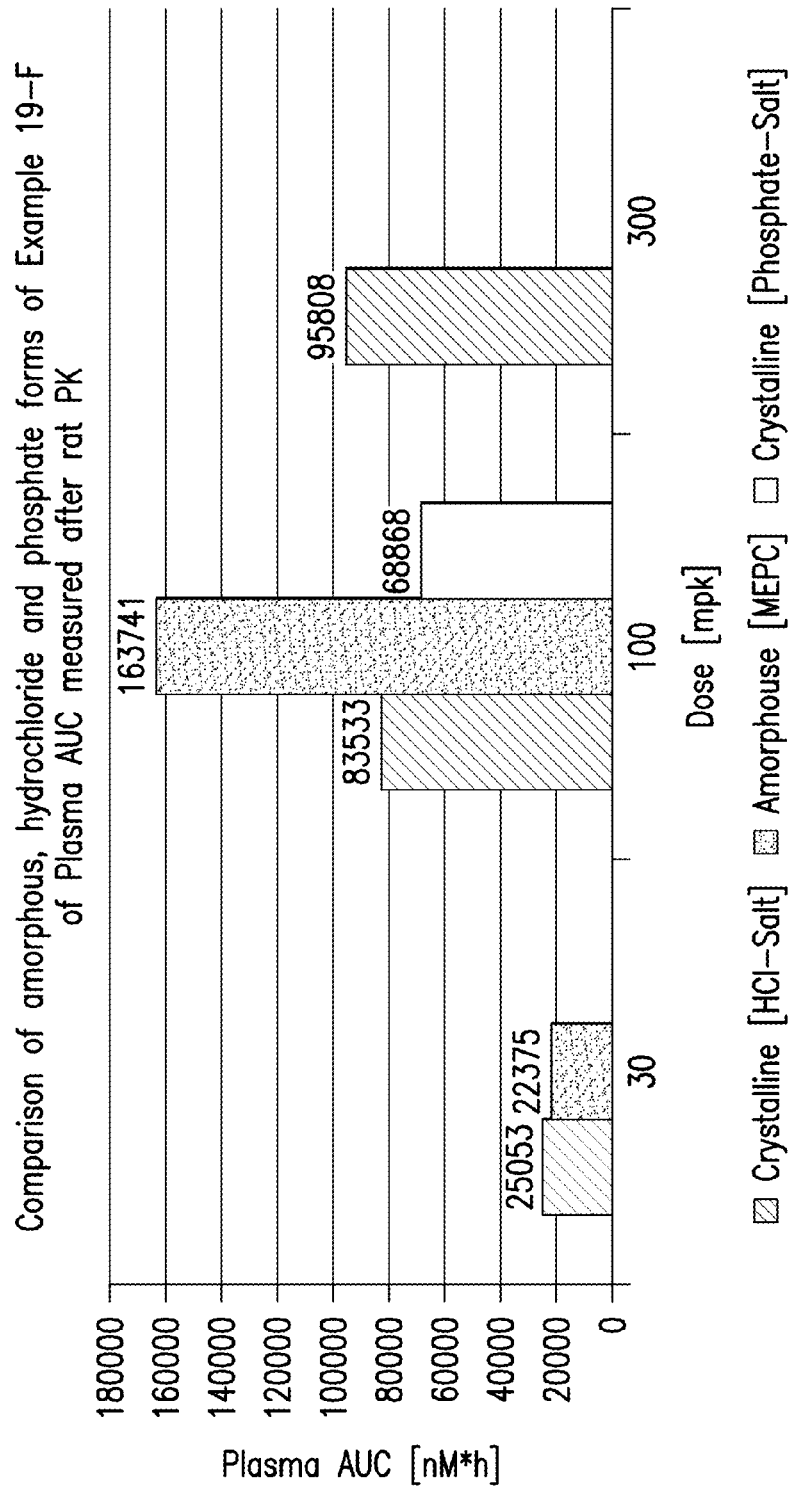
FIG. 25. Comparison of amorphous, hydrochloride and phosphate forms of Example 19-F of Plasma AUC measured after rat PK.

Example 19-F Hydrochloride Form B (30 and 100 mpk) and Example 19-F Phosphate Form C (100 mpk) have been dosed in a suspension formulation (0.1% Tween80/0.5% MC) at 100 mpk in Sprague Dawley Rats. At 30 mpk the HCl salt has similar plasma exposure levels to those observed after a microemulsion dose. The exposure at 100 mpk was lower from the salt forms compared to the microemulsion. The plasma exposure after a 300 mpk dose of the HCl salt is approximately the same as after the 100 mpk dose. The date from this experiment is summarized in FIG. 25.

The Example 19-F Hydrochloride Form B suspension particle size was d(0.5) and d(0.9) were 4.3 µm and 13.8 µm respectively. The Example 19-F Phosphate Form C suspension particle size was d(0.5) and d(0.9) were 8.5 µm and 37.0 µm respectively. After 24 hrs, the solids in suspension had become mostly amorphous.

EXAMPLE 91

Solvate of Example 55-G

To 100 mg of free base Example 55-G, 1000 µL of 10% EtOAc in heptane was added. On stirring a fine suspension is formed. Suspension was heated to 50° C. at 1° C./min and held for 30 minutes at which point it was cooled at 0.5° C./min to 5° C. where it was held for 30 minutes. The resulting solid was collected by filtration washed with 1000 µL cold heptane and dried at 40° C. under vacuum for 72 hours.

This form is crystalline by XRPD with a melting point of 134.8° C. and a concurrent weight loss of 4.3%. XRPD is shown in FIG. 26. DSC and TGA are shown in FIG. 27.

Powder X-Ray Diffraction Peaks of Example 55-G from 10% EtOAc in Heptane

| Angle 2θ | d value Å | Relative Intensity % |
|---|---|---|
| 6.805 | 12.99 | 13.7 |
| 7.752 | 11.41 | 18.4 |
| 8.75 | 10.11 | 17.7 |
| 10.211 | 8.66 | 19.6 |
| 10.909 | 8.11 | 14 |
| 11.635 | 7.61 | 24.6 |
| 12.485 | 7.09 | 26.9 |
| 12.972 | 6.82 | 18.6 |
| 14.159 | 6.26 | 79.2 |
| 14.831 | 5.97 | 29.2 |
| 15.714 | 5.64 | 21.8 |
| 16.227 | 5.46 | 45.3 |
| 17.249 | 5.14 | 100 |
| 17.899 | 4.96 | 35 |
| 18.411 | 4.82 | 35.4 |
| 19.351 | 4.59 | 28.1 |
| 20.094 | 4.42 | 31.3 |
| 22.443 | 3.96 | 21.7 |
| 23.089 | 3.85 | 49.9 |
| 23.813 | 3.74 | 30.7 |
| 24.303 | 3.66 | 22.8 |
| 25.326 | 3.52 | 25.9 |
| 25.809 | 3.45 | 30.2 |
| 27.193 | 3.28 | 24.3 |
| 27.973 | 3.19 | 25.3 |
| 28.863 | 3.09 | 20 |

EXAMPLE 92

Tri-Hydrate of Example 55-G

To 600 mg of free base Example 55-G, 7500 µL of 50% MeOH in water was added. On stirring a fine suspension is formed which is amorphous in nature. Suspension was heated to 50° C. at 1° C./min and held for 30 minutes at which point it was cooled at 0.5° C./min to 5° C. where it was held for 30 minutes. The resulting solid was collected by filtration then dried at 40° C. under vacuum for 72 hours. Yield was approximately 92%

This form is crystalline by XRPD with a melting point of 123.7° C. and a weight loss on heating of 6.6%. Water content is 7.5% by Karl Fischer. The XRPD is shown in FIG. 28. The DSC and TGA are shown in FIG. 29. The sealed pan DSC is shown in FIG. 30.

Powder X-Ray Diffraction Peaks of FIG. 55-G from 50% MeOH in Water

| Angle 2θ | d value Å | Relative Intensity % |
|---|---|---|
| 6.602 | 13.39 | 17.9 |
| 8.161 | 10.83 | 100 |
| 9.746 | 9.08 | 19.2 |
| 12.689 | 6.98 | 62.2 |
| 13.109 | 6.75 | 39.9 |
| 13.91 | 6.37 | 20.2 |
| 14.544 | 6.09 | 29.1 |
| 16.441 | 5.39 | 20.9 |
| 16.999 | 5.22 | 27.9 |
| 17.517 | 5.06 | 22.9 |
| 19.318 | 4.59 | 29.4 |
| 21.222 | 4.19 | 34.3 |
| 22.71 | 3.92 | 37.8 |
| 23.065 | 3.86 | 29.5 |
| 24.253 | 3.67 | 23.4 |
| 25.351 | 3.51 | 31.9 |
| 27.787 | 3.21 | 30.8 |

EXAMPLE 93

Sulfate of Example 55-G

To 100 mg of free base Example 55-G, 1M equivalent of sulfuric acid and 1000 µL of acetone was added. On stirring a clear solution is formed. This solution was heated to 50° C. at 1° C./min and held for 30 minutes at which point it was cooled at 0.5° C./min to 5° C. where it was held for 30 minutes. The resulting solid was collected by cold filtration then dried at 40° C. under vacuum for 72 hours.

This form is weakly crystalline hemisulfate with a melting point of 131.4° C. and a concurrent weight loss of 1.8% up to 200° C. XRPD is shown in FIG. 31. DSC and TGA are shown in FIG. 32.

Powder X-Ray Diffraction Peaks of Example 55-G Sulfate

| Angle 2θ | d value Å | Relative Intensity % |
|---|---|---|
| 5.227 | 16.91 | 100 |
| 6.198 | 14.26 | 29.4 |
| 8.648 | 10.23 | 42.1 |
| 10.047 | 8.80 | 82.2 |
| 11.452 | 7.73 | 42.6 |
| 12.769 | 6.93 | 63.4 |
| 14.551 | 6.09 | 68.4 |
| 16.203 | 5.47 | 63.1 |
| 17.059 | 5.20 | 56.1 |
| 17.827 | 4.98 | 56.1 |
| 19.214 | 4.62 | 55.9 |
| 19.952 | 4.45 | 55.1 |

EXAMPLE 94

Tosylate of Example 55-G

To 600 mg of free base Example 55-G, 1M equivalent of p-toluenesulfonic hydrate acid and 7500 µL of acetone was added. On stirring a clear solution is formed. This solution was heated to 50° C. at 1° C./min and held for 30 minutes at which point it was cooled at 0.5° C./min to 5° C. where it was held for 30 minutes. The resulting solid was collected by filtration then dried at 40° C. under vacuum for 72 hours. Yield was approximately 75%.

This form is weakly crystalline 1:1 tosylate salt with a melting point of 143.8° C. and a concurrent weight loss of 1.2% up to 200° C. XRPD is shown in FIG. 33. DSC and TGA are shown in FIG. 34.

Powder X-Ray Diffraction Peaks of Example 55-G Tosylate

| Angle 2θ | d value Å | Relative Intensity % |
|---|---|---|
| 4.157 | 21.25 | 64.4 |
| 6.405 | 13.80 | 47.6 |
| 8.264 | 10.70 | 51.4 |
| 9.769 | 9.05 | 47.3 |
| 12.366 | 7.16 | 57.6 |
| 13.724 | 6.45 | 72.2 |
| 14.639 | 6.05 | 87.5 |
| 16.026 | 5.53 | 77.1 |
| 18.069 | 4.91 | 100 |
| 18.889 | 4.70 | 82.4 |

EXAMPLE 95

Besylate of Example 55-G

To 100 mg of free base Example 55-G, 1M equivalent of benzene sulfonic acid and 1000 µL of acetone was added. On stirring a clear solution is formed. This solution was heated to 50° C. at 1° C./min and held for 30 minutes at which point it was cooled at 0.5° C./min to 5° C. where it was held for 30 minutes. The resulting solid collected by filtration and dried at 40° C. under vacuum for 72 hours.

This form is crystalline, 1:1 besylate salt acetone solvate with a melting point of 155.7° C. There is a lower temperature endotherm at 85.9° C. with a concurrent weight loss of 5.4% which likely corresponds to loss of acetone. XRPD is shown in FIG. 35. DSC and TGA are shown in FIG. 36.

Powder X-Ray Diffraction Peaks of Example 55-G Besylate

| Angle 2θ | d value Å | Relative Intensity % |
|---|---|---|
| 6.799 | 13.00 | 22.1 |
| 7.624 | 11.60 | 14.9 |
| 8.215 | 10.76 | 26 |
| 9.196 | 9.62 | 40.7 |
| 10.674 | 8.29 | 22.8 |
| 11.177 | 7.92 | 11.3 |
| 11.715 | 7.55 | 11.3 |
| 13.324 | 6.65 | 28.5 |
| 13.71 | 6.46 | 100 |
| 14.352 | 6.17 | 24.9 |
| 14.912 | 5.94 | 49.6 |
| 15.358 | 5.77 | 35 |
| 16.169 | 5.48 | 54.2 |
| 16.706 | 5.31 | 21.8 |
| 17.16 | 5.17 | 27.6 |
| 17.465 | 5.08 | 52.4 |
| 17.737 | 5.00 | 33.1 |
| 18.952 | 4.68 | 14 |
| 19.915 | 4.46 | 46.3 |
| 21.568 | 4.12 | 17.1 |
| 22.119 | 4.02 | 69 |
| 22.422 | 3.97 | 35.4 |
| 23.656 | 3.76 | 18 |
| 24.45 | 3.64 | 76.1 |
| 25.535 | 3.49 | 17.3 |
| 27.668 | 3.22 | 19.9 |

-continued

| Angle 2θ | d value Å | Relative Intensity % |
|---|---|---|
| 28.393 | 3.14 | 32.3 |
| 29.209 | 3.06 | 18.5 |
| 29.832 | 2.99 | 18.1 |
| 30.595 | 2.92 | 18.5 |
| 33.143 | 2.70 | 17.7 |

EXAMPLE 96

MTBE Solvate of Example 55-G

To 100 mg of free base Example 55-G, 1000 μL of 10% MTBE in heptane (or neat MTBE may also be used) was added. On stirring a fine suspension is formed. Suspension was heated to 50° C. at 1° C./min and held for 30 minutes at which point it was cooled at 0.5° C./min to 5° C. where it was held for 30 minutes. The resulting solid was collected by filtration and dried at 40° C. under vacuum for 72 hours.

This form is crystalline with a melting point of 134.2° C. with a concurrent weight loss of 6.9% corresponding to loss of MTBE. XRPD is shown in FIG. 37. DSC and TGA are shown in FIG. 38.

Powder X-Ray Diffraction Peaks of Example 55-G MTBE Solvate

| Angle 2θ | d value Å | Relative Intensity % |
|---|---|---|
| 4.074 | 21.69 | 13.9 |
| 6.728 | 13.14 | 22.3 |

-continued

| Angle 2θ | d value Å | Relative Intensity % |
|---|---|---|
| 7.659 | 11.54 | 36.3 |
| 8.627 | 10.25 | 26.8 |
| 10.148 | 8.72 | 27 |
| 10.853 | 8.15 | 19.4 |
| 11.418 | 7.75 | 39.3 |
| 12.313 | 7.19 | 31.9 |
| 12.889 | 6.87 | 27.3 |
| 14.043 | 6.31 | 88.8 |
| 14.684 | 6.03 | 27.6 |
| 15.969 | 5.55 | 61.2 |
| 16.689 | 5.31 | 50.7 |
| 17.149 | 5.17 | 100 |

-continued

| Angle 2θ | d value Å | Relative Intensity % |
|---|---|---|
| 17.842 | 4.97 | 39.2 |
| 18.338 | 4.84 | 43.1 |
| 19.119 | 4.64 | 33.9 |
| 19.752 | 4.49 | 32 |
| 23.113 | 3.85 | 37.6 |
| 24.397 | 3.65 | 22.2 |
| 25.187 | 3.54 | 22 |
| 25.794 | 3.45 | 24.9 |
| 27.159 | 3.28 | 20.3 |

EXAMPLE 97

Moisture Sorption Properties of Different Crystalline Example 55-G Forms Compared to the Amorphous Free Form

| DVS % Weight gain | amorphous | Di-hydrate | Sulfate | tosylate | Besylate (acetone solvate) | Hydrate |
|---|---|---|---|---|---|---|
| 40% RH | 1.9 | −1 | 3.5 | 2.2 | −3.5 | 7.1 |
| 90% RH | 3.3 | −0.2 * | 9 | 5.3 | −2 * | 9.3 |

Solubility of Different Crystalline Example 55-G Forms Compared to the Amorphous Free Form

| mg/mL (pH) | amorphous | Di-hydrate | tosylate | Besylate (acetone solvate) | hydrate |
|---|---|---|---|---|---|
| pH 1.2 | >10 [1.2] | 5.698 (1.59) | 1.618 (1.47) | 3.161 (1.44) | 4.402 (1.7) |
| pH 4.5 | 0.01 [4.8] | <0.0005 (4.46) | <0.0005 (4.54) | <0.0005 (4.39) | <0.0005 (4.54) |
| pH 6.8 | <0.0005 [6.8] | 0.041 (3.82) | 0.257 (2.97) | 0.075 (3.57) | <0.0005 (6.63) |
| SGF | >10 [1.6] | 6.603 (1.33) | 2.034 (1.31) | 3.179 (1.31) | 7.061 (1.4) |
| FeSSIF (pH 5.5) | 1.2 [5.6] | <0.0005 (4.51) | <0.0005 (5.1) | <0.0005 (5.5) | 0.001 (5.75) |
| FaSSIF (pH 6.5) | 0.07 [6.9] | 0.081 (3.54) | <0.0005 (5.7) | <0.0005 (5.98) | <0.0005 (6.56) |
| Water | <0.0005 [6.2] | 0.451 (2.64) | 0.495 (2.42) | 0.457 (2.57) | <0.0005 (6.12) |

EXAMPLE 98

In Vivo Data

Example 55-G hydrate was dosed in a suspension formulation (0.1% Tween80/0.5% MC) at 30 and 100 mpk to Sprague Dawley Rats. At 30 mpk the hydrate has similar plasma exposure levels to those observed after a dose of microemulsion or amorphous form suspension. The exposure at 100 mpk was slightly lower from the crystalline hydrate compared to the microemulsion or amorphous suspension. However the increase in exposure was proportional with dose for the hydrate suggesting the form would be suitable for use in higher dose in vivo work. The results of this experiment are summarized in FIG. 39.

EXAMPLE 99

FLIPR Assay

Compounds were tested for their ability to inhibit C5a-mediated calcium mobilization using a stable cell line over expressing the human C5aR & the Gα15 protein on the FLIPR (Fluorescent Imaging Plate Reader) Tetra system. Cells were maintained in culture media containing DMEM (Dulbecco's Modified Eagle Medium) with 4.5 g/L glucose, 10% fetal bovine serum, 100 U/mL, 1× non-essential amino acid, and 250 μg/mL G418 (Geneticin). Prior to testing of compounds, cells were plated at 10,000 cells/well in clear bottom 384-well black plate, and incubated overnight at 37° C. with 5% $CO_2$. On the day of experiment, culture media was removed, and replaced with assay buffer HBSS (Hanks' Balanced Salt Solution) with 20 mM HEPES (4-(2-hydroxyethyl)-1-piperazineethanesulfonic acid) and 0.1% BSA (bovine serum albumin) BSA containing calcium 5 dye (Molecular Devices) and 2.5 mM probenecid. After 1 hour incubation at 37° C., 5% $CO_2$ for 60 min, cells were pre-incubated with compounds for 30 minutes at room temperature, in 1% DMSO (dimethyl sulfoxide). Human C5a at the EC50 (0.1-0.25 nM) concentration was then added and changes in calcium mobilization were detected using FLIPR

| Example number | FLIPR $IC_{50}$ (nM) |
|---|---|
| 23-I | 0.5 |
| 17-M | 30 |
| 29 | 2 |
| 19-F | 4 |
| 16-I | 48 |
| 20-D | 164 |
| 21-AJ | 6 |
| 21-R | 1 |
| 24-G | 7 |
| 17-Y | 160 |
| 21-AF | 4 |
| 23-H | 1 |
| 30-A | 16 |
| 17-T | 54 |
| 19-AE | 4 |
| 17-AP | 10 |
| 17-H | 10 |
| 22-C | 2 |
| 21-AH | 1 |
| 24-I | 464 |
| 17-AN | 31 |
| 31-I | 9 |
| 54-B | 2 |
| 17-AM | 2 |
| 17-R | 10 |
| 43-A | 56 |
| 23-G | 2 |
| 16-V | 338 |
| 17-AI | 19 |
| 21-AG | 1 |
| 24-D | 91 |
| 42-K | 217 |
| 19-AD | 2 |
| 44-E | 38 |
| 19-N | 29 |
| 21-D | 0.5 |
| 40-L | 180 |
| 47-B | 56 |
| 21-AK | 5 |
| 42-H | 58 |
| 17-G | 4 |
| 42-I | 14 |
| 23-F | 5 |
| 50-E | 790 |
| 24-L | 6 |
| 40-Q | 868 |
| 24-E | 75 |
| 44-D | 131 |
| 17-AY | 9 |
| 16-O | 90 |
| 17-AQ | 16 |
| 19-AF | 1 |
| 17-AJ | 94 |
| 43-D | 802 |
| 17-BK | 163 |
| 46-B | 42 |
| 46-A | 20 |
| 19-AI | 2 |
| 40-S | 78 |
| 42-L | 4 |
| 21-Q | 1 |
| 40-M | 11 |
| 21-X | 308 |
| 23-D | 8 |
| 40-D | 132 |
| 45 | 27 |
| 19-AC | 4 |
| 21-M | 56 |
| 33-C | 79 |
| 40-P | 37 |
| 19-AB | 17 |
| 31-H | 77 |
| 28-D | 4 |
| 41-F | 550 |
| 21-S | 30 |
| 41-E | 21 |
| 21-E | 23 |
| 19-AK | 31 |
| 24-C | 31 |
| 25-C | 5 |
| 19-L | 746 |
| 32-B | 2 |
| 53 | 18 |
| 17-AS | 46 |
| 25-F | 23 |
| 55-I | 1 |
| 23-K | 64 |
| 55-G | 2 |
| 19-Q | 112 |
| 17-BG | 15 |
| 17-BE | 415 |
| 55-L | 3 |
| 48 | 198 |
| 28-B | 3 |
| 21-P | 7 |
| 19-AH | 4 |
| 41-G | 3 |
| 41-D | 49 |
| 21-AB | 4 |
| 21-AE | 9 |
| 21-AI | 1 |
| 41-J | 22 |
| 26-B | 20 |
| 17-P | 13 |
| 19-K | 65 |
| 19-X | 47 |
| 52-C | 1 |
| 17-AZ | 39 |
| 17-AV | 12 |
| 55-H | 4 |
| 23-J | 8 |
| 55-J | 5 |
| 24-J | 8 |
| 39-D | 74 |
| 32-A | 6 |
| 55-M | 1 |
| 51-D | 197 |
| 23-C | 40 |
| 56-C | 1 |
| 56-B | 2 |
| 21-N | 2 |

| Example number | FLIPR IC$_{50}$ (nM) |
|---|---|
| 21-K | 2 |
| 63-E | 23 |
| 56-F | 1 |
| 21-AM | 1 |
| 55-N | 6 |
| 55-G | 4 |
| 68-C | 16 |
| 69-M | 8 |
| 46-C | 25 |
| 69-H | 4 |
| 70-G | 9 |
| 65-H | 4 |
| 21-AL | 1 |
| 56-E | 2 |
| 68-B | 2 |
| 65-B | 2 |
| 65-K | 2 |
| 63-G | 31 |
| 63-I | 32 |
| 65-A | 1 |
| 70-J | 12 |
| 69-L | 1 |
| 65-I | 1 |
| 69-J | 67 |
| 69-I | 4 |
| 70-K | 20 |
| 71-B | 2 |

EXAMPLE 100

Human Whole Blood CD11b Up-Regulation Assay

Whole blood was collected in sodium heparin tubes and the assay started within 2 hours of the blood draw. The blood was incubated with compounds in 1% DMSO (dimethyl sulfoxide) at room temperature for 10 minutes with gentle rocking. 2 nM of human C5a was then added for 15 minutes at room temperature with gentle rocking. Following the C5a incubation period cells were washed once with cold FACS (fluorescence-activated cell sorting) buffer (phosphate buffered saline+0.5% bovine serum albumin) FITC (fluorescein isothiocyanate) mouse anti-human CD15 and PE-Cy5 (phycoerythrin-cyanine 5) mouse anti-human CD11b antibodies (Becton Dickinson) were gently mixed with the cells and allowed to incubate for 30 minutes on ice protected from the light. Cells were then washed three times with cold FACS buffer. Red blood cells (RBC) were lysed by incubating with BD FACS lysis buffer (Becton Dickinson) for 10 minutes at room temperature. Cells were pelleted and the lysing procedure was repeated until all RBCs were lysed. The remaining leukocytes were resuspended in BD lysis buffer. Samples were acquired on the LSR[11] flow cytometer and 10,000 events of the CD15+ granulocyte population were collected. The CD11b median fluorescence intensity of the CD 15+ cell population was evaluated using FACSDiva software (Becton Dickinson).

| Example number | hCD11b IC$_{50}$ (nM) |
|---|---|
| 23-I | 22 |
| 19-F | 13 |
| 29 | 300 |
| 17-AN | 423 |
| 31-I | 18 |
| 24-E | 385 |
| 21-AJ | 15 |
| 21-R | 15 |
| 24-G | 670 |
| 55-G | 23 |
| 21-AF | 28 |
| 54-B | 19 |
| 17-R | 42 |
| 43-A | 178 |
| 56-C | 6 |
| 23-G | 25 |
| 21-AG | 22 |
| 24-D | 1500 |
| 19-AD | 26 |
| 44-E | 188 |
| 23-H | 24 |
| 30-A | 5785 |
| 17-T | 451 |
| 19-AE | 22 |
| 17-AP | 513 |
| 17-H | 300 |
| 22-C | 17 |
| 21-AH | 6 |
| 17-AY | 45 |
| 55-H | 4 |
| 16-O | 2250 |
| 17-AQ | 277 |
| 19-AF | 6 |
| 17-BK | 40 |
| 56-B | 45 |
| 46-B | 224 |
| 46-A | 1987 |
| 19-AI | 7 |
| 40-S | 793 |
| 21-Q | 7 |
| 21-D | 7 |
| 47-B | 1420 |
| 21-AK | 51 |
| 17-G | 114 |
| 42-I | 2120 |
| 23-F | 28 |
| 24-L | 391 |
| 19-AB | 26 |
| 31-H | 72 |
| 28-D | 58 |
| 21-S | 180 |
| 21-E | 422 |
| 19-AK | 30 |
| 25-C | 183 |
| 32-B | 24 |
| 17-AS | 67 |
| 55-L | 36 |
| 28-B | 107 |
| 21-N | 8 |
| 21-K | 11 |
| 23-C | 95 |
| 23-J | 38 |
| 21-AL | 19 |
| 63-E | 29 |
| 40-M | 69 |
| 23-D | 18 |
| 40-D | 264 |
| 45 | 583 |
| 19-AC | 50 |
| 21-M | 181 |
| 33-C | 238 |
| 21-P | 26 |
| 19-AH | 17 |
| 41-G | 70 |
| 41-D | 153 |
| 21-AB | 11 |
| 21-AE | 93 |
| 21-AI | 8 |
| 41-J | 302 |
| 26-B | 907 |
| 23-K | 11 |
| 17-P | 70 |

-continued

| Example number | hCD11b IC$_{50}$ (nM) |
|---|---|
| 52-C | 178 |
| 24-J | 423 |
| 32-A | 63 |
| 55-M | 15 |
| 65-K | 26 |
| 63-G | 197 |
| 56-F | 11 |
| 21-AM | 7 |
| 55-N | 12 |
| 55-G | 5 |
| 68-C | 69 |
| 69-M | 45 |
| 76-C | 46 |
| 69-H | 196 |
| 70-G | 19 |
| 68-B | 17 |
| 71-B | 10 |
| 63-I | 60 |
| 65-A | 30 |
| 70-J | 39 |
| 69-L | 54 |
| 65-I | 19 |
| 69-J | 112 |
| 69-I | 25 |
| 70-K | 37 |
| 65-H | 56 |
| 65-B | 16 |
| 70-H | 41 |
| 70-I | 38 |

What is claimed is:

1. A compound, or pharmaceutically acceptable salt thereof, according to the formula:

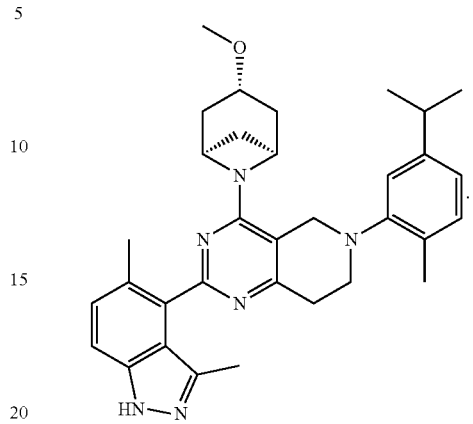

2. A pharmaceutical composition comprising one or more pharmaceutically acceptable carriers and a therapeutically effective amount of a compound of claim 1.

3. A method of treating age related macular degeneration comprising administering to a subject in need thereof an effective amount of a composition comprising a compound of claim 1.

* * * * *